United States Patent
McLeod et al.

(10) Patent No.: US 11,964,944 B2
(45) Date of Patent: Apr. 23, 2024

(54) COMPOUNDS AND METHODS FOR TREATING, DETECTING, AND IDENTIFYING COMPOUNDS TO TREAT APICOMPLEXAN PARASITIC DISEASES

(71) Applicants: The University of Chicago, Chicago, IL (US); University of Leeds, Leeds (GB); The J. Craig Venter Institute, Rockville, MD (US); Institute For Systems Biology, Seattle, WA (US); U.S. Government, as represented by The Secretary of The Army Medical Command (MEDCOM), Fort Detrick, MD (US); The University of Strathclyde, Glasgow (GB)

(72) Inventors: Rima McLeod, Chicago, IL (US); Martin McPhillie, Leeds (GB); Colin W. G. Fishwick, Leeds (GB); Hernan Alejandro Lorenzi, Rockville, MD (US); Kai Wang, Seattle, WA (US); Taek-Kyun Kim, Seattle, WA (US); Yong Zhou, Seattle, WA (US); Leroy E. Hood, Seattle, WA (US); Ying Zhou, Chicago, IL (US); Kamal El Bissati, Chicago, IL (US); Mark Hickman, Silver Spring, MD (US); QiGui Li, Silver Spring, MD (US); Craig Roberts, Glasgow (GB)

(73) Assignees: The University of Chicago, Chicago, IL (US); J. Craig Venter Institute, Inc., Ajolla, CA (US); The University of Sheffield (GB); Institute for Systems Biology, Seattle, WA (US); The University of Leeds (GB); The University of Strathclyde (GB); The Government of the United States, Fort Detrick, MD (US)

( * ) Notice: Subject to any disclaimer, the term of this patent is extended or adjusted under 35 U.S.C. 154(b) by 0 days.

(21) Appl. No.: 17/831,049

(22) Filed: Jun. 2, 2022

(65) Prior Publication Data

US 2023/0140413 A1    May 4, 2023

Related U.S. Application Data

(62) Division of application No. 16/063,877, filed as application No. PCT/US2016/067795 on Dec. 20, 2016, now Pat. No. 11,414,385.

(60) Provisional application No. 62/306,385, filed on Mar. 10, 2016, provisional application No. 62/270,264, filed on Dec. 21, 2015.

(51) Int. Cl.
| | | |
|---|---|---|
| *C07D 215/233* | (2006.01) | |
| *A61P 33/06* | (2006.01) | |
| *C07D 401/12* | (2006.01) | |
| *C07D 405/12* | (2006.01) | |
| *C07D 471/04* | (2006.01) | |
| *C07D 487/04* | (2006.01) | |

(52) U.S. Cl.
CPC .......... *C07D 215/233* (2013.01); *A61P 33/06* (2018.01); *C07D 401/12* (2013.01); *C07D 405/12* (2013.01); *C07D 471/04* (2013.01); *C07D 487/04* (2013.01)

(58) Field of Classification Search
CPC .................................................. C07D 215/233
See application file for complete search history.

(56) References Cited

FOREIGN PATENT DOCUMENTS

| WO | 2007/012598 | | 2/2007 |
|---|---|---|---|
| WO | 2008/150029 | A1 | 12/2008 |
| WO | 2010/065905 | A1 | 6/2010 |
| WO | 2011/117271 | | 9/2011 |
| WO | 2012/167237 | | 6/2012 |
| WO | 2012/167237 | A2 | 12/2012 |

OTHER PUBLICATIONS

International Search Report for International Application No. PCT/US2016/067795 dated May 25, 2017, 4 pages.
Nilsen et al., "Discovery, Synthesis, and Optimization of Antimalarial 4(1H)-Quinolone-3-Diarylethers" Journal of Medicinal Chemistry 57(9):3818-34 (Apr. 2014).
Pidathala et al., "Identification, Design and Biological Evaluation of Bisaryl Quinolones Targeting Plasmodium falciparum Typ1 II NADH: Quinone Oxidoreductase (PfNDH2)" Journal of Medicinal Chemistry 57(5):1831-43 (Feb. 2012).
Stickles et al., "Subtle changes in endochin-like quinolone structure alter the site of inhibition within the cytochrome pc1 complex of Plasmodium falciparum" Antimicrobial Agents and Chemotherapy 59(4):1977-82 (Apr. 2015).
Supplementary European Search Report for European Application No. EP 16 87 9977; completed Aug. 8, 2019, pp. 1-3.

*Primary Examiner* — Paul V Ward
(74) *Attorney, Agent, or Firm* — McDonnell Boehnan Hulbert & Berghoff LLP

(57) ABSTRACT

Disclosed herein are novel compounds for treating apicomplexan parasite related disorders, methods for their use; cell line and non-human animal models of the dormant parasite phenotype and methods for their use in identifying new drugs to treat apicomplexan parasite related disorders, and biomarkers to identify disease due to the parasite and its response to treatment.

17 Claims, 22 Drawing Sheets

Specification includes a Sequence Listing.

Fig. 1A
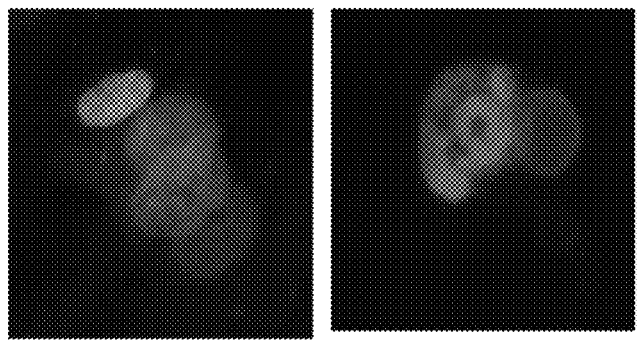
Fig. 1B
No. of genes
(1% FDR & Fold>±2)
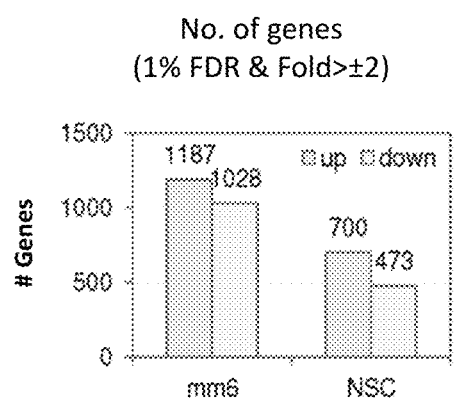
Fig. 1C
Up-regulated genes    Down-regulated genes
Fig. 1D
MiRs most altered
| MiR | logFC (cont) | Log cpm | P value | FDR |
|---|---|---|---|---|
| hsa-mir-708 | -11.46 | 5.67 | 6.11E-22 | 2.54E-18 |
| hsa-mir-29b | -5.46 | 5.99 | 1.85E-15 | 2.56E-12 |
| ENST00000474173 | -9.95 | 4.25 | 7.09E-15 | 7.34E-12 |
| hsa-mir-32 | -5.48 | 7.42 | 8.85E-15 | 7.34E-12 |
| hsa-mir-142 | -4.62 | 10.49 | 1.77E-13 | 1.23E-10 |
| hsa-mir-3656 | -9.66 | 4.01 | 2.28E-11 | 1.05E-08 |

Fig. 2B
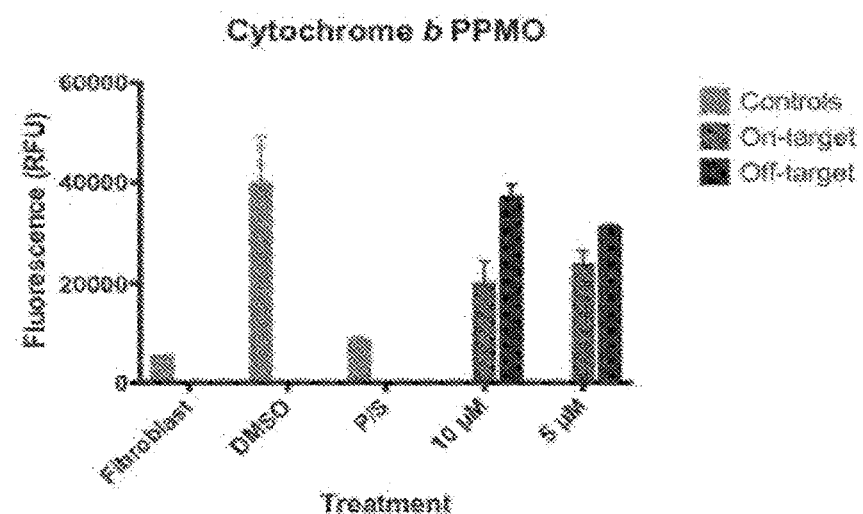
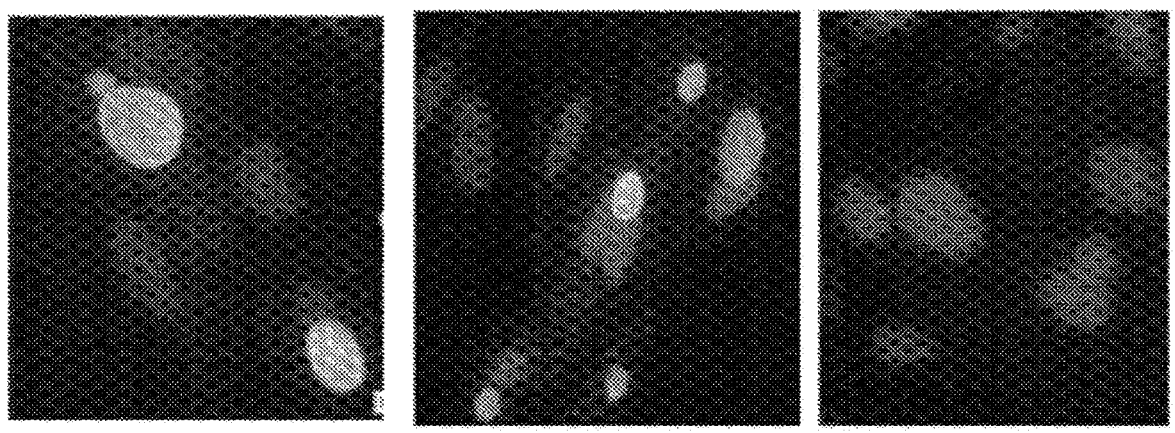

Fig. 3A
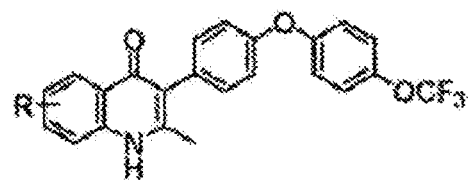
R = H　　　　　　　ELQ-271 (1)
R = 6-Cl, 7-OMe　ELQ-300 (2)
R = 6-F, 7-OMe　　ELQ-316 (3)
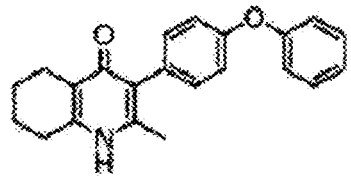
Tetrahydroquinolone MJM170 (4)
Fig. 3B
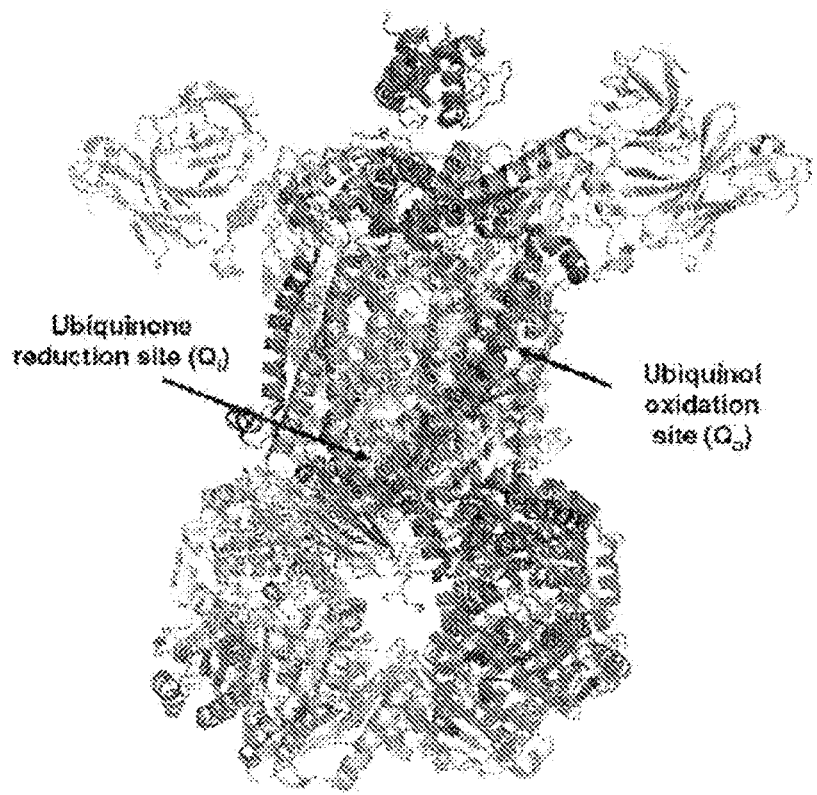

Fig. 6C

Cytochrome b Qi mutants

| P. falciparum | Yeast | T. gondii | Bovine |
|---|---|---|---|
| G33A G33V | G37 | A37 | G38 |
| F210 | M221K M221Q | F215 | F220 |

Cytochrome b sequences (UniProtKb):Toxo: O20672; Human: P00156;Pf: Q02768;Yeast: P00163; Bovine: P00157. Both reported Qi resistant mutants (G33A and M221K) steric clash with Qi inhibitors for a loss of binding affinity. Both are useful indicators for target confirmation. Adapted and modified from reference ___ with permission

Goal: To test if JAG21 and/or Tafenoquine be able to kill the dormant stage of T. gondii: rps13

Experiment design:

```
   -1        0       0-13           14-on
    |        |         |               |
   Taf    quine    rps13    JAG21/DMSO daily    Tet in water
```

| 4 groups: 5/group | D-1: Inject Tafenoquine | D0 Inject rps13 | D0-D13 daily Inject JAG21 | D0-D13 daily Inject DMSO |
|---|---|---|---|---|
| Control | | x | | x |
| Tafenoquine | x | x | | x |
| JAG21 | | x | x | |
| T+J | x | x | x | |

| 4 groups: 5/group | D14 Give tet water | |
|---|---|---|
| Control | x | Monitor the mice |
| Tafenoquine | x | Take out the spleen once the |
| JAG21 | x | mouse is really sick for histopath |
| T+J | x | |

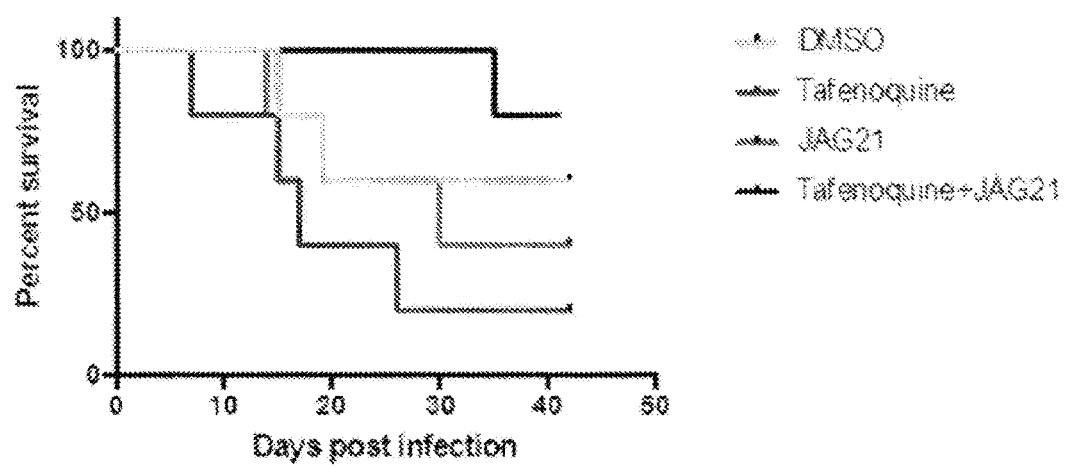

Fig. 14A
| Pt | Ethnicity | New Seizure | Macular Disease | Increase Dye Test | Elevated CSF Protein |
|---|---|---|---|---|---|
| 1a | Caucasian | Yes (myoclonic) | Yes | Yes | Yes |
| 1b | Caucasian | No | No | ND | ND |
| 2a | Filipino/Caucasian | Yes (myoclonic) | Yes | Yes | Yes |
| 2b | Filipino/Caucasian | No | No | ND | ND |
| 3a | Hispanic | Yes (hypsarrhythmia) | Yes | ND | ND |
| 3b | Hispanic | No | No | ND | ND |
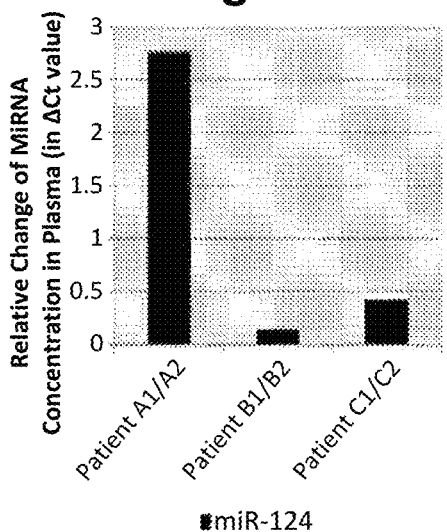
Fig. 14B
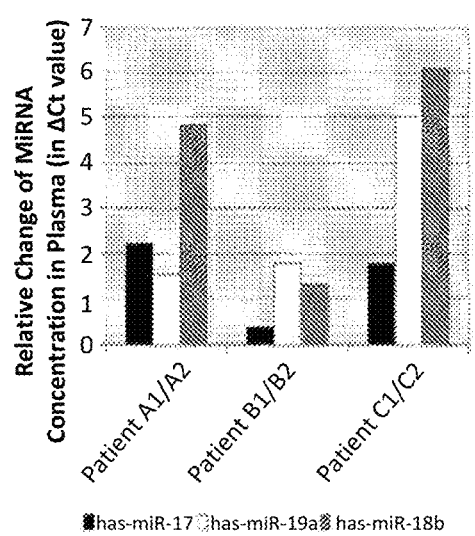
Fig. 14C

COMPOUNDS AND METHODS FOR TREATING, DETECTING, AND IDENTIFYING COMPOUNDS TO TREAT APICOMPLEXAN PARASITIC DISEASES

CROSS REFERENCE

This application is a divisional application of U.S. patent application Ser. No. 16/063,877, filed Jun. 19, 2018, which is a U.S. national phase application of International Patent Application no. PCT/US2016/067795, filed on Dec. 20, 2016, which claims the benefit of U.S. Provisional Patent Application No. 62/270,264, filed Dec. 21, 2015, and U.S. Provisional Application No. 62/306,385, filed Mar. 10, 2016, each incorporated by reference herein in their entirety.

STATEMENT OF GOVERNMENT RIGHTS

This invention was made with government support under National Institutes of Health (NIH) contract number HHNS272200900007C, NIH, National Institute of Allergy and Infectious Diseases of the National Institutes of Health (NIAID) award numbers R01AI071319 (NIAID) and R01AI027530 (NIAID); NIAID contract Number HHNS272200900007C; NIAID award number U19AI110819: NIAID award numbers U01 AI077887 (NIAID) and U01AI082180 (NIAID); National Institute of Diabetes and Digestive and Kidney Diseases (NIDDK) Grant #5T35DK062719-28: Defense Threat Reduction Agency award number 13-C-0055, and Department of Defense award numbers W911NF-09-D0001 and W911SR-07-C0101. The government has certain rights in the invention.

BACKGROUND

Apicomplexan parasitic infections, such as *Toxoplasma gondii* infections, can cause systemic symptoms, damage and destroy tissues, especially eye and brain and cause fatalities. Primary infections may be asymptomatic, or cause fever, headache, malaise, lymphadenopathy, and rarely meningoencephalitis, myocarditis, or pericarditis. Retinochoroiditis and retinal scars develop in up to 30% of infected persons, and epilepsy may occur. In immune-compromised and congenitally infected persons, active infection frequently is harmful. Recrudescence arises from incurable, dormant cysts throughout life. Current treatments against active *T. gondii* tachyzoites can have side effects such as hypersensitivity, kidney stones, and bone marrow suppression, limiting their use. Latent bradyzoites are not significantly affected by any medicines. Atovaquone partially, and transiently, limits cyst burden in mice, but resistance develops with clinical use. Thus, *T. gondii* infection is incurable with recrudescence from latent parasites posing a continual threat. Estimates of costs for available, suboptimal medicines to treat active, primary ocular, gestational and congenital infections, in just the U.S. and Brazil, exceed $5 billion per year.

Improved medicines are needed urgently. Molecular targets shared by *T. gondii* and Plasmodia make re-purposing compounds a productive strategy.

SUMMARY OF THE INVENTION

In one aspect, the invention provides compounds of the structure of Formula (I), pharmaceutical compositions thereof, and methods for their use in treating apicomplexan parasite related disorders):

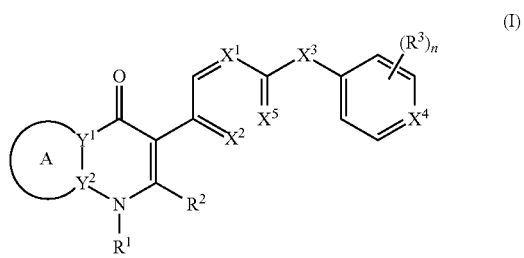

or a stereoisomer thereof, or a pharmaceutically acceptable salt thereof,
wherein
ring A combines with $Y^1$ and $Y_2$ to form a $C_{3-7}$cycloalkenyl or heteroaryl ring,
  wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;
$Y^1$ is C or N;
$Y^2$ is C or N;
$X^1$ is $C(R^{x1})$ or N,
  wherein $R^{x1}$ is hydrogen, halogen, $C_{1-3}$alkyl, $C_{1-3}$alkoxy or $C_{1-3}$haloalkyl;
$X^2$ is $C(R^{x2})$ or N,
  wherein $R^{x2}$ is hydrogen, halogen, $C_{1-3}$alkyl, $C_{1-3}$alkoxy or $C_{1-3}$haloalkyl;
$X^3$ is O, N(R), S or $C_{1-3}$alkyl;
$X^4$ is C or N;
$X^5$ is C or N;
$R^1$ is hydrogen or $C_{1-3}$alkyl;
R2 is hydrogen, $C_{1-3}$alkyl, $C_{1-3}$haloalkyl, —$CH_2OH$, —$CH_2OR$ or —C(O)OR;
n is 0, 1, 2, 3 or 4;
each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or $SF_5$;
or two $R^3$ groups, together with the carbons to which they are attached, form a 1,3-dioxolane; and
each R is independently hydrogen or $C_{1-3}$alkyl.

In another aspect, the invention provides cell lines infected with an apicomplexan parasite, wherein the apicomplexan parasite genome comprises a gene encoding an Apetela 2 IV-4 protein with an M=>I modification at residue 570 ("AP2 IV-4 M570I") compared to its orthologous gene on the reference *T. gondii* ME49 strain (gene ID: TGME49_318470), non-human animal models comprising cell lines of the invention, and methods for use of each in identifying compounds for treating an apicomplexan parasitic infection.

In another aspect, the invention provides methods for treating an apicomplexan parasite infection (such as a *T. gondii* infection), comprising administering to a subject in need thereof an amount effective to treat the infection of an inhibitor (of up-regulated genes) or an activator (of down-regulated genes) of 1 or more up-regulated genes as discussed herein.

In a further aspect, the invention provides methods for identifying test compounds for apicomplexan parasite therapy, comprising identifying test compounds that reduce expression (for up-regulated genes), or increase expression (for down-regulated genes) of 1 or more apicomplexan parasite genes as discussed herein.

In one aspect, the invention provides a plurality of isolated probes that in total selectively bind to at least 2, 3, 4, 5, 6, 7, 8, 9, 10, 15, 20, 25, 30, 35, 40, 45, 100, 150, 200, 250, 500, or all of the markers as discussed herein, complements thereof, or their expression products, or functional equivalents thereof wherein at least 10%, 20%, 30%, 40%, 50%, 60%, 70%, 80%, 90%, 95%, or all of the probes in total are selective for markers that are upregulated in the EGS strain of T. gondii after infection of human fibroblasts, neuronal stem cells or monocytic lineage cells.

In another aspect, the invention provides a plurality of isolated probes that in total selectively bind to at least 2, 3, 4, 5, 6, 7, 8, 9, 10, 15, 20, 25, 30, 35, 40, 45, 100, 150, 200, 250, 500, or all of the markers as discussed herein, complements thereof, or their expression products, or functional equivalents thereof, wherein at least 10%, 20%, 30%, 40%, 50%, 60%, 70%, 80%, 90%, 95%, or all of the probes in total are selective for markers that are upregulated in human fibroblasts, neuronal stem cells or monocytic lineage cells after infection with T. gondii, including but not limited to infection with the EGS strain of T. gondii.

In another aspect, the invention provides methods for monitoring T. gondii infection in a subject, comprising monitoring levels in a blood sample from the subject of one or more markers selected from the group consisting of clusterin, oxytocin, PGLYRP2 (N-acetylmuramoyl-L-alanine amidase), Apolipoprotein A1 (apoA1), miR-17-92, and miR-124, wherein a change in levels of the one or more circulating markers compared to control correlates with T. gondii infection in the subject.

In another aspect, the invention provides methods for treating a T. gondii infection, comprising administering to a subject with a T. gondii infection an amount effective to treat the infection of ApoA1.

DESCRIPTION OF THE FIGURES

FIG. 1A-1D. EGS morphology and effect on host cell transcriptomes FIG. 1a. EGS in human MM6 cells and NSC form cysts. Left NSC with EGS. Right MM6 with EGS. Note green dolichos cyst walls and BAG1 (red) in NSC. DAPI stained nuclei(blue). FIG. 1B, FIG. 1C. Effects of EGS infection on MM6 and NSC transcriptomes: EGS transcripts in MM6 compared with NSC shows overlap of, as well as unique patterns of, transcripts. Differentially expressed genes in MM6 and NSC cells infected with EGS parasite were identified based on criteria of 1% FDR and absolute fold-change ≥2. Number of DEGs in each cell line are presented with bar graph (FIG. 1B) and Venn diagram are used to show general comparison of DEGs identified between the two cell lines (FIG. 1B). There is both communality, overlap in genes modulated and independence in others between cell types indicating cell type also influences cell type. Red and green colors were used to represent up- and down-regulated genes, cell line used is indicated on bottom (FIG. 1B-FIG. 1C). Functional enrichment analysis was performed for gene ontology (GO) biological process and KEGG pathways. P-values derived from analysis were −log 10 transformed and presented as a heat map. Pink and blue colors indicate GO terms or KEGG pathways enriched by up- and down-regulated genes, respectively. Enriched pathways or biological processes are listed on right of panels and cell lines are indicated on top. FIG. 1D. Host cell miR-seq analysis reveals that EGS regulates host cell miR-NAs critical in pathogenesis and latency. An especially interesting down-modulated miRNA is hsa-miR-708-5p which is expressed particularly in brain and retina cells causing apoptosis[65]. When T. gondii downmodulates this as an encysted bradyzoite in neuronal cells, it would prevent hosts from initiating apoptosis to eliminate chronically infected neurons. f. Parasite genetics and human host cell type have a profound influence on T. gondii gene expression. MDS plot comparing T. gondii gene expression profiles from MM6 and NSC cells infected with EGS, GT1, ME49 and VEG strains for 18 hours and HFF cell cultures infected with EGS strain for 2, 18 and 48 hours.

FIG. 2A-2B. Differential Gene Expression (DGE) analyses and effects of inhibition of cytochrome bc1. FIG. 2A. DGE analysis of bradyzoite- and tachyzoite-specific markers during EGS infections of HFF cultures at 2, 18 and 48 hours (top panel), MM6 cells at 18 hours (middle panel) or NSC cultures at 18 hours (bottom panel) versus infections of same host cells with canonical strains GT1, ME49 or VEG at 18 hours (averaged across the three canonical strains for HFF infections). Genes reported as being over- or under-expressed during bradyzoite differentiation is indicated with red or green arrows respectively. "*", q-value ≤0.05; Log FC, logarithm of the fold change in gene expression. CST1, SAG-related sequence SRS44$^{S114}$; LDH2, lactate dehydrogenase 2$^{S115}$; LDH1, lactate dehydrogenase 1$^{S115}$; ENO2, enolase 2; ENO1, enolase 1$^{S116}$; SAG1, SAG-related sequence SRS29B; BAG1, bradyzoite antigen BAG1$^{S115}$. FIG. 2B. Effect of known cytochrome b inhibitors on EGS. Morpholino conjugated to a Vivoporter (called PPMO) designed to knock down cytochrome b compared with off target control has a significant effect in reducing replication of YFP RH strain tachyzoites at 5 and 10 µM (p<0.05) but only a very small effect on size and number of EGS cysts in HFF. As a poorly soluble inhibitor of cytochrome b, ELQ271 was reported to partially reduce cyst numbers in mice[27] and is shown herein also to reduce the EGS cysts in vitro at 10 µM in this novel model. This demonstrates the utility of this novel in vitro model by indicating that inhibition of cytochrome b Qi is associated with reduction of cysts in vivo in a mouse model, even when there are serious limitations caused by insolubility of this inhibitory compound. This poor solubility significantly limits ELQ271 as a candidate for progression to a medicine. Increasing selectivity for the parasite enzyme with our new scaffold is another critical challenge.

FIG. 3A-3B. FIG. 3A. Structures of the ELQ class (1-3) and the tetrahydroquinolone scaffold (4).[27,45,49,53] Low solubility of the ELQs has been a serious concern going into preclinical evaluation for treatment of malaria.[27] FIG. 3B. Saccharomyces cerevisiae cytochrome $bc_1$ X-ray structure (PDB ID: 1KB9)[5] The complex contains 11 subunits and 3 respiratory subunits (cytochrome b, cytochrome c1 and Rieske protein). The cytochrome b subunit provides both quinone binding sites ($Q_o$ and $Q_i$) highlighted as grey and pink surfaces respectively.

FIG. 4A. MJM170 markedly reduces RH YFP tachyzoites in tissue culture robustly at low nanoM levels. (Standard curve left and effect on RH YFP, right panel). FIG. 4B, FIG. 4C. MJM170 markedly reduces EGS bradyzoites in cysts in vitro. Inhibition of cytochrome b Qi eliminates cysts in HFF infected with EGS. Without inhibitory compound in HFF (note, oval cyst with green border staining dolichos) and adjacent panel with inhibitory MJM170 compound (note absence of cysts with small amount of amorphous residual dolichos). MJM170 eliminated tachyzoites followed to 10 days of culture and bradyzoites in cysts in vitro. Summary comparison of each of the compounds tested in vitro and their ADMET is in Table 2. Note improvement in solubility, properties amenable for compounds to cross blood brain barrier with new scaffold. FIG. 4D. EGS transfected with stage specific reporters for fluors, red tachyzoite SAG1, Green bradyzoite LDH2.

FIG. 5A: 25 mg/kg daily MJM170 administered intraperitoneally eliminates active infection due to RH tachyzoites stably transfected with YFP in mice (RFU control vs rx with MJM 170, p<0.004). For the standard curve in the inset, RFU increase with increasing concentrations of fluorescent tachyzoites ($R^2$=0.99). FIG. 5B. MJM 170 25 mg/kg daily reduces Type 2 parasites. FIG. 5C. MJM 170 reduces cysts in mice infected 2.5 months earlier and treated for 17 days with 12.5 mg/kg daily then without compound for 3 days:cyst count of wet prep of brain homogenate. FIG. 5D. Zebra fish can be used to visualize fluorescent tachyzoites and cysts in more chronic infections.

FIG. 6A-6G. MJM170 targets apicomplexan cytochrome $bc_1$ Qi: modelling, yeast surrogate assays, target validation, co-crystallography and nanoM inhibition of $P.$ $falciparum$ and $T.$ $gondii$ FIG. 6A. Modeling: MJM170 (yellow) modelled within cytochrome b $Q_i$ site (grey) highlighting residues (green) involved in binding. FIG. 6B. Mutations for yeast, $P.$ $falciparum$, predicted for $T.$ $gondii$ and bovine enzyme. Relevant mutations are indicated by colored dots in $Q_i$ domains on the bottom of the image of mitochondrion membrane for $S.$ $cerevesiae$ and $P.$ $falciparum$, and where those amino acids are in $T.$ $gondii$, human and bovine enzymes. Red dot marks G33A/V in $Q_i$ domain of $P.$ $falciparum$. FIG. 6C. Cytochrome b mutants and sequence accession numbers. FIG. 6D. MJM 170 inhibits wild-type but not mutant yeast. Compounds MJM 170 and ELQ 271 with wild type and mutant yeast validate predictions that M221 K/Q would create a steric clash and resistance. FIG. 6E. MJM170 is a potent low nM inhibitor of $Plasmodium$ $falciparum$. In Table 2, wild type $P.$ $falciparum$ also are tested and is inhibited at <50 nM by this scaffold. D6 is a drug sensitive strain from Sierra Leone, C235 is a multi-drug resistant strain from Thailand, W2 is a chloroquine resistant strain from Thailand, and C2B has resistance to a variety of drugs including atovaquone. Mutant G33V did not confirm prediction of a steric clash. FIG. 6F-6G. MJM170 binds within $Q_i$ site of bovine cytochrome $bc_1$ as shown by X-ray crystallography. FIG. 6F. An omit Fo-Fc electron density map (green) at 5σ allows unambiguous positioning of MJM170 (magenta) within the $Q_i$ site with the tetrahydroquinolone group near heme $b_H$ (white) and diphenyl ether directed out of the channel. FIG. 6G MJM 170 molecule is included into the structure, the 2Fo-Fc electron density map at 1σ (grey) allows placement of the planar head between heme $b_H$ and Phe220 with the carbonyl group positioned in a polar region surrounded by Ser35 and Asp228.

FIG. 7A. MJM170 is highly potent (Dd2, black curve, $EC_{50}$=29.5 nM) without cross-resistance in previously reported cytochrome b drug-resistant mutant parasite lines including ubiquinone reduction site mutants ($Dd2^{G33A}$ and $Dd2^{G33V}$, light blue and dark blue curves, respectively). Dose-response curve from representative assay. MJM170 cannot inhibit a parasite supplemented with a yeast cytosolic DHODH (scDHODH, green curve) demonstrating that its primary activity in $P.$ $falciparum$ is to inhibit electron transport necessary for pyrimidine biosynthesis. Inset Table. Dose-response phenotypes of a panel of $P.$ $falciparum$ cytochrome b mutant parasite lines. $EC_{50}$ values were calculated using whole-cell SYBR Green assay and listed as mean±standard deviation of three biological replicates, each with triplicate measurements. FIG. 7B., FIG. 7C. Isobolograms with MJM170 plus atovaquone or cycloguanil or $Q_i$ inhibitor BRD6323: FIG. 7B. Combinations were with atovaquone (ATV) or cycloguanil (CYG) at multiple fixed volumetric ratios (10:0, 8:2, 6:4, 4:6, 2:8, and 0:10) in Dd2 parasites. Slight synergy observed with combinations of MJM170 and atovaquone while MJM170 and cycloguanil dosed in combination showed additive effect. Fractional inhibitory concentrations (FIC) for each drug were calculated and plotted. Shown is a representative isobologram for each combination of compounds. Table below lists FICs for each compound and ratio tested (values are mean from three independent assays±standard deviation). Synergy was defined as a combined FIC<1.0, additivity as FIC=1.0, and antagonism as FIC>1.0. FIG. 7C. Isobologram Figure: MJM170 was tested in combination with previously reported reduction site inhibitor BRD6323 at multiple fixed volumetric ratios (10:0, 8:2, 6:4, 4:6, 2:8, and 0:10) in Dd2 parasites. Antagonism was observed with combinations of MJM170 and BRD6323, another bulky inhibitor of cytochrome bc, as opposed to synergy observed with oxidation site inhibitor atovaquone. Fractional inhibitory concentrations (FIC) for each drug were calculated and plotted. Representative isobologram of three independent assays is shown. Table below lists FICs for each compound and ratio tested (values are means from three independent assays±standard deviation). Definitions as in b.

FIG. 10A-FIG. 10C) Graphs comparing the effects of JAG050 and JAG021 on EGS.

FIG. 13. Tafenoquine and JAG21 are both needed to contain RPS13Δ. One additional mouse in the tafenoquine and JAG21 died outside the time on this graph others remained healthy.

FIG. 14A-14D. Serum biomarkers from boys with active brain disease due to *Toxoplasma* reflect infection and neurodegeneration. FIG. 14A. Tabular clinical summary: Three pairs of children, matched demographically; one in each pair had severe disease and one mild or no manifestations. One pair dizygotic, discordant twins. Each ill child had new myoclonic or hypsarrythmic seizures. Two children had T2 weighted abnormalities on brain MRIs similar to active inflammatory and parasitic disease in murine model[8] FIG. 14B-FIG. 14D. Protein and miR serum biomarkers: Panel of nanoproteomics and miR sequencing performed on serum obtained at time of new illness. MiRNA concentration measured and difference in concentration graphed. Abundance of peptides measured. Note: Presence of markers of neurodegeneration, inflammation, and protein misfolding include clusterin, diminished ApoJ, serum amyloid, and oxytocin in ill children compared with their healthy controls.

DETAILED DESCRIPTION OF THE INVENTION

Figure 2A:
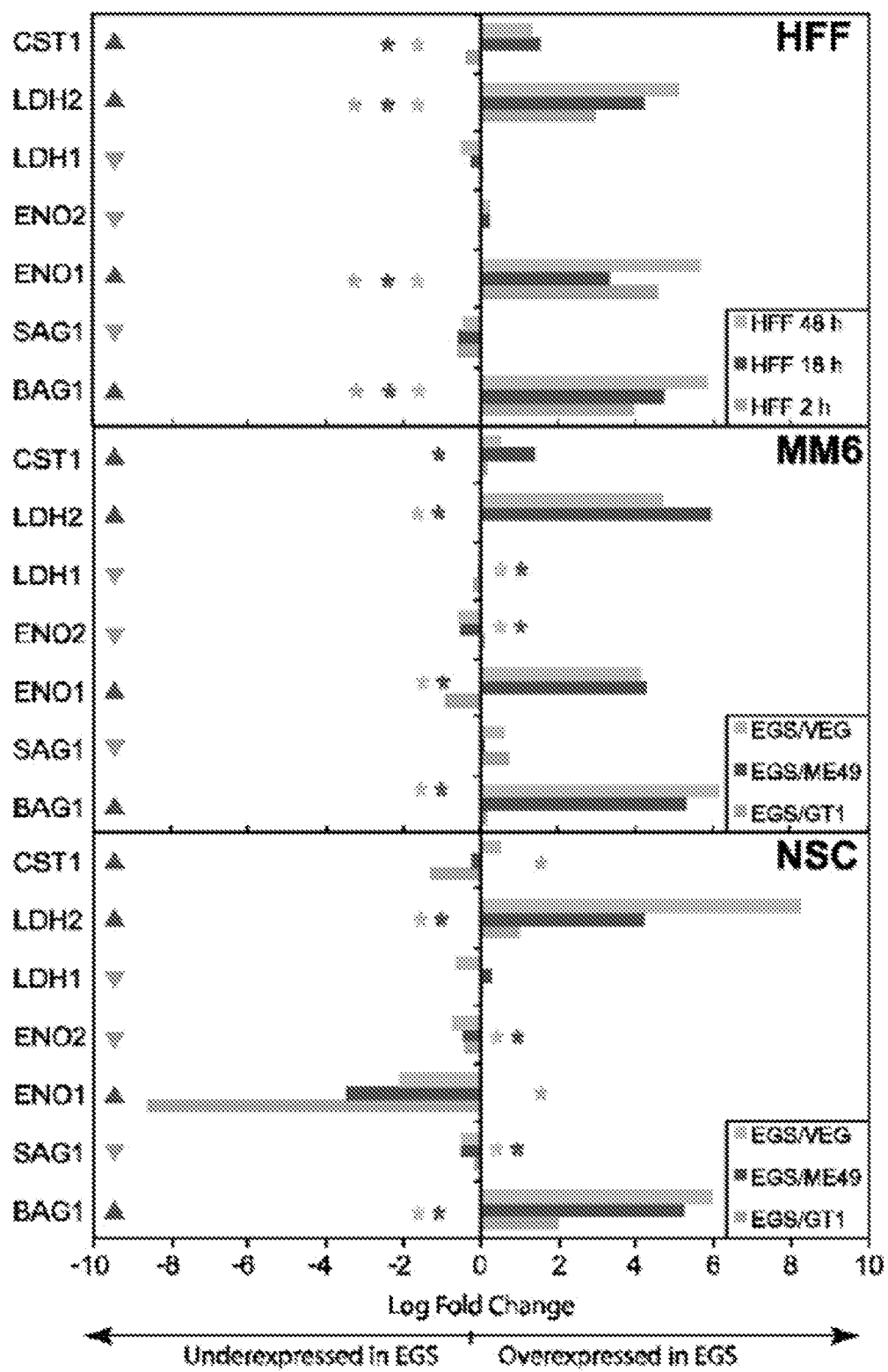
Figure 4A:
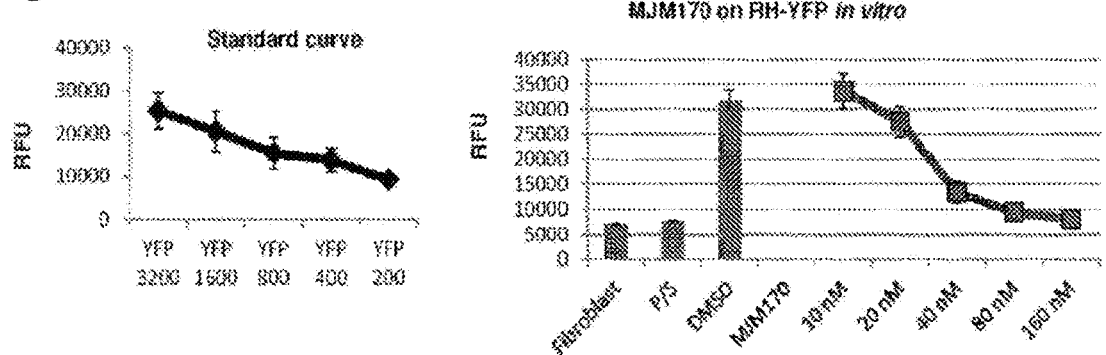
FIG. 4A-4E. ELQ inhibitors provide a new scaffold and approach yielding compounds that are potent inhibitors of tachyzoites and cysts in vitro. Study of Inhibitors in vitro is summarized in Table 2 and led to selection of MJM170 as a promising novel scaffold for both tachyzoites and bradyzoites.
Figure 4B:
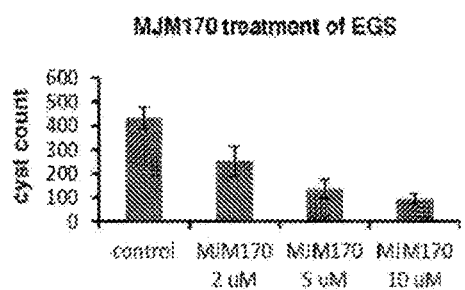
Figure 4C:
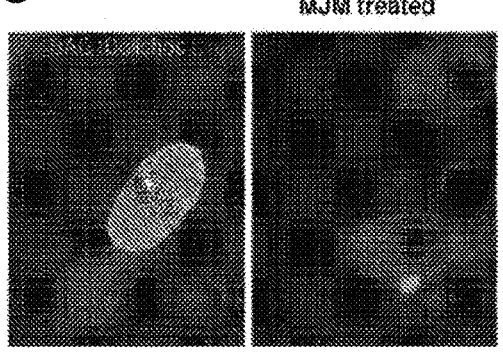
Figure 4D:
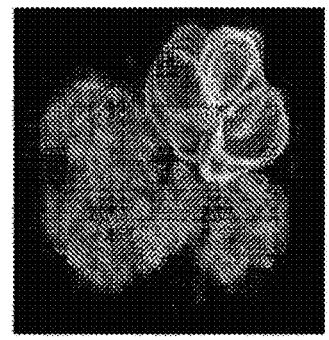
Figure 4E:
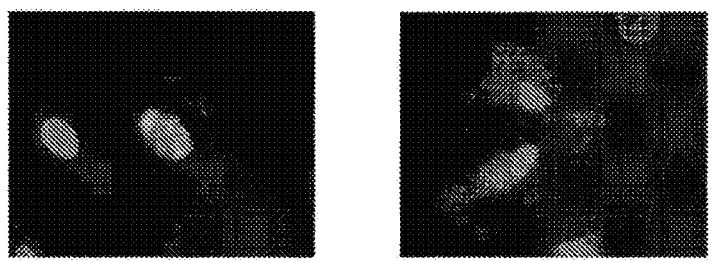

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R. I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In one aspect, the invention provides cell lines infected with an apicomplexan parasite, wherein the apicomplexan parasite genome comprises a gene encoding an Apetela 2 IV-4 protein with an M=>I modification at residue 570 ("AP2 IV-4 M570I") compared to its orthologous gene on the reference *T. gondii* ME49 strain (gene ID: TGME49_318470). As described in the examples that follow, Apetela 2 (AP2) IV-iv is known to be a bradyzoite gene expression repressor[56], and the AP2 IV-4 M570I mutant results in an apicomplexan parasite that remains as a bradyzoite in tissue cultures passaged extensively, capable of producing oocysts when administered to cats definitively proving its true bradyzoite phenotype.

As further described in the examples that follow, critical flaws and limitations of available methods and models for developing medicines to cure apicomplexan infections, such as *T. gondii* infections, include lack of in vitro culture systems for cysts and scalable, easy to use animal models for screening compounds. The cell lines of this aspect of the invention unexpectedly possess a true, dormant parasite phenotype in tissue culture and can be used, for example, to screen for drugs that can be used to treat apicomplexan parasitic infections, as well as a research tool for studying apicomplexan parasites in the dormant phenotype. The cell lines can be used, for example, as a model of bradyzoite infection. A generalized apicomplexan life cycle comprises a rapidly growing tachyzoite and slow-growing, latent bradyzoite that forms tissue cysts (i.e.: dormant phenotype). Such dormant parasites are present in the brains of 2 billion persons worldwide across their lifetimes and are incurable. Quite remarkably, the inventors have discovered that in human cells this encysted parasite turns on host cell pathways important for altering ribosomal function, miss-splicing of transcripts, oxidative pathways, and, those pathways found to be altered in Alzheimer's and Parkinson's diseases. Extensive details on the model are described in the examples that follow.

In one embodiment, the apicomplexan parasite genome comprises a gene encoding AP2 IV-4 M570I that further differs from its orthologous gene on the reference *T. gondii* ME49 strain (gene ID: TGME49_318470) in encoding the amino acid sequence GGNRPHYH-VAKQEWRVRYYMNGKRKMRTYSAKFYGYETAHT-MAEDFAHYVDKH E (SEQ ID NO: 1) beginning at residue 821. In a further embodiment, the gene encoding AP2 IV-4 M570I encodes the following amino acid sequence, or functional equivalents thereof:

```
                                              (SEQ ID NO: 2)
MAAPAPSAEARPAKRRCFPLPRETPVSSEDETRKTLQHDTLGCLPRSS

SGQPELAAASAASQVGHLSSAALLQLVQTQSAGGVPQAVLRNLFSSIH

RNPKPLPANALAATPNSSLYASLTSLSSAAALPGAGPAYSQAPSPASA

DLLQSEQFGSAAKNPSPNEASPILALLGEAARAATTPRTVPALSAVCP

AASSGVSLPSASDTLALAQSSLSSSTGCASDVKASRPEEHPAFASGTA

NRQSLLQALLLSTAPLAFSGPSLSSASTTLPASSGAVSSRNAGAYQFE

RLLQAEAAKVKALLPNATSKSMSQSSVPQRDLTRKTSLFPDPRGLSAD

DASRRYNTRGANSGGAGLRRGTGVHATTEQSGALDAGERTRPFGAGED

ESAQGKPDSRGRQRPGALDASNILGLLAAFQPSQAPAIRDLSAPSHLS

AAATGALPLTASFTASALASSQCLPAGTPASSSASPPFSEVLSTTEES

STTKETDASASTLLAFLQKYSAVSGLGGASDFLGQLQGKSSLPPLSLA

EPSSALPSSFLGGSDGGTIDTRNGNGEKTTPPIHLFQSAFRIPSPSQQ

NLLDALLASSCTTATSRSDGSGNLGCPVVDERNAKLAGPAHPLPCSFP

QISSSSGEPGRKTGGRVHRQGTSQSGGRVRSGKNGGSAAPPRQSSSEN

VPSTPTVSSHEAPHRAGFPSQTPYELSASPSHQLDLLRLGAFLGGAGK
```

-continued

```
QDASVHSDETGTLSGEPSHRSCSLSRGLTQESVLQLSDTTSTSREGEP

NEPSQGCVNVAASLPAFGPQPSSGAAKAREGRRGAGGAGAAPPVPLRA

DVTLGGNRPHYHVAKQEWRVRYYMNGKRKMRTYSAKFYGYETAHTMAE

DFAHYVDKHEALPDSMMMTAMMLQAQANSAASSGQTVPLARGIRASSA

SAGAGGHVSKSATKGSVAASSEGSTSMGSDATRSQEGEAAELCPLAAG

LSRPLASMHSAAGNAVAQGRQESKEEAPGGQAWFGEPGKFRASSEAAL

CGSGSSAEGRDGHESEVLWATLGKVHDASQGKKIKPEKPLTVARGRLA

LGAEDKSQNLGVDLGDSGGAQGLPGVRQPRQMKNSEECSLRDSDKGMA

LSKRFGFLPSQTPSCDSMTLPFPGGFDALSLSSALSSCASLPVAHEGN

NFQKGHTGDIVALASQSGTQRPASVVLSRDANVSGSSPSHPTWQREGA

AVSGRADEFSSLSVTPSTVPLSSFTMEDIKGEEGDPSRRFALVGESMK

NVSAPEVQALFPTSSIANAELLPVDFLHSNSCSADKLESSIPRGLAGN

NPSMTATAVAATAVSHQIFDTITLFGEFLREFAKEKVNEFHEYGLEAS

PLTVEASPEVSLFGKATFGRCPVAGGSTPAGISKMSGETLSGLSASEL

SLVSARTNTTTGEEQFALARGLFPGDSEGDRDEKKPQLSQQELLVLSH

ALVNLTSSTYVLMHTLKASLSKSTEAVQLHQPLLEAASEAKATDEAKT

REEQESSECDHEYPPGSSLEATTGALPFRLSPALSASSKDLPSLSASA

SLESVTPFAGLPLEEGTLSASVGLASSDDEHDTSLLFKTEAAKKRSLF

STAADGDESRTYNDGLGQPMEEEIRSCVSTSCGEAVATTTLSAIGPGT

GASGALLDSESRESLGEKPGAALRAGAHTPAPSRAPTPSRTFSFTSSS

TATSAALLCDSNVVHEKLSAQGKDSEAGERKGDSEKEEEVEMWKEEDE

EVQRCTGSAETDSTEATRGEEAWRRGKQSEKKPSVITTALNLLETHRH

LALTISQLKRPVAQQLRFILPIAAPQLLPCILPPASFQGTGESGDGKA

EAEAKGSSSLGQVLETALGHGTRLAPSASAMVPPRKDEAASAVPEAKT

LTGLANAGVTREAASRTLEAEQVSRKRSREEVVDSETAGDEGDMENVP

ETRDGTTRPGSRQYDTSPSNDGTKPPATAKSRVIRDQAALERLLLAPF

QDTPTCSCTDRPCPCDRQQVADMIYLFYAVPARQQAESSKEGSTQRLQ

FAARDTNERKDARTGEETQGGETEAKEVIRDPEERGVCEGSSSQNAHT

QFDAETASSSMSSDPRADKESNAQDAHMADKTSFVSDLPQPSGEFAPS

LLSETSLDVAMADSRGTPSEIHGFFTRSDEQKRASFSSSSLLAAGHAV

ASFSSSLAGVVSGAGERRECAGPSLGDLSTIGLLSLSYPAMLAFILPL

QSLLHTVSGMILTLHKKLIHRFICAHLRLVLDDDMRRPAGGALKSRGA

HGDTEAAEAQVERRRREHEREETTNLAIGYREGNAEAANTFPLVDTVS

SLLSPGSLRQENSEVERRDNDEERLELITGIARESPKPSEKDSVSPFL

STAPCPGTEAESSDCSASSACSGTPTEGTEGGETGDIASFLSPSGEVK

QTIMLA
```

The mutations at residue 570 and beginning at residue 821 compared to the Apetela 2 IV-4 orthologous protein encoded by the reference *T. gondii* ME49 strain (gene ID: TGME49_318470) are presented in bold font and underlining in the above sequence. A "functional equivalent" is a gene encoding an Apetela 2 IV-4 protein that is at least 70%, 75%, 80%, 85%, 90%, 91%, 92%, 93%, 94%, 95%, 96%, 97%, 98%, or 99% identical to the amino acid sequence provided above, includes the noted mutations at residue 570 and beginning residues 821-874, and that does not represses bradyzoite gene expression in a tachyzoite in an apicomplexan parasite.

As used here, "apicomplexan parasites" are a phylum of the kingdom Protista (formerly a division of protozoa called *Sporozoa*); named for a complex of cell organelles (apical microtubule complex) at the apex of the sporozoite form that can penetrate host cells. It includes, but is not limited to, the medically important genera *Plasmodium, Toxoplasma, Cryptosporidium*, and *Isospora*. Thus, in one embodiment, the apicomplexan parasite is selected from the group consisting of *Plasmodium, Toxoplasma, Cryptosporidium*, and *Isospora*. In a specific embodiment, the apicomplexan is a wild type, mutant, or recombinant *Toxoplasma gondii* strain. In various further embodiments, the apicomplexan parasite is *Toxoplasma gondii* of clade B.

In another embodiment, the apicomplexan parasite is a GO arrested parasite, including but not limited to s *Toxoplasma gondii* strain RPS 13 delta (Hutson et al., PLoS One. Nov. 22, 2010; dx.doi.org/10.1371/journal.pone.0014057). This cell line can be used, for example, to identify companion compounds for THQ that eliminate the GO arrested stage of *T. gondii* along with the active and the slowly growing bradyzoite stage.

In another embodiment, the apicomplexan parasite is *Toxoplasma gondii* strain EGS (ATCC® Number:PRA-396™). As described in the examples that follow, the EGS strain was extensively characterized in vitro to show that true cysts develop, making the EGS strain especially useful for drug development.

In all embodiments of this aspect of the invention, the cell line can be any suitable cell line capable of supporting apicomplexan parasitic infection, including but not limited to mammalian cells (mouse, rat, human, etc.), zebrafish cells, etc. In one specific embodiment, the cell line is a human cell line; exemplary human cell lines for use in this aspect of the invention include, but are not limited to fibroblasts, stem cells, neurons, monocytes, and ocular cells 9 including primary human cells). As described in the examples that follow, the apicomplexan parasites form cysts in the host cell lines that enlarge over time and then destroy host cell monolayers as single cell organisms. As such, the cell lines of the invention are extremely useful as in vitro models of apicomplexan parasite infection. Such models can be used, for example, to test for candidate compounds that inhibit cyst formation and/or destruction of host cell monolayers; such candidate compounds would be useful in treating apicomplexan parasite infection.

In another embodiment, the apicomplexan parasite genome is recombinantly engineered to express a reporter polypeptide, including but not limited to fluorescent or luminescent proteins. This embodiment permits ready visualization of the parasite and facilitates automated quantitative analysis. In one embodiment, the reporter polypeptide is operatively linked to a promoter that is activated in the bradyzoite stage or a promoter that is activated in the merozoite stage. Any suitable promoter that is activated in the bradyzoite stage or merozoite stage may be used. In one embodiment the promoter that is activated in the bradyzoite stage is the *T. gondii* BAG1 encoding gene promoter or a functional equivalent thereof. The BAG1 promoter sequence can be obtained as disclosed in Bohne et al., Molecular and Biochemical Parasitology 85 (1997) 89-98. In one embodiment, the BAG promoter comprises SEQ ID NO:3, or functional equivalent thereof, from the *T. gondii* VEG strain.

A "functional equivalent" of the BAG1 promoter is a promoter from any strain of *T. gondii* that promotes expression of BAG1 in the VEG strain, as well as an promoter nucleic acid sequence that is 50%, 60%, 70%, 75%, 80%, 85%, 90%, 91%, 92%, 93%, 94%, 95%, 96%, 97%, 98%, or 99% identical to SEQ ID NO:3 and drives expression of a BAG1 gene in a *T. gondii* strain.

As described in the examples that follow, the cell lines of the invention can be administered to/ingested by non-human animal models to provide an in vivo model of apicomplexan parasitic infection that develop the classic, gold standard bradyzoite phenotype of producing oocysts. This, in another aspect, the invention provides non-human animal models of apicomplexan parasitic infection, comprising a non-human animal that has ingested or otherwise comprises the cell line of any embodiment or combination of embodiments of the invention. In one embodiment, the non-human animal produces oocysts. Any suitable non-human animal model that produces oocysts can be used, including but not limited to cats.

In another aspect, the invention provides non-human animal models of apicomplexan parasitic infection, comprising a non-human animal that has ingested or otherwise comprises oocysts produced by the non-human animal model that has ingested or otherwise comprises the cell line of any embodiment or combination of embodiments of the invention. As described in detail in the examples that follow, oocysts given to non-human animal models such as mice created an illness and histopathology phenotypically characteristic for typical, virulent parasites causing dose related proliferation of the parasite (exemplified by *T. gondii*) with necrosis in terminal ileum, pneumonia at 9-10 days, with brain parasites by 17 days and dose-related mortality. Thus, the non-human animal models of this aspect of the invention are particularly useful in screening for drugs to treat the effects of apicomplexan parasite infection.

As will be understood by those of skill in the art, the oocysts do not need to be isolated prior to ingestion; they may be present, for example, in tissue (including but not limited to brain tissue) taken from the non-human animals that have ingested or otherwise comprise the cell lines of the invention, which then produce oocysts. Any suitable non-human animal model can be used, including but not limited to mice, rats, cats, zebrafish, non-human primates, cattle, sheep, and pigs. In one specific embodiment, the non-human animal is a mouse.

In another aspect the present invention provides methods of identifying compounds for treating an apicomplexan parasitic infection, comprising contacting one or more test compounds to the cell line of any embodiment or combination of embodiments of the invention, wherein those positive test compounds that reduce bradyzoite cyst amounts in the cell line are candidates to treat an apicomplexan parasitic infection. As disclosed above, the cell lines of the invention unexpectedly possess a true, dormant parasite phenotype in tissue culture and can be used to screen for drugs that can be used to treat apicomplexan parasitic infections. Any reduction in bradyzoite cyst amounts in the cell line indicates that the test compound may be useful for treating an apicompl- exan parasitic infection. In various embodiments, positive test compounds are those that reduce bradyzoite cyst amounts by at least 5%, 10%, 15%, 20%, 25%, 50%, 75%, 90%, or more.

In another aspect the present invention provides methods of identifying compounds for treating an apicomplexan parasitic infection, comprising administering one or more test compounds to the animal model of any aspect or embodiment of the invention, wherein those positive test compounds that reduce one or more symptoms of the infection and/or reduce parasitic titer in the animal model are candidates to treat an apicomplexan parasitic infection. In one embodiment, those positive test compounds that reduce oocyst production and/or reduce bradyzoite cyst amounts in the animal model are candidates to treat an apicomplexan parasitic infection. Any reduction in oocysts production and/or bradyzoite cyst amounts indicate that the test compound may be useful for treating an apicomplexan parasitic infection. In various embodiments, positive test compounds are those that reduce oocysts production and/or bradyzoite cyst amounts by at least 5%, 10%, 15%, 20%, 25%, 50%, 75%, 90%, or more.

In one embodiment of any of the methods of identifying compounds for treating an apicomplexan parasitic infection of the invention, positive test compounds are candidates for treating *Toxoplasma gondii* or *Plasmodium falciparum*: infection, including drug resistant strains and or other plas- modial infections. The methods can be used to test any suitable type of candidate compound, including but not limited to polypeptides, antibodies, nucleic acids, organic compounds, etc. Treatment effects of the test compounds may be assessed relative to a suitable control, such as the cell lines or non-human animal models of the invention that are not treated with the test compound. It is well within the level of those of skill in the art to determine a suitable control in light of the teachings herein.

In one specific embodiment, the cell line, or non-human animal model that has ingested or otherwise comprises the cell line, comprises a G0 arrested parasite (such as RPS 13 delta) and is used to identify companion compounds for tetrahydroquinolones (THQ) that eliminate the G0 arrested stage of an apicomplexan parasite, such as *T. gondii*, along with the active and the slowly growing bradyzoite stage.

RPS 13 Δ is a genetically engineered conditional knock- out parasite that has a unique transcriptome documenting its G0 state, G1 arrest in the absence of tetracycline but grows normally in the presence of tetracycline which removes the repressor from the promoter. The method may utilize, for example, a system that when there is no anhydrotetracycline to remove the engineered tetracycline responsive repressor from the 4 tetracycline response elements engineered in tandem in the promoter; these parasites persist in tissue culture for long times (months). This embodiment is based on the observation that this conditional knockout RPS13 delta parasite when it is in its arrested in G1 state is not susceptible to the effect of any inhibitors that effect pro- cesses essential to the tachyzoite or bradyzoite form includ- ing those tested in vitro so far. In this embodiment the conditional knockout RPS13 delta parasite is amenable to testing inhibitors of hypnozoite like organisms by culturing them without tetracycline in the presence of the compound and determining whether any parasites can be rescued by adding tetracycline to determine whether they are still capable of persisting and becoming tachyzoites that grow rapidly in the presence of tetracycline. Furthermore, the methods may comprise testing RPS13 delta in mice, and involves the observations that when RPS13 delta is admin- istered to wild type mice without tetracycline the RPS13 delta parasite induces a protective immune response as a vaccine dependent on interferon gamma and has no adverse effect on the mice, nor can it be rescued with tetracycline or inhibitors of iNOS (intracellular nitrogen oxide synthase) such as LNAME (L-N$^G$-Nitroarginine methyl ester) which abrogate effects of interferon gamma after 7 days. For example, that in interferon gamma knock out mice or mice treated with antibody to interferon, RPS13 delta is lethal for the mice, where the attenuated organism persists, can be observed, until mice succumb slowly. Another example may be a SCID mouse or a steroid treated mouse that is more susceptible due to immune compromise.

In another embodiment, RPS13 delta can be used to test compounds in vitro against this G0 truly dormant stage, and against compounds that can target the hypnozoite state but that must be metabolized in the liver to produce toxic electron containing compounds in vivo.

In all these embodiments, the methods can be used to determine if compounds have parasiticidal effects on hypnozoite forms and be used in conjunction with THQ compounds, such as tafenoquine, known in primate models and in humans as the only compound besides primaquine which has a lethal effect on the malaria hypnozoite in primates or in humans. However, tafenoquine is not active against actively proliferating organisms and requires a compound that is effective against more rapidly and slowly growing forms to produce radical cure of malaria.

In another embodiment, the THQ compound may be primaquine, a compound that has a similar effect when metabolized and is ineffective against *T. gondii* tachyzoites in tissue culture and can therefore be utilized in the same manner as tafenoquine to inhibit the hypnozoite form of apicomplexan parasites to produce radical cure.

Compounds identified using the methods of these various embodiment of the invention can be used together the THQ compound(s) to treat/cure the active tachyzoite, the slowly growing bradyzoite, and the G0 arrested hypnozoite-like phase of the apicomplexan infections the active tachyzoite, the slowly growing bradyzoite, and the G0 arrested hypnozoite-like phase of the apicomplexan infections As described in detail in the examples that follow, the inventors carried out transcriptome analysis of both the apicomplexan parasite and the host cells after parasite infection of the host cells. The resulting transcriptomes provide a signature for apicomplexan parasites (such as *T. gondii* strains EGS), which helps in identification of targets for drug development, as well as a signature for infected host cells (such as human foreskin fibroblasts (HFF) human monocytic cells (ex: MM6), and human primary neuronal stem cells (NSC)), which helps in identification of targets for treating apicomplexan infection. As shown in the examples, EGS transcription was influenced by host cell type (FIGS. 1A-1D). Transcriptomics using host mRNA and miR profiling of EGS cultures in MM6, and NSC cells for 18 hours demonstrated that this parasite modulates host transcripts involved in protein misfolding, neurodegeneration, endoplasmic reticulum stress, spliceosome alteration, ribosome biogenesis, cell cycle, epilepsy, and brain cancer among others (FIGS. 1A-1D). The number of genes significantly up or down regulated in MM6 and NSC cells compared to uninfected controls are depicted in FIGS. 1A-1D. Overexpressed genes differ from those of GT1, ME49 and VEG tachyzoite-infected human NSC cells, but modify the same or connected pathways. Hsa-miR-708-5p was the most affected miRNA (down-modulated) by EGS (FIG. 1D. miR-708-5p is a regulator that promotes apoptosis in neuronal and retinal cells, which could maintain a niche for EGS-like encysted bradyzoites to persist.

The genes identified in the host transcriptome study are thus targets for anti-parasite therapy, as well as markers of apicomplexan parasite infection (such as *T. gondii* infection). In various embodiments, the invention may thus comprise methods for treating an apicomplexan parasite infection (such as a *T. gondii* infection), comprising administering to a subject in need thereof an amount effective to treat the infection of an inhibitor (of up-regulated genes) or an activator (of down-regulated genes) of 1 or more (i.e.: 1, 2, 3, 4, 5, 6, 7, 8, 9, 10, or more) of the up-regulated genes listed discussed herein (protein encoding genes or miRNA). In various non-limiting embodiments, the inhibitor is selected from the group consisting of a target-specific inhibitory antibody, aptamer, siRNA, shRNA, antisense oligonucleotide, or small molecule.

In one embodiment, the target is miR-708-5p. In various further embodiments the targets are one or more of the genes listed in Table 1 below, or as discussed herein, which provide a more complete list of up-regulated or down-regulated genes involved in specific host cell pathways or indications. The table shows up-regulated or down-regulated genes involved in specific host cell pathways or indications ("KEGG pathway"), such as systemic lupus erythematosus, (SLE), Parkinson's disease, etc. In an exemplary embodiment, the methods comprise administering to the subject in need thereof an inhibitor (of up-regulated genes) or an activator (of down-regulated genes) of one or more (1, 2, 3, 4, 5, 6, 7, 8, 9, 10, 11, 12, or all 13) of genes HIST2H2AA3, HIST1H2AC, HIST1H2BC, ACTN4, SNRPD3, ELANE, ClR, HIST1H2BK, H2AFZ, SNRPB, H2AFX, CTSG, and HIST1H4H, to treat apicomplexan parasite infection-associated SLE. One of skill in the art will understand from the table that the methods may be used to treat apicomplexan parasite infection-associated Parkinson's, Huntington's disease, Alzheimer's disease, etc. using an inhibitor (of up-regulated genes) or an activator (of down-regulated genes) against 1 or more (i.e., 1, 2, 3, 4, 5, 6, 7, 8, 9, 10, 11, 12, or more, such as all) of the target genes listed for the specific indication. Similarly, one of skill in the art will understand from the table that the methods may be used to treat apicomplexan parasite infection-associated disorders relating to ribosomal assembly, spliceosome assembly, oxidative phosphorylation, etc. using an inhibitor (of up-regulated genes) or an activator (of down-regulated genes) against 1 or more (i.e., 1, 2, 3, 4, 5, 6, 7, 8, 9, 10, 11, 12, or more, such as all) of the target genes listed for the specific indication.

TABLE 1

| KEGG id | KEGG pathway | P-value | Genes |
|---|---|---|---|
| hsa03010 | Ribosome | 4.6E−07 | RPL35A, RPL36A, RPL35, RPS9, RPL27, RPS27L, RPL38, RPS25, RPS27, RPL30, RPL23, RPS29, RPL21, RPS20, RPS21, UBA52, RPL36AL |
| hsa05322 | Systemic lupus erythematosus | 0.00082 | HIST2H2AA3, HIST1H2AC, HIST1H2BC, ACTN4, SNRPD3, ELANE, C1R, HIST1H2BK, H2AFZ, SNRPB, H2AFX, CTSG, HIST1H4H |
| hsa04621 | NOD-like receptor signalling pathway | 0.01458 | IL6, CCL2, XIAP, NFKBIB, NFKBIA, TNFAIP3, BIRC3, CCL5 |

TABLE 1-continued

| KEGG id | KEGG pathway | P-value | Genes |
|---|---|---|---|
| hsa03040 | Spliceosome | 4.1E−06 | SNRPA1, CCDC12, MAGOH, SNRPD3, LSM6, LSM7, SNRPB2, SNRPD2, PPIH, SNRPB, PQBP1, SYF2, LSM5, U2AF1, MAGOHB, THOC2, SNRPF, SNRPE, SNRPG |
| hsa00190 | Oxidative phosphorylation | 6.4E−16 | ATP5E, NDUFB4, ATP6V0E1, NDUFB6, NDUFB9, COX7C, ATP6V1G1, ATP5G1, UQCRQ, NDUFB1, NDUFB2, NDUFS5, NDUFS4, ATP5L, NDUFS3, COX17, ATP5H, ATP5J, NDUFA4, NDUFA5, NDUFA2, NDUFA3, COX7A1, NDUFA6, COX8A, NDUFC2, NDUFC1, NDUFA1, ATP6V1F, NDUFV2, COX6A1, UQCRB |
| hsa05012 | Parkinson's disease | 2.4E−14 | ATP5E, NDUFB4, NDUFB6, NDUFB9, COX7C, ATP5G1, UQCRQ, NDUFB1, NDUFB2, NDUFS5, NDUFS4, HTRA2, NDUFS3, ATP5H, ATP5J, NDUFA4, NDUFA5, NDUFA2, NDUFA3, COX7A1, NDUFA6, COX8A, NDUFC2, NDUFC1, UBE2L3, NDUFA1, VDAC3, NDUFV2, COX6A1, UQCRB |
| hsa05016 | Huntington's disease | 2.2E−13 | ATP5E, NDUFB4, POLR2F, NDUFB6, POLR2K, NDUFB9, POLR2J, COX7C, ATP5G1, UQCRQ, NDUFB1, NDUFB2, NDUFS5, NDUFS4, TGM2, CREB3L1, NDUFS3, ATP5H, ATP5J, NDUFA4, NDUFA5, NDUFA2, NDUFA3, COX7A1, NDUFA6, COX8A, NDUFC2, NDUFC1, NDUFA1, VDAC3, SOD2, NDUFV2, COX6A1, UQCRB |
| hsa05010 | Alzheimer's disease | 9E−11 | ATP5E, NDUFB4, NDUFB6, NDUFB9, COX7C, ATP5G1, UQCRQ, NDUFB1, NDUFB2, NDUFS5, NDUFS4, PPP3CA, NDUFS3, ATP5H, ATP5J, NDUFA4, NDUFA5, NDUFA2, NDUFA3, COX7A1, NDUFA6, COX8A, NDUFC2, NDUFC1, ITPR3, NDUFA1, NDUFV2, COX6A1, UQCRB |
| hsa04623 | Cytosolic DNA-sensing pathway | 0.0077 | MAVS, IL6, POLR3K, NFKBIB, IRF7, NFKBIA, POLR1C, CCL5 |

In one embodiment, the invention provides methods for treating an apicomplexan parasite infection, comprising treating a subject with an apicomplexan parasite infection an amount effective to inhibit activity or expression from the apicomplexan parasite of one or more proteins as discussed herein.

In another embodiment, the invention provides methods for identifying a compound to treat an apicomplexan infection, comprising identifying a compound that inhibits activity or expression of one or more proteins as discussed herein from an apicoimplexan parasite present in an infected host cell.

Certain proteins as discussed herein are believed to be particularly important for apicomplexan parasite bradyzoite development and/or survival in the host. Thus, targeting expression and/or activity of these proteins from the apicomplexan parasite will be effective to inhibit bradyzoite development and/or survival in the host.

EGS transcripts in HHF, MM6, and NSC cells were enriched for genes transcribed in bradyzoites, including known bradyzoite transcripts, certain Apetela 2s and cytochrome b and other cytochromes. Among transcripts with the most increased fold change in EGS across all three cell lines were: cytochrome b; cytochrome c oxidase subunit III subfamily protein; apocytochrome b; cytochrome b, putative; and cytochrome b (N-terminal)/b6/petB subfamily protein. Other over-expressed genes include bradyzoite transcription factor AP2IX-9 and plant-like heat-shock protein BAG1 (FIG. 2A). The up- or down-regulated genes identified in the parasite transcriptome study are thus targets against which to identify drugs for anti-apicomplexan parasite (such as T. gondii) therapy, by identifying test compounds that reduce expression of over-expressed genes, or promote expression of down-regulated genes. In various embodiments, positive test compounds are those that reduce expression (for up-regulated genes), or decrease expression (for down-regulated genes) of 1 or more (i.e.: 1, 2, 3, 4, 5, 6, 7, 8, 9, 10, 50, 100, or more) of the up-regulated apicomplexan parasite genes as discussed herein after host cell infection by at least 5%, 10%, 15%, 20%, 25%, 50%, 75%, 90%, or more. The drug screening assays may employ the cell lines and non-human animal models of the present invention. In one embodiment, the methods comprise identifying test compounds that reduce expression from the apicomplexan parasite after cell infection of 1 or more of cytochrome b; cytochrome c oxidase subunit III subfamily protein; apocytochrome b, cytochrome b, putative, cytochrome b (N-terminal)/b6/petB subfamily protein, bradyzoite transcription factor AP2IX-9 and plant-like heat-shock protein BAG1.

In another aspect, the invention provides compositions comprising a plurality of isolated probes that in total selectively bind to at least 2, 3, 4, 5, 6, 7, 8, 9, 10, 15, 20, 25, 30, 35, 40, 45, 100, 150, 200, 250, 500, or all of certain markers as discussed herein, complements thereof, or their expression products, or functional equivalents thereof wherein at least 10%, 20%, 30%, 40%, 50%, 60%, 70%, 80%, 90%, 95%, or all of the probes in total are selective for markers that are upregulated in the EGS strain of T. gondii after infection of human fibroblasts, neuronal stem cells or monocytic lineage cells.

Functional equivalents are allelic variants of the recited marker from other T. gondii strains. In one embodiment, the markers include two or more of apetela 2 transcription factors, cytochrome b, cytochrome oxidase, or functional equivalents thereof. The markers may further comprise one or more of enolase 1, lactate dehydrogenase 2, bradyzoite antigen 1 and cyst wall protein, or functional equivalents thereof. In another embodiment, In a further aspect, the invention provides a plurality of isolated probes that in total selectively bind to at least 2, 3, 4, 5, 6, 7, 8, 9, 10, 15, 20, 25, 30, 35, 40, 45, 100, 150, 200, 250, 500, or all of certain markers as discussed herein, complements thereof, or their expression products, or functional equivalents thereof, wherein at least 10%, 20%, 30%, 40%, 50%, 60%, 70%, 80%, 90%, 95%, or all of the probes in total are selective for markers that are upregulated in human fibroblasts, neuronal stem cells or monocytic lineage cells after infection with *T. gondii*, including but not limited to infection with the EGS strain of *T. gondii*.

In one embodiment of each of these aspects, the plurality of isolated probes comprises polynucleotide probes. In another embodiment, the plurality of isolated probes comprises antibody probes. In all of the above embodiments, the isolated probes can be labelled with a detectable label. Methods for detecting the label include, but are not limited to spectroscopic, photochemical, biochemical, immunochemical, physical or chemical techniques. Any suitable detectable label can be used.

The compositions can be stored frozen, in lyophilized form, or as a solution. In one embodiment, the compositions can be placed on a solid support, such as in a microarray or microplate format; this embodiment facilitates use of the compositions in various detection assays.

The compositions of the invention can be used, for example, to test patient samples for up-regulation or down-regulation of the one or more markers disclosed in the figures, to assist in diagnosing a subject as having an apicomplexan parasite infection (such as *T. gondii*) or to monitor treatment of a subject receiving therapy for an apicomplexan-associated disorder. In one embodiment, such methods comprise testing the patient samples for increased expression of at least 1, 2, 3, 4, 5, 6, or all 7 of apetela 2 transcription factors, cytochrome b, cytochrome oxidase, enolase 1, lactate dehydrogenase 2, bradyzoite antigen 1 and cyst wall protein, or functional equivalents thereof.

In one embodiment, the transcriptome provides the signature of cytochrome b as an important part of the bradyzoite transcriptional pathways and a signature that demonstrates effective inhibition of cytochrome b with abrogation of the signature when treatment is with an inhibitor of cytochrome b, which when used early after infection can confirm selectivity of compound. Cytochrome b functions for pyrimidine synthesis in *Plasmodium falciparum* so that it will be synergistic or additive in effect with inhibitors of DHODH.

The invention thus also provides pathway to improved inhibitors of cytochrome b through co-crystallography that defines the chemical space and pi stacking which facilitates design of improved medicines and their delivery into tachyzoites and bradyzoites using molecular transporters such as octaargine, or carbonate, and also improves their solubility and access to encysted bradyzoites.

In various embodiments, the methods for monitoring treatment of an apicomplexan parasitic infection (such as a *T. gondii* infection), comprising monitoring expression, protein in serum or plasma, and/or activity of 1, 2, 3, 4, 5, 6, 7, 8, 9, 10, or all of certain markers as discussed herein (such as a human subject) being treated for an apicomplexan parasitic infection, wherein a decrease or increase in expression and/or presence and/or activity of the one or more markers indicates that the treatment is effective. In one exemplary embodiment, infection is in the subject's brain or other neurologic tissue.

In another aspect, the present disclosure provides compounds having the structure of Formula (I):

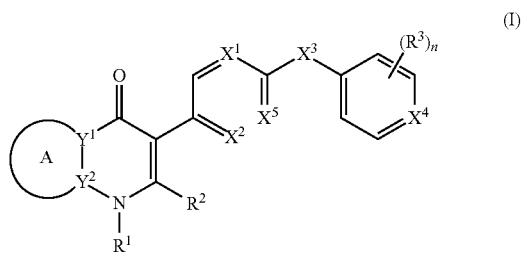

or a stereoisomer thereof, or a pharmaceutically acceptable salt thereof,
wherein
ring A combines with $Y^1$ and $Y_2$ to form a $C_{3-7}$cycloalkenyl or heteroaryl ring,
wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;
$Y^1$ is C or N;
$Y^2$ is C or N;
$X^1$ is $C(R^{x1})$ or N,
wherein $R^{x1}$ is hydrogen, halogen, $C_{1-3}$alkyl, $C_{1-3}$alkoxy or $C_{1-3}$haloalkyl;
$X^2$ is $C(R^{x2})$ or N,
wherein $R^{x2}$ is hydrogen, halogen, $C_{1-3}$alkyl, $C_{1-3}$alkoxy or $C_{1-3}$haloalkyl;
$X^3$ is O, N(R), S or $C_{1-3}$alkyl;
$X^4$ is C or N;
$X^5$ is C or N;
$R^1$ is hydrogen or $C_{1-3}$alkyl;
$R^2$ is hydrogen, $C_{1-3}$alkyl, $C_{1-3}$haloalkyl, —CH$_2$OH, —CH$_2$OR or —C(O)OR;
n is 0, 1, 2, 3 or 4;
each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or SF$_5$;
or two $R^3$ groups, together with the carbons to which they are attached, form a 1,3-dioxolane; and
each R is independently hydrogen or $C_{1-3}$alkyl.

The compounds of the invention have been demonstrated in the examples herein as useful, for example, in treating diseases associated with apicomplexan parasite infection.

In some embodiments, the compounds are of Formula (Ia):

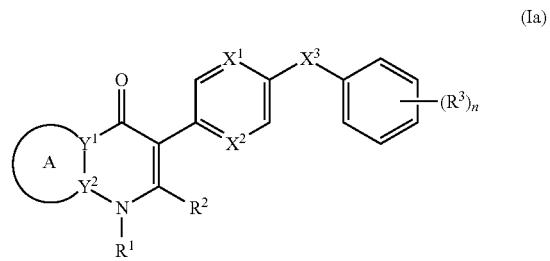

or a stereoisomer thereof, or a pharmaceutically acceptable salt thereof, wherein ring A combines with $Y^1$ and $Y_2$ to form a $C_{3-7}$cycloalkenyl or heteroaryl ring, wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;

$Y^1$ is C or N;

$Y^2$ is C or N;

$X^1$ is $C(R^{x1})$ or N, wherein $R^{x1}$ is hydrogen, halogen, $C_{1-3}$alkyl, $C_{1-3}$alkoxy or $C_{1-3}$haloalkyl;

$X^2$ is $C(R^{x2})$ or N, wherein $R^{x2}$ is hydrogen, halogen, $C_{1-3}$alkyl, $C_{1-3}$alkoxy or $C_{1-3}$haloalkyl;

$X^3$ is O, N(R), S or $C_{1-3}$alkyl;

$R^1$ is hydrogen or $C_{1-3}$alkyl;

$R^2$ is hydrogen, $C_{1-3}$alkyl or —C(O)OR;

n is 0, 1, 2, 3 or 4;

each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or $SF_5$; and each R is independently hydrogen or $C_{1-3}$alkyl.

In some embodiments, the compounds are of Formula (Ib):

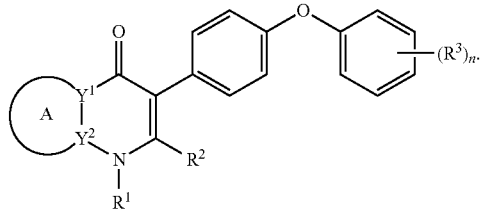

In some embodiments, the compounds are of Formula (Ic):

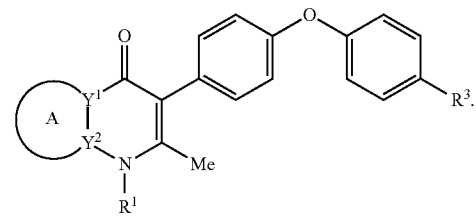

In some embodiments, the compounds are of Formula (II):

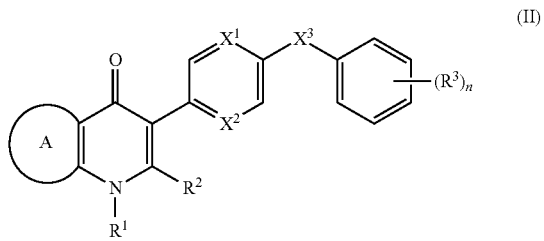

wherein ring A combines with the carbon atoms with which it is attached to form a $C_{3-7}$cycloalkenyl.

In some embodiments, the compounds are of Formula (IIa):

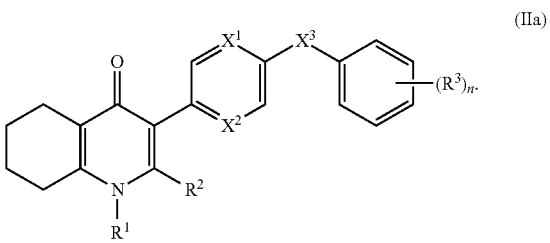

In some embodiments, the compounds are of Formula (IIa-1):

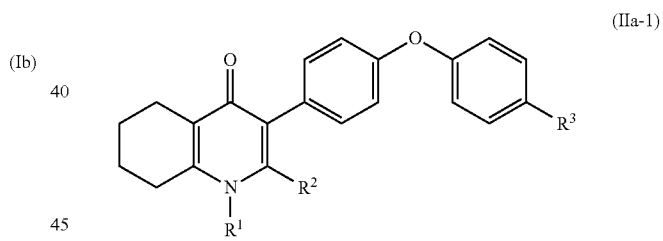

wherein $R^3$ is hydrogen, halogen, $C_{1-3}$alkyl or $C_{1-3}$haloalkyl.

In some embodiments, the compounds are of Formula (III):

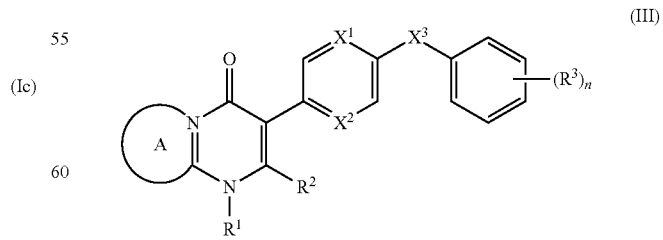

wherein ring A combines with the nitrogen atom and carbon atom with which it is attached to form a heteroaryl ring.

In some embodiments, the compounds are of Formula (IIIa):

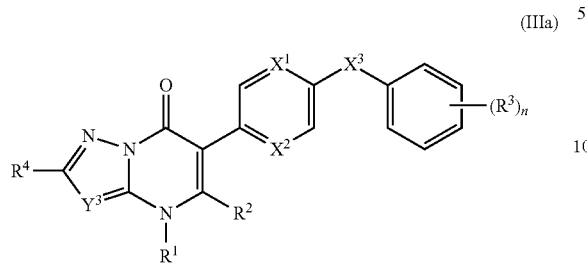

wherein
Y³ is C(R⁵) or N; and
R⁴ and R⁵ are independently hydrogen, halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl.

In some embodiments, the compounds are of Formula (IIIb):

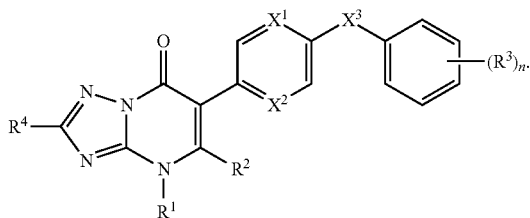

In some embodiments, the compounds are of R⁴ is hydrogen or $C_{1-3}$alkyl.

In some embodiments, the compounds are of Formula (IIIb-1):

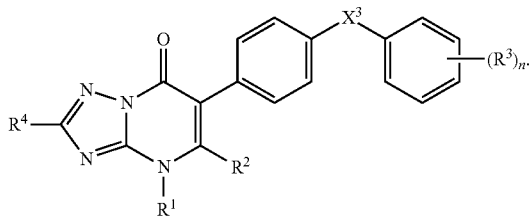

In some embodiments, the compounds are of Formula (IIIc):

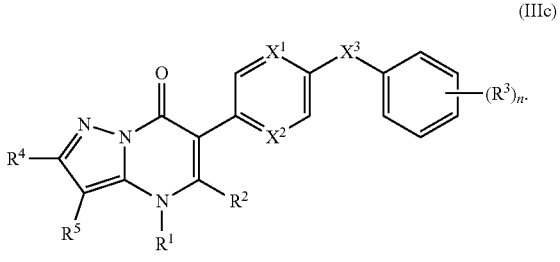

In some embodiments,
R⁴ is hydrogen or $C_{1-3}$alkyl or phenyl; and
R⁵ is hydrogen or cyano.

In some embodiments, the compounds are of Formula (IIIc-1):

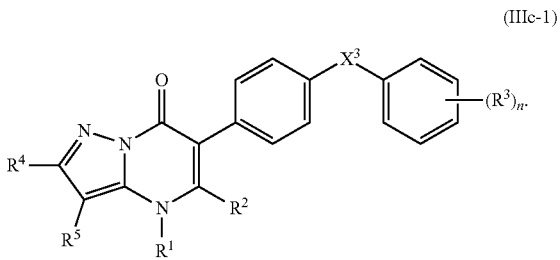

In some embodiments, the compounds are of Formula (IV):

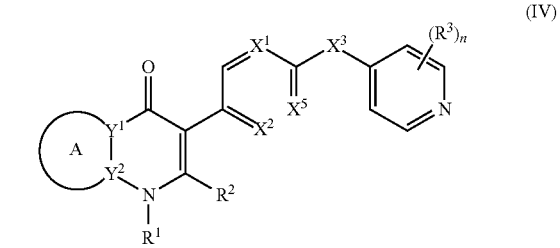

or a stereoisomer thereof, or a pharmaceutically acceptable salt thereof,
wherein
ring A combines with Y¹ and Y₂ to form a $C_{3-7}$cycloalkenyl or heteroaryl ring, wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;
Y¹ is C or N;
Y² is C or N;
X¹ is C(R^{x1}) or N,
   wherein R^{x1} is hydrogen, halogen, $C_{1-3}$alkyl, $C_{1-3}$alkoxy or $C_{1-3}$haloalkyl;
X² is C(R^{x2}) or N,
   wherein R^{x2} is hydrogen, halogen, $C_{1-3}$alkyl, $C_{1-3}$alkoxy or $C_{1-3}$haloalkyl;
X³ is O, N(R), S or $C_{1-3}$alkyl;
X⁵ is C or N;
R¹ is hydrogen or $C_{1-3}$alkyl;

R2 is hydrogen, $C_{1-3}$alkyl, $C_{1-3}$haloalkyl, —$CH_2OH$, —$CH_2OR$ or —C(O)OR;

n is 0, 1, 2, 3 or 4;

each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or $SF_5$; and each R is independently hydrogen or $C_{1-3}$alkyl.

In some embodiments, the compounds are of Formula (IVa):

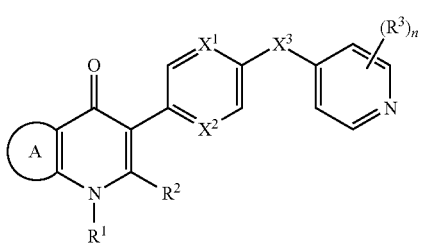

(IVa)

wherein
ring A combines with the carbon atoms with which it is attached to form a $C_{3-7}$cycloalkenyl.

In some embodiments, the compounds are of Formula (IVb):

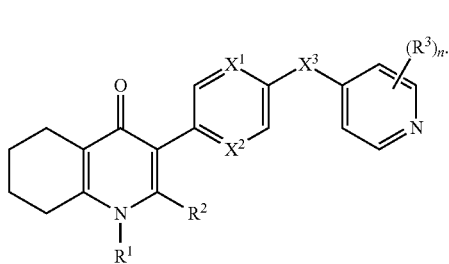

(IVb)

In some embodiments, $Y^1$ is C. In other embodiments, $Y^1$ is N.

In some embodiments, $Y^2$ is C. In other embodiments, $Y^2$ is N.

In some embodiments, $Y^1$ is C. In other embodiments, $Y^1$ is N.

In some embodiments, $X^1$ is $C(R^{x1})$ wherein $R^{x1}$ is hydrogen, halogen, $C_{1-3}$alkyl, $C_{1-3}$alkoxy or $C_{1-3}$haloalkyl. In other embodiments, $X^1$ is N.

In some embodiments, $X^1$ is $C(R^{x1})$ wherein $R^{x1}$ is selected from any of groups (1a)-(1x):
(1a) hydrogen, halogen, $C_{1-3}$alkyl, $C_{1-3}$alkoxy or $C_{1-3}$haloalkyl;
(1b) halogen, $C_{1-3}$alkyl, $C_{1-3}$alkoxy or $C_{1-3}$haloalkyl;
(1c) hydrogen;
(1d) halogen or $C_{1-3}$haloalkyl;
(1e) halogen or $C_{1-3}$alkyl;
(1f) $C_{1-3}$alkyl;
(1g) hydrogen, methyl or ethyl;
(1h) methyl or ethyl;
(1i) methyl;
(1j) ethyl;
(1k) propyl;
(1l) hydrogen, methyl or propyl;
(1m) methyl or propyl;
(1n) hydrogen, ethyl or propyl;
(1o) ethyl or propyl;
(1p) $C_{1-3}$haloalkyl;
(1q) $C_{1-3}$fluoroalkyl;
(1r) fluoromethyl
(1s) difluoromethyl
(1t) trifluoromethyl
(1u) fluoromethyl
(1v) fluoropropyl
(1w) —$CH_2OH$;
(1x) —$CH_2OR$;

In some embodiments, $X^2$ is $C(R^{x2})$ wherein $R^{x2}$ is hydrogen, halogen, $C_{1-3}$alkyl, $C_{1-3}$alkoxy or $C_{1-3}$haloalkyl. In other embodiments, $X^2$ is N.

In some embodiments, $X^2$ is $C(R^{x2})$ wherein $R^{x2}$ is selected from any of groups (2a)-(2x):
(2a) hydrogen, halogen, $C_{1-3}$alkyl, $C_{1-3}$alkoxy or $C_{1-3}$haloalkyl;
(2b) halogen, $C_{1-3}$alkyl, $C_{1-3}$alkoxy or $C_{1-3}$haloalkyl;
(2c) hydrogen;
(2d) halogen or $C_{1-3}$haloalkyl;
(2e) halogen or $C_{1-3}$alkyl;
(2f) $C_{1-3}$alkyl;
(2g) hydrogen, methyl or ethyl;
(2h) methyl or ethyl;
(2i) methyl;
(2j) ethyl;
(2k) propyl;
(2l) hydrogen, methyl or propyl;
(2m) methyl or propyl;
(2n) hydrogen, ethyl or propyl;
(2o) ethyl or propyl;
(2p) $C_{1-3}$haloalkyl;
(2q) $C_{1-3}$fluoroalkyl;
(2r) fluoromethyl
(2s) difluoromethyl
(2t) trifluoromethyl
(2u) fluoromethyl
(2v) fluoropropyl
(2w) —$CH_2OH$;
(2x) —$CH_2OR$;

In some embodiments, $X^3$ is selected from any of groups (3a)-(3p):
(3a) O, N(R), S or $C_{1-3}$alkyl;
(3b) O, N(R) or S;
(3c) O or N(R);
(3d) O;
(3e) N(R);
(3f) S or $C_{1-3}$alkyl;
(3g) O, N(R), or $C_{1-3}$alkyl;
(3h) O or $C_{1-3}$alkyl;
(3i) N(R), S or $C_{1-3}$alkyl;
(3j) N(R) or $C_{1-3}$alkyl;
(3k) O or $C_{1-3}$alkyl;
(3l) $C_{1-3}$alkyl;
(3m) methylene
(3n) ethylene;
(3o) propylene;
(3p) NH.

In some embodiments, $X^4$ is C. In other embodiments, $X^4$ is N.

In some embodiments, $X^5$ is C. In other embodiments, $X^5$ is N.

In some embodiments, $R^1$ is selected from any of groups (4a)-(4l):
(4a) hydrogen or $C_{1-3}$alkyl;
(4b) hydrogen;
(4c) $C_{1-3}$alkyl;
(4d) hydrogen, methyl or ethyl;

(4e) methyl or ethyl;
(4f) methyl;
(4g) ethyl;
(4h) propyl;
(4i) hydrogen, methyl or propyl;
(4j) methyl or propyl;
(4k) hydrogen, ethyl or propyl;
(4l) ethyl or propyl;

In some embodiments, R2 is selected from any of groups (5a)-(5gg):
  (5a) hydrogen, $C_{1-3}$alkyl, $C_{1-3}$haloalkyl, —$CH_2OH$, —$CH_2OR$ or —C(O)OR;
  (5b) $C_{1-3}$alkyl, $C_{1-3}$haloalkyl, —$CH_2OH$, —$CH_2OR$ or —C(O)OR;
  (5c) hydrogen, $C_{1-3}$haloalkyl, —$CH_2OH$, —$CH_2OR$ or —C(O)OR;
  (5d) hydrogen, $C_{1-3}$alkyl, —$CH_2OH$, —$CH_2OR$ or —C(O)OR;
  (5e) hydrogen, $C_{1-3}$alkyl, $C_{1-3}$haloalkyl, —$CH_2OR$ or —C(O)OR;
  (5f) hydrogen, $C_{1-3}$alkyl, $C_{1-3}$haloalkyl, —$CH_2OH$, or —C(O)OR;
  (5g) hydrogen, $C_{1-3}$alkyl, $C_{1-3}$haloalkyl, —$CH_2OH$, or —$CH_2OR$;
  (5h) hydrogen or $C_{1-3}$alkyl;
  (5i) hydrogen;
  (5j) $C_{1-3}$alkyl;
  (5k) hydrogen, methyl or ethyl;
  (5l) methyl or ethyl;
  (5m) methyl;
  (5n) ethyl;
  (5o) propyl;
  (5p) hydrogen, methyl or propyl;
  (5q) methyl or propyl;
  (5r) hydrogen, ethyl or propyl;
  (5s) ethyl or propyl;
  (5t) $C_{1-3}$haloalkyl, —$CH_2OH$, —$CH_2OR$ or —C(O)OR;
  (5u) $C_{1-3}$haloalkyl;
  (5v) $C_{1-3}$fluoroalkyl;
  (5w) fluoromethyl
  (5x) difluoromethyl
  (5y) trifluoromethyl
  (5z) fluoromethyl
  (5aa) fluoropropyl
  (5bb) —$CH_2OH$;
  (5cc) —$CH_2OR$;
  (5dd) —C(O)OR;
  (5ee) —C(O)OH;
  (5ff) —C(O)OMe;
  (5gg) —C(O)OEt In some embodiments, n is selected from any of groups (6a)-(6k):
  (6a) n is 1, 2, 3, or 4.
  (6b) n is 0, 1, 2, or 3.
  (6c) n is 0, 1, or 2.
  (6d) n is 0 or 1.
  (6e) n is 1 or 2.
  (6f) n is 2 or 3.
  (6g) n is 1.
  (6h) n is 2.
  (6i) n is 3.
  (6j) n is 4.
  (6k) n is 0.

In some embodiments, $R^3$ is selected from any of groups (7a)-(7cc):
  (7a) each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, $SF_5$, or two $R^3$ groups, together with the carbons to which they are attached, form a 1,3-dioxolane;
  (7b) each $R^3$ is independently $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or $SF_5$;
  (7c) each $R^3$ is independently halogen, $C_{1-3}$alkoxy, $C_{1-3}$haloalkyl, —O—$C_{1-3}$haloalkyl, —S—$C_{1-3}$haloalkyl, —C(O)OR or $SF_5$;
  (7d) each $R^3$ is independently halogen, $C_{1-3}$alkyl, $C_{1-3}$haloalkyl, —O—$C_{1-3}$haloalkyl, —S—$C_{1-3}$haloalkyl, —C(O)OR or $SF_5$;
  (7e) each $R^3$ is independently halogen, $C_{1-3}$haloalkyl, —O—$C_{1-3}$haloalkyl, —S—$C_{1-3}$haloalkyl, —C(O)OR or $SF_5$;
  (7f) each $R^3$ is independently halogen, $C_{1-3}$alkyl, $C_{1-3}$alkoxy, —O—$C_{1-3}$haloalkyl, —S—$C_{1-3}$haloalkyl, —C(O)OR or $SF_5$;
  (7g) each $R^3$ is independently $C_{1-3}$alkyl, $C_{1-3}$alkoxy, —O—$C_{1-3}$haloalkyl, —S—$C_{1-3}$haloalkyl, —C(O)OR or $SF_5$;
  (7h) each $R^3$ is independently —O—$C_{1-3}$haloalkyl, —S—$C_{1-3}$haloalkyl, —C(O)OR or $SF_5$;
  (7i) each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or $SF_5$;
  (7j) each $R^3$ is independently halogen, $C_{1-3}$haloalkyl, —O—$C_{1-3}$haloalkyl, —C(O)OR, or two $R^3$ groups, together with the carbons to which they are attached, form a 1,3-dioxolane;
  (7k) each $R^3$ is independently halogen, $C_1$haloalkyl, —O-$C_1$haloalkyl, —C(O)OR, or two $R^3$ groups, together with the carbons to which they are attached, form a 1,3-dioxolane;
  (7l) each $R^3$ is independently fluoro, chloro, $C_{1-3}$haloalkyl, —O—$C_{1-3}$haloalkyl, —C(O)OR, or two $R^3$ groups, together with the carbons to which they are attached, form a 1,3-dioxolane;
  (7m) each $R^3$ is independently fluoro, chloro, trifluoromethyl, —O—$C_{1-3}$haloalkyl, —C(O)OR, or two $R^3$ groups, together with the carbons to which they are attached, form a 1,3-dioxolane;
  (7n) each $R^3$ is independently fluoro, chloro, trifluoromethyl, —$OCF_3$, —C(O)OR, or two $R^3$ groups, together with the carbons to which they are attached, form a 1,3-dioxolane;
  (7o) each $R^3$ is independently fluoro, chloro, trifluoromethyl, —$OCF_3$, —C(O)OH, or two $R^3$ groups, together with the carbons to which they are attached, form a 1,3-dioxolane;
  (7p) each $R^3$ is independently trifluoromethyl, —$OCF_3$, —C(O)OH, or two $R^3$ groups, together with the carbons to which they are attached, form a 1,3-dioxolane;
  (7q) each $R^3$ is independently fluoro, chloro, —$OCF_3$, —C(O)OH, or two $R^3$ groups, together with the carbons to which they are attached, form a 1,3-dioxolane;
  (7r) each $R^3$ is independently fluoro, chloro, trifluoromethyl, —$OCF_3$, or two $R^3$ groups, together with the carbons to which they are attached, form a 1,3-dioxolane;
  (7s) each $R^3$ is independently fluoro, chloro, trifluoromethyl or —$OCF_3$;
  (7t) each $R^3$ is independently fluoro, chloro, trifluoromethyl, —$OCF_3$ or —C(O)OH;
  (7u) each $R^3$ is independently fluoro, chloro, trifluoromethyl or —$OCF_3$;

(7v) each $R^3$ is independently fluoro, chloro or trifluoromethyl;
(7w) each $R^3$ is independently fluoro or chloro;
(7x) each $R^3$ is independently fluoro;
(7y) each $R^3$ is independently chloro;
(7z) each $R^3$ is trifluoromethyl;
(7aa) each $R^3$ is —$OCF_3$;
(7bb) each $R^3$ is —C(O)OH;
(7cc) two $R^3$ groups, together with the carbons to which they are attached, form a 1,3-dioxolane;

In some embodiments, R is selected from any of groups (8a)-(8l):
(8a) hydrogen or $C_{1-3}$alkyl;
(8b) hydrogen;
(8c) $C_{1-3}$alkyl;
(8d) hydrogen, methyl or ethyl;
(8e) methyl or ethyl;
(8f) methyl;
(8g) ethyl;
(8h) propyl;
(8i) hydrogen, methyl or propyl;
(8j) methyl or propyl;
(8k) hydrogen, ethyl or propyl;
(8l) ethyl or propyl;

In some embodiments, the compound is of Formula (I), (Ia), (Ib) or (Ic), and $X^1$, $X^2$, $X^3$, $R^1$, $R^2$, $R^3$ and n are selected from any combination of groups (1a)-(8l).

In some embodiments, the compound is of Formula (II), (IIa) or (IIa-1), and $X^1$, $X^2$, $X^3$, $R^1$, $R^2$, $R^3$ and n are selected from any combination of groups (1a)-(8l).

In some embodiments, the compound is of Formula (III), (IIIa), (IIIb), (IIIb-1), (IIIc) or (IIIc-1), and $X^1$, $X^2$, $X^3$, $R^1$, $R^2$, $R^3$ and n are selected from any combination of groups (1a)-(8l).

In some embodiments, the compound is of Formula (IV), (IVa) or (IVb) and $X^1$, $X^2$, $X^3$, $R^1$, $R^2$, $R^3$ and n are selected from any combination of groups (1a)-(8l).

In some embodiments, the compound is:

| No. | ID | Structure | Name |
|---|---|---|---|
| ELQ-type systems | | | |

| PA1 | MJM102/ MJM113 (ELQ-271) | 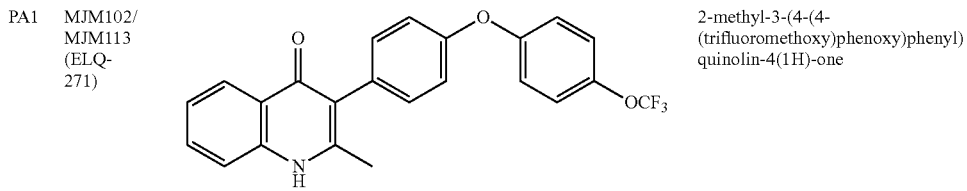 | 2-methyl-3-(4-(4-(trifluoromethoxy)phenoxy)phenyl)quinolin-4(1H)-one |
| PA2 | MJM 129 | 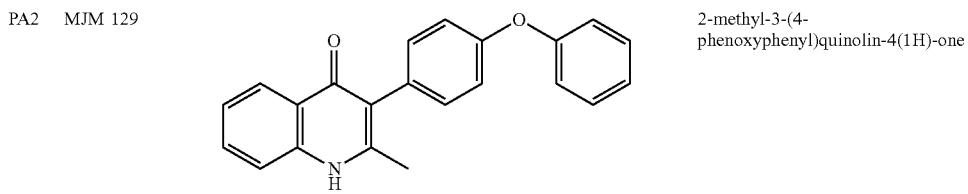 | 2-methyl-3-(4-phenoxyphenyl)quinolin-4(1H)-one |
| PA3 | JM10 | 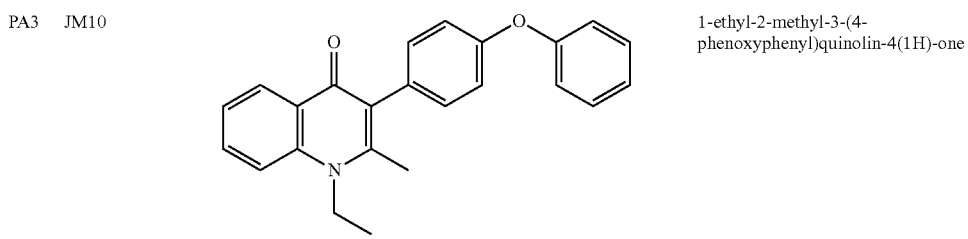 | 1-ethyl-2-methyl-3-(4-phenoxyphenyl)quinolin-4(1H)-one |

| No. | ID | Structure | Name |
|---|---|---|---|
| PA4 | RG38 | | 3-(4-(4-chlorophenoxy)-3-hydroxyphenyl)-2-methylquinolin-4(1H)-one |

5,6-fused pyridone systems

| No. | ID | Structure | Name |
|---|---|---|---|
| 1 | MJM136 | 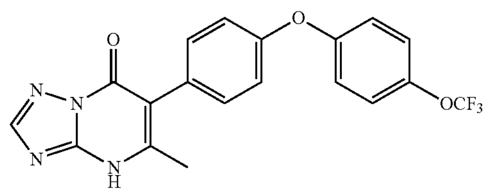 | 5-methyl-6-(4-(4-(trifluoromethoxy)phenoxy)phenyl)-[1,2,4]triazolo[1,5-a]pyrimidin-7(4H)-one |
| 2 | MJM141 | 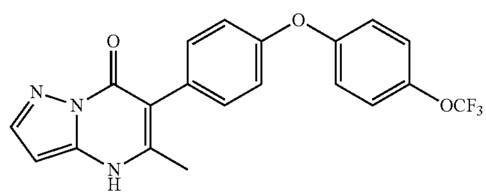 [SMILES: Cc1[nH]c2ccnn2c(=O)c1-c1ccc(Oc2ccc(OC(F)(F)F)cc2)cc1] | 5-methyl-6-(4-(4-(trifluoromethoxy)phenoxy)phenyl)pyrazolo[1,5-a]pyrimidin-7(4H)-one |
| 3 | JAG006 | 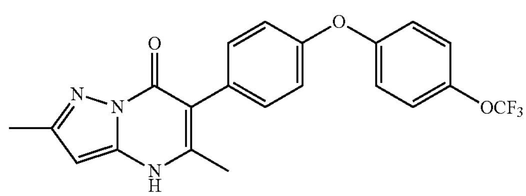 [SMILES: Cc1cc2[nH]c(C)c(-c3ccc(Oc4ccc(OC(F)(F)F)cc4)cc3)c(=O)n2n1] | 2,5-dimethyl-6-(4-(4-(trifluoromethoxy)phenoxy)phenyl)pyrazolo[1,5-a]pyrimidin-7(4H)-one |
| 4 | JAG013 | 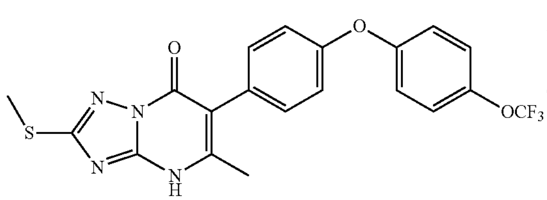 [SMILES: CSc1nc2[nH]c(C)c(-c3ccc(Oc4ccc(OC(F)(F)F)cc4)cc3)c(=O)n2n1] | 5-methyl-2-(methylthio)-6-(4-(4-(trifluoromethoxy)phenoxy)phenyl)-[1,2,4]triazolo[1,5-a]pyrimidin-7(4H)-one |
| 5 | JAG014 | 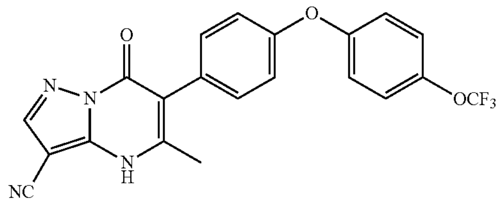 [SMILES: Cc1[nH]c2c(C#N)cnn2c(=O)c1-c1ccc(Oc2ccc(OC(F)(F)F)cc2)cc1] | 5-methyl-7-oxo-6-(4-(4-(trifluoromethoxy)phenoxy)phenyl)-4,7-dihydropyrazolo[1,5-a]pyrimidine-3-carbonitrile |

-continued

| No. | ID | Structure | Name |
|---|---|---|---|
| 6 | JAG015 | | 5-methyl-2-phenyl-6-(4-(4-(trifluoromethoxy)phenoxy)phenyl)pyrazolo[1,5-a]pyrimidin-7(4H)-one |

Tetrahydroquinolones (THQ)

| No. | ID | Structure | Name |
|---|---|---|---|
| 7 | MJM170 | 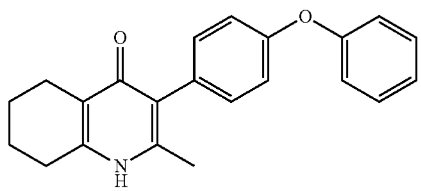 [SMILES: Cc1[nH]c2c(c(=O)c1-c1ccc(Oc3ccccc3)cc1)CCCC2] | 2-methyl-3-(4-phenoxyphenyl)-5,6,7,8-tetrahydroquinolin-4(1H)-one |
| 8 | JAG21 | 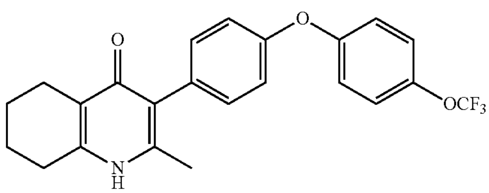 [SMILES: Cc1[nH]c2c(c(=O)c1-c1ccc(Oc3ccc(OC(F)(F)F)cc3)cc1)CCCC2] | 2-methyl-3-(4-(4-(trifluoromethoxy)phenoxy)phenyl)-5,6,7,8-tetrahydroquinolin-4(1H)-one |
| 9 | JAG039 | 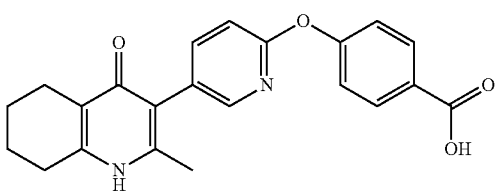 | 4-((5-(2-methyl-4-oxo-1,4,5,6,7,8-hexahydroquinolin-3-yl)pyridin-2-yl)oxy)benzoic acid |
| 10 | JAG046 | 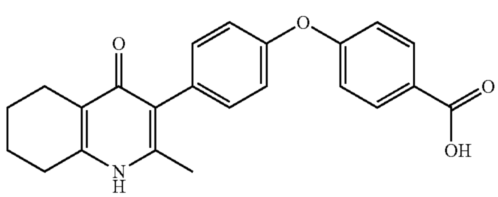 [SMILES: Cc1[nH]c2c(c(=O)c1-c1ccc(Oc3ccc(C(=O)O)cc3)cc1)CCCC2] | 4-(4-(2-methyl-4-oxo-1,4,5,6,7,8-hexahydroquinolin-3-yl)phenoxy)benzoic acid |
| 11 | JAG047 | 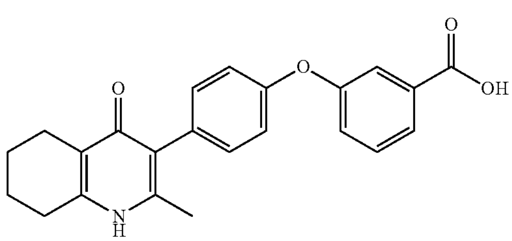 [SMILES: Cc1[nH]c2c(c(=O)c1-c1ccc(Oc3cccc(C(=O)O)c3)cc1)CCCC2] | 3-(4-(2-methyl-4-oxo-1,4,5,6,7,8-hexahydroquinolin-3-yl)phenoxy)benzoic acid |
| 12 | JAG50 | 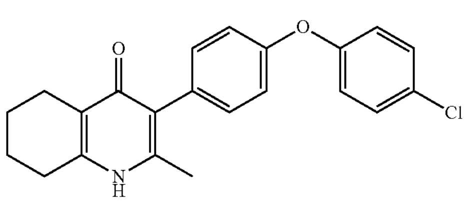 [SMILES: Cc1[nH]c2c(c(=O)c1-c1ccc(Oc3ccc(Cl)cc3)cc1)CCCC2] | 3-(4-(4-chlorophenoxy)phenyl)-2-methyl-5,6,7,8-tetrahydroquinolin-4(1H)-one |

-continued

| No. | ID | Structure | Name |
|---|---|---|---|
| 13 | JAG58 | 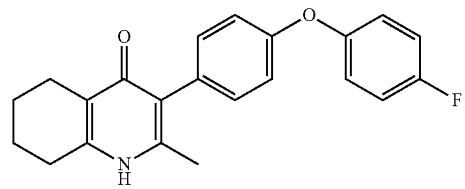 [SMILES: Cc1[nH]c2c(c(=O)c1-c1ccc(Oc3ccc(F)cc3)cc1)CCCC2] | 3-(4-(4-fluorophenoxy)phenyl)-2-methyl-5,6,7,8-tetrahydroquinolin-4(1H)-one |
| 14 | JAG63 | 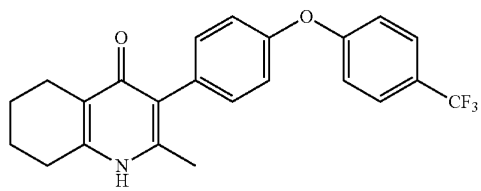 [SMILES: Cc1[nH]c2c(c(=O)c1-c1ccc(Oc3ccc(C(F)(F)F)cc3)cc1)CCCC2] | 2-methyl-3-(4-(4-(trifluoromethyl)phenoxy)phenyl)-5,6,7,8-tetrahydroquinolin-4(1H)-one |
| 15 | JAG062 | 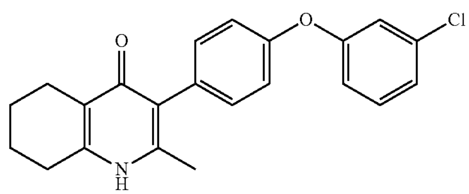 [SMILES: Cc1[nH]c2c(c(=O)c1-c1ccc(Oc3cccc(Cl)c3)cc1)CCCC2] | 3-(4-(3-chlorophenoxy)phenyl)-2-methyl-5,6,7,8-tetrahydroquinolin-4(1H)-one |
| 16 | JAG067 | 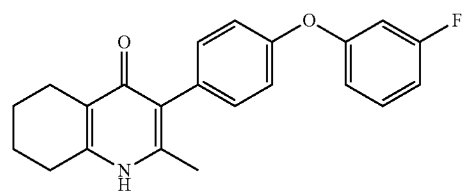 [SMILES: Cc1[nH]c2c(c(=O)c1-c1ccc(Oc3cccc(F)c3)cc1)CCCC2] | 3-(4-(3-fluorophenoxy)phenyl)-2-methyl-5,6,7,8-tetrahydroquinolin-4(1H)-one |
| 17 | JAG023 | 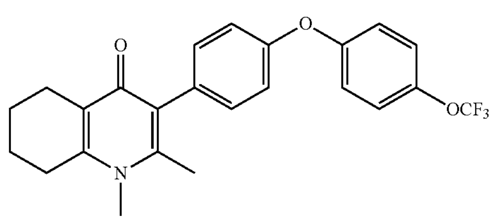 [SMILES: Cc1c(-c2ccc(Oc3ccc(OC(F)(F)F)cc3)cc2)c(=O)c2c(n1C)CCCC2] | 1,2-dimethyl-3-(4-(4-(trifluoromethoxy)phenoxy)phenyl)-5,6,7,8-tetrahydroquinolin-4(1H)-one |
| 18 | JAG077 | 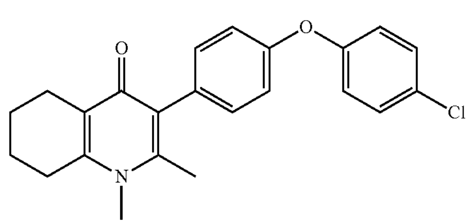 [SMILES: Cc1c(-c2ccc(Oc3ccc(Cl)cc3)cc2)c(=O)c2c(n1C)CCCC2] | 3-(4-(4-chlorophenoxy)phenyl)-1,2-dimethyl-5,6,7,8-tetrahydroquinolin-4(1H)-one |
| 19 | AS006 | 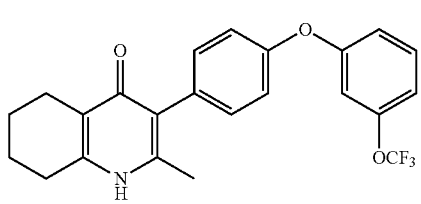 [SMILES: Cc1[nH]c2c(c(=O)c1-c1ccc(Oc3cccc(OC(F)(F)F)c3)cc1)CCCC2] | 2-methyl-3-(4-(3-(trifluoromethoxy)phenoxy)phenyl)-5,6,7,8-tetrahydroquinolin-4(1H)-one |

| No. | ID | Structure | Name |
|---|---|---|---|
| 20 | AS0012 | 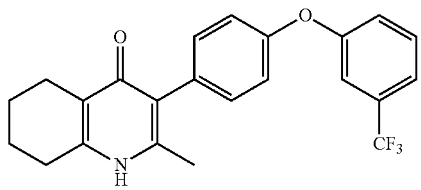 | 2-methyl-3-(4-(3-(trifluoromethyl)phenoxy)phenyl)-5,6,7,8-tetrahydroquinolin-4(1H)-one |
| 21 | AS021 | 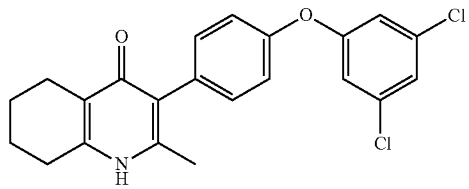 [SMILES: Cc1[nH]c2c(c(=O)c1-c1ccc(Oc3cc(Cl)cc(Cl)c3)cc1)CCCC2] | 3-(4-(3,5-dichlorophenoxy)phenyl)-2-methyl-5,6,7,8-tetrahydroquinolin-4(1H)-one |
| 22 | AS022 | | 3-(4-(3-chloro-4-fluorophenoxy)phenyl)-2-methyl-5,6,7,8-tetrahydroquinolin-4(1H)-one | or a stereoisomer thereof or a pharmaceutically acceptable salt thereof.

In some embodiments, the compound is:

| ID | Structure | Name |
|---|---|---|
| MJM136 | 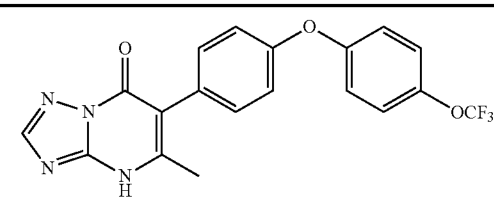 | 5-methyl-6-(4-(4-(trifluoromethoxy)phenoxy)phenyl)-[1,2,4]triazolo[1,5-a]pyrimidin-7(4H)-one |
| MJM141 | 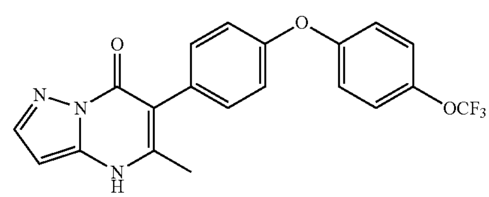 [SMILES: Cc1[nH]c2ccnn2c(=O)c1-c1ccc(Oc2ccc(OC(F)(F)F)cc2)cc1] | 5-methyl-6-(4-(4-(trifluoromethoxy)phenoxy)phenyl)pyrazolo[1,5-a]pyrimidin-7(4H)-one |
| JAG006 | 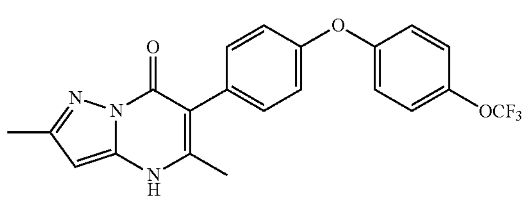 [SMILES: Cc1cc2[nH]c(C)c(-c3ccc(Oc4ccc(OC(F)(F)F)cc4)cc3)c(=O)n2n1] | 2,5-dimethyl-6-(4-(4-(trifluoromethoxy)phenoxy)phenyl)pyrazolo[1,5-a]pyrimidin-7(4H)-one |
| JAG013 | 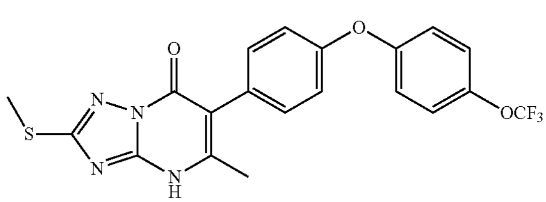 [SMILES: CSc1nc2[nH]c(C)c(-c3ccc(Oc4ccc(OC(F)(F)F)cc4)cc3)c(=O)n2n1] | 5-methyl-2-(methylthio)-6-(4-(4-(trifluoromethoxy)phenoxy)phenyl)-[1,2,4]triazolo[1,5-a]pyrimidin-7(4H)-one |

-continued

| ID | Structure | Name |
| --- | --- | --- |
| JAG014 | 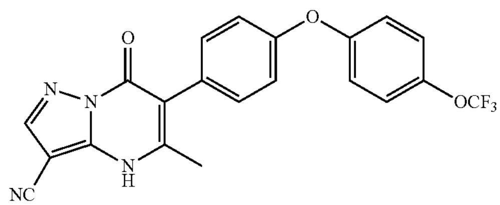 [SMILES: Cc1[nH]c2c(C#N)cnn2c(=O)c1-c1ccc(Oc2ccc(OC(F)(F)F)cc2)cc1] | 5-methyl-7-oxo-6-(4-(4-(trifluoromethoxy)phenoxy)phenyl)-4,7-dihydropyrazolo[1,5-a]pyrimidine-3-carbonitrile. |
| JAG015 | 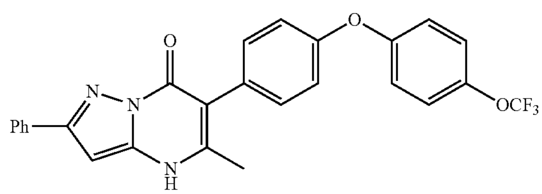 [SMILES: Cc1[nH]c2cc(-c3ccccc3)nn2c(=O)c1-c1ccc(Oc2ccc(OC(F)(F)F)cc2)cc1] | 5-methyl-2-phenyl-6-(4-(4-(trifluoromethoxy)phenoxy)phenyl)pyrazolo[1,5-a]pyrimidin-7(4H)-one. |
| MJM170 | 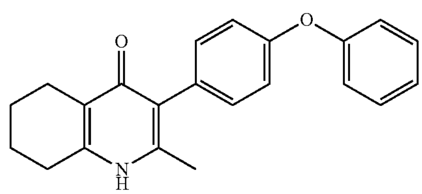 | 2-methyl-3-(4-phenoxyphenyl)-5,6,7,8-tetrahydroquinolin-4(1H)-one |
| JAG21 | 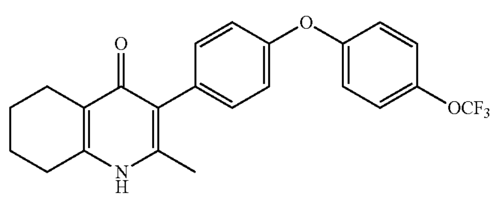 [SMILES: Cc1[nH]c2c(c(=O)c1-c1ccc(Oc3ccc(OC(F)(F)F)cc3)cc1)CCCC2] | 2-methyl-3-(4-(4-(trifluoromethoxy)phenoxy)phenyl)-5,6,7,8-tetrahydroquinolin-4(1H)-one |
| JAG039 | 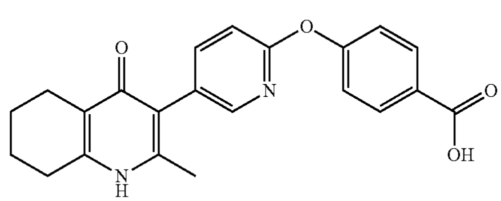 [SMILES: Cc1[nH]c2c(c(=O)c1-c1ccc(Oc3ccc(C(=O)O)cc3)nc1)CCCC2] | methyl 3-((5-(4-ethoxy-2-methyl-5,6,7,8-tetrahydroquinolin-3-yl)pyridin-2-yl)oxy)benzoate |
| JAG046 | 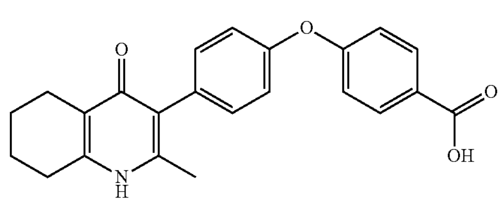 [SMILES: Cc1[nH]c2c(c(=O)c1-c1ccc(Oc3ccc(C(=O)O)cc3)cc1)CCCC2] | 4-(4-(2-methyl-4-oxo-1,4,5,6,7,8-hexahydroquinolin-3-yl)phenoxy)benzoic acid |
| JAG047 | 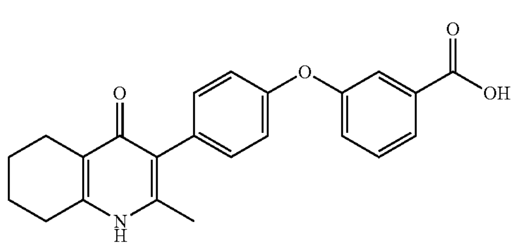 [SMILES: Cc1[nH]c2c(c(=O)c1-c1ccc(Oc3cccc(C(=O)O)c3)cc1)CCCC2] | 3-(4-(2-methyl-4-oxo-1,4,5,6,7,8-hexahydroquinolin-3-yl)phenoxy)benzoic acid |

-continued

| ID | Structure | Name |
|---|---|---|
| JAG50 | 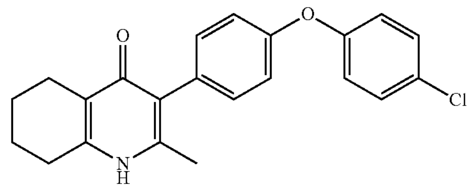 [SMILES: Cc1[nH]c2c(c(=O)c1-c1ccc(Oc3ccc(Cl)cc3)cc1)CCCC2] | 3-(4-(4-chlorophenoxy)phenyl)-2-methyl-5,6,7,8-tetrahydroquinolin-4(1H)-one |
| JAG58 | 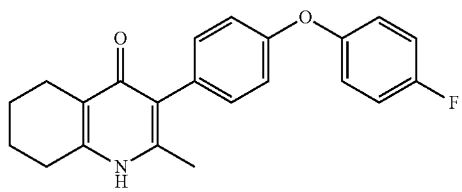 [SMILES: Cc1[nH]c2c(c(=O)c1-c1ccc(Oc3ccc(F)cc3)cc1)CCCC2] | 3-(4-(4-Fluorophenoxy)phenyl)-2-methyl-5,6,7,8-tetrahydroquinolin-4(1H)-one |
| JAG63 | 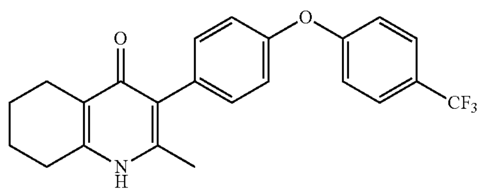 [SMILES: Cc1[nH]c2c(c(=O)c1-c1ccc(Oc3ccc(C(F)(F)F)cc3)cc1)CCCC2] | 2-Methyl-3-(4-(4-(trifluoromethyl)phenoxy)phenyl)-5,6,7,8-tetrahydroquinolin-4(1H)-one |
| JAG062 | 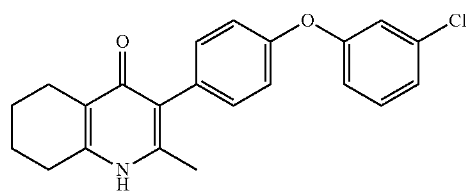 [SMILES: Cc1[nH]c2c(c(=O)c1-c1ccc(Oc3cccc(Cl)c3)cc1)CCCC2] | 3-(4-(3-Chlorophenoxy)phenyl)-2-methyl-5,6,7,8-tetrahydroquinolin-4(1H)-one |
| JAG069 | 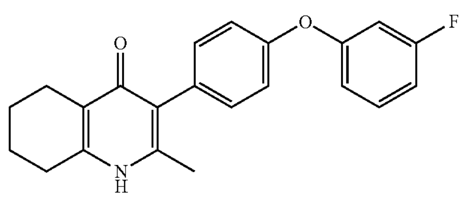 [SMILES: Cc1[nH]c2c(c(=O)c1-c1ccc(Oc3cccc(F)c3)cc1)CCCC2] | 3-(4-(3-Fluorophenoxy)phenyl)-2-methyl-5,6,7,8-tetrahydroquinolin-4(1H)-one |
| JAG023 | 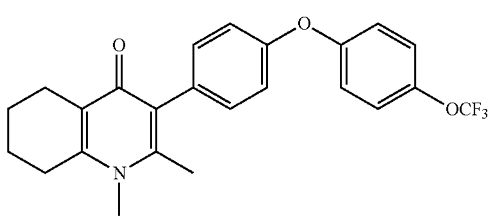 [SMILES: Cc1c(-c2ccc(Oc3ccc(OC(F)(F)F)cc3)cc2)c(=O)c2c(n1C)CCCC2] | 1,2-dimethyl-3-(4-(4-(trifluoromethoxy)phenoxy)phenyl)-5,6,7,8-tetrahydroquinolin-4-one |
| AS006/ JAG143 | 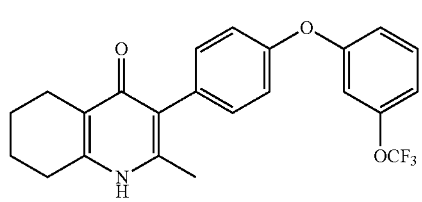 | 3-(4-(3,4-Dichlorophenoxy)phenyl)-2-methyl-5,6,7,8-tetrahydroquinolin-4(1H)-one |
| AS012/ JAG144 | 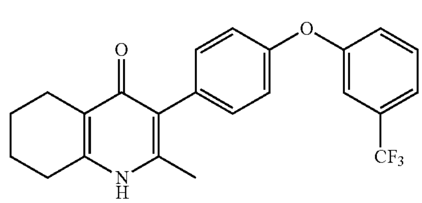 | 3-(4-(3,4-Dichlorophenoxy)phenyl)-2-methyl-5,6,7,8-tetrahydroquinolin-4(1H)-one |

-continued

| ID | Structure | Name |
|---|---|---|
| AS021/ JAG145 | 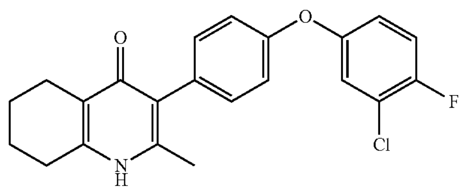 [SMILES: Cc1[nH]c2c(c(=O)c1-c1ccc(Oc3ccc(F)c(Cl)c3)cc1)CCCC2] | 3-[4-(3-chloro-4-fluorophenoxy)phenyl]-2-methyl-5,6,7,8-tetrahydro-1H-quinolin-4-one |
| AS034/ JAG148 | 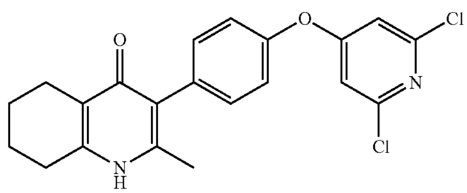 [SMILES: Cc1[nH]c2c(c(=O)c1-c1ccc(Oc3cc(Cl)nc(Cl)c3)cc1)CCCC2] | 3-{4-[(2,6-dichloropyridin-4-yl)oxy]phenyl}-2-methyl-5,6,7,8-tetrahydro-1H-quinolin-4-one |
| AS022 | 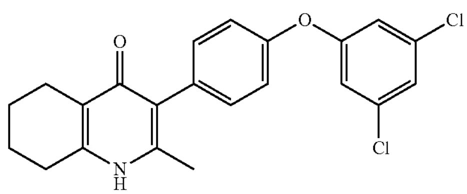 [SMILES: Cc1[nH]c2c(c(=O)c1-c1ccc(Oc3cc(Cl)cc(Cl)c3)cc1)CCCC2] | 3-[4-(3,5-dichlorophenoxy)phenyl]-2-methyl-5,6,7,8-tetrahydro-1H-quinolin-4(1H)-one |
| JAG084 | 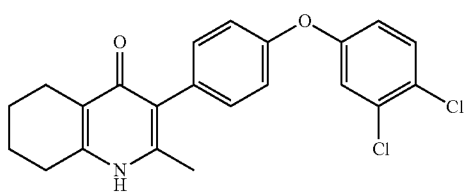 [SMILES: Cc1[nH]c2c(c(=O)c1-c1ccc(Oc3ccc(Cl)c(Cl)c3)cc1)CCCC2] | 3-(4-(3,4-Dichlorophenoxy)phenyl)-2-methyl-5,6,7,8-tetrahydroquinolin-4(1H)-one |
| JAG091 | 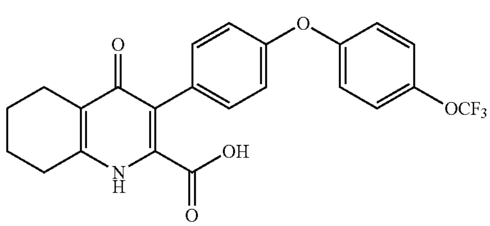 [SMILES: O=C(O)c1[nH]c2c(c(=O)c1-c1ccc(Oc3ccc(OC(F)(F)F)cc3)cc1)CCCC2] | 3(4-(4-Trifluoromethoxyphenoxy)phenyl)-2-(carboxylate)-5,6,7,8-tetrahydroquinolin-4(1H)-one |
| JAG092 | 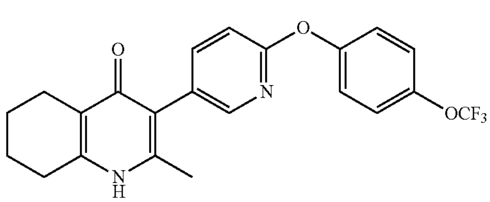 [SMILES: Cc1[nH]c2c(c(=O)c1-c1ccc(Oc3ccc(OC(F)(F)F)cc3)nc1)CCCC2] | 3-(6-(4-Trifluoromethoxyphenoxy)pyrdin-3-yl)-2-methyl-5,6,7,8-tetrahydroquinolin-(4)-one |
| JAG095 | 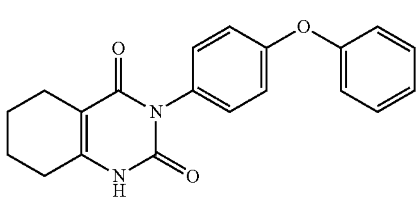 [SMILES: O=c1[nH]c2c(c(=O)n1-c1ccc(Oc3ccccc3)cc1)CCCC2] | 3-(4-Phenonxyphenyl)-1,2,3,4,5,6,7,8-octahydroquinazoline-2,4,dione |

-continued

| ID | Structure | Name |
|---|---|---|
| JAG099 | 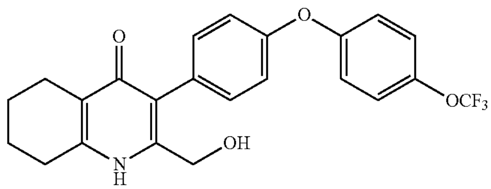 [SMILES: O=c1c2c([nH]c(CO)c1-c1ccc(Oc3ccc(OC(F)(F)F)cc3)cc1)CCCC2] | 3(4-(4-Trifluoromethoxyphenoxy)phenyl)-2-(methylhydroxy)-5,6,7,8-tetrahydroquinolin-4(1H)-one |
| AS032 | 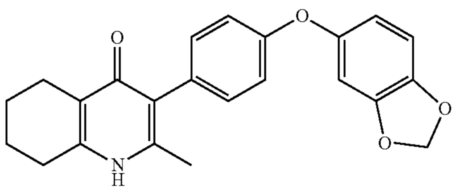 [SMILES: Cc1[nH]c2c(c(=O)c1-c1ccc(Oc3ccc4c(c3)OCO4)cc1)CCCC2] | 3-[4-(2H-1,3-benzodioxo1-5-yloxy)phenyl]-2-methyl-5,6,7,8-tetrahydro-1H-quinolin-4-one |
| JAG100 | 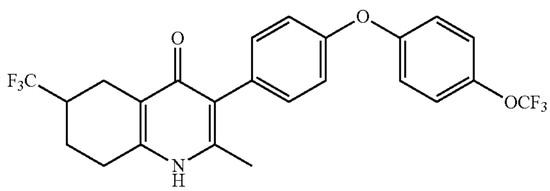 [SMILES: Cc1[nH]c2c(c(=O)c1-c1ccc(Oc3ccc(OC(F)(F)F)cc3)cc1)CC(C(F)(F)F)CC2] | 6-Ethyl-3-(4-(4-trifluoromethoxyphenoxy)phenyl)-2-methyl-5,6,7,8-tetrahydroquinolin-4(1H)-one |
| JAG106 | 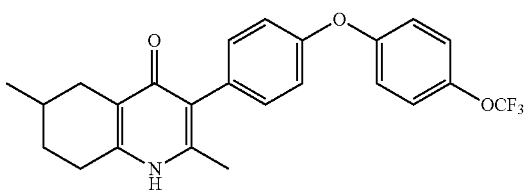 [SMILES: Cc1[nH]c2c(c(=O)c1-c1ccc(Oc3ccc(OC(F)(F)F)cc3)cc1)CC(C)CC2] | 3(4-(4-Trifluoromethoxyphenoxy)phenyl)-2,6-dimethyl-5,6,7,8-tetrahydroquinolin-4(1H)-one |
| JAG107 | 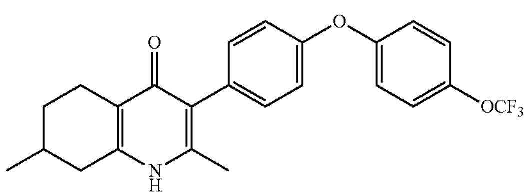 [SMILES: Cc1[nH]c2c(c(=O)c1-c1ccc(Oc3ccc(OC(F)(F)F)cc3)cc1)CCC(C)C2] | 3(4-(4-Trifluoromethoxyphenoxy)phenyl)-2,7-dimethyl-5,6,7,8-tetrahydroquinolin-4(1H)-one |
| JAG121 | 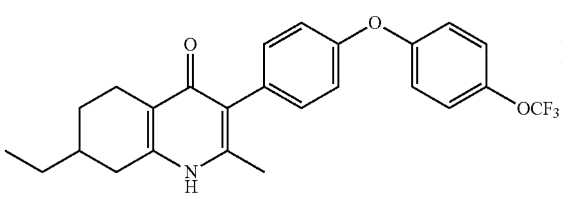 [SMILES: CCC1CCc2c([nH]c(C)c(-c3ccc(Oc4ccc(OC(F)(F)F)cc4)cc3)c2=O)C1] | 7-Ethyl-2-methyl-3(4-(4-trifluoromethoxyphenoxy)phenyl)-5,6,7,8-tetrahydroquinolin-4(1H)-one |
| JA129 | 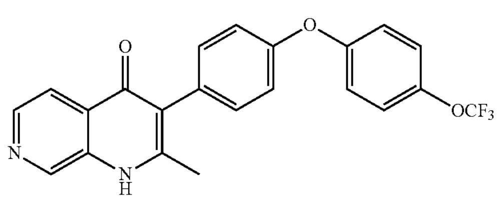 [SMILES: Cc1[nH]c2cnccc2c(=O)c1-c1ccc(Oc2ccc(OC(F)(F)F)cc2)cc1] | 3(4-(4-trifluoromethoxyphenoxy)phenyl)-2-methyl-1,7-napthyrid-4(1H)-one |
| JAG162 | | 7-Trifluromethyl-2-methyl-3(4-(4-trifluoromethoxyphenoxy)phenyl)-5,6,7,8-tetrahydroquinolin-4(1H)-one | or a stereoisomer thereof, or a pharmaceutically acceptable salt thereof.

In another aspect, the invention provides prodrugs of a compound of Formula (I). The term "prodrug" is intended to represent covalently bonded carriers, which are capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein an amino, hydroxy, carboxylic or a similar group is modified. Examples of prodrugs include, but are not limited to esters (e.g., acetate, formate, and benzoate), carbamates (e.g., N,N-dimethylaminocarbonyl), amides (e.g., trifluoroacetylamino, acetylamino, and the like), and the like. A complete discussion of prodrugs is found in Huttunen, K. M. and Rautio J. *Current Topics in Medicinal Chemistry*, 2011, 11, 2265-2287 and Stella, V. J. et al. (2007). *Prodrugs: Challenges and Awards Part 1*. New York: Springer. The disclosure of both references is herein incorporated by reference in its entirety.

In some embodiments, the prodrug of a compound of Formula (I) has the structure of Formula (I-p):

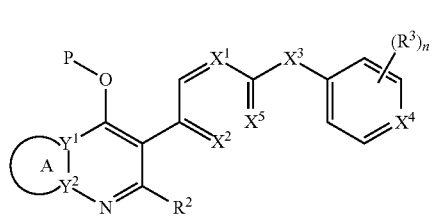

(I-p)

or a stereoisomer thereof, or a pharmaceutically acceptable salt thereof, wherein
ring A, $Y^1$, $Y^2$, $X^1$, $X^2$, $X^3$, $X^4$, $X^5$, R, $R^3$ and n are as described above;
R2 is hydrogen, $C_{1-3}$alkyl, $C_{1-3}$haloalkyl, —$CH_2OH$, —$CH_2OR$, —C(O)OR or —$CH_2OP$; and
P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (Ia-p):

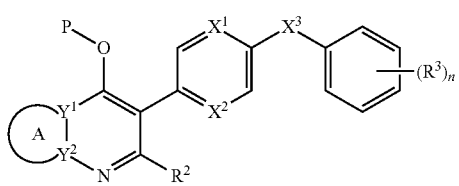

(Ia-p)

or a stereoisomer thereof, or a pharmaceutically acceptable salt thereof, wherein
ring A, $Y^1$, $Y^2$, $X^1$, $X^2$, $X^3$, R, $R^2$, $R^3$ and n are as described above;
$R^2$ is hydrogen, $C_{1-3}$alkyl, $C_{1-3}$haloalkyl, —$CH_2OH$, —$CH_2OR$, —C(O)OR or —$CH_2OP$; and P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (Ib-p):

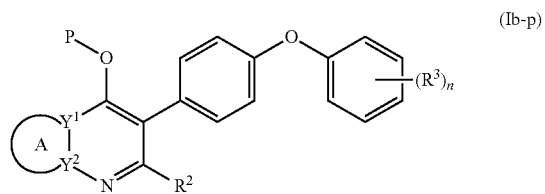

(Ib-p)

or a stereoisomer thereof, or a pharmaceutically acceptable salt thereof, wherein
ring A, $Y^1$, $Y^2$, R, $R^2$, $R^3$ and n are as described above;
$R^2$ is hydrogen, $C_{1-3}$alkyl, $C_{1-3}$haloalkyl, —$CH_2OH$, —$CH_2OR$, —C(O)OR or —$CH_2OP$; and
P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (Ic-p):

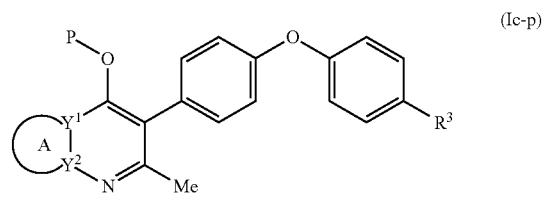

(Ic-p)

or a stereoisomer thereof, or a pharmaceutically acceptable salt thereof, wherein
ring A, $Y^1$, $Y^2$, R and $R^3$ are as described above; and
P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (II-p):

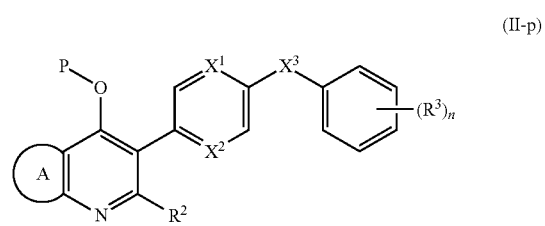

(II-p)

or a stereoisomer thereof, or a pharmaceutically acceptable salt thereof, wherein
ring A, $X^1$, $X^2$, $X^3$, R, $R^2$, $R^3$ and n are as described above;
$R^2$ is hydrogen, $C_{1-3}$alkyl, $C_{1-3}$haloalkyl, —$CH_2OH$, —$CH_2OR$, —C(O)OR or —$CH_2OP$; and
P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (IIa-p):

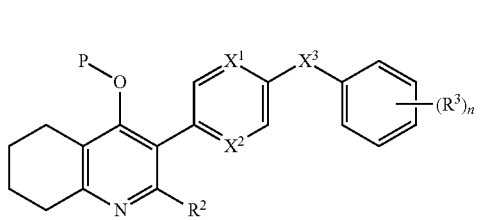

(IIa-p)

or a stereoisomer thereof, or a pharmaceutically acceptable salt thereof, wherein $X^1$, $X^2$, $X^3$, R, $R^2$, $R^3$ and n are as described above;

$R^2$ is hydrogen, $C_{1-3}$alkyl, $C_{1-3}$haloalkyl, —CH$_2$OH, —CH$_2$OR, —C(O)OR or —CH$_2$OP; and P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (IIa-1-p):

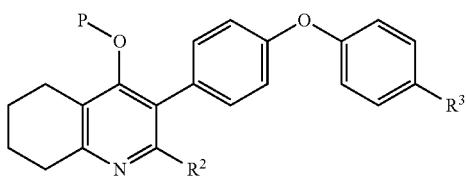

(IIa-1-p)

or a stereoisomer thereof, or a pharmaceutically acceptable salt thereof, wherein R, $R^2$, $R^3$ and n are as described above;

$R^2$ is hydrogen, $C_{1-3}$alkyl, $C_{1-3}$haloalkyl, —CH$_2$OH, —CH$_2$OR, —C(O)OR or —CH$_2$OP; and P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (IIa-2-p):

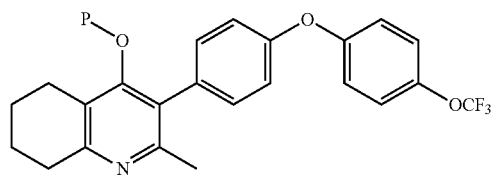

(IIa-2-p)

or a stereoisomer thereof, or a pharmaceutically acceptable salt thereof, wherein P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (IIa-3-p):

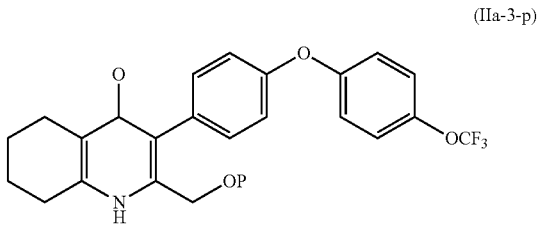

(IIa-3-p)

or a stereoisomer thereof, or a pharmaceutically acceptable salt thereof, wherein P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (III-p):

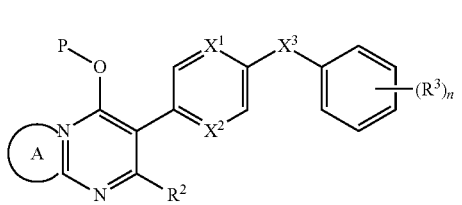

(III-p)

or a stereoisomer thereof, or a pharmaceutically acceptable salt thereof, wherein ring A, $X^1$, $X^2$, $X^3$, R, $R^2$, $R^3$ and n are as described above;

$R^2$ is hydrogen, $C_{1-3}$alkyl, $C_{1-3}$haloalkyl, —CH$_2$OH, —CH$_2$OR, —C(O)OR or —CH$_2$OP; and P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (IIIa-p):

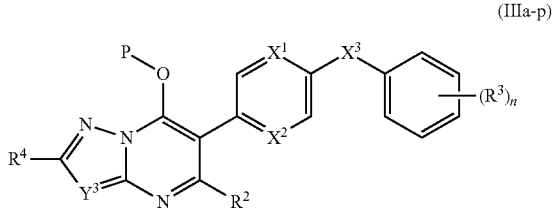

(IIIa-p)

or a stereoisomer thereof, or a pharmaceutically acceptable salt thereof, wherein $Y^3$, X, $X^2$, $X^3$, R, $R^2$, $R^3$, $R^4$ and n are as described above;

$R^2$ is hydrogen, $C_{1-3}$alkyl, $C_{1-3}$haloalkyl, —CH$_2$OH, —CH$_2$OR, —C(O)OR or —CH$_2$OP; and P is —C(O)OR', —C(O)R', —C(O)NR'$_2$ or —OP(O)(OR')OR', wherein each R' is independently hydrogen or $C_{1-3}$alkyl.

In some embodiments, the prodrug is a compound of Formula (IIIb-p):

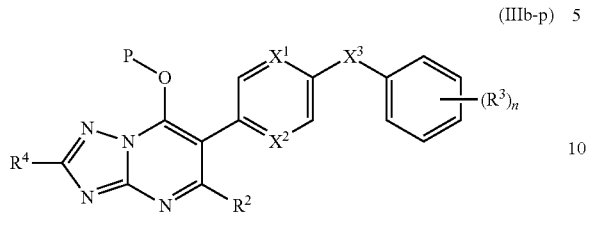

(IIIb-p)

or a stereoisomer thereof, or a pharmaceutically acceptable salt thereof, wherein
X¹, X², X³, R, R², R³, R⁴ and n are as described above;
R² is hydrogen, C₁₋₃alkyl, C₁₋₃haloalkyl, —CH₂OH, —CH₂OR, —C(O)OR or —CH₂OP; and
P is —C(O)OR', —C(O)R', —C(O)NR'₂ or —OP(O)(OR')OR', wherein each R' is independently hydrogen or C₁₋₃alkyl.

In some embodiments, the prodrug is a compound of Formula (IIIb-1-p):

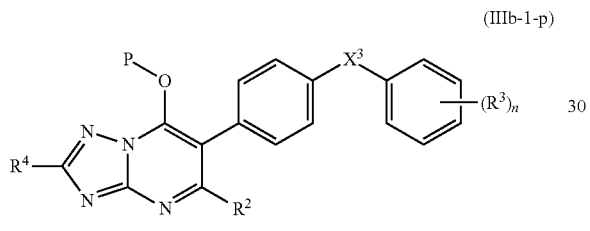

(IIIb-1-p)

or a stereoisomer thereof, or a pharmaceutically acceptable salt thereof, wherein
X³, R, R², R³, R⁴ and n are as described above;
R² is hydrogen, C₁₋₃alkyl, C₁₋₃haloalkyl, —CH₂OH, —CH₂OR, —C(O)OR or —CH₂OP; and
P is —C(O)OR', —C(O)R', —C(O)NR'₂ or —OP(O)(OR')OR', wherein each R' is independently hydrogen or C₁₋₃alkyl.

In some embodiments, the prodrug is a compound of Formula (IIIc-p):

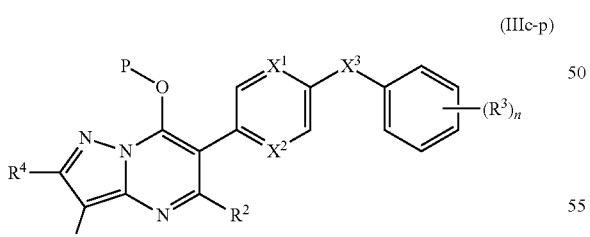

(IIIc-p)

or a stereoisomer thereof, or a pharmaceutically acceptable salt thereof, wherein
X¹, X², X³, R, R², R³, R⁴, R⁵ and n are as described above;
R² is hydrogen, C₁₋₃alkyl, C₁₋₃haloalkyl, —CH₂OH, —CH₂OR, —C(O)OR or —CH₂OP; and
P is —C(O)OR', —C(O)R', —C(O)NR'₂ or —OP(O)(OR')OR', wherein each R' is independently hydrogen or C₁₋₃alkyl.

In some embodiments, the prodrug is a compound of Formula (IIIc-1-p):

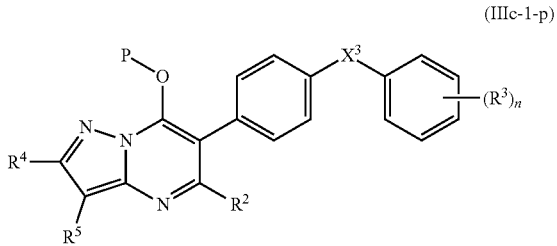

(IIIc-1-p)

or a stereoisomer thereof, or a pharmaceutically acceptable salt thereof, wherein
X³, R, R², R³, R⁴, R⁵ and n are as described above;
R² is hydrogen, C₁₋₃alkyl, C₁₋₃haloalkyl, —CH₂OH, —CH₂OR, —C(O)OR or —CH₂OP; and
P is —C(O)OR', —C(O)R', —C(O)NR'₂ or —OP(O)(OR')OR', wherein each R' is independently hydrogen or C₁₋₃alkyl.

In some embodiments, the prodrug is a compound of Formula (IV-p):

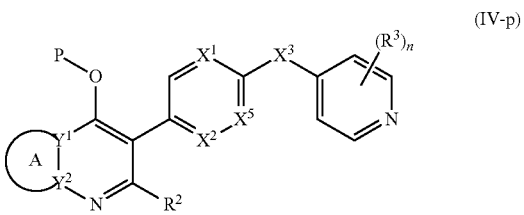

(IV-p)

or a stereoisomer thereof, or a pharmaceutically acceptable salt thereof, wherein
ring A, Y¹, Y², X¹, X², X³, X⁵, R, R², R³ and n are as described above;
R² is hydrogen, C₁₋₃alkyl, C₁₋₃haloalkyl, —CH₂OH, —CH₂OR, —C(O)OR or —CH₂OP; and
P is —C(O)OR', —C(O)R', —C(O)NR'₂ or —OP(O)(OR')OR', wherein each R' is independently hydrogen or C₁₋₃alkyl.

In some embodiments, the prodrug is a compound of Formula (IVa-p):

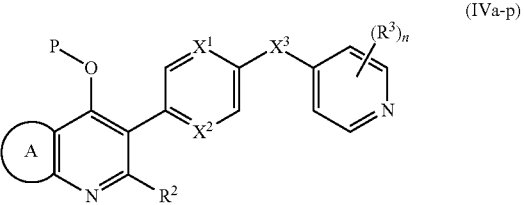

(IVa-p)

or a stereoisomer thereof, or a pharmaceutically acceptable salt thereof, wherein
ring A, X¹, X², R, R², R³ and n are as described above;
R² is hydrogen, C₁₋₃alkyl, C₁₋₃haloalkyl, —CH₂OH, —CH₂OR, —C(O)OR or —CH₂OP; and
P is —C(O)OR', —C(O)R', —C(O)NR'₂ or —OP(O)(OR')OR', wherein each R' is independently hydrogen or C₁₋₃alkyl.

In some embodiments, the prodrug is a compound of Formula (IVb-p)

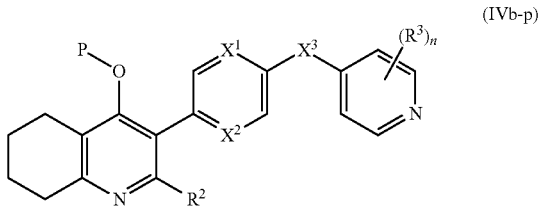

(IVb-p)

or a stereoisomer thereof, or a pharmaceutically acceptable salt thereof, wherein $X^1$, $X^2$, $X^3$, R, $R^2$, $R^3$ and n are as described above;

$R^2$ is hydrogen, $C_{1-3}$alkyl, $C_{1-3}$haloalkyl, —CH$_2$OH, —CH$_2$OR, —C(O)OR or —CH$_2$OP; and P is —C(O)OR', —C(O)R', —C(O)NR'$_2$ or —OP(O)(OR')OR', wherein each R' is independently hydrogen or $C_{1-3}$alkyl.

In some embodiments, the compound is of any of Formulae (I-p), (Ia-p), (Ib-p), (Ic-p), (II-p), (Ia-p), (IIa-1-p), (IIa-2-p), (IIa-3-p), (III-p), (IIIa-p), (IIIb-p), (IIIb-1-p), (IIIc-p), (IIIc-1-p), (IV-p), (Iva-p) or (IVb-p), and $X^1$, $X^2$, $X^3$, $R^1$, $R^2$, $R^3$ and n are selected from any combination of groups (1a)-(8l).

In some embodiments, the compound is of Formulae (I-p), (Ia-p), (Ib-p), (Ic-p), (II-p), (Ia-p), (IIa-1-p), (IIa-2-p), (IIa-3-p), (III-p), (IIIa-p), (IIIb-p), (IIIb-1-p), (IIIc-p), (IIIc-1-p), (IV-p), (Iva-p) or (IVb-p), $X^1$, $X^2$, $X^3$, $R^1$, $R^2$, $R^3$ and n are selected from any combination of groups (1a)-(8l), and P is —C(O)$_2$R'.

In some embodiments, the compound is of Formulae (I-p), (Ia-p), (Ib-p), (Ic-p), (II-p), (Ia-p), (IIa-1-p), (IIa-2-p), (IIa-3-p), (III-p), (IIIa-p), (IIIb-p), (IIIb-1-p), (IIIc-p), (IIIc-1-p), (IV-p), (Iva-p) or (IVb-p), $X^1$, $X^2$, $X^3$, $R^1$, $R^2$, $R^3$ and n are selected from any combination of groups (1a)-(8l), and P is —C(O)R'.

In some embodiments, the compound is of Formulae (I-p), (Ia-p), (Ib-p), (Ic-p), (II-p), (Ia-p), (IIa-1-p), (IIa-2-p), (IIa-3-p), (III-p), (IIIa-p), (IIIb-p), (IIIb-1-p), (IIIc-p), (IIIc-1-p), (IV-p), (Iva-p) or (IVb-p), $X^1$, $X^2$, $X^3$, $R^1$, $R^2$, $R^3$ and n are selected from any combination of groups (1a)-(8l), and P is —C(O)NR'$_2$.

In some embodiments, the compound is of Formulae (I-p), (Ia-p), (Ib-p), (Ic-p), (II-p), (Ia-p), (IIa-1-p), (IIa-2-p), (IIa-3-p), (III-p), (IIIa-p), (IIIb-p), (IIIb-1-p), (IIIc-p), (IIIc-1-p), (IV-p), (Iva-p) or (IVb-p), $X^1$, $X^2$, $X^3$, $R^1$, $R^2$, $R^3$ and n are selected from any combination of groups (1a)-(8l), and P is —OP(O)(OR')OR'.

In another aspect, the invention provides a pharmaceutical composition comprising a compound of Formula (I-p) and a pharmaceutically acceptable diluent, excipient, or carrier.

In some embodiments, the pharmaceutical composition is a combination comprising a compound of Formula (I), an 8-Aminoquinoline drug and a pharmaceutically acceptable diluent, excipient, or carrier.

In some embodiments, the pharmaceutical composition is a combination comprising a compound of Formula (I), tafenoquine and a pharmaceutically acceptable diluent, excipient, or carrier.

In some embodiments, the pharmaceutical composition is a combination comprising a compound of Formula (I-p), an 8-Aminoquinoline drug and a pharmaceutically acceptable diluent, excipient, or carrier.

In some embodiments, the pharmaceutical composition is a combination comprising a compound of Formula (I-p), tafenoquine and a pharmaceutically acceptable diluent, excipient, or carrier.

In another aspect, the invention provides a pharmaceutical composition comprising a compound of claim Formula (I) and a pharmaceutically acceptable diluent, excipient, or carrier. In another aspect, the invention provides a method for treating an apicomplexan parasitic infection, comprising administering to a subject (such as a human subject) in need thereof an amount effective to treat the infection of the compound of Formula (I) or a pharmaceutical composition comprising a compound of Formula (I). In some embodiments of the method, the infection comprises a *Toxoplasma gondii* infection and/or a *Plasmodium falciparum* infection. In some embodiments of the method, the infection comprises an infection in the subject's brain and/or the subject's eye. In some embodiments of the method, the compound is a prodrug of Formula (I-p).

In another aspect, the invention provides a method for treating an apicomplexan parasitic infection, comprising administering to a subject (such as a human subject) in need thereof an amount effective to treat the infection of a combination comprising a compound of Formula (I) and a 8-Aminoquinoline drug or a pharmaceutical composition comprising a compound of Formula (I) and a 8-Aminoquinoline drug. In some embodiments of the method, the infection comprises a *Toxoplasma gondii* infection and/or a *Plasmodium falciparum* infection. In some embodiments of the method, the infection comprises an infection in the subject's brain and/or the subject's eye. In some embodiments of the method, the compound is a prodrug of Formula (I-p). In some embodiments of the method, the 8-Aminoquinoline drug is tafenoquine.

In some embodiments of the method, the subject is immune compromised. In some embodiments of the method, the subject is immune compromised due to cancer/cancer treatment, autoimmune disease, and/or AIDS. In some embodiments of the method, the subject has malaria, and the treating comprises reducing severity of one or more symptoms of malaria, and/or reducing recurrence of symptoms of malaria. In some embodiments of the method, the subject has toxoplasmosis, and the treating comprises reducing severity of one or more symptoms of toxoplasmosis, and/or reducing recurrence of symptoms of toxoplasmosis. In some embodiments of the method, the treating comprises reducing parasitic load in the subject. In some embodiments of the method, the treating comprises reducing the bradyzoite form and/or the tachyzoite form of the parasite in the subject. In some embodiments of the method, the method further comprises administering to the subject one or more additional compounds in an amount effective to treat the infection. In some embodiments of the method, the one or more additional compounds are selected from the group consisting of pyrimethamine, sulfadiazine, cycloguanil, inhibitors of kcalcium kinases or dense granules or vacuolar atpases, atovoquone, and bulky cytochrome Qi inhibitors, itraconazole and other inhibitors of *T. gondii*.

In another aspect, the invention provides a method for monitoring treatment of an apicomplexan parasitic infection (including but not limited to any of the treatments of claims 23-33), comprising monitoring expression, protein in serum or plasma, and/or activity of 1, 2, 3, 4, 5, 6, 7, 8, 9, 10, or all of the markers listed in Table and figures in Example 8/FIGS. 3A-3B in the Appendix in a subject (such as a human subject) being treated for an apicomplexan parasitic infection, wherein a decrease or increase in expression and/or presence and/or activity of the one or more markers indicates that the treatment is effective.

In some embodiments of the method, the infection is a *T. gondii* infection. In some embodiments of the method, the infection is in the subject's brain or other neurologic tissue.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, alkyl, alkyl-, and -alkyl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The terms "cyano" and "nitrile" as used herein refers to a —CN group. "Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "hydroxy" as used herein, means an —OH group.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a parasite with a compound includes the administration of a compound described herein to an individual or patient, such as a human, infected with the parasite, as well as, for example, introducing a compound into a sample containing a cellular or purified preparation containing the parasite.

In another aspect, the invention provides methods for monitoring *T. gondii* infection in a subject, comprising monitoring levels in a blood sample from the subject of one or more markers selected from the group consisting of clusterin, oxytocin, PGLYRP2 (N-acetylmuramoyl-L-alanine amidase), Apolipoprotein A1 (apoA1), miR-17-92, and miR-124, wherein a change in levels of the one or more circulating markers compared to control correlates with *T. gondii* infection in the subject. The inventors have discovered these specific markers of active *T. gondii* infection, as described in the examples that follow.

The blood sample can be whole blood, serum, blood plasma, or any other suitable blood sample in which circulating IgG from a person with toxoplasmosis may be present. For example, the blood sample may be a plasma sample. As used herein, a "plasma sample" means blood plasma, the liquid component of blood, and is prepared, for example, by centrifugation of whole blood to remove blood cells. As used herein, a plasma sample also includes a blood serum sample, in which blood clotting factors have been removed.

Any suitable control can be used, including but not limited to a reference value obtained from one or more subjects that either do not have a *T. gondii* infection, or that are known to have a *T. gondii* infection, a previous blood sample obtained from the same subject, or any other suitable control. It is well within the level of those of skill in the art to determine an appropriate control for an intended use in light of the teachings herein. The change in level from control that correlates with *T. gondii* infection in the subject may be a difference of 10%, 25%, 50%, 100%, or more. In one embodiment, the difference is a statistically significant increase as judged by standard statistical analysis.

The level (e.g., quantity or amount) of a particular biomarker can be measured in the blood sample using a variety of methods known to those of skill in the art. Such methods include, but are not limited to, flow cytometry, ELISA using red blood cell, platelet, or white blood cell lysates (e.g., lymphocyte lysates), and radioimmunoassay.

In one embodiment, the method is used to monitor effect on the subject of a therapy for *T. gondii* infection. In this embodiment, the subject is receiving therapy for a *T. gondii* infection, and the methods permit attending medical personnel to assess efficacy of the therapy. In this embodiment, the blood sample test may, for example, be carried out periodically over time during the course of therapy. In another embodiment, the method is used to diagnose whether the subject is suffering from a *T. gondii* infection. In this embodiment, the subject is suspected of suffering from a *T. gondii* infection based on the presence of one or more symptoms, and the methods can be used to assist in providing a more definitive diagnostic, along with all other factors to be considered by an attending physician.

In various embodiments of these methods:
(a) an increase in level of one or more of clusterin, oxytocin, miR-17-92, or miR-124 compared to control correlates with active *T. gondii* infection; and/or
(b) a decrease in level of one or more of PGLYRP2 or ApoA1 compared to control correlates with active *T. gondii* infection.

In further embodiments of these methods:
(a) a decrease in level of one or more of clusterin, oxytocin, miR-17-92, or miR-124 compared to a level of the one or more markers in a serum sample obtained from the subject at an earlier time point correlates with a positive effect of the therapy in treating active *T. gondii* infection; and/or
(b) an increase in level of one or more of PGLYRP2 or ApoA1 compared to a level of the one or more markers in a serum sample obtained from the subject at an earlier time point correlates with a positive effect of the therapy in treating correlates with active *T. gondii* infection.

In one embodiment, the *T. gondii* infection involves neuronal damage and/or retinal damage in the subject. For example, the *T. gondii* infection may involve neuronal damage selected from the group consisting of neurodegeneration and/or seizures.

In another aspect, the invention provides methods for treating a *T. gondii* infection, comprising administering to a subject with a *T. gondii* infection an amount effective to treat the infection of ApoA1. As shown in the examples that follow, a reduction in apoA1 closely correlates with active *T. gondii* infection. The apoA1 may be administered as a protein therapeutic, or may be administered in an expression construct (such as a recombinant viral vector, etc.) that expresses apoA1 (i.e.: gene therapy).

In one embodiment, the subject to be treated has a decreased level of serum ApoA1 compared to control.

```
UniProtKB-P02647 (APOA1_HUMAN)
                                        (SEQ ID NO: 4)
MKAAVLTLAV LFLTGSQARH FWQQDEPPQS PWDRVKDLAT

VYVDVLKDSG RDYVSQFEGS ALGKQLNLKL LDNWDSVTST

FSKLREQLGP VTQEFWDNLE KETEGLRQEM SKDLEEVKAK

VQPYLDDFQK KWQEEMELYR QKVEPLRAEL QEGARQKLHE

LQEKLSPLGE EMRDRARAHV DALRTHLAPY SDELRQRLAA

RLEALKENGG ARLAEYHAKA TEHLSTLSEK AKPALEDLRQ

GLLPVLESFK VSFLSALEEY TKKLNTQ.
```

As used herein, the term "individual" or "patient," or "subject" used interchangeably, refers to any animal, including mammals, preferably mice, rats, other rodents, rabbits, dogs, cats, swine, cattle, sheep, horses, or primates, and most preferably humans.

As used herein, the phrase "amount effective", "therapeutically effective amount" or "effective to treat" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease;
  (2) inhibiting the disease; for example, inhibiting a disease, condition or disorder in an individual who is experiencing or displaying the pathology or symptomatology of the disease, condition or disorder; or
  (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., reducing parasitic loador adverse effects the parasite is causing in the human it infects).

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluene-sulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Example 1. New Paradigms for Understanding and Step Changes in Treating Active and Chronic, Persistent Apicomplexan Infections Abstract

*Toxoplasma gondii*, the most common parasitic infection of human brain and eye, persists across lifetimes, can progressively damage sight, and is currently incurable. New, curative medicines are needed urgently. Herein, we develop novel models to facilitate drug development: EGS strain *T. gondii* forms cysts in vitro that induce oocysts in cats, the gold standard criterion for cysts. These cysts highly express cytochrome b. Using these models, we envisioned, and then created, novel 4-(1H)-quinolone scaffolds that target the cytochrome $bc_1$ complex $Q_i$ site, of which, a substituted 5,6,7,8-tetrahydroquinolin-4-one inhibits active infection ($IC_{50}$, 30 nM) and cysts ($IC_{50}$, 4 µM) in vitro, and in vivo (25 mg/kg), and drug resistant *Plasmodium falciparum*: (IC50, <30 nM), with clinically relevant synergy. Mutant yeast and co-crystallographic studies demonstrate binding to the $bc_1$ complex $Q_i$ site. Our results have direct impact on improving outcomes for those with toxoplasmosis, malaria, and ~2 billion persons chronically infected with encysted bradyzoites.

*Toxoplasma gondii* infections can cause systemic symptoms, damage and destroy tissues[1-1], especially eye and brain[1-10] and cause fatalities[S1-20] Primary infections may be asymptomatic, or cause fever, headache, malaise, lymph-adenopathy, and rarely meningoencephalitis, myocarditis, or pericarditis[9,11,12]. Retinochoroiditis and retinal scars develop in up to 30% of infected persons[1,7,13] and epilepsy may occur[6,14] In immune-compromised and congenitally infected persons, active infection frequently is harmful[1-10]. Recrudescence arises from incurable, dormant cysts throughout life[6,7,9,10] In rodents, chronic infection alters fear, smell, reward pathways, neurotransmitters such as GABA and dopamine, and causes abnormal neurologic functions[15]. Although this parasite is present in the brains of 2-3 billion persons worldwide, consequences are unknown. Neurobehavioral abnormalities and differences in serum cytokines, chemokines, and growth factors were associated with seropositivity in humans[16, 17].

Current treatments against active *T. gondii* tachyzoites can have side effects such as hypersensitivity, kidney stones, and bone marrow suppression, limiting their use[10]. Latent bradyzoites are not significantly affected by any medicines[6]. Atovaquone partially, and transiently, limits cyst burden in mice[18], but resistance develops with clinical use[19]-2[4]. Thus, *T. gondii* infection is incurable with recrudescence from latent parasites posing a continual threat. Estimates of costs for available, suboptimal medicines to treat active, primary ocular, gestational and congenital infections, in just the U.S. and Brazil, exceed $5 billion per year. Improved medicines are needed urgently. Molecular targets shared by *T. gondii* and Plasmodia make re-purposing compounds a productive strategy.

Critical flaws and limitations of available methods and models for developing medicines to cure *T. gondii* infections include lack of in vitro culture systems for cysts and scalable, easy to use animal models for screening compounds. To address these challenges, we characterized the EGS parasite, isolated in 1994 from amniotic fluid of a congenitally infected Brazilian fetus[24a], that form cyst-like structures in vitro[25]. In our characterization of EGS in vitro, herein, we discovered that true cysts develop, making EGS especially useful for drug development. EGS parasites can infect zebrafish, and we have characterized this, as well as a fluorescent tachyzoite and cyst assay in this new model[26]. Further, cytochrome $bc_1$ expression is markedly increased in encysted EGS bradyzoites suggesting cytochrome $bc_1$ might be a viable drug target for this life stage. This mitochondrial membrane bound protein complex cytochome $bc_1$, part of the electron transport chain responsible for generating ubiquinone for pyrimidine biosynthesis in *Plasmodium*, is the molecular target of the naphthoquinone, atovaquone[27-52]. Partial efficacy, rapid emergence of drug resistance in malaria and toxoplasmosis limit clinical usefulness of atovaquone. We present new 4-(1H)-quinolone scaffolds that target the $Q_i$ site of cytochrome bc1 in apicomplexan parasites. Our lead 5,6,7,8-tetrahydroquinolin-4-one compound, MJM170, is highly effective against apicomplexan parasites and has substantially enhanced solubility compared with other reported quinolones due to its' new scaffold. Direct visualisation in the crystallographic structure opens the way to design a new generation of compounds for both parasites.

Results

Characterization of EGS Strain Develops Novel In Vitro Models to Test Compounds.

Genotyping and Phylogenetic Analysis of EGS: We isolated and sequenced genomic DNA from the EGS[25] (25) parasite, which formed cysts when grown in human foreskin fibroblasts (HFF) in culture. Phylogenetic analysis based on 796,168 SNPs across 62 *T. gondii* genomes revealed that EGS is closely related to other Brazilian strains including TgCatBr1, TgCatBr18 and TgCatBr25 and ancient South American MAS. All these grouped to clade B, haplogroup 4 and 8. Full genome sequence analysis of EGS compared with canonical and geographically closely related parasite genomic sequences reveal a non-synonymous mutation and disordered c terminal sequence in Apetela 2 (AP2) IV-iv, a bradyzoite repressor. EGS differs from other isolates by non-synonymous SNPs in Apetela 2 IV-iv, M=>I (570) and a disordered area beginning at 821, GGNRPHYH-VAKQEWRVRYYMNGKRKMRTYSAKFY GYETAHT-MAEDFAHYVDKHE (SEQ ID NO: 1). AP2 IV-iv is a member of the plant-like transcription factor family unique to apicomplexan parasites. This AP2 represses tachyzoite to bradyyzoite conversion,[56] among other differences. Because AP2 IV-iv is a bradyzoite gene expression repressor[56], a mutation could create a parasite like EGS that remains as an encysted bradyzoite.

Phenotypes of EGS in Human cells in vitro, and in Cats and Mice:

EGS in human foreskin fibroblasts (HFF). In vitro, these EGS parasites form cysts that enlarge over ~48-96 hours and then destroy monolayers as single cell organisms. This created novel, useful in vitro models. Cyst walls are thick in electron micrographs (data not shown). Cyst-like structures' perimeters demonstrate dolichos, with bradyzoites within them staining with BAG1 and nuclei with Dapi. Kinetic analysis of EGS in HFF cultures, 2, 18, and 72 hours after infection, RNA-seq and MiR-seq results demonstrated varied expression signatures over time in culture with expression of bradyzoite markers by 18 hours and Apetela 2 signatures by 2 hours.

Cats fed EGS in HFF cultures or mouse brain produce oocysts. When HFF tissue cultures with these cyst structures were fed to cats, they developed the classic, gold standard bradyzoite phenotype of producing oocysts in two replicate experiments. All other T. gondii strains cultured for more than 30 passages, as EGS was since the 1990s, lose the ability to produce oocysts when fed to cats (JP Dubey, personal observations). This experiment established that these were true bradyzoites in cysts formed in vitro under standard culture conditions. Oocysts also formed 10 days after feeding cats mouse brains infected with EGS stably transfected with tachyzoite SAG1 promoter-driven mcherry, and bradyzoite BAG1 promoter-driven green fluorescent protein (GFP), and merozoite promoter-driven blue fluorescent protein, engineered to facilitate creation of automated, scalable in vitro and in vivo assays. In vitro, these promoters did not provide a fluorescence signal robust enough to detect differences between 2×10[5] and 650 parasites useful in scalable assays (data not shown).

EGS is virulent in Mice. When these EGS oocysts were fed to mice they produced disease indistinguishable from other virulent Brazilian strains. Oocysts given to mice per-orally created an illness and histopathology phenotypically characteristic for typical, virulent parasites causing dose related proliferation of T. gondii with necrosis in terminal ileum, pneumonia at 9-10 days, with brain parasites by 17 days and dose-related mortality.

EGS has a bradyzoite/cyst morphology and alters the transcriptomes of the biologically relevant human monocytic cell line MM6 and human primary neuronal stem cells (NSC). Human cells particularly relevant to human toxoplasmosis were infected with different strains of T. gondii to better characterize EGS parasites. Immunofluorescence staining of EGS-infected MM6 and NSC cultures revealed the development of cysts (FIG. 1A) and accordingly, EGS gene expression resembled that of bradyzoites when compared to equivalent infections done with GT1, ME49 or VEG strains. Interestingly, EGS transcription was influenced by host cell type (FIGS. 1A-1D). Transcriptomics using host mRNA and miR profiling of EGS cultures in MM6, and NSC cells for 18 hours demonstrated that this parasite modulates host transcripts involved in protein misfolding, neurodegeneration, endoplasmic reticulum stress, spliceosome alteration, ribosome biogenesis, cell cycle, epilepsy, and brain cancer among others (FIGS. 1A-1D). The number of genes significantly up or down regulated in MM6 and NSC cells compared to uninfected controls are depicted in FIGS. 1A-1D. Overexpressed genes differ from those of GT1, ME49 and VEG tachyzoite-infected human NSC cells (FIG. 2A), but modify the same or connected pathways (McLeod et al, unpublished observations). Hsa-miR-708-5p was the most affected miRNA (down-modulated) by EGS (FIG. 1D). miR-708-5p is a regulator that promotes apoptosis in neuronal and retinal cells, which could maintain a niche for EGS-like encysted bradyzoites to persist.

EGS transcripts demonstrate importance of cytochromes and key Apetela 2 transcription factors in this life cycle stage. EGS transcripts in HHF, MM6, and NSC cells were enriched for genes transcribed in bradyzoites, including known bradyzoite transcripts, certain Apetela 2s and cytochrome b and other cytochromes. Among transcripts with the most increased fold change in EGS across all three cell lines were: cytochrome b; cytochrome c oxidase subunit III subfamily protein; apocytochrome b; cytochrome b, putative; and cytochrome b (N-terminal)/b6/petB subfamily protein. Other over-expressed genes include bradyzoite transcription factor AP2IX-9 and plant-like heat-shock protein BAG1 (FIG. 2A).

Identifying Novel and Efficacious Compounds Against T. gondii Cytochrome $Bc_1$, Increased expression of cytochromes in EGS made it pertinent to synthesize and test an endochin-like quinolone (ELQ) 271, which was previously reported to inhibit T. gondii cytochrome $bc_1$ $Q_i$ site and reduce, but not eliminate, brain cyst numbers in mice[27]. ELQ271 also inhibited EGS in vitro (FIG. 2B bottom) demonstrating that our in vitro model correlates with previously reported partial activity of ELQ271 against bradyzoites in cysts in mouse brain. Vivoporter-PMOs inhibiting cytochrome $bc_1$ had a modest effect on tachyzoite replication and a small effect on size and number of EGS cysts (FIG. 2B top). Minimal effect might be related to limited entry of vivoporter into cysts or mitochondria.

ELQs have been a focus for drug development for malaria (ELQ 300) and toxoplasmosis (ELQ 271 and 316) as they were reported to be potent and selective (versus human cytochrome $bc_1$) inhibitors of P. falciparum cytochrome $bc_1$ at nanomolar concentrations[27]. ELQs are part of the 4-(1H)-quinolone class of cytochrome $bc_1$ inhibitor[36,42,40,45,49,52,53,54,56-62] and (Dogget et al, 13th International Toxoplasmosis Meeting Abstract. Gettysburg Pennsylvania, June 2015), a scaffold that suffers from limited aqueous solubility. Another aspect of inhibitor design for this system is minimizing the inhibition of mammalian cytochrome $bc_1$, which shares ~40% sequence identity to the T. gondii ortholog within the Q substrate sites. Thus, we set out to design potent and selective inhibitors of T. gondii cytochrome $bc_1$ with improved solubility (FIGS. 3A and 3B) compared to known quinolone-based inhibitors. Noting the previous work of GSK on the preclinical development of Clopidol derivatives which led to terminating studies secondary to toxicity in the rat models, as another serious deficiency[63] and the incorporation of the diphenyl ether group onto the central 4-(1H)-quinolone core as reported by Riscoe et al.[27], we focused on the central core ring system. Doggett, Riscoe et al's[27] ELQ 271 (FIGS. 3A and 3B) was reported to be ineffective against yeast with a mutation in the $Q_i$ site. Nonetheless, it recently was shown that ELQs can bind both $Q_i$ and $Q_o$ depending on subtle chemical changes[61-3]. As a result of our initial efforts, a 5,6,7,8-tetrahydroquinolone (MJM170, 2) displayed promising results. (FIGS. 3A and 3B; Table 2). We chose ELQ271 for comparison because it had the greatest activity at the lowest dose (5 mg/kg) in the mouse model of Doggett despite the higher cytotoxicity toward human fibroblasts in the in vitro toxicity studies.[27]

MJM170 is a potent inhibitor of *T. gondii* tachyzoites (RH—YFP strain, $IC_{50}$ 0.03 μM) and bradyzoites (EGS strain, $IC_{50}$ 4 μM), equipotent to ELQ271 (Table 2, FIG. 4A-4E). MJM170 showed 10-fold improved aqueous kinetic solubility (pH 7.4) over ELQ 271 (Table 2), 3-fold improved FaSSIF/FeSSIF (pH 6.5) solubility, with similar human microsomal stability profiles (146 vs 172 minutes). A different method from that in reference[49] was used. MJM170 has a significantly decreased mouse microsomal stability compared to ELQ 271 (20 vs>200 minutes). MJM170 was further evaluated with MDCK-MDR1 cells (a measure of blood-brain barrier permeability) and results suggest that MJM170 could cross the blood brain barrier and not suffer from P-glycoprotein efflux These data highlight the potential of the 5,6,7,8-tetrahydroquinolin-4-one scaffold for further hit-to-lead development.

Figure 5A:
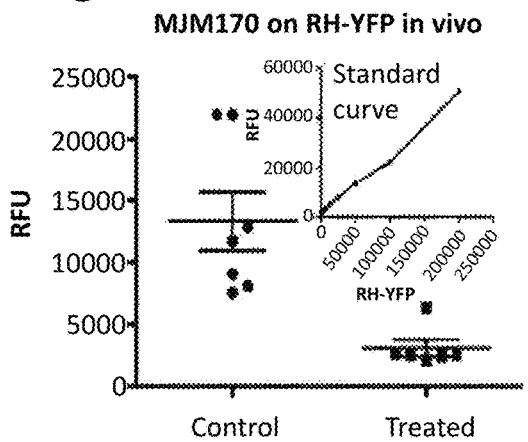
FIG. 5A-5D. MJM170 is also effective against RH and Prugneaud tachyzoites and Me49 bradyzoites, in vivo with translucent zebrafish providing a novel model with potential for scalable in vivo assays in which tachyzoites with fluorescent reporters and bradyzoites in cysts can be visualized efficiently.
Figure 5B:
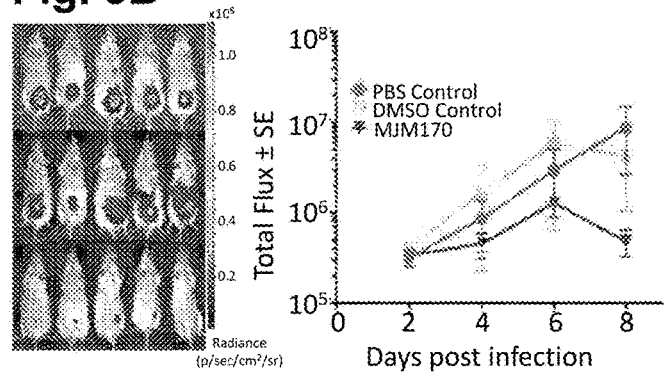
Figure 5C:
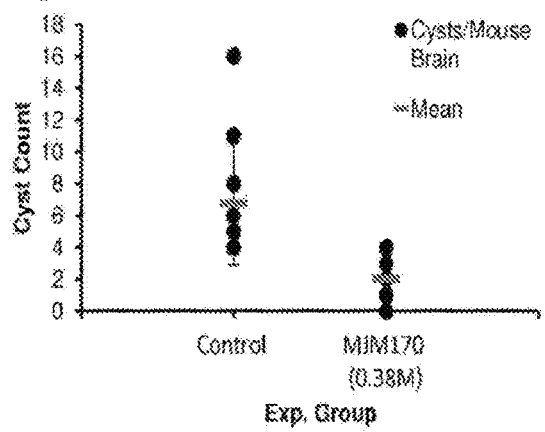
Figure 5D:
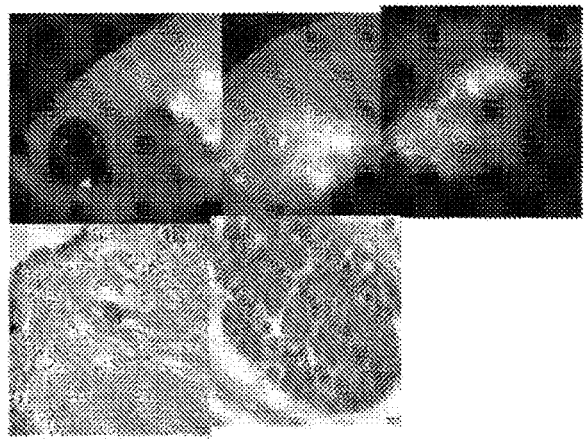

(data not shown). Translucent zebra fish can be infected with EGS, other *T. gondii* that make cysts, and RH YFP preparing for a novel model for scalable screening (FIG. 5D).

Figure 6A:
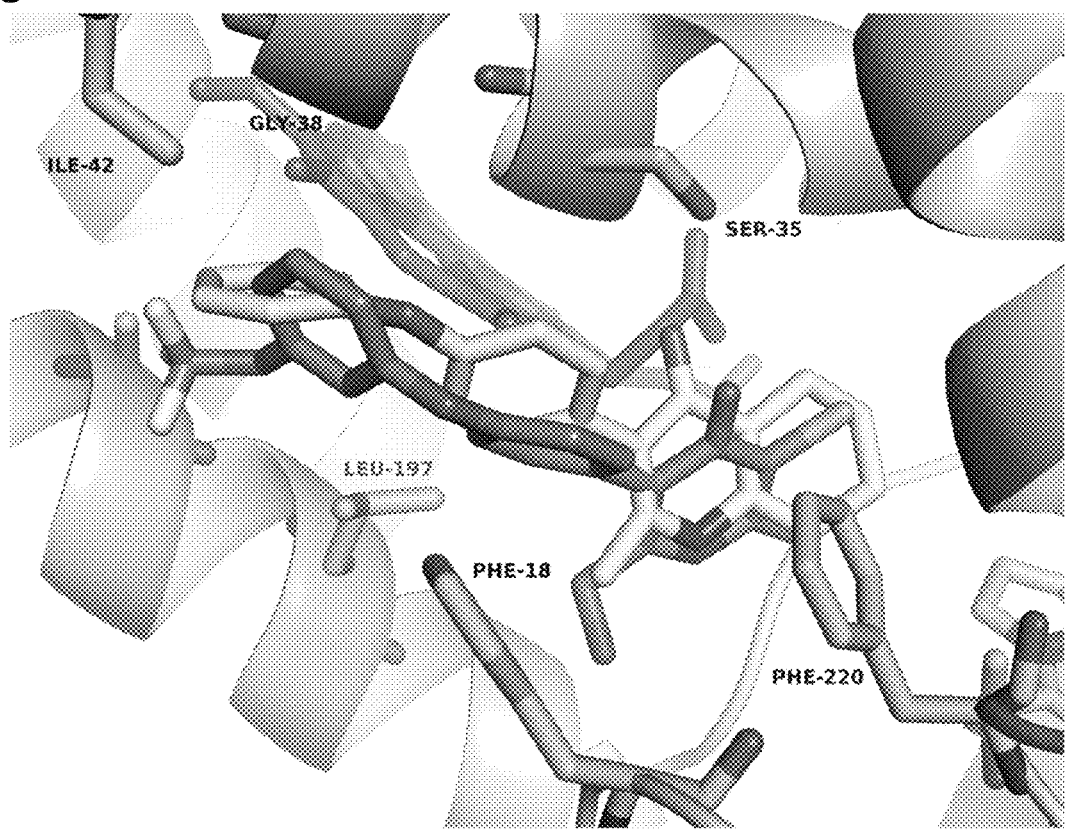
Figure 6B:
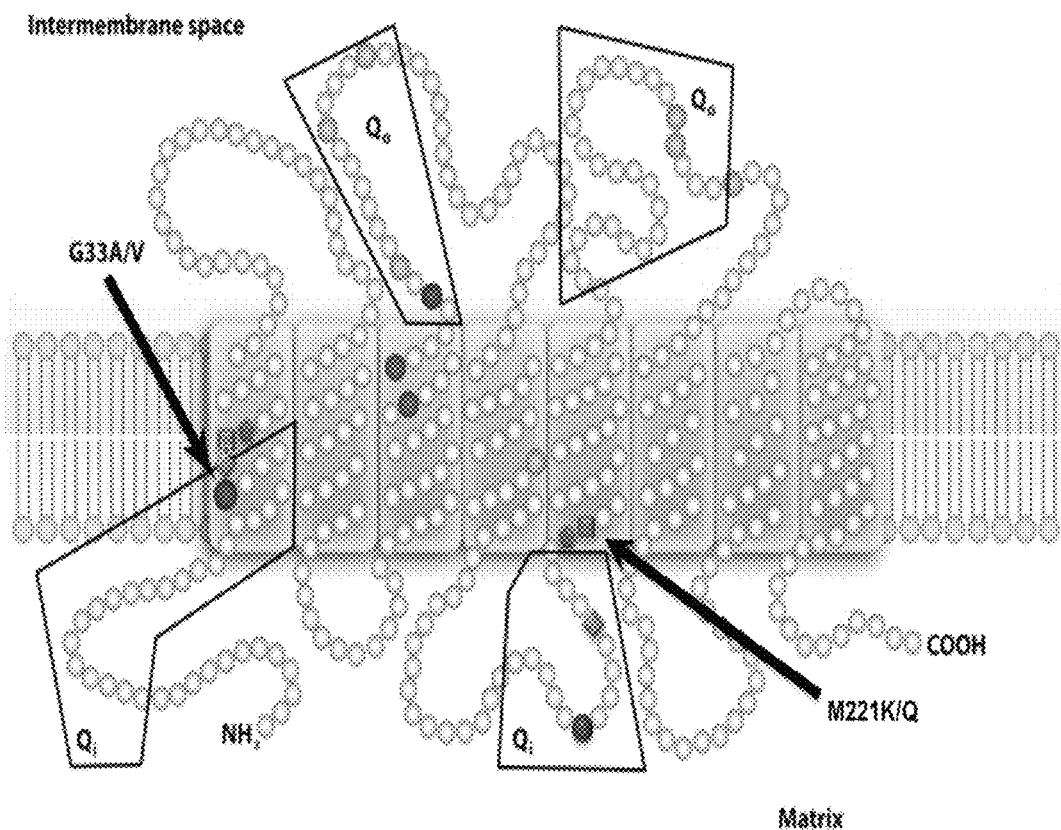

Cytochrome $bc_1$ $Q_i$ is the binding site of MJM170 which is potent against *Plasmodium falciparum*: and yeast. Tetrahydroquinolone binds to the $Q_i$ site of cytochrome $bc_1$: Studies to determine whether cytochrome $bc_1$ $Q_i$ is the molecular target of MJM170 initially included studies of resistance of yeast and *P. falciparum* with known cytochrome b $Q_i$ mutations predicted to cause a steric clash with MJM170 (FIGS. 6A-6G). Recently, we reported co-crystal structures of GSK's cytochrome $bc_1$ inhibitors bound to bovine cytochrome $bc_1$ at the $Q_i$ site[52] demonstrating that these pyridone inhibitors and other structurally related inhibitors bind to an alternative site to atovaquone on cytochrome $bc_1$. This structure allowed us to model MJM170 within the $Q_i$ site using the Maestro Suite from Schrödinger. This molecular modelling predicted steric clashes in mutant yeast and *P. falciparum* cytochrome $bc_1$ with MJM170 (FIG. 6A).

Co-crystallization of MJM170 with bovine cytochrome $bc_1$ and modelling of the *T. gondii* enzyme confirm the target. Co-crystallization validates predictions made with modelling and confirmed using assays with *S. cerevesiae*

TABLE 2

Comparison of ELQ 271 and MJM170 in our biological assays: inhibition of apicomplexan parasites and ADME/Tox. ELQ 271 was synthesised in-house.

| Compound | ELQ 271 | MJM170 |
|---|---|---|
| Structure | 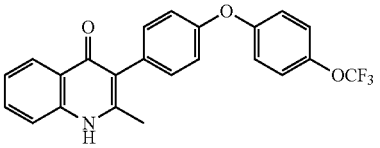 [SMILES: Cc1[nH]c2ccccc2c(=O)c1-c1ccc(Oc2ccc(OC(F)(F)F)cc2)cc1] | 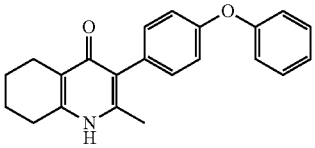 |
| Mol. Wt. | 411.4 | 331.4 |
| *T. gondii* Tachyzoite $IC_{50}$ μM | 0.03 | 0.03 |
| *T. gondii* Bradyzoite $IC_{50}$ μM | 1 | 4 |
| *P. falciparum* $IC_{50}$ μM[a] | 0.03 (D6) 0.09 (TM91C235) 0.10 (W2) 0.13 (C2B) | 0.01 (D6) 0.03 (TM91C235) 0.03 (W2) 0.01 (C2B) |
| HFF Toxicity $CC_{50}$ μM | 20 | 20 |
| Kinetic Solubility PBS pH 7.4 μM [b] | 0.15 | 1.97 |
| FaSSIF Solubility pH 6.5 μM [b] | 3.4 | 9.8 |
| Human microsomal stability $T_{1/2}$ mins [b] | 171.9 | 146.3 |
| Mouse microsomal stability $T_{1/2}$ mins [b] | >200 | 21.0 |
| MDCK-MDR1 $P_{app}$A-B × $10^6$ cm/s [b] | N.D. | 32.1 |
| MDCK-MDR1 Efflux Ratio [b] | N. D. | 1.23 |

[a] The D6 strain (Sierra Leone) is drug sensitive, the TM91C235 (Thailand) is multi-drug resistant, the W2 strain (Thailand) is chloroquine resistant, and the C2B strain is multi-drug resistant with pronounced resistance to atovaquone.
[b] ADME carried out by ChemPartner Shanghai Ltd. N.D. not determined. Human and mouse microsomal stability differs as is known to occur for other compounds such as TMP/SMX.

Figure 6E:
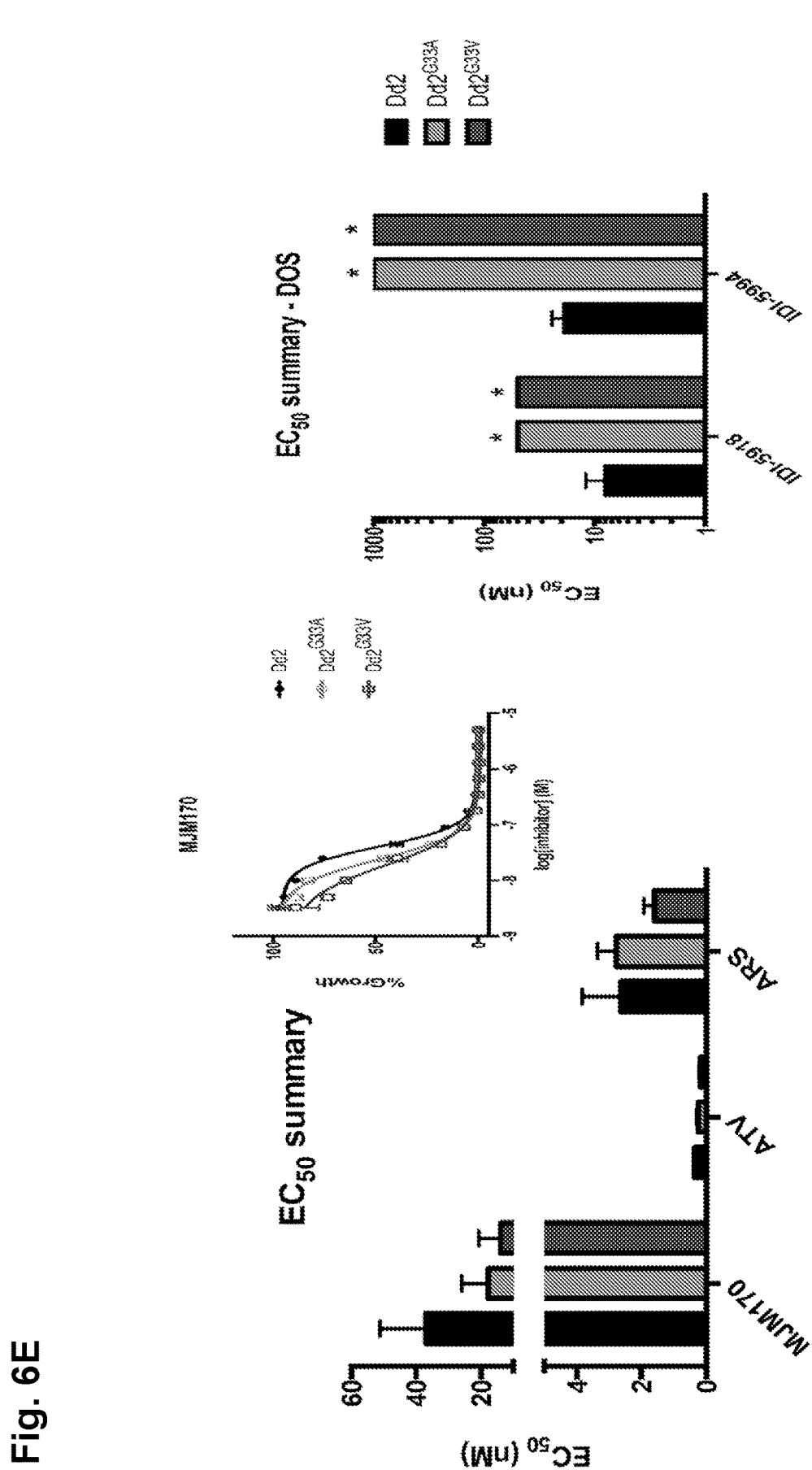
Figure 6F:
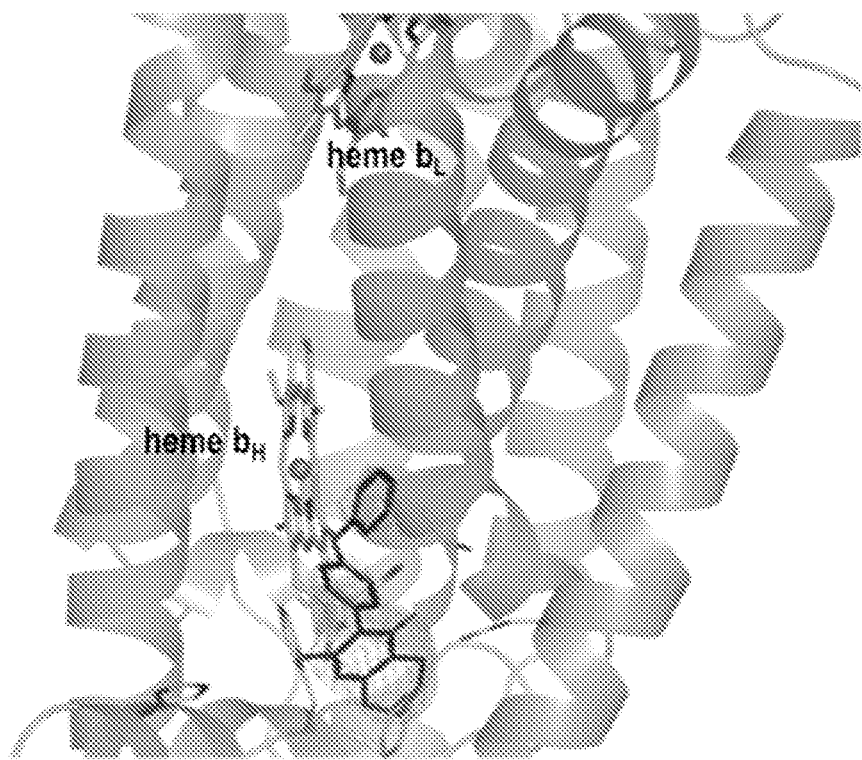
Figure 6G:
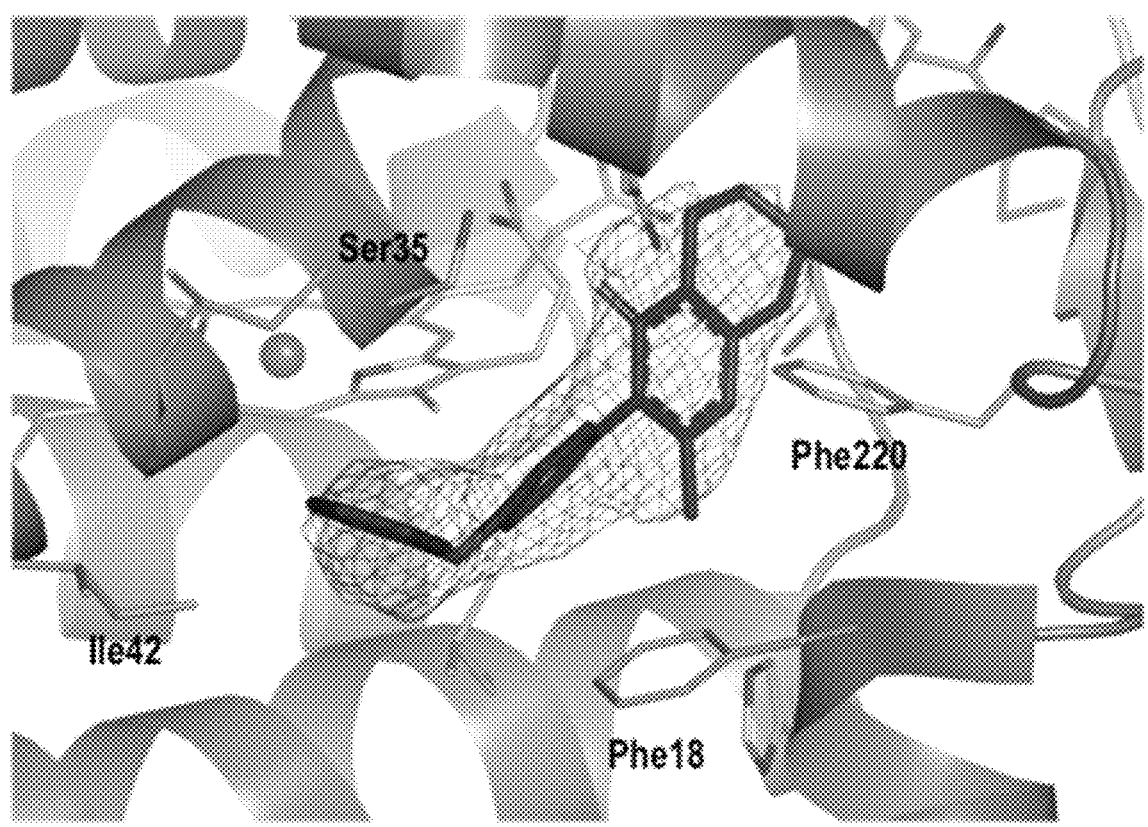

MJM 170 is effective in vivo against tachyzoites, and modestly against bradyzoites in cysts of mice, and development of a scalable zebrafish assay. MJM170 was highly efficacious against RH (FIG. 5A) and Prugniaud (FIG. 5B) strain tachyzoites in mice at 25 mg/kg without toxicity for 5 days (p<0.00), and modestly reduced numbers of Me49 strain cysts established >2 months earlier when treated with 12.5-25 mg mg/kg for 17 days (p<0.002) (FIG. 5C). In analysis of parallel histopathology, there was a similar trend mutants (FIG. 6D). There was no steric clash for *P. falciparum*—model based upon this crystal structure, consistent with in vitro assays (FIGS. 6E-6F). MJM170 was co-crystallized with bovine cytochrome $bc_1$ and the resulting good quality electron density maps allowed for unambiguous placement of MJM170 within the $Q_i$ site (FIG. 6F). The planar region of the quinolone group is held between heme $b_H$ and Phe220 and the additional ring further extends into the hydrophobic cavity at the apex of the binding site towards Pro24 and Ile27. The carbonyl group of the compound is surrounded by Ser35, Asp228 and the carbonyl of Trp31, while its amine moiety lies between His201 and Ser205. The diphenyl ether group extends outwards towards the hydrophobic residues Ile39 and Ile42 and forms a stacking interaction with Phe18 (FIG. 6G).

Surrogate assays demonstrate efficacy of compounds, providing target validation and added value as MJM170 is effective against wild type but not M221Q(F) mutant yeast. Mutants of *S. cerevesiae* were used to further confirm the molecular target of MJM170 (FIG. 6D), and documented that the $Q_i$ domain in cytochrome b is essential for its efficacy. This approach provided insight into binding of compounds to the enzyme. Crystallographic structure of bovine cytochrome $bc_1$ with GSK932121[52] indicates that certain amino acids are critical in tetrahydroquinolone binding and explains why there is inhibition by certain compounds. Previous studies reported that no cross-resistance is observed between ELQs and atovaquone in *P. falciparum*. This is rationalised as atovaquone binds the $Q_o$ site on cytochrome $bc_1$. A yeast M221Q substitution within the $Q_i$ site displayed resistance to ELQ inhibition further confirming that this to be the target site[27]. MJM170 and ELQ271 were effective against *S. cerevisiae* wild type parental AD1-9 strain at 1 mM, 100, 5 and 1 µM when grown on non-fermentable, glycerol medium forcing reliance on ATP production for respiration. Yeast strains with point mutations in the cytochrome b gene that substitute methionine by glutamine (M221Q) or phenylalanine (M221F) at position 221 in the $Q_i$ site predicted to yield a steric clash upon inhibitor binding were resistant to MJM170 (FIG. 6D).

Figure 7A:
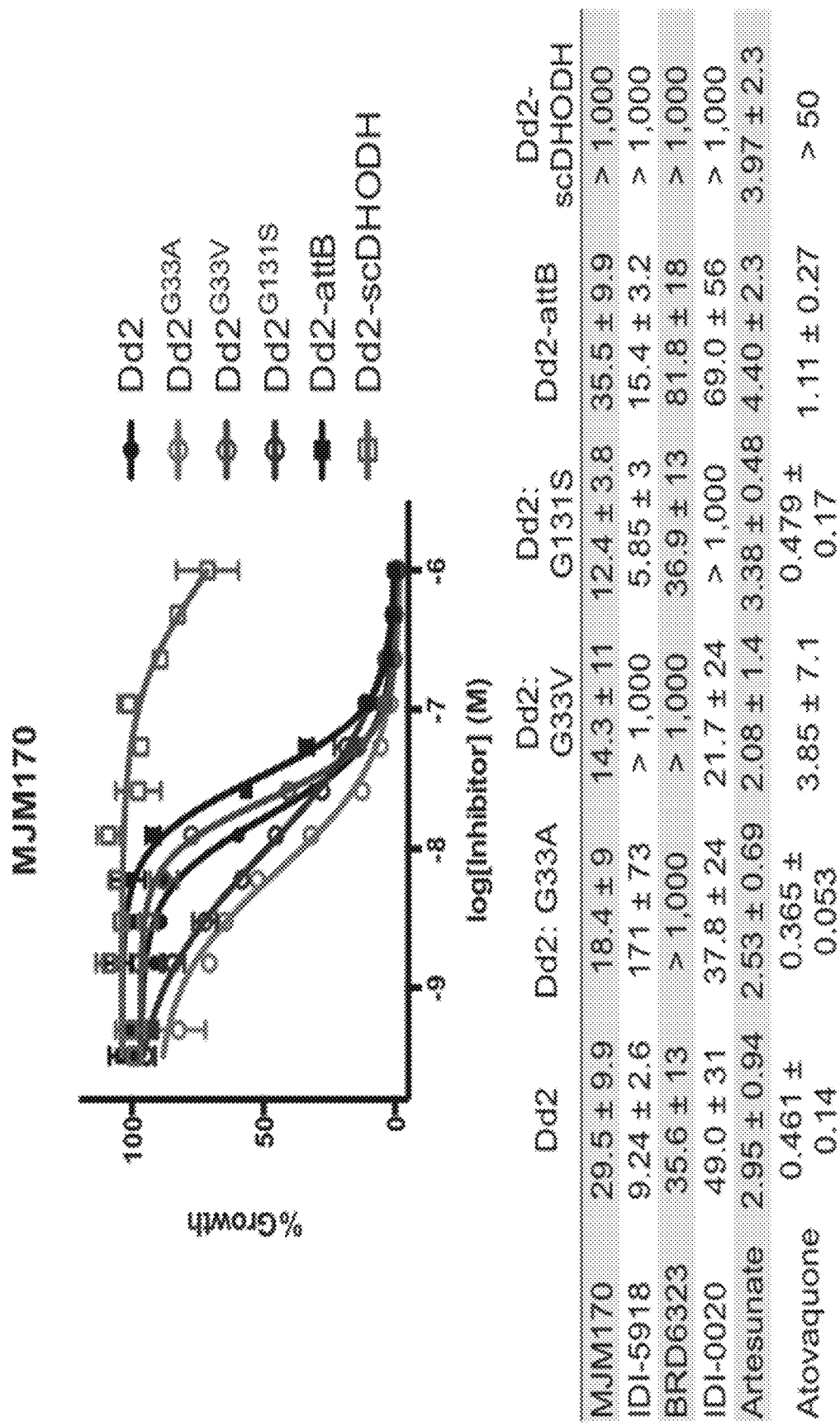
FIG. 7A-7C. MJM170 potently inhibits $P.$ $falciparum$ mitochondrial electron transport important for synthesis of pyrimidines, is modestly synergistic with atovaquone, additive with cycloguanil and antagonistic with $Q_i$ inhibitor.
Figure 7B:
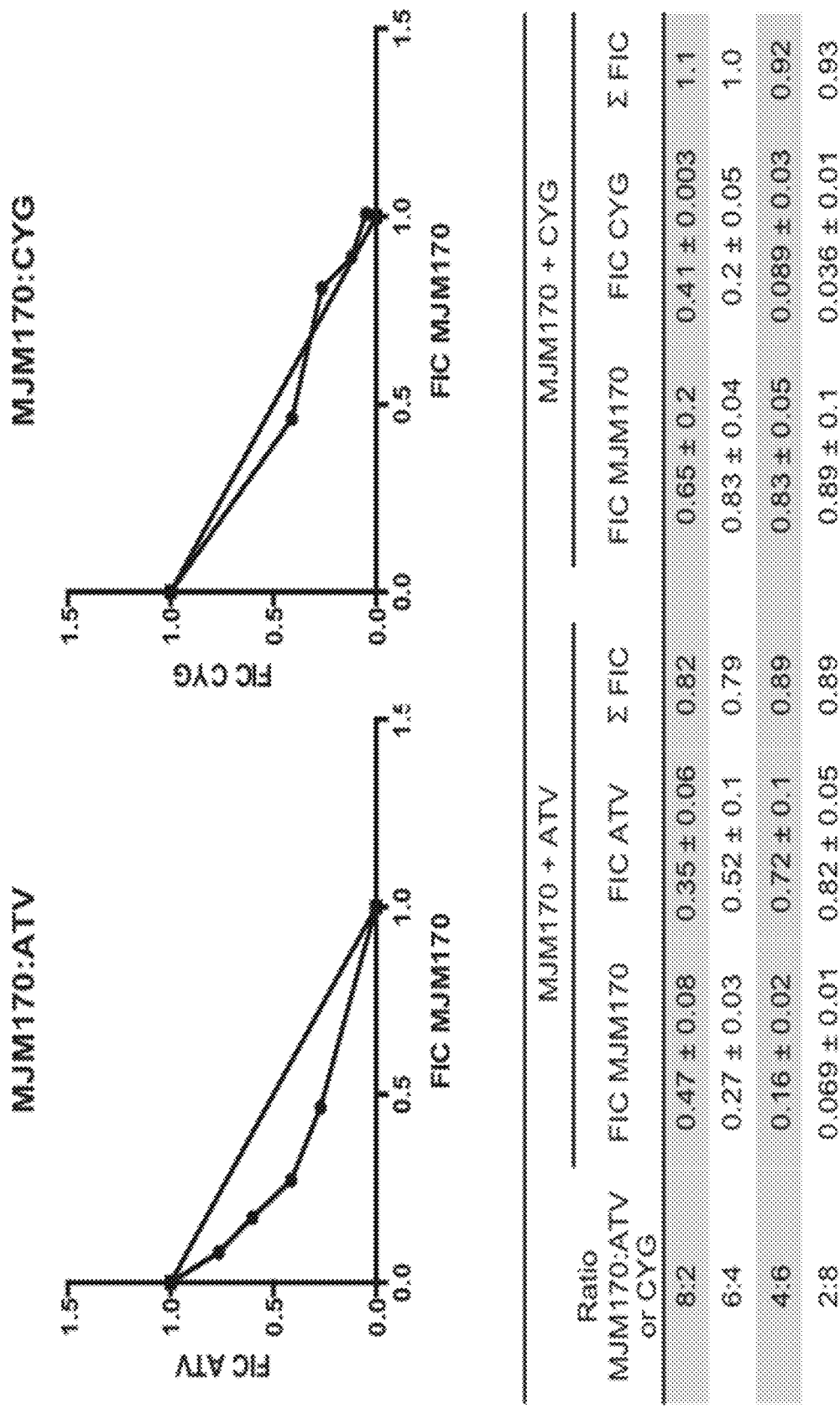
Figure 7C:
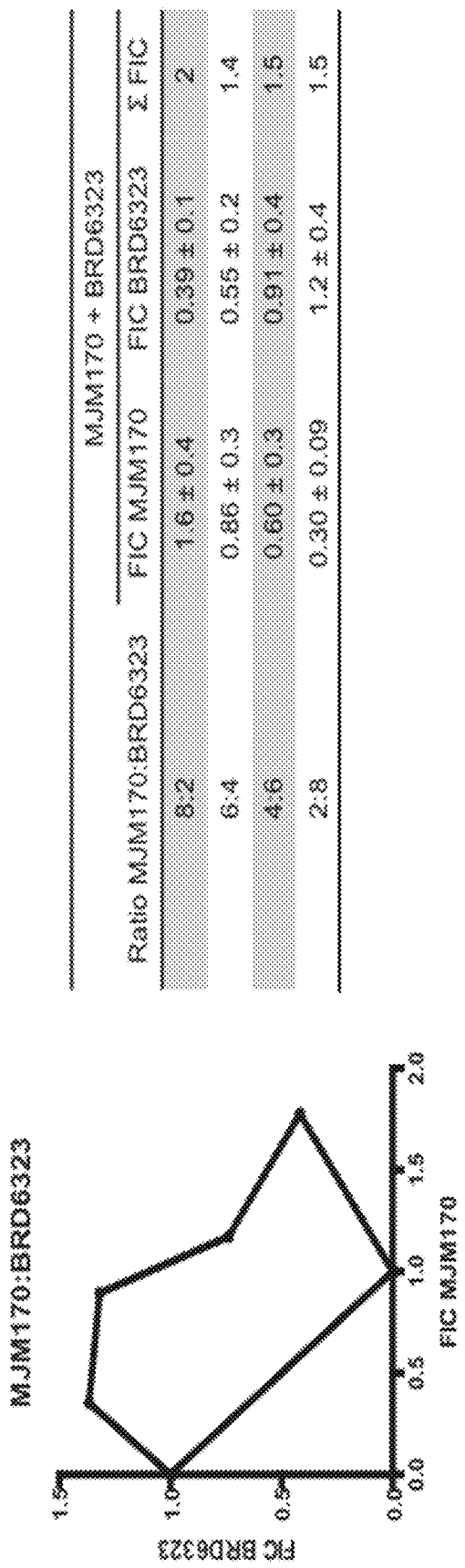

Tetrahydroquinolones are potent against wild type *P. falciparum*, and *P. falciparum* G33A/V and other drug resistant mutants but not DHODH mutant. MJM170 is highly effective against *P. falciparum* (Table 2) including multiple strains resistant to available antimicrobials and a cytochrome $bc_1$ $Q_i$ mutant (FIGS. 7A-7C). Resistance against transgenic *P. falciparum* yeast DHODH mutant strain indicates MJM170 affects mitochondria suggesting that the mode of action against *P. falciparum* is through inhibition of electron transport (FIG. 7A).

Potentially clinically useful combinations with tetrahydroquinolone demonstrated in synergy studies. To determine whether there might be clinically relevant synergies and additive effects, combinations of MJM170 with other clinically available and useful compounds also were tested. Earlier, we had found cycloguanil and related biguanide tnazines[64] were active against *T. gondii* tachyzoites and *P. falciparum* making it relevant to test them in combination with MJM170. We observed modest synergy in vitro for atovaquone, additive effect with cycloguanil, and antagonism with BRD6323, a $Q_i$ inhibitor for *P. falciparum* (FIG. 7B). Combining atovaquone with proguanil (active component cycloguanil) as Malarone[R] for malaria provides an approach to reduce selection of drug resistant *plasmodium* mutants.

Discussion

The results presented here offer a molecular understanding and therapeutic strategies for one of the most common parasitic infections of human brain and eye, and that persists across lifetimes in around 2 billion people worldwide. We have developed new models to facilitate discovery of curative treatments for toxoplasmosis. We have characterized the Brazilian *T. gondii* isolate called EGS that was known to be morphologically similar to encysted bradyzoites in tissue culture. We further validate the cystic nature of these EGS infected cultures, since they are able to induce the intraintestinal life cycle when fed to cats ultimately resulting in oocyst secretion. This is the first such description of this phenotype and provides definitive proof that this unique parasite has a true cyst phenotype when maintained in vitro. Our data also provide a number of other major conceptual advances on EGS by demonstrating the following: (i) Genome sequencing of this EGS isolate demonstrates that EGS has a typical Brazilian virulent genotype and phylogeny, (ii) EGS is a haplogroup 4 *T. gondii*. Consistent with a genotype that is known to be pathogenic and virulent for mice, we demonstrate that EGS oocyst induced infection is similar to that of other virulent Brazilian parasites. For example, mice fed EGS oocysts demonstrated ileal parasites causing necrosis, as well as pneumonitis, encephalitis and systemic infection leading to death. This indicates that the ability to form cysts in culture does not alter the pathogenicity of EGS in mice. However, potentially relevant to its in vitro bradyzoite phenotype, full genome sequencing revealed that it has nonsynonymous single nucleotide repeat sequence differences from other Brazilian and canonical U.S. and European parasites which do not share its in vitro bradyzoite phenotype. EGS has a non-synonymous mutation in a bradyzoite repressor, Apetela 2 (AP2) IV-iv, plant like transcription factor. AP2s interact with HATs and HDACs to modulate transcriptional signatures in apicomplexan parasites[55]. This Apetela 2, plant-like transcription factor gene, AP2IV-4, represses bradyzoite genes during the tachyzoite cell cycle, thereby preventing commitment to the bradyzoite developmental pathway[56]. If the observed substitution or disordered N terminus results in a defective or non-functional molecule, this could provide an explanation for the observed bradyzoite phenotype of EGS parasites. This is consistent with our findings that EGS in HFF forms cysts by 24 hours, characterized by BAG1, and *Dolichos* staining at 24, 48, and 96 hours after infection. These cysts gradually enlarge until 48-96 hrs in culture, when single *T. gondii* begin to destroy HFF monolayers. These are the cultures of bradyzoites in cysts that when fed to cats ~48 hours after infection form oocysts which are virulent in mice, providing definitive proof of an in vitro bradyzoite phenotype for the EGS strain of *T. gondii*.

The transcriptomic studies with this EGS isolate have provided critical insights into host cell mechanisms that are a prominent part of the ability of the encysted parasite to persist in this untreatable life cycle stage, and biologic consequences of such persistent infection. RNAseq and miR seq of EGS infected human host cells included human fibroblasts, monocytic and neuronal stem cells with this encysted EGS strain parasite. These provide an understanding of the types of perturbations of biologically relevant host cells this bradyzoite life cycle stage can cause, providing insights into unique aspects of pathogenesis of this infection with untreatable cysts and its consequences. We found that EGS modifies critical host cell pathways. For example we find in vitro modulations of host cell pathways in human, primary neuronal stem cells are the same as those associated with modulation of host cell replication as seen with malignancies, and in neurodegenerative diseases. Further, it is noteworthy that the level of a microRNA that specifies apoptosis in eye and brain cells is markedly down modulated by this EGS bradyzoite which would inhibit host protective apoptotic mechanisms allowing parasites to persist in brain and eye without a critical protective mechanism. EGS, as an encysted bradyzoite, clearly alters biologic processes including cell cycle, cell death, alternative splicing, protein synthesis, protein folding and ubiquitination and down regulates hsa-miR-708-5p that specifies apoptosis in neuronal and retinal cells[65].

RNA and MiR sequencing and transcriptomic analyses of the EGS parasites also identified molecular targets that are critical for the bradyzoite life cycle stage in the parasite as well. These molecular targets include cytochrome b, as critically increased in dormant, encysted parasites. Cytochrome b was increased along with known cyst constituents like enolase 1, Cyst wall protein, Lactate dehydrogenase 2, bradyzoite antigen 1, Apetela 2 plant like transcription factors not present in animals, such as AP2 IX-ix, and cytochrome oxidase. Our work provides a new means to identify stage specific molecular targets, and emphasizes that cytochrome bc 1 complex is a critical target. The transcriptome of EGS parasites in HFF over time are similar to those of in vivo bradyzoites in terms of known critical genes modified. Finally, EGS presents a much-needed assay for identifying novel molecular targets present in bradyzoites in vitro. EGS was also useful to evaluate the effect of inhibitors on encysted bradyzoites in vitro.

Recent crystallographic studies with the bovine cytochrome $bc_1$ complex allowed us to rationally design a novel compound to target the $Q_i$ site of cytochrome b. Our novel compound was designed to address issues with poor solubility of existing quinolone/pyridone $Q_i$ inhibitors. One of these compounds MJM170, a substituted 5,6,7,8-tetrahydroquinolin-4-one inhibits active infection ($IC_{50}$ 30 nM) and cysts ($IC_{50}$ 4 μM) in vitro, and in vivo (25 mg/kg). It is predicted to cross the blood brain barrier with no efflux as demonstrated in an in vitro MDR1-MDCK permeability assay (Table 2), indicating this class of compounds have promise for treatment of central nervous system infections. When we tested MJM170 against wild type and multi-drug resistant P. falciparum, we found it was also potent ($IC_{50}$<30 nM against all strains). In combination studies, MJM170 was identified as additive with cycloguanil and modestly synergistic with atovoquone. Studies of yeast and malaria mutants, as surrogate assays, and co-crystallography studies with bovine cytochrome $bc_1$ confirm the mechanism of action/target for MJM170. The co-crystal structure of MJM170 in complex with bovine cytochrome $bc_1$ reveals a clear binding mode within the $Q_i$ site. Using homology models of the apicomplexan Qi sites, there are clear differences between the binding sites of the apicomplexan and mammalian orthologs which can be used to fine-tune the selectivity of our scaffold towards apicomplexan $bc_1$. The larger binding pocket of the apicomplexan versus the mammalian $bc_1$ may provide a way forward to increase selectivity. Our work provides a conceptual and a practical step change forward that provides a foundation for further testing and improvements to efficacy, toxicity, solubility, oral absorption, large animal toxicology that will be needed to reach the clinic. Our work reported herein not only provides new and important insights into the biology of T. gondii, especially the bradyzoite life cycle stage and the remarkable effects of this parasite on its human host's cells, but also provides critical molecular targets and new methods to identify others. Armed with this information, a novel scaffold with intrinsically higher solubility than the equivalent quinolone has been designed with holds promise towards developing a much-needed curative medicine for those with toxoplasmosis, malaria, and ~2 billion persons chronically infected with presently incurable, encysted bradyzoites which persist and can recrudesce lifelong.

Methods

All methods were carried out in accordance with approved guidelines set at the University of Leeds by the Education & Training Resources office and all experimental protocols were approved by the IRB committees; University of Chicago Institutional Animal Care and Use Committee (IACUC) and all experimental protocols were approved by the IRB committee; United States Department of Agriculture IACUC and all experimental protocols were approved by the IRB committees; J Craig Venter Institute Research ethics committee; University of Liverpool UK Office for Research Integrity (UKRIO) and all experimental protocols were approved by the IRB committees; Harvard School of Public Health HMS IACUC and all experimental protocols were approved by the IRB committees; The Broad Institute IACUC and all experimental protocols were approved by the IRB committees; Walter Reed Army Institute of Research Division of Human Subjects Protection (DHSP) and all experimental protocols were approved by the IRB committees; Oregon State University IACUC and all experimental protocols were approved by the IRB committees; Institute for Systems Biology ethics committee; Albert Einstein College of Medicine IACUC and all experimental protocols were approved by the IRB committees; Strathclyde University Ethics Committee (UEC) and all experimental protocols were approved by the IRB committees; Institute for Integrative Biology of the Cell IACUC and all experimental protocols were approved by the IRB committees, and the Centre national de la recherche scientifique IACUC and all experimental protocols were approved by the IRB committees.

Cells and Parasites for Work with T. gondii

Cells: The cells utilized for T. gondii assays included human foreskin fibroblasts (HFF), Human MonoMac 6 cells (MM6), and Neuronal Stem cells (NSC) from a temporal lobe biopsy.

Toxoplasma gondii. The strains of T. gondii utilized in this work were: RH—YFP Tachyzoites of the RH—YFP strain were passaged in human foreskin fibroblasts (HFF cells); EGS-Bradyzoite assays use the EGS strain, isolated from amniotic fluid of human with congenital toxoplasmosis; Other strains used are: Me49; Prugniaud; Beverly; Veg; GT1. All other than EGS are T. gondii tachyzoites. These parasites are passaged in HFF.

Isolation of DNA and RNA. EGS single celled organisms were grown in Human Foreskin Fibroblasts, filtered free of host cells. gDNA was isolated and processed for sequencing as described. For isolation of RNA RIN scores were >8.

Gene Sequencing, Genomics, RNA and MiR Sequencing, Systems Analysis, Metabolomics Genome sequencing of T. gondii EGS strain. A single Illumina paired-end barcoded library was prepared from tachyzoite gDNA with Illumina TrueSeq library preparation kit. The library was then sequenced using 100 bp pared-end reads in one ninth of a lane of an Illumina HiSeq 2000 machine to generate ~2 Gbp of genome sequence.

Single nucleotide polymorphism (SNP) identification and annotation. Illumina genome sequencing reads from EGS or downloaded from GenBank SRA database for GT1 (SRR516419), VEG (SRR516406) and TgCatBr1 (SRR350737) were aligned to the T. gondii ME49 reference genome assembly (ABPA02000000, ToxoDB release 13.0) with Bowtie2 and realigned around gaps using the GATK toolkit. SNP calls were done simultaneously across all four strains with samtools utility mpileup, requiring a minimum SNP coverage of 5 reads and an alternative allele frequency of 0.8 or higher, given the haploid nature of these genomes. Thereafter, SnpEff and a gff3 file containing the annotation of *T. gondii* ME49 downloaded from ToxoDB v13.0 were used to classify the different types of mutations identified in each strain. Allelic variants that were different between EGS and the rest of the strain were considered EGS-specific.

Phylogenetic network analysis. A total of 790,168 single nucleotide polymorphisms spanning the entire *T. gondii* genome from 62 different strains representing all major haplogroups were downloaded from ToxoDB, combined with SNP data from the same sites from the EGS strain and directly incorporated as a FASTA file into SplitsTree v4.13.1 to generate unrooted phylogenetic networks using a neighbor-net method.

Differential gene expression (DGE) analysis. Total RNA extracted from human cell cultures infected (or not) with a number of *T. gondii* strains for 2 h, 18 h or 48 h was treated with miRNeasy Mini Kit columns (Qiagen) following manufacturer instructions to separate mRNA and miRNA fractions. Afterwards, Illumina barcoded sequencing libraries were constructed with TruSeq RNA Sample Preparation Kits v2 (Illumina) for mRNA and miRNA TruSeq Small RNA Library Preparation Kit (Illumina) for miRNA. Libraries were sequenced as 100 bp single reads with Illumina HiSeq 2000 apparatus in pulls of 6 or 9 samples per lane for mRNA (yield ~3 Gbp per sample) and miRNA (yield ~2 Gbp per sample) libraries respectively. For protein coding genes, reads were mapped to the human (release GRCh38) and *T. gondii* ME49 strain (ToxoDB release 13.0) reference genome assemblies and annotations with CLC Genomic Workbench software (CLC Bio-Qiagen, Aarhus, Denmark) and raw read counts per gene were then analyzed with the R package EdgeR using a generalized linear model likelihood ratio test to identify genes that are differentially expressed among samples.

For miRNA DGE analysis, reads were depleted of adaptor and primer sequences and mapped to the human reference genome assembly (GRCh38) and the miRNA annotation from miRBase v21 (see the mirbase web site) with CLC Genomic Workbench software. Identification of human miRNA genes that are differentially expressed across treatments was carried out with EdgeR from raw read counts per miRNA gene using a generalized linear model likelihood ratio test.

For both mRNA and miRNA DGE analyses p-values were adjusted for multiple hypotheses testing using the False Discovery Rate method. MDS plots and heat maps were generated with the plotMDS tool from EdgeR and the R tool heatmap. Differentially expressed genes (DEGs) in MM6 and NSC cell lines infected with EGS parasites were identified under the criteria of 1% FDR and absolute log 2-fold-change >1.5 (i.e. fold-change >2 and <0.5 for up- and down-regulated genes, respectively).

Functional enrichment analysis GO enrichment analyses were performed for up- or down-regulated genes, by using the Database for Annotation, Visualization and Integrated Discovery (DAVID) v6.7. GO slim enrichment analysis was performed for genes carrying potential change-of-function mutations in EGS that were absent in strains ME49, VAND or TgCatBr1. GO slim database was downloaded from QuickGO provided by EMBL-EBI. Using taxonomy id "508771" for the ME49 strain, relevant GO slim terms were retrieved. GO slim enrichment analysis was performed with Fisher's exact test based on the GO slim terms.

Assay for oocyst development in cats. Oocysts were collected from feces of *Toxoplasma*-free cats 3-14 days after feeding infected cell cultures or infected mouse brains. Oocysts were separated from feces by sugar floatation, sporulated in 2% sulfuric acid by aeration at room temperature for 1 week. After removing sulfuric acid oocysts were inoculated orally in to Swiss Webster albino mice. All tissues of mice that died or euthanized were studied histologically after staining with hematoxylin and eosin and by BAG1 antibodies to *T. gondii* as described. (Dubey J P, Ferreira L R, Martins J, McLeod R. Oral oocyst-induced mouse model of toxoplasmosis: effect of infection with *Toxoplasma gondii* strains of different genotypes, dose, and mouse strains (transgenic, out-bred, inbred) on pathogenesis and mortality. Parasitology 139:1-13, Epub 2011. PMID: 22078010; also referred t herein as S39)

Chemical Synthesis. Final compounds had >95% purity determined by high performance liquid chromatography (HPLC) and 300 and/or 500 MHz NMR spectrometers. Liquid chromatography-mass spectrometry (LC-MS) and high resolution mass spectrometers (HRMS) analytical systems were used to determine integrity and purity of all intermediates and final compounds.

Synthesis of 2-methyl-5,6,7,8-tetrahydroquinolin-4-one (6) Platinum oxide (100 mg, 10 mol %) was added to a solution of 4-hydroxy-2-methylquinoline (5, 1.00 g, 6.28 mmol, 1.00 eq) in glacial acetic acid (10.0 ml). The heterogeneous mixture was catalytically hydrogenated under a balloon of hydrogen. After 22 hrs, TLC (10% MeOH-DCM) confirmed complete reaction. The mixture was filtered through celite under vacuum, washing thoroughly with EtOAc. The filtrate was concentrated and the resulting residue purified by column chromatography (10% MeOH-DCM) to give the desired product as a pale yellow oil (917 mg, 5.65 mmol, 89%); Rr 0.14 (10% MeOH-DCM); $\delta_H$ (300 MHz, CDCl$_3$) 1.74-1.76 (4H, m, CH$_2$), 2.29 (3H, s, Me), 2.49-2.52 (2H, m, CH$_2$), 2.67-2.70 (2H, m, CH$_2$), 6.16 (1H, s, Ar—H); $\delta_C$ (125 MHz, CDCl$_3$) 19.0 (Me), 21.8 (CH$_2$), 22.1 (CH$_2$), 27.1 (CH$_2$), 112.5 (CH), 122.4 (Cq), 146.4 (Cq), 147.0 (Cq), 178.3 (Cq); Spectroscopic data consistent with literature values (JMC, 1993, 36, 1245-54).

Synthesis of 2-methyl-3-iodo-5,6,7,8-tetrahydroquinolin-4-one (7) Butylamine (6.20 ml, 62.8 mmol, 10.0 eq) was added to a suspension of 2-methyl-5,6,7,8-tetrahydroquinolin-4-one (6, 1.02 g, 6.28 mmol, 1.00 eq) in DMF (10.0 ml). To this heterogeneous mixture was added 12 (1.60 g, 6.28 mmol, 1.00 eq) in a saturated solution of KI (6.00 ml). After 20 hrs stirring at R.T., a precipitate formed in the orange solution, Excess iodine was quenched with 0.1 M sodium thiosulfate solution. The precipitate was filtered by vacuum filtration, washed with distilled H$_2$O and dried (Na$_2$SO$_4$) to give the desired product as a colourless solid (1.76 g, 6.09 mmol, quantative yield); $\delta_H$ (300 MHz, DMSO-d$_6$) 1.61-1.70 (4H, m, CH$_2$), 2.29 (2H, t, J 6.0, CH$_2$), 2.43 (2H, s, CH$_2$), CH$_3$ under DMSO peak.

Synthesis of 2-methyl-3-iodo-4-ethoxy-5,6,7,8-tetrahydroquinoline (8) Potassium carbonate (1.53 g, 11.1 mmol, 2.00 eq) was added to a heterogeneous mixture of 2-methyl-3-iodo-5,6,7,8-tetrahydroquinolin-4-one (7, 1.60 g, 5.56 mmol, 1.00 eq) in DMF (15.0 ml), and the reaction heated to 50° C. for 30 mins. The R.B. flask was removed from the heating mantle and ethyl iodide was added dropwise. The reaction was then heated at 50° C. for 18 hrs. The reaction was cooled to R.T., quenched with water (40 ml). The resulting emulsion formed which was extracted with EtOAc (50 ml). EtOAc layer were washed with water (3×30 ml), brine (3×30 ml), dried (Na$_2$SO$_4$) and concentrated to give a pale yellow oil (1.09 g, 3.44 mmol, 61%); Rr 0.88 (1:1 Pet-EtOAc); HPLC (RT=1.67 mins); LCMS (Method A), (RT=1.6 min, m/z (ES) Found MH$^+$ 318.0); $\delta_H$ (500 MHz, CDCl$_3$) 1.49 (3H, t, J 7.0, ethoxy CH$_3$), 1.73-1.78 (2H, m, CH$_2$) 1.84-1.88 (2H, m, CH$_2$), 2.78-2.69 (5H, m, CH$_2$ &

$CH_3$), 2.84 (2H, t, J 6.5, $CH_2$), 3.97 (2H, q, J 7.0, $OCH_2$); $\delta_C$ (125 MHz, $CDCl_3$) 15.6 ($CH_3$), 22.3 ($CH_2$), 22.8 ($CH_2$), 23.6 ($CH_2$), 29.3 ($CH_3$), 32.0 ($CH_2$), 68.4 ($OCH_2$), 90.9 (Cq), 124.5 (Cq), 158.3 (Cq), 158.9 (Cq), 163.9 (Cq).

Synthesis of 2-methyl-3-(4-phenoxyphenyl)-4-ethoxy-5,6,7,8-tetrahydroquinoline (10) 2-Methyl-3-iodo-4-ethoxy-5,6,7,8-tetrahydroquinoline (8, 0.266 g, 0.839 mmol, 1.00 eq), $Pd(PPh_3)_4$ (0.048 mg, 0.0419 mmol, 5 mol %) and 4-phenoxyphenylboronic acid (9, 0.270 mg, 1.26 mmol, 1.50 eq) were charged to a R.B. flask under $N_2(g)$[49]. Degassed DMF (10.0 ml) was added to the flask followed by 2M $K_2CO_3$ (1.60 ml). The flask was heated to 85° C. under $N_2(g)$. After 15 mins, TLC (4:1 Pet-EtOAc) confirmed reaction was complete. The reaction was cooled and diluted with EtOAc (15 ml), filtered through celite and partitioned between EtOAc (10 ml) and $H_2O$ (25 ml). Combined organics were washed with $H_2O$ (3×30 ml), then brine (3×30 ml), dried ($Na_2SO_4$) and concentrated to give a red oil which was purified by column chromatography (3:1 Pet-EtOAc), to give the desired product as a pale yellow oil (0.235 mg, 0.655 mmol, 78%); Rr 0.31 (3:1 Pet-EtOAc); HPLC (RT=3.08 mins); $\delta_H$ (300 MHz, $CDCl_3$) 1.04 (3H, t, J 7.0, ethoxy $CH_3$), 1.76-1.93 (4H, m, 2×$CH_2$), 2.32 (3H, s, $CH_3$) 2.72 (2H, t, J 6.0, $CH_2$), 2.91 (2H, t, J 6.5, $CH_2$), 3.50 (2H, q, J 7.0, $OCH_2$), 7.05-7.16 (5H, m, Ar—H), 7.20-7.29 (2H, m, Ar—H), 7.31-7.43 (2H, m, Ar—H); $\delta_C$ (125 MHz, $CDCl_3$) 15.7 ($CH_3$), 22.5 ($CH_2$), 23.0 ($CH_3$), 23.3 ($CH_2$), 23.4 ($CH_2$), 32.7 ($CH_2$), 68.2 ($OCH_2$), 118.6 (CH), 118.9 (CH), 123.4 (CH), 126.8 (Cq), 129.8 (CH), 131.5 (CH), 154.9 (Cq), 156.5 (Cq), 157.1 (Cq), 157.3 (Cq); m/z (ES) (Found: $MH^+$, 360.1973. $C_{24}H_{26}NO_2$ requires MH, 360.1964).

Synthesis of 2-methyl-3-(4-phenoxyphenyl)-4-ethoxy-5,6,7,8-tetrahydroquinoline (MJM170, 4)[49] Aqueous hydrobromic acid (>48%) (1.00 ml) was added to a solution of 2-methyl-3-(4-phenoxyphenyl)-4-ethoxy-5,6,7,8-tetrahydroquinoline (10, 0.226 mg, 0.630 mmol, 1.00 eq) in glacial acetic acid (2 ml). The reaction was stirred at 90° C. for 5 days, monitoring by LMCS. The reaction was cooled to R.T. and the pH adjusted to pH5 with 2M NaOH. The precipitate was collected by vacuum filtration and recrystallized from $MeOH:H_2O$ to give the desired product as an off-white solid (0.155 g, 0.467 mmol, 74%); HPLC (RT=2.56 mins); $\delta_H$ (500 MHz, DMSO-$d_6$) 1.66-1.72 (4H, m, 2×$CH_2$), 2.08 (3H, s, $CH_3$) 2.31 (2H, t, J 6.0, $CH_2$), 2.56 (2H, t, J 6.0, $CH_2$), 6.99 (2H, d, J 8.5, Ar—H), 7.06 (2H, d, J 7.5, Ar—H), 7.14-7.18 (3H, m, Ar—H), 7.40-7.43 (2H, m, Ar—H), 11.0 (1H, s, NH); $\delta_C$ (125 MHz, DMSO-$d_6$) 17.7 ($CH_3$), 21.5 ($CH_2$), 21.8 ($CH_2$), 21.9 ($CH_2$), 26.2 ($CH_2$), 117.8 (CH), 118.6 (CH), 121.2 (Cq), 123.3 (CH), 123.7 (Cq), 130.0 (CH), 131.4 (Cq), 132.3 (CH), 142.3 (Cq), 143.2 (Cq), 155.0 (Cq), 156.8 (Cq), 175.4 (Cq); nm/z (ES) (Found: $MH^+$, 332.1654. $C_{22}H_{22}NO_2$ requires MH, 332.1645).

ADME studies of inhibitors: Compounds that were highly effective in vitro ($IC_{50}$ <1 µM) were tested for ADME profiling[S43-58] by Shanghai ChemPartner Ltd. Initial studies focused on aqueous kinetic solubility pH 7.4, microsomal metabolic stability (human and mouse) and Blood-Brain Barrier (BBB) permeability (performed with MDCK-MDR1 cells as described).

In Vitro Assays
Cytotoxicity Assay

Toxicity Analysis. Lack of toxicity for mammalian host cells was demonstrated first by visual inspection of monolayers following giemsa staining, in separate methods by incorporation of a mitochondrial cell death reagent called WST we used successfully for this purpose and in separate experiments.

Toxicity assays were conducted using WST-1 cell proliferation reagent (Roche). HFF were grown on a flat, clear-bottomed, black 96-well plate. Confluent HFF were treated with inhibitory compounds at concentrations equal to those being tested in challenge assays. Compounds were diluted in IMDM-C, and 20 µl were added to each designated well, with triplicates for each condition. A gradient of 2 fold-decreasing concentrations of DMSO in clear IMDM-C was used as a control. The plate was incubated for 72 hours at 37° C. 10 µl of WST-1 reagent (Roche) were added to each well and the cells were incubated for 30 to 60 minutes. Absorbance was read using a fluorometer at 420 nm. A higher degree of color change (and absorbance) indicated mitochondrial activity and cell viability.

In Vitro Cellular Assays for Effects on *T. gondii*

Vivo PMO: Vivo-PMO (Vivo porter linked to morpholinos) to knock down cytochrome b and an off-target PPMO (Vivo porter) were utilized at concentrations of 5 and 10 µM as previously described with both cultures of RH—YFP tachyzoites and EGS. Morpholino sequence for cytochrome b/c knockdown is 5' AGTGTTCTCGAAAC-CATGCTAACAC 3' (SEQ ID NO: 5), and for unrelated sequence, off target, is 5' CCTCTTACCTCAGTTACAAT-TTATA 3' (SEQ ID NO: 6).

Tetrahydroquinolone Compounds: Compounds synthesized at the University of Leeds were initially prepared in 10 mM Stock solutions made with 100% Dimethyl Sulfoxide (DMSO) [Sigma Aldrich], and working concentrations were made with IMDM-C (1×, [+]glutamine, [+] 25 mM HEPES, [−] Phenol red, 10% FBS) [Gibco, Denmark]).

Tachyzoite Assays:

Type 1 parasites. Human foreskin fibroblasts (HFF) were cultured on a flat, clear-bottomed, black 96-well plate to 90% to 100% confluence. IMDM (1×, [+] glutamine, [+] 25 mM HEPES, [+] Phenol red, 10% FBS [gibco, Denmark]) was removed from each well and replaced with IMDM-C (1×, [+] glutamine, [+] 25 mM HEPES, [−] Phenol red, 10% FBS)[Gibco, Denmark]). Type I RH parasites expressing Yellow Fluorescent Protein (RH—YFP) were lysed from host cells by double passage through a 27-gauge needle. Parasites were counted and diluted to 32,000/mL in IMDM-C. Fibroblast cultures were infected with 3200 tachyzoites of the Type I RH—YFP strain and returned to incubator at 37° C. for 1-2 hours to allow for infection. Diluted solutions of the compounds were made using IMDM-C, and 20 µl were added to each designated well, with triplicates for each condition. Controls included pyrimethamine/sulfadiazine (current standard of treatment), DMSO only, fibroblast only, and an untreated YFP gradient with 2 fold dilutions of the parasite. Cells were incubated at 37° C. for 72 hours. The plates were read using a fluorimeter (Synergy H4 Hybrid Reader, BioTek) To ascertain the amount of yellow fluorescent protein, in relative fluorescence units (RFU), as a measure of parasite burden after treatment. Compounds were not considered effective or pursued for further analysis if there were no signs of inhibition at 1 µM. Data was collected using Gen5 software and analyzed with Excel.

Type II parasites. To test type II parasites, *T. gondii* ME49 and Prugneaud parasites expressing luciferase or GFP. We tested them in vitro and in vivo as we have described.

EGS strain Bradyzoite Assay. HFF cells were grown in IMDM (1×, [+] glutamine, [+] 25 mM HEPES, [+] Phenol red, 10% FBS, [Gibco, Denmark]) on removable, sterile glass disks in the bottom of a clear, flat-bottomed 24-well plate. Cultures were infected with 3×10⁴ parasites (EGS strain) per well, in 0.5 mL media and plate was returned to incubator at 37° C. overnight. The following day, the media was removed and clear IMDM and compounds were added to making various concentrations of the drug, to a total volume of 0.5 mL. Two wells were filled with media only, as a control. Plates were returned to the 37° C. incubator for 72 hours.

Efficacy was determined following fixation. Staining was used to determine the numbers of cysts in cultures without and with treatment with the test compounds. Cells were fixed using 4% paraformaldehyde and stained with Fluorescein-labeled *Dolichos biflorus* Agglutinin, DAPI, and anti-BAG1, and anti-SAG1. Disks were removed and mounted onto glass slides and visualized using microscopy (Nikon T17). Slides were also scanned using a CRi Pannoramic Scan Whole Slide Scanner and viewed using Panoramic Viewer Software.

When cysts that had dolichos in their cyst wall were eliminated or markedly reduced in size and number, a compound was considered efficacious against bradyzoites in cysts.

Statistical Analyses. Significance of differences were determined using Student's t-test. $P<0.05$ was considered significant. Every experiment was replicated at least twice. A Pearson test was used to confirm a correlation between increasing dose and increasing inhibition. An ANOVA and subsequent pair wise comparison with Dunnett correction was used to determine whether or not inhibition or toxicity at a given concentration was statistically significant. Stata/SE 12.1 was used for this analysis. This study was approved by the University of Chicago IRB, IBC, and IACUC.

In Vivo Analysis (Mice and Zebrafish):

Initial screening with tachyzoites using IVIS, fluorescence, and histopathology: Ability of compounds to abrogate tachyzoites multiplication was assessed using an in vivo imaging system (IVIS). To facilitate this we have *T. gondii* strains from each of the 3 major lineages expressing the luciferase gene. In these studies mice are injected intraperitoneally with tachyzoites and parasite proliferation followed up to 30 days post infection. Removal of brains at 30 days allows parasite quantitation by bioluminescence ex vivo using the IVIS. As an alternative method to improve screening efficiency and scalability it is possible for initial screening to use zebrafish with histopathology and visualization as shown in FIGS. 1A-1D. Quantitation also was performed using QT PCR as described for mice or in translucent Casper zebrafish with parasites with fluors or luciferase to screen rapidly. Tachyzoites and bradyzoites in cysts were used for IP infection and compounds given intraperitoneally.

Type II parasites. To test type II parasites, we used *T. gondii* Me49 and Prugneaud parasites[S39].

Encephalitis: The ability of compounds to reduce cyst burden and prevent encephalitis induced by the Type II strain of *T. gondii* were tested. Encephalitis was assessed by histological analyses and parasite burdens evaluated by quantitation of cysts.

Oocyst induced disease: The oocyst challenge model is ideal for this study because oocysts can be diluted at one time and stored at 4° C. for 12 months without loss of infectivity titer. For treatment of chronic infection there were 5 to 10 mice per group treated 2 months after infection was established by compound in DMSO for parenteral administration administered once per day. Treatment was for 17 days.

Zebrafish Zebrafish were acclimatized to 37 degrees a degree a day and then infected with tachyzoites or cysts of RH YFP, Me49, Veg *T. gondii* as described. The use of RH YFP was performed for the first time herein in order to develop a rapidly scalable assay for drug development. This is the initial demonstration of cyst formation by 10 days in Zebrafish.

Tissue processing and histopathology: All organs including eyes and brains were fixed in 0.1M phosphate buffer (pH 7.4) containing 4% formaldehyde. Sections were cut from paraffin-embedded tissues and stained with Hematoxylin and Eosin (H&E) or immunoperoxidase stained. All sections were examined and assessed without knowledge of the group from which they originated[S39].

Testing of Cytochrome b $Q_i$ Mutant Yeast

Target Validation with Mutant *S. cerevisiae* (Growth Inhibition):

Three *S. cerevisiae* strains were used: M221Q and M221F cytochrome b mutants and wild type. They share the same nuclear genetic background deriving from AD1-9 (kindly given by M. Ghislain, UCL, Belgium). AD1-9 harbors multiple deletions in the ABC transporter genes that render the strain more sensitive to drugs than standard yeast strainss[S65].

Cytochrome b mutant M221F was generated by mitochondrial transformation as described. M221Q was selected as suppressor from a respiratory deficient mutant. Analysis of revertants from respiratory deficient mutants within the center N of cytochrome b in *Saccharomyces cerevisiae*.

Protocol: Yeast strains were grown over 48 hours at 33° C. in liquid YPG medium [1% yeast extract, 2% (wt/vol) peptone, and 3% (vol/vol) glycerol). Cultures were diluted to an $OD_{600}$ of 0.05 and grown for 2 hrs. Cultures were then combined with YPG containing 6% melted agar for a total volume of 15-20 mL and poured onto OmniTray single-well rectangular plates that measured 86 mm by 128 mm (ThermoScientific). Filter paper disks (7 mm diameter, 3 um thick) were placed onto the cooled agar plates. Compounds were dissolved in DMSO in diluted concentrations (1 mM, 500 µM, 100 µM, and 10 µM) and 10 microliters were applied to a disk. A single disk with DMSO on each plate was used as a control. Plates were incubated at 33° C. Images were obtained after 4 days using GelDoc XR Imaging System (BioRad) and Quantity One software. Drug effect was assessed by the presence and size of a zone of inhibition around the disks.

Testing of *P. falciparum*: D6 is a drug sensitive strain from Sierra Leone, C235 is a multi-drug resistant strain from Thailand, W2 is a chloroquine resistant strain from Thailand, and C2B has resistance to a variety of drugs including atovaquone.

Testing of *P. falciparum* Cytochrome b Qi and DHODH Mutants and Drug Combinations for *P. falciparum*

Parasite Strains and Culture Maintenance. We used the following parasite line from the MR4 repository of the American Type Culture Collection (ATCC): Dd2 (MRA-156). Mutant Dd2 parasites harboring a G33A or G33V substitution in cytochrome b were as reported. Dd2 parasites with a G131S mutation in cytochrome b and transgenic lines expressing a chromosomally integrated copy of the *S. cerevisiae* DHODH were utilized as previously described. Parasites were cultured by standard methods in RPMI media supplemented with 5% human O⁺ serum and 0.25% AlbuMAX® II (Life Technologies 11021-045).

In Vitro Drug Sensitivity and $EC_{50}$ Determinations

Drug susceptibility was measured using the SYBR Green method. Twelve point curves based on 2-fold dilutions of the test compound were carried out in triplicate each day and replicated on at least three different days. $EC_{50}$ values were calculated using a nonlinear regression curve fit in Prism 6.0 for Mac (GraphPad Software, Inc.).

Studies of compound, drug combinations in vitro. Isobologram experiments were performed in similar fashion utilizing the modified fixed ratio methodology. Briefly, MJM170 and either atovaquone or cycloguanil or BRD6323 were mixed at multiple fixed volumetric ratios (10:0, 8:2, 6:4, 4:6, 2:8, and 0:10) and then serially diluted in 12-point 2-fold dilutions and dispensed in triplicate to 384-well assay plates and replicated on three different days. $EC_{50}$ values were calculated as above, and FICs were calculated for each drug combination as described[S76]. Synergy was defined as an FIC<1.0, additivity as FIC=1.0, and antagonism as FIC>1.0.

Molecular Modelling/Chemogenomics. X-ray structures of the cytochrome $bc_1$ complex are available from the Protein DataBank[S80]. An Homology model of the *T. gondii* cytochrome $bc_1$ complex was generated using the Phyre webserver. Molecular modelling and docking was performed on high performance Linux clusters at the University of Leeds, using specialist software: SPROUT[S82] & eHiTs[S83] (SymBioSis), Maestro & Glide[S84] (Schrodinger), AutoDock (Scripps Institute), ROCS/EON[S85] & VIDA[S86] (OpenEye) and the Marvin/JChem suites (ChemAxon).

X-ray crystallography: Cytochrome $bc_1$ was purified usig standard techniques. Crude bovine mitochondria were isolated from fresh cow heart and solubilised in DDM. The solution was clarified by ultracentrifugation at 200,000 g for 1 hour at 4° C. and the supernatant applied to a DEAE CL-6B sepharose column ca. 50 ml pre-equilibrated in 50 mM KPi (pH 7.5), 250 mM NaCl, 3 mM $NaN_3$, 0.1 g/L DDM, washed with two CV and eluted along a gradient from 250 mM to 500 mM NaCl. Cyt. $bc_1$ containing fractions were pooled and concentrated before loading on a Sepharose S300 column ca. 120 ml equilibrated with 20 mM KMOPS (pH 7.2), 100 mM NaCl, 0.5 mM EDTA, 0.1 g/L DDM at 0.5 ml/min. 10 mM MJM170 stock in DMSO was added to the eluted protein in a two-fold molar excess and allowed to incubate at 4° C. for 1 hour. Increasing amounts of PEG4000 were then added to precipitate cyt. $bc_1$ and separate remaining contaminants. The cyt. $bc_1$ was then resuspended before buffer exchange into a final buffer (25 mM KPi (pH 7.5), 3 mM $NaN_3$, 0.015% DDM) and concentrated to 40 mg/ml. 1.6% HECAMEG was added to the protein solution prior tp crystals growing by the hanging drop vapour diffusion method against a reservoir of 50 mM KPi (pH 6.8), 100 mM NaCl, 3 mM $NaN_3$, 9% PEG4000, 0.16% HECMAEG. Crystals were flash frozen in 23% glycerol in reservoir solution as a cryoprotectant. Multiple wedges of data were collected at 100K from different points on the same crystal at 124 Diamond Light Source using 0.9686 Å X-rays with a Pilatus3 6M detector.

Datasets were processed in iMosflm and combined using Blend to produce a complete merged dataset. Refinement was carried out with Refmac using Prosmart to generate secondary structure restraints to assist in the low-resolution refinement. The ligand MJM170 was produced using JLigand[S92] and modelled in the $Q_i$ site of cyt. $bc_1$ using Coot. Cycles of alternating Refmac5 and manual modelling resulted in a completed model. Data collection and refinement statistics are summarised In table 1A. For 3715 residues 95.2% are Ramachandran favored, 4.6% allowed and 0.3% outliers.

Interpretation of Data and Statistical Analyses (1) Sample size and number of experiments. There were 3 replicate samples per group for in vitro experiments. All experiments were performed with sufficient sample sizes to have an 80% power to detect differences at the 5% level of significance.

(2) Statistics. Groups included untreated or mock treated controls. Results were compared using students T test, Chi square analysis or Fisher's exact test as appropriate for the data set. When there were more than two groups, pairwise comparisons were made only when F-test for the ANOVA was significant at the 5% levels using protected least significant difference (LSD) test approach.

REFERENCES FOR EXAMPLE 1

1. Arevalo, J. F., Belfort, R. Jr., Muccioli, C. & Espinoza, J. V. Ocular toxoplasmosis in the developing world. Int Ophthalmol Clin. 50, 57-69 (2010).
2. Mulanovich, V. E. et al. Toxoplasmosis in allo-SCT patients: Risk factors and outcomes at a transplantation center with a low incidence. *Bone Marrow Transplant.* 46, 273-277 (2011).
3. Porter, S. B. & Sande, M. A. Toxoplasmosis of the central nervous system in the acquired immunodeficiency syndrome. *N Engl J Med.* 327, 1643-1648 (1992).4. McLeod, R. et al. Toxoplasmosis presenting as brain abscesses: Diagnosis by computerized tomography and cytology of aspirated purulent material. *Am. J Med.* 67, 711-714 (1979).
5. McLeod, R. et al. Levels of pyrimethamine in sera and cerebrospinal and ventricular fluids from infants treated for congenital toxoplasmosis: Toxoplasmosis Study Group. *Antimicrob Agents Chemother.* 36, 1040-1048 (1992).
6. McAuley, J. et al. Early and longitudinal evaluations of treated infants and children and untreated historical patients with congenital toxoplasmosis: the Chicago Collaborative Treatment Trial. *Clin Infect Dis.* 18, 38-72 (1994).
7. Delair, E. et al. Clinical Manifestations of Ocular Toxoplasmosis. *Ocul Immunol Inflamm.* 2, 91-102 (2011).
8. Boyer, K. et al. Unrecognized ingestion of *Toxoplasma gondii* oocysts leads to congenital toxoplasmosis and causes epidemics in North America. *Clin Infect Dis.* 53, 1081-1089 (2011).
9. McLeod, R. et al. Prematurity & Severity Associate with *T. gondii* Alleles (NCCCTS, 1981-2009). *Clin Infect Dis.* 54, 1595-1605 (2012).
10. McLeod, R. et al. Severe sulfadiazine hypersensitivity in a child with reactivated congenital toxoplasmic chorioretinitis. *Pediatr. Infect. Dis. J.* 25, 270-272 (2006).
11. Demar, M. et al. Acute toxoplasmosis in immunocompetent patients hospitalized in an intensive care unit in French Guiana. *Clinical Microbiology and Infection.* 18(7), E221-231 (July 2012).
12. Townsend, J. J., Wolinsky, J. S., Baringer, J. R. & Johnson, P. C. Acquired toxoplasmosis: A neglected cause of treatable nervous system disease. *Arch Neurol.* 32(5), 335-343 (May 1975).
13. Dubey, J. P., Lago, E. G., Gennari, S. M., Su, C. & Jones, J. L. Toxoplasmosis in humans and animals in Brazil: high prevalence, high burden of disease, and epidemiology. *Parasitology.* 139, 1375-1424 (September 2012).
14. Stommel, E. W. et al. Cryptogenic Epilepsy: An Infectious Etiology? *Epilepsia.* 42, 436-438 (March 2001).
15. Hermes, G. et al. Neurological and behavioral abnormalities, ventricular dilatation, altered cellular functions, inflammation, and neuronal injury in brains of mice due to common, persistent, parasitic infection. *J Neuroinflammation*. 5, 48 (2008).
16. Gajewski, P. D., Falkenstein, M., Hengstler, J. G. & Golka, K. *Toxoplasma gondii* impairs memory in infected seniors. *Brain, Behavior, and Immunity*. 36, 193-199 (February 2014).
17. Pernas, L., Ramirez, R., Holmes, T. H., Montoya, J. & Boothroyd, J. C. Immune Profiling of Pregnant *Toxoplasma*-Infected US and Colombia Patients Reveals Surprising Impacts of Infection on Peripheral Blood Cytokines. *JID*. 210, 923-931 (2014).
18. Araujo, F. G., Huskinson-Mark, J., Gutteridge, W. E. & Remington, J. S. In vitro and in vivo activities of the hydroxynaphthoquinone 566C80 against the cyst form of *Toxoplasma gondii*. *Antimicrob Agents Chemother*. 36, 326-330 (1992).
19. Torres, R. A. et al. Atovaquone/Toxoplasmic Encephalitis Study Group Atovaquone for salvage treatment and suppression of toxoplasmic encephalitis in patients with AIDS. *Chin InfectDis*. 24, 422-429 (1997).
20. Chirgwin, K. et al. Randomized phase II trial of atovaquone with pyrimethamine or sulfadiazine for treatment of toxoplasmic encephalitis in patients with acquired immunodeficiency syndrome: ACTG 237/ANRS 039 Study. AIDS Clinical Trials Group 23. *Clin Infect Dis*. 34, 1243-1250 (2002).
21. Winterhalter, S. et al. Does atovaquone prolong the disease-free interval of toxoplasmic retinochoroiditis? *Graefes Arch Clin Ex Ophthalmol*. 248, 1187-1192 (2010).
22. Djurković-Djaković, O., Milenković, V., Nikolić, A., Bobić, B. & Grujić, J. Efficacy of atovaquone combined with clindamycin against murine infection with a cystogenic (Me49) strain of *Toxoplasma gondii*. *J Antamicrob Chemother*. 50, 981-987 (2002).
23. Meneceur, P. et al. In vitro susceptibility of various genotypic strains of *Toxoplasma gondii* to pyrimethamine, sulfadiazine, and atovaquone. *Antimicrob Agents Chemother*. 52, 1269-1277 (2008).
24. McFadden, D. C., Seeber, F. & Boothroyd, J. C. Use of *Toxoplasma gondii* expressing beta-galactosidase for colorinetric assessment of drug activity in vitro. *Antimicrob Agents Chemother*. 41, 1849-1853 (1997).
24a. (CASTRO F. C. Correlacáo do diagnóstico pósnatal da toxoplasmose congenita com a reacao em cadeia da polime-rase no liquido amniótico, inoculaqáo em camundongo e achados anatomopatológicos da placenta. Thesis, Belo Horizonte, Brazil, 1999)
25. Paredes-Santos, T. C. et al. Spontaneous cystogenesis in vitro of a Brazilian strain of *Toxoplasma gondii*. Parasitol Int. 62(2), 181-188 (April 2013).
26. Sanders, I. et al. The zebrafish, *Danio rerio*, as a model for *Toxoplasma gondii*: an initial description of infection in fish. *J Fish Dis*. 38(7), 675-679 (July 2015).
27. Doggett, J. S. et al. Endochin-like quinolones are highly efficacious against acute and latent experimental toxoplasmosis. *Proc Natl Acad Sci USA*. 109(39) 15936-15941 (September 2012).
28. Salzer, W., Timmler, H. & Andersag, H. A new type of compound active against avian malaria. *Chem Ber*. 81, 12-19 (1948).
29. Gingrich, W. D. & Darrow, E. M. The effect of endochin on experimental toxoplasmosis. *Am J Trop Med Hyg*. 31, 12-17 (1951).
30. Kikuth, W. & Mudrow-Reichenow, L. Ueber kausalprophylaktisch bei Vogelmalaria wirksame Substanzen. *Z Hyg Infektionskr*. 127(1-2), 151-165 (1947).
31. Fieser, L. & Richardson, A. P. Naphthoquinone antimalarials; correlation of structure and activity against *P. lophurae* in ducks. *J Am Chem Soc*. 70(10), 3156-3165 (1948).
32. Looareesuwan, S. et al. Clinical studies of atovaquone, alone or in combination with other antimalarial drugs, for treatment of acute uncomplicated malaria in Thailand. *Am. J. Trop. Med. Hyg*. 54, 62-66 (1996).
33. Pudney, M., Yeates, C., Pearce, J., Jones, L. & Fry, M. New 4-pyridone antimalarials which potentiate the activity of atovaquone (566C80). *Proceedings of the XIIIth International Congress for Tropical Medicine and Malaria, Jomtien, Pattaya, Thailand*. Abstract 149 (November 29-Dec. 4, 1992)
34. Vercesi, A. E., Rodrigues, C. O., Uyemura, S. A., Zhong, L. & Moreno, S. N. Respiration and oxidative phosphorylation in the apicomplexan parasite *Toxoplasma gondii*. *J Biol Chem*. 273, 31040-31047 (1992).
35. Winter, R. W. et al. Evaluation and lead optimization of anti-malarial acridones. *Exp Parasitol*. 114, 47-56 (2006).
36. Winter, R. W. et al. Antimalarial quinolones: synthesis, potency, and mechanistic studies. *Exp Parasitol*. 118, 487-497 (2008).
37. Yeates, C. L. et al. Synthesis and structure-activity relationships of 4-pyridones as potential antimalarials. *J. Med. Chem*. 51, 2845-2852 (2008).
38. Mphahlele, M. J. & Mtshemla, V. 2-Aryl-4-chloro-3-iodoquinolines as substrates for the synthesis of 2,3-diaryl-4-methoxyquinolines. *J. Chem. Res*. 2008(8), 437-440 (2008).
39. Bajohr, L. L. el al. In vitro and in vivo activities of 1-hydroxy-2-alkyl-4(1H)quinolone derivatives against *Toxoplasma gondii*. *Antimicrob Agents Chemother*. 54, 517-521 (2010).
40. Cross, R. M. et al. Endochin optimization: structure-activity and structure-property relationship studies of 3-substituted 2-methyl-4(1H)-quinolones with antimalarial activity. *J Med Chem*. 53, 7076-7094 (2010).
41. Korsinczky, M. et al. Mutations in *Plasmodium falciparum* cytochrome b that are associated with atovaquone resistance are located at a putative drug-binding site. *Antimicrob Agents Chemother*. 44(8), 2100-2108 (2000).
42. Winter, R. et al. Optimization of endochin-like quinolones for antimalarial activity. *Exp Parasitol*. 127, 545-551 (2011).
43. Cross, R. M. et al. Optimization of 1,2,3,4-tetrahydroacridin-9(10H)-ones as antimalarials utilizing structure-activity and structure-property relationships. *J Med Chem*. 54 4399 (2011).
44. Fry, M. & Pudney, M. Site of action of the antimalarial hydroxynaphthoquinone, 2-[trans-4-(4'-chlorophenyl)cyclohexyl]-3-hydroxy-1,4-naphthoquinone (566C80). *Biochem Pharmacol*. 43, 1545 (1992).
45. Riscoe, M. K. et al., inventors; Oregon Health & Science University, assignee. Compounds having antiparasitic or anti-infectious activity. International patent WO 2010/065905 A2. 2010 June 10.
46. Vallieres, C. et al. HDQ, A potent inhibitor of *Plasmodium falciparum* proliferation binds to the Qi site of the bc1 complex. *Antimicrob Agents Chemother*. 56, 3739-3747 (2012).
47. Biagini, G. A. et al. Generation of quinolone antimalarials targeting the *Plasmodium falciparum* mitochon- 48. LaCrue, A. N. et al. 4(1H)-Quinolones with Liver Stage Activity against *Plasmodium berghei*. *Antimicrob Agents Chemother.* 57, 417 (2013).
49. Nilsen, A. et al. Discovery, Synthesis, and Optimization of Antimalarial 4(1H)-Quinolone-3-Diarylethers. *J Med Chem.* 57(9), 3818-3834 (2014).
50. Lukens, A. et al. Diversity-Oriented Synthesis Probe Targets *Plasmodium falciparum* Cytochrome b Ubiquinone Reduction Site and Synergizes With Oxidation Site Inhibitors. *J InfectDis.* 211(7), 1097-1103 (2015).
51. Boyom, F. F et al. Repurposing the Open Access Malaria Box To Discover Potent Inhibitors of *Toxoplasma gondii* and *Entamoeba histolytica*. Antimicrob Agents Chemother. 58(10), 5848-5854 (2014).
52. Capper, M. J. et al. *Antimalarial* 4(1H)-pyridones bind to the Qi site of cytochrome bc1. *Proc. Nati. Acad. Sci. USA.* 112(3), 755-760 (2015).
53. Nilsen, A. et al. Quinolone-3-diarylethers: anew class of antimalarial drug. *Sci Transl Med.* 5(177) 177ra37 (2013).
54. Brasseur, G. & Brivet-Chevillotte, P. Characterization of mutations in the mitochondrial cytochrome b gene of *Saccharomyces cerevisiae* affecting the quinone reductase site ($Q_N$). *Eur J Biochem.* 230, 1118-1124 (1995).
55. Hutson, S. L. et al. *T. gondii* RP promoters & knockdown reveal molecular pathways associated with proliferation and cell-cycle arrest. *PLoS One.* 5(11), e14057 (2010).
56. Smilkstein, M. J. et al. A drug-selected *Plasmodium falciparum* lacking the need for conventional electron transport. *Mol Biochem Parasitol.* 159(1), 64-68 (2008).
57. Ke, H. et al. Variation among *Plasmodium falciparum* strains on mitochondrial electron transport chain function. *Eukaryot Cell.* 10(8), 1053-1061 (2011).
58. Trumpower, B. L. & Edwards, C. A. Purification of a reconstitutively active iron-sulfur protein (oxidation factor) from succinate cytochrome c reductase complex of bovine heart mitochondria. *J. Biol. Chem.* 254, 8697-8706 (1979).
59. White, N. J. et al. Malaria. *Lancet.* 383, 723-735 (2014).
60. Burrows, J. N. et al. Antimalarial drug discovery—the path towards eradication. *Parasitology.* 141, 128-139 (2014).
61. Stickles, A. M. et al. Inhibition of cytochrome bc1 as a strategy for single-dose, multi-stage antimalarial therapy. *Am J Trop Med Hyg.* 92(6), 1195-1201 (2015).
62. Stickles, A. M. et al. Subtle changes in endochin-like quinolone structure alter the site of inhibition within the cytochrome bc1 complex of *Plasmodium falciparum*. *Antimicrob Agents Chemother.* 59(4), 1977-1982 (2015).
63. Bueno, J. M. et al. Exploration of 4(1H)-pyridones as a novel family of potent antimalarial inhibitors of the plasmodial cytochrome bc1. *Future Medicinal Chemistry.* 4(18), 2311-2323(2012) (doi: 10.4155/fmc.12.177).
64. Mui, E. et al. Novel triazine JPC-2067-B inhibits *Toxoplasma gondii* in vitro and in in vivo. *PLoS Negl Trop Dis.* 2(3):e190 (2008).
65. Saini, S. et al. MicroRNA-708 induces apoptosis and suppresses tumorigenicity in renal cancer cells. *Cancer Res.* 71, 6208-6219 (2011).
66. Radke, J. B., Transcriptional control of *Toxoplasma* development. PhD dissertation, University of South Florida (2014).

Example 2. Potent anti-apicomplexan tetrahydroquinolone

Summary: Apicomplexan infections cause substantial morbidity and mortality. Herein, we created a next generation tetrahydroquinolone that we found to be an anti-apicomplexan, mature, lead compound. We utilized sphere-like 3D space and predicted flexibility conferred by eliminating double bonds in this lead compound. This was to optimize ADMET and create a compound, JAG21, that is potent against *Toxoplasma gondii* tachyzoites (IC 90<125 nM) and bradyzoites (IC 90 500 nM), and drug resistant *Plasmodium falciparum* in vitro (IC 90<50 nM), not toxic to human HepG cells (>17 µM). Further, we demonstrate metabolic stability with assays for human and mouse liver microsomal activity and logs improved aqueous solubility at pH 7.4. This compound displays a balanced set of physicochemical and pharmacologic properties, including clean hERG, CYP profile, and a long (days in humans), predicted half-life and predicted ability to cross blood brain barrier. This allowed progression towards in vivo studies. In vivo *Toxoplasma* tachyzoites were cleared from mice at a dose of 5 mg/kg/day (IP). JAG21 acted in conjunction with tafenoquine (3 mg/kg single dose) to protect against a G0 arrested parasite that could persist in interferon ϒ knockout mice similar to the effect of tafenoquine for malaria hypnozoites. There was cure with oral dosing, 0.625 mg/kg, 3 oral doses of JAG21, and cure with a single dose of 2.5 mg/kg, of *P. berghei* sporozoite, blood and liver stages in mice. There was no parasitemia and 100% survival at 30 days. This mature lead compound has improved solubility and diminished toxicity relative to other cytochrome b Qi inhibitors, without formulation as a pro-drug. Selectivity for apicomplexan enzyme relative to mammalian enzymes was demonstrated with co-crystallography, binding and enzyme assays. This compound has real promise as a mature, lead compound.

Malaria results in death of one child every eleven seconds and 1 million children a year, with drug resistance eliminating usefulness of successive generations of new medicines each decade. The related apicomplexan parasite, *Toxoplasma gondii*, is the most frequent parasitic infection of humans, in the world. It is the second most frequent, single cause of food born associated death in the United States; It is the most frequent infectious cause of destruction of the back of the human eye; It is a cause of death and illness from recrudescent disease from its latent form in those who are immune compromised or immunologically immature; It has been estimated that in a ten year period, there are 1.9 million new cases of this congenital infection globally, causing 12 million disability adjusted life years from damage to the fetal brain and eye. This is a neglected, rarely diagnosed, and thus often untreated or mistreated disease. There are approximately 2 billion people throughout the world who have this parasite in their brain lifelong. No medicine eliminates this chronic encysted form of the parasite which causes epilepsy and may contribute to neurodegenerative disease. Certainly, new and improved medicines are greatly needed for both these diseases, These two apicomplexan parasites, *Plasmodia* and *Toxopalsma*, often share molecular targets inhibited by the same inhibitory compounds.

Herein we identify a mature lead compound that is highly efficacious against *T. gondii* tachyzoites and bradyzoites in vitro, tachyzoites in vivo, likely to be active against cysts in vivo with experiments ongoing, all drug resistant forms of *Plasmodium falciparum, Plasmodium berghei* in mouse model in single or three doses at low amounts against the sporozoite, blood and liver stages of plasmodium when administered orally at 2.5 mg/kg and at 1.25 mg kg for 100% of mice with three doses. It was found to add to protection in conjunction with tafenoquine in immune compromised mice infected with a G0/tachyzoite form of *T. gondii* which resembles the malaria hypnozoite when treated with tafenoquine in conjunction with anti-blood stage parasite compounds. The data which follow present the creation and characterization of this broad spectrum anti-apicomplexan lead compound.

Materials and Methods

*Toxoplasma gondii*

Tachyzoites of the RH—YFP strain were passaged in human foreskin fibroblasts (HFF cells)(15). Bradyzoite assays use the EGS strain, isolated from a human with congenital toxoplasmosis (16,17). These parasites are also passaged in human foreskin fibroblasts. RPS13 delta was prepared and utilized as described (Hutson, McLeod et al 2010)

Tetrahydroquinolone (THQ) Compounds

The THQ compounds were synthesized at the University of Leeds as described in Example 3. 10 mM stock solutions were made with 100% Dimethyl Sulfoxide (DMSO) [Sigma Aldrich] and working concentrations were made with IMDM-C (1×, [+] glutamine, [+] 25 mM HEPES, [−] Phenol red, 10% FBS)[Gibco, Denmark]). Compounds are shown herein.

In Vitro Challenge Assay for *Toxoplasma* Tachyzoites

Protocol adapted from Fomovska, et. al. (18,19). Human foreskin fibroblasts (HFF) were cultured on a flat, clear-bottomed, black 96-well plate to 90% to 100% confluence. IMDM (1×, [+] glutamine, [+] 25 mM HEPES, [+] Phenol red, 10% FBS [gibco, Denmark]) was removed from each well and replaced with IMDM-C (1×, [+] glutamine, [+] 25 mM HEPES, [−] Phenol red, 10% FBS)[gibco, Denmark]). Type I RH parasites expressing Yellow Fluorescent Protein (RH—YFP) were lysed from host cells by double passage through a 27-gauge needle. Parasites were counted and diluted to 32,000/mL in IMDM-C. Fibroblast cultures were infected with 3200 tachyzoites of the Type I RH strain expressing Yellow Fluorescent Protein (RH—YFP) and returned to incubator at 37° C. for 1-2 hours to allow for infection (15). Various concentrations of the compounds were made using IMDM-C, and 20 µl were added to each designated well, with triplicates for each condition. Controls included pyrimethamine/sulfadiazine (current standard of treatment), 0.1% DMSO only, fibroblast only, and an untreated YFP gradient with 2 fold dilutions of the parasite. Cells were incubated at 37° C. for 72 hours. Plates were read using a fluorimeter (Synergy H4 Hybrid Reader, BioTek) to ascertain the amount of yellow fluorescent protein, in relative fluorescence units (RFU), as a measure of parasite burden after treatment. Data was collected using Gen5 software. $IC_{50}$ was calculated by graphical analysis in Excel.

An initial screening assay of 10 µM, 1 µM, 100 nM, and 10 nM was performed. Compounds were not considered effective or pursued for further analysis if there were no signs of inhibition of tachyzoites at 1 µM. If compounds did appear to be effective at 1 µM, another experiment was conducted to assess effect at 1 µM, 500 nM, 250 nM, 125 nM, 62.5 nM, and 31.25 nM.

Cytotoxicity Assay

Toxicity assays were conducted using WST-1 cell proliferation reagent (Roche) as described in Fomovska, et. al. (18,19). HFF were grown on a flat, clear-bottomed, black 96-well plate. Confluent HFF were treated with inhibitory compounds at concentrations of 10 µM and 50 µM. Compounds were diluted in IMDM-C, and 20 µl were added to each designated well, with triplicates for each condition. A gradient of 2 fold-decreasing concentrations of DMSO from 10% to 0% in clear IMDM-C was used as a control. The plate was incubated for 72 hours at 37° C. 10 µl of WST-1 reagent (Roche) were added to each well and the cells were incubated for 30 to 60 minutes. Absorbance was read using a fluorimeter at 420 nm. A higher degree of color change (and absorbance) indicated mitochondrial activity and cell viability.

In Vitro Challenge Assay for Bradyzoites

HFF cells were grown in IMDM (1×, [+] glutamine, [+] 25 mM HEPES, [+] Phenol red, 10% FBS, [gibco, Denmark]) on removable, sterile glass disks in the bottom of a clear, flat-bottomed 24-well plate. Cultures were infected with $3\times10^4$ parasites (EGS strain) per well, in 0.5 mL media and plate was returned to incubator at 37° C. overnight. The following day, the media was removed and clear IMDM and compounds were added to making various concentrations of the drug, to a total volume of 0.5 mL. 2 wells were filled with media only, as a control. Plates were returned to the 37° C. incubator for 72 hours, and checked once every 24 hours. If tachyzoites were visible in the control before 72 hours, the cells were fixed and stained.

Cells were fixed using 4% paraformaldehyde and stained with Fluorescein-labeled *Dolichos biflorus* Agglutinin, DAPI, and BAG1. Disks were removed and mounted onto glass slides and visualized using microscopy (Nikon T17). Slides were scanned using a CRi Pannoramic Scan Whole Slide Scanner and viewed using Panoramic Viewer Software. Effects of the compounds were quantified by counting cysts in the controls and treated cells. Cysts and persisting organisms were counted in a representative field of view and then multiplied by a factor determined by the total area of the disk in order to estimate the number of cysts and organisms in each condition.

Assessment of Compound Degradation and Microbicidal Effect on *Toxoplasma*

HFF were cultured in a 96-well plate and infected with RH—YFP as described above on Day 0, 20 µL of compound was added to 9 wells for each compound and concentration (3 conditions, 3 wells per condition). In condition I, media was removed and replaced with fresh media on Day 3. In condition II, media was removed and replaced with fresh media and more compound on Day 3. In condition III, media was not replaced on Day 3, nor was the compound refreshed. On Day 6, media was removed and replaced with clean media in all wells. On Day 3, 6, and 9 plate was read in the fluorimeter and analyzed graphically in Prism (GraphPad Software).

*Toxoplasma* In Vivo

IVIS. Mice were infected intraperitoneally with $20\times10^3$ *Toxoplasma gondii* (Pru strain expressing luciferase) tachyzoites. Treatment commenced 2 hours later with JAG21 (5 mg/kg) which was dissolved in DMSO and administered intraperitoneally in a total volume of 0.05 ml. Mice were imaged every second day starting on day 4 post infection using a IVIS Spectrum (Caliper Life Sciences) for a 1 minute exposures, with medium binning, 20 minutes post injection with 150 mg/kg of D-luciferin potassium salt solution.

Brain cysts: Mice were infected intraperitoneally with $20\times10^3$. Treatment commenced 2 hours later with JAG21 (5 mg/kg) which was dissolved in DMSO and administered intraperitoneally in a total volume of 0.05 ml. After 30 days, treatment with JAG21 was begun each day for 14 days intraperitoneally. In experiments when tafenoquine was administered alone or with JAG21 in some groups 3 mg/kg tafenoquine was administered once on day −1. Cysts in brain were quantitated after concluding treatment RPS13 Δ. This G0 arrested parasite persists in tissue culture for prolonged times in the absence of tetracycline. The design of this experiment is shown in FIG. 13. The parasite (x) was used to infect interferon gamma knockout mice. For the first y days no tetracycline was administered. After that time tetracycline was administered. Mice were observed and at the time they appeared ill or at the termination of the experiment they were euthanized and tissues fixed in formalin and stained with hematoxylin and eosin or immunoperoxidase stained and parasite burden was assessed.

Malaria Assays

Methods for enzyme assays[21-3]: Professor Giancarlo A. Biagini, Dr Richard S. Priestley, Department of Parasitology, Liverpool School of Tropical Medicine, Pembroke Place, Liverpool, L3 5QA, UK.

Materials

*Plasmodium* falciparum: 3D7 strain was obtained from the Liverpool School of Tropical Medicine. Protease cocktail inhibitor was obtained from Roche. Bradford protein assay dye reagent was obtained from Bio-Rad. All other reagents were obtained from Sigma-Aldrich. Decylubiquinol was produced as per Fisher et al. (Fisher et al. 2004)[21]. In brief, 25 mg of decylubiquinone were dissolved in 400 µl of nitrogen-saturated hexane. An equal volume of aqueous 1 M sodium dithionite was added, and the mixture vortexed until colorless. The organic phase containing the decylubiquinol was collected, the solvent was evaporated under $N_2$ and the decylubiquinol finally dissolved in 100 µl of 96% ethanol (acidified with 10 mM HCl). Concentrations of decylubiquinol was determined spectrophotometrically on a Cary 300 Bio UV/visible spectrophotometer (Varian, UK) from absolute spectra, using 8288-320=8.1 mM-1 cm$^{-1}$. Decylubiquinol was stored at −80° C. and used within two weeks.

*Plasmodium falciparum*: Culture and Extract Preparation

*Plasmodium falciparum*: strain 3D7 blood-stage cultures were maintained by the method of Trager and Jensen (Trager & Jensen 2005)[23]. Cultures contained a 2% suspension of O+ human erythrocytes in RPMI 1640 medium containing L-glutamine and sodium carbonate, and supplemented with 10% pooled human AB+ serum, 25 mM HEPES (pH 7.4) and 20 µM gentamicin sulphate. Cultures were grown under a gaseous headspace of 4% O2 and 3% $CO_2$ in $N_2$ at 37° C. Cultures were grown to a parasitaemia of 5% before use.

The protocol for the preparation of parasite extract was adapted from Fisher et al. (Fisher et al. 2009)[22]. Free parasites were prepared from infected erythrocytes pooled from five T75 flasks, by adding 5 volumes of 0.15% (w/v) saponin in phosphate-buffered saline (137 mM NaCl, 2.7 mM KCl, 1.76 mM $K_2HPO_4$, 8.0 mM $Na_2HPO_4$, 5.5 mM D-glucose, pH 7.4) for 5 min, followed by three washes by centrifugation in RPMI containing HEPES (25 mM), and a final resuspension in potassium phosphate buffer (50 mM $K_2HPO_4$, 50 mM $KH_2PO_4$, 2 mM EDTA, pH7.4) containing a protease inhibitor cocktail (Complete Mini; Roche). Parasite extract was then prepared by disruption with a sonicating probe for 5 s, followed by a 1 min rest period on ice to prevent the sample overheating. This process was performed three times. The parasite extract was used immediately. The protein concentration of the parasite extract was determined by Bradford protein assay (Bio-Rad).

Pfbc$_1$ Native Assay

*Plasmodium falciparum*: bc$_1$ complex cytochrome c reductase (Pfbc$_1$) activity was measured by monitoring cytochrome c reduction at 550 versus 542 nm using a Cary 300 Bio UV-Visible Spectrophotometer (Varian, UK), using a protocol adapted from Fisher et al. (Fisher et al. 2009)[21-23]. The assay was performed in potassium phosphate buffer in a quartz cuvette and in a final volume of 700 µL. Potassium cyanide (10 µM), oxidised cytochrome c (30 µM), parasite extract (100 µg protein) and compound/DMSO were added sequentially to the cuvette, with mixing between each addition. Test compounds were added to a final concentration of 1 µM. DMSO (0.1% v/v) and atovaquone (1 µM), a known malarial cytochrome bc$_1$ complex inhibitor, were used as negative and positive controls respectively. The reaction was initiated by the addition of 50 µM decylubiquinol and allowed to proceed for 3 min.

Data Analysis

Malaria

In vitro studies: D6 is a drug sensitive strain from Sierra Leone, C235 is a multi-drug resistant strain from Thailand, W2 is a chloroquine resistant strain from Thailand, and C2B has resistance to a variety of drugs including atovaquone. These assays were performed as described.

Compound Activity Against *Plasmodium falciparum*:

Compound activity against *P. falciparum*, a causative agent of malaria, was tested using the Malaria SYBR Green I—Based Fluorescence (MSF) Assay. This; microtiter plate drug sensitivity assay uses the presence of malarial DNA as a measure of parasitic proliferation in the presence of antimalarial drugs or experimental compounds based on modifications of previously described methods by Plouffe et al (20) and Johnson et al. As the intercalation of SYBR Green I dye and its resulting fluorescence is relative to parasite growth, a test compound that inhibits the growth of the parasite will result in a lower fluorescence.

Selected compounds were examined for activity against four strains of *P. falciparum*: D6 (CDC/Sierra Leone), a drug-sensitive strain readily killed by chloroquine, TM91-C235, a multi-drug resistant strain resistant to chloroquine, W2, a chloroquine resistant strain from Thailand, and C2B has resistance to a variety of drugs including atovaquone.

*P. berghei* Model Sporozoite, Blood Stage, and Liver Stage Model.

*P. berghei* sporozoites. The methods that follow are taken directly from[24,25]: From laboratory-reared female *Anopheles stephensi*, isolation, inoculation and viability check *Plasmodium berghei* sporozoites (luciferase expressing) were obtained and maintained at 18° C. for 17 to 22 days after feeding on malaria-infected Swiss CD-1/ICR mice. From malaria-infected mosquitoes, salivary glands were extracted and sporozoites obtained. Briefly, mosquitoes were separated into head/thorax and abdomen. Thoraxes and heads were triturated with a mortar and pestle and suspended in medium RPMI 1640 containing 1% C57BL/6 mouse serum (Rockland Co, Gilbertsville, PA, USA). 50-80 heads with glands total were placed into a 0.5 ml Osaki tube on top of glass wool with enough dissection media to cover the heads. Until all mosquitoes had been dissected, the Osaki tube was kept on ice. Sporozoites that were isolated from the same batch of mosquitoes were inoculated into C57BL/6, 2D knock-out and 2D knock-out/2D6 knock-in C57BL/6 mice on the same day to control for biological variability in sporozoite preparations. On day 0, each mouse was inoculated intravenously in the tail vein with approximately 10,000 sporozoites suspended in 0.1 ml volume. They were stained with a vital dye containing fluorescein diacetate (50 mg/ml in acetone) and ethidium bromide (20 µg/ml in phosphate buffered saline; Sigma Chemical Co, St. Louis, MO, USA) and counted in a haemocytometer to ensure that inoculated sporozoites were viable following the isolation procedure. Viability of the sporozoites ranged from 90 to 100%.

Animals

The mice used in these experiments were Swiss Webster females. The animals were acclimated for seven days (quarantine) on arrival. The animals were housed in a cage maintained in a room with 34-68% relative humidity, a temperature range of 64-79° F., and a 12-hr light/dark cycles. Water and food were provided during quarantine and throughout the study. The mice were fed a standard rodent maintenance diet. All animal studies were performed under protocols that are IACUC-approved. All animal care, handling, and use was performed in accordance with the current Guide for the Care and Use of Laboratory Animals (1996).

Test Compounds and Administration

At the time of preparation of the suspension solution, compounds tested in these experiments were dosed based on the body weight. The suspension solution of oral agents, using homogenizer (PRO Scientific Inc, Monroe, CT, USA) with 10 mm open-slotted generator to homogenize drug powder mixture at 20,000-22,000 rpm for 5 min in ice bath, were prepared in 0.5% (w/v) hydroxyethyl cellulose and 0.2% (0.5% HECT, v/v) Tween-80 in distilled water.

A three consecutive day-treatment regimen (−1, 0, 1 day) or a once-a-day, one dose on day 0 was used in assessments. Drug suspensions were transferred to a 20-ml bottle, drawn into a 1-ml syringe, and delivered to the designated recipient via intragastric feeder (18 gauge).

1 hour after intravenous administration of 10,000 *P. berghei* sporozoites, single dose causal prophylaxis in 5 C57BL/6 albino mice at 2.5 mpk dosed on day 0. In 5 C57BL/6 albino mice, 3 dose causal prophylaxis treatment at 0.6 mpk dosed on days −1, 0, and +1.

In Vivo Imaging System Spectrum

All of the in vivo imaging system (IVIS) methods utilized have been described previously [6]. Briefly TQ and NPC-1161B were administered orally on days −1, 0 and 1 with respect to sporozoite inoculation. All inoculated mice were tested using the Xenogen IVIS-200 Spectrum (Caliper Life Sciences, Hopkinton, MA, USA) IVIS instrument at 24, 48 and 72 hr post-sporozoite infection. Additionally, using a flow cytometry system (FC500 MPL, Beckman Coulter, Miami, FL, USA), blood-stage infections were measured. For the IVIS calibration in each test, positive and negative controls were used. D-Luciferin potassium salt, (Xenogen, California and Goldbio, St Louis, MO, USA), the luciferase substrate, was inoculated intraperitoneally into mice at a concentration of 200 mg/kg 15 min before luminescence analysis. Three min post-luciferin administration the mice were anesthetized using isoflurane. The mice, in the IVIS on the 37° C. platform, were then positioned ventral side up. Through nose cone delivery, the mice continued to receive isoflurane. The exposure time of the camera was 5 min for the 24, 48 and 72 hr time points with f-stop=1 and large binning setting. Using Living Image® 3.0 software, photons emitted from specific regions were quantified.

Parasitemia was measured after days of IVIS imaging. During a total of 30 days, mice were observed and parasitemia level determined using FACs analysis. (Pybus et al. Malaria Journal 2013, 12:212; Marcsisin et al. Malaria Journal 2014, 13:2).

Bovine Cytochrome bc1 Purification Protocol

Preparation of crude mitochondria: Whole bovine heart was collected directly from slaughter and transported on ice to the cold room. All work was carried out at 4° C. Fat and other tissues were removed leaving only lean muscle that was then cut into small cubes. The cubes were then transferred to a waring blender and homogenisation buffer (250 mM sucrose; 20 mM $K_2HPO_4$; 2 mM succinic acid; 0.5 mM EDTA) was added at a ration of 2.6 L buffer per 1 L of muscle tissue. The solution was then homogenised. The resulting homogenate was adjusted to pH 7.8 using 2 M Tris and PMSF was added to a concentration of 0.1 mM. The homogenate was then centrifuged in a Sorvall GS-3 rotor at 3000 rpm for 20 mins. The resulting supernatant was then transferred to a Sorvall GSA rotor and centrifuged at 12,000 rpm for 20 mins. The pellet was then re-suspended and washed in buffer 1 (50 mM KPi (pH 7.5); 0.1 mM PMSF) before centrifugation under the same conditions again. The pellet was collected and frozen at −80° C. for use later.

Solubilisation of membrane proteins: The frozen mitochondria were thawed and re-suspended in buffer 2 (50 mM KPi (pH 7.5); 150 mM NaCl; 3 mM $NaN_3$; 0.1 mM PMSF) and a sample taken for a BCA assay. The remaining sample was centrifuged at 42,000 rpm in a Beckman Ti70 rotor for 60 mins. The pellet was re-suspended in the same wash buffer to a volume of 70 ml with the addition 0.1 mg DDM per 1 mg of protein and centrifuged at 42,000 rpm in a Beckman Ti70 rotor for 60 mins. The pellet was then re-suspended in the same wash buffer to a final volume of 215 ml with the addition of 0.9 mg DDM per 1 mg of protein and centrifuged for a final time at 42,000 rpm in a Beckman Ti70 rotor for 60 mins. The supernatant was collected.

Purification of cytochrome $bc_1$: Whilst being purified, the presence of protein was determined using 280 nm absorbance and the presence of haem was determined using 415 nm soret band peak and 462 nm absorbance. The solubilised protein solution was first applied to a DEAE-Sepharose CL-6B column (ca. 50 ml) pre-equilibrated in buffer A (50 mM KPi (pH 7.5); 150 mM NaCl; 0.03% DDM; 3 mM $NaN_3$) washed with 2 CV buffer A and eluted along a gradient with buffer B (50 mM KPi (pH 7.5); 350 mM NaCl; 0.03% DDM; 3 mM $NaN_3$). The collected protein was pooled and diluted twofold with buffer C (50 mM KPi (pH 7.5); 0.03% DDM; 3 mM $NaN_3$) before application to a hydroxyapatite column (ca. 15 ml) pre-equilibrated with buffer C. The column was washed with 10 CV of buffer C before elution along a gradient with Buffer C* (1000 mM KPi (pH 7.5); 0.03% DDM; 3 mM $NaN_3$). Fractions containing cytochrome $bc_1$, as identified by 415 nm absorbance, were then collected, pooled and concentrated to 1.5 ml using an Amicon Ultra-15 (Amicon, MWCO 100,000). The sample was then applied to a Sephacryl-S300 column (ca. 120 ml) pre-equilibrated in buffer D (25 mM KPi (pH 7.5); 100 mM NaCl; 0.015% DDM; 3 mM $NaN_3$) and ran at a flow rate of 0.5 ml/min. Purified cytochrome $bc_1$ fractions were then collected and concentrated to 30 mg/m.

Bovine Enzyme crystallography: Compounds designed using structure-based analyses of cytochrome b co-crystalized with JAG21 as described un Example 1[26]. This was done to optimize medicine-like properties using structure activity principles and analyses. Compounds synthesized as above were used in these assays as follows: 0.10 mM stock solutions were made with 100% Dimethyl Sulfoxide (DMSO) [Sigma Aldrich] and working concentrations were made with IMDM-C (1×, [+] glutamine, [+] 25 mM HEPES, [−] Phenol red, 10% FBS)[gibco, Denmark]).

Statistical Analysis: A Pearson test was used to confirm a correlation between increasing dose and increasing inhibition. An ANOVA and subsequent pairwise comparison with Dunnett correction was used to determine whether or not inhibition or toxicity at a given concentration was statistically significant. Stata/SE 12.1 was used for this analysis.

Results

Figure 8:
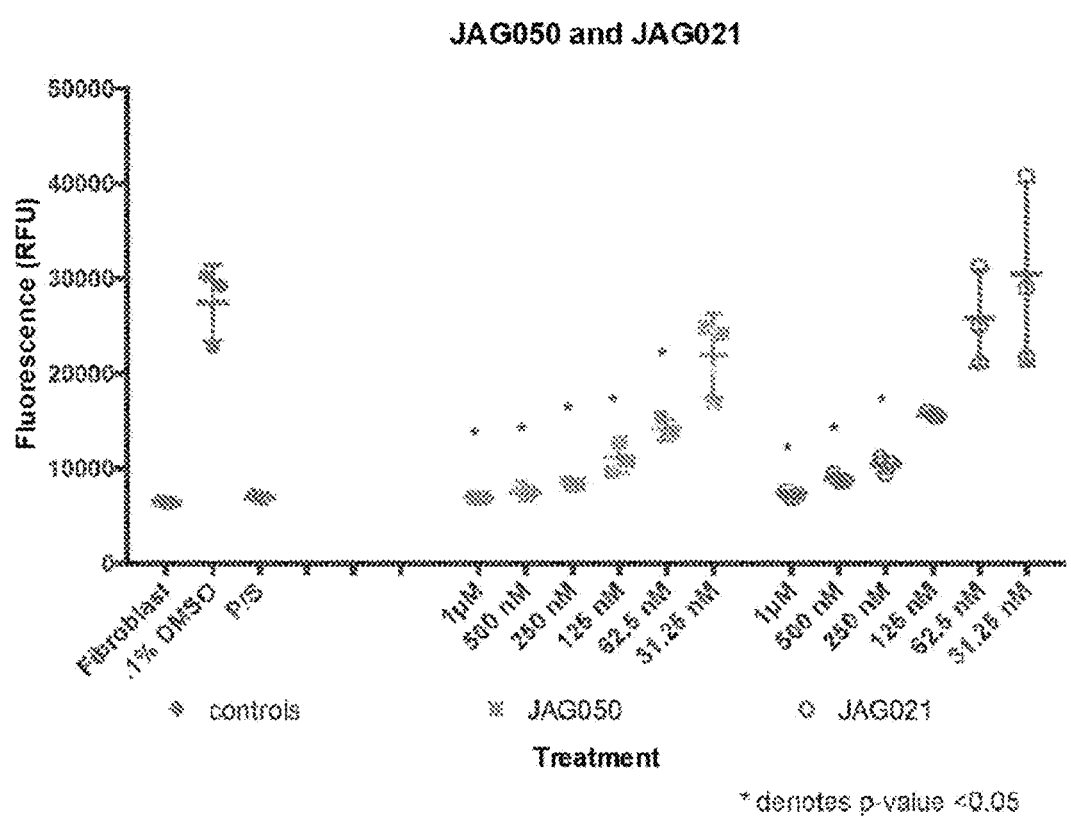
FIG. 8. Effects of compounds against RH—YFP. Graph is a representative example of an experiment testing two of the compounds against tachyzoites (RH—YFP). On the vertical axis is fluorescence in relative fluorescence units, where decrease in fluorescence compared to the DMSO control indicates parasite inhibition. On the horizontal axis are the different treatment conditions.

Tetrahydroquinolone Compounds:

In Vitro Challenge Assay for Tachyzoites: Seven compounds (Table 1) were tested and each compound was tested at least twice. JAG021 and JAG050 demonstrated effect below 1 µM, and were tested at lower concentrations. A representative graph of this data is shown in FIG. 8. JAG050 and JAG021 were identified as lead compounds because the $IC_{50}$ values were 55 and 188 nM respectively. Correlation between concentration of compound and inhibition of parasite growth and activity (as measured by fluorescence) was observed for all compounds except JAG046.

Figure 9:
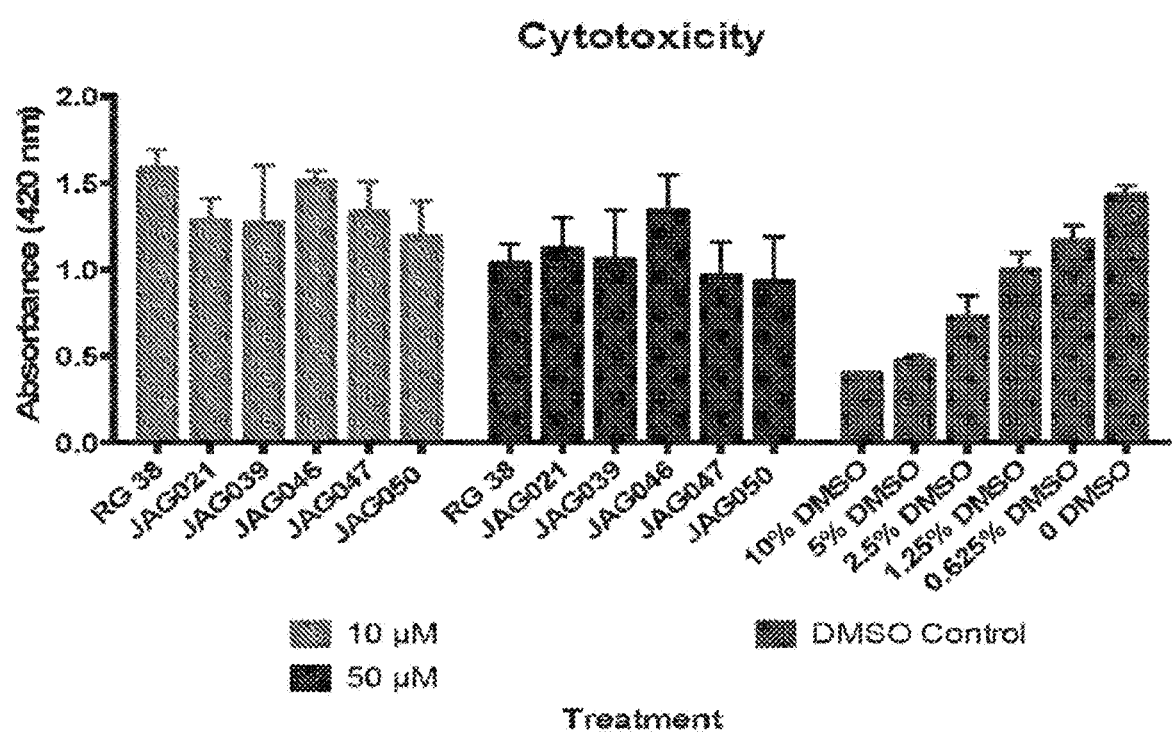
FIG. 9. The results of a cytotoxicity assay. 10 μM solution of compound was compared to the DMSO control closest to 0.1% DMSO (0% DMSO) and the 50 μM solution was compared to the DMSO control closest to 0.5% DMSO (0.625% DMSO). The differences were not found to be statistically significant.

Cytotoxicity Assay using HFF and WST-1 and IC50 with HEP G cells: Because *T. gondii* grows inside cells, if a compound was toxic to host Human Foreskin Fibroblast Cells (HFF), then it would make the compound appear to be spuriously effective; in actuality only toxicity for the host cell would be measured. Cytotoxicity to human foreskin fibroblasts was therefore assessed for all compounds at 10 µM and 50 µM. Results of this experiment are in FIG. 9 and Table 3. A two-way ANOVA and subsequent pairwise comparison found none of the differences in absorbance, compared to the controls, to be statistically significant ($p>0.05$). This suggests that these compounds are not toxic at 10 µM or 50 µM and that toxicity to cells is attributed to DMSO in the solution, not the compound. IC50 with HEP G cells was performed as described and toxicity was: HEP G2 IC50 17.70 microM ($r^2=0.97$) JAG 21; JAG 50 7.1 microM $r^2=0.98$.

In Vitro Challenge Assay for Bradyzoites

Figure 10A:
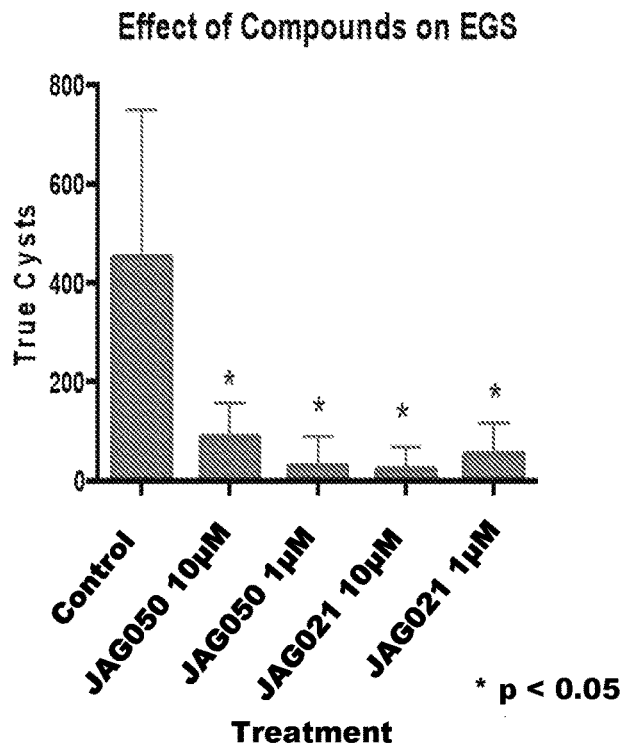
FIG. 10A-10C. Effects of compounds against EGS.
Figure 10B:
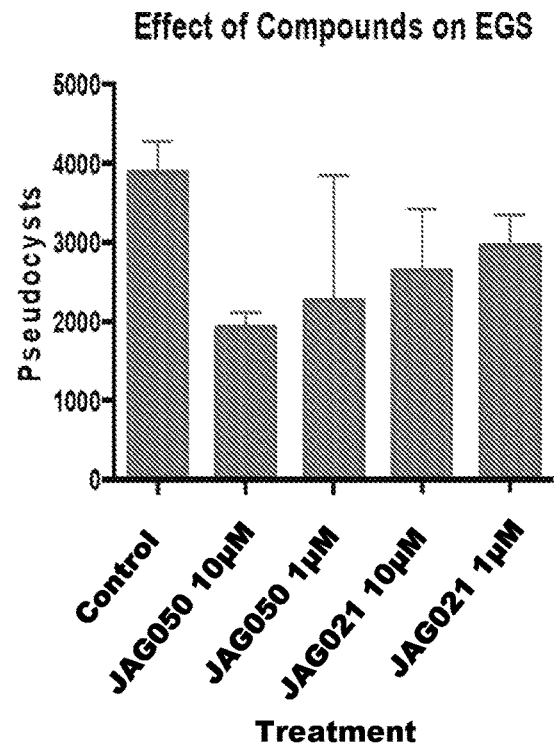
Figure 10C:
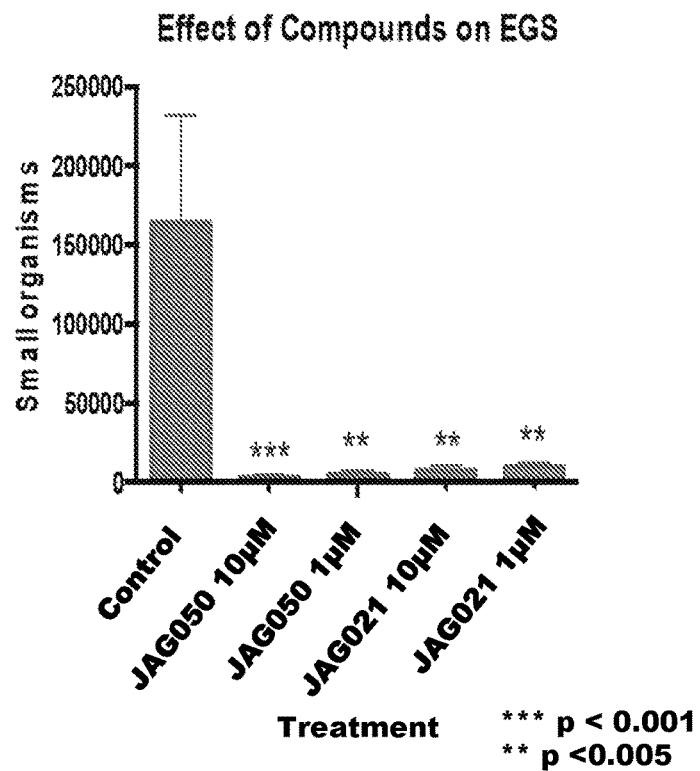

Lead compounds JAG050 and JAG021 were tested against EGS because of their effects on tachyzoites (RH—YFP). Under immunofluorescence microscopy, the following forms were observed: "true cysts" with a dolichos-staining wall, "pseudocysts" or tight clusters of parasites, and small organisms. If there were fewer than four parasites visible in a cluster, the organisms were counted individually (as "small organisms"). A statistically significant reduction in the number of true cysts and small organisms was observed at 1 µM and 10 µM for both compounds ($p<0.05$, $p<0.005$, FIGS. 10A-10C).

ADME properties of THQs. In vitro ADME analyse of the THQ compounds were outsourced to ChemPartner Shanghai Ltd. ELQ-271 was tested as a comparison. THQs which were potent inhibitors of *T. gondii* tachyzoites were assessed for their kinetic solubility, metabolic stability in human and mouse liver microsomes, and their ability to permeate across MDCK-MDK1 cell membranes (in vitro measure of blood-brain barrier (BBB) permeability). Solubility, half-life and BBB permeability/efflux results are shown in Table 4. The kinetic solubility (PBS, pH 7.4) of compounds JAG021 and JAG050, 7 and 16 µM respectively, were higher than MJM170 (2 µM) and ELQ-271 (0.2 µM). JAG021 was the most metabolically stable compound in human liver microsomes (>99% remaining after 45 mins) compared with other THQs and ELQ-271, although it displayed a much shorter half-life of 101 mins in mouse liver microsomes. All THQs tested in the MDK1 (MJM170, JAG021 and JAG050) MDCK-MDK1 system exhibit high permeability ($P_{app}>10\times 10^6$ cm/s) and low efflux (efflux ratio <1.5).

TABLE 4

Chart compares properties of solubility and half-life of JAG050 and JAG021 to parent compounds ELQ 271 and MJM170.

| Compound | Solubility (pH 7.4)* | Human liver microsomes[#] | Mouse liver microsomes[#] |
|---|---|---|---|
| ELQ271 | 0.15 µM | 171.93 min | 448.13 min |
| MJM170 | 1.97 µM | 146.33 min | 20.97 min |

TABLE 3

Cytotoxicity to human foreskin fibroblasts was therefore assessed for all compounds at 10 µM and 50 µM. Graph is representative of replicate experiment.

| Observation | Control | JAG050 10 µM | JAG050 1 µM | JAG021 10 µM | JAG021 1 µM |
|---|---|---|---|---|---|
| a | | | | | |
| True Cysts | 4.67 ± 3.06 [2-8] | 1 ± 0.82 [0-2] | 0.25 ± 0.5 [0-1] | 0.25 ± 0.5 [0-1] | 0.5 ± 0.6 [0-1] |
| Pseudocysts | 40.3 ± 11.4 [31-53] | 20.5 ± 2.9 [17-24] | 23.25 ± 10.31 [14-38] | 25.5 ± 5.1 [19-30] | 29 ± 6 [21-34] |
| Small organisms | 1600 ± 436 [1100-1900] | 31 ± 16 [8-43] | 58 ± 24 [27-85] | 73.25 ± 30.9 [30-101] | 90.5 ± 33.5 [63-137] |
| b | | | | | |
| True Cysts | 452 | 88 | 29 | 22 | 54 |
| Pseudocysts | 3884 | 1921 | 2269 | 2638 | 2955 |
| Small organisms | 16404 | 3018 | 5086 | 7309 | 9734 |

TABLE 4-continued

Chart compares properties of solubility and half-life of JAG050 and JAG021 to parent compounds ELQ 271 and MJM170.

| Compound | Solubility (pH 7.4)* | Human liver microsomes# | Mouse liver microsomes# |
|---|---|---|---|
| JAG021 | 7.07 µM | ∞ | 101.09 min |
| JAG050 | 16.41 µM | 99.04 min | 68.55 min |

The test system was 100 mM Phosphate Buffer (pH 7.4).:
<10 µM is low solubility,
10-80 µM is moderate solubility and
>80 µM is high solubility.
A $T_{1/2}$
< 30 minutes indicates susceptibility to metabolism,
between 30 and 120 minutes indicates moderate metabolism and
>120 minutes indicates stability in the liver.

Enzyme assays: Enzyme reduction of cytochrome c by the parasite extract is mediated by *P. falciparum* $bc_1$ complex cytochrome c reductase ($Pfbc_1$). All three compounds (1 µM) significantly inhibited the reduction of cytochrome c by the parasite extract, (JAG021=86.4±3.2; JAG099=81.3±6.0; MJM170=69.7±11.3% atovaquone response). This clearly demonstrates the compounds are inhibitors of $Pfbc_1$. Additional data demonstrating effect on bovine and *Plasmodium falciparum* enzyme are shown in Table 5. There is selectivity for the malaria enzyme.

TABLE 5

Inhibition of $Pfbc_1$ by compounds.

| Compound (1 µM) | Inhibition of cytochrome c reduction (% atovaquone response) |
|---|---|
| JAG021 | 86.4 ± 3.2 |
| JAG099 | 81.3 ± 6.0 |
| MJM170 | 69.7 ± 11.3 |

Data shown are mean ± s.e.m. of 4 independent experiments performed in triplicate.

Figure 11:
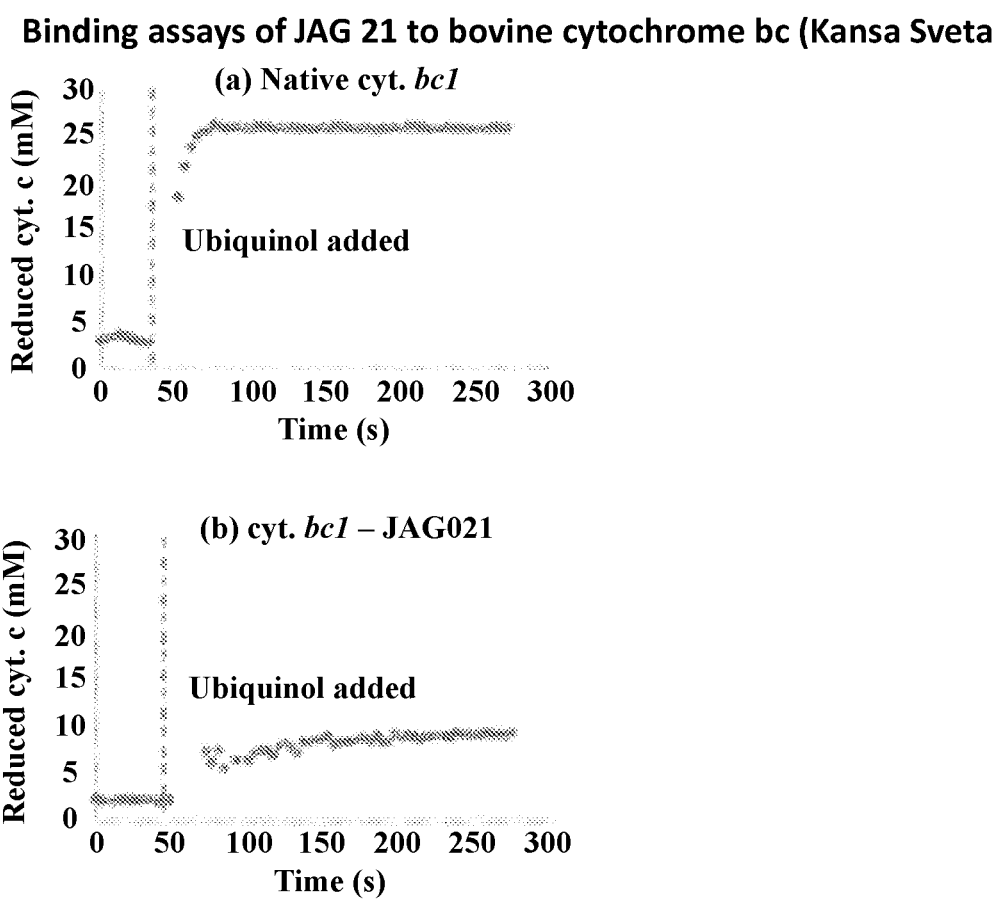
FIG. 11. Binding assays show selectivity with binding to the bovine enzyme which is not as robust as has been seen with other cytbc inhibitors FIG. 12A-12D. JAG21 is a mature lead that protects against $Toxoplasma$ $gondii$ tachyzoites and cures $Plasmodium$ $bergheii$ sprorozoites, blood and liver stages with oral administration of single dose 2.5 mg/kg and 3 doses protect at 0.5 mg/kg. Single dose causal prophylaxis in 5 C57BL/6 albino mice at 2.5 mpk dosed on day 0, 1 hour after intravenous administration of 10,000 $P.$ $berghei$ sporozoites. 3 dose causal prophylaxis treatment in 5 C57BL/6 albino mice at 0.6 mpk dosed on days −1, 0, and +1. A representative figure for higher dose (5 mg/kg) is shown, but all experiments with the amounts mentioned above had efficacy measured as cure measured as survival, luminesence and parasitemia quantitated by flow cytometry are similar to these.
Figure 12A:
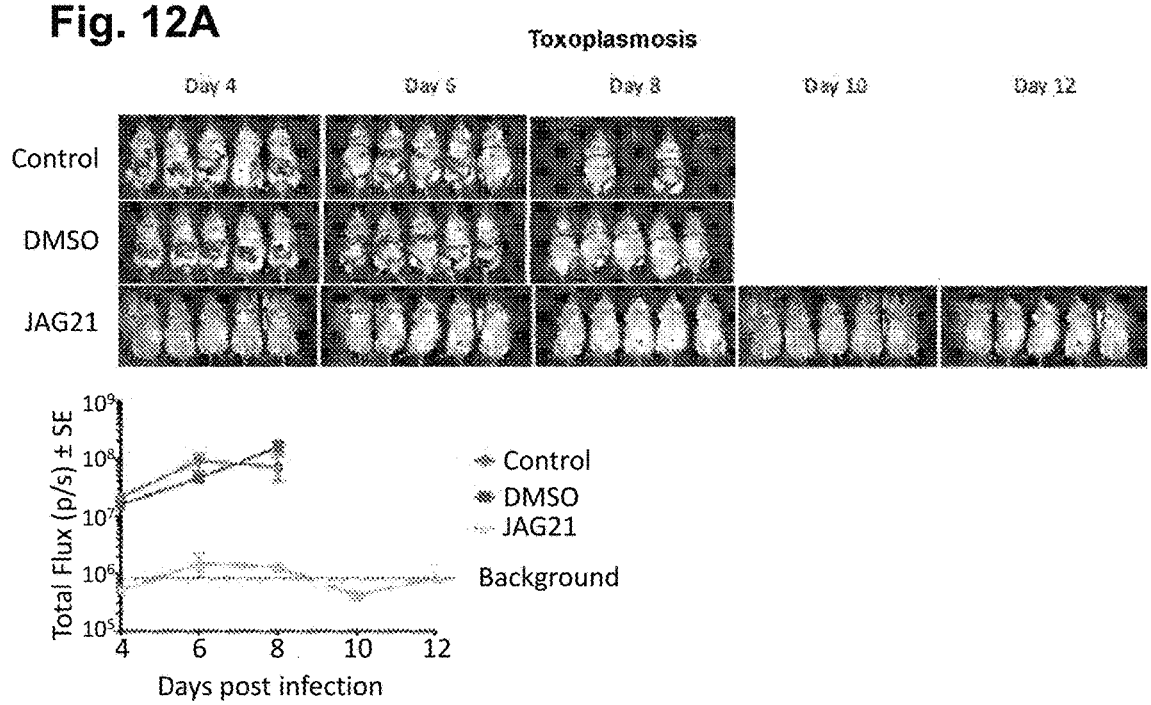
Figure 12B:
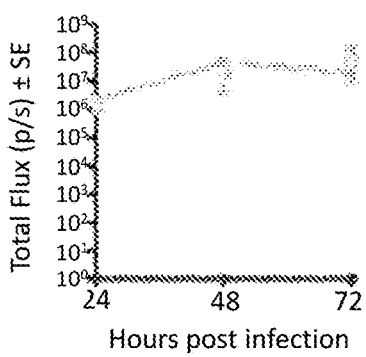
Figure 12C:
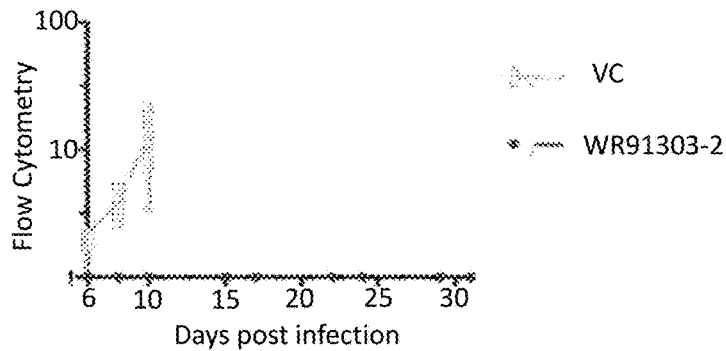
Figure 12D:
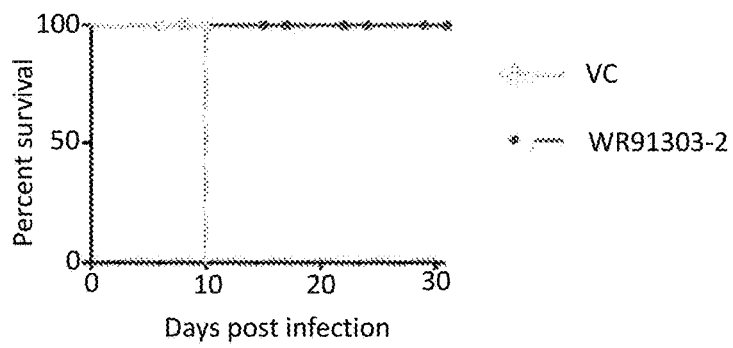

Binding assays and co crystallography. JAG021 has lower binding affinity to bovine cytochrome bc in comparison with previous compounds that we have tested. JAG 21 'inhibits' Cytbc1 but not fully, indicating that it will be less toxic for bovine/human cyt bc (FIG. 11)

Assessment of Compound Degradation and Microbicidal Effect on *Toxoplasma gondii* Compounds JAG050 and JAG021 were observed for degradation and microbicidal effect. Neither compound was found to be microbicidal; when media was replaced with clean media, the parasites appeared to resume activity and replication. In comparing the 6-day exposure with no addition of compound to the 6-day exposure with the addition of compound, it did not appear that the compound was being degraded over time. In condition II, in which the compound is refreshed, there appears to be a rise in fluorescence on day 6 in the 1 µM treatment group for both compounds. However, these differences were not found to be statistically significant (p>0.05).

Effective of JAG21 on *Toxoplasma gondii*. JAG21 at 5 mg/kg eliminates *T. gondii* tachyzoites seen in luminescence studies (FIGS. 12A-12D).

JAG21 against G0 arrested and normal (no tet repressor) *Toxoplasma* RPS13 delta in Interferon gamma knockout mice plus and minus tetracycline. Our data show that the combination of JAG21 and tafenoquine treatment is superior to either alone against RPS13Δ minus tetracycline (FIG. 13). The data indicates that this appears to be a dormant parasite that is less susceptible to JAG21 than either the slowly growing EGS bradyzoites or the rapidly proliferating tachyzoites.

Malaria:

In vitro. Results are shown in Table 6. JAG 21 is a 40-65 nM inhibitor of *Plasmodium falciparum* including effect against all drug resistant strains. The effects of the other compounds are also shown in this table and are in the range of 50-200 nM.

TABLE 6

Inhibition of *P falciparum* in vitro including drug resistant isolates

| Compound ID | SYBR Green D6 IC50 (uM) | SYBR D6 $R^2$ | SYBR Green C235 IC50 (uM) | SYBR TM91C235 $R^2$ | SYBR Green W2 IC50 (uM) | SYBR W2 $R^2$ | SYBR Green C2B IC50 (uM) | SYBR C2B $R^2$ |
|---|---|---|---|---|---|---|---|---|
| JAG006 | 0.29 | 0.90 | 0.88 | 0.92 | 2.46 | 0.92 | 1.66 | 0.94 |
| JAG021 | 0.01435 | 0.9572 | 0.06164 | 0.9706 | 0.05518 | 0.9727 | 0.04042 | 0.9847 |
| JAG050 | 0.04664 | 0.9138 | 0.06913 | 0.9562 | 0.03136 | 0.9693 | 0.03635 | 0.9427 |
| JAG047 | 3.746 | 0.9738 | 12.56 | 0.9218 | 9.072 | 0.9358 | 7.781 | 0.9575 |
| JAG039 | 9.595 | 0.9532 | >20 | N/A | >20 | N/A | >20 | N/A |
| JAG046 | 6.716 | 0.9844 | >20 | N/A | >20 | N/A | >20 | N/A |
| RG38 | 2.84 | 0.8936 | 13.66 | 0.8338 | 9.245 | 0.7954 | >20 | N/A |

In vivo. Single dose causal prophylaxis in 5 C57BL/6 albino mice at 2.5 mpk dosed on day 0, 1 hour after intravenous administration of 10,000 *P. berghei* sporozoites. 3 dose causal prophylaxis treatment in 5 C57BL/6 albino mice at 0.6 mpk dosed on days −1, 0, and +1. A representative figure for higher dose (5 mg/kg) is shown, but all experiments with the amounts mentioned above had efficacy measured as cure measured as survival, luminesence and parasitemia quantitated by flow cytometry are similar to these. (FIGS. 12A-12D)

Discussion

JAG050 and JAG021 were identified as lead compounds, demonstrating potent inhibition of tachyzoites and bradyzoites and no toxicity to human foreskin fibroblasts in our in vitro model. While compounds inhibited parasite replication and activity, there did not appear to be a microbicidal effect.

Toxoplasmosis is highly prevalent and the impact of this disease can be devastatingly severe. Current treatments have toxic side effects and are not curative. JAG050 and JAG021 are lead compounds in the search for a new curative medicine because they demonstrate effect on both life stages and were not toxic to the human cells in our in vitro model.

Experiments testing the compounds against the EGS strain had some surprising findings. While true cysts in vitro appeared to be completely eliminated by treatment, or their number significantly reduced, parasites did persist in tight, clustered, cyst-like structures, or pseudo-cysts, and small punctate life forms that resemble tachyzoites. One possible explanation is that the dolichos-staining organisms that remain 48 hours after treatment are in a separate, hypnozoite-like life stage that is not affected by the compounds.

JAG050 and JAG021 do not appear to have a microbicidal effect on the RH—YFP parasites. However, in comparing the two conditions in which cells and parasites were exposed to the drug for 6 days, it does not appear that the parasites or host cells are degrading the compounds. In order to cure toxoplasmosis, a companion drug that can work synergistically with the compounds of the present invention may be helpful. Primaquine and tafenoquine, which are the only medicines that can treat the hypnozoite stage of *Plasmodium vivax* and *P. ovale*, may be potential candidates. We had demonstrated synergy with an earlier generation compound with atovaquone and additive effect with cycloguanil.[26]

JAG21 demonstrated high efficacy against Toxopalsma tachyzoites in our vitro and in vivo models, low nanoM efficacy against drug resistant *P. falciparum*, and single dose causal prophylaxis in a mouse model of *P. berghei* sporozoites infection

REFERENCES FOR EXAMPLE 2

1. CDC—Toxoplasmosis [Internet]. [cited 2015 Jul. 1].
2. Montoya J, Liesenfeld O. Toxoplasmosis. The Lancet [Internet]. 2004 Jun. 12 [cited 2015 Jul. 1]; 363(9425): 1965-76.
3. McLeod R, Vantubbergen C, Boyer K. Toxoplasmosis (*Toxoplasma gondii*). In: Nelson Textbook of Pediatrics. 20th ed. Elsevier; 2015.
4. Jones J L, Holland G N. Annual Burden of Ocular Toxoplasmosis in the United States. Am J Trop Med Hyg [Internet]. 2010 March [cited 2015 Jul. 1]; 82(3):464-5.
5. Wallon M, Garweg J G, Abrahamowicz M, Cornu C, Vinault S, Quantin C, et al. Ophthalmic outcomes of congenital toxoplasmosis followed until adolescence. Pediatrics. 2014 March; 133(3):e601-8.
6. Roberts F, McLeod R. Pathogenesis of toxoplasmic retinochoroiditis. Parasitol Today Pers Ed. 1999 February; 15(2):51-7.
7. McLeod R, Khan A R, Noble G A, Latkany P, Jalbrzikowski J, Boyer K. SEVERE SULFADIAZINE HYPERSENSITIVITY IN A CHILD WITH REACTIVATED CONGENITAL TOXOPLASMIC CHORIORETINITIS: Pediatr Infect Dis J [Internet]. 2006 March [cited 2015 Jun. 16]; 25(3):270-2.
8. Waxman S, Herbert V. Mechanism of pyrimethamine-induced megaloblastosis in human bone marrow. N Engl J Med. 1969 Jun. 12; 280(24):1316-9.
9. Caumes E, Bocquet H, Guermonprez G, Rogeaux O, Bricaire F, Katlama C, et al. Adverse cutaneous reactions to pyrimethamine/sulfadiazine and pyrimethamine/clindamycin in patients with AIDS and toxoplasmic encephalitis. Clin Infect Dis Off Publ Infect Dis Soc Am. 1995 September; 21(3):656-8.
10. Phan L, Kasza K, Jalbrzikowski J, Noble A G, Latkany P, Kuo A, et al. Longitudinal study of new eye lesions in children with toxoplasmosis who were not treated during the first year of life. Am J Ophthalmol. 2008 September; 146(3).
11. Vercesi A E, Rodrigues C O, Uyemura S A, Zhong L, Moreno S N J. Respiration and Oxidative Phosphorylation in the Apicomplexan Parasite *Toxoplasma gondii*. J Biol Chem [Internet]. 1998 Nov. 20 [cited 2015 Jun. 16]; 273(47):31040-7.
12. Khan A A, Nasr M, Araujo F G. Two 2-hydroxy-3-alkyl-1,4-naphthoquinones with in vitro and in vivo activities against *Toxoplasma gondii*. Antimicrob Agents Chemother. 1998 September; 42(9):2284-9.
13. Doggett J S, Nilsen A, Forquer I, Wegmann K W, Jones-Brando L, Yolken R H, et al. Endochin-like quinolones are highly efficacious against acute and latent experimental toxoplasmosis. Proc Natl Acad Sci USA. 2012 Sep. 25; 109(39):15936-41.
14. Capper M J, O'Neill P M, Fisher N, Strange R W, Moss D, Ward S A, et al. Antimalarial 4(1H)-pyridones bind to the Qi site of cytochrome bc1. Proc Natl Acad Sci USA. 2015 Jan. 20; 112(3):755-60.
15. Gubbels M-J, Li C, Striepen B. High-Throughput Growth Assay for *Toxoplasma gondii* Using Yellow Fluorescent Protein. Antimicrob Agents Chemother [Internet]. 2003 January [cited 2015 Jul. 8]; 47(1):309-16.
16. Vidigal P V T, Santos D V V, Castro F C, Couto J C de F, Vitor R W de A, Brasileiro Filho G. Prenatal toxoplasmosis diagnosis from amniotic fluid by PCR. Rev Soc Bras Med Trop [Internet]. 2002 February [cited 2015 Jul. 8]; 35(1):1-6.
17. Silva L A, Brandao G P, Pinheiro B V, Vitor R W A. Immunosuppression with cyclophosphamide favors reinfection with recombinant *Toxoplasma gondii* strains. Parasite J Societe Fr Parasitol [Internet]. 2012 August [cited 2015 Jul. 8]; 19(3):249-57.
18. Fomovska A, Huang Q, El Bissati K, Mui E J, Witola W H, Cheng G, et al. Novel N-Benzoyl-2-Hydroxybenzamide Disrupts Unique Parasite Secretory Pathway. Antimicrob Agents Chemother [Internet]. 2012 May [cited 2015 Jul. 8]; 56(5):2666-82.
19. Fomovska A, Wood R D, Mui E, Dubey J P, Ferreira L R, Hickman M R, et al. Salicylanilide inhibitors of *Toxoplasma gondii*. J Med Chem. 2012 Oct. 11; 55(19):8375-91.
20. Galen P. Miley, Sovitj Pou, Rolf Winter, Aaron Nilsen, Yuexin Li, Jane X. Kelly, Allison M. Stickles, Michael W. Mather, c Isaac P. Forquer, a April M. Pershing, Karen White, David Shackleford, Jessica Saunders, Gong Chen, Li-Min Ting, Kami Kim, N. Zakharov, Cristina Donini, Jeremy N. Burrows, Akhil B. Vaidya Susan A. Charman, Michael K. Risco, ELQ-300 Prodrugs for Enhanced Delivery and Single-Dose Cure of Malaria 2015 AAC 59: 5555-556
21. Fisher, N. et al., 2009. Chapter 17 Type II NADH: Quinone Oxidoreductases of *Plasmodium Falciparum* and *Mycobacterium Tuberculosis*: Kinetic and High-Throughput Assays. In B. T.-M. in Enzymology, ed. *Mitochondrial Function, Part A: Mitochondrial Electron Transport Complexes and Reactive Oxygen Species*. Academic Press, pp. 303-320.
22. Fisher, N. et al., 2004. Human disease-related mutations in cytochrome b studied in yeast. *The Journal of biological chemistry*, 279(13), pp. 12951-12958.
23. Trager, W. & Jensen, J. B., 2005. Human malaria parasites in continuous culture. 1976. *The Journal of parasitology*, 91(3), pp. 484-486.

24. Pybus et al. Malaria Journal 2013, 12:212.
25. Marcsisin et al. Malaria Journal 2014, 13:2.
26. McPhillie M SREP(Nature) Jume 2016

Example 3: Synthesis and Activity of Compounds

All reagents and solvents were purchased from commercial sources. All commercial reagents and solvents were used as received without further purification. The reactions were monitored using analytical thin layer chromatography (TLC) with 0.25 mm EM Science silica gel plates (60F-254). The developed TLC plates were visualized by short wave UV light (254 nm) or immersion in potassium permanganate solution followed by heating on a hot plate. Flash chromatography was performed with Selecto Scientific silica gel, 32-63 μm particle sizes. All reactions were performed in flame or oven-dried glassware under a nitrogen atmosphere. All reactions were stirred magnetically at ambient temperature unless otherwise indicated. $^1$H NMR spectra were obtained with a Bruker DRX400, Varian VXR400 or VXR300. $^1$H NMR spectra were reported in parts per million (δ) relative to TMS (0.0), DMSO-d6 (2.50) or CD$_3$OD (4.80) as an internal reference. All $^1$H NMR spectra were taken in CDCl3 unless otherwise indicated.

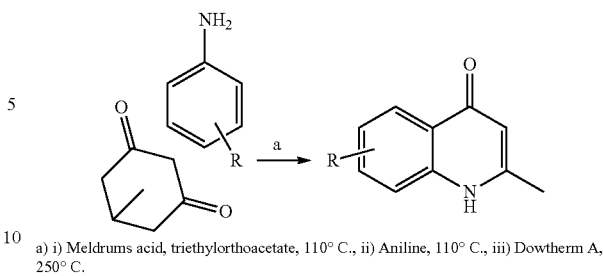

a) i) Meldrums acid, triethylorthoacetate, 110° C., ii) Aniline, 110° C., iii) Dowtherm A, 250° C.

General Method A 2,2-Dimethyl-1,3-dioxane-4,6-dione (1.5 equiv.) was dissolved in trimethylorthoacetate (2 equiv.) and heated to 115° C. for 2 hrs. The reaction was cooled to allow the addition of the aniline (1 equiv.) before being heated to 115° C. for a further 2 hrs. The reaction mixture was then allowed to cool and was concentrated in vacuo, remaining solvent was washed off with cold methanol. The precipitate was then dissolved in minimum volume of Dowtherm A and refluxed

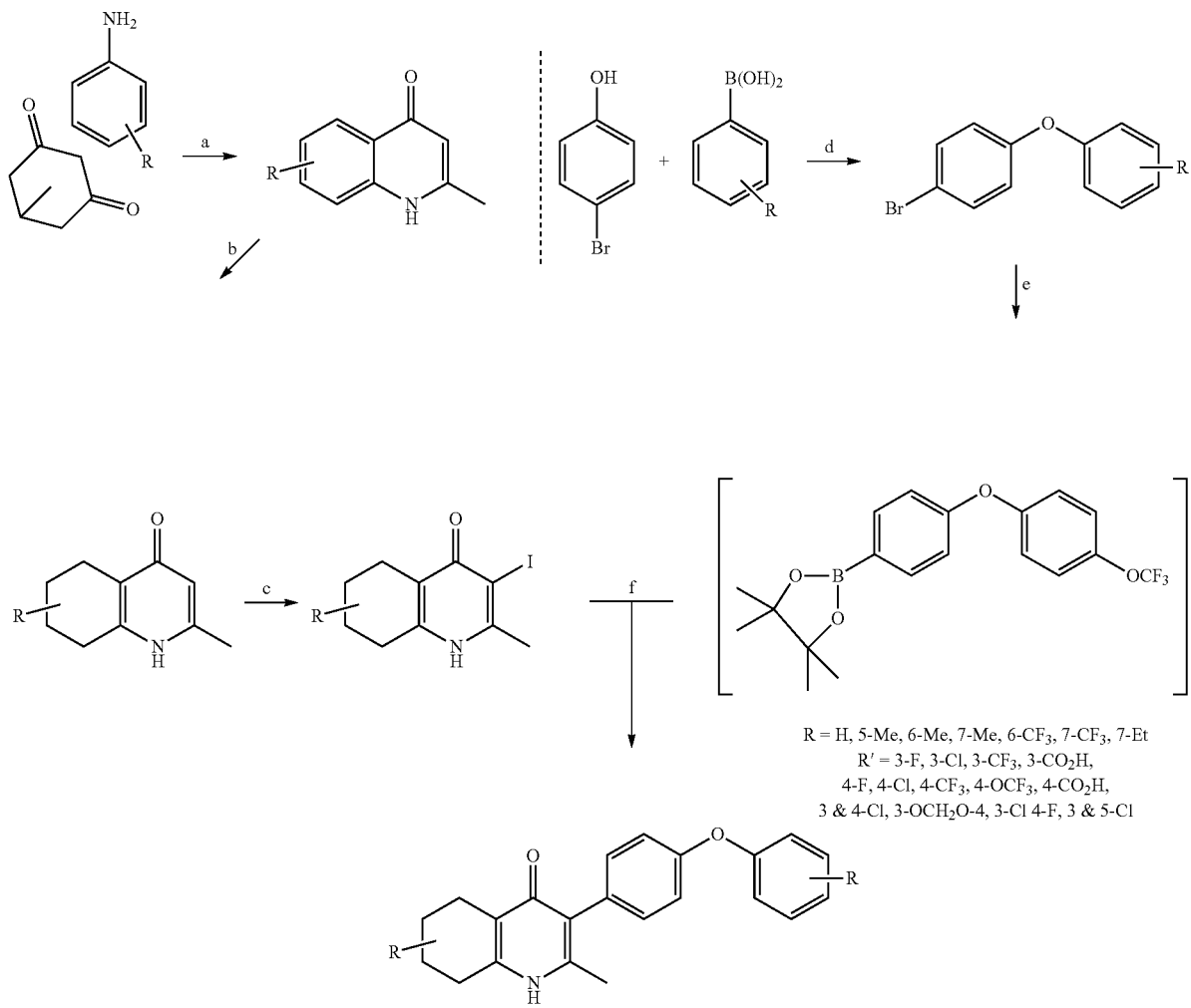

R = H, 5-Me, 6-Me, 7-Me, 6-CF$_3$, 7-CF$_3$, 7-Et
R' = 3-F, 3-Cl, 3-CF$_3$, 3-CO$_2$H,
4-F, 4-Cl, 4-CF$_3$, 4-OCF$_3$, 4-CO$_2$H,
3 & 4-Cl, 3-OCH$_2$O-4, 3-Cl 4-F, 3 & 5-Cl a) i) Meldrums acid, triethylorthoacetate, 110° C., ii) Aniline, 110° C., iii) Dowtherm A, 250° C., b) PtO$_2$, H$_2$, AcOH, c) NIS, Acetonitrile, 80° C., d) Cu(OAc)$_2$, Pyridine, TEA, DCM, e) Pd(dppf)Cl$_2$, Bispincolatodiborane, KOAc, DMF, 80° C. f) Pd(dppf)Cl$_2$, Na$_2$CO$_3$, DMF, 80° C.

at 250° C. for 1.5 hours. The reaction mixture was allowed to cool and the precipitate filtered followed by washing with hexane to afford the title compound.

2-Methyl-6-(trifluoromethyl)quinolin-4(1H)-one

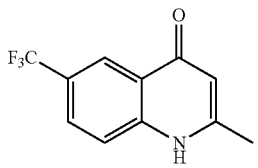 [SMILES: Cc1cc(=O)c2cc(C(F)(F)F)ccc2[nH]1]

The title compound was synthesised by general method A using 4-trifluoromethyl aniline (2.00 g, 12.4 mmol) to yield the title compound as a white amorphous solid (466 mg, 2.05 mmol, 17%). $^1$H NMR (300 MHz, MeOD) δ 8.42 (s, 1H), 7.81 (dd, J=8.8 Hz, 2.1 Hz, 1H), 7.60 (d, J=8.8 Hz, 1H), 6.16 (s, 1H), 2.40 (s, 3H); M/Z (ESI+); 228.06 (Found MH$^+$228.0634, C$_{11}$H$_8$F$_3$NO requires 228.0630).

7-ethyl-2-methylquinolin-4(1H)-one

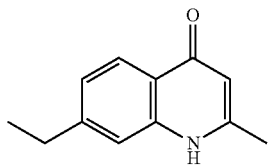

The title compound was synthesised following general procedure A from 3-ethylaniline (1.4 mL, 11.1 mmol). The title compound was isolated as a colourless solid (210 mg, 1.12 mmol, 10%). $^1$H NMR (500 MHz, CDCl3) δ 9.72 (s, 1H), 8.17 (d, J=8.3 Hz, 1H), 7.16 (s, 1H), 7.10 (d, J=8.3 Hz, 1H), 6.07 (s, 1H), 2.66 (q, J=7.6 Hz, 2H), 2.33 (s, 3H), 1.18 (t, J=7.6 Hz, 3H);

2,7-Dimethylquinolin-4(1H)-one

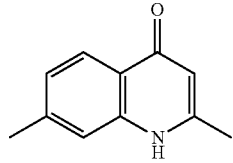

The title compound was synthesised following general procedure A from 3-methylaniline (7.5 mL, 42 mmol). The title compound was isolated as a colourless solid (370 mg, 2.13 mmol, 5%). $^1$H NMR (400 MHz, CDCl3) δ 9.58 (s, 1H), 8.24 (d, J=8.3 Hz, 1H), 7.22 (s, 1H), 7.16 (d, J=8.3 Hz, 1H), 6.15 (s, 1H), 2.46 (s, 3H), 2.41 (s, 3H).

7-trifluormethyl-2-methylquinolin-4(1H)-one

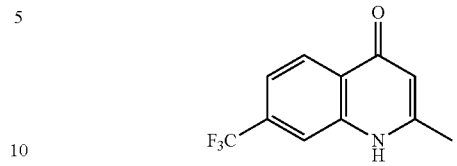

The title compound was synthesised following general procedure A from 3-trifluoromethyl-aniline (3 mL, 24 mmol). The title compound was isolated with its regiomer and separation was not achieved and so was carried forwards as a mixture (1.5 g).

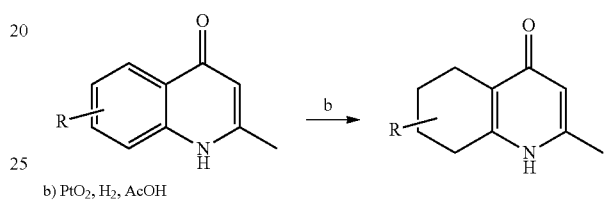

b) PtO$_2$, H$_2$, AcOH

General Method B

The 4-hydroxylquinolone (1 equiv.) was dissolved in acetic acid (10.0 mL) under inert conditions. platinum dioxide (5% weight equiv.) was added and a hydrogen balloon was attached. The reaction was left to proceed for 12 hours. The resulting suspension was filtered through a pad of Celite and washed with ethyl acetate (10.0 mL). The filtrate was concentrated in vacuo to afford a yellow/brown oil. Purification by column chromatography (10% methanol in chloroform) afforded the title compound.

2-methyl-5,6,7,8-tetrahydroquinolin-4(1H)-one

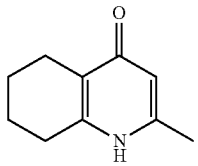

A solution of 4-hydroxyl 2-methyl-quinolone (1.00 g, 6.28 mmol) in acetic acid (10.0 mL) was catalytically hydrogenated over platinum dioxide (0.10 g, 0.44 mmol) for 12 hours. The resulting suspension was filtered through a pad of Celite and washed with ethyl acetate (10.0 mL). The filtrate was concentrated in vacuo to afford a yellow/brown oil. Purification by column chromatography (10% methanol in chloroform) afforded the title compound as a colourless amorphous solid. (1.02 g, 6.25 mmol, 99%). δ H NMR; (500 MHz, Chloroform-d); δ 6.29 (s, 1H), 2.71 (t, J=6.1 Hz, 2H), 2.48 (t, J=6.1 Hz, 2H), 2.32 (s, 3H), 1.78-1.69 (m, 4H); M/Z (ESI+); 164.1122 (Found MH+, 164.11 C$_{10}$H$_{13}$NO requires 164.1075).

2-Methyl-6-(trifluoromethyl)-5,6,7,8-tetrahydroquinolin-4(1H)-one

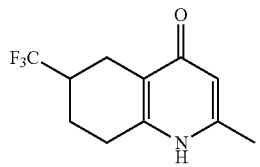 [SMILES: Cc1cc(=O)c2c([nH]1)CCC(C(F)(F)F)C2]

The title compound was synthesised following general procedure B from 2-methyl-6-(trifluoromethyl)quinolin-4(1H)-one (466 mg, 2.0 mmol), The title compound was isolated as colourless solid (230 mg, 0.99 mmol, 49%). $^1$H NMR (500 MHz, MeOD) δ 6.32 (s, 1H), 2.94 (dd, J=16.7, 5.1 Hz, 1H), 2.86 (dd, J=8.4, 4.1 Hz, 2H), 2.65-2.52 (m, 1H), 2.41 (dd, J=22.8, 11.5 Hz, 1H), 2.36 (s, 3H), 2.28-2.15 (m, 1H), 1.75 (tt, J=12.8, 9.1 Hz); M/Z (ESI+); 232.10 (Found MH$^+$; 232.0955, C$_{11}$H$_{12}$F$_3$NO requires 232.0949).

2,6-Dimethyl-5,6,7,8-tetrahydroquinolin-4(1H)-one

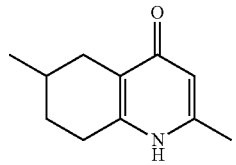

The title compound was synthesised following general procedure B from 2,6-dimethyl-quinolin-4(1H)-one (1.0 g, 5.78 mmol), The title compound was isolated as a colourless solid (780 mg, 4.30 mmol, 76%). $^1$H NMR (400 MHz, CDCl3) δ 12.26 (s, 1H), 6.09 (s, 1H), 2.88-2.64 (m, 3H), 2.30 (s, 3H), 1.98 (dd, J=16.9, 10.1 Hz, 1H), 1.87 (d, J=12.4 Hz, 1H), 1.77 (m, 1H), 1.39 (ddd, J=23.9, 11.1, 6.0 Hz, 1H), 1.08 (d, J=6.5 Hz, 3H); M/Z (ESI+); 178.13 (Found MH$^+$; 178.1280, C$_{11}$H$_{15}$NO requires 177.1154).

2,7-Dimethyl-5,6,7,8-tetrahydroquinolin-4(1H)-one

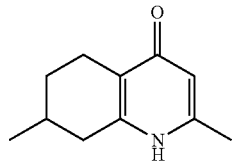

The title compound was synthesised following general procedure B from 2,7-Dimethyl-quinolin-4(1H)-one (350 mg, 2.0 mmol). The title compound was isolated as a colourless solid (311 mg, 1.75 mmol, 88%). $^1$H NMR (500 MHz, MeOD) δ 6.31 (s, 1H), 2.78 (dd, J=17.0, 5.1 Hz), 2.73 (ddd, J=17.7, 5.2, 2.7 Hz), 2.45-2.31 (m, 2H), 2.00-1.87 (m, 2H), 2.37 (s, Me), 1.37 (m, 2H), 1.13 (d, J=6.6 Hz, 3H); M/Z (ESI+); 178.13 (Found MH$^+$; 178.1278, C$_{11}$H$_{15}$NO requires 177.1154).

7-ethyl-2-methyl-5,6,7,8-tetrahydroquinolin-4(1H)-one

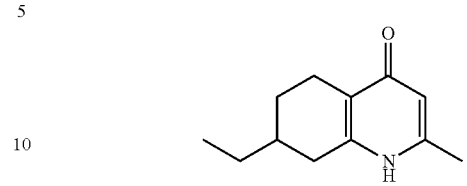

The title compound was synthesised following general procedure B from 7-ethyl-2-methylquinolin-4(1H)-one (420 mg, 1.78 mmol). The title compound was isolated as a colourless solid (360 mg, 1.5 mmol, 84%). H NMR (400 MHz, CDCl3) δ 12.20 (s, 1H), 6.09 (s, 1H), 2.88-2.66 (m, 2H), 2.46-2.19 (m, 5H, 2-Me), 1.95 (d, J=13.0 Hz, 1H), 1.63 (s, 1H), 1.38 (td, J=13.9, 6.9 Hz, 2H), 1.33-1.22 (m, 1H) 0.94 (t, J=7.4, 3H); M/Z (ESI+); 192.14 (Found MH$^+$; 192.1378 C$_{12}$H$_{17}$NO requires 192.1383).

7-trifluormethyl-2-methyl-5,6,7,8-tetrahydroquinolin-4(1H)-one

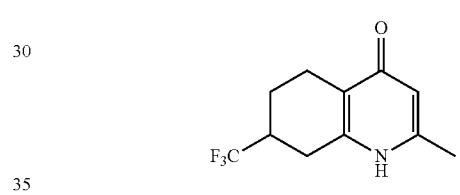

The title compound was synthesised following general procedure B from a mixture of 7-trifluormethyl-2-methylquinolin-4(1H)-one & 5-trifluormethyl-2-methylquinolin-4 (1H)-one (1.5 g). The title compound was isolated as a colourless solid (495 mg, 2.14 mmol). $^1$H NMR (500 MHz, CDCl$_3$/MeOD, 1:1) δ 5.99 (s, 1H), 2.73-2.60 (m, 2H), 2.53 (dd, J=16.3, 12.0 Hz, 1H), 2.35 (s, 1H), 2.20 (ddd, J=17.7, 11.4, 5.9 Hz, 1H), 2.11 (s, 3H), 2.09-2.01 (m, 1H), 1.42 (ddd, J=25.0, 12.1, 5.7 Hz, 1H); M/Z (ESI+); 232.10 (Found MH$^+$; 232.0953, C$_{11}$H$_{12}$F$_3$NO requires 232.0949).

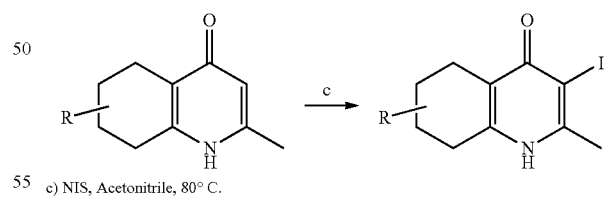

c) NIS, Acetonitrile, 80° C.

General Method C

Potassium iodide solution (sat aq, 5.60 mL mmol$^{-1}$) and n-butylamine (10 equiv.) were added to a solution of the tetrahydroquinolin-4(1H)-one (1 equiv.) and iodine (1 equiv.) in DMF (10.0 mL). The reaction mixture was stirred at room temperature for 16 hours. Observed colour change from dark purple to orange. Sodium thiosulphate (250 mg in

4(1H), 3-iodo-2-methyl-5,6,7,8-tetrahydroquinolin-4(1H)-one

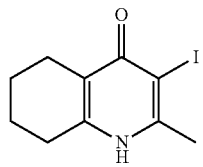

Saturated potassium iodide solution (sat aq, 5.60 mL) and n-butylamine (5.80 mL, 58.3 mmol) was added to a solution of 2-methyl-5,6,7,8-tetrahydroquinolin-4(1H)-one (0.95 g, 5.83 mmol) and iodine (1.48 g, 5.83 mmol) in DMF (10.0 mL). The reaction mixture was stirred at room temperature for 16 hours. Observed colour change from dark purple to orange. Sodium thiosulphate (250 mg in 10.0 mL water) was then added followed by filtration (washed 2×10 mL water) to afford the title compound (39) as colourless microcrystals (1.45 g, 5.02 mmol, 86%). 1H NMR (500 MHz, methanol-d4); δ 2.53 (t, J=6.1 Hz, 2H), 2.44 (s, 3H), 2.30 (t, J=6.1 Hz, 2H), 1.73-1.67 (m, 2H), 1.67-1.61 (m, 2H); M/Z (ESI+); 290.00 (Found MH+, 290.0037 $C_{10}H_{12}INO$ requires 290.0036).

3-Iodo-2-methyl-6-(trifluoromethyl)-5,6,7,8-tetrahydroquinolin-4(1H)-one

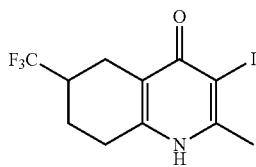 [SMILES: Cc1[nH]c2c(c(=O)c1I)CC(C(F)(F)F)CC2]

The title compound was synthesised following general procedure C from 2-methyl-6-(trifluoromethyl)-5,6,7,8-tetrahydroquinolin-4(1H)-one (230 mg, 1.0 mmol). The title compound was isolated as colourless solid (300 mg, 0.84 mmol, 84%). $^1$H NMR (400 MHz, DMSO) δ 11.58 (s, 1H), 2.75 (d, J=5.6 Hz, 1H), 2.72-2.67 (m, 2H), 2.62 (dd, J=7.4, 5.8 Hz, 1H), 2.46 (s, 3H), 2.31 (d, J=22.7 Hz, 1H), 2.15 (dd, J=16.4, 11.1 Hz, 1H), 2.07 (dd, J=6.6, 5.4 Hz, 1H), 1.68-1.51 (m, 1H); M/Z (ESI+); 357.99 (Found MH+; 357.9914, $C_{11}H_{11}F_3INO$ requires 357.9910).

3-Iodo-2·6-dimethyl-5,6,7,8-tetrahydroquinolin-4(1H)-one

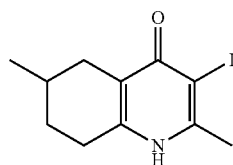

The title compound was synthesised following general procedure C from 2,6-dimethyl-5,6,7,8-tetrahydro quinolin-4(1H)-one (750 mg, 4.24 mmol). The title compound was isolated as colourless solid (740 mg, 2.44 mmol, 58%). $^1$H NMR (500 MHz, CDCl₃/MeOD) δ 2.36 (dd, J=17.3, 4.8 Hz), 2.25 (d, J=4.8 Hz, 2H), 2.15 (s, 3H), 1.57 (dd, J=17.3, 10.4 Hz, 1H), 1.51 (d, J=10.9 Hz, 1H), 1.36 (s, 1H), 1.09-0.94 (m, 1H), 0.69 (d, J=6.6 Hz, 3H); M/Z (ESI+); 304.02 (Found MH+; 304.0190, $C_{11}H_{14}INO$ requires 304.0193).

3-Iodo-7-ethyl-2-methyl-5,6,7,8-tetrahydroquinolin-4(1H)-one

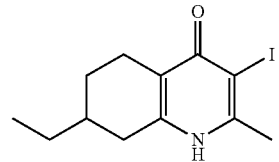

The title compound was synthesised following general procedure C from 7-ethyl-2-methyl-5,6,7,8-tetrahydroquinolin-4(1H)-one (110 mg, 0.57 mmol). The title compound was isolated as colourless solid (180 mg, 0.57 mmol, 99%). $^1$H NMR (400 MHz, MeOD) δ 2.62 (dd, J=17.2, 4.4 Hz, 2H), 2.47 (s, 3H), 2.34-2.22 (m, 1H), 2.18 (dd, J=17.8, 9.6 Hz, 1H), 1.92-1.81 (m, 1H), 1.64-1.50 (m, 1H), 1.34 (dtd, J=14.1, 7.2, 2.2 Hz, 2H), 1.21 (ddd, J=24.1, 10.9, 5.6 Hz, 1H), 0.91 (t, J=7.4 Hz, 3H); M/Z (ESI+); 318.03 (Found MH+; 318.0261, C12H16INO requires 318.0349).

3-Iodo-7-trifluormethyl-2-methyl-5,6,7,8-tetrahydroquinolin-4(1H)-one

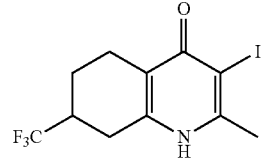 [SMILES: Cc1[nH]c2c(c(=O)c1I)CCC(C(F)(F)F)C2]

The title compound was synthesised following general procedure C from 7-trifluormethyl-2-methylquinolin-4(1H)-one (480 mg, 2.10 mmol). The title compound was isolated as a colourless solid (688 mg, 1.92 mmol, 91%). $^1$H NMR (500 MHz, CDCl₃/MeOD, 1:1) δ 2.40 (dd, J=16.0, 4.9 Hz, 2H), 2.24 (dd, J=17.9, 8.3 Hz, 1H), 2.20-2.12 (m, 1H), 2.12 (s, 2H), 2.00-1.86 (m, 1H), 1.94 (s, 1H), 1.75 (s, 1H), 1.74 (dd, J=13.5, 5.9 Hz, 1H), 1.13 (ddd, J=19.4, 12.1, 5.8 Hz, 1H). M/Z (ESI+); 357.99 (Found MH+; 357.9915, $C_{11}H_{11}F_3INO$ requires 357.9910).

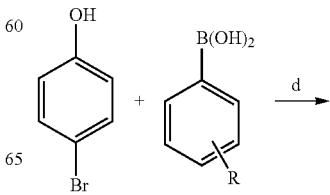

-continued

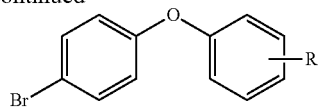

d) Cu(OAc)$_2$, Pyridine, TEA, DCM,

General Procedure d

Copper (II) acetate (1 equiv.), triethylamine (5 equiv.), and pyridine (5 equiv.) was added to a solution of the boronic acid (1.5 equiv.) and phenol (1 equiv.) in dichloromethane (10 mL mmol$^{-1}$) over heat-activated 4 Å molecular sieves. The reaction mixture was stirred over 16 hours at room temperature. The reaction mixture was quenched with HCl (0.5 M, 20 mL mmol$^{-1}$) and filtered through a pad of Celite, followed by repeated washing with water (10 mL mmol$^{-1}$). The organic layer was extracted with brine, dried over magnesium sulphate, and concentrated in vacuo. Purification by silica gel chromatography (ethyl acetate/hexane) afforded the title compound.

1-Bromo-4-(4-(trifluoromethoxy)phenoxy)benzene

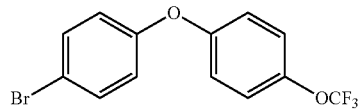

The title compound was synthesised, from 4-bromophenol (0.42 g, 2.43 mmol) and 4-trifluoromethoxy benzene boronic acid (1.00 g, 4.68 mmol), according to general procedure d as a colourless oil (70%, 0.53 g, 1.63 mmol). δ H NMR (500 MHz, Chloroform-d) δ 7.37 (d, J=9.0 Hz, 2H), 7.10 (d, J=9.1 Hz, 2H), 6.91 (d, J=9.1 Hz, 2H), 6.80 (d, J=9.0 Hz, 2H);

Methyl 3-(4-bromophenoxy)benzoate

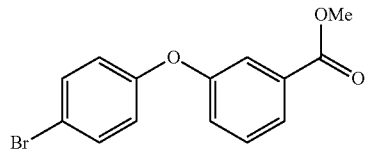 [SMILES: COC(=O)c1cccc(Oc2ccc(Br)cc2)c1]

The title compound was synthesised, from 4-bromo-pehonl (0.42 g, 2.43 mmol) and 3-methoxycarbonyl phenyl boronic acid (0.43 g, 2.43 mmol), according to general procedure D. The title compound (43) was isolated as colourless glassy solid (0.21 g, 0.69 mmol, 28%). $^1$H NMR (500 MHz, CDCl$_3$) δ 7.73 (dt, J=7.7, 1.2 Hz, 1H), 7.59-7.53 (m, 1H), 7.38 (d, J=9.0 Hz, 2H), 7.34 (t, J=8.4 Hz, 2H), 7.13 (ddd, J=8.4, 2.5, 0.9 Hz, 1H), 6.82 (d, J=9.0 Hz, 2H), 3.83 (s, 3H); M/Z (ESI+); 307.00 (Found MH$^+$, 306.9962 C$_{14}$H$_{11}$BrO$_3$ requires; 306.9964).

1-bromo-4-(4-chlorophenoxy)benzene

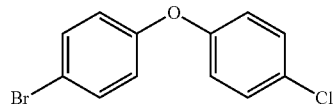 [SMILES: Clc1ccc(Oc2ccc(Br)cc2)cc1]

The title compound was synthesised, from 4-bromophenol (0.5 g, 2.80 mmol) and 4-trifluoromethoxy benzene boronic acid (0.6 g, 4.20 mmol), according to general procedure D. The title compound was isolated as a colourless needles (160 mg, 0.56 mmol, 20%). 1H NMR (500 MHz, CDCl$_3$) δ 7.43 (d, J=9.0 Hz, 2H), 7.30 (d, J=9.0 Hz, 2H), 6.93 (d, J=9.0 Hz, 2H), 6.86 (d, J=9.0 Hz, 2H).

Methyl 4-(4-bromophenoxy)benzoate

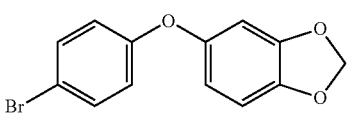 [SMILES: Brc1ccc(Oc2ccc3c(c2)OCO3)cc1]

The title compound was synthesised, from 4-bromo-pehonl (0.42 g, 2.43 mmol) and 4-methoxycarbonyl phenyl boronic acid (0.43 g, 2.43 mmol), according to general procedure D. The title compound was isolated as colourless plate crystals (0.25 g, 0.81 mmol, 33%). 1H NMR (500 MHz, CDCl$_3$) δ 7.94 (d, J=8.9 Hz, 2H), 7.41 (d, J=8.9 Hz, 2H), 6.91 (d, J=8.8 Hz, 2H), 6.87 (d, J=8.9 Hz, 2H), 3.83 (s, 3H); M/Z (ESI+); 307.00 (Found MH$^+$, 306.9961 C$_{14}$H$_{11}$BrO$_3$ requires 306.9964).

5-(4-bromophenoxy)-2H-1,3-benzodioxole

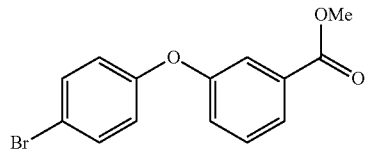 [SMILES: COC(=O)c1cccc(Oc2ccc(Br)cc2)c1]

The title compound was synthesised, from 4-bromo-pehonl (500 mg, 2.89 mmol) and 3,4-methyleneoxy-phenylboronic acid (719 mg, 4.34 mmol according to general procedure D. The title compound was isolated as a pale yellow oil (196 mg, 0.67 mmol, 23%). δ $^1$H NMR (500 MHz, Chloroform-d) δ 7.43 (d, J 8.5 Hz, 2H), 6.86 (d, J 8.5 Hz, 2H), 6.79 (d, J 8.5 Hz, 1H), 6.59 (d, J 2.5 Hz, 1H), 6.51 (dd, J 8.5 & 2.5 Hz, 1H), 6.00 (s, 2H);

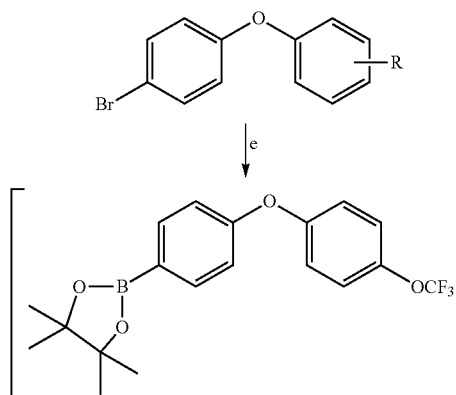
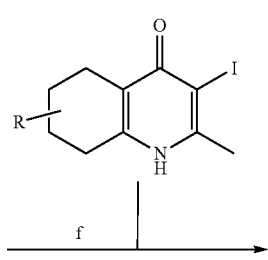

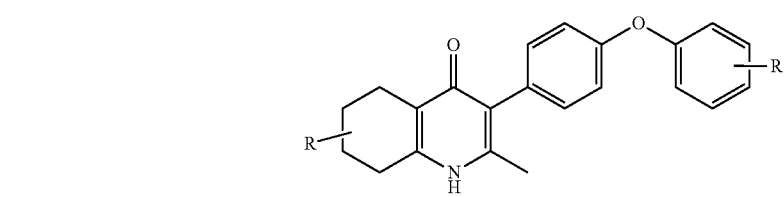

e) Pd(dppf)Cl₂, Bispinocolatodiborane, KOAc, DMF, 80° C. f) Pd(dppf)Cl₂, Na₂CO₃, DMF, 80° C.

1.1 General Method E &F

A flask charged with the 4-bromo-diarylether (1 equiv.), bispinocolatodiborane (1.1 equiv.), KOAc (3 equiv.) and Pd(dppf)Cl₂ (3 mol %) was flushed with nitrogen. DMF (2.00 mL) was added and the reaction was stirred at 80° C. for 18 hours. After cooling the solution to room temperature, 3-iodotetrahydroquinoline (2 equiv.), PdCl₂(dppf) (3 mol %) and Na₂CO₃ (2M, 5 equiv.) were added and the mixture was stirred at 80° C. under nitrogen for a further 24 hours. The solution was cooled to room temperature, the product was extracted with Et₂O (15.0 mL). The organic layers were combined and washed with H₂O (15.0 mL), brine and dried over MgSO₄ and concentrated in vacuo. This was followed by purification by silica gel chromatography (ethyl acetate/petroleum ether).

2-methyl-3-(4-(4-(trifluoromethoxy)phenoxy)phenyl)-5,6,7,8-tetrahydroquinolin-4(1H)-one

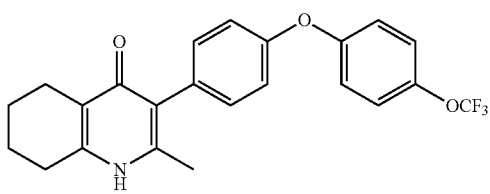

The title compound was synthesised following general procedure E&F from 3-iodo-5,6,7,8-tetrahydroquinolin-4(1H)-one (260 mg, 0.9 mmol) and 4-bromo(4-trifluoromethoxyphenoxy)phenyl (200 mg, 0.6 mmol). The title compound was isolated as colourless solid (38 mg, 0.09 mmol, 15%). ¹H NMR (500 MHz, DMSO) δ 11.07 (s, 1H), 7.40 (d, J=8.5 Hz, 2H), 7.19 (d, J=8.6 Hz, 2H), 7.13 (d, J=9.0 Hz, 2H), 7.02 (d, J=8.5 Hz, 2H), 2.54 (t, J=6.0 Hz, 2H, H-8), 2.28 (t, J=5.9 Hz, 2H), 2.07 (s, 3H), 1.71 (m, 2H), 1.65 (m, 2H); M/Z (ESI+); 416.15 (Found MH⁺, 416.1492 C₂₃H₂₀F₃NO₃ requires 416.1473).

3(4-(4-trifluoromethoxyphenoxy)phenyl)-2,6-dimethyl-5,6,7,8-tetrahydroquinolin-4(1H)-one

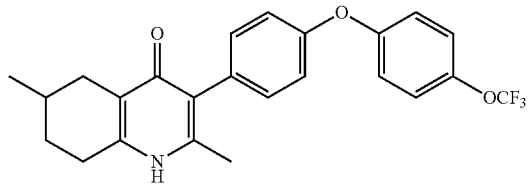 [SMILES: Cc1[nH]c2c(c(=O)c1-c1ccc(Oc3ccc(OC(F)(F)F)cc3)cc1)CC(C)CC2]

The title compound was synthesised following general procedure E&F from 3-iodo-2,6-dimethyl-5,6,7,8-tetrahydroquinolin-4(1H)-one (270 mg, 0.9 mmol) and 4-bromo(4-trifluromethoxyphenoxy)phenyl (200 mg, 0.6 mmol). The title compound was isolated as colourless solid (40 mg, 0.09 mmol, 15%). ¹H NMR (500 MHz, CDCl₃/MeOD) δ 6.86 (d, J=8.3 Hz, 4H), 6.79-6.64 (m, 4H), 2.43 (dd, J=17.5, 4.9 Hz, 1H), 2.37 (s, 2H), 1.81 (s, 3H), 1.70-1.54 (m, 2H), 1.45 (m, 1H), 1.09 (dt, J=20.7, 10.5 Hz, 1H), 0.76 (d, J=6.6 Hz, 3H); M/Z (ESI+); 452.14 (Found MNa⁺; 452.1446 C₂₄H₂₂F₃NO₃ requires 452.1444).

3(4-(4-trifluoromethoxyphenoxy)phenyl)-2,7-dimethyl-5,6,7,8-tetrahydroquinolin-4(1H)-one

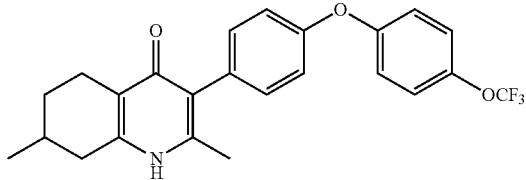 [SMILES: Cc1[nH]c2c(c(=O)c1-c1ccc(Oc3ccc(OC(F)(F)F)cc3)cc1)CCC(C)C2]

The title compound was synthesised following general procedure E&F from 3-iodo-2,7-dimethyl-5,6,7,8-tetrahydroquinolin-4(1H)-one (120 mg, 0.4 mmol) and 4-bromo(4-trifluromethoxyphenoxy)phenyl (87 mg, 0.27 mmol). The title compound was isolated as colourless solid (30 mg, 0.07 mmol, 26%). $^1$H NMR (400 MHz, DMSO) δ 10.90 (s, 1H), 7.41 (d, J=8.5 Hz, 2H), 7.20 (d, J=7.9 Hz, 2H), 7.14 (d, J=8.5 Hz, 2H), 7.03 (d, J=7.9 Hz, 2H), 2.61 (m, 2H), 2.20 (dd, J=16.4, 9.6 Hz, 2H), 2.08 (s, 3H), 1.81 (m, 2H), 1.24 (s, 1H), 1.04 (d, J=5.9 Hz, 3H); M/Z (ESI+); 452.14 (Found MNa$^+$; 452.1446 $C_{24}H_{22}F_3NO_3$ requires 452.1444).

6-Ethyl-3-(4-(4-trifluoromethoxyphenoxy)phenyl)-2-methyl-5,6,7,8-tetrahydroquinolin-4(1H)-one

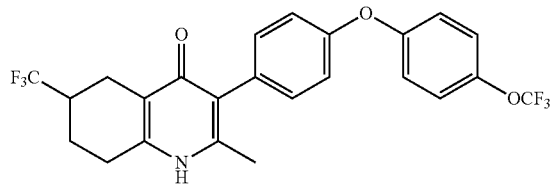 [SMILES: Cc1[nH]c2c(c(=O)c1-c1ccc(Oc3ccc(OC(F)(F)F)cc3)cc1)CC(C(F)(F)F)CC2]

The title compound was synthesised following general procedure E&F from 3-iodo-2-methyl-6-(trifluoromethyl)-5,6,7,8-tetrahydroquinolin-4(1H)-one (300 mg, 0.84 mmol) and 4-bromo-(4-trifluoromethoxyphenoxy)phenyl (185 mg, 0.56 mmol). The title compound was afforded as a colourless solid. (20 mg, 0.04 mmol, 7%). $^1$H NMR (500 MHz, TFA) δ 7.39 (d, J=7.7 Hz, 4H), 7.34 (d, J=7.1 Hz, 2H), 7.24 (d, J=8.5 Hz, 2H), 3.32 (d, J=14.9 Hz, 2H), 3.21 (dd, J=13.8, 5.6 Hz, 1H), 2.89 (dd, J=18.0, 9.6 Hz, 1H), 2.73 (dd, J=15.3, 6.9 Hz, 1H), 2.57 (s, 3H), 2.52 (d, J=13.5 Hz, 1H), 2.07 (d, J=16.0 Hz, 1H, H-7b); M/Z (ESI+); 484.14 (Found MH$^+$ 484.1358, $C_{24}H_{19}F_6NO_3$ requires 484.1342).

7-Ethyl-2-methyl-3(4-(4-trifluoromethoxyphenoxy)phenyl)-5,6,7,8-tetrahydroquinolin-4(1H)-one

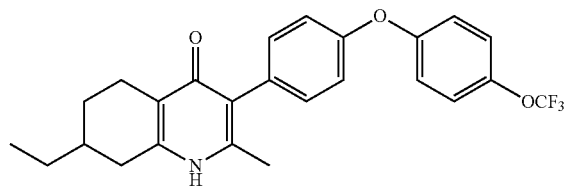 [SMILES: CCC1CCc2c([nH]c(C)c(-c3ccc(Oc4ccc(OC(F)(F)F)cc4)cc3)c2=O)C1]

The title compound was synthesised following general procedure E&F from 7-ethyl-2-methylquinolin-4(1H)-one (170 mg, 0.54 mmol) and 4-bromo-(4-trifluromethoxyphenoxy)phenyl (120 mg, 0.36 mmol). The title compound was isolated as a colourless solid (17 mg, 0.04 mmol, 11%). $^1$H NMR (500 MHz, CDCl$_3$) δ 11.50 (s, 1H), 7.16 (dd, J=15.3, 8.2 Hz, 4H), 6.94 (dd, J=16.6, 8.3 Hz, 4H), 2.78 (d, J=16.1 Hz, 1H), 2.60 (d, J=21.4 Hz, 1H), 2.39 (s, 1H), 2.13 (dd, J=15.8, 10.8 Hz, 1H), 1.96 (s, 3H), 1.59 (s, 1H), 1.43-1.32 (m, 2H), 1.32-1.18 (m, 2H), 0.94 (t, J=7.2 Hz, 3H); M/Z (ESI+); 444.18 (Found MH$^+$; 444.1784, $C_{25}H_{24}F_3NO_3$ requires 444.1781).

7-trifluromethyl-2-methyl-3(4-(4-trifluoromethoxyphenoxy)phenyl)-5,6,7,8-tetrahydroquinolin-4(1H)-one

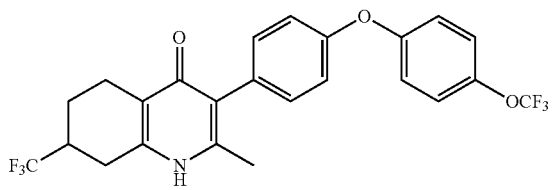 [SMILES: Cc1[nH]c2c(c(=O)c1-c1ccc(Oc3ccc(OC(F)(F)F)cc3)cc1)CCC(C(F)(F)F)C2]

The title compound was synthesised following general procedure x from 7-trifluormethyl-2-methylquinolin-4(1H)-one (360 mg, 0.99 mmol) and 4-bromo-(4-trifluromethoxyphenoxy)phenyl (220 mg, 0.66 mmol). The title compound was isolated as a colourless solid (95 mg, 0.20 mmol, 30%). M/Z (ESI+); 484.14 (Found MH+484.1358, $C_{24}H_{19}F_6NO_3$ requires 484.1342).

3-[4-(2H-1,3-benzodioxol-5-yloxy)phenyl]-2-methyl-5,6,7,8-tetrahydro-1H-quinolin-4-one

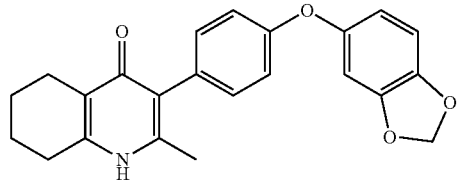 [SMILES: Cc1[nH]c2c(c(=O)c1-c1ccc(Oc3ccc4c(c3)OCO4)cc1)CCCC2]

The title compound was synthesised from 5-(4-bromophenoxy)-2H-1,3-benzodioxole (200 mg, 0.68 mmol) and 3-iodo-5,6,7,8-tetrahydroquinolin-4(1H)-one (288 mg, 1.02 mmol). The title compound was isolated as a pale grey solid (40 mg, 0.11 mmol, 16%). HPLC; 3.28 min (86%); δ $^1$H NMR (500 MHz, TFA) δ 7.35 (d, J 8.5 Hz, 2H), 7.31-7.29 (m, 3H), 6.98 (s, 1H), 6.79 (s, 1H), 6.10 (s, 2H), 3.09 (t, J 5.0 Hz, 2H), 2.90 (t, J 5.0 Hz, 2H), 2.52 (s, 3H), 2.11-2.05 (m, 4H); M/Z (ESI); 375.1563, ($C_{23}H_{21}NO_4$ requires 375.1471).

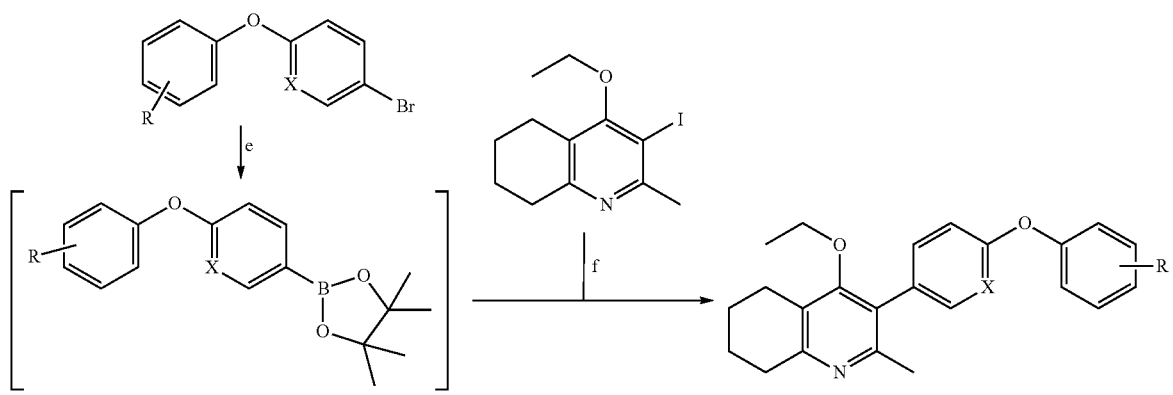

e) Pd(dppf)Cl₂, Bispinocolatodiborane, KOAc, DMF, 80° C. f) Pd(dppf)Cl₂, Na₂CO₃, DMF, 80° C., g) HBr, AcOH 120° C.

1.2 General Method E &F

A flask charged with the 4-bromo-diarylether (1 equiv.), bispinocolatodiborane (1.1 equiv.), KOAc (3 equiv.) and Pd(dppf)Cl₂ (3 mol %) was flushed with nitrogen. DMF (2.00 mL) was added and the reaction was stirred at 80° C. for 18 hours. After cooling the solution to room temperature, 3-iodotetrahydroquinoline (2 equiv.), PdCl₂(dppf) (3 mol %) and Na₂CO₃ (2M, 5 equiv.) were added and the mixture was stirred at 80° C. under nitrogen for a further 24 hours. The solution was cooled to room temperature, the product was extracted with Et₂O (15.0 mL). The organic layers were combined and washed with H₂O (15.0 mL), brine and dried over MgSO₄ and concentrated in vacuo. This was followed by purification by silica gel chromatography (ethyl acetate/petroleum ether).

4-ethoxy-2-methyl-3-(4-(4-(trifluoromethoxy)phenoxy)phenyl)-5,6,7,8-tetrahydro quinoline

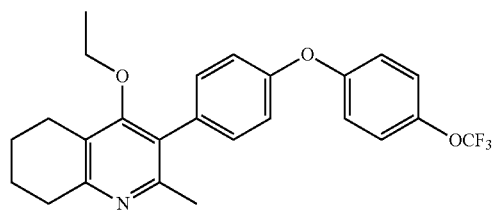 [SMILES: CCOc1c2c(nc(C)c1-c1ccc(Oc3ccc(OC(F)(F)F)cc3)cc1)CCCC2]

The title compound was synthesised from 1-Bromo-4-(4-(trifluoromethoxy)phenoxy)benzene (100 mg, 0.30 mmol) according to general procedure E&F, to afford the title compound as a colourless gum/viscous oil (30 mg, 0.07 mmol, 23%). ¹H NMR (500 MHz, Acetone) δ 7.28 (d, J=8.7 Hz, 2H), 7.26 (d, J=9.1 Hz, 2H), 7.09 (d, J=9.1 Hz, 2H), 7.07 (d, J=8.7, 2H), 3.52 (q, J=7.0 Hz, 2H), 2.85 (t, J=6.5 Hz, 2H), 2.78 (t, J=6.2 Hz, 2H), 2.26 (s, 3H), 1.89-1.81 (m, 2H), 1.81-1.72 (m, 2H), 0.93 (t, J=7.0 Hz, 3H); M/Z (ESI+); 444.18 (Found MH⁺, 444.1792 C₂₅H₂₄F₃NO₃ requires 444.1781).

Methyl 4-(4-(4-ethoxy-2-methyl-5,6,7,8-tetrahydroquinolin-3-yl)phenoxy)benzoate

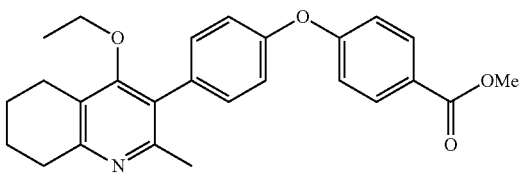 [SMILES: CCOc1c2c(nc(C)c1-c1ccc(Oc3ccc(C(=O)OC)cc3)cc1)CCCC2]

The title compound was synthesised from methyl 4-(4-bromophenoxy)benzoate (150 mg, 0.49 mmol) according to general procedure E&F. The title compound was isolated as colourless microcrystals (56 mg, 0.13 mmol, 27%). ¹H NMR (500 MHz, CDCl₃) δ 8.03 (d, J=8.7 Hz, 2H), 7.29 (d, J=8.4 Hz, 2H), 7.11 (d, J=8.4 Hz, 2H), 7.03 (d, J=8.7 Hz, 2H), 3.90 (s, 3H), 3.51 (q, J=7.0 Hz, 2H), 2.91 (t, J=6.2 Hz, 2H), 2.72 (t, J=6.0 Hz, 2H), 2.32 (s, 3H), 1.91-1.84 (m, 2H), 1.83-1.76 (m, 2H), 1.04 (t, J=7.0 Hz, 3H); M/Z; 418.20 (ESI+); 418.20 (Found MH⁺, 418.2037 C₂₆H₂₇NO₄ requires 418.2018).

Methyl 4-((5-(4-ethoxy-2-methyl-5,6,7,8-tetrahydroquinolin-3-yl)pyridin-2-yl)oxy) benzoate

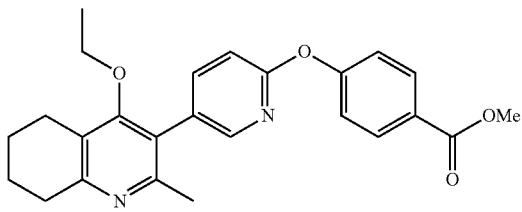 [SMILES: CCOc1c2c(nc(C)c1-c1ccc(Oc3ccc(C(=O)OC)cc3)nc1)CCCC2]

The title compound was synthesised from methyl 3-((5-bromopyridin-2-yl)oxy)benzoate (100 mg, 0.33 mmol) according to general procedure E&F. The title compound was isolated as a colourless gum/semisolid (30 mg, 0.07 mmol, 21%). 1H NMR (500 MHz, CDCl$_3$) δ 8.13 (d, J=2.3 Hz, 1H, H-6'), 8.10 (d, J=8.7 Hz, 2H), 7.67 (dd, J=8.4, 2.4 Hz, 1H, H-4'), 7.24 (d, J=8.7 Hz, 2H), 7.05 (d, J=8.4 Hz, 1H), 3.91 (s, 3H), 3.53 (q, J=7.0 Hz, 2H), 2.92 (t, J=6.3 Hz, 2H), 2.71 (t, J=6.2 Hz, 2H), 1.06 (t, J=7.0 Hz, 3H); M/Z (ESI+); 419.20 (Found MH$^+$, 419.1993 C$_{25}$H$_{26}$N$_2$O$_4$ requires 419.1970).

Methyl 3-(4-(4-ethoxy-2-methyl-5,6,7,8-tetrahydroquinolin-3-yl)phenoxy)benzoate

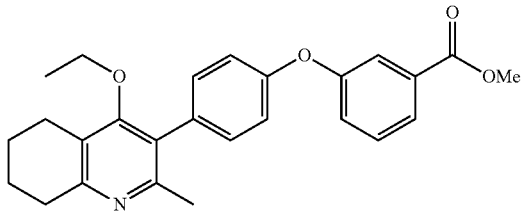 [SMILES: CCOc1c2c(nc(C)c1-c1ccc(Oc3cccc(C(=O)OC)c3)cc1)CCCC2]

The title compound was synthesised from methyl 3-(4-bromophenoxy)benzoate (150 mg, 0.49 mmol) according to general procedure E&F. The title compound was isolated as colourless crystals (50 mg, 0.12 mmol, 25%). 1H NMR (500 MHz, CDCl$_3$) δ 7.73 (d, J=7.7 Hz, 1H), 7.65-7.60 (m, 1H), 7.37 (t, J=7.9 Hz, 1H), 7.19 (m, 3H), 7.00 (d, J=8.6 Hz, 2H), 3.83 (s, J=, 3H), 3.45 (q, J=7.0 Hz, 2H), 2.85 (t, J=6.3 Hz, 2H), 2.65 (t, J=6.2 Hz, 2H), 2.26 (s, 3H), 1.88-1.78 (m, 2H), 1.76-1.67 (m, 2H), 0.99 (t, J=7.0 Hz, 3H); M/Z (ESI+); 418.20 (Found MH$^+$ 418.2030, C$_{26}$H$_{27}$NO$_4$ requires 418.2018).

Formation of: 3-(4-(4-chlorophenoxy)phenyl)-4-ethoxy-2-methyl-5,6,7,8-tetrahydroquinoline

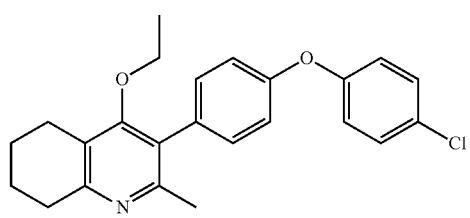 [SMILES: CCOc1c2c(nc(C)c1-c1ccc(Oc3ccc(Cl)cc3)cc1)CCCC2]

The title compound was synthesised from 1-bromo-4-(4-chlorophenoxy)benzene (70 mg, 0.24 mmol) according to general procedure E&F. The title compound was isolated as colourless oil (20 mg, 0.05 mmol, 27%). $^1$H NMR (500 MHz, CDCl$_3$) δ 7.25 (d, J=8.9 Hz, 2H), 7.17 (d, J=8.7 Hz, 2H), 6.98 (d, J=8.7 Hz, 2H), 6.93 (d, J=8.9 Hz, 2H), 3.45 (q, J=7.0 Hz, 2H), 2.89 (t, J=6.3 Hz, 2H), 2.65 (t, J=6.1 Hz, 2H), 2.28 (s, 3H), 1.90-1.61 (m, 4H), 0.98 (t, J=7.0 Hz, 3H); M/Z (ESI+); 394.16 (Found MH+394.1575, C$_{24}$H$_{24}$ClNO$_2$ requires 394.1568).

1.3 General Method G

To a solution of the 4-ethoxy-3-(diaryl ether)-hydroxyquinolone (1 equiv.) in acetic acid (2 mL mmol$^{-1}$) was added hydrogen bromide (>48% w/v (aq)) (1 mL mmol$^{-1}$). The reaction mixture was then heated to 90° C. and left to reflux for 72 hours. The reaction mixture was neutralised with sodium hydroxide (2 M, 30.0 mL) and precipitate formed. The reaction mixture was then filtered to afford the title compound and purified.

Methyl 3-((5-(4-ethoxy-2-methyl-5,6,7,8-tetrahydroquinolin-3-yl)pyridin-2-yl)oxy) benzoate

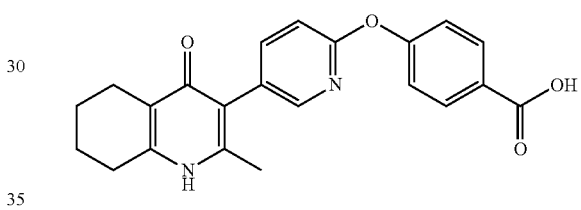

The title compound was synthesised from methyl 4-((5-(4-ethoxy-2-methyl-5,6,7,8-tetrahydroquinolin-3-yl)pyridin-2-yl)oxy) benzoate (30 mg, 0.07 mmol) according to general procedure G. The title compound was isolated as colourless semi solid (13 mg, 0.03 mmol, 45%). $^1$H NMR (500 MHz, DMSO) δ 12.83 (s, 1H, NH), 11.03 (s, 1H, CO$_2$H), 8.00 (d, J=8.7 Hz, 2H), 7.99 (s, 1H) 7.73 (dd, J=8.4, 2.4 Hz, 1H), 7.24 (d, J=8.7 Hz, 2H), 7.12 (d, J=8.4 Hz, 1H), 2.56 (t, J=5.8 Hz, 2H), 2.30 (t, J=5.8 Hz, 2H), 2.11 (s, 3H), 1.82-1.51 (m, 4H); M/Z (ESI+); 377.15 (Found MH$^+$, 377.1497 C$_{22}$H$_{20}$N$_2$O$_4$ requires 377.1496).

4-(4-(2-methyl-4-oxo-1,4,5,6,7,8-hexahydroquinolin-3-yl)phenoxy)benzoic Acid

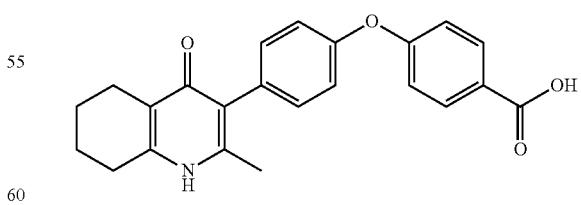

The title compound was synthesised from methyl 4-(4-(4-ethoxy-2-methyl-5,6,7,8-tetrahydroquinolin-3-yl)phenoxy) benzoate (50 mg, 0.17 mmol) according to general procedure G. The title compound was isolated as colourless crystals (33 mg, 0.09 mmol, 48%). $^1$H NMR (500 MHz, DMSO) δ 13.79 (s, 1H), 12.80 (s (b), 1H), 7.99 (d, J=8.8 Hz, 2H), 7.36 (d, J=8.7 Hz, 2H), 7.24 (d, J=8.7 Hz, 2H), 7.14 (d, J=8.8 Hz, 2H), 2.92 (t, J=5.1 Hz, 2H), 2.62 (t, J=5.0 Hz, 2H), 2.31 (s, 3H), 1.90-1.76 (m, 4H); M/Z (ESI+); 376.16 (Found MH$^+$, 376.1550, $C_{23}H_{21}NO_4$ requires 376.1543).

3-(4-(2-methyl-4-oxo-1,4,5,6,7,8-hexahydroquinolin-3-yl)phenoxy)benzoic Acid

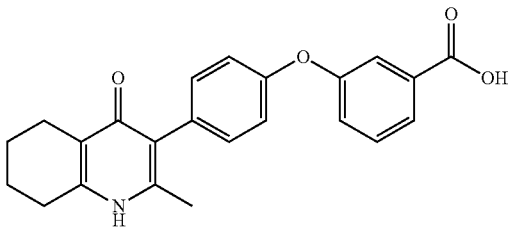 [SMILES: Cc1[nH]c2c(c(=O)c1-c1ccc(Oc3cccc(C(=O)O)c3)cc1)CCCC2]

The title compound was synthesised from 3 methyl 3-(4-(4-ethoxy-2-methyl-5,6,7,8-tetrahydroquinolin-3-yl)phenoxy)benzoate (50 mg, 0.17 mmol) according to general procedure G. The title compound was isolated as colourless crystals (7 mg, 0.02 mmol, 12%). $^1$H NMR (500 MHz, DMSO) δ 13.00 (s, 1H), 11.31 (s, 1H), 7.70 (d, J=7.9 Hz, 1H), 7.52 (t, J=7.9 Hz, 1H), 7.48 (dd, J=2.2, 1.6 Hz, 1H), 7.31 (dd, J=7.9, 1.6 Hz, 1H), 7.21 (d, J=8.6 Hz, 2H), 7.04 (d, J=8.6 Hz, 2H), 2.58 (t, J=5.8 Hz, 2H), 2.32 (t, J=5.8 Hz, 2H), 2.09 (s, 3H), 1.76-1.59 (m, 4H); M/Z (ESI+); 376.15 (Found MH$^+$ 376.1547, $C_{23}H_{21}NO_4$ requires 376.1543).

3-(4-(4-chlorophenoxy)phenyl)-2-methyl-5,6,7,8-tetrahydroquinolin-4(1H)-one

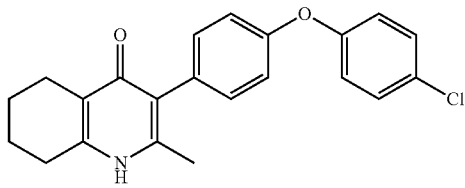 [SMILES: Cc1[nH]c2c(c(=O)c1-c1ccc(Oc3ccc(Cl)cc3)cc1)CCCC2]

The title compound was synthesised from 3-(4-(4-chlorophenoxy)phenyl)-4-ethoxy-2-methyl-5,6,7,8-tetrahydroquinoline (20 mg, 0.5 mmol) according to general procedure G. The title compound was isolated as colourless solid (18 mg, 0.05 mmol, 95%). $^1$H NMR (500 MHz, DMSO) δ 10.99 (s, 1H), 7.44 (d, J=8.9 Hz, 2H), 7.18 (d, J=8.6 Hz, 2H), 7.05 (d, J=8.9 Hz, 2H), 7.04 (d, J=8.6 Hz, 2H), 2.56 (t, J=5.3 Hz, 2H), 2.29 (t, J=5.3 Hz, 2H), 2.07 (s, 3H), 1.78-1.55 (m, 4H); M/Z (ESI+); 366.13 (Found MH$^+$ 366.1262, $C_{22}H_{21}ClNO_2$ requires 366.1253).

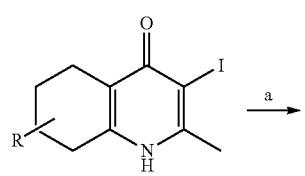

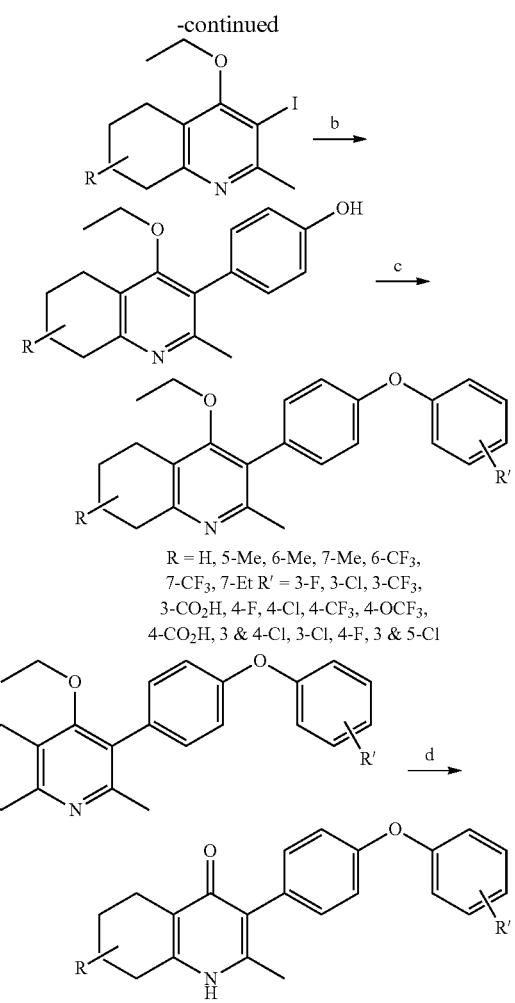

R = H, 5-Me, 6-Me, 7-Me, 6-CF$_3$, 7-CF$_3$, 7-Et R' = 3-F, 3-Cl, 3-CF$_3$, 3-CO$_2$H, 4-F, 4-Cl, 4-CF$_3$, 4-OCF$_3$, 4-CO$_2$H, 3 & 4-Cl, 3-Cl, 4-F, 3 & 5-Cl a) EtI, K$_2$CO$_3$, DMF, 80° C., b) 4-Hydroxyphenyl boronic acid, Pd(PPH$_3$)$_4$, Na$_2$CO$_3$, DMF, 80° C., c) Phenyl boronic acid, Cu(OAc)$_2$, Pyridine, TEA, DCM, d) HBr (40% aq), Acetic acid, 120° C.

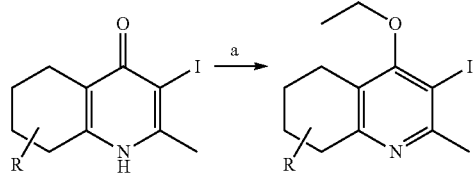

a) EtI, K$_2$CO$_3$, DMF, 80° C.

4-ethoxy-3-iodo-2-methyl-5,6,7,8-tetrahydroquinoline

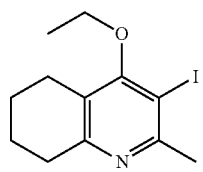

A suspension of 4(1H), 3-iodo-2-methyl, 5,6,7,8-tetrahydroquinolinone (2.20 g, 7.61 mmol) and Potassium carbonate (2.10 g, 15.2 mmol) in DMF (20.0 mL) was heated to 50° C. and stirred for 45 minutes. The reaction mixture was removed from the heat and ethyl iodide (0.89 mL, 11.4 mmol) was added dropwise. The reaction mixture was then heated to 50° C. and stirred for a further 18 hours. Formation of a yellow emulsion was observed. The reaction mixture was then quenched with water (40.0 mL). The organic phase was extracted using the polar extraction technique (ethyl acetate, 3×40.0 mL), and the resulting organic layers were combined and dried over MgSO$_4$ and concentrated in vacuo to afford the title compound as an orange oil. (2.00 g, 6.32 mmol, 83%). δ H NMR (500 MHz, Chloroform-d); δ 3.96 (q, J=7.0 Hz, 2H), 2.84 (t, J=6.3 Hz, 2H), 2.74 (t, J=6.3 Hz, 2H), 2.71 (s, 3H), 1.89-1.82 (m, 2H), 1.78-1.72 (m, 2H), 1.49 (t, J=7.0 Hz, 3H); M/Z (ESI+); 318.04 (Found MH$^+$, 318.0350, C$_{12}$H$_{17}$INO requires 318.0349).

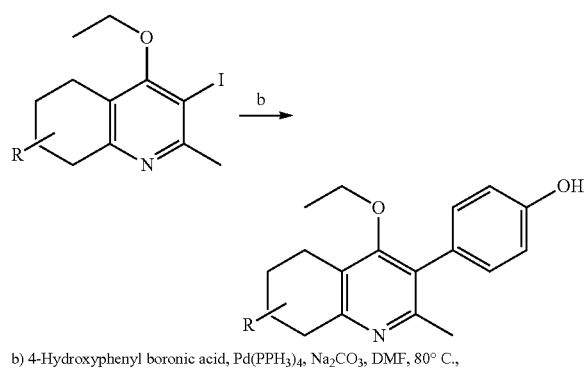

b) 4-Hydroxyphenyl boronic acid, Pd(PPH$_3$)$_4$, Na$_2$CO$_3$, DMF, 80° C., 4-(4-Ethoxy-2-methyl-5,6,7,8-tetrahydroquinolin-3-yl)phenol

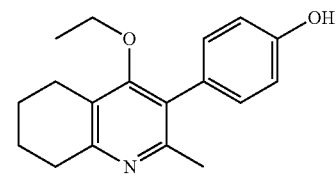 [SMILES: CCOc1c2c(nc(C)c1-c1ccc(O)cc1)CCCC2]

To a nitrogen flushed flask charged with 4-ethoxy-3-iodo-2-methyl-5,6,7,8-tetrahydroquinoline (400 mg, 1.26 mmol), 4 hydroxybenzene boronic acid (260 mg, 1.89 mmol) and palladium tetra(triphenylphosphine) (73 mg, 0.06 mmol) was added degassed DMF (10 mL). Potassium carbonate (aq) (3 mL, 2 M) was added and the reaction mixture brought up to 80° C. and stirred for 3 hours. The reaction mixture was then cooled to room temperature and diluted with water (10 mL). The organic phase was then extracted using ethyl acetate (3×20 mL). The organic phases were combined and washed with water (3×20 mL) and then dried with brine (1×10 mL) and MgSO$_4$, before concentration in vacuo. The resulting reddish brown solid was then recrystallized in ethyl acetate. To yield the title compound as a colourless solid (220 mg, 0.78 mmol, 61%). $^1$H NMR (500 MHz, MeOD) δ 7.07 (d, J=8.6 Hz, 2H), 6.86 (d, J=8.6 Hz, 2H), 3.51 (q, J=7.0 Hz, 2H), 2.83 (t, J=6.3 Hz, 2H), 2.72 (t, J=6.1 Hz, 2H), 2.23 (s, 3H), 1.95-1.72 (m, 4H), 1.00 (t, J=7.0 Hz, 3H); M/Z (ESI+); 284.17 (Found MH$^+$ 284.1664, C$_{18}$H$_{21}$NO$_2$ requires 284.1651).

4-ethoxy-2-methyl-3-(4-phenoxyphenyl)-5,6,7,8-tetrahydroquinoline

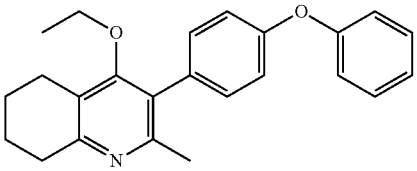 [SMILES: CCOc1c2c(nc(C)c1-c1ccc(Oc3ccccc3)cc1)CCCC2]

A solution of 4-ethoxy, 3-iodo, 2-methyl, 5,6,7,8-tetrahydro, quinolone (1.00 g, 3.16 mmol), 4-phenoxy phenyl boronic acid (1.01 g, 4.73 mmol), Palladium (II) tetra(tri-phenylphosphine) (0.18 g, 0.16 mmol) and dipotassium carbonate (2.00 M, 6.40 mL) dissolved in degassed DMF (20.0 mL) was heated to 85° C. and stirred for 12 hours. Observed colour change from yellow to black. The reaction mixture was allowed to cool to room temperature before dilution with ethyl acetate (15.0 mL). The organic layer was extracted using polar extraction technique, before being collected and dried over MgSO$_4$. The solution was then concentration in vacuo to afford the title compound as colourless fine needles (0.45 g, 1.25 mmol, 40%). δ H NMR (126 MHz, Chloroform-d); δ 7.35 (t, J=7.6 Hz, 2H), 7.23 (d, J=8.5 Hz, 2H), 7.11 (t, J=7.6 Hz, 1H), 7.05 (d, 4H) 3.42 (q, J=7.0 Hz, 2H), 2.82 (t, J=6.4 Hz, 2H), 2.62 (t, J=6.3 Hz, 2H), 2.23 (s, 3H), 1.80-1.74 (m, 2H), 1.73-1.67 (m, 2H), 1.49 (t, J=7.0 Hz, 3H); M/Z (ESI+); 360.20 (Found MH$^+$, 360.1963, C$_{24}$H$_{26}$NO$_2$ requires 360.1958).

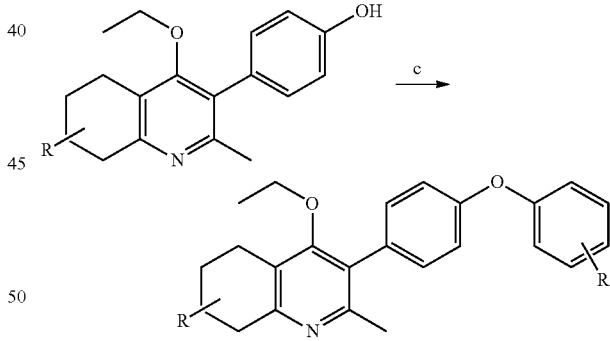

c) Phenyl boronic acid, Cu(OAc)$_2$, Pyridine, TEA, DCM

General Method C

Copper (II) acetate (1 equiv.), triethylamine (5 equiv.), and pyridine (5 equiv.) was added to a solution of the boronic acid (1.5 equiv.) and phenol (1 equiv.) in dichloromethane (10 mL mmol$^{-1}$) over heat-activated 4 Å molecular sieves. The reaction mixture was stirred over 16 hours at room temperature. The reaction mixture was quenched with HCl (0.5 M, 20 mL mmol$^{-1}$) and filtered through a pad of Celite, followed by repeated washing with water (10 mL mmol$^{-1}$). The organic layer was extracted with brine, dried over magnesium sulphate, and concentrated in vacuo. Purification by silica gel chromatography (ethyl acetate/hexane) afforded the title compound.

4-Ethoxy-3-(4-(4-fluorophenoxy)phenyl)-2-methyl-5,6,7,8-tetrahydroquinoline

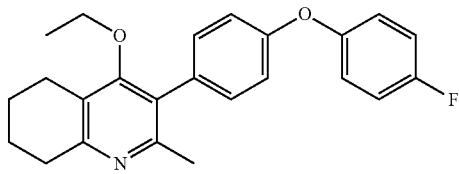 [SMILES: CCOc1c2c(nc(C)c1-c1ccc(Oc3ccc(F)cc3)cc1)CCCC2]

The title compound was synthesised from 4-(4-ethoxy-2-methyl-5,6,7,8-tetrahydroquinolin-3-yl)phenol (60 mg, 0.21 mmol) and 4-fluorobenzene boronic acid (45 mg, 0.31 mmol), according to general procedure C as pink micro crystals (70%, 55 mg, 0.15 mmol). $^1$H NMR (500 MHz, Chloroform-d) δ 7.14 (d, J=8.6 Hz, 2H), 6.97 (m, 6H), 3.44 (q, J=7.0 Hz, 2H), 2.87 (t, J=6.2 Hz, 2H), 2.64 (t, J=6.1 Hz, 2H), 2.26 (s, 3H), 1.78 (m, 4H), 0.97 (t, J=7.0 Hz, 3H); M/Z (ESI+); 378.19 (Found MH$^+$ 378.1877, $C_{24}H_{24}FNO_2$ requires).

3-(4-(3-Chlorophenoxy)phenyl)-4-ethoxy-2-methyl-5,6,7,8-tetrahydroquinoline

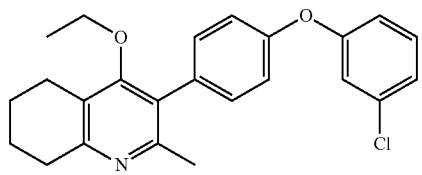 [SMILES: CCOc1c2c(nc(C)c1-c1ccc(Oc3cccc(Cl)c3)cc1)CCCC2]

The title compound was synthesised from 4-(4-ethoxy-2-methyl-5,6,7,8-tetrahydroquinolin-3-yl)phenol (250 mg, 0.88 mmol) and 3-chlorobenzene boronic acid (205 mg, 1.32 mmol), according to general procedure C as a viscous orange oil (78%, 270 mg, 0.68 mmol). 1H NMR (500 MHz, CDCl$_3$) δ 7.28-7.22 (m, 1H), 7.20 (d, J=8.3 Hz, 2H), 7.02 (d, J=8.3 Hz, 2H), 6.81-6.72 (m, 2H), 6.67 (dd, J=10.2, 2.1 Hz, 1H), 3.44 (q, J=7.0 Hz, 2H), 2.86 (t, J=6.2 Hz, 2H), 2.65 (t, J=6.1 Hz, 2H), 2.26 (s, 3H), 1.82 (m, 2H), 1.77-1.69 (m, 2H), 0.98 (t, J=7.0 Hz, 3H); M/Z (ESI+); 394.16 (Found MH$^+$; 394.1588, $C_{24}H_{24}ClNO_2$ requires 394.1574).

4-Ethoxy-2-methyl-3-(4-(4-(trifluoromethyl)phenoxy)phenyl)-5,6,7,8-tetrahydroquinoline

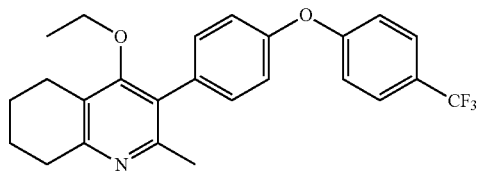 [SMILES: CCOc1c2c(nc(C)c1-c1ccc(Oc3ccc(C(F)(F)F)cc3)cc1)CCCC2]

The title compound was synthesised from 4-(4-ethoxy-2-methyl-5,6,7,8-tetrahydroquinolin-3-yl)phenol (60 mg, 0.21 mmol) and 4-trifluoromethylbenzene boronic acid (62 mg, 0.29 mmol), according to general procedure C as a viscous orange oil (55%, 47 mg, 0.11 mmol). 1H NMR (500 MHz, CDCl$_3$) δ 7.61 (d, J=8.7 Hz, 2H), 7.28 (d, J=8.5 Hz, 2H), 7.15-7.06 (m, 5H), 3.54 (q, J=7.0 Hz, 2H), 2.98 (t, J=6.3 Hz, 2H), 2.72 (t, J=6.2 Hz, 2H), 2.37 (s, 3H), 1.94-1.85 (m, 2H), 1.84-1.77 (m, 2H), 1.06 (t, J=7.0 Hz, 3H), M/Z (ESI+); 428.18 (Found MH$^+$ 428.1842, $C_{25}H_{24}F_3NO_2$ requires 428.1832).

4-Ethoxy-3-(4-(3-fluorophenoxy)phenyl)-2-methyl-5,6,7,8-tetrahydroquinoline

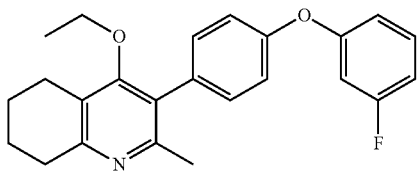 [SMILES: CCOc1c2c(nc(C)c1-c1ccc(Oc3cccc(F)c3)cc1)CCCC2]

The title compound was synthesised from 4-(4-ethoxy-2-methyl-5,6,7,8-tetrahydroquinolin-3-yl)phenol (250 mg, 0.88 mmol) and 3-fluorobenzene boronic acid (184 mg, 1.32 mmol), according to general procedure G as a yellow oil (57%, 190 mg, 0.50 mmol). $^1$H NMR (500 MHz, CDCl$_3$) δ 7.25 (dd, J=15.0, 8.2 Hz, 1H), 7.18 (d, J=8.6 Hz, 2H), 7.04 (d, J=8.6 Hz, 2H), 6.81-6.75 (m, 2H), 6.69 (dt, J=10.1, 2.3 Hz, 1H), 3.49 (q, J=7.0 Hz, 2H), 3.04 (m, 2H), 2.65 (t, J=6.2 Hz, 2H), 2.39 (s, 3H), 1.87-1.79 (m, 2H), 1.79-1.70 (m, 2H), 1.02 (t, J=7.0 Hz, 3H); M/Z (ESI+); 378.19 (Found MH$^+$ 378.1877, $C_{24}H_{24}FNO_2$ requires).

4-Ethoxy-3-(4-(3,4-dichlorophenoxy)phenyl)-2-methyl-5,6,7,8-tetrahydroquinoline

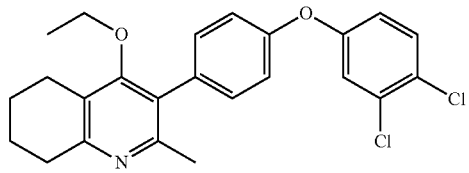 [SMILES: CCOc1c2c(nc(C)c1-c1ccc(Oc3ccc(Cl)c(Cl)c3)cc1)CCCC2]

The title compound was synthesised from 4-(4-ethoxy-2-methyl-5,6,7,8-tetrahydroquinolin-3-yl)phenol (100 mg, 0.34 mmol) and 3,4-dichlorobenzene boronic acid (93 mg, 0.51 mmol), according to general procedure C as an orange oil (49%, 70 mg, 0.16 mmol). $^1$H NMR (300 MHz, CDCl$_3$) δ 7.34 (d, J=8.8 Hz, 1H), 7.20 (dd, J=7.1, 1.6 Hz, 2H), 7.06 (d, J=2.8 Hz, 1H), 7.03-6.97 (m, 2H), 6.85 (dd, J=8.8, 2.8 Hz, 1H), 3.46 (q, J=7.0 Hz, 2H), 2.91 (t, J=6.2 Hz, 2H), 2.65 (t, J=6.1 Hz, 2H), 2.29 (s, 3H), 1.90-1.62 (m, 4H), 0.99 (t, J=7.0 Hz, 3H); M/Z (ESI+); 428.12 (Found MH$^+$; 428.1202, $C_{24}H_{23}Cl_2NO_2$ requires 428.1184).

4-Ethoxy-3-(4-(3-chloro-4-fluorophenoxy)phenyl)-2-methyl-5,6,7,8-tetrahydroquinoline

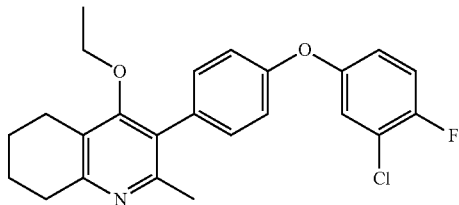 [SMILES: CCOc1c2c(nc(C)c1-c1ccc(Oc3ccc(F)c(Cl)c3)cc1)CCCC2]

The title compound was synthesised from 4-(4-ethoxy-2-methyl-5,6,7,8-tetrahydroquinolin-3-yl)phenol (250 mg, 0.88 mmol) and 3-chloro-4-fluorophenylboronic acid (230 mg, 1.32 mmol), according to general procedure C. The title compound was collected as a pale orange solid (104 mg, 0.25 mmol, 29%). $^1$H NMR (400 MHz, CDCl$_3$) δ 7.26 (d, J=8.2 Hz, 2H), 7.17-7.11 (t, J=8.7 Hz, 1H), 7.09 (dd, J=6.1, 2.9 Hz, 1H), 7.04 (d, J=8.3 Hz, 2H), 6.97-6.91 (m, 1H), 3.50 (dd, J=14.0, 7.0 Hz, 1H), 2.91 (t, J=6.2 Hz, 2H), 2.72 (t, J=5.9 Hz, 2H), 2.31 (s, 3H), 1.95-1.84 (m, 2H), 1.81 (m, 2H), 1.04 (t, J=7.0 Hz, 3H); M/Z (ESI); 412.1489, C$_{24}$H$_{23}$ClFNO$_2$ requires 411.1401.

4-Ethoxy-3-(4-(3-trifluoromethoxyphenoxy)phenyl)-2-methyl-5,6,7,8-tetrahydroquinoline

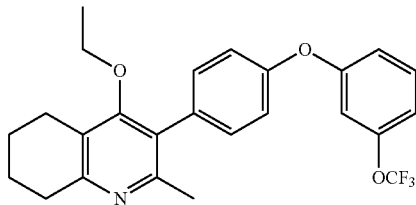 [SMILES: CCOc1c2c(nc(C)c1-c1ccc(Oc3cccc(OC(F)(F)F)c3)cc1)CCCC2]

The title compound was synthesised from 4-(4-ethoxy-2-methyl-5,6,7,8-tetrahydroquinolin-3-yl)phenol (200 mg, 0.71 mmol) and 3-trifluoromethoxyphenylboronic acid (218 mg, 1.06 mmol) according to general procedure C. The title compound was collected as a purple/brown oil (132 mg, 0.32 mmol, 42%); $^1$H NMR (400 MHz, CDCl$_3$) δ 7.29 (t, J=8.3 Hz, 1H), 7.21 (d, J=8.3 Hz, 2H), 7.03 (d, J=8.2 Hz, 2H), 6.90 (d, J=8.2 Hz, 2H), 6.81 (s, 1H), 3.44 (dd, J=14.0, 7.0 Hz, 2H), 2.84 (t, J=6.2 Hz, 2H), 2.65 (t, J=6.0 Hz, 2H), 2.25 (s, 3H), 1.86-1.78 (m, 2H), 1.74 (dd, J=10.2, 4.6 Hz, 2H), 0.97 (t, J=7.0 Hz, 3H); M/Z (ESI); 444.1786, C$_{25}$H$_{25}$F$_3$NO$_3$ requires 444.1781.

4-Ethoxy-3-(4-(3-trifluoromethylphenoxy)phenyl)-2-methyl-5,6,7,8-tetrahydroquinoline

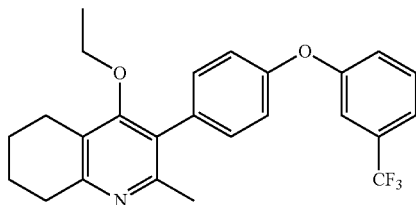

The title compound was synthesised from 4-(4-ethoxy-2-methyl-5,6,7,8-tetrahydroquinolin-3-yl)phenol (300 mg, 1.06 mmol) and 3-trifluoromethylphenyl boronic acid (302 mg, 1.59 mmol) according to general procedure C. The title compound was collected as a yellow oil (198 mg, 0.46 mmol, 44%). $^1$H NMR (400 MHz, CDCl$_3$) δ 7.44-7.38 (m, 1H), 7.32 (d, J=7.8 Hz, 1H), 7.17 (s, 2H), 7.12 (d, J=8.3 Hz, 2H), 7.01 (d, J=8.4 Hz, 2H), 3.45 (q, J=7.0 Hz, 2H), 2.85 (t, J=6.0 Hz, 2H), 2.62 (t, J=5.7 Hz, 2H), 2.25 (s, 3H), 1.73 (m, 4H), 1.00 (t, J=7.0 Hz, 3H); M/Z (ESI); 427.1852, C$_{25}$H$_{24}$F$_3$NO$_2$ requires 427.1759.

3-[4-(3,5-dichlorophenoxy)phenyl]-4-ethoxy-2-methyl-5,6,7,8-tetrahydroquinoline

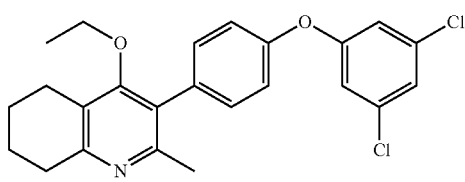 [SMILES: CCOc1c2c(nc(C)c1-c1ccc(Oc3cc(Cl)cc(Cl)c3)cc1)CCCC2]

The title compound was synthesised from 4-(4-ethoxy-2-methyl-5,6,7,8-tetrahydroquinolin-3-yl)phenol (250 mg, 0.88 mmol) and 3,5-dichlorophenylboronic acid (278 mg, 1.32 mmol according to general procedure C. The title compound was collected as a yellow solid (50 mg, 0.12 mmol, 13%). δ $^1$H NMR (500 MHz, Chloroform-d) δ 7.34-7.32 (m, 2H), 7.13-7.11 (m, 3H), 6.93 (d, J=1.8 Hz, 2H), 3.54 (q, J=7.0 Hz, 2H), 2.94 (t, J=6.1 Hz, 2H), 2.75 (t, J=6.3 Hz), 2.39 (s, 3H), 1.95-1.81 (m, 4H), 1.08 (t, J=7.0 Hz, 3H); M/Z (ESI); 428.1194, C$_{24}$H$_{24}$Cl$_2$NO$_2$ requires 428.1179.

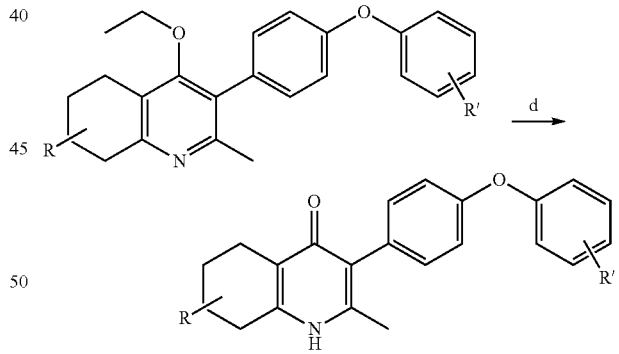

d) HBr (40% aq), Acetic acid, 120° C.

1.4 General Method D

To a solution of the 4-ethoxy-3-(diaryl ether)-hydroxy-quinoline (1 equiv.) in acetic acid (2 mL mmol$^{-1}$) was added hydrogen bromide (>48% w/v (aq)) (1 mL mmol$^{-1}$). The reaction mixture was then heated to 90° C. and left to reflux for 72 hours. The reaction mixture was neutralised with sodium hydroxide (2 M, 30.0 mL) and precipitate formed. The reaction mixture was then filtered to afford the title compound and purified.

Formation of 2-methyl-3-(4-phenoxyphenyl)-5,6,7,8-tetrahydroquinolin-4(1H)-one

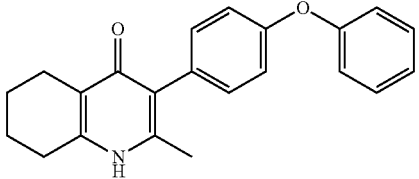 [SMILES: Cc1[nH]c2c(c(=O)c1-c1ccc(Oc3ccccc3)cc1)CCCC2]

The title compound was synthesised from 4-ethoxy,3-(4-phenoxy, benzene),2-methy,5,6,7,8-hydroquinolone (0.43 g, 1.20 mmol) following general procedure D to afford the title compound as colourless microcrystals (0.39 g, 1.20 mmol, 99%). $^1$H NMR (500 MHz, DMSO-$d_6$); δ 7.38 (t, J=7.9 Hz, 2H, H-3" & 5"), 7.17 (d, J=8.5 Hz, 2H), 7.14 (t, J=7.4 Hz, 1H), 7.05 (d, J=7.9 Hz, 2H), 6.98 (d, J=8.5 Hz, 2H), 2.56 (t, J=5.9 Hz, 2H), 2.30 (t, J=6.1 Hz, 2H), 2.08 (s, 3H), 1.75-1.68 (m, 2H), 1.68-1.62 (m, 2H M/Z (ESI+); 332.17 (Found MH$^+$, 332.1673, $C_{22}H_{21}NO_2$ requires 332.1650).

3-(4-(4-Fluorophenoxy)phenyl)-2-methyl-5,6,7,8-tetrahydroquinolin-4(1H)-one

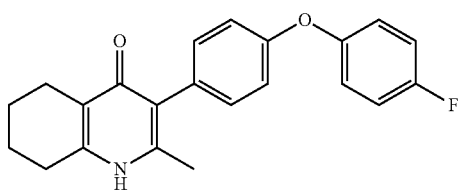 [SMILES: Cc1[nH]c2c(c(=O)c1-c1ccc(Oc3ccc(F)cc3)cc1)CCCC2]

The title compound was synthesised from 4-ethoxy-3-(4-(4-fluorophenoxy)phenyl)-2-methyl-5,6,7,8-tetrahydroquinoline (45 mg, 0.12 mmol) according to general procedure D. The title compound was isolated as colourless solid (25 mg, 0.07 mmol, 60%). $^1$H NMR (500 MHz, DMSO) δ 7.25 (t, J=8.7 Hz, 2H), 7.17 (d, J=8.5 Hz, 2H), 7.11 (dd, J=8.9, 4.5 Hz, 2H), 6.96 (d, J=8.5 Hz, 2H), 2.59-2.53 (m, 2H), 2.30 (t, J=5.2 Hz, 2H), 2.08 (s, 3H), 1.72 (m, 2H), 1.66 (m, 2H); M/Z (ESI+); 350.16 (Found MH$^+$ 350.1562, $C_{22}H_{20}FNO_2$ requires 350.1550).

3-(4-(3-Chlorophenoxy)phenyl)-2-methyl-5,6,7,8-tetrahydroquinolin-4(1H)-one

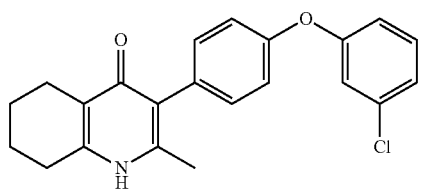 [SMILES: Cc1[nH]c2c(c(=O)c1-c1ccc(Oc3cccc(Cl)c3)cc1)CCCC2]

The title compound was synthesised from 3-(4-(3-chlorophenoxy)phenyl)-4-ethoxy-2-methyl-5,6,7,8-tetrahydroquinoline (200 mg, 0.51 mmol) according to general procedure D. The title compound was isolated as colourless solid (120 mg, 0.33 mmol, 66%). $^1$H NMR (500 MHz, DMSO) δ 11.71 (s, 1H), 7.44 (t, J=8.2 Hz, 1H), 7.25 (d, J=8.6 Hz, 2H), 7.22 (ddd, J=8.0, 1.9, 0.8 Hz, 1H), 7.10 (t, J=2.0 Hz, 1H), 7.09 (d, J=8.6 Hz, 2H), 7.03 (ddd, J=8.2, 2.3, 0.6, 1H), 2.65 (t, J=5.9 Hz, 2H), 2.39 (t, J=5.2 Hz, 2H), 2.14 (s, 3H), 1.84-1.59 (m, 4H); M/Z (ESI+); 366.13 (Found MH$^+$ 366.1262, $C_{22}H_{20}ClNO_2$ requires 366.1255).

2-Methyl-3-(4-(4-(trifluoromethyl)phenoxy)phenyl)-5,6,7,8-tetrahydroquinolin-4(1H)-one

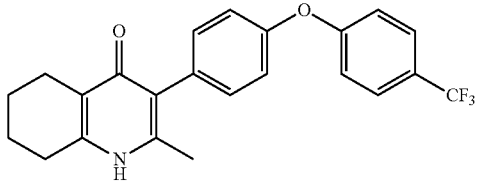 [SMILES: Cc1[nH]c2c(c(=O)c1-c1ccc(Oc3ccc(C(F)(F)F)cc3)cc1)CCCC2]

The title compound was synthesised from 4-ethoxy-2-methyl-3-(4-(4-(trifluoromethyl)phenoxy)phenyl)-5,6,7,8-tetrahydroquinoline (47 mg, 0.12 mmol) according to general procedure D. The title compound was isolated as colourless solid (25 mg, 0.07 mmol, 60%). $^1$H NMR (500 MHz, DMSO) δ 11.14 (s, 1H), 7.77 (d, J=8.6 Hz, 2H), 7.26 (d, J=8.6 Hz, 2H), 7.19 (d, J=8.6 Hz, 2H), 7.12 (d, J=8.6 Hz, 2H), 2.59 (t, J=5.8 Hz, 2H), 2.33 (t, J=6.4 Hz, 2H), 2.12 (s, 3H), 1.73 (m, 2H), 1.70-1.64 (m, 2H); M/Z (ESI+); 400.15 (Found MH$^+$; 400.1528, $C_{23}H_{20}F_3NO_2$ requires 400.1519).

3-(4-(3-Fluorophenoxy)phenyl)-2-methyl-5,6,7,8-tetrahydroquinolin-4(1H)-one

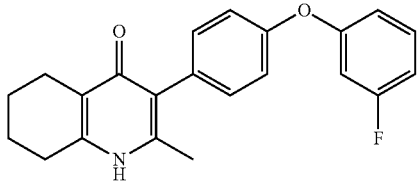 [SMILES: Cc1[nH]c2c(c(=O)c1-c1ccc(Oc3cccc(F)c3)cc1)CCCC2]

The title compound was synthesised from 4-ethoxy-3-(4-(3-fluorophenoxy)phenyl)-2-methyl-5,6,7,8-tetrahydroquinoline (170 mg, 0.45 mmol) according to general procedure D. The title compound was isolated as colourless solid (110 mg, 0.31 mmol, 70%). $^1$H NMR (500 MHz, DMSO) δ 7.47 (dt, J=8.6, 7.1 Hz, 1H), 7.31 (d, J=8.7 Hz, 2H), 7.17 (d, J=8.7 Hz, 2H), 7.02 (tdd, J=8.5, 2.3, 0.7 Hz, 1H), 6.97-6.88 (m, 2H), 2.83 (t, J=6.1 Hz, 2H), 2.54 (t, J=5.8 Hz, 2H), 2.25 (s, 3H), 1.87-1.69 (m, 4H); M/Z (ESI+); 350.16 (Found MH$^+$; 350.1569, $C_{22}H_{21}FNO_2$ requires 350.1556).

3-(4-(3,4-Dichlorophenoxy)phenyl)-2-methyl-5,6,7,8-tetrahydroquinolin-4(1H)-one

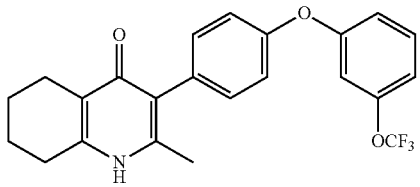 [SMILES: Cc1[nH]c2c(c(=O)c1-c1ccc(Oc3cccc(OC(F)(F)F)c3)cc1)CCCC2]

The title compound was synthesised from 4-Ethoxy-3-(4-(3-trifluoromethoxyphenoxy)phenyl)-2-methyl-5,6,7,8-tetrahydroquinoline (100 mg, 0.23 mmol) according to general procedure D. The title compound was isolated as colourless solid (72 mg, 0.16 mmol, 76%). $^1$H NMR (501 MHz, DMSO) δ 11.27 (s, 1H, NH), 7.51 (t, J=8.3 Hz, 1H), 7.22 (d, J=8.5 Hz, 2H), 7.12 (d, J=7.6 Hz, 1H), 7.07 (d, J=8.5 Hz, 2H), 7.03 (dd, J=8.6, 1.7 Hz, 1H), 7.00 (s, 1H), 2.58 (t, J=5.2 Hz, 2H), 2.32 (t, J=6.2 Hz, 2H), 2.09 (s, 3H), 1.76-1.69 (m, 2H), 1.69-1.61 (m, 2H); M/Z (ESI+); 416.15 (Found MH$^+$; 416.1469, $C_{23}H_{21}F_3NO_3$ requires 416.1468).

3-(4-(3,4-Dichlorophenoxy)phenyl)-2-methyl-5,6,7,8-tetrahydroquinolin-4(1H)-one

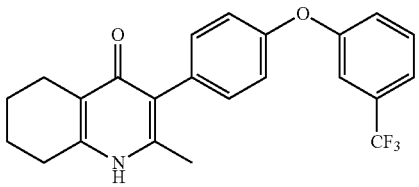 [SMILES: Cc1[nH]c2c(c(=O)c1-c1ccc(Oc3cccc(C(F)(F)F)c3)cc1)CCCC2]

The title compound was synthesised from 4-Ethoxy-3-(4-(3-trifluoromethylphenoxy)phenyl)-2-methyl-5,6,7,8-tetrahydroquinoline (193 mg, 0.45 mmol) according to general procedure D. The title compound was isolated as colourless solid (174 mg, 0.44 mmol, 96%). $^1$H NMR (501 MHz, DMSO) δ 11.15 (s, 1H), 7.63 (t, J=8.6 Hz, 1H), 7.48 (d, J=8.2 Hz, 1H), 7.30 (s, 2H), 7.22 (d, J=8.4 Hz, 2H), 7.07 (d, J=8.4 Hz, 2H), 2.56 (t, J=3.3 Hz, 2H), 2.30 (t, J=5.3 Hz, 2H), 2.08 (s, 3H), 1.71 (dd, J=6.0, 4.6 Hz, 2H), 1.68-1.60 (m, 2H); M/Z (ESI+); 400.15 (Found MH$^+$; 400.1519 requires $C_{23}H_{21}F_3NO_2$ requires 400.1519).

3-(4-(3,4-Dichlorophenoxy)phenyl)-2-methyl-5,6,7,8-tetrahydroquinolin-4(1H)-one

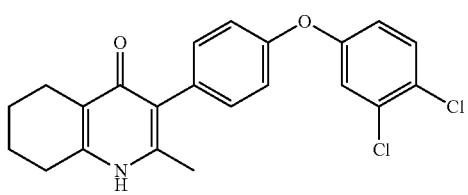 [SMILES: Cc1[nH]c2c(c(=O)c1-c1ccc(Oc3ccc(Cl)c(Cl)c3)cc1)CCCC2]

The title compound was synthesised from 4-ethoxy-3-(4-(3,4-dichloro phenoxy)phenyl)-2-methyl-5,6,7,8-tetrahydroquinoline (60 mg, 0.15 mmol) according to general procedure D. The title compound was isolated as colourless solid (35 mg, 0.08 mmol, 59%). $^1$H NMR (500 MHz, DMSO) δ 10.95 (s, 1H), 7.66 (d, J=8.5 Hz, 1H), 7.31 (s, 1H), 7.23 (d, J=8.2 Hz, 2H), 7.08 (d, J=7.6 Hz, 2H), 7.04 (d, J=8.9 Hz, 1H), 2.55 (m, 2H), 2.30 (m, Hz, 2H), 2.09 (s, 3H), 1.72 (m, 2H), 1.66 (m, 2H); M/Z (ESI+); 400.09 (Found MH$^+$; 400.0881, $C_{22}H_{20}Cl_2NO_2$ requires 400.0866).

3-[4-(3-chloro-4-fluorophenoxy)phenyl]-2-methyl-5,6,7,8-tetrahydro-1H-quinolin-4-one

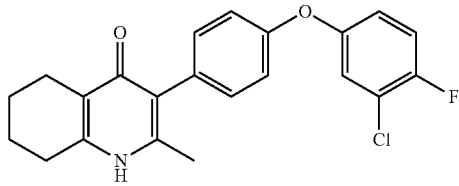

The title compound was synthesised from 4-Ethoxy-3-(4-(3-chloro-4-fluorophenoxy)phenyl)-2-methyl-5,6,7,8-tetrahydroquinoline (90 mg, 2.18 mmol) The title compound was isolated as a pale grey precipitate (55 mg, 0.14 mmol, 66%). 1H NMR (500 MHz, TFA) δ 7.39 (d, J 8.6 Hz, 2H), 7.32 (d, J 8.5 Hz, 2H), 7.27-7.24 (m, 2H), 7.12-7.09 (m, 1H), 3.10 (t, J 5.8 Hz, 2H), 2.91 (t, J 5.9 Hz, 2H), 2.54 (s, 3H), 2.15-2.03 (m, 4H); M/Z (ESI); 384.1167, ($C_{22}H_{20}ClFNO_2$ requires 384.1161).

3-[4-(3,5-dichlorophenoxy)phenyl]-2-methyl-5,6,7,8-tetrahydro-1H-quinolin-4(1H)-one

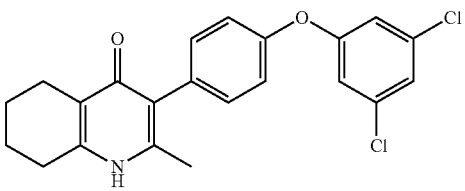

The title compound was synthesised from 3-[4-(3,5-dichlorophenoxy)phenyl]-4-ethoxy-2-methyl-5,6,7,8-tetrahydroquinoline (40 mg, 0.93 mmol) according to general procedure D. The title compound was isolated as colourless solid (31 mg, 0.08 mmol, 83%). δ $^1$H NMR (500 MHz, TFA) δ 7.44 (d, J=8.5 Hz, 2H), 7.39 (d, J=8.0 Hz, 2H), 7.30 (s, 1H), 7.10 (s, 2H), 3.12 (t, J=5.5 Hz, 2H), 2.93 (t, J=5.5 Hz, 2H), 2.57 (s, 3H), 2.09-2.00 (m, 4H); M/Z (ESI); 400.0874, $C_{22}H_{20}Cl_2NO_2$ requires 400.0866.

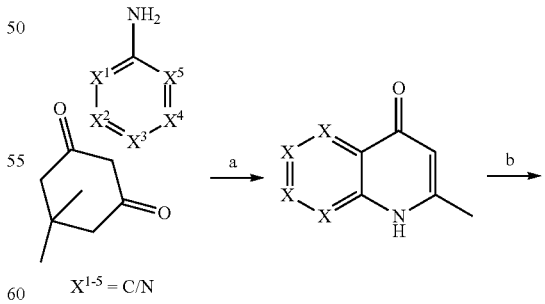

$X^{1-5}$ = C/N

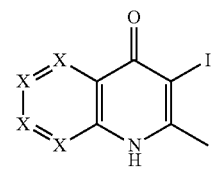

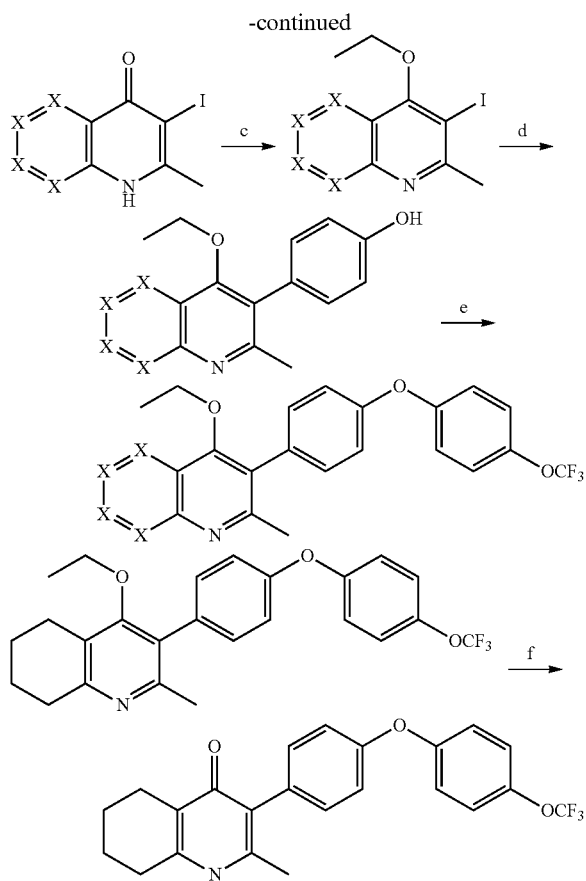

a) i) Meldrums acid, triethylorthoacetate, 110° C., ii) Aniline, 110° C., iii) Dowtherm A, 250° C., b) NIS, Acetonitrile, 80° C., c) EtI, K$_2$CO$_3$, DMF, 80° C., d) 4-Hydroxyphenyl boronic acid, Pd(PPH$_3$)$_4$, Na$_2$CO$_3$, DMF, 80° C., e) Phenyl boronic acid, Cu(OAc)$_2$, Pyridine, TEA, DCM, f) HBr (40% aq), Acetic acid, 120° C.

General Method A 2,2-Dimethyl-1,3-dioxane-4,6-dione (1.5 equiv.) was dissolved in trimethylorthoacetate (2 equiv.) and heated to 115° C. for 2 hrs. The reaction was cooled to allow the addition of the aniline (1 equiv.) before being heated to 115° C. for a further 2 hrs. The reaction mixture was then allowed to cool and was concentrated in vacuo, remaining solvent was washed off with cold methanol. The precipitate was then dissolved in minimum volume of Dowtherm A and refluxed at 250° C. for 1.5 hours. The reaction mixture was allowed to cool and the precipitate filtered followed by washing with hexane to afford the title compound.

2-Methyl-1,7-napthyrid-4(1H)-one

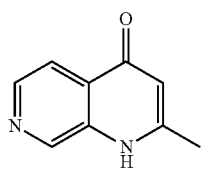

The title compound was synthesised using 3-amino pyridine (3.0 g, 32 mmol) following general procedure A. To give the title compound as colourless solid (489 mg, 3.1 mmol, 10%). 1H NMR (500 MHz, CDCl$_3$) δ 8.52 (s, 1H, H-8), 7.72 (d, J=8.0 Hz, 1H, H-5), 7.59-7.31 (m, 1H, H-6), 6.18 (s, 1H, H-3), 2.28 (s, 3H, Me). M/Z (ESI+); (Found MH$^+$; requires).

General Method B

2-Methyl-napthyrid-4(1H)-one (1 equiv.) and N-Iodosuccinamide (1.2 equiv.) were dissolved in acetonitrile (5 mL mmol$^{-1}$) and stirred and heated at 80° C. for 3 hours. The reaction mixture was then allowed to cool and the mixture filtered, the precipitate was then washed with water (15 mL) to afford the title compound as a colourless solid.

3-Iodo-2-methyl-1,7-napthyrid-4(1H)-one

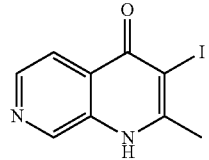

The title compound was synthesised using 2-Methyl-1,7-napthyrid-4(1H)-one (480 mg, 3.0 mmol) following general procedure B. To give the title compound as colourless solid (740 mg, 2.6 mmol, 86%). $^1$H NMR (500 MHz, CDCl$_3$) δ 8.36-7.91 (m, 1H), 7.49 (dd, J=8.4, 1.1 Hz, 1H), 7.18 (dd, J=8.6, 4.2 Hz, 1H), 2.27 (s, 3H). M/Z (ESI+); (Found MH$^+$; requires).

General Method C

A suspension of the 4(1H), 3-Iodo-2-methyl-napthyrid-4(1H)-one (1 equiv.) and potassium carbonate (2 equiv.) in DMF (20.0 mL) was heated to 50° C. and stirred for 45 minutes. The reaction mixture was removed from the heat and ethyl iodide (1.5 equiv.) was added dropwise. The reaction mixture was then heated and kept at 50° C. with stirring for a further 18 hrs. Formation of a yellow emulsion was observed. The reaction mixture was then quenched with water (40.0 mL). The organic phase was extracted using the polar extraction technique (ethyl acetate, 3×40.0 mL), and the resulting organic layers were combined and dried over MgSO$_4$ and concentrated in vacuo to afford the title compound.

4-Ethoxy-3-iodo-2-methyl-1,7-napthyridine

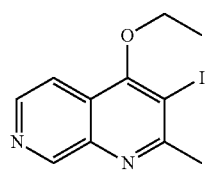

The title compound was synthesised using, 3-Iodo-2-methyl-napthyrid-4(1H)-one (720 mg, 2.5 mmol) following general procedure C. To give the title compound as brown gum (244 mg, 0.8 mmol, 33%). $^1$H NMR (500 MHz, CDCl$_3$) δ 8.87 (dd, J=4.0, 1.5 Hz, 1H), 8.31 (dd, J=8.5, 1.6 Hz, 1H), 7.63 (dd, J=8.5, 4.1 Hz, 1H), 4.84 (q, J=7.0 Hz, 2H), 3.00 (s, 3H), 1.59 (t, J=7.0 Hz, 3); M/Z (ESI+); (Found MH+; requires).

General Method F

To a nitrogen flushed flask charged with the 4-Ethoxy-3-iodo-2-methyl-napthyridine (400 mg, 1.26 mmol), 4-hydroxybenzene boronic acid (260 mg, 1.89 mmol) and palladium tetra(triphenylphosphine) (73 mg, 0.06 mmol) was added degassed DMF (10 mL). Potassium carbonate (3 mL, 2 M$_{(aq)}$) was added and the reaction mixture brought up to 80° C. and stirred for 3 hours. The reaction mixture was then cooled to room temperature and diluted with water (10 mL). The organic phase was then extracted using ethyl acetate (3×20 mL). The organic phases were combined and washed with water (3×20 mL) and then dried with brine (1×10 mL) and MgSO$_4$, before concentration in vacuo. The resulting solid was then recrystallized in ethyl acetate to afford the title compound.

4-Ethoxy-3-phenol-2-methyl-1,7-napthyridine

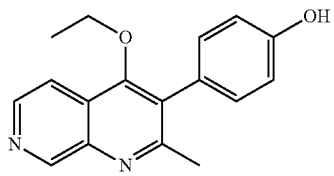 [SMILES: CCOc1c(-c2ccc(O)cc2)c(C)nc2cnccc12]

The title compound was synthesised using, 4-Ethoxy-3-iodo-2-methyl-1,7-napthyridine (230 mg, 0.73 mmol) following general procedure F. To give the title compound an orange powder (80 mg, 0.8 mmol, 28%). 1H NMR (400 MHz, MeOD) δ 8.78 (dd, J=4.1, 1.4 Hz, 1H), 8.24 (dd, J=8.6, 1.4 Hz, 1H), 7.64 (dd, J=8.6, 4.2 Hz, 1H), 7.08 (d, J=8.5 Hz, 2H), 6.84 (d, J=8.5 Hz, 2H), 4.12 (q, J=7.0 Hz, 2H), 2.39 (s, 3H), 1.05 (t, J=7.0 Hz, 3H); M/Z (ESI+); (Found MH+; requires).

General Method G

Copper (II) acetate (1 equiv.), triethylamine (5 equiv.), and pyridine (5 equiv.) was added to a solution of the boronic acid (1.5 equiv.) and phenol (1 equiv.) in dichloromethane (10 mL mmol$^{-1}$) over heat-activated 4 Å molecular sieves. The reaction mixture was stirred over 16 hours at room temperature. The reaction mixture was quenched with HCl (0.5 M, 20 mL mmol$^{-1}$) and filtered through a pad of Celite, followed by repeated washing with water (10 mL mmol$^{-1}$). The organic layer was extracted with brine, dried over magnesium sulphate, and concentrated in vacuo. Purification by silica gel chromatography (ethyl acetate/hexane) afforded the title compound.

4-Ethyl-3(4-(4-trifluoromethoxyphenoxy)phenyl)-2-methyl-1,7-napthyridone

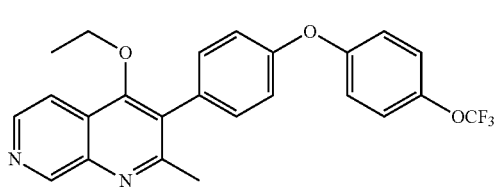 [SMILES: CCOc1c(-c2ccc(Oc3ccc(OC(F)(F)F)cc3)cc2)c(C)nc2cnccc12]

The title compound was synthesised using 4-Ethoxy-3-iodo-2-methyl-1,7-napthyridine (70 mg, 0.25 mmol) and 4-trifluoromethoxybenzenboronic acid (79 mg, 0.38 mmol) following general procedure G. To give the title compound as a red crystalline solid (34 mg, 0.08 mmol, 20%). 1H NMR (400 MHz, CDCl$_3$) δ 8.90 (dd, J=4.0, 1.3 Hz, 1H), 8.33 (dd, J=8.5, 1.3 Hz, 1H), 7.61 (dd, J=8.5, 4.1 Hz, 1H), 7.31 (d, J=8.5 Hz, 2H), 7.24 (d, J=8.7 Hz, 2H), 7.13 (d, J=8.7 Hz, 2H), 7.10 (d, J=9.1 Hz, 2H), 4.43 (q, J=7.0 Hz, 2H), 2.54 (s, 3H), 1.19 (t, J=7.0 Hz, 3H); M/Z (ESI+); (Found MH+; requires).

General Method J

To a solution of the 4-Ethyl-3(4-(4-trifluoromethoxyphenoxy)phenyl)-2-methylnapthyridone (1 equiv.) in acetic acid (2 mL mmol$^{-1}$) was added hydrogen bromide (>48% w/v (aq)) (1 mL mmol$^{-1}$). The reaction mixture was then heated to 90° C. and left to reflux for 72 hours. The reaction mixture was neutralised with sodium hydroxide (2 M, 30.0 mL) and precipitate formed. The reaction mixture was then filtered to afford the title compound.

3(4-(4-trifluoromethoxyphenoxy)phenyl)-2-methyl-1,7-napthyrid-4(1H)-one

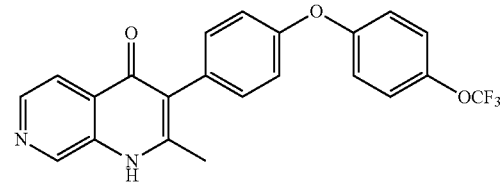 [SMILES: Cc1[nH]c2cnccc2c(=O)c1-c1ccc(Oc2ccc(OC(F)(F)F)cc2)cc1]

The title compound was synthesised from 4-Ethyl-3(4-(4-trifluoromethoxyphenoxy)phenyl)-2-methyl-1,7-napthyridone (31 mg, 0.07 mmol). To give the title compound as a colourless solid (13 mg, 0.03 mmol, 45%). $^1$H NMR (400 MHz, CDCl$_3$) δ 8.44 (d, J=3.6 Hz, 1H), 7.75 (d, J=8.2 Hz, 1H), 7.36 (dd, J=8.3, 4.1 Hz, 1H), 7.02 (d, J=8.6 Hz, 2H), 6.96 (d, J=8.5 Hz, 2H), 6.83 (d, J=9.2 Hz, 4H), 2.09 (s, 3H); M/Z (ESI+); 413.11 (Found MH+; 413.1104 C$_{22}$H$_{15}$F$_3$N$_2$O$_3$ requires 413.1107).

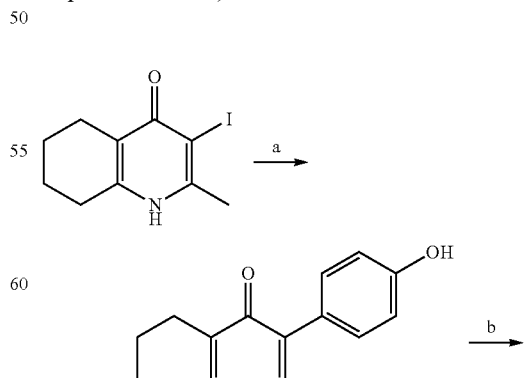

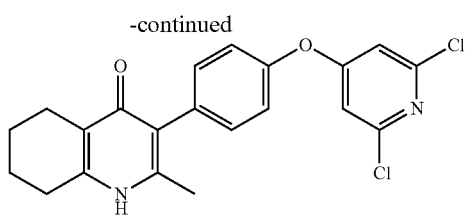

a) 4-Hydroxybenzene boronic acid, Pd(PPH₃)₄, Na₂CO₃ (aq), DMF 80° C., b) 2,4,6 trichloropyridine, K₂CO₃, DMF, 100° C.

3-phenol-2-methyl-5,6,7,8-tetrahydroquinolin-4(1H)-one

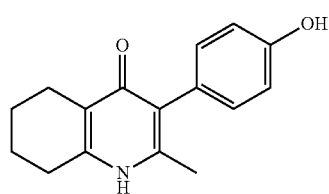 [SMILES: Cc1[nH]c2c(c(=O)c1-c1ccc(O)cc1)CCCC2]

The title compound was synthesised from 4(1H)-3-iodo-2-methyl-5,6,7,8-tetrahydroquinolin-4(1H)-one (500 mg, 1.73 mmol) and 4-hydroxyphenylboronic acid (318 mg, 2.30 mmol) and palladium tetra(triphenylphosphine) (73 mg, 0.06 mmol) was added degassed DMF (10 mL). Potassium carbonate (aq) (3 mL, 2 M) was added and the reaction mixture brought up to 80° C. and stirred for 3 hours. The reaction mixture was then cooled to room temperature and diluted with water (10 mL). Organics were extracted with ethyl acetate (3×10 mL). The aqueous layer was neutralised using hydrochloric acid (2 M), causing the title compound, a grey precipitate to crash out which was collected by vacuum filtration (150 mg, 0.58 mmol, 44%). ¹H NMR (400 MHz, MeOD) δ 6.91 (d, J=8.6 Hz, 2H), 6.71 (d, J=8.6 Hz, 2H), 2.57 (t, J=6.0 Hz), 2.39 (t, J=5.6 Hz, 2H), 2.03 (s, 3H), 1.77-1.61 (m, 4H); M/Z (ESI); 255.1341 ($C_{16}H_{17}NO_2$ requires 255.1259).

3-{4-[(2,6-dichloropyridin-4-yl)oxy]phenyl}-2-methyl-5,6,7,8-tetrahydro-1H-quinolin-4-one

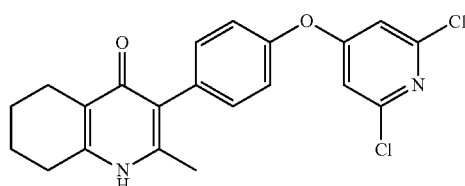

3-phenol-2-methyl-5,6,7,8-tetrahydroquinolin-4(1H)-one (120 mg, 0.47 mmol) and potassium carbonate (78 mg, 0.56 mmol) were dissolved in DMF (3 mL) and the reaction mixture was stirred for 15 mins. Following this, 2,4,6-Trichloropyridine (86 mg, 0.47 mmol) was added and the mixture was heated to 100° C. and stirred for 18 hours under an inert atmosphere. The reaction mixture was allowed to cool to room temperature and was diluted with water (5 ml). The resulting pale grey precipitate was collected by vacuum filtration, washed with water (5 ml) and dried (118 mg, 0.29 mmol, 63%). δ ¹H NMR (500 MHz, TFA) δ 7.66 (d, J 8.5 Hz, 2H), 7.56 (d, J 8.5 Hz, 2H), 7.44 (s, 2H), 3.10 (t, J 5.0 Hz, 2H), 2.90 (t, J 5.0 Hz, 2H), 2.55 (s, 3H), 2.10-2.08 (m, 4H); M/Z (ESI); 400.0826, ($C_{21}H_{18}Cl_2N_2O_2$ requires 400.0745).

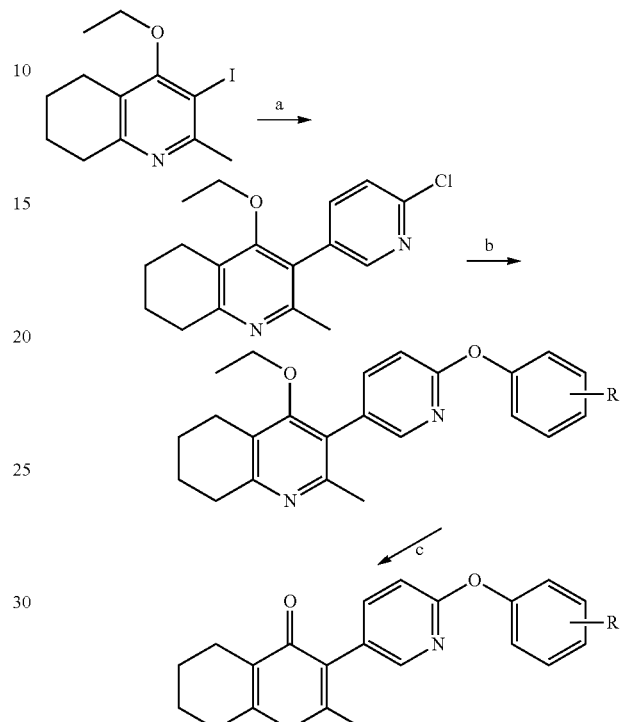

a) 2-Chlorpyridine-5-boronic acid, Pd(PPH₃)₄, Na₂CO₃ (aq), DMF 80° C., b) Phenol, K₂CO₃, DMF, 100° C.

4-Ethoxy-3-(6-chloropyrdin-3-yl)-2-methyl-5,6,7,8-tetrahydroquinoline

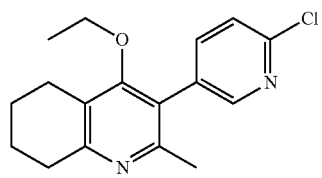 [SMILES: CCOc1c2c(nc(C)c1-c1ccc(Cl)nc1)CCCC2]

To a nitrogen flushed flask charged with 4-ethoxy-3-iodo-2-methyl-5,6,7,8-tetrahydroquinoline (1.5 g, 4.7 mmol), 2-chloropyridine-5-boronic acid (1.12 g, 7.1 mmol) and palladium tetra(triphenylphosphine) (271 mg, 0.24 mmol) was added degassed DMF (20 mL). Potassium carbonate (3 mL, 2 $M_{(aq)}$) was added and the reaction mixture brought up to 80° C. and stirred for 3 hours. The reaction mixture was then cooled to room temperature and diluted with water (10 mL). The organic phase was then extracted using ethyl acetate (3×20 mL). The organic phases were combined and washed with water (3×20 mL) and then dried with brine (1×10 mL) and MgSO₄, before concentration in vacuo. The resulting residue was purified by column chromatography (Pet:EtOAc), to yield the title compound as a yellow platelets (330 mg, 1.09 mmol, 23%). HPLC; 2.17 min (100% ref area); ¹H NMR (500 MHz, CDCl₃) δ 8.33 (d, J=2.4 Hz, 1H), 7.60 (dd, J=8.2, 2.4 Hz, 1H), 7.44-7.42 (d, J=8.2, 1H), 3.53 (q, J=7.0 Hz, 2H), 2.98 (t, J=6.2 Hz, 2H), 2.72 (t, J=6.2 Hz, 2H), 2.35 (s, 3H), 1.93-1.85 (m, 2H), 1.84-1.76 (m, 2H), 1.06 (t, J=7.0 Hz, 3H); M/Z (ESI+); 303.13 (Found MH⁺; 303.1266, C₁₇H₁₉ClN₂O requires 303.1259).

4-Ethoxy-3-(6-(4-trifluoromethoxyphenoxy)pyridin-3-yl)-2-methyl-5,6,7,8-tetrahydroquinoline

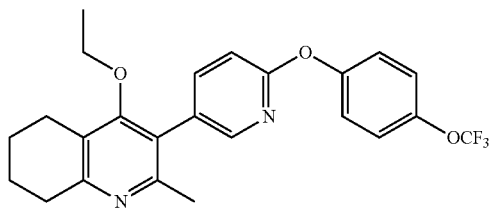

4-Ethoxy-3-(6-chloropyrdin-3-yl)-2-methyl-5,6,7,8-tetrahydroquinoline (250 mg, 0.82 mmol), 4-trifluoromethoxyphenol (178 mg, 1.0 mmol) and potassium carbonate (276 mg, 1.7 mmol) were dissolved in DMF and refluxed at 110° C. for 24 hrs. The reaction mixture was then cooled to room temperature and diluted with water (10 mL). The organic phase was then extracted using ethyl acetate (3×20 mL). The organic phases were combined and washed with water (3×20 mL) and then dried with brine (1×10 mL) and MgSO₄, before concentration in vacuo. The resulting residue was purified by reverse phase column chromatography (H₂O: acetonitrile), to yield the title compound as a yellow oil (75 mg, 0.17 mmol, 20%). 1H NMR (400 MHz, CDCl₃) δ 8.03 (d, J=2.2 Hz, 1H), 7.58 (dd, J=8.4, 2.2 Hz, 1H), 7.29-7.07 (m, 4H), 6.95 (d, J=8.4 Hz, 1H), 3.46 (q, J=7.0 Hz, 2H), 2.85 (t, J=6.3 Hz, 2H), 2.64 (t, J=6.1 Hz, 2H), 2.25 (s, 3H), 1.81 (dt, J=12.2, 6.3 Hz, 2H), 1.77-1.68 (m, 2H), 0.99 (t, J=7.0 Hz, 3H); M/Z (ESI+); 445.18 (Found MH⁺; 445.1759, C₂₄H₂₃F₃N₂O₃ requires 445.1739).

3-(6-(4-Trifluoromethoxyphenoxy)pyridin-3-yl)-2-methyl-5,6,7,8-tetrahydroquinolin-(4)-one

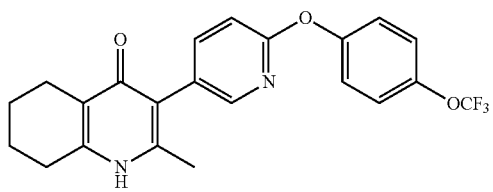

The title compound was synthesised from 4-ethoxy-3-(6-(4-trifluoromethoxyphenoxy)pyridin-3-yl)-2-methyl-5,6,7,8-tetrahydroquinoline (70 mg, 0.15 mmol) according to general procedure J. The title compound was isolated as colourless solid (13 mg, 0.03 mmol, 20%). ¹H NMR (400 MHz, DMSO) δ 11.07 (s, 1H), 7.94 (d, J=2.2 Hz, 1H), 7.70 (dd, J=8.4, 2.4 Hz, 1H), 7.43 (d, J=8.7 Hz, 2H), 7.29 (d, J=9.0 Hz, 2H), 7.09 (d, J=8.4 Hz, 1H), 2.56 (t, J=5.1 Hz, 2H), 2.30 (t, J=5.9 Hz, H), 2.10 (s, 3H), 1.79-1.57 (m, 4H); M/Z (ESI+); 417.14 (Found MH⁺; 417.1432, C₂₂H₁₉F₃N₂O₃ requires 417.1421).

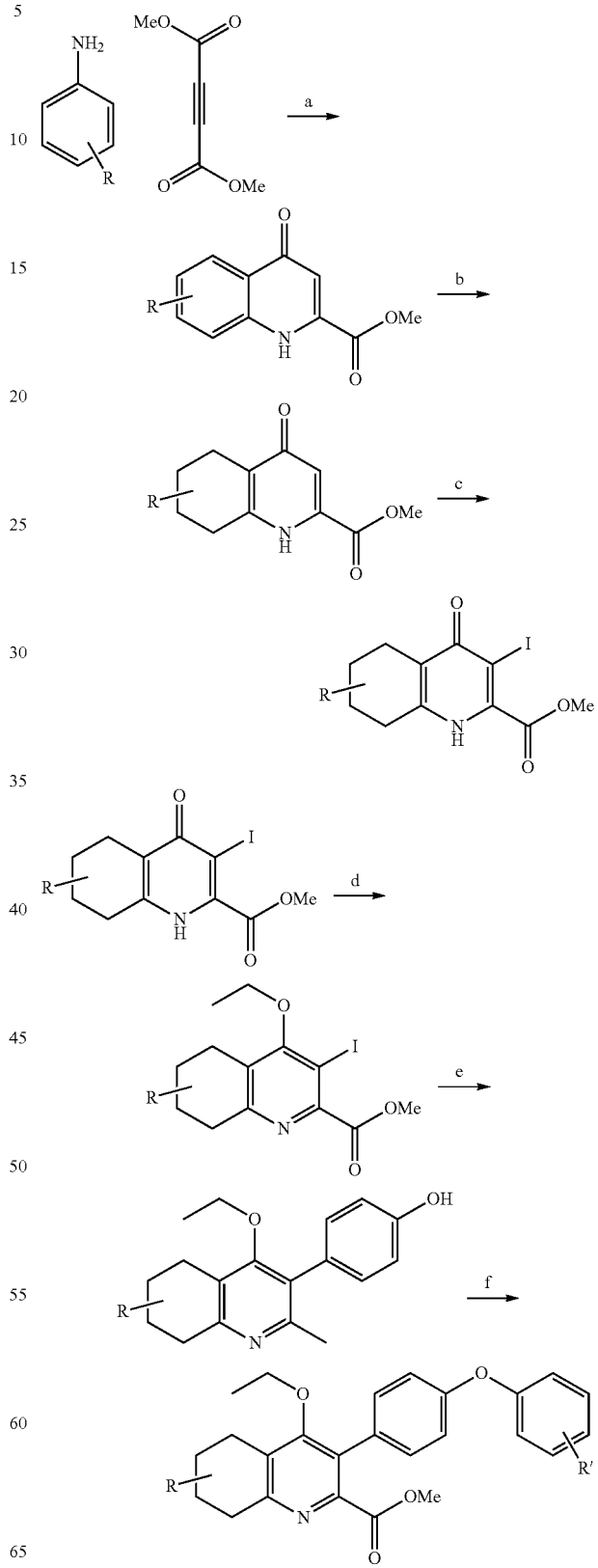

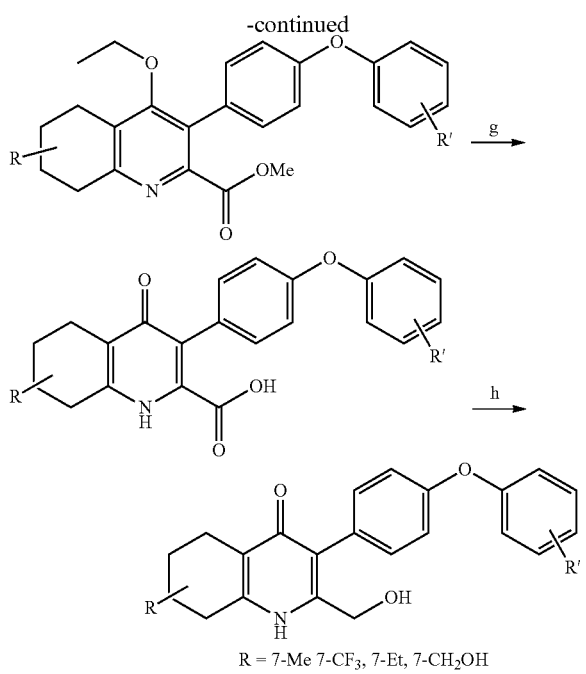

R = 7-Me 7-CF$_3$, 7-Et, 7-CH$_2$OH a) i) Ethanol, ii) Dowtherm A, 250° C., b) PtO$_2$, H$_2$, AcOH, c) NIS, Acetonitrile, 80° C., D) EtI, K$_2$CO$_3$, DMF, 80° C., e) 4-Hydroxyphenyl boronic acid, Pd(PPH$_3$)$_4$, DMF, 80° C., f) Phenyl boronic acid, Cu(OAc)$_2$, Pyridine, TEA, DCM, g) HBr (40% aq), Acetic acid, 120° C., h) i) MeOH, ii) DiBAl.

General Method B

The 4-hydroxylquinolone (1 equiv.) was dissolved in acetic acid (10.0 mL) under inert conditions. platinum dioxide (5% weight equiv.) was added and a hydrogen balloon was attached. The reaction was left to proceed for 12 hours. The resulting suspension was filtered through a pad of Celite and washed with ethyl acetate (10.0 mL). The filtrate was concentrated in vacuo to afford a yellow/brown oil. Purification by column chromatography (10% methanol in chloroform) afforded the title compound.

2-(Methoxycarboxylate)-5,6,7,8-tetrahydro quinolin-4(1H)-one

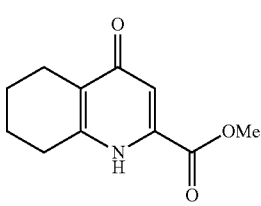 [SMILES: COC(=O)c1cc(=O)c2c([nH]1)CCCC2]

The title compound was synthesised following general procedure B from 2-(methoxycarboxylate)quinolin-4(1H)-one (500 mg, 2.5 mmol). The title compound was isolated as colourless solid (470 mg, 2.4 mmol, %). $^1$H NMR (500 MHz, CDCl$_3$) δ 8.89 (s, 1H), 7.07 (s, 1H), 3.95 (s, 3H), 2.74 (t, J=6.1 Hz, 2H), 2.56 (t, J=6.2 Hz, 2H), 1.82 (dt, J=8.0, 6.1 Hz, 1H), 1.79-1.69 (m, 1H); M/Z (ESI+); 208.10 (Found MH$^+$; 208.0977, C$_{11}$H$_{13}$NO$_3$ requires 208.0974).

1.5 General Method C

The tetrahydroquinolin-4(1H)-one (1 equiv.) and N-Iodo-succinamide (1.2 equiv.) were dissolved in acetonitrile (5 mL mmol$^{-1}$) and stirred and heated at 80° C. for 3 hours. The reaction mixture was then allowed to cool and the mixture filtered, the precipitate was then washed with water (15 mL) to afford the title compound as a colourless solid 3-Iodo-2-(methoxycarboxylate)-5,6,7,8-tetrahydro quinolin-4(1H)-one

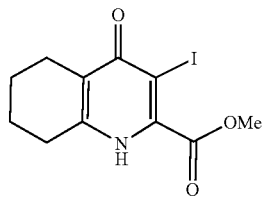 [SMILES: COC(=O)c1[nH]c2c(c(=O)c1I)CCCC2]

The title compound was synthesised following general procedure C from 2-(methoxycarboxylate)-5,6,7,8-tetrahydro quinolin-4(1H)-one (450 mg, 2.20 mmol). The title compound was isolated as colourless solid (612 mg, 1.8 mmol, 84%). $^1$H NMR (400 MHz, DMSO) δ 11.93 (s, 1H), 3.91 (s, 3H), 2.58 (s, 2H), 2.34 (t, 2H), 1.90-1.45 (m, 4H); M/Z (ESI+); 333.99 (Found MH$^+$; 333.9935, C$_{11}$H$_{12}$INO$_3$ requires; 333.9935).

General Method D

A suspension of the 4(1H), 3-iodo-tetrahydroquinolinone (1 equiv.) and potassium carbonate (2 equiv.) in DMF (20.0 mL) was heated to 50° C. and stirred for 45 minutes. The reaction mixture was removed from the heat and ethyl iodide (1.5 equiv.) was added dropwise. The reaction mixture was then heated and kept at 50° C. with stirring for a further 18 hrs. Formation of a yellow emulsion was observed. The reaction mixture was then quenched with water (40.0 mL). The organic phase was extracted using the polar extraction technique (ethyl acetate, 3×40.0 mL), and the resulting organic layers were combined and dried over MgSO$_4$ and concentrated in vacuo to afford the title compound.

4-Ethoxy-3-iodo-2-(methoxycarboxylate)-5,6,7,8-tetrahydroquinoline

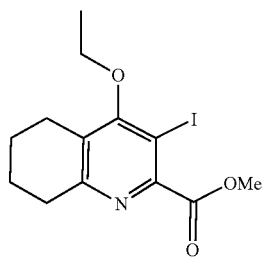 [SMILES: CCOc1c(I)c(C(=O)OC)nc2c1CCCC2]

The title compound was synthesised following general procedure D from 3-iodo-2-(methoxycarboxylate)-5,6,7,8-tetrahydro quinolin-4(1H)-one (500 mg, 1.5 mmol). The title compound was isolated as colourless crystals (450 mg, 1.25 mmol, 83%). $^1$H NMR (300 MHz, CDCl$_3$) δ 3.94 (q, J=7.0 Hz, 2H), 3.90 (s, 3H), 2.84 (t, J=6.4 Hz, 2H), 2.73 (t, J=6.2

Hz, 2H), 1.87-1.64 (m, 4H), 1.43 (t, J=7.0 Hz, 3H); M/Z (ESI+); 362.03 (Found MH+; 362.0256, C$_{13}$H$_{16}$INO$_3$ requires 362.0248).

1.6 General Method E

To a nitrogen flushed flask charged with the 4-ethoxy-3-iodo-tetrahydroquinoline (400 mg, 1.26 mmol), 4-hydroxybenzene boronic acid (260 mg, 1.89 mmol) and palladium tetra(triphenylphosphine) (73 mg, 0.06 mmol) was added degassed DMF (10 mL). Potassium carbonate (3 mL, 2 M$_{(aq)}$) was added and the reaction mixture brought up to 80° C. and stirred for 3 hours. The reaction mixture was then cooled to room temperature and diluted with water (10 mL). The organic phase was then extracted using ethyl acetate (3×20 mL). The organic phases were combined and washed with water (3×20 mL) and then dried with brine (1×10 mL) and MgSO$_4$, before concentration in vacuo. The resulting solid was then recrystallized in ethyl acetate to afford the title compound.

4-(4-Ethoxy-(methoxycarboxylate)-5,6,7,8-tetrahydroquinolin-3-yl)phenol

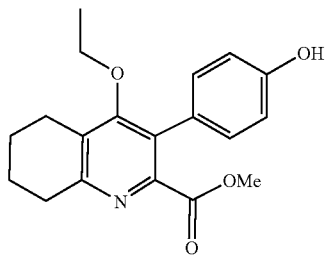 [SMILES: CCOc1c2c(nc(C(=O)OC)c1-c1ccc(O)cc1)CCCC2]

The title compound was synthesised following general procedure E from 4-ethoxy-3-iodo-2-(methoxycarboxylate)-5,6,7,8-tetrahydro quinoline (400 mg, 1.11 mmol). The title compound was isolated as a solid (200 mg, 0.61 mmol, 55%). $^1$H NMR (500 MHz, CDCl$_3$) δ 7.11 (d, J=8.6 Hz, 2H), 6.77 (d, J=8.6 Hz, 2H), 3.60 (s, 3H), 3.43 (q, J=7.0 Hz, 2H), 2.91 (t, J=6.4 Hz, 2H), 2.71 (t, J=6.3 Hz, 2H), 1.82 (m, 2H), 1.78-1.69 (m, 2H), 0.98 (t, J=7.0 Hz, 3H); M/Z (ESI+); 328.16 (Found MH+; 328.1551, C$_{19}$H$_{21}$NO$_4$ requires; 328.1543).

General Method F

Copper (II) acetate (1 equiv.), triethylamine (5 equiv.), and pyridine (5 equiv.) was added to a solution of the boronic acid (1.5 equiv.) and phenol (1 equiv.) in dichloromethane (10 mL mmol$^{-1}$) over heat-activated 4 Å molecular sieves. The reaction mixture was stirred over 16 hours at room temperature. The reaction mixture was quenched with HCl (0.5 M, 20 mL mmol$^{-1}$) and filtered through a pad of Celite, followed by repeated washing with water (10 mL mmol$^{-1}$). The organic layer was extracted with brine, dried over magnesium sulphate, and concentrated in vacuo. Purification by silica gel chromatography (ethyl acetate/hexane) afforded the title compound.

4-Ethoxy-3(4-(4-trifluoromethoxyphenoxy)phenyl)-2-(methoxycarboxylate)-5,6,7,8-tetrahydroquinoline

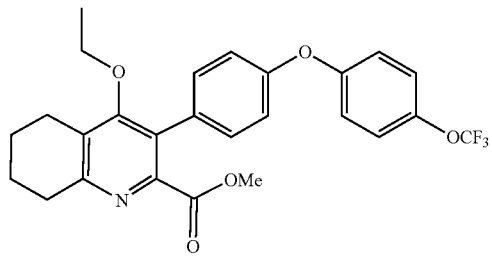 [SMILES: CCOc1c2c(nc(C(=O)OC)c1-c1ccc(Oc3ccc(OC(F)(F)F)cc3)cc1)CCCC2]

The title compound was synthesised following general procedure F from 4-(4-ethoxy-(methoxycarboxylate)-5,6,7,8-tetrahydroquinolin-3-yl)phenol (180 mg, 0.55 mmol). The title compound was isolated as a yellow oil (210 mg, 0.43 mmol, 78%). $^1$H NMR (500 MHz, CDCl$_3$) δ 7.32 (d, J=8.6 Hz, 2H), 7.22 (d, J=8.6 Hz, 2H), 7.05 (dd, J=8.8, 3.0 Hz, 4H), 3.73 (s, 3H), 3.55 (q, J=7.0 Hz, 2H), 3.05 (t, J=4.7 Hz, 2H), 2.80 (t, J=6.2 Hz, 2H), 1.99-1.88 (m, 2H), 1.88-1.79 (m, 2H), 1.09 (t, J=7.0 Hz, 3H).

General Method G

To a solution of the 4-ethoxy-3-(diaryl ether)-hydroxyquinoline (1 equiv.) in acetic acid (2 mL mmol$^{-1}$) was added hydrogen bromide (>48% w/v (aq)) (1 mL mmol$^{-1}$). The reaction mixture was then heated to 90° C. and left to reflux for 72 hours. The reaction mixture was neutralised with sodium hydroxide (2 M, 30.0 mL) and precipitate formed. The reaction mixture was then filtered to afford the title compound.

3(4-(4-Trifluoromethoxyphenoxy)phenyl)-2-(carboxylate)-5,6,7,8-tetrahydroquinolin-4(1H)-one

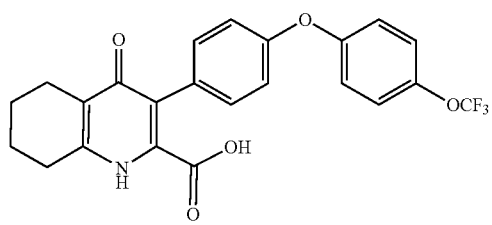 [SMILES: O=C(O)c1[nH]c2c(c(=O)c1-c1ccc(Oc3ccc(OC(F)(F)F)cc3)cc1)CCCC2]

The title compound was synthesised following general procedure G from 4-ethoxy-3(4-(4-trifluoromethoxyphenoxy)phenyl)-2-(methoxycarboxylate)-5,6,7,8-tetrahydroquinoline (200 mg, 0.42 mmol). The title compound was isolated as a colourless solid (80 mg, 0.18 mmol, 43%). $^1$H NMR (400 MHz, DMSO) δ 7.41 (d, J=8.8 Hz, 2H), 7.21 (d, J=8.3 Hz, 2H), 7.12 (d, J=8.8 Hz, 2H), 7.01 (d, J=8.3 Hz, 2H), 2.64 (t, J=5.6 Hz, 2H), 2.35 (t, J=5.6 Hz, 2H), 1.94-1.33 (m, 4H); M/Z (ESI+); 446.12 (Found MH+; 446.1207, C$_{23}$H$_{18}$F$_3$NO$_5$ requires 446.1210).

3(4-(4-Trifluoromethoxyphenoxy)phenyl)-2-(methylhydroxy)-5,6,7,8-tetrahydroquinolin-4(1H)-one

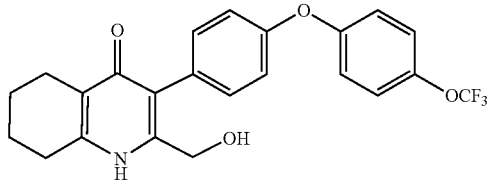 [SMILES: O=c1c2c([nH]c(CO)c1-c1ccc(Oc3ccc(OC(F)(F)F)cc3)cc1)CCCC2]

3(4-(4-trifluoromethoxyphenoxy)phenyl)-2-(carboxylate)-5,6,7,8-tetrahydroquinolin-4(1H)-one (80 mg, 0.17 mmol) was dissolved in methanol (5 mL) with the addition of HCl (1 mL, conc.) heated to 80° C. for 24 hours. The reaction mixture was diluted with water (10 mL) and the organics extracted with EtOAc (3×10 mL) before being dried and concentrated in vacuo. The crude material was then dissolved in dry THF under inert atmosphere and cooled to 0° C. Diisobutylaluminium hydride was then added slowly with stirring. After two hours the reaction pH was lowered to 3 through addition of HCl (2M). Dilution of the solution with water caused precipitation. The title compound was isolated as via filtration as a pale yellow solid (38 mg, 0.09 mmol, 55%). 1H NMR (400 MHz, DMSO) δ 11.06 (s, 1H), 7.41 (d, J=8.8 Hz, 2H), 7.25 (d, J=8.6 Hz, 2H), 7.15 (d, J=9.1 Hz, 2H), 7.05 (d, J=8.6 Hz, 2H), 5.53 (s, 1H), 4.25 (s, 2H), 2.67 (t, J=5.6 Hz, 2H), 2.35 (t, J=6.2 Hz, 2H), 1.82-1.56 (m, 4H); M/Z (ESI+); 432.14 (Found MH+; 432.1445, $C_{23}H_{20}F_3NO_4$ requires 432.1423).

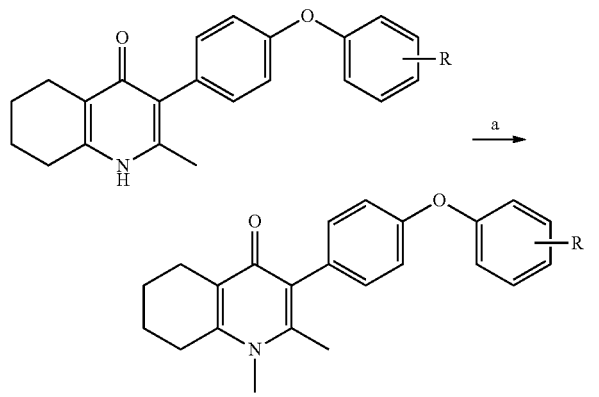

a) MeI, NaH, DMF, 90° C.

1,2-dimethyl-3-(4-(4-(trifluoromethoxy)phenoxy)phenyl)-5,6,7,8-tetrahydroquinolin-4-one

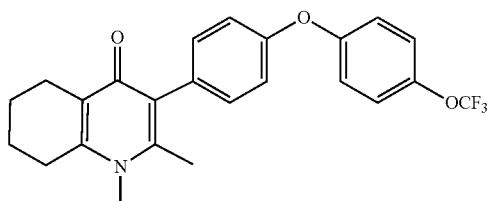

2-methyl-3-(4-(4-(trifluoromethoxy)phenoxy)phenyl)-5,6,7,8-tetrahydroquinolin-4(1H)-one (60 mg, 0.14 mmol) was dissolved in DMF (0.1 mL) under Nitrogen. Sodium Hydride (4 mg, 0.17 mmol) was added and the reaction heated to 90° C. for 30 minutes. Methyl iodide (80 mg, 0.56 mmol) was added and the reaction continued for a further 2 hours. Reaction mixture was allowed to cool and organics extracted with ethyl acetate, followed by drying with brine and magnesium sulphate. Organics were concentrated in vacuo and purified by column chromatography (DCM). To give the title compound as a colourless solid (20 mg, 0.04 mmol, 35%). $^1$H NMR (400 MHz, DMSO) δ 7.41 (d, J=8.6 Hz, 2H), 7.19-7.08 (m, 4H), 7.06 (d, J=8.5 Hz, 2H), 3.53 (s, 3H), 2.71 (t, J=6.2 Hz, 2H), 2.38 (t, J=6.0 Hz, 2H), 2.19 (s, 3H), 1.75 (d, J=5.7 Hz, 2H), 1.66-1.56 (m, 2H).

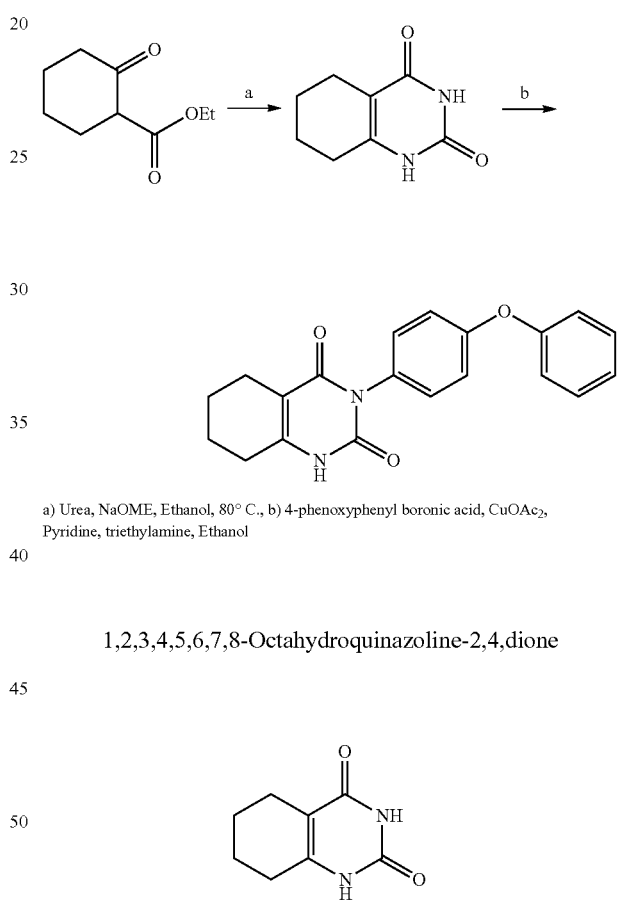

a) Urea, NaOME, Ethanol, 80° C., b) 4-phenoxyphenyl boronic acid, CuOAc$_2$, Pyridine, triethylamine, Ethanol

1,2,3,4,5,6,7,8-Octahydroquinazoline-2,4,dione

Urea (0.48 g, 8.0 mmol) and ethyl-2-oxocyclohexancarbonylate (1.0 g, 6.0 mmol) were dissolved in ethanol (10 mL). Sodium methoxide (3 mL, 12.0 mmol) was added and the reaction mixture refluxed at 80° C. for 15 hours. The reaction mixture was allowed to cool and the resulting precipitate was washed with diethyl ether (2×10 mL) to afford the title compound as a white solid. (526 mg 3.17 mmol, 53%). $^1$H NMR (501 MHz, DMSO) δ 10.72 (s, 1H), 8.50 (s, 1H), 2.28 (t, J=6.2 Hz, 2H), 2.12 (t, J=6.2 Hz, 2H), 1.69-1.60 (m, 2H), 1.59-1.51 (m, 2H); M/Z (ESI+); 167.08 (Found MH$^+$; 167.0815, $C_8H_{10}N_2O_2$ requires 167.0815).

3-(4-Phenoxyphenyl)-1,2,3,4,5,6,7,8-octahydroquinazoline-2,4,dione

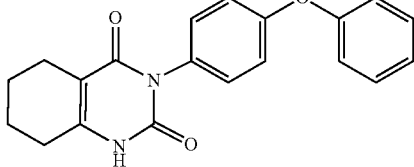

1,2,3,4,5,6,7,8-Octahydroquinazoline-2,4,dione (300 mg, 1.8 mmol), 4phenoxyphenyl boronic acid (600 mg, 2.7 mmol) and copper acetate (330 mg, 1.8 mmol) were dissolved in ethanol (20 mL). Triethylamine (1.2 mL, 9.0 mmol), and pyridine (0.66 mL, 9.0 mmol) were added immediately and the reaction stirred overnight. The reaction was filtered through celite neutralised with HCl (0.5 M, 60 mL) to give crude solid, this was then recrystallized in DCM to afford product as colourless needles (60 mg, 0.18 mmol, 10%). $^1$H NMR (500 MHz, DMSO) δ 11.04 (s, 1H), 7.45 (t, J=7.1 Hz, 2H), 7.20 (d, J=7.5 Hz, 3H), 7.09 (d, J=7.8 Hz, 2H), 7.04 (d, J=7.9 Hz, 2H), 2.39 (s, 2H), 2.22 (s, 2H), 1.68 (m, 4H); M/Z (ESI+); 335.14 (Found MH$^+$; 335.1394, $C_{20}H_{18}N_2O_3$ requires 335.1390).

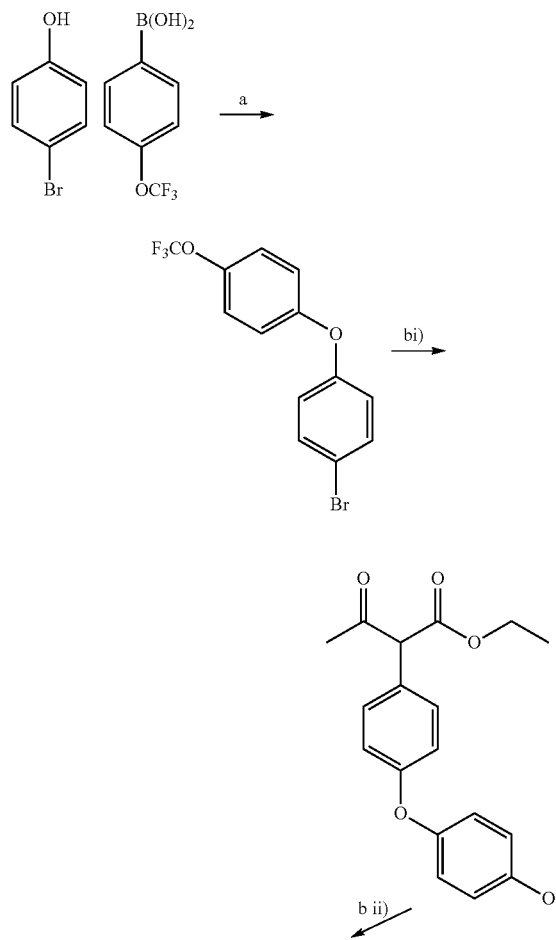

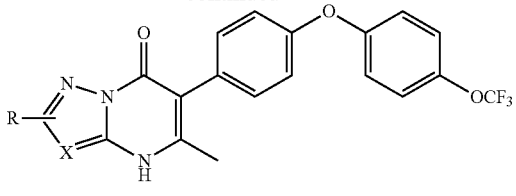

R = SMe, Me, CN, Ph
X = C/N a) Cu(OAc)$_2$, Pyridine, TEA, DCM, b)i) Ethylacetoacetate, PdOAc$_2$, JohnPhos, K$_3$PO$_4$, Tol, 90° C., b)ii) pyrazole/triazole, AcOH, 120° C.

General Procedure B

Toluene (2.00 mL) was added to a flask flushed with nitrogen and charged with 1-Bromo-4-(4-trifluoromethoxy) phenoxy)benzene (0.30 g, 0.90 mmol), ethyl acetoacetate (0.252 mL, 0.99 mmol), palladium acetate (10.1 mg, 0.045 mmol), (2-Biphenyl)di-tert-butylphosphine (26.8 mg, 0.09 mmol) and potassium phosphate (0.252 g, 1.2 mmol). The reaction mixture was then heated to 90° C. for 16 hours. The reaction mixture was cooled to room temperature followed by dilution in DCM (15.0 mL) and filtration through a pad of Celite. The reaction mixture was then concentrated in vacuo and passed through a silica plug. The resulting oil containing crude ethyl 3-oxo-2-4-(4-(trifluoromethoxy)phenoxy)phenyl)butanoate (1 equiv.) was dissolved in acetic acid (2.00 ml). 3-amino-tria-/pyrazole (1 equiv.) was added to the solution. The solution was heated to 120° C. and refluxed for 16 hours. The reaction mixture was then allowed to cool to room temperature. Addition of H$_2$O (2.00 ml) caused precipitation of a white solid. Precipitate was filtered and washed with H$_2$O (2×10.0 mL). The solid was then recrystallized in appropriate solvent to give the title compound.

2,5-dimethyl-6-(4-(4-(trifluoromethoxy)phenoxy)phenyl)pyrazolo[1,5-a]pyrimidin-7(4H)-one

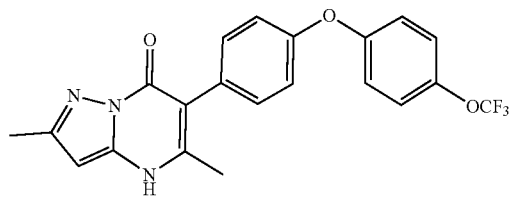 [SMILES: Cc1cc2[nH]c(C)c(-c3ccc(Oc4ccc(OC(F)(F)F)cc4)cc3)c(=O)n2n1]

The title compound was synthesised from 3-amino-5 methyl-pyrazole (30.0 mg, 0.31 mmol) according to general procedure B (recrystallized in EtOAc) to afford the title compound as colourless platelets (47.0 mg, 0.11 mmol, 36%). δ H NMR (500 MHz, Chloroform-d); δ 7.27 (d, J=8.6 Hz, 2H), 7.16 (d, J=8.7 Hz, 2H), 6.99 (d, J=8.9 Hz, 2H), 6.95 (d, J=8.6 Hz, 2H), 5.80 (s, 1H), 2.34 (s, 3H), 2.21 (s, 3H) M/Z (ESI); 419.12 (Found MH$^+$ 416.1221, $C_{21}H_{16}F_3N_3O_3$ requires 416.1217).

5-methyl-2-(methylthio)-6-(4-(4-(trifluoromethoxy)
phenoxy)phenyl)-[1,2,4]triazolo [1,5-a]pyrimidin-7
(4H)-one

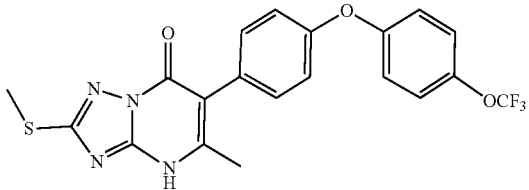 [SMILES: CSc1nc2[nH]c(C)c(-c3ccc(Oc4ccc(OC(F)(F)F)cc4)cc3)c(=O)n2n1]

The title compound was synthesised from 3-amino-5-me-thio-1,2,4triazole (30.0 mg, 0.31 mmol) according to general procedure B to afford the title compound as colourless flake crystals (recrystallized EtOAc) (54.0 mg, 0.12 mmol, 39%). δ H NMR (500 MHz, Chloroform-d); δ 7.30 (d, J=8.6 Hz, 2H), 7.22 (d, J=8.7 Hz, 2H), 7.09 (d, J=8.7 Hz, 2H), 7.07 (d, J=8.6 Hz, 2H), 2.74 (s, 3H), 2.49 (s, 2H); M/Z (ESI); 449.09 (Found MH$^+$ 449.0893, $C_{20}H_{15}F_3N_4O_3S$ requires 449.0893).

5-methyl-7-oxo-6-(4-(4-(trifluoromethoxy)phenoxy)
phenyl)-4,7-dihydropyrazolo[1,5-a]pyrimidine-3-
carbonitrile

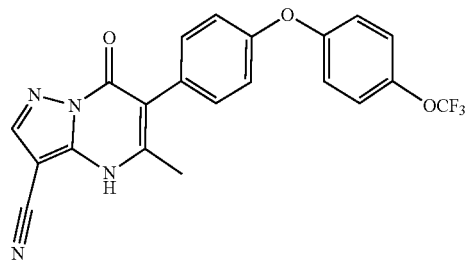 [SMILES: Cc1[nH]c2c(C#N)cnn2c(=O)c1-c1ccc(Oc2ccc(OC(F)(F)F)cc2)cc1]

The title compound was synthesised from 3-amino-4-carbo-nitrile-1,2,pyrazole (45 mg, 0.42 mmol) according to general procedure B to afford the title compound as white flake crystals (recrystallized EtOAc), (43 mg, 0.10 mmol, 23%); $^1$H NMR (500 MHz, DMSO) δ 8.49 (s, 1H), 7.51 (d, J=8.9 Hz, 2H), 7.44 (d, J=8.6 Hz, 2H), 7.28 (d, J=8.9, Hz, 2H), 7.20 (d, J=8.6 Hz, 2H), 2.32 (s, 3H). M/Z (ESI+); 427.10 (Found MH$^+$ 427.1018, $C_{21}H_{13}F_3N_4O_3$ requires 427.1012).

5-methyl-2-phenyl-6-(4-(4-(trifluoromethoxy)phe-
noxy)phenyl)pyrazolo[1,5-a]pyrimidin-7(4H)-one

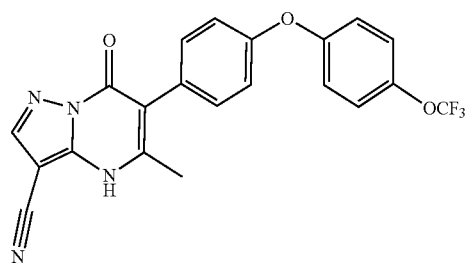 [SMILES: Cc1[nH]c2c(C#N)cnn2c(=O)c1-c1ccc(Oc2ccc(OC(F)(F)F)cc2)cc1]

The title compound was synthesised from 3-amino-4-carbo-nitrile-1,2,pyrazole (0.067 g, 0.42 mmol) according to general procedure B (recrystallized in DMSO) to afford the title compound as a grey micro crystals (0.15 g, 0.31 mmol, 74%). $^1$H NMR (500 MHz, DMSO) δ 12.47 (s, 1H, NH), 8.01 (d, J=6.8 Hz, 2H, H-2* & 6*), 7.53-7.40 (m, 5H, H-3*, 4*, 5*,2' & 6'), 7.38 (d, J=8.7 Hz, 2H, H-2" & 6"), 7.20 (d, J=9.1 Hz, 2H, H-3' & 5'), 7.11 (d, J=8.7 Hz, 2H, H-3" & 5"), 6.62 (s, 1H, H-3), 2.22 (s, 3H, Me); M/Z (ESI+); 478.1378 (Found MH+, $C_{26}H_{18}F_3N_3O_3$ requires 478.1373).

In Vitro Challenge Assay for *Toxoplasma* Tachyzoites

Protocol adapted from Fomovska, et. al. (Fomovska A, Huang Q, El Bissati K, Mui E J, Witola W H, Cheng G, et al. Novel N-Benzoyl-2-Hydroxybenzamide Disrupts Unique Parasite Secretory Pathway. Antimicrob Agents Chemother [Internet]. 2012 May [cited 2015 Jul. 8]; 56(5):2666-82; Fomovska A, Wood R D, Mui E, Dubey J P, Ferreira L R, Hickman M R, et al. Salicylanilide inhibitors of *Toxoplasma gondii*. J Med Chem. 2012 Oct. 11; 55(19):8375-91). Human foreskin fibroblasts (HFF) were cultured on a flat, clear-bottomed, black 96-well plate to 90% to 100% confluence. IMDM (1×, [+] glutamine, [+] 25 mM HEPES, [+] Phenol red, 10% FBS [gibco, Denmark]) was removed from each well and replaced with IMDM-C (1×, [+] glutamine, [+] 25 mM HEPES, [−] Phenol red, 10% FBS)[gibco, Denmark]). Type I RH parasites expressing Yellow Fluorescent Protein (RH—YFP) were lysed from host cells by double passage through a 27-gauge needle. Parasites were counted and diluted to 32,000/mL in IMDM-C. Fibroblast cultures were infected with 3200 tachyzoites of the Type I RH strain expressing Yellow Fluorescent Protein (RH—YFP) and returned to incubator at 37° C. for 1-2 hours to allow for infection (Gubbels M-J, Li C, Striepen B. High-Throughput Growth Assay for *Toxoplasma gondii* Using Yellow Fluo-rescent Protein. Antimicrob Agents Chemother [Internet]. 2003 January [cited 2015 Jul. 8]; 47(1):309-16). Various concentrations of the compounds were made using IMDM-C, and 20 µl were added to each designated well, with triplicates for each condition. Controls included pyrimeth-amine/sulfadiazine (current standard of treatment), 0.1% DMSO only, fibroblast only, and an untreated YFP gradient with 2 fold dilutions of the parasite. Cells were incubated at 37° C. for 72 hours. Plates were read using a fluorimeter (Synergy H4 Hybrid Reader, BioTek) to ascertain the amount of yellow fluorescent protein, in relative fluores-cence units (RFU), as a measure of parasite burden after treatment. Data was collected using Gen5 software. IC50 was calculated by graphical analysis in Excel.

In Vitro Challenge Assay for Bradyzoites

HFF cells were grown in IMDM (1×, [+] glutamine, [+] 25 mM HEPES, [+] Phenol red, 10% FBS, [gibco, Den-mark]) on removable, sterile glass disks in the bottom of a clear, flat-bottomed 24-well plate. Cultures were infected with 3×104 parasites (EGS strain) per well, in 0.5 mL media and plate was returned to incubator at 37° C. overnight. The following day, the media was removed and clear IMDM and compounds were added to making various concentrations of the drug, to a total volume of 0.5 mL. 2 wells were filled with media only, as a control. Plates were returned to the 37° C. incubator for 72 hours, and checked once every 24 hours. If tachyzoites were visible in the control before 72 hours, the cells were fixed and stained. Cells were fixed using 4% paraformaldehyde and stained with Fluorescein-labeled *Dolichos biflorus* Agglutinin, DAPI, and BAG1. Disks were removed and mounted onto glass slides and visualized using microscopy (Nikon T17). Slides were scanned using a CRi Pannoramic Scan Whole Slide Scanner and viewed using Panoramic Viewer Software. Effects of the compounds were quantified by counting cysts in the controls and treated cells. Cysts and persisting organisms were counted in a representative field of view and then multiplied by a factor determined by the total area of the disk in order to estimate the number of cysts and organisms in each condition. Data was collected using Gen5 software. IC50 was calculated by graphical analysis in Excel.

| ID | Structure | Tachy IC$_{50}$ μM | Brady IC$_{50}$ μM | Pf D6 IC$_{50}$ μM |
|---|---|---|---|---|
| MJM136 | 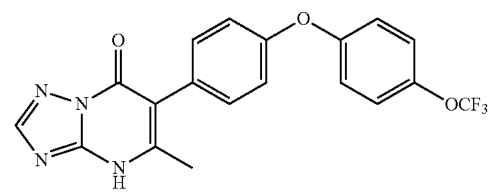 | 1.0-10.0 | >10 | 0.2 |
| MJM141 | 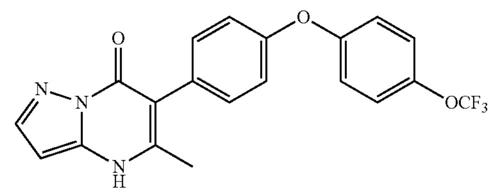 | 1.0-10.0 | 1.0-10.0 | 0.16 |
| JAG006 | 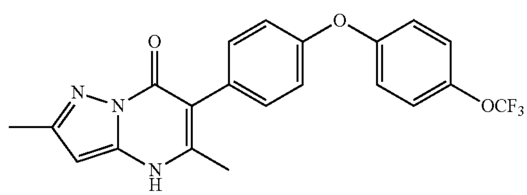 [SMILES: Cc1cc2[nH]c(C)c(-c3ccc(Oc4ccc(OC(F)(F)F)cc4)cc3)c(=O)n2n1] | >1 | N.D. | 0.29 |
| JAG013 | 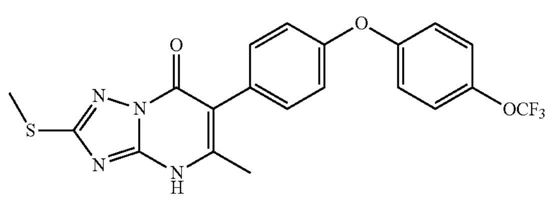 [SMILES: CSc1nc2[nH]c(C)c(-c3ccc(Oc4ccc(OC(F)(F)F)cc4)cc3)c(=O)n2n1] | >1 | N.D. | 1.31 |
| JAG014 | 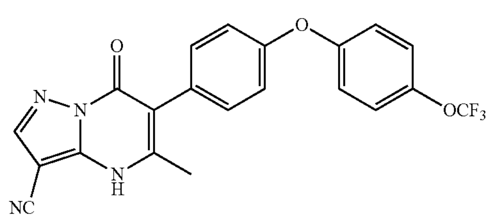 [SMILES: Cc1[nH]c2c(C#N)cnn2c(=O)c1-c1ccc(Oc2ccc(OC(F)(F)F)cc2)cc1] | >1 | N.D. | 0.71 |
| JAG015 | 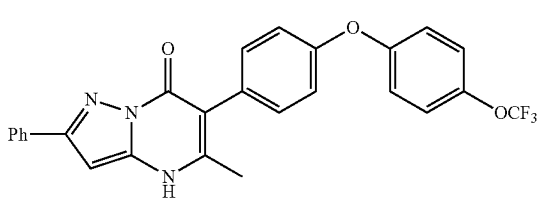 [SMILES: Cc1[nH]c2cc(-c3ccccc3)nn2c(=O)c1-c1ccc(Oc2ccc(OC(F)(F)F)cc2)cc1] | >1 | N.D. | >20 |
| MJM170 | 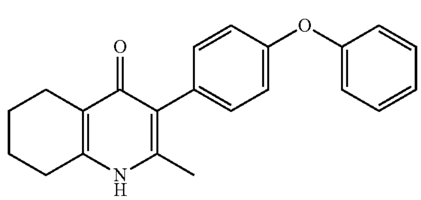 [SMILES: Cc1[nH]c2c(c(=O)c1-c1ccc(Oc3ccccc3)cc1)CCCC2] | 0.03 | 1.0-10.0 | 0.01 |

-continued
| ID | Structure | Tachy IC$_{50}$ μM | Brady IC$_{50}$ μM | Pf D6 IC$_{50}$ μM |
|---|---|---|---|---|
| JAG21 | 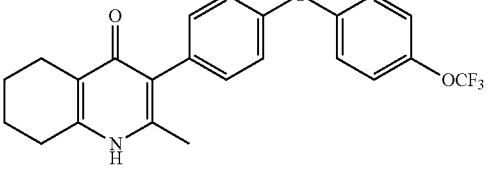 | 0.09 | N.D. | 0.01435 |
| JAG039 | 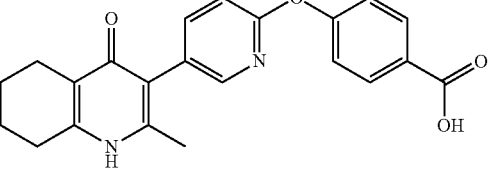 | 7.6 | N.D. | 9.595 |
| JAG046 | 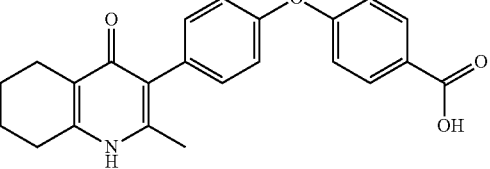 | >10 | N.D. | 6.716 |
| JAG047 | 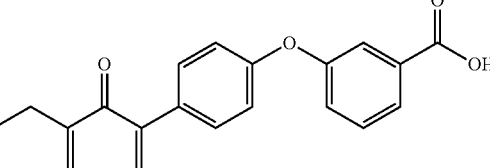 | >10 | N.D. | 3.746 |
| JAG50 | 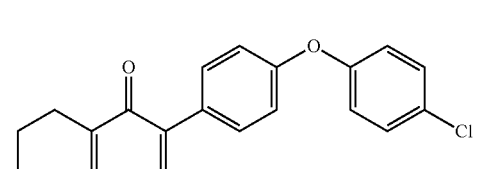 | 0.055 | N.D. | 0.04664 |
| JAG58 | 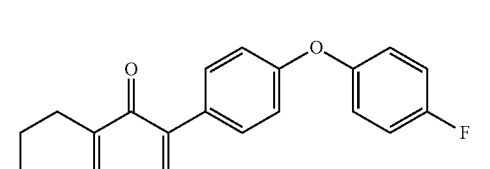 | 0.04-0.08 | N.D. | Awaiting Testing |
| JAG63 | 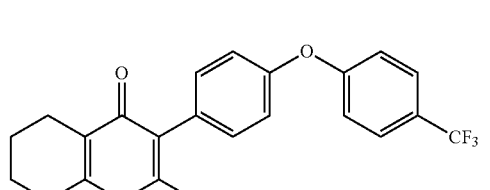 | 0.1-0.3 | N.D. | Awaiting Testing |

| ID | Structure | Tachy IC$_{50}$ μM | Brady IC$_{50}$ μM | Pf D6 IC$_{50}$ μM |
|---|---|---|---|---|
| JAG062 | 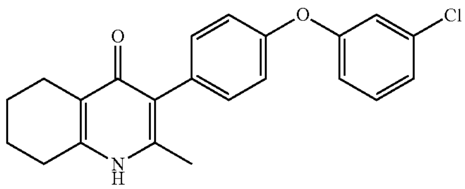 [SMILES: Cc1[nH]c2c(c(=O)c1-c1ccc(Oc3cccc(Cl)c3)cc1)CCCC2] | 0.016 | N.D. | N.D. |
| JAG069 | 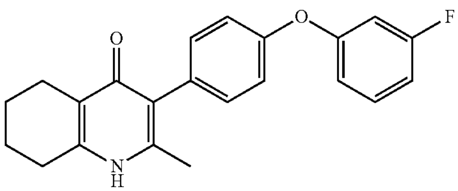 [SMILES: Cc1[nH]c2c(c(=O)c1-c1ccc(Oc3cccc(F)c3)cc1)CCCC2] | 0.02 | N.D. | N.D. |
| JAG023 | 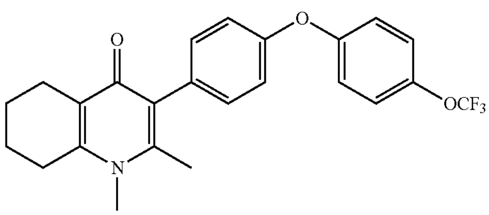 [SMILES: Cc1c(-c2ccc(Oc3ccc(OC(F)(F)F)cc3)cc2)c(=O)c2c(n1C)CCCC2] | 1 | N.D. | N.D. |
| AS006/ JAG143 | 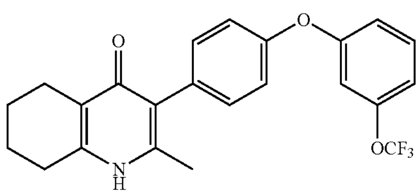 | 0.06-0.08 | N.D. | N.D. |
| AS012/ JAG144 | 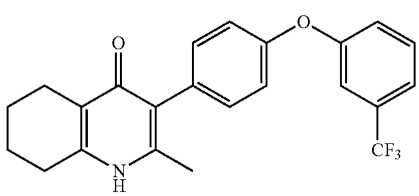 | 0.3 | N.D. | N.D. |
| AS021/ JAG145 | 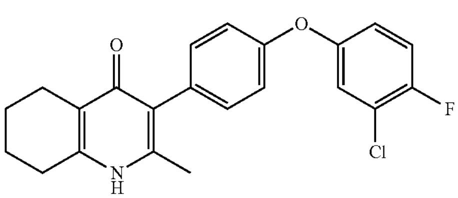 [SMILES: Cc1[nH]c2c(c(=O)c1-c1ccc(Oc3ccc(F)c(Cl)c3)cc1)CCCC2] | 0.08 | N.D. | N.D. |
| AS034/ JAG148 | 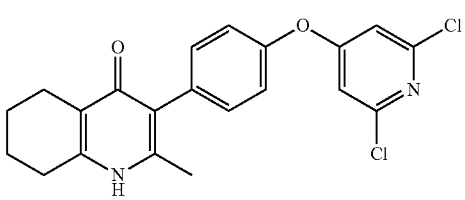 [SMILES: Cc1[nH]c2c(c(=O)c1-c1ccc(Oc3cc(Cl)nc(Cl)c3)cc1)CCCC2] | 0.1-0.5 | N.D. | N.D. |

-continued

| ID | Structure | Tachy IC$_{50}$ μM | Brady IC$_{50}$ μM | Pf D6 IC$_{50}$ μM |
|---|---|---|---|---|
| AS022 | 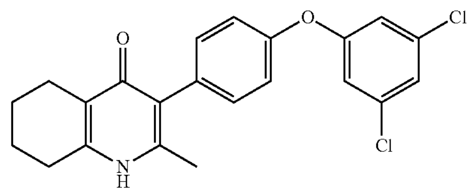 [SMILES: Cc1[nH]c2c(c(=O)c1-c1ccc(Oc3cc(Cl)cc(Cl)c3)cc1)CCCC2] | 0.02-0.04 | N.D. | N.D. |
| JAG084 | 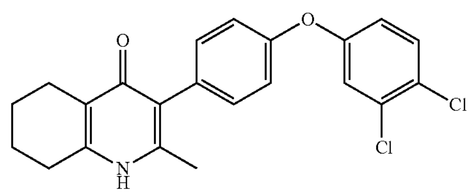 [SMILES: Cc1[nH]c2c(c(=O)c1-c1ccc(Oc3ccc(Cl)c(Cl)c3)cc1)CCCC2] | 0.04-0.08 | N.D. | N.D. |
| JAG091 | 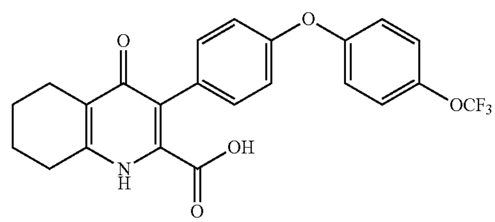 [SMILES: O=C(O)c1[nH]c2c(c(=O)c1-c1ccc(Oc3ccc(OC(F)(F)F)cc3)cc1)CCCC2] | >1 | N.D. | N.D. |
| JAG092 | 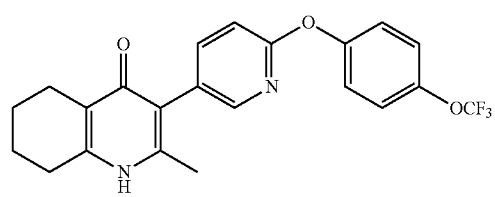 | 1 | N.D. | N.D. |
| JAG095 | 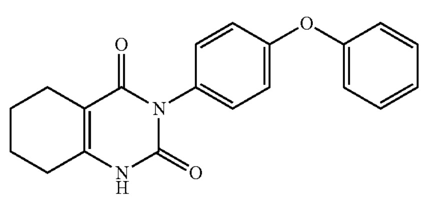 [SMILES: O=c1[nH]c2c(c(=O)n1-c1ccc(Oc3ccccc3)cc1)CCCC2] | >10 | N.D. | N.D. |
| JAG099 | 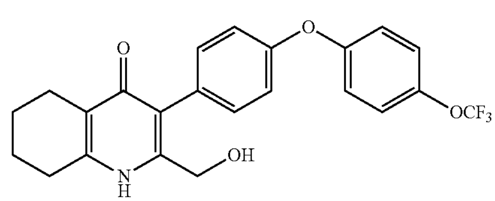 [SMILES: O=c1c2c([nH]c(CO)c1-c1ccc(Oc3ccc(OC(F)(F)F)cc3)cc1)CCCC2] | 0.32 | N.D. | N.D. |
| AS032 | 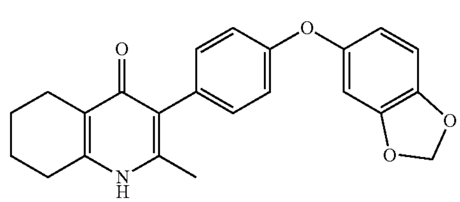 [SMILES: Cc1[nH]c2c(c(=O)c1-c1ccc(Oc3ccc4c(c3)OCO4)cc1)CCCC2] | 0.1-0.3 | N.D. | N.D. |

| ID | Structure | Tachy IC$_{50}$ μM | Brady IC$_{50}$ μM | Pf D6 IC$_{50}$ μM |
|---|---|---|---|---|
| JAG100 | 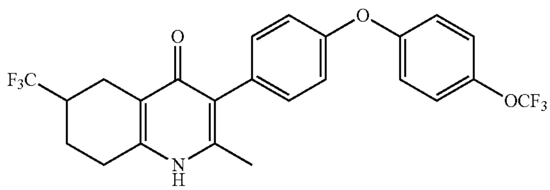 [SMILES: Cc1[nH]c2c(c(=O)c1-c1ccc(Oc3ccc(OC(F)(F)F)cc3)cc1)CC(C(F)(F)F)CC2] | >10 | N.D. | N.D. |
| JAG106 | 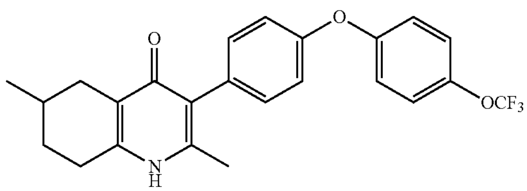 [SMILES: Cc1[nH]c2c(c(=O)c1-c1ccc(Oc3ccc(OC(F)(F)F)cc3)cc1)CC(C)CC2] | ~1 | N.D. | N.D. |
| JAG107 | 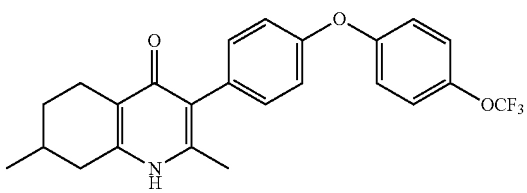 [SMILES: Cc1[nH]c2c(c(=O)c1-c1ccc(Oc3ccc(OC(F)(F)F)cc3)cc1)CCC(C)C2] | 1 | N.D. | N.D. |
| JAG121 | 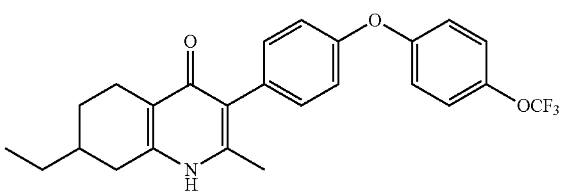 [SMILES: CCC1CCc2c([nH]c(C)c(-c3ccc(Oc4ccc(OC(F)(F)F)cc4)cc3)c2=O)C1] | 0.1 | N.D. | N.D. |
| JAG129 | 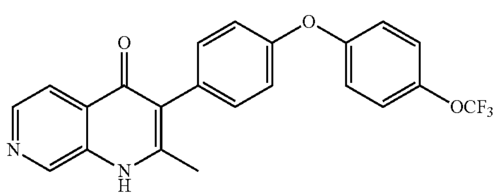 [SMILES: Cc1[nH]c2cnccc2c(=O)c1-c1ccc(Oc2ccc(OC(F)(F)F)cc2)cc1] | 0.1 | N.D. | N.D. |
| JAG162 | 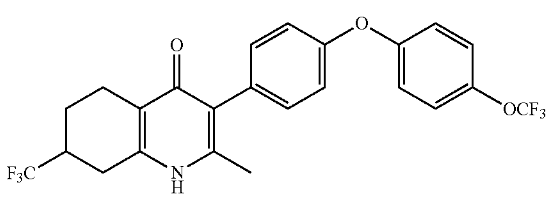 [SMILES: Cc1[nH]c2c(c(=O)c1-c1ccc(Oc3ccc(OC(F)(F)F)cc3)cc1)CCC(C(F)(F)F)C2] | 0.5 | N.D. | N.D. |
| JAG094 | 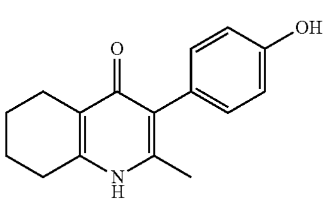 [SMILES: Cc1[nH]c2c(c(=O)c1-c1ccc(O)cc1)CCCC2] | 1 | N.D. | N.D. |

Biological Activity Studies
Malaria In Vitro Studies:

D6 is a drug sensitive strain from Sierra Leone, C235 is a multi-drug resistant stain from Thailand, W2 is a chloroquine resistant strain from Thailand, and C2B has resistance to a variety of drugs including atovaquone. These assays were performed using standard protocols.

Compound Activity Against *Plasmodium* falciparum

Compound activity against *P. falciparum*, a causative agent of malaria, was tested using the Malaria SYBR Green I—Based Fluorescence (MSF) Assay. This; microtiter plate drug sensitivity assay uses the presence of malarial DNA as a measure of parasitic proliferation in the presence of antimalarial drugs or experimental compounds based on modifications of previously described methods known in the art. As the intercalation of SYBR Green I dye and its resulting fluorescence is relative to parasite growth, a test compound that inhibits the growth of the parasite will result in a lower fluorescence. Selected compounds were examined for activity against four strains of *P. falciparum*: D6 (CDC/Sierra Leone), a drugsensitive strain readily killed by chloroquine, TM91-C235, a multi-drug resistant strain resistant to chloroquine, W2, a chloroquine resistant strain from Thailand, and C2B has resistance to a variety of drugs including atovaquone.

| ID | Parasite strains | SYBR Green D6 IC50 (uM) | SYBR D6 $R^2$ | SYBR Green C235 IC50 (uM) | SYBR TM91C235 $R^2$ |
|---|---|---|---|---|---|
| MJM129 | D6, C235, W2, C2B | 0.03 | 0.94 | 0.07 | 0.94 |
| MJM136 | D6, C235, W2, C2B | 0.20 | 0.99 | 0.58 | 0.98 |
| MJM141 | D6, C235, W2, C2B | 0.16 | 0.96 | 0.57 | 0.95 |
| MJM170 | D6, C235, W2, C2B | 0.01 | 0.98 | 0.03 | 0.99 |
| JAG006 | D6, C235, W2, C2B | 0.29 | 0.90 | 0.88 | 0.92 |
| JAG013 | D6, C235, W2, C2B | 1.31 | 0.98 | 2.60 | 0.96 |
| JAG014 | D6, C235, W2, C2B | 0.71 | 0.94 | 1.35 | 0.99 |
| JAG015 | D6, C235, W2, C2B | >20 | N/A | >20 | N/A |
| JM10 | D6, C235, W2, C2B | 0.88 | 0.94 | 4.48 | 0.97 |
| JAG021 | D6, C235, W2, C2B | 0.01435 | 0.9572 | 0.06164 | 0.9706 |
| JAG047 | D6, C235, W2, C2B | 3.746 | 0.9738 | 12.56 | 0.9218 |
| JAG046 | D6, C235, W2, C2B | 6.716 | 0.9844 | >20 | N/A |
| JAG039 | D6, C235, W2, C2B | 9.595 | 0.9532 | >20 | N/A |
| JAG050 | D6, C235, W2, C2B | 0.04664 | 0.9138 | 0.06913 | 0.9562 |
| RG38 | D6, C235, W2, C2B | 2.884 | 0.8936 | 13.66 | 0.8338 |

| ID | Parasite strains | SYBR Green W2 IC50 (uM) | SYBR W2 $R^2$ | SYBR Green C2B IC50 (uM) | SYBR C2B $R^2$ |
|---|---|---|---|---|---|
| MJM129 | D6, C235, W2, C2B | 0.08 | 0.93 | 0.01 | 0.94 |
| MJM136 | D6, C235, W2, C2B | 0.55 | 0.98 | 0.38 | 0.99 |
| MJM141 | D6, C235, W2, C2B | 0.63 | 0.88 | 0.48 | 0.95 |
| MJM170 | D6, C235, W2, C2B | 0.03 | 0.99 | 0.01 | 0.99 |
| JAG006 | D6, C235, W2, C2B | 2.46 | 0.92 | 1.66 | 0.94 |
| JAG013 | D6, C235, W2, C2B | 2.35 | 0.96 | 1.39 | 0.94 |
| JAG014 | D6, C235, W2, C2B | 1.27 | 0.99 | 0.92 | 0.98 |
| JAG015 | D6, C235, W2, C2B | >20 | N/A | >20 | N/A |
| JM10 | D6, C235, W2, C2B | 5.36 | 0.90 | 6.75 | 0.81 |
| JAG021 | D6, C235, W2, C2B | 0.05518 | 0.9727 | 0.04042 | 0.9847 |
| JAG047 | D6, C235, W2, C2B | 9.072 | 0.9358 | 7.781 | 0.9575 |
| JAG046 | D6, C235, W2, C2B | >20 | N/A | >20 | N/A |
| JAG039 | D6, C235, W2, C2B | >20 | N/A | >20 | N/A |
| JAG050 | D6, C235, W2, C2B | 0.03136 | 0.9693 | 0.03635 | 0.9427 |
| RG38 | D6, C235, W2, C2B | 9.245 | 0.7954 | >20 | N/A |

Example 5: Effect of Active Forms of *T. gondii* on Transcriptomes, Proteomes and Mechanisms Whereby this Occurs and Reflection of the Same Type of Damage to Neuronal Cells in Circulating Biomarkers from Children Since we found signature pathways reflecting influence of the bradyzoite stage (characteristic of the chronic *Toxoplasma gondii* infection) in primary human neuronal stem cells in tissue culture on pathways of neurodevelopment, neuroplasticity, and neurotoxicity, we asked whether the active form of the parasite would also affect those pathways. It did. We found alterations in pathways similar to those shown with EGS bradyzoites in transcriptomics and proteomics (FIGS. 14A-14D with explanatory figure legends and methods). These abnormalities suggested that there might be circulating biomarkers reflecting such damage to neuronal cells in patients. In that context we then asked whether serum biomarkers from ill children would reflect neuronal damage and neurodegeneration.

Methods.

Biomarkers: Serum collection was from children in the National Collaborative Congenital ToxoplasmosisStudy (NCCCTS). Children have serum drawn at each visit. Sera characterized were obtained at a visit when new seizures were noted for ill children. These sera were analyzed with nano proteomic and miR analyses as described earlier by Hood, Wang et al. This was done using a panel of markers known to be abnormal in patients with Alzheimer's and other neurodegenerative diseases. This was done to determine whether the same biomarkers present in serum or plasma from persons with these neurodegenerative disease might be present in sera from the ill children. The children are described more fully in the figure legend.

Murine study of Apolipoprotein A1: Wildtype mice on a C57Bl6/J background, mice in which the Apolipoprotein A1 gene was knocked out (Apo A1-/-) were utilized in this experiment. They were immunized with an attenuated strain of the RH strain of *Toxoplasma* in which ribosomal proteins small subunit 13 was placed under the control of a tetracycline repressor by placing 4 tet 0 elements in the promoter and a tetracycline regulatable repressor with YFP was stably transfected. This immunized the mice and subsequently the mice were challenged with the Me49 strain *T. gondii* and cysts were counted or luminescence in brain measured.

EGS and Canonical Type 1,2,3 transcriptomics details and Type 1, 2, 3 proteomics, analysis of alternatively spliced genes, and immunoflurescense studies: Details of the specific genes with altered transcription caused by EGS in Example 1 are discussed above. Trascriptomics were carried out as described in Example 1.

iTRAQ data from *T. gondii* infected cell cultures. Protein quantified, extracted, subjected to mass spectroscopy, and sequence analysis from each flask, ~180-190 ug proteins were extracted and 50 ug were used for 8-plex iTRAQ. A raw table listing relative ratios for all peptide identified in 8 samples was created. The ratio should be 0.125 (1.000/8) if one peptide/protein evenly distributes in 8 samples. Ratios of peptides from the same proteins are then calculated to protein ratios. A "Ratio to Channel 0" then included a total of 4,367 proteins identified with iTRAQ ratio. The protein ratios crossed 8 samples (4 conditions in duplicates) and were raw data from mass spec and converted to ratios against Channel 0, i.e. Control sample. They are then normalized and ratios made. "Prot with high score" has 3,359 proteins identified by more than 1 peptide and with ProteinProphet probability >0.8 (=FDR<1%). Among these 3,3359 proteins with high confidence, 10 proteins up >2-fold in either of the 3 infected cells vs. controls, while 28 proteins down >2-fold were identified. Occurrence of differences in alternative splicing between infected and uninfected cells was done with rMATS. Method for IFA are as described in Example 1. The antibodies are to SAG1, P50-NFkB.

Figure 14D:
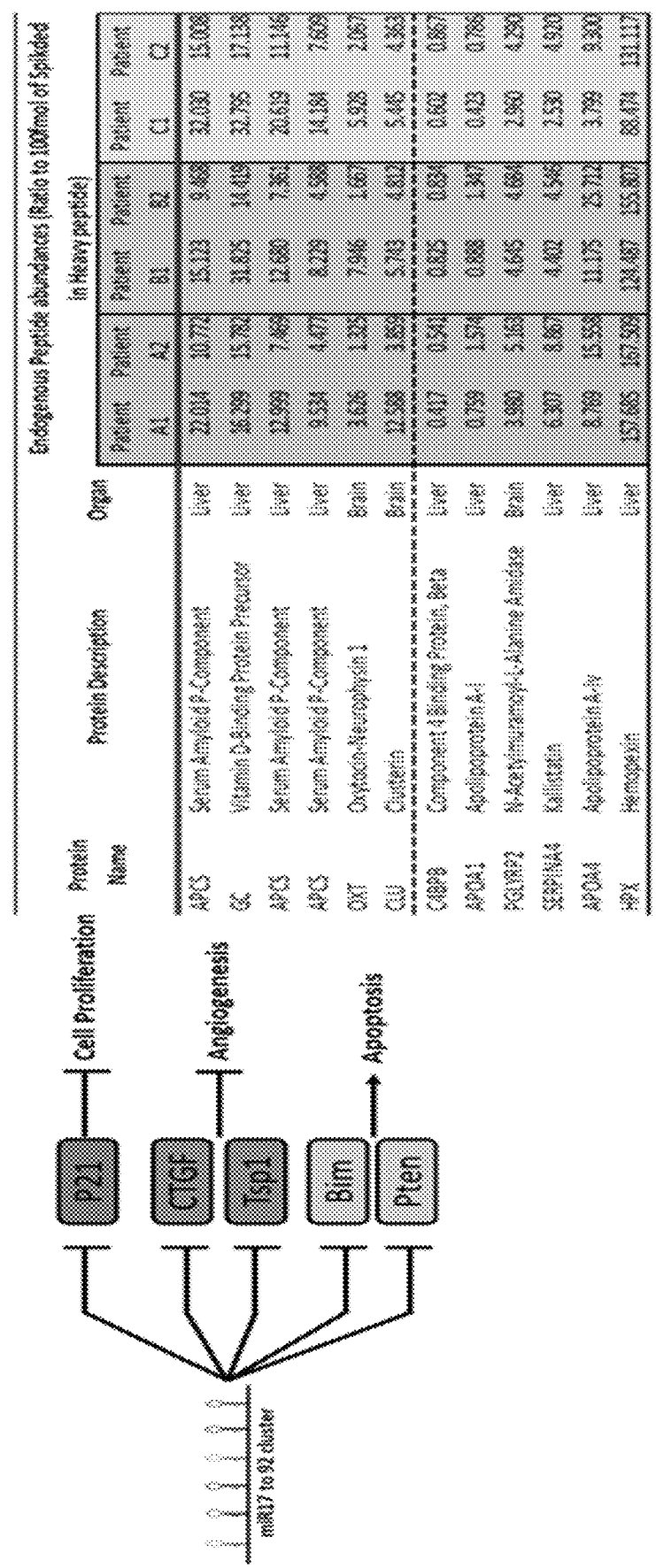

Results:

Human serum biomarkers in ill congenitally infected children reflect *T. gondii* infection and neuronal damage. Three pairs of children were studied. In each demographically-matched pair, one child had severe disease and the other had mild or no clinical illness. Each child had serum stored from evaluations at the same ages. The second pair are dizygotic, discordant twins. Each of the three ill children had new myoclonic-"infantile" spasms, or hypsarrhythmic seizures. For two, this was associated with a rise in or high *T. gondii* specific IgG antibody titers (FIG. 14A). IgG was not measured for the third ill child. A panel of nanoproteomics and miR sequencing was performed on serum obtained at the time of this new illness. The two ill children diagnosed more recently had T2 weighted abnormalities on brain MRIs similar to active inflammatory and parasitic caused brain disease seen in a murine model. Ill children compared with their paired healthy controls had alterations in miRs and increases in serum proteins associated with neurodegeneration, inflammation, a misfolded protein response and protein misfolding. Elevated proteins included clusterin, and oxytocin (FIGS. 14A-14D). PGLYRP2 (N-acetylmuramoyl-L-alanine amidase) and Apolipoprotein B1 were depressed. miR-17-92, which *T. gondi* RH strain markedly increases in HFF cultures, also was increased in sera of the ill children, as was miR-124 (FIGS. 14B-14C). miR-124 is associated with neurodegeneration. This indicates active brain destruction by the parasite or the response to it. These circulating proteins and miRs are clinically useful biomarkers to identify active toxoplasmic brain (and possibly retinal) disease.

To determine whether the presence of one of these biomarkers could be confirmed, a murine model was used. In this example of biomarkers in a murine experiment recapitulating the data of biomarkers in the serum of the ill children, APOA1 knockout and wild type mice were infected with *Toxoplasma*. The wild type and uninfected mice had less radiance from luciferase parasites and fewer cysts, and less immunologic reaction to the lower parasite burden in brain (data not shown). This demonstrates that the circulating ApoA1 diminishing in the boys who were ill as a biomarker. This provides evidence that these biomarkers that were abnormal in the children had counterparts in murine models.

To determine whether similar pathways as were abnormal in EGS Example 1 were perturbed by the canonical U.S./European types of parasites and mechanisms whereby this might occur, transcriptomics, proteomics, analysis of alternatively spliced genes and immunofluorescent were also preformed. Experimental data showed similar perturbation of pathways by canonical U.S./European type parasites that infected the children with the biomarkers through similar transcriptomics analyses demonstrating biological effect of Type I, II, III parasites on localization of NFkB, STAT 3 and STAT 6 in primary human neuronal stem cells. These abnormalities are caused by the canonical U.S. and European types of parasites growing as tachyzoites in the human primary neuronal stem cells and monocytic cells. These finding along with those demonstrated by the Omic studies of EGS (Example 1) suggest a mechanism whereby circulating biomarkers reflecting damage to neuronal cells in patients can occur. Placed in this context, we hypothesize that serum biomarkers from ill children reflect neuronal damage and neurodegeneration, as confirmed by our murine models, and findings seen in tissue culture and/or in patients.

Discussion

The signature pathways we noted in studies of human primary neuronal stem cells which reflected abnormalities and gene products associated with neurodegenerative disease and the mechanisms whereby *T. gondii* can cause such pathology prompted study of biomarkers in a small number of ill versus well children. Biomarkers of active brain *T. gondii* infection in humans were found. The serum biomarkers shown in FIGS. 14A-14D are increased (e.g., clusterin, oxytocin, amyloid, and mir 17-92 and mir 124) or diminished, including PGLYRP2 (N-acetylmuramoyl-L-alanine amidase) and Apolipooprotein-A1 which are indicative of infection. These are consistent with the transcriptome demonstrating signature pathways in GO slim and KEGG analyses with effect on ribosomes, alternative splicing and neurodegenerative diseases, including Alzheimer's disease, Huntingtons disease, and Parkinson's disease by encysted EGS, and for example pathways of response to oxidative stress, regulation of apotosis, and alternative splicing of toll receptors that were abnormal in the same cells infected by the canonical US/European parasites (active tachyzoites) that the children had. Other manifestations of active disease in the brain diminished with treatment and are not abnormal in the dizygotic healthy twin of one child or demographically matched well children. This is consistent with these biomarkers being selected to be assayed with MiR sequencing and proteomics based on their differences in diseases of neurodegeneration. These ill children had developed new seizures, elevations in antibody titer, elevated cerebrospinal fluid protein in one child, and abnormal T2 weighted alterations in T2 weighted brain magnetic resonance imaging. The biomarkers that were characteristic of neurodegeneration in the ill children and when diminished were associated with greater severity of disease in a murine model will be useful to monitor disease and response to treatment of disease due to this parasite. Restoration to normal values being indicative of favorable response to treatment and presence may also mark recrudescence of disease. ApoA1 may also be a useful treatment.

We claim:
1. A compound of the structure of
(a) Formula (I):

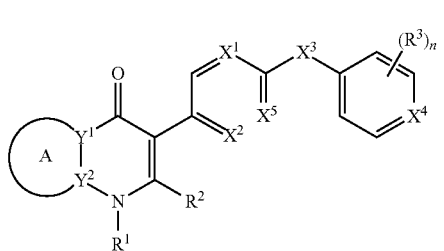

or a stereoisomer thereof, or a pharmaceutically acceptable salt thereof,
wherein
ring A combines with $Y^1$ and $Y_2$ to form a $C_{3-7}$cycloalkenyl or heteroaryl ring,
  wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;
$Y^1$ is N;
$Y^2$ is C or N;
$X^1$ is $C(R^{x1})$ or N,
  wherein $R^{x1}$ is hydrogen, halogen, $C_{1-3}$alkyl, $C_{1-3}$alkoxy or $C_{1-3}$haloalkyl;
$X^2$ is $C(R^{x2})$ or N,
  wherein $R^{x2}$ is hydrogen, halogen, $C_{1-3}$alkyl, $C_{1-3}$alkoxy or $C_{1-3}$haloalkyl;
$X^3$ is O, N(R), S or $C_{1-3}$alkyl;
$X^4$ is C or N;
$X^5$ is C or N;
$R^1$ is hydrogen or $C_{1-3}$alkyl;
$R^2$ is hydrogen, $C_{1-3}$alkyl, $C_{1-3}$haloalkyl, —CH$_2$OH, —CH$_2$OR or —C(O)OR;
n is 0, 1, 2, 3 or 4;
each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or SF$_5$;
or two $R^3$ groups, together with the carbons to which they are attached, form a 1,3-dioxolane; and
each R is independently hydrogen or $C_{1-3}$alkyl; or
(b) Formula (I-p):

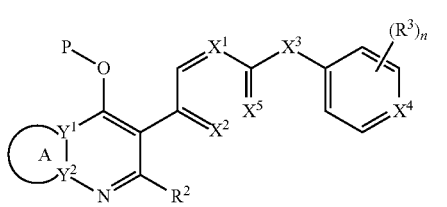

or a stereoisomer thereof, or a pharmaceutically acceptable salt thereof,
wherein
  ring A combines with $Y^1$ and $Y_2$ to form a $C_{3-7}$cycloalkenyl or heteroaryl ring, wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;
$Y^1$ is N;
$Y^2$ is C or N;
$X^1$ is $C(R^{x1})$ or N,
  wherein $R^{x1}$ is hydrogen, halogen, $C_{1-3}$alkyl, $C_{1-3}$alkoxy or $C_{1-3}$haloalkyl;
$X^2$ is $C(R^{x2})$ or N,
  wherein $R^{x2}$ is hydrogen, halogen, $C_{1-3}$alkyl, $C_{1-3}$alkoxy or $C_{1-3}$haloalkyl;
$X^3$ is O, N(R), S or $C_{1-3}$alkyl;
$X^5$ is C or N;
P is —C(O)OR', —C(O)R', —C(O)NR'$_2$, wherein R' is hydrogen, $C_{1-3}$alkyl or —CH$_2$OR;
$R^2$ is hydrogen, $C_{1-3}$alkyl, $C_{1-3}$haloalkyl, —CH$_2$OH, —CH$_2$OR, —C(O)OR or —CH$_2$OP;
P is —C(O)OR', —C(O)R', —C(O)NR'$_2$ or —OP(O)(OR')OR', wherein each R' is independently hydrogen or $C_{1-3}$alkyl;
n is 0, 1, 2, 3 or 4;
each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or SF$_5$;
or two $R^3$ groups, together with the carbons to which they are attached, form a 1,3-dioxolane; and
each R is independently hydrogen or $C_{1-3}$alkyl.
2. The compound of claim 1, having the structure of (I):

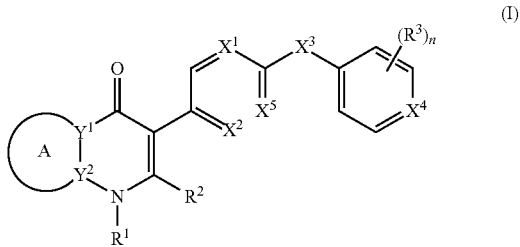

or a stereoisomer thereof, or a pharmaceutically acceptable salt thereof,
wherein
ring A combines with $Y^1$ and $Y^2$ to form a $C_{3-7}$cycloalkenyl or heteroaryl ring,
  wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;
$Y^1$ is N;
$Y^2$ is C or N;
$X^1$ is $C(R^{x1})$ or N,
  wherein $R^{x1}$ is hydrogen, halogen, $C_{1-3}$alkyl, $C_{1-3}$alkoxy or $C_{1-3}$haloalkyl;
$X^2$ is $C(R^{x2})$ or N,
  wherein $R^{x2}$ is hydrogen, halogen, $C_{1-3}$alkyl, $C_{1-3}$alkoxy or $C_{1-3}$haloalkyl;
$X^3$ is O, N(R), S or $C_{1-3}$alkyl;
$X^4$ is C or N;
$X^5$ is C or N;
$R^1$ is hydrogen or $C_{1-3}$alkyl;
$R^2$ is hydrogen, $C_{1-3}$alkyl, $C_{1-3}$haloalkyl, —CH$_2$OH, —CH$_2$OR or —C(O)OR;
n is 0, 1, 2, 3 or 4;
each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or SF$_5$;

or two R³ groups, together with the carbons to which they are attached, form a 1,3-dioxolane; and each R is independently hydrogen or $C_{1-3}$alkyl.

3. The compound of claim 1, having the structure of (Ia):

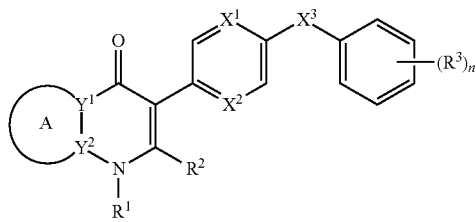

(Ia)

or a stereoisomer thereof, or a pharmaceutically acceptable salt thereof, wherein ring A combines with $Y^1$ and $Y^2$ to form a $C_{3-7}$cycloalkenyl or heteroaryl ring, wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;

$Y^1$ is N;

$Y^2$ is C or N;

$X^1$ is $C(R^{x1})$ or N,
  wherein $R^{x1}$ is hydrogen, halogen, $C_{1-3}$alkyl, $C_{1-3}$alkoxy or $C_{1-3}$haloalkyl;

$X^2$ is $C(R^{x2})$ or N,
  wherein $R^{x2}$ is hydrogen, halogen, $C_{1-3}$alkyl, $C_{1-3}$alkoxy or $C_{1-3}$haloalkyl;

$X^3$ is O, N(R), S or $C_{1-3}$alkyl;

$R^1$ is hydrogen or $C_{1-3}$alkyl;

$R^2$ is hydrogen, $C_{1-3}$alkyl or —C(O)OR;

n is 0, 1, 2, 3 or 4;

each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or $SF_5$; and each R is independently hydrogen or $C_{1-3}$alkyl.

4. The compound of claim 3, having (a) the structure of Formula (Ib):

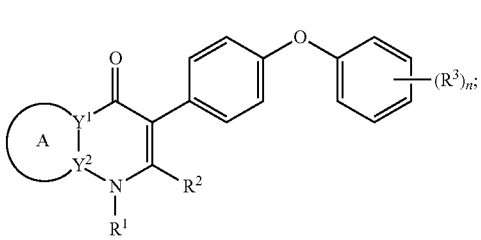

(Ib)

(b) the structure of Formula (Ic):

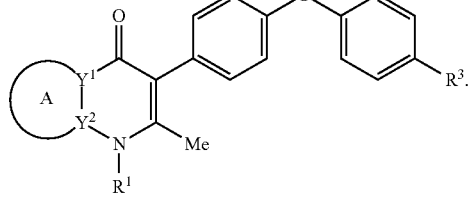

(Ic)

5. The compound of claim 3, having the structure of Formula (III):

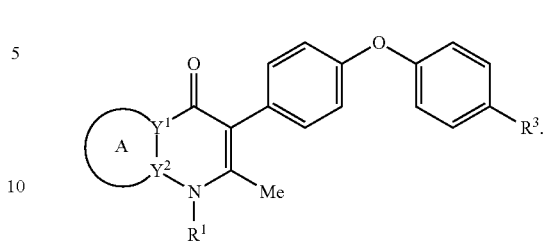

(III)

wherein ring A combines with the nitrogen atom and carbon atom with which it is attached to form a heteroaryl ring.

6. The compound of claim 5, having the structure of Formula (IIIa):

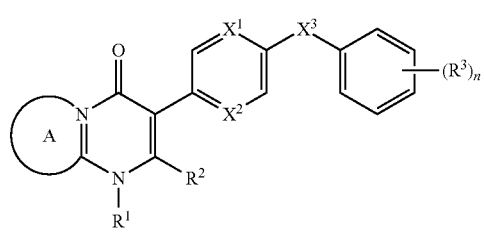

(IIIa)

wherein $Y^3$ is $C(R^5)$ or N; and $R^4$ and $R^5$ are independently hydrogen, halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl.

7. The compound of claim 6, having the structure of Formula (IIIb):

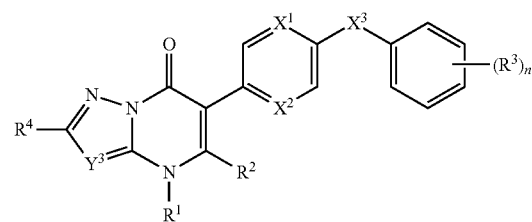

(IIIb)

8. The compound of claim 7, wherein $R^4$ is hydrogen or $C_{1-3}$alkyl.

9. The compound of claim 7, having the structure of Formula (IIIb-1):

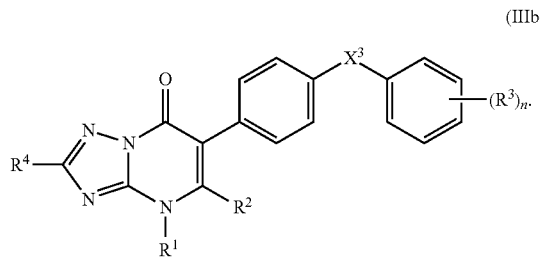

(IIIb-1)

10. The compound of claim 6, having the structure of Formula (IIIc):

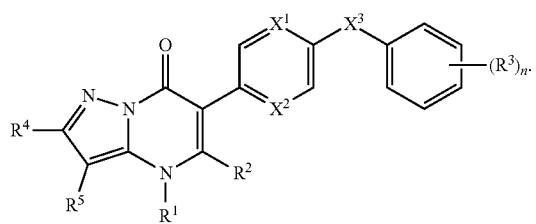

(IIIc)

11. The compound of claim 10, wherein
$R^4$ is hydrogen or $C_{1-3}$alkyl or phenyl; and
$R^5$ is hydrogen or cyano.

12. The compound of claim 10, having the structure of Formula (IIIc-1):

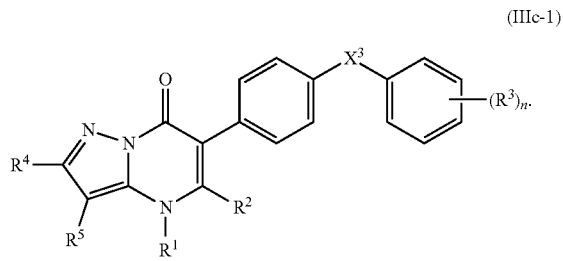

(IIIc-1)

13. The compound of claim 1, having the structure of Formula (IV):

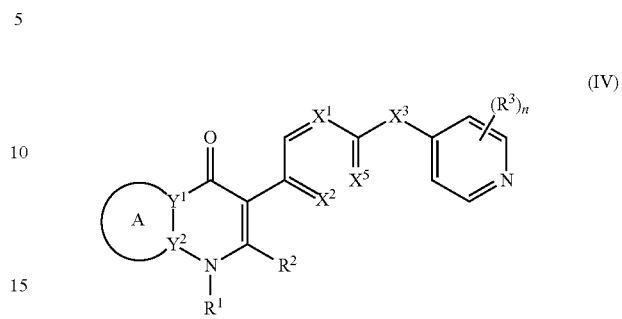

(IV)

or a stereoisomer thereof, or a pharmaceutically acceptable salt thereof, wherein ring A combines with $Y^1$ and $Y_2$ to form a $C_{3-7}$cycloalkenyl or heteroaryl ring, wherein the $C_{3-7}$cycloalkenyl or heteroaryl is optionally substituted by halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR, cyano or phenyl;

$Y^1$ is N;

$Y^2$ is C or N;

$X^1$ is $C(R^{x1})$ or N, wherein $R^{x1}$ is hydrogen, halogen, $C_{1-3}$alkyl, $C_{1-3}$alkoxy or $C_{1-3}$haloalkyl;

$X^2$ is $C(R^{x2})$ or N, wherein $R^{x2}$ is hydrogen, halogen, $C_{1-3}$alkyl, $C_{1-3}$alkoxy or $C_{1-3}$haloalkyl;

$X^3$ is O, N(R), S or $C_{1-3}$alkyl;

$X^5$ is C or N;

$R^1$ is hydrogen or $C_{1-3}$alkyl;

$R^2$ is hydrogen, $C_{1-3}$alkyl, $C_{1-3}$haloalkyl, —CH$_2$OH, —CH$_2$OR or —C(O)OR;

n is 0, 1, 2, 3 or 4;

each $R^3$ is independently halogen, $C_{1-3}$alkyl, $C_{1-3}$alkoxy, $C_{1-3}$haloalkyl, —O—$C_{1-3}$haloalkyl, —S—$C_{1-3}$haloalkyl, —C(O)OR or SF$_5$; and each R is independently hydrogen or $C_{1-3}$alkyl.

14. A compound that is:

| Structure | Name |
|---|---|
| ![structure] | 5-methyl-6-(4-(4-(trifluoromethoxy)phenoxy)phenyl)-[1,2,4]triazolo[1,5-a]pyrimidin-7(4H)-one |

| Structure | Name |
|---|---|
| 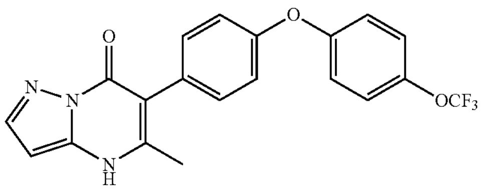 [SMILES: Cc1[nH]c2ccnn2c(=O)c1-c1ccc(Oc2ccc(OC(F)(F)F)cc2)cc1] | 5-methyl-6-(4-(4-(trifluoromethoxy)phenoxy)phenyl)pyrazolo[1,5-a]pyrimidin-7(4H)-one |
| 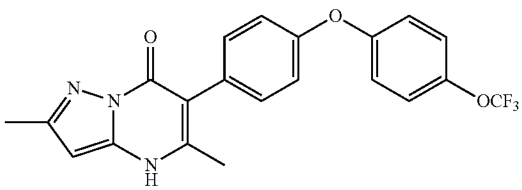 [SMILES: Cc1cc2[nH]c(C)c(-c3ccc(Oc4ccc(OC(F)(F)F)cc4)cc3)c(=O)n2n1] | 2,5-dimethyl-6-(4-(4-(trifluoromethoxy)phenoxy)phenyl)pyrazolo[1,5-a]pyrimidin-7(4H)-one |
| | 5-methyl-2-(methylthio)-6-(4-(4-(trifluoromethoxy)phenoxy)phenyl)-[1,2,4]triazolo[1,5-a]pyrimidin-7(4H)-one |
| | 5-methyl-7-oxo-6-(4-(4-(trifluoromethoxy)phenoxy)phenyl)-4,7-dihydropyrazolo[1,5-a]pyrimidine-3-carbonitrile |
| 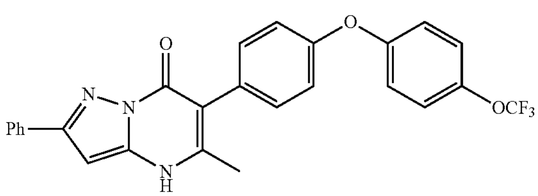 [SMILES: Cc1[nH]c2cc(-c3ccccc3)nn2c(=O)c1-c1ccc(Oc2ccc(OC(F)(F)F)cc2)cc1] | 5-methyl-2-phenyl-6-(4-(4-(trifluoromethoxy)phenoxy)phenyl)pyrazolo[1,5-a]pyrimidin-7(4H)-one |

5-methyl-6-(4-(4-(trifluoromethoxy)phenoxy)phenyl)-[1,2,4]triazolo[1,5-a]pyrimidin-7(4H)-one;

5-methyl-6-(4-(4-(trifluoromethoxy)phenoxy)phenyl)pyrazolo[1,5-a]pyrimidin-7(4H)-one;

2,5-dimethyl-6-(4-(4-(trifluoromethoxy)phenoxy)phenyl)pyrazolo[1,5-a]pyrimidin-7(4H)-one;

5-methyl-2-(methylthio)-6-(4-(4-(trifluoromethoxy)phenoxy)phenyl)-[1,2,4]triazolo [1,5-a]pyrimidin-7(4H)-one;

5-methyl-7-oxo-6-(4-(4-(trifluoromethoxy)phenoxy)phenyl)-4,7-dihydropyrazolo[1,5-a]pyrimidine-3-carbonitrile;

5-methyl-2-phenyl-6-(4-(4-(trifluoromethoxy)phenoxy)phenyl)pyrazolo[1,5-a]pyrimidin-7(4H)-one;

or a stereoisomer thereof, or a pharmaceutically acceptable salt thereof.

15. A pharmaceutical composition comprising a compound of claim 1 and a pharmaceutically acceptable diluent, excipient, or carrier.

16. A method for treating an apicomplexan parasitic infection, comprising administering to a subject (such as a human subject) in need thereof an amount effective to treat the infection of the compound or pharmaceutical composition of claim 1.

17. An invention selected from the group consisting of:
(a) a method for monitoring treatment of an apicomplexan parasitic infection, such as *T. gondii* infection (including but not limited to any of the treatment of claim 16), comprising monitoring expression, protein in serum or plasma, and/or activity of 1, 2, 3, 4, 5, 6, 7, 8, 9, 10, or all of the markers listed in FIGS. 1-2 in a subject (such as a human subject) being treated for an apicomplexan parasitic infection, wherein a decrease or increase in expression and/or presence and/or activity of the one or more markers indicates that the treatment is effective;
(b) a cell line infected with an apicomplexan parasite, wherein the apicomplexan parasite genome comprises a gene encoding an Apetela 2 IV-4 protein with an M=>I modification at residue 570 ("AP2 IV-4 M570I") compared to its orthologous gene on the reference *T. gondii* ME49 strain (gene ID: TGME49_318470);
(c) a method for treating an apicomplexan parasite infection (such as a *T. gondii* infection), comprising administering to a subject in need thereof an amount effective to treat the infection of an inhibitor (of up-regulated genes) or an activator (of down-regulated genes) of 1 or more of the up-regulated genes listed in FIG. 1 or FIG. 2;

(d) a method for identifying test compounds for apicomplexan parasite therapy, comprising identifying test compounds that reduce expression (for up-regulated genes), or increase expression (for down-regulated genes) of 1 or more of the apicomplexan parasite genes in FIGS. 3-5;

(e) a plurality of isolated probes that in total selectively bind to at least 2, 3, 4, 5, 6, 7, 8, 9, 10, 15, 20, 25, 30, 35, 40, 45, 100, 150, 200, 250, 500, or all of the markers listed in FIGS. 3-5, complements thereof, or their expression products, or functional equivalents thereof wherein at least 10%, 20%, 30%, 40%, 50%, 60%, 70%, 80%, 90%, 95%, or all of the probes in total are selective for markers that are upregulated in the EGS strain of *T. gondii* after infection of human fibroblasts, human neuronal stem cells or human monocytic lineage cells;

(f) a plurality of isolated probes that in total selectively bind to at least 2, 3, 4, 5, 6, 7, 8, 9, 10, 15, 20, 25, 30, 35, 40, 45, 100, 150, 200, 250, 500, or all of the markers listed in FIG. 1-2, complements thereof, or their expression products, or functional equivalents thereof, wherein at least 10%, 20%, 30%, 40%, 50%, 60%, 70%, 80%, 90%, 95%, or all of the probes in total are selective for markers that are upregulated in human fibroblasts, human neuronal stem cells or human monocytic lineage cells after infection with *T. gondii*, including but not limited to infection with the EGS strain of *T. gondi*.

* * * * *

UNITED STATES PATENT AND TRADEMARK OFFICE
CERTIFICATE OF CORRECTION

PATENT NO. : 11,964,944 B2
APPLICATION NO. : 17/831049
DATED : April 23, 2024
INVENTOR(S) : Rima McLeod et al.

It is certified that error appears in the above-identified patent and that said Letters Patent is hereby corrected as shown below:

In the Specification

Delete Column 1, Lines 18-32 and replace with the following:
This invention was made with government support under U01 AI082180, HHSN272200900007C, and U19 AI110819 awarded by the National Institutes of Health. The government has certain rights in the invention.

Signed and Sealed this
Twenty-eighth Day of May, 2024

Katherine Kelly Vidal
*Director of the United States Patent and Trademark Office*

SEQUENCE LISTING

<160> NUMBER OF SEQ ID NOS: 27

<210> SEQ ID NO 1
<211> LENGTH: 54
<212> TYPE: PRT
<213> ORGANISM: Homo sapiens

<400> SEQUENCE: 1

Gly Gly Asn Arg Pro His Tyr His Val Ala Lys Gln Glu Trp Arg Val
1               5                   10                  15

Arg Tyr Tyr Met Asn Gly Lys Arg Lys Met Arg Thr Tyr Ser Ala Lys
            20                  25                  30

Phe Tyr Gly Tyr Glu Thr Ala His Thr Met Ala Glu Asp Phe Ala His
        35                  40                  45

Tyr Val Asp Lys His Glu
    50

<210> SEQ ID NO 2
<211> LENGTH: 2406
<212> TYPE: PRT
<213> ORGANISM: Homo sapiens

<400> SEQUENCE: 2

Met Ala Ala Pro Ala Pro Ser Ala Glu Ala Arg Pro Ala Lys Arg Arg
1               5                   10                  15

Cys Phe Pro Leu Pro Arg Glu Thr Pro Val Ser Ser Glu Asp Glu Thr
            20                  25                  30

Arg Lys Thr Leu Gln His Asp Thr Leu Gly Cys Leu Pro Arg Ser Ser
            35                  40                  45

Ser Gly Gln Pro Glu Leu Ala Ala Ala Ser Ala Ala Ser Gln Val Gly
        50                  55                  60

His Leu Ser Ser Ala Ala Leu Leu Gln Leu Val Gln Thr Gln Ser Ala
65                  70                  75                  80

Gly Gly Val Pro Gln Ala Val Leu Arg Asn Leu Phe Ser Ser Ile His
                85                  90                  95

Arg Asn Pro Lys Pro Leu Pro Ala Asn Ala Leu Ala Ala Thr Pro Asn
            100                 105                 110

Ser Ser Leu Tyr Ala Ser Leu Thr Ser Leu Ser Ser Ala Ala Ala Leu
        115                 120                 125

Pro Gly Ala Gly Pro Ala Tyr Ser Gln Ala Pro Ser Pro Ala Ser Ala
    130                 135                 140

Asp Leu Leu Gln Ser Glu Gln Phe Gly Ser Ala Ala Lys Asn Pro Ser
145                 150                 155                 160

Pro Asn Glu Ala Ser Pro Ile Leu Ala Leu Leu Gly Glu Ala Ala Arg
                165                 170                 175

Ala Ala Thr Thr Pro Arg Thr Val Pro Ala Leu Ser Ala Val Cys Pro
            180                 185                 190

Ala Ala Ser Ser Gly Val Ser Leu Pro Ser Ala Ser Asp Thr Leu Ala
        195                 200                 205

Leu Ala Gln Ser Ser Leu Ser Ser Thr Gly Cys Ala Ser Asp Val
    210                 215                 220

Lys Ala Ser Arg Pro Glu Glu His Pro Ala Phe Ala Ser Gly Thr Ala
225                 230                 235                 240

Asn Arg Gln Ser Leu Leu Gln Ala Leu Leu Leu Ser Thr Ala Pro Leu
                245                 250                 255

Ala Phe Ser Gly Pro Ser Leu Ser Ser Ala Ser Thr Thr Leu Pro Ala

```
                260                 265                 270
Ser Ser Gly Ala Val Ser Ser Arg Asn Ala Gly Ala Tyr Gln Phe Glu
            275                 280                 285
Arg Leu Leu Gln Ala Glu Ala Ala Lys Val Lys Ala Leu Leu Pro Asn
            290                 295                 300
Ala Thr Ser Lys Ser Met Ser Gln Ser Ser Val Pro Gln Arg Asp Leu
305                 310                 315                 320
Thr Arg Lys Thr Ser Leu Phe Pro Asp Pro Arg Gly Leu Ser Ala Asp
                325                 330                 335
Asp Ala Ser Arg Arg Tyr Asn Thr Arg Gly Ala Asn Ser Gly Gly Ala
            340                 345                 350
Gly Leu Arg Arg Gly Thr Gly Val His Ala Thr Glu Gln Ser Gly
            355                 360                 365
Ala Leu Asp Ala Gly Glu Arg Thr Arg Pro Phe Gly Ala Gly Glu Asp
            370                 375                 380
Glu Ser Ala Gln Gly Lys Pro Asp Ser Arg Gly Arg Gln Arg Pro Gly
385                 390                 395                 400
Ala Leu Asp Ala Ser Asn Ile Leu Gly Leu Leu Ala Ala Phe Gln Pro
                405                 410                 415
Ser Gln Ala Pro Ala Ile Arg Asp Leu Ser Ala Pro Ser His Leu Ser
            420                 425                 430
Ala Ala Ala Thr Gly Ala Leu Pro Leu Thr Ala Ser Phe Thr Ala Ser
            435                 440                 445
Ala Leu Ala Ser Ser Gln Cys Leu Pro Ala Gly Thr Pro Ala Ser Ser
            450                 455                 460
Ser Ala Ser Pro Pro Phe Ser Glu Val Leu Ser Thr Thr Glu Glu Ser
465                 470                 475                 480
Ser Thr Thr Lys Glu Thr Asp Ala Ser Ala Ser Thr Leu Leu Ala Phe
                485                 490                 495
Leu Gln Lys Tyr Ser Ala Val Ser Gly Leu Gly Gly Ala Ser Asp Phe
            500                 505                 510
Leu Gly Gln Leu Gln Gly Lys Ser Ser Leu Pro Pro Leu Ser Leu Ala
            515                 520                 525
Glu Pro Ser Ser Ala Leu Pro Ser Ser Phe Leu Gly Gly Ser Asp Gly
            530                 535                 540
Gly Thr Ile Asp Thr Arg Asn Gly Asn Gly Glu Lys Thr Thr Pro Pro
545                 550                 555                 560
Ile His Leu Phe Gln Ser Ala Phe Arg Ile Pro Ser Pro Ser Gln Gln
                565                 570                 575
Asn Leu Leu Asp Ala Leu Leu Ala Ser Ser Cys Thr Thr Ala Thr Ser
            580                 585                 590
Arg Ser Asp Gly Ser Gly Asn Leu Gly Cys Pro Val Val Asp Glu Arg
            595                 600                 605
Asn Ala Lys Leu Ala Gly Pro Ala His Pro Leu Pro Cys Ser Phe Pro
            610                 615                 620
Gln Ile Ser Ser Ser Gly Glu Pro Gly Arg Lys Thr Gly Gly Arg
625                 630                 635                 640
Val His Arg Gln Gly Thr Ser Gln Ser Gly Arg Val Arg Ser Gly
                645                 650                 655
Lys Asn Gly Gly Ser Ala Ala Pro Pro Arg Gln Ser Ser Ser Glu Asn
            660                 665                 670
Val Pro Ser Thr Pro Thr Val Ser Ser His Glu Ala Pro His Arg Ala
            675                 680                 685
```

-continued

Gly Phe Pro Ser Gln Thr Pro Tyr Glu Leu Ser Ala Ser Pro Ser His
690                 695                 700

Gln Leu Asp Leu Leu Arg Leu Gly Ala Phe Leu Gly Gly Ala Gly Lys
705                 710                 715                 720

Gln Asp Ala Ser Val His Ser Asp Glu Thr Gly Thr Leu Ser Gly Glu
                725                 730                 735

Pro Ser His Arg Ser Cys Ser Leu Ser Arg Gly Leu Thr Gln Glu Ser
            740                 745                 750

Val Leu Gln Leu Ser Asp Thr Thr Ser Thr Ser Arg Glu Gly Glu Pro
        755                 760                 765

Asn Glu Pro Ser Gln Gly Cys Val Asn Val Ala Ala Ser Leu Pro Ala
770                 775                 780

Phe Gly Pro Gln Pro Ser Ser Gly Ala Ala Lys Ala Arg Glu Gly Arg
785                 790                 795                 800

Arg Gly Ala Gly Gly Ala Gly Ala Ala Pro Pro Val Pro Leu Arg Ala
                805                 810                 815

Asp Val Thr Leu Gly Gly Asn Arg Pro His Tyr His Val Ala Lys Gln
            820                 825                 830

Glu Trp Arg Val Arg Tyr Tyr Met Asn Gly Lys Arg Lys Met Arg Thr
        835                 840                 845

Tyr Ser Ala Lys Phe Tyr Gly Tyr Glu Thr Ala His Thr Met Ala Glu
850                 855                 860

Asp Phe Ala His Tyr Val Asp Lys His Glu Ala Leu Pro Asp Ser Met
865                 870                 875                 880

Met Met Thr Ala Met Met Leu Gln Ala Gln Ala Asn Ser Ala Ala Ser
                885                 890                 895

Ser Gly Gln Thr Val Pro Leu Ala Arg Gly Ile Arg Ala Ser Ser Ala
            900                 905                 910

Ser Ala Gly Ala Gly Gly His Val Ser Lys Ser Ala Thr Lys Gly Ser
        915                 920                 925

Val Ala Ala Ser Ser Glu Gly Ser Thr Ser Met Gly Ser Asp Ala Thr
930                 935                 940

Arg Ser Gln Glu Gly Glu Ala Ala Glu Leu Cys Pro Leu Ala Ala Gly
945                 950                 955                 960

Leu Ser Arg Pro Leu Ala Ser Met His Ser Ala Ala Gly Asn Ala Val
                965                 970                 975

Ala Gln Gly Arg Gln Glu Ser Lys Glu Glu Pro Gly Gly Gln Ala
            980                 985                 990

Trp Phe Gly Glu Pro Gly Lys Phe Arg Ala Ser Ser Glu Ala Ala Leu
        995                 1000                1005

Cys Gly Ser Gly Ser Ser Ala Glu Gly Arg Asp Gly His Glu Ser
    1010                1015                1020

Glu Val Leu Trp Ala Thr Leu Gly Lys Val His Asp Ala Ser Gln
    1025                1030                1035

Gly Lys Lys Ile Lys Pro Glu Lys Pro Leu Thr Val Ala Arg Gly
    1040                1045                1050

Arg Leu Ala Leu Gly Ala Glu Asp Lys Ser Gln Asn Leu Gly Val
    1055                1060                1065

Asp Leu Gly Asp Ser Gly Gly Ala Gln Gly Leu Pro Gly Val Arg
    1070                1075                1080

Gln Pro Arg Gln Met Lys Asn Ser Glu Glu Cys Ser Leu Arg Asp
    1085                1090                1095

-continued

```
Ser Asp Lys Gly Met Ala Leu Ser Lys Arg Phe Gly Phe Leu Pro
    1100                1105                1110

Ser Gln Thr Pro Ser Cys Asp Ser Met Thr Leu Pro Phe Pro Gly
    1115                1120                1125

Gly Phe Asp Ala Leu Ser Leu Ser Ser Ala Leu Ser Ser Cys Ala
    1130                1135                1140

Ser Leu Pro Val Ala His Glu Gly Asn Asn Phe Gln Lys Gly His
    1145                1150                1155

Thr Gly Asp Ile Val Ala Leu Ala Ser Gln Ser Gly Thr Gln Arg
    1160                1165                1170

Pro Ala Ser Val Val Leu Ser Arg Asp Ala Asn Val Ser Gly Ser
    1175                1180                1185

Ser Pro Ser His Pro Thr Trp Gln Arg Glu Gly Ala Ala Val Ser
    1190                1195                1200

Gly Arg Ala Asp Glu Phe Ser Ser Leu Ser Val Thr Pro Ser Thr
    1205                1210                1215

Val Pro Leu Ser Ser Phe Thr Met Glu Asp Ile Lys Gly Glu Glu
    1220                1225                1230

Gly Asp Pro Ser Arg Arg Phe Ala Leu Val Gly Glu Ser Met Lys
    1235                1240                1245

Asn Val Ser Ala Pro Glu Val Gln Ala Leu Phe Pro Thr Ser Ser
    1250                1255                1260

Ile Ala Asn Ala Glu Leu Leu Pro Val Asp Phe His Leu His Ser Asn
    1265                1270                1275

Ser Cys Ser Ala Asp Lys Leu Glu Ser Ser Ile Pro Arg Gly Leu
    1280                1285                1290

Ala Gly Asn Asn Pro Ser Met Thr Ala Thr Ala Val Ala Ala Thr
    1295                1300                1305

Ala Val Ser His Gln Ile Phe Asp Thr Ile Thr Leu Phe Gly Glu
    1310                1315                1320

Phe Leu Arg Glu Phe Ala Lys Glu Lys Val Asn Glu Phe His Glu
    1325                1330                1335

Tyr Gly Leu Glu Ala Ser Pro Leu Thr Val Glu Ala Ser Pro Glu
    1340                1345                1350

Val Ser Leu Phe Gly Lys Ala Thr Phe Gly Arg Cys Pro Val Ala
    1355                1360                1365

Gly Gly Ser Thr Pro Ala Gly Ile Ser Lys Met Ser Gly Glu Thr
    1370                1375                1380

Leu Ser Gly Leu Ser Ala Ser Glu Leu Ser Leu Val Ser Ala Arg
    1385                1390                1395

Thr Asn Thr Thr Thr Gly Glu Glu Gln Phe Ala Leu Ala Arg Gly
    1400                1405                1410

Leu Phe Pro Gly Asp Ser Glu Gly Asp Arg Asp Glu Lys Lys Pro
    1415                1420                1425

Gln Leu Ser Gln Gln Glu Leu Leu Val Leu Ser His Ala Leu Val
    1430                1435                1440

Asn Leu Thr Ser Ser Thr Tyr Val Leu Met His Thr Leu Lys Ala
    1445                1450                1455

Ser Leu Ser Lys Ser Thr Glu Ala Val Gln Leu His Gln Pro Leu
    1460                1465                1470

Leu Glu Ala Ala Ser Glu Ala Lys Ala Thr Asp Glu Ala Lys Thr
    1475                1480                1485

Arg Glu Glu Gln Glu Ser Ser Glu Cys Asp His Glu Tyr Pro Pro
```

-continued

```
              1490                1495                1500
Gly Ser Ser Leu Glu Ala Thr Thr Gly Ala Leu Pro Phe Arg Leu
    1505                1510                1515
Ser Pro Ala Leu Ser Ala Ser Ser Lys Asp Leu Pro Ser Leu Ser
    1520                1525                1530
Ala Ser Ala Ser Leu Glu Ser Val Thr Pro Phe Ala Gly Leu Pro
    1535                1540                1545
Leu Glu Glu Gly Thr Leu Ser Ala Ser Val Gly Leu Ala Ser Ser
    1550                1555                1560
Asp Asp Glu His Asp Thr Ser Leu Leu Phe Lys Thr Glu Ala Ala
    1565                1570                1575
Lys Lys Arg Ser Leu Phe Ser Thr Ala Ala Asp Gly Asp Glu Ser
    1580                1585                1590
Arg Thr Tyr Asn Asp Gly Leu Gly Gln Pro Met Glu Glu Glu Ile
    1595                1600                1605
Arg Ser Cys Val Ser Thr Ser Cys Gly Glu Ala Val Ala Thr Thr
    1610                1615                1620
Thr Leu Ser Ala Ile Gly Pro Gly Thr Gly Ala Ser Gly Ala Leu
    1625                1630                1635
Leu Asp Ser Glu Ser Arg Glu Ser Leu Gly Glu Lys Pro Gly Ala
    1640                1645                1650
Ala Leu Arg Ala Gly Ala His Thr Pro Ala Pro Ser Arg Ala Pro
    1655                1660                1665
Thr Pro Ser Arg Thr Phe Ser Phe Thr Ser Ser Thr Ala Thr
    1670                1675                1680
Ser Ala Ala Leu Leu Cys Asp Ser Asn Val Val His Glu Lys Leu
    1685                1690                1695
Ser Ala Gln Gly Lys Asp Ser Glu Ala Gly Glu Arg Lys Gly Asp
    1700                1705                1710
Ser Glu Lys Glu Glu Glu Val Glu Met Trp Lys Glu Glu Asp Glu
    1715                1720                1725
Glu Val Gln Arg Cys Thr Gly Ser Ala Glu Thr Asp Ser Thr Glu
    1730                1735                1740
Ala Thr Arg Gly Glu Glu Ala Trp Arg Arg Gly Lys Gln Ser Glu
    1745                1750                1755
Lys Lys Pro Ser Val Ile Thr Thr Ala Leu Asn Leu Leu Glu Thr
    1760                1765                1770
His Arg His Leu Ala Leu Thr Ile Ser Gln Leu Lys Arg Pro Val
    1775                1780                1785
Ala Gln Gln Leu Arg Phe Ile Leu Pro Ile Ala Ala Pro Gln Leu
    1790                1795                1800
Leu Pro Cys Ile Leu Pro Pro Ala Ser Phe Gln Gly Thr Gly Glu
    1805                1810                1815
Ser Gly Asp Gly Lys Ala Glu Ala Glu Ala Lys Gly Ser Ser Ser
    1820                1825                1830
Leu Gly Gln Val Leu Glu Thr Ala Leu Gly His Gly Thr Arg Leu
    1835                1840                1845
Ala Pro Ser Ala Ser Ala Met Val Pro Pro Arg Lys Asp Glu Ala
    1850                1855                1860
Ala Ser Ala Val Pro Glu Ala Lys Thr Leu Thr Gly Leu Ala Asn
    1865                1870                1875
Ala Gly Val Thr Arg Glu Ala Ala Ser Arg Thr Leu Glu Ala Glu
    1880                1885                1890
```

```
Gln Val Ser Arg Lys Arg Ser Arg Glu Glu Val Val Asp Ser Glu
1895                1900                    1905

Thr Ala Gly Asp Glu Gly Asp Met Glu Asn Val Pro Glu Thr Arg
1910                1915                    1920

Asp Gly Thr Thr Arg Pro Gly Ser Arg Gln Tyr Asp Thr Ser Pro
1925                1930                    1935

Ser Asn Asp Gly Thr Lys Pro Pro Ala Thr Ala Lys Ser Arg Val
1940                1945                    1950

Ile Arg Asp Gln Ala Ala Leu Glu Arg Leu Leu Leu Ala Pro Phe
1955                1960                    1965

Gln Asp Thr Pro Thr Cys Ser Cys Thr Asp Arg Pro Cys Pro Cys
1970                1975                    1980

Asp Arg Gln Gln Val Ala Asp Met Ile Tyr Leu Phe Tyr Ala Val
1985                1990                    1995

Pro Ala Arg Gln Gln Ala Glu Ser Ser Lys Gly Ser Thr Gln
2000                2005                    2010

Arg Leu Gln Phe Ala Ala Arg Asp Thr Asn Glu Arg Lys Asp Ala
2015                2020                    2025

Arg Thr Gly Glu Glu Thr Gln Gly Gly Glu Thr Glu Ala Lys Glu
2030                2035                    2040

Val Ile Arg Asp Pro Glu Glu Arg Gly Val Cys Glu Gly Ser Ser
2045                2050                    2055

Ser Gln Asn Ala His Thr Gln Phe Asp Ala Glu Thr Ala Ser Ser
2060                2065                    2070

Ser Met Ser Ser Asp Pro Arg Ala Asp Lys Glu Ser Asn Ala Gln
2075                2080                    2085

Asp Ala His Met Ala Asp Lys Thr Ser Phe Val Ser Asp Leu Pro
2090                2095                    2100

Gln Pro Ser Gly Glu Phe Ala Pro Ser Leu Leu Ser Glu Thr Ser
2105                2110                    2115

Leu Asp Val Ala Met Ala Asp Ser Arg Gly Thr Pro Ser Glu Ile
2120                2125                    2130

His Gly Phe Phe Thr Arg Ser Asp Glu Gln Lys Arg Ala Ser Phe
2135                2140                    2145

Ser Ser Ser Ser Leu Leu Ala Ala Gly His Ala Val Ala Ser Phe
2150                2155                    2160

Ser Ser Ser Leu Ala Gly Val Val Ser Gly Ala Gly Glu Arg Arg
2165                2170                    2175

Glu Cys Ala Gly Pro Ser Leu Gly Asp Leu Ser Thr Ile Gly Leu
2180                2185                    2190

Leu Ser Leu Ser Tyr Pro Ala Met Leu Ala Phe Ile Leu Pro Leu
2195                2200                    2205

Gln Ser Leu Leu His Thr Val Ser Gly Met Ile Leu Thr Leu His
2210                2215                    2220

Lys Lys Leu Ile His Arg Phe Ile Cys Ala His Leu Arg Leu Val
2225                2230                    2235

Leu Asp Asp Asp Met Arg Arg Pro Ala Gly Gly Ala Leu Lys Ser
2240                2245                    2250

Arg Gly Ala His Gly Asp Thr Glu Ala Ala Glu Ala Gln Val Glu
2255                2260                    2265

Arg Arg Arg Arg Glu His Glu Arg Glu Glu Thr Thr Asn Leu Ala
2270                2275                    2280
```

```
Ile Gly Tyr Arg Glu Gly Asn Ala Glu Ala Ala Asn Thr Phe Pro
    2285                2290                2295

Leu Val Asp Thr Val Ser Ser Leu Leu Ser Pro Gly Ser Leu Arg
2300                2305                2310

Gln Glu Asn Ser Glu Val Glu Arg Arg Asp Asn Asp Glu Glu Arg
    2315                2320                2325

Leu Glu Leu Ile Thr Gly Ile Ala Arg Glu Ser Pro Lys Pro Ser
2330                2335                2340

Glu Lys Asp Ser Val Ser Pro Phe Leu Ser Thr Ala Pro Cys Pro
    2345                2350                2355

Gly Thr Glu Ala Glu Ser Ser Asp Cys Ser Ala Ser Ser Ala Cys
2360                2365                2370

Ser Gly Thr Pro Thr Glu Gly Thr Glu Gly Gly Glu Thr Gly Asp
    2375                2380                2385

Ile Ala Ser Phe Leu Ser Pro Ser Gly Glu Val Lys Gln Thr Ile
2390                2395                2400

Met Leu Ala
    2405

<210> SEQ ID NO 3
<211> LENGTH: 1217
<212> TYPE: DNA
<213> ORGANISM: Homo sapiens

<400> SEQUENCE: 3
tatccagttg cccggctctg tctaccttct tctcgatgta gcggcggcgt tctgtgttcc      60
ttagagcgag tccacgcacc agcctcgtgg agtcgaacag ttttcgccag agcggggaca     120
gccggtggaa gacagaacag gagggattca ccgtcacctc gtttgcttcc ttctggtgat     180
ggagggaata agccgacaga ctcacttctt aacagttcat ggcagagggg caacgacgtc     240
accatccagc tttccattca cttaaccgca caagcgttct gctcgttagt caagcctcac     300
tcgccagtcg aaagccatta aaagttcgcg tttctggctc tcgtttgtgc cggaagtctg     360
ccaaagcaaa caaaggatct gaaaccgagt agcagtgaac gcgtgacagt gcagaggggt     420
gcccgcgtcg gcgtcctctc tgtccacgaa cagccacaat tctcatcacg agaagtcctc     480
ctcccctgga tcttcctcca gttccccatg actgcctccg gttctcgcac ggacggcgat     540
ccgccttcac gctccccggc ctttgccagt tttgtgcaag aaggtcgccc gtcttattct     600
tgtcacgttc cctgtatcta ctcggttcac tgcgctctac agaagctctt cttcgccttc     660
tactgatcag tgcactctac gagatgcact atcatcagtc ctgaactcca tgtttgggtg     720
gaaacctggg cgtgctgtgt cgcagcgagt cgcgagattg ccggcctgtc gacgagttcc     780 cgttttcct gcactggcta cagcgtagcg gcttcgcctg ctcactggcg acggtactgg      840
ccgcacggtt tcacgatcct gaggtcggcg agatgccct gtctggcgag gccttttgtc      900
tacgcagcga cctctgtcta ctagagaaag gcagaaggcc ggagcgtttt tcagatgtg      960 ctactctttg tcttctgcga tcttccgtgc gttcagctgt gcttttgcca aggagacct     1020 gtgtgcagag gacttcgctg ctaaaaagca gaagagtgcg cggcgtgtgt agctcagtgg     1080
catttcggga ctcggtcttg cgtcgttcgc gactggacgt cgtcgtctgt gagagcgtca     1140
aactagggag aaggggcggg ccagagcgtt cggaaaatta tctgcaaagc ccaggtcccg     1200
tatgatattc aaaaaag                                                   1217

<210> SEQ ID NO 4
```

```
<211> LENGTH: 267
<212> TYPE: PRT
<213> ORGANISM: Homo sapiens

<400> SEQUENCE: 4

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 5
<211> LENGTH: 25
<212> TYPE: DNA
<213> ORGANISM: Homo sapiens

<400> SEQUENCE: 5
agtgttctcg aaaccatgct aacac                                        25

<210> SEQ ID NO 6
<211> LENGTH: 25
<212> TYPE: DNA
<213> ORGANISM: Homo sapiens

<400> SEQUENCE: 6
cctcttacct cagttacaat ttata                                        25

<210> SEQ ID NO 7
```

```
<211> LENGTH: 968
<212> TYPE: PRT
<213> ORGANISM: Homo sapiens

<400> SEQUENCE: 7

Met Leu Ser Arg Arg Cys Lys Arg Ser Ala Glu Asp Ser Gly Ala
1               5                   10                  15

Asn Glu Val Gly Ala Asn Ala Asp Gln Ser Lys Arg Leu Arg His Ser
            20                  25                  30

Leu Asp Ser Ile Ile Glu Lys Gly Gly Asp Pro Val Asn His Asp Ser
        35                  40                  45

Ala Met Leu Leu Asp Cys Ala Pro Thr Gln Thr Gly Arg Ala Phe Ala
    50                  55                  60

Phe Leu Ser Met Pro Ala Pro Ile Glu Pro Ser Gly Asn Glu Glu Ser
65              70                  75                  80

Ala Pro Ala Val His Arg Asp Ser Gly Val Gly Ile Asp Tyr Pro
                85                  90                  95

Arg Pro Val Ala Ser Ile Ser Val Glu Ser Ser Gln Val Val Ala
            100                 105                 110

Pro Arg Asp Glu Asn Pro Ser Ala Ser Tyr Gln Arg Arg Gly Asp Ser
        115                 120                 125

Pro Pro Ser Leu Arg Asn Gly Gly Asp Arg Gln Glu Arg Lys Arg Thr
    130                 135                 140

Ala Val Ala Pro Glu Ala Asn Glu Pro Gln Asp Asn Glu Thr Lys Asn
145                 150                 155                 160

Glu Glu Trp Leu Gln Leu Ala Arg Leu Lys Pro Lys Val Glu Gly Val
                165                 170                 175

Cys Phe Asp Arg Phe Arg Arg Trp Val Ala Lys Arg Ala Gly Leu
            180                 185                 190

Lys Lys Val Tyr Phe Pro Val Tyr Lys Tyr Gly Phe Asp Arg Ala Tyr
        195                 200                 205

Glu Leu Ala Val Ala Thr Arg Arg Gly Leu Glu Asn Asp Ala Ala Ala
    210                 215                 220

Gly Ile Arg Ala Val Gly Ala Leu Arg Pro Arg Ile Ser Glu Ala Ala
225                 230                 235                 240

Gly Cys Thr Ser Ser Pro Gly Met Leu Ser Glu Asp Ala Cys Pro Glu
                245                 250                 255

Lys Pro Pro Val Pro Val Gln Pro Pro Arg Thr Leu Ser Thr Arg Ala
            260                 265                 270

Thr Ala Ala Gln Ala Glu Val Lys Ser Gly Asp Ser Ala Glu Ser Thr
        275                 280                 285

Lys Asn Asp Ser Glu Gly Ala His Val Leu Glu Gly Ala Glu Leu Gln
    290                 295                 300

Thr Pro Glu Arg Ser Thr Ser Asn Thr Ile Cys Trp Ala Thr Ala Ala
305                 310                 315                 320

Glu Gly Ser Ile Ser Lys Thr Asp Gly Phe Gln Asn Arg Ser Ser Pro
                325                 330                 335

Ser Gly Phe Gly His Gly Ser Arg Asn Lys Pro Glu Leu Ser Gln Gln
            340                 345                 350

Lys Val Glu Thr Thr Ser Arg Gly Ile Arg Ser Ala Ser Ala Ser Cys
        355                 360                 365

Asn Arg Glu Lys Asp Gln Gly Gly Ser Ala Cys Ser Val Leu Ser Ile
    370                 375                 380

Ala Ser Phe Ser Leu Ser Gln Ile Asp Glu Glu Leu Glu Gly Ile Asn
```

```
                385                 390                 395                 400
Asp Glu Ala Tyr Glu Ala Glu Arg Leu Gln Ala Asp Glu Asp Arg Ser
                    405                 410                 415

His Ala Pro Ala Ala Ser His Gly Glu Gly Gly Thr Ser Ala Gly Glu
            420                 425                 430

Ser Thr Ala Ala Ser Thr Thr Gly Ser Glu Asp Ser Gly Pro Leu Arg
                435                 440                 445

Ala Ala Thr Ser Pro Leu Met Phe Pro Gln Gly Ser Glu Gly Ser Ala
        450                 455                 460

Ser Ser Ala Ser Thr Glu Ile Met Val Leu Asp Asp Glu Ser Met Gln
465                 470                 475                 480

Gln Ala Leu Val Thr Ala Ser Ala Glu Thr Leu Asn Lys Leu Arg Ser
                485                 490                 495

Thr Leu Pro Ala Gly Val His Phe Asp Phe Ala Ser Lys Arg Trp Phe
            500                 505                 510

Ala Val Tyr Ser Ser His Glu Ser Pro Glu Ala Thr Gln Arg Asp Pro
                515                 520                 525

Val Arg Pro Lys Glu Arg Val Arg Ile Phe Asp Pro Thr Gln Tyr Glu
    530                 535                 540

Gly Ser Met Leu Lys Ala Phe His Ala Cys Arg Ser Phe Cys Gly Ser
545                 550                 555                 560

Val Glu Ala Gly Ala Ser Asp Trp Asp Ser Val Pro Gln Leu Val Pro
                565                 570                 575

Glu Gln Arg Lys Gln Gly Glu Cys Gln Asp Thr Ser Gly Ser Ser Asp
            580                 585                 590

Gln Gly Ala Asn Arg Leu Ser Pro Thr Glu Thr Glu Asn Pro Pro Thr
        595                 600                 605

Ala Asp His Pro Arg Ser Leu Ser Ala Thr Thr Arg Pro Glu Gly Ser
    610                 615                 620

Leu Glu Gln Thr Gln His Pro Gln Arg Asn Arg Gly Ile Leu Gly Ile
625                 630                 635                 640

Gln Pro Gly Glu Thr Glu Gly Leu Gln Val Pro Ser Asn Gly His Gly
                645                 650                 655

Val Asn Ala Gly Asp Ile Glu Thr Asn Leu Leu Asp Ala Glu Phe Gly
            660                 665                 670

Ser Glu Thr Arg Ala Arg Thr Thr Ala Leu Pro His Leu Arg Arg Ser
                675                 680                 685

Gln Arg Arg Ala Asp Pro Ala Arg Ser Val His Ser Asn Thr Phe Ala
    690                 695                 700

Gly Gln Glu Leu His Gln Ser Pro Lys Pro Gly Asn Gln Thr Ser Arg
705                 710                 715                 720

Gly Glu Ser Gly Arg Ser Ser Leu Arg Arg Lys Asn Gln Val Ser Thr
                725                 730                 735

Asn Glu Lys Gly Leu Pro Gly Glu Gly Gly Cys Arg Thr Asp Glu Lys
            740                 745                 750

Ser Lys Gln Val Ser Tyr Val Ser Phe Ser Glu Pro Ile Thr Val Arg
                755                 760                 765

Tyr Gln Gln Val Pro Thr Glu Ser Ala Ser Thr Arg Gly Cys Ser Gln
    770                 775                 780

Arg Arg Pro Gln Asn Ala Glu Glu Leu Glu Asp Arg Arg Ser Pro Leu
785                 790                 795                 800

Thr Arg Gln Glu Glu Arg Thr Glu Ser Asp Pro Arg Thr Thr Ala Gly
                805                 810                 815
```

-continued

Leu Cys Gln Glu Asn Pro His Pro Ser Tyr Arg Phe Leu Arg Gln Gln
                820                 825                 830

Ser Arg Glu Leu Ala Val Arg Cys Leu Leu Val Ile Phe Gly Asn Leu
            835                 840                 845

Ala Asp Val Cys Thr Pro Ala Leu Phe Arg Leu Phe Pro Gln Asp Arg
        850                 855                 860

Cys Arg Arg Val Arg Ala Val Leu Gln His Arg Asp Leu Leu Gln Ser
865                 870                 875                 880

Gly Lys His Thr Arg Val Leu Leu Ser Ala Tyr Phe Gln Leu Phe Trp
                885                 890                 895

Pro Leu Leu Glu Thr Arg Thr Leu Pro Gln His Tyr Ser Ala Asp Tyr
            900                 905                 910

Ile Arg Arg Leu Leu Asn Gly Met His Asn Val Ala Ala Met His Lys
        915                 920                 925

Ser Leu Phe Pro Glu Tyr Pro Leu Arg Gly Glu Leu Asp Asn Arg Glu
    930                 935                 940

Gly Pro Tyr Ala Phe Leu Asp Asp Thr Ala Ala Glu Gly Ile Asn Phe
945                 950                 955                 960

Phe Glu Thr Asp Phe Asp Glu Pro
                965

<210> SEQ ID NO 8
<211> LENGTH: 425
<212> TYPE: PRT
<213> ORGANISM: Homo sapiens

<400> SEQUENCE: 8

Met Ala Tyr Gln Arg Arg Ala Ala Ala Cys Thr Ile Glu Val Ser
1               5                   10                  15

Arg Asp Leu Phe Ser Pro Glu Arg Asn Leu His Asp Asn Phe Ser Ser
                20                  25                  30

Leu Ala Ile Thr Met Ala Phe Arg Thr Val Ser Lys Val Leu Pro Thr
            35                  40                  45

Leu Ser His Cys Phe Pro Gly Pro Leu Ser Val Ala Ala Ser Ser Ser
        50                  55                  60

Leu Pro Gly His Ser Lys Gly Glu Ser Val Pro Cys Arg Val His
65                  70                  75                  80

Arg Ser Phe Arg Leu Ser Pro Val Ala Asp His Glu Ala Glu Ala Leu
                85                  90                  95

Ser Gly Ser Gly Asn Asp Thr Ser Gly Cys Ser Gln Arg Asp Arg Phe
            100                 105                 110

Cys Ala Gly Asn Gly Ser Asp Cys Lys Ala Arg Arg Thr Ser Asp Gly
        115                 120                 125

Asn Gly Ser Pro Pro Thr Asn Ala Arg Met Ser Glu Lys Leu Ser Leu
    130                 135                 140

Phe Lys Asn His Ala Tyr Ser Cys Leu Glu Gln Arg Ala Cys Pro Ala
145                 150                 155                 160

Ser Asn Arg Asn Leu Gly Asp Thr Ala Ala Cys Pro Leu Ser Ala Phe
                165                 170                 175

Cys Arg Ser Leu Val Arg Arg Thr Pro Ser Arg Leu Trp Leu Pro Pro
            180                 185                 190

Gln Cys Ser Leu Leu Ser Gly Cys Ser Ala Arg Ser Cys Pro Pro Lys
        195                 200                 205

Ile Ser Val Arg Ala Thr Asn Gly Ala Ser Glu Gln Ala Ser Trp Gln

```
            210                 215                 220
Asp Phe His Pro Ala Leu Gly Arg Ala Val Pro Leu Ser Leu Ser
225                 230                 235                 240

Gly Arg Gly Thr Ala Gly Thr His Leu Val Arg Lys Phe Gly Thr Gln
                245                 250                 255

Arg Val Val Gln Lys Arg Arg His Gln Met Arg Ile Leu His Pro Ala
            260                 265                 270

Gln Thr Ala Tyr Val Pro Val Glu Gln Arg Pro Pro Ile Pro His
        275                 280                 285

Ser Leu Thr Ala Ser Ser Thr Val Lys Arg Leu Leu Asn Asn Asn Thr
290                 295                 300

Val Ala Ala Lys Glu Ala Ala Lys Arg Ile Asn Trp Gly Ala Tyr Ile
305                 310                 315                 320

Ser His Gln Arg Gly Val Arg Trp His Pro Gln Gly Ala Trp Arg Val
                325                 330                 335

Gln Phe Ser Arg Arg Asn His Glu Arg Asn Phe Phe Val Arg Cys Glu
            340                 345                 350

Cys Tyr Phe Arg Val Gly Thr Tyr Gly Phe Gln Met Ala Lys Asp Leu
        355                 360                 365

Ala Ile Arg Tyr Arg Gln Arg Leu Glu Lys Glu Trp Glu Glu Leu Gln
370                 375                 380

Glu Gln Trp Thr Lys Leu Asp Ile Leu Glu Ala Glu Gln Arg Ala Lys
385                 390                 395                 400

Tyr Lys Glu Lys Arg Glu Glu His Leu Leu Gly Ala Gly Glu Glu
                405                 410                 415

Pro Glu Leu His Ser Arg Arg Ser Lys
            420                 425

<210> SEQ ID NO 9
<211> LENGTH: 2674
<212> TYPE: PRT
<213> ORGANISM: Homo sapiens

<400> SEQUENCE: 9

Met Asp Gly Ser Gly Glu Ser Ser Gly His Leu Phe Lys Pro Gly His
1               5                   10                  15

Gly Glu Ala Arg Val Ser Val His Arg Gly Ser Leu Thr Asp Ser Gly
                20                  25                  30

Ser Leu Pro Ala Ala Ser Arg Cys His Ser Gln Asp Asn Lys Leu Ser
            35                  40                  45

Leu Pro Cys Ala Gly Ser Met Leu Pro Ala Ser Ser Gly Arg Phe Ser
        50                  55                  60

Cys Asp Ser Ala Leu Phe Gly Gly Pro Val Asp Ser Ala Cys Ser Ser
65                  70                  75                  80

Asp Trp Thr Pro Val Val Ser Pro Ser Arg Asp Leu Ser Ala Asp Gly
                85                  90                  95

Thr Asp Ser Ser Ser Val Ser Gly Ser Arg Gly Ser Ser Leu Pro Phe
            100                 105                 110

Gly Ser Pro Thr Ser Ala Leu Leu Arg Pro Ser Ser Glu Ala Ser Ala
        115                 120                 125

Asn Phe Pro Arg Leu His Lys Ser Val His Ala Leu Asp Asp Lys Met
    130                 135                 140

Arg Gly Leu Asp Ala Gln Leu Tyr Val Arg Pro His Gln Thr Leu Pro
145                 150                 155                 160
```

```
Leu Gln Pro Arg Leu Arg Glu Thr Asp Leu Cys Arg Asn Gly Glu Asp
                165                 170                 175
Gly Arg Pro Gly Lys Phe Asp Ser Pro His Leu Gly Ser Ser Ala Gly
            180                 185                 190
Pro Tyr Gly His Ser Phe Leu Ala Asn Pro Gln Leu Thr Pro Phe Val
        195                 200                 205
Pro Gln His Leu Ser Ser Ser Pro Gln Pro Val Leu Ser Pro Pro
    210                 215                 220
Gly Glu Glu Gly Arg Asn Ser Ala Ala Phe Gly Lys Thr Val Ser Arg
225                 230                 235                 240
Leu Asn Thr Gly Gly Gly Glu Arg Gln Asp Ser Ser Glu Asp Gln Val
                245                 250                 255
Gly Gly Thr Gly Arg Gln Ser Asp Gln Ala Thr Lys Ala Asn Ser Gly
            260                 265                 270
Ser Thr Pro Ala Gly Cys Ala Gln Thr Ala Gly Leu Leu Thr Asp Val
        275                 280                 285
Gln Ser Ser Gly Thr Asn Val Glu His Gly Arg Glu His Phe Ser Thr
    290                 295                 300
Pro Gln Lys Pro Ala Asp Gly Ser Ala Arg Thr Cys Gly Phe Arg Glu
305                 310                 315                 320
Thr Arg Val Ser Pro Ser Asn Ser Ser Leu Pro Arg Thr Ala Cys Arg
                325                 330                 335
Ser Arg Leu Asp Ala Phe Leu Pro Gln Lys Ser Val Ser Pro Asp His
            340                 345                 350
Glu His Val Arg Gly Thr Gly Ala Arg Ala Phe Val Gly Gly Asp
        355                 360                 365
Ser Pro Phe Pro Glu Lys Pro Asp Thr Leu Pro Ala Thr Val Thr Ala
    370                 375                 380
Glu Leu Ala Thr Glu Ala Pro Pro Ala Ser Arg Asp Pro Pro Val Glu
385                 390                 395                 400
Glu Phe Pro Gly Ala His Glu Leu Glu Ser Leu Pro Pro Pro His Val
                405                 410                 415
Asn Ser Gly Arg Pro Pro Ile Gly Glu Lys Asp Gly Ala Ala Ala Ser
            420                 425                 430
Pro Gly Val Ser Arg Leu Pro Ser Gln Glu Arg Val His Thr Leu Leu
    435                 440                 445
Tyr Pro Asn Glu Lys Asp Ala Ser Ser Leu Ser Arg Cys Cys Pro Ser
    450                 455                 460
Ser Met Gln Pro Pro Ala Gly Pro Arg Gln Glu Glu Ala Arg Ser
465                 470                 475                 480
Phe Ser Val Ser Ala Ala Ser Ala Pro Gly Ala Pro Pro Gly Ile Val
                485                 490                 495
Tyr Gln Ala Ser Ala Cys Ala Ser Pro Ala Thr Val Ala Ser Phe Ala
            500                 505                 510
Thr Pro Leu Thr Thr Pro Val Gly Ala Ser Ala Gln Ser Glu Pro Ala
    515                 520                 525
Ala Leu His Ala His Ser Arg Ser Arg Thr Gly Ala His Pro Glu Ala
    530                 535                 540
Leu Pro Pro Gly Val Pro Val Thr Ser Gln Leu Gly Arg Gly Ala
545                 550                 555                 560
Arg Gly Asp Arg Glu Thr Leu Ala Gly Ala Arg Pro Gly Gln Asp
                565                 570                 575
Gly Val Cys Glu Arg Arg Gly Asp Val Ala Arg Gly Arg Leu Gly Gly
```

```
            580                 585                 590
Val Ser Val Ala Gly Asp Glu Ala Glu Gly Thr Ser His Lys Ala
        595                 600                 605
Ala Leu Glu Gly Ala Tyr Val Gln Asp Gly Cys Ser Pro Gln Pro Leu
    610                 615                 620
Asn Pro His Ala Pro Ser Gly Ile Ser Ala Pro Thr Asn Gly Ser Ser
625                 630                 635                 640
Glu Leu Ala Ser Ser Ala Ile Pro Ala Ser Thr Cys His Asp Ala Phe
            645                 650                 655
Val Arg Ser Pro Val Ser Gly Ser Asp Cys Met Ser Val Ala Asn Pro
        660                 665                 670
Gly Gly Pro Pro Gly Ala Leu Gly Leu Phe Pro Ser Pro Arg Gly
        675                 680                 685
Pro Ser Gly Pro Arg Pro Thr Pro His Pro Ala Gln Met Ala Phe Ala
        690                 695                 700
Phe Val Gly Gln Gln Pro Val Phe Pro Gly Phe Asp Ala Ser Gln Pro
705                 710                 715                 720
Ala Gly Ser Thr Phe Gln Tyr Pro Pro Ile Arg Gly Ala Val Ser Gly
            725                 730                 735
Val Ser Pro Pro Pro Met His Pro Ser Ser Phe Ala Gln Pro Val
        740                 745                 750
Trp Ser Pro Thr Ser Val Pro Ser Ser Val Ser Ser Val Ser
        755                 760                 765
Ser Ser Gly Val Ser Ser Ala Pro Pro Leu Ala Val Gly Phe
    770                 775                 780
Gln Asn Pro Cys Pro Trp Arg Pro Thr Ala Pro Arg Asp Arg Ser Glu
785                 790                 795                 800
Gly Gly Ala Gly Ser Pro Gly Val Ser Cys Gly Ser Ala Pro Pro Ala
            805                 810                 815
Pro Thr His Pro Thr Gly Lys Gly Gly Ala Ala Gly Arg Ala Gly Lys
            820                 825                 830
Gln Leu Gly Gln Ala Thr Arg Phe Leu Ser Ser Val Ser Gly Val Val
        835                 840                 845
Tyr Asp Lys Gly Gly Glu Lys Trp Ile Ala Arg Trp Ser Glu Asn Gly
        850                 855                 860
Lys Pro Phe Lys Lys Thr Phe Ala Val Gly Lys His Gly Phe Asp Ala
865                 870                 875                 880
Ala Arg Lys Met Ala Glu Asp Cys Arg Leu Gln Ala Leu Tyr Ala Lys
            885                 890                 895
Arg Trp Asn Ser Ala Ser Gly Leu Pro Ala Ser Phe Ser Lys Ser Asn
        900                 905                 910
Ser Leu Gly Arg Ser Thr Pro Gly Asp Arg Gly Lys Thr Glu Ser Thr
        915                 920                 925
Asn Ser Ala Lys Cys Lys Arg Asp Thr Ser Gly Glu Ser Gly Cys Thr
945                 935                 940
Asp Thr Gly Leu Arg Ser Leu His Met Gly Gly Ala Gly Asp Leu Ser
945                 950                 955                 960
Ser Leu Gly His Pro Gly Thr Pro Pro Arg Asp Gln Glu Gly Ala Pro
            965                 970                 975
Ala Ser Phe Leu Leu Glu Gly Thr Gly Val Val Arg Ser Ser Gln Val
        980                 985                 990
Gln Thr Pro Phe Arg Leu Tyr Asp Ser Val Pro Ser Pro Leu Arg Ser
        995                 1000                1005
```

```
Gly Asp Ala Leu Gly Ala Gln Arg Gly Leu Val Pro Gln Leu Leu
1010            1015            1020

Asn Asn Ala Leu Val Gly Val Pro Phe Ala Pro Pro Pro Gly Ala
1025            1030            1035

Ser His Ser Gly Cys Ser Ala Ala Leu Pro Pro Gly Pro Gly Ala
1040            1045            1050

Pro Val Gln Val Ser Ser Pro His Thr Gly Phe Val Ala Pro Ala
1055            1060            1065

Asp Val Asp Ala Pro Pro Arg Asp Gly Leu Glu Gly Leu Gly Gly
1070            1075            1080

Ala Ala Glu Val Ser Pro Gln Ile Ala Val Gln Asp Gly Gly Lys
1085            1090            1095

Lys Gly Glu Gly Leu Leu Gly Ser Ala Ser Leu Ser Val Arg Arg
1100            1105            1110

Arg Arg Lys Arg Glu Pro Asp Glu Lys Phe Ser Pro Gly Glu Ser
1115            1120            1125

Asn Ala Ala Val Lys Lys Thr Pro Arg Pro Gly Ser Phe His Pro
1130            1135            1140

His Ser Cys Pro Gly Ser Glu Gly Phe Arg Ser His Asp Gly Pro
1145            1150            1155

Gly Asp Ser Thr Glu Ala Arg Cys Ala Gly Leu Pro Ala Phe Gln
1160            1165            1170

His Ala Thr Ala Pro Ser Ser Val Cys Trp Pro Ser Thr Ala Ser
1175            1180            1185

Leu Pro Ser Leu Asp Lys Ala Gly Gln Arg Ala Glu His Ala Gly
1190            1195            1200

Pro Ser Ala Phe Ser Ser Phe Ser Ser Val Gln Gln Ser Pro Gly
1205            1210            1215

Ser Val Glu Thr Trp Arg Pro Glu Gly Asp Gly Gly Pro Ala Ser
1220            1225            1230

Pro Ala Arg Asp Ala Gly Arg Arg Gly Ala Glu Ser Glu Glu Arg
1235            1240            1245

Glu Thr Gly Glu Leu Ala Gly Pro Phe Ala Gly Val Ser Ala Ser
1250            1255            1260

Ala Gly Ser Ala Ser Arg Lys Gly Gln Gln Lys Gln Leu Thr Arg
1265            1270            1275

Gln Ile Gln Arg Gln Gln Gln Leu Tyr Arg Gln Gln Glu Ala Leu
1280            1285            1290

Leu Gln Asn Gln Glu Glu Leu Phe Ser Arg Leu Leu Arg Arg Arg
1295            1300            1305

Ser Arg Gln Glu Arg Ser Asp Val Arg Arg Met Gln Arg Asp
1310            1315            1320

Val Ser Ser Leu Arg Arg Leu Pro Ala Met Leu Leu Ser Pro Leu
1325            1330            1335

Arg Asp Thr Leu Val Ala Ser Ala Ala Arg Leu Pro Leu Ala Thr
1340            1345            1350

Arg Gly Thr Lys Arg Glu Ser Gln Lys Glu Arg Arg Asp Cys Gly
1355            1360            1365

Ala Gly Ile Gly Gly Glu Thr Ala Ser Glu Lys Lys Glu Met Ala
1370            1375            1380

Glu Pro Val Arg Val His Arg Arg Asp Arg Gly Gly Ala Arg Asp
1385            1390            1395
```

```
Glu Glu Lys Pro Ser Thr Glu Gly Val Arg Gln Ala Asp Pro Lys
    1400            1405                1410

Gly Arg Lys Ala Glu Gly Phe Pro Thr Trp Val Ile Pro Pro Asn
    1415            1420                1425

Glu Glu Leu Lys Ala Ala Gln Val Leu Arg Ala Leu Arg Val Gln
    1430            1435                1440

Arg Arg Ala Ala Ala Arg Glu Gly Lys Leu Leu Glu Ser Leu Leu
    1445            1450                1455

Val His Arg Gly Glu Gly Glu Gly Thr Phe Ser Glu Glu Thr Glu
    1460            1465                1470

Gly Asn Thr Gly Ile Glu Asp Ala Gly Thr Glu Ser Asp Ala Thr
    1475            1480                1485

Val Thr Gln Glu Thr Ala Glu Lys Val Val Glu Asn Val Gln Lys
    1490            1495                1500

Met Glu Glu Leu Glu Ser Lys Val Glu Lys Glu Asn Glu Arg Arg
    1505            1510                1515

Arg Glu Ala Glu Asp Glu Thr Pro Lys Gln Ser Ser Glu Glu Ala
    1520            1525                1530

Pro Gly Val Gln Gln Ser Pro His Lys Leu Ser Thr Asn Asn Glu
    1535            1540                1545

Asn Asp Ala Ser Pro Gln Lys Leu Thr Lys Ser Val Arg Phe Ala
    1550            1555                1560

Glu Ser Val Ala Gly Ser Ser Ala Val Gln Thr Ala Gly Ala
    1565            1570                1575

Ala Asp Glu Glu Pro Leu Ala Thr Glu Thr Leu Glu Gly Arg Arg
    1580            1585                1590

Val Gly Gly Ile Pro Val Pro Ala Thr Ser Ser Pro Ala Pro Val
    1595            1600                1605

Phe Pro Cys Thr Ala Ala Gln Leu Gly Asp Leu Cys Met Asp Thr
    1610            1615                1620

Leu Tyr Ala Leu Gly Thr Val Arg Pro Gln Trp Arg Arg Gln Asp
    1625            1630                1635

His Arg Arg Ala Phe Gly Trp His Leu Ser Gln Ile Lys Pro Asp
    1640            1645                1650

Leu Ile Leu Pro Ser Leu His Ala Ser Arg Val Leu Arg Arg Leu
    1655            1660                1665

Ser Pro Arg Pro Ser Asn Ala Val Glu Phe Pro Arg Glu Glu Leu
    1670            1675                1680

Ala Ala Ala Ser Ser Ala Ala Gly Leu Val Tyr Gly Glu Gly Leu
    1685            1690                1695

Ser Ser His His Thr Leu Arg Ser Tyr Val Asp Ala Phe Arg Pro
    1700            1705                1710

Leu Phe Ser Ser Pro Ser Ser Pro Pro Leu Glu Phe Leu His Leu
    1715            1720                1725

Ser Ser Gly Asp Leu Leu Met Ser Leu Trp Gln Leu Glu Glu Gly
    1730            1735                1740

Gly Arg Ala Ala Val Ile Asp Asn Val Leu Leu Ala Leu Asp Ala
    1745            1750                1755

Leu Tyr Glu Arg His Thr Gly Arg Arg Leu Arg Gly Thr Ala Pro
    1760            1765                1770

Pro Pro Phe Ala Val Ser Ser Pro Ser Ser Ala Pro Ser Ser Leu
    1775            1780                1785

Phe Ala Leu Ala His Leu Gln Gly Gly Ala Thr Ser Thr Thr Pro
```

```
                1790                1795                1800

Leu Pro Ala Thr Ala Leu Pro Ser Pro Pro Phe Pro Arg Val Ser
    1805                1810                1815

Ser Ala Pro Asp Ser Pro Val Phe Ala Pro Asp Ala Ser His Gly
    1820                1825                1830

Pro Ser Gln Arg Arg Gln Val Ser Pro His Val Thr Phe Glu Thr
    1835                1840                1845

Pro Pro Thr His Pro Arg Asp Arg Asp Ser Glu Thr Ser Val Glu
    1850                1855                1860

Arg Asn Ala Ser Pro Glu Ala Ser Pro Gln Ala Ala Thr Leu Ala
    1865                1870                1875

Ala Pro Ala Pro Cys Asp Gly Asp Arg Glu Glu Asn Phe Val Leu
    1880                1885                1890

Ala Tyr Asn Pro Glu Ala Lys Ala Leu Arg Gln Val Asn Phe Leu
    1895                1900                1905

Ala Val Gly Val Arg Val Phe Leu His Leu Glu Val Val Glu Glu
    1910                1915                1920

Met Leu His Leu Gln Ala Lys Met Gln Arg Thr Pro Gly Arg Asp
    1925                1930                1935

Asp Arg Ala Thr Ala Ser Ser Gly Pro Ser Val Asp Asp Gly Ser
    1940                1945                1950

Gly Leu Met Thr Ser Leu Pro Ser Thr Cys Ser Gly Val Ser Gly
    1955                1960                1965

Lys Lys Asp Pro Met His Trp Ser Ala Leu Phe Val Thr Val Pro
    1970                1975                1980

Ala Pro Ser Val Ser Thr Ala Ala Ser Lys Pro Leu Phe Val Val
    1985                1990                1995

Ala Glu Met Val Asp Arg Arg Leu Gln Val Pro Cys Gly Glu Gln
    2000                2005                2010

Leu Leu Phe Arg Pro Leu Pro Leu Ser Pro Ala Ala Pro Ser Ala
    2015                2020                2025

Leu Leu Ala Phe Ala Pro Ala Arg Val Cys Gln Leu Leu Arg Ala
    2030                2035                2040

Gly Ala Met Cys Leu Thr Arg Phe Thr Glu Lys Glu Gly Gly Lys
    2045                2050                2055

Arg Pro Arg Gly Ser Ala Gln Arg Cys Ser Ala Ala Ser Ser Phe
    2060                2065                2070

Phe Tyr Ser Pro Pro Leu Asp Leu Ser His Leu Ala Ser Phe
    2075                2080                2085

Ala Pro Ala Ala Ser Thr Leu Thr Pro Pro Ser Ser Pro Ala Ser
    2090                2095                2100

Ser Pro Ser Ala Ser Ala Ser Gln Thr Gly Pro Gly Arg Ala Lys
    2105                2110                2115

Ser Arg Gly Thr Ser Pro Val Gly Pro Glu Ser Pro Glu Ala Ala
    2120                2125                2130

Ser Thr Thr Ser Asp Gly Leu Ala Val Pro Gly Ser Ala Ser Ala
    2135                2140                2145

Val Ser Thr Pro Gly Val Pro Ala Gly Ala Ser Gly Ala Ser Leu
    2150                2155                2160

Gly Ala Pro Ala Pro Ser Pro Met Ala Ser Pro Gly Gly Ser Pro
    2165                2170                2175

Gly Arg Pro Pro Lys Pro Val Cys Cys Pro Ala Ala Pro Gly Ile
    2180                2185                2190
```

```
Glu Thr Ala Trp Arg Cys Lys Cys Ser His Arg His Glu Leu
    2195                2200                2205

Gln Leu Glu Ile Lys Gln Lys Leu Arg Gln Asp Lys Lys Arg Cys
    2210                2215                2220

Leu Ala Leu Ile Arg Glu Tyr Pro Asp Leu Ser Leu Leu Val Gly
    2225                2230                2235

Ala Pro Pro Ala Thr Pro Arg Glu Lys Glu Thr Gly Ala Lys Arg
    2240                2245                2250

Gln Ala Pro Glu Gly Arg Arg Thr Ala Thr Pro Ser Gly Ser Gly
    2255                2260                2265

Thr Leu Thr Ala Lys Gly Gly Asp Leu Gln Gly Ser Thr Pro Ser
    2270                2275                2280

Gly Ala Gly Leu Leu Ser Leu Ala Arg Thr Ser Gln Leu Glu Met
    2285                2290                2295

Leu Ala Tyr Leu Val Glu Val Asp Pro Trp Lys Tyr Ala Lys Asn
    2300                2305                2310

Arg Gln Asp Ala Pro Lys Pro Glu Glu Ile Pro Gly Leu Leu Ala
    2315                2320                2325

Lys Tyr Lys Ala Ala Val Arg Thr Ala Glu Tyr Gly Arg Met Leu
    2330                2335                2340

Gln Lys Trp Arg Ala Gly Gln Ser Arg Glu Asp Glu Gly Arg Gly
    2345                2350                2355

Gly Ala Asp Gly Arg Lys Glu Gly Asp Gly Leu Leu Ser Pro Thr
    2360                2365                2370

Ala Ser Pro Pro Ser Arg Arg Lys Gln Gly Lys Asp Ser Ser Pro
    2375                2380                2385

Asn Ser Ala Ser Ser Gln Ala Ser Gly Pro Ala Pro Ser Pro Ser
    2390                2395                2400

Leu Ser Pro Gly Ala Gly Ala Ala Val Leu Glu Ala Glu Lys
    2405                2410                2415

Pro Glu Pro Gln Ser Pro Gln Glu Ser Pro Cys Pro Leu Glu Pro
    2420                2425                2430

Ala Ala Gly Gln Glu Pro Arg Ala Thr Ser Ser Ala Leu Pro Ala
    2435                2440                2445

Gly Ser Pro Pro Trp Ala Leu Pro Leu Val Pro Pro Gly Gly Ser
    2450                2455                2460

Pro Arg Ala Ser Val Ser Pro Ser Val Leu Glu Glu Leu Leu Arg
    2465                2470                2475

Ile Gln Thr Ala Met Ser Gln Leu Ala Ile Gly Thr Ala Ile Cys
    2480                2485                2490

Val Arg Val Lys Ala Leu Leu Gly Leu Pro Ala Gly Ala Glu Gln
    2495                2500                2505

His Ile Arg Gly Val Val Thr Arg Asn Ala Leu Lys Phe Pro Trp
    2510                2515                2520

Glu Lys Pro Ala Ala Pro Gln Val Gln Ala Ala Gly Pro Ser Val
    2525                2530                2535

Gly Ala Ser Arg Thr Ser Pro Ser Arg Arg Leu Ser Gly Gly Val
    2540                2545                2550

Leu Pro Gly Asp Glu Ala Gly Glu Arg Arg Glu Lys Gly Gly Ala
    2555                2560                2565

Arg Arg Gly Val Ala Glu Gly Asp Thr Glu Lys Lys Glu Asp Glu
    2570                2575                2580
```

-continued

```
Gly Thr Ala Leu Cys Ala Gly Ser Arg Glu Thr Glu Ala Asp Gly
    2585                2590                2595

Ala Gly Tyr Leu Thr Leu Ser Leu Asn Asn Arg Lys Glu Glu Phe
2600                2605                2610

Ile Leu Ser Phe Arg Glu Val Gln Cys Leu Val Ala Gln Asp Asp
    2615                2620                2625

Leu Arg Leu Val Arg Thr Arg Ala Arg Gln Trp Val Ser Ser Phe
    2630                2635                2640

Gly Pro Gln Pro Ser Ala Asp Arg Lys Gly Glu Arg Glu Glu Glu
    2645                2650                2655

Lys Glu Thr Gly Gly Arg Thr Arg Lys Phe Val Val Asp Glu Asp
    2660                2665                2670

Phe
```

```
<210> SEQ ID NO 10
<211> LENGTH: 2282
<212> TYPE: PRT
<213> ORGANISM: Homo sapiens

<400> SEQUENCE: 10

Met Asp Ser Gly Arg Asp Val Lys Asp Gly Thr Ala Gly Ser Arg Pro
1               5                   10                  15

Lys Asp Gly Gly Asp Gly Val Gly Glu Thr Arg Ala Ser Gly Arg Glu
            20                  25                  30

Ser Glu Glu Arg Ser Leu Gln Leu Glu Ala Asn Glu Cys Pro Gly Ala
        35                  40                  45

Val Met Ser Arg Arg Glu Asp Glu Ala Glu Pro Gln Ser Ser Pro Ser
    50                  55                  60

Ser Ser Pro Pro Arg Glu Glu Gly Pro Gln Asn Val Asp Asp Ala Asp
65                  70                  75                  80

Thr Ala Asn Gly Ser Gly Glu Ala Gly Leu Gln Arg Pro Pro Gln Lys
                85                  90                  95

Arg Arg Leu Glu Gln Gly Leu Glu Ala Glu Ala Gly Val Gly Ser Ser
            100                 105                 110

Arg Val Glu Glu Val Glu Ala Val Cys Arg Lys Arg Pro Ala Phe Ser
        115                 120                 125

Gly Val Ala Asp Ala Phe Leu Glu Arg Pro Val Thr Leu Lys Asn Ser
    130                 135                 140

Ser Glu Glu Asp Ala Ala Arg Leu Ser Gly Asp Asp Ala Ala Gly Ala
145                 150                 155                 160

Ser Leu Leu Ser Val Arg Ser Ala Gly Ala Leu Thr Gly Asp Phe Pro
                165                 170                 175

Ser Ser Ser Arg Leu Pro Ala Met Leu Ser Gly Ala Arg Gly Glu
            180                 185                 190

Asn Ala Glu Glu Ser Val Arg Asp Ala His Thr Pro Ala Gln Asp Ser
        195                 200                 205

Arg Asp Ser Ala Leu Ala Ser Phe Ala Pro Thr Leu Ala Pro Gly Gln
    210                 215                 220

Glu Ser Glu Tyr Thr Arg Ala Lys Leu Trp Ser Ile Glu Lys Ala Phe
225                 230                 235                 240

Asp Ala Phe Leu Ala Asp Gln Lys Ala Asn Gly Arg Arg Gln Gly Ser
                245                 250                 255

Arg Ser Met Arg Glu Pro Ser His Ala His Pro Gly Leu Ser Ala Glu
            260                 265                 270
```

-continued

```
Arg Glu Thr Ser Ser Gly Ala Ser Ala Ala Thr Ser Asp Leu Ser Arg
        275                 280                 285

Glu Asp Val Glu Glu Leu Phe Arg Gln His Gly Val Ser Pro Arg Glu
290                 295                 300

Leu Val Arg Met Leu Ser Gly Arg Arg Asp Gly Pro Gly Thr Ser Pro
305                 310                 315                 320

Glu Glu Leu Arg Ala Ala Val Ala Trp Ala Arg Gln Leu Phe Pro Ala
                325                 330                 335

Ala Pro Arg Ser Pro Ser Glu Leu Arg Met Tyr Leu Gln Arg Ala Val
                340                 345                 350

Leu Asp Arg Gln Lys Arg Leu Arg Glu Arg Trp Gly Ala Glu Ala Asn
                355                 360                 365

Pro Cys Gly Asp Ala Ser Val Tyr Gly Asp Glu Lys Leu Arg Glu His
            370                 375                 380

Leu Ser Asp Leu Ser Ala Phe Met Pro His Leu Asp Ala Gly Arg Glu
385                 390                 395                 400

Val Tyr Met Gln Trp Gln Arg Ser Arg Gly Arg Arg Asp Phe Asp Ala
                405                 410                 415

Phe Val Arg Pro Pro Gly Leu Thr Pro Phe Arg Asp Ser Ser Ser Arg
                420                 425                 430

Gln Gly Asp Phe Ala Ala Ser Pro Leu Tyr Ser Phe Ser Ser Arg Thr
            435                 440                 445

Pro Trp Ala Ser Ala Cys Lys Glu Ala Ser Thr Pro Pro Ala Ala Lys
    450                 455                 460

Gln Gln Ala Pro Pro Ser Leu Trp Asn Leu Pro Asn Arg Pro Gln
465                 470                 475                 480

Pro Tyr Thr Leu Ala Asp Val Gln Glu Ala Met Glu Gly Pro Glu Gly
                485                 490                 495

Val Leu Arg Val Ala Arg Pro Leu Thr Gly Phe Gly Glu Asp Ala Glu
                500                 505                 510

Ser Leu Ser Phe Ala Ser Leu Pro Lys Gly Ala Glu Thr Leu Phe Trp
            515                 520                 525

Ser Ser Gly Arg Gly Leu Tyr Phe Leu Arg His Leu Glu Arg Thr Lys
    530                 535                 540

Ala Gly Glu His Asp Val Val Gly Glu Ala Gly Val Trp Val Ala Ala
545                 550                 555                 560

Ser Glu Glu Glu Phe Gly Gly Phe Ile Ile His Arg Lys Phe Ser Val
                565                 570                 575

Ala Lys Phe Gly Phe Glu Arg Ala Lys Met Leu Ala Cys Arg Trp Tyr
            580                 585                 590

Asn Asp Arg Gln Glu Ala Arg Arg Gly Gln His Ala Leu Pro His Arg
        595                 600                 605

Glu Lys Pro Lys Gly Ile Met Ser Ser Asp Arg Pro Leu Ser Arg Glu
    610                 615                 620

Ala Ala Pro Glu Ala Ser Arg Phe Ser Ala Ser Arg Ala Gly Glu Leu
625                 630                 635                 640

Ser Gly Lys Ala Gln Glu Ala Pro Lys Ser Thr Gly Gly Thr Ala Ala
                645                 650                 655

Glu His Pro Arg Ala Ser Gln Lys Cys Arg Val Met Asp Thr Thr Cys
            660                 665                 670

Pro Val Pro Gly Val Arg Tyr Asp Ser Arg Asp Arg Ala Trp Leu Ala
            675                 680                 685

Thr Trp His Asp Gly Val Arg Gln Tyr Lys Arg Cys Phe Ser Ile Lys
```

-continued

```
            690                 695                 700
Lys Tyr Gly Phe Ala Lys Ala Lys Glu Cys Ala Ile Arg Met Lys Met
705                     710                 715                 720

Ser Leu Val Gly Gln Pro Gly Val Ser Gln Ser Gly Arg Gln Ala Pro
                    725                 730                 735

Phe Pro Val Arg Pro Phe Thr Ser Arg Ala Cys Ser Pro Leu Gln Asp
                740                 745                 750

Phe Phe Arg Glu Gly Asp Arg Arg Val Ala Ala Ser Ser Phe Ser Leu
            755                 760                 765

Leu Pro Ser Gly Arg Gly Glu Pro Arg Gly Ser Leu Gly Ser Ser Gln
770                 775                 780

Gly Ala Asp Asp Glu Arg Ser Lys Pro Gln Ser Cys Arg Gly Leu Val
785                 790                 795                 800

Glu Gln Leu Leu Ala Arg Phe Gln Asp Ser Glu Gly Phe Thr Arg Gly
                805                 810                 815

Leu Pro Gly Asp Asp Glu Asn Arg Gly Lys Arg Leu Ser Lys Gln Ala
            820                 825                 830

Gln Asp Asp Phe Gln Ser Trp Arg Pro Pro Gly Ala Arg Phe Gly
            835                 840                 845

Ser Ala Ala Gln Ala Ser Arg His Ser Thr Asp Glu Val Gly Gly Phe
850                 855                 860

Ala Gly Phe Pro Gly Phe Ala Ala Ser His Cys Gly Glu Lys Pro Gly
865                 870                 875                 880

Gly Glu Gly Pro Ser Phe Leu Gln Lys Ser Gly Phe Val Gln Glu Asn
                885                 890                 895

Ala Phe Ser Pro Pro Ser Glu Arg Phe Glu Thr Gly Val His Arg Arg
                900                 905                 910

Val Pro Ser Leu Ser Ser Glu Leu Ala Asn Pro Gln Val Thr Glu Glu
            915                 920                 925

Val Glu Glu Phe Leu Phe Ser Leu Ser Thr Arg Ala Arg Gln Ser Leu
            930                 935                 940

Leu Ala Ser Leu Arg Arg Gly Ala Glu Asp Ser Arg Arg Ser Ala Trp
945                 950                 955                 960

Pro Gly Ala Ser Arg Asp Cys His Thr Gly Ala Gly Thr Pro Gly Gly
                965                 970                 975

Thr Asp Val Ala Asp Arg Arg Ala Thr Arg Glu Thr Arg Asp Arg
                980                 985                 990

Glu Gly Glu Glu Ser Thr Ser Glu Asp Gly Thr Val Arg Arg Glu Thr
            995                 1000                1005

Asp Ala Gly Ala Val Ser Pro Asp Glu Val Ser Arg Ala Asn Ala
    1010                1015                1020

Glu Glu Arg Ala Ala Gly Glu Lys Thr Arg Ser Ser Glu Arg Ile
    1025                1030                1035

Trp Thr Gly Glu Gly Glu Arg Ser Ala Gly Asp Arg Asp Asp Lys
    1040                1045                1050

Gly Glu Gly Glu Gly Gly Gly Val Val Glu Gly Arg Thr Glu
    1055                1060                1065

Lys Gly Gly Asp Asp Lys Lys Pro Gly Glu Glu Glu Ser Ala
    1070                1075                1080

Glu Arg Glu Glu Glu Leu Lys Asn Asp Ala Tyr Ala Tyr Phe Thr
    1085                1090                1095

His Leu Thr Asn Arg Glu Trp Asp Leu Leu Asp Tyr Leu Asp Thr
    1100                1105                1110
```

```
Leu Asp Phe Glu Thr Val Asp Leu Asp Ala Val Met Pro Phe Ile
1115                1120                1125

Asn Gln Val Pro Lys Val Arg Gly Val Cys Phe Asp Arg Lys Gly
    1130                1135                1140

Leu Tyr Trp Ile Ser Gln Trp His Ser Gln Gln Lys Lys His Arg
    1145                1150                1155

Glu Trp Phe Gly Val Lys Arg Leu Gly Phe Arg Lys Ala Trp Ala
1160                1165                1170

Leu Ala Val Cys Val Arg Arg Asp Ala Glu Lys Val Glu Asp Glu
1175                1180                1185

Pro Val Asp Tyr Pro Lys Leu Pro Asp Tyr Glu Glu Val Leu Gly
1190                1195                1200

Val Thr Tyr Ala Arg Phe Ala Ser Gly Arg Tyr Trp Val Ala His
1205                1210                1215

Tyr Met Arg Pro Ala Ala Pro Ser Ser Gly Cys Leu Gly Ser Val
1220                1225                1230

Gly Arg Lys Leu Phe Pro Val Ser Glu Ser Ser Phe Glu Glu Ala
1235                1240                1245

Arg Ser Gln Ala Val Ala Val Ala Thr Ala Phe Pro Leu Pro Leu
1250                1255                1260

Ala Phe Phe Val Asp Pro Glu Arg Arg Ala Thr Ser Ala Phe Glu
1265                1270                1275

Ser Ala Arg Ala Glu Asn Leu Gln Gly Asp Lys Gln Val Leu Leu
    1280                1285                1290

Ser Lys Asn Cys Leu Phe Asn Val Phe Thr Trp Leu Asn Gly Gly
1295                1300                1305

Ala Ser Trp Thr Asn Val Arg Arg Trp Ala His Ala Lys Arg Met
1310                1315                1320

Gln Leu Ala Glu Asp Asp Trp Pro Gln Gln Phe Phe Ser Leu Pro
1325                1330                1335

Ser Pro Ala Lys Gly Asp Ser Phe Ala Glu Ala Glu Lys Glu Arg
1340                1345                1350

Ala Glu Glu Arg Thr Gly Gly Glu Glu Val Lys Ala Asn Ser Ala
1355                1360                1365

Ser Arg Ala Ala Ala Lys Ser Glu Trp Pro Val Ala Ser Thr Thr
1370                1375                1380

Ser Pro Ala Glu Asp Leu Ala Ser Ser Gly Ser Pro Arg Asp Leu
1385                1390                1395

Gln Lys Leu Ser Pro Leu Leu Ala Asp Ser Ser Leu Thr Lys Glu
1400                1405                1410

Leu Leu Gly Gly Asp Arg Glu Leu Gly Asn Ala Met Asp Gly Ala
1415                1420                1425

Arg Gly Pro Arg Gly Leu Asp Thr Ala Lys Gly Arg Ala Lys Asp
1430                1435                1440

Glu Glu Arg Leu Thr Ala Lys Asp Ala Glu Ser Arg Gln Ala Thr
1445                1450                1455

Leu Pro Gly Gly Arg Ala Ala His Gly Gly Gly Val Gly Gly Ser
1460                1465                1470

Leu Gly Thr Ala Cys Glu Glu Glu Leu Asp Glu Pro Leu Ser Pro
1475                1480                1485

Leu Asp Ile Glu Ser Ile Val Ala Asp Ala Tyr Glu Ser Phe Ser
1490                1495                1500
```

-continued

```
Asp Glu Asp Ala Glu Gly Glu Gly Asp Gly Gly Lys Pro Gly Lys
1505                1510                1515

Arg Ile Arg Leu Pro Lys Ile Gly Gly Val Tyr Tyr Lys Arg Asp
    1520                1525                1530

Gly Asn Tyr Lys Ala Trp Ala Ala Ser Trp His Ile Gln Gly Lys
    1535                1540                1545

Arg Thr Arg Arg Tyr Phe Thr Val Lys Lys His Gly Phe Arg Asn
    1550                1555                1560

Ala Tyr Leu Lys Ala Val Arg Ala Arg Arg Glu Ala Glu Arg His
    1565                1570                1575

Glu Gly Ile Ser Val Lys His Arg His His Ala Leu Val Pro Gly
    1580                1585                1590

His Pro Gly Asn Met Leu Gly Ala Ser Lys Val Cys Ala Glu Ser
    1595                1600                1605

His Glu Val Ser Gly Phe Pro His Gly Asp Glu Asp Ser Arg Leu
    1610                1615                1620

Thr Arg Gly Gly Ala Ser His Ala Ala Val Ala Pro Gly Arg Val
    1625                1630                1635

Asn Arg Glu Arg Ser Val Ala Leu Val Asp Arg Ala Thr Lys Asp
    1640                1645                1650

Asp Glu Asp Asp Glu Arg Asp Leu Gln Arg Glu Lys Thr Gly Ala
    1655                1660                1665

Gly Gly Gly Glu Ala Cys Ser Gly Glu Ser Val Lys Val Ala Leu
    1670                1675                1680

Gly Thr Arg His Asp Ser Phe Ser Asp Gly Ser Cys Arg Thr Leu
    1685                1690                1695

Asp Lys Leu Ser Thr Gln Phe Glu Gln Lys Pro Arg Gly Gly Ala
    1700                1705                1710

Gly Glu Glu Ala Glu His Pro Thr Arg Lys Gln Gly Gln Glu Thr
    1715                1720                1725

Gly Gly Val Asp Glu Pro Leu Ser Arg Ala Ala Ser Ile Val Gly
    1730                1735                1740

Gly Arg Glu Val Arg Leu Thr Ser Gly Val Ser Val His Leu Thr
    1745                1750                1755

Pro Leu Glu Arg Val Ala Lys Ala Val Asp Val Asp Leu Lys Glu
    1760                1765                1770

Leu Thr Asp Arg Val Ser Arg Ala Ala Phe Arg Gly Gly Asp Ser
    1775                1780                1785

Arg Leu Phe His Arg Thr Val Asp Asn Cys Glu Gly Glu Ala Asp
    1790                1795                1800

Glu Val Ala Gln Gly Leu Asp Thr His Arg Glu Asp Val Asp Val
    1805                1810                1815

Thr Arg Asn Leu Glu Phe Ala Met Ala Arg Glu Thr Leu Asp Val
    1820                1825                1830

Leu Leu Ser Asp Leu Tyr Ser Val Val Ala Lys Leu Ser Gly Ala
    1835                1840                1845

Gly Arg Trp Thr Ser Leu Val Ser Pro Thr Ala Ala Glu Ala Glu
    1850                1855                1860

Pro Leu Val Ser Ala Trp Asp Arg Ser Ala Arg Glu Glu Arg Arg
    1865                1870                1875

Glu Lys Phe Glu Asp Thr Asn Ala Ala Ser Asp Glu Pro Gly Tyr
    1880                1885                1890

Pro Thr Ser Ser Ala Gln Ile His Val Ala Ile Gln Leu Val Val
```

-continued

```
            1895                1900                1905
Ile Lys His Tyr Leu Ala Thr Val Arg Thr Ala Asn Arg Val Glu
        1910                1915                1920

Gln Ile Ala Pro Leu Leu Ala Leu Phe Glu Pro Cys Ile Lys Gln
        1925                1930                1935

Gly Met Leu Pro His Glu Cys Ala Leu Pro Arg Leu Arg Trp Leu
        1940                1945                1950

Val Cys Gln Leu Cys Arg Ala Ser Leu Pro Trp Leu Asp Glu Ser
        1955                1960                1965

Asp Val Leu Thr Asp Ala Leu Leu Tyr Arg His Leu Glu Glu Leu
        1970                1975                1980

Val Glu Thr Glu Glu Ala Glu Ala Pro Gln Glu Gly Val Pro Pro
        1985                1990                1995

Gly Gly Gln Ile Val Phe Ser Ala Gly Phe Ala Glu Gly Asn Ser
        2000                2005                2010

Thr Val Ala Ser Arg Asn Val Phe Thr Gly Glu Ser Arg Val Ala
        2015                2020                2025

Gly Gly Phe Arg Thr Asp Ser Glu Lys Glu Ser Gly Ile Asp Asp
        2030                2035                2040

Arg Asp Glu Ala Ser Leu Ala Ala Leu Ile Cys Leu Pro Gly Lys
        2045                2050                2055

Gly Lys Lys Leu Arg Glu Glu Ala Asp Val Glu Lys Asp Asp Thr
        2060                2065                2070

Ser Ala Ser Leu Asn Cys Glu Ser Gly Lys Lys Thr Glu Ala Glu
        2075                2080                2085

Ser Gln His Ser Arg Ser Pro Thr Glu Val Ala Ala Ser Ser Val
        2090                2095                2100

Ser Gly Ser Glu Gly Lys Asp Gly Ser Ser Asp Asn Glu Arg Ser
        2105                2110                2115

Gly Asp Ala Asp Asp Ala Thr Glu Gly Ser Glu Lys Cys Glu Lys
        2120                2125                2130

Thr Arg Gly Gly Asp Gln Arg Arg Ala Ala Pro Arg Thr Ser Ser
        2135                2140                2145

Ala Ser Thr Ala Ser Gly Glu Thr Pro Glu Lys Ser Lys Asn Arg
        2150                2155                2160

Gly Ser Asp Ala Leu Lys Gly Lys Asn Glu Gly Ala Thr Gly
        2165                2170                2175

Thr Ser Gly Glu Gln Arg Asp Asp Glu Asp Arg Asp Leu Glu Asn
        2180                2185                2190

Val Glu Ile Ser Lys Asp Thr Arg Ala Gly Ser Gly Gly Arg Arg
        2195                2200                2205

Arg Thr Gly Glu Arg Gly Gln Arg Phe Cys Ala Ser Gly Gly
        2210                2215                2220

Glu Leu Arg Val Ser Glu Glu Ser Pro Asp Arg Ala Lys Thr Glu
        2225                2230                2235

Lys Ser Lys Gly Glu Pro Val Arg Asp Ser Leu Ser Pro Asp Ala
        2240                2245                2250

Ser Ser Arg Leu Pro Ser Arg Cys Gly Thr Pro Pro Pro Ala Ala
        2255                2260                2265

Ala Thr Gly Ser Cys Ala Thr Val Glu Ser Asp Val Pro Ala
        2270                2275                2280
```

<210> SEQ ID NO 11

```
<211> LENGTH: 3236
<212> TYPE: PRT
<213> ORGANISM: Homo sapiens

<400> SEQUENCE: 11

Met Thr Thr Val Ser Arg Ala His Ala Ser Arg Ser Arg Arg Lys Ser
1               5                   10                  15

Arg Asp Glu Asp Ser Glu Gly Ser Ser Leu Pro Ala Val Gly Ile His
            20                  25                  30

Glu Thr Gln Ser Pro Val Phe Ser Arg Glu Gly His Gly Asp Arg
        35                  40                  45

Ala Ala Gln Pro Glu Asp Val Val Ala Ala Glu Ser His Ser Asn Pro
50                  55                  60

Gln Trp Pro Thr Pro Leu Asp Thr Gly Phe Asp Lys Gly Ala Pro Pro
65                  70                  75                  80

Leu Gly Cys Ser Arg Ser Glu Glu Leu Arg Ser Pro Pro Met Ala Ser
                85                  90                  95

Gly Ser Phe His Gly Ser Gly Thr Gly Gly Asp Gly Gly Cys Leu Leu
            100                 105                 110

Ser Leu Glu Ala His Ala Val Ser Lys Asp Ser Glu Arg Gln Val Asn
        115                 120                 125

Ser Gly Leu Pro Gly Gly Asp Glu Ile Ser Gly Arg Leu Ser Pro
130                 135                 140

Ser Cys Ala Ser Leu Pro Leu Val Ala Ala Ala Leu Ser Pro Val Glu
145                 150                 155                 160

Asp Thr Arg Leu Glu Arg Asp Ser Ser Ile Pro Val Leu Lys Pro Ser
                165                 170                 175

Leu Ser Ile Pro Asn Leu Leu Val Thr Ser Pro Ser Leu Thr Ser Val
            180                 185                 190

Ser Tyr Val Cys Glu Ala Asp Arg Ser Ala Glu Gly Lys Ala Pro Ser
        195                 200                 205

Met Asp Ala Leu Pro Pro Ser His Ser Ala Ala Pro Glu Ser Gly Leu
210                 215                 220

Trp Arg Glu Cys Asp Glu Arg Gly Lys Asn Ser Phe Phe Ser Ser Gly
225                 230                 235                 240

Leu Pro Ala His Pro Glu Gly Asn Gly Glu Arg Ala Gly Glu Gly Gln
                245                 250                 255

Asp Pro Arg Ser Gly Asp Phe Glu Thr Pro Glu Glu Ala Ala Phe Ser
            260                 265                 270

Val Gln Arg Ile Leu Gln Glu Ser Glu Glu Leu Phe Leu Leu Ser Gly
        275                 280                 285

Cys Ala Arg Glu Asp Arg Gly Gly Glu Ser Asp Ala Ala Phe Lys Thr
290                 295                 300

Met Thr Arg Ser Glu Gly Ala Phe Ser Arg Glu Pro Ala His Arg His
305                 310                 315                 320

Ala Phe Ala Lys Pro Gly Asn Gly Gly Glu Ser Glu Pro Phe Met Ser
                325                 330                 335

Ile Asp Glu Glu Arg Ala Ala Ser Pro Ser Ala Ser Gly Pro Ser Ser
            340                 345                 350

Tyr Ala Phe Leu Ser Phe Glu Thr Ser Ala Gly Ser Arg Arg Ser
        355                 360                 365

Pro Asp Ala Gln Ser Pro Pro Leu Ser Gly His Leu Ser Asp Gly Asp
370                 375                 380

Arg Thr Gln Arg Lys Ala Gly Glu Arg Phe Leu Glu Asp Pro Arg Gly
```

```
            385                 390                 395                 400
        Asn Leu Lys Arg Ser Arg Ser Pro Leu Ile Ala Arg Asp Cys Asn Arg
                        405                 410                 415

Ser Leu Gly Thr Cys Asp Ser Ser Leu Thr Thr Arg Gly Pro Val Ala
                        420                 425                 430

Ser Asp Thr Ser Pro Arg Arg Gly Tyr Thr Asp Gln Trp His Ser His
                        435                 440                 445

Arg Lys Ala Gln Ser Pro Gly Arg Phe Arg Arg Thr Asn Thr Glu Gly
                        450                 455                 460

Asn Ala Thr Pro Val Asp Ser Gln Ser Ser Pro Pro Ser Lys Lys Arg
        465                 470                 475                 480

Cys Cys Leu Ala Glu Arg Phe Ala Phe Glu Arg Arg Gln Pro Pro
                        485                 490                 495

Val Pro Leu Pro Ser Val Ala Ser Ala Val Ala Ala Leu Ala Gln
                        500                 505                 510

Phe Pro Pro Gly Ala Cys Thr Ala Ala Val Glu Arg Ala Asp Asp Val
                        515                 520                 525

Pro Pro Glu Gly Ser Gly Asn Gly Val Leu Pro Gly Gly Glu Val Ser
                530                 535                 540

Asp Leu Ser Leu Ser Asp Arg Lys Ser Gly Ala Ser Pro Arg Gln Thr
        545                 550                 555                 560

Leu Asp Thr Phe Leu Pro Ala Lys Gly Ala Ser Ala Leu Lys Gln
                        565                 570                 575

Glu Gly Ser Ser Ser Glu Ile Gly Glu Gly Cys Pro Ala Ser Asp Asp
                        580                 585                 590

Ala Ala Val Ala Ala Thr Leu Ser Gly Trp Lys Arg Gly Arg Gly Pro
                        595                 600                 605

Arg Ser Gly Cys Val Ser Gly Ser Ser Arg Ala Ser Ser Leu Glu His
                        610                 615                 620

Ala Gly Ala Arg Arg Ser Gly Val Glu Arg Lys Arg Arg Glu Lys
        625                 630                 635                 640

Arg Lys Ala Ala Leu Ala Thr Ala Ala Val Ser Ala Ser Val Arg
                        645                 650                 655

Arg Leu Ala Leu Val Ala Ala Pro Cys Leu Val Glu Asn Thr Leu Arg
                        660                 665                 670

Gln Trp Trp Arg Leu Gln Glu Gln Val Gly Asp Glu Leu Asp Asn Gly
                        675                 680                 685

Gly Val Ser Glu Glu Gln Thr Thr Gly Arg Ser Gly Arg Arg Thr Gly
                        690                 695                 700

Lys Asn Pro Ile Val Gly Gly Arg Val Lys Glu Gly Glu Gln Ser Val
        705                 710                 715                 720

Arg Leu Glu Ile Glu Arg Ser Gly Asp Ser Pro Arg Asn Thr Ala Lys
                        725                 730                 735

Thr Glu Pro Gly Asp Gln Gly Ala Ala Gln Gly Gln Gly Pro Glu
                        740                 745                 750

Gln Ile Ala Glu Asn Glu Ser Gly Thr Glu Arg Met Glu Thr Ser Gln
                        755                 760                 765

Thr Lys Gln Glu Ala Gln Asp Leu Pro Leu His Arg Glu Ala Ala Ser
                        770                 775                 780

Ala Ser Ala Thr Pro Phe Ile Pro Glu Gly Arg Thr Gln Glu Arg Asp
        785                 790                 795                 800

Ser Tyr Leu Arg Val Thr Leu Phe Ala Ala Ser Gln Val Leu Asn Ser
                        805                 810                 815
```

```
Gly Gln Phe Arg Gln Ala Ile Arg Met Phe Pro Gly Ala Asp Ser Pro
            820                 825                 830

Arg Gly Asp Gln Arg Ser Arg Cys Val Val Arg Val Tyr Lys Gln Ser
            835                 840                 845

Leu Arg Lys Arg Arg Leu Ser Gly Asp Arg Asn Arg Arg Val Gly Glu
        850                 855                 860

Asp Gly Asn Leu Val Ser Val Ser Leu Arg Asp Leu Leu Ala Asn Ser
865                 870                 875                 880

Gly Glu Asp Trp Glu Pro Ser Pro Ser Ala Ala Thr Arg Pro Leu
                885                 890                 895

Pro Leu Ala Pro Ser Ala Leu Ser Ala His Gln Ala Arg Ser Ser Phe
            900                 905                 910

Gly Ser Phe Ser Arg Arg Ser Ala Glu Gly Val Pro Gly Pro Ser Pro
            915                 920                 925

Trp Gly Gly Asp Cys Ser Pro Thr Ala Ala Arg Ser Pro Leu Pro Leu
    930                 935                 940

Ser Thr Ser His Asp Leu Arg Arg Arg Val Cys Pro Pro Arg Arg
945                 950                 955                 960

Arg Tyr Ser Pro Ser Glu Ser Val His Ser Ser Asp Gly Arg Gly Gly
                965                 970                 975

Ala Cys Ala Ile Ala Ala Lys Lys Pro Lys Gly Arg Arg Ser Arg Gly
            980                 985                 990

Arg Glu Glu Gln Thr Arg Glu Glu  Val Ser Glu Ser Arg  Cys Ser Thr
        995                 1000                1005

Pro Arg  Ser Cys Ser Ser Val  Arg Tyr Ala Val Ser  Asp Gly Ser
    1010                1015                1020

Pro Ala  Ser Ser Arg Ala His  Leu Gly Arg Pro Asp  Asp Glu Gly
    1025                1030                1035

Asp Glu  Arg Met Thr Gly Gly  Gln Arg Thr Pro Arg  Gly Thr Pro
    1040                1045                1050

Gln Glu  Gly Glu Asp Ser Asp  Phe Leu Pro Ala Gly  Met Ser Gly
    1055                1060                1065

Leu Arg  Gly Gly Thr Leu Pro  Leu Asp Gln Leu Gly  Glu Arg Ser
    1070                1075                1080

Arg Ser  Ala Glu Arg Trp Met  Pro Ala Pro Ser Val  Ala Val Val
    1085                1090                1095

Pro Phe  Ala Pro Asn Ile Leu  Ala Lys Lys His Ala  Glu Asp Val
    1100                1105                1110

Glu Asn  Gln Leu Asp Gly Gly  Lys Met Ser Leu Asp  Gly Val Gly
    1115                1120                1125

Gln Lys  Glu Cys Gly Leu Val  Glu Thr Gly Asp Thr  Gly Glu Gln
    1130                1135                1140

Glu Ala  Ala Val Ala Ala Ser  Glu Lys Arg Arg Pro  Leu Glu Ala
    1145                1150                1155

Gln Thr  Pro Gly Arg His Gly  Thr Thr Val Leu Met  Lys Gly Glu
    1160                1165                1170

Gly Leu  Leu Ala Gly Arg Thr  Ser Glu Val Asp Gly  Asp Arg Thr
    1175                1180                1185

Gly Glu  Lys Thr Thr Gln Ile  Ser Pro Phe Ser Glu  Ala Thr Gly
    1190                1195                1200

Ile Cys  Ile Leu Arg Arg Ser  Pro Arg Arg Val Gln  Ser Asn Ser
    1205                1210                1215
```

-continued

```
Ser Glu Ala Ser Arg Thr Ala Val Arg Ser Thr Glu Gly Leu Glu
    1220                1225                1230

Thr Ser Asp Lys Leu Gly Val Asp Val Gly Thr Thr Asn Lys Glu
    1235                1240                1245

Ala Asp Ser Phe Ser Ala Ser Cys Asp Ser Pro Arg Asp Ser Leu
    1250                1255                1260

Glu Arg Asn Val Gly Glu Ile Val Ala Ile Trp Ala Arg Ala Arg
    1265                1270                1275

Asp Ala Lys Gln Gly Gly Arg Ile Arg Arg Arg Val Trp Leu Pro
    1280                1285                1290

Pro Gly Met Ala Thr His Gly Gly His Glu Gly Asn Glu Gln Asn
    1295                1300                1305

Asn Glu Ala Ile Cys Gly Gly Gly Ala Thr Pro Met Met Lys Thr
    1310                1315                1320

Glu Arg Ala Met Glu Glu Gly Arg Gly Asp Ala Lys Thr His Pro
    1325                1330                1335

Val Gly Gly Thr Tyr Ala Glu Thr Glu Lys Lys Val Val Asp Glu
    1340                1345                1350

Met Lys Ala Trp Trp Ser Lys Leu Thr Cys Ala Ser Val Glu Ala
    1355                1360                1365

Val Pro Val Gln Thr Leu Thr Leu Asp Asp Phe Ala Arg Ala Phe
    1370                1375                1380

Ser Thr Val Ala Asn Arg Ala Val Asp Leu Leu Cys Leu Ala Phe
    1385                1390                1395

Arg Ala Arg Gly Ala Gly Pro Val Phe Arg Pro Val Leu Ser Ser
    1400                1405                1410

Ser Pro Lys Gln Gln Gly Asn Ser Pro Gln Pro Glu Ser Glu Asp
    1415                1420                1425

Val Glu Thr Arg Ile Glu Thr Tyr Arg Gln Gln Val Arg Arg Leu
    1430                1435                1440

Tyr Arg Arg Arg Gln Gln Leu His Glu Ala Thr Gly Asn Ser Pro
    1445                1450                1455

Phe Ser Ser Ser Arg Val Gly Gly Ala Leu Gln Arg Arg Ile Gly
    1460                1465                1470

Glu Leu Gln Arg Leu Arg Glu Ala His Gly Arg Val Asp Ile Pro
    1475                1480                1485

Asn Glu Gly Pro Arg Arg Glu Glu Asp Ser Glu Lys Cys Pro Ala
    1490                1495                1500

Ser Leu Trp Asp Val Pro Leu Arg Gln Arg Lys Gln Gly Arg Lys
    1505                1510                1515

Arg Val Ser Pro Trp Tyr Ser Val Gly Val Arg Trp Leu Ala Asp
    1520                1525                1530

Phe Ser Ala Phe Glu Tyr Phe Val Val Lys Asn Tyr Arg Lys Glu
    1535                1540                1545

Asp Leu Gly Ala Thr Val Ser Leu Ser Asn Arg Gly Glu Ala Ser
    1550                1555                1560

Asp Thr Thr Trp Ser Val Asp Gly Thr Gly Ser Gln Arg Ala Pro
    1565                1570                1575

Val Pro Cys Leu Ser Arg Ala Gly Thr Pro Arg Thr Val Ser Pro
    1580                1585                1590

Ser Pro Pro Ser Ala Asp Ala Met Asn Leu Trp Ala Gln Ala Tyr
    1595                1600                1605

Ala Pro Ser Leu Asn Gln Pro Arg Gly Met Ser Pro Ala Thr Thr
```

-continued

```
            1610                1615                1620

Pro Pro Leu Ser Glu Ser Ala Thr Pro Arg Gly Asn Val Ser Pro
        1625                1630                1635

Pro Phe Ser Glu Ala Ser Ser Ser Gly Gln Arg Gly Lys Lys Val
        1640                1645                1650

Ala Pro Gly Pro Ser Ala Asp Glu Lys Lys Asp Glu Asp Tyr Gln
        1655                1660                1665

Ser Ala Gly Ser Leu Arg Trp Glu Val Asp Gly Gly Gln Arg Arg
        1670                1675                1680

Gln Val Gln Val Arg Ser Arg Leu Leu Leu His Glu Leu Leu Gln
        1685                1690                1695

Pro Pro Ser Leu Asp Ala Thr Gly Leu Arg Thr Ala Leu Val Leu
        1700                1705                1710

Ile Val Leu Arg Leu Gln Arg Phe Leu Arg Leu Lys Glu Gly Gly
        1715                1720                1725

Val Asn Asn Arg Gly Arg Gly Gln Arg Ser Glu Arg Lys Arg Arg
        1730                1735                1740

Cys Arg Ala Met Pro Pro Ile Phe Ile Phe Arg Asp Asp Ser Asn
        1745                1750                1755

Ala Phe Gln Glu Ala Leu Leu Ala Lys Lys Leu Asp Ile Arg Leu
        1760                1765                1770

Asp Ser Asp Ser Pro His Thr Asp Val Pro Ser Arg Arg Ser Leu
        1775                1780                1785

Asp Gly Glu Val Gly Asp Glu Arg Arg Arg Leu Arg Ser Val Lys
        1790                1795                1800

Pro Thr Asn Ser Asn Asp Leu Ser Asp Glu Arg Gly Pro Pro Pro
        1805                1810                1815

Pro Ser Thr Met Ser Pro His Ser Leu Gly Ser Gly Pro Cys Asp
        1820                1825                1830

Thr Gln Glu Gly Val Gln Asn Leu Gln Gln Asp Ala Ser Leu Phe
        1835                1840                1845

Ser Pro Ala Leu Ala Gln Gly Gln Ala His Ala His Thr Asp Ala
        1850                1855                1860

Val Pro Gly Ala Arg His Asp Asp Val Leu Pro Arg Ser Pro Arg
        1865                1870                1875

Phe Pro Val Val Asp Ala Gly Pro Glu Glu Thr Pro Arg Pro Glu
        1880                1885                1890

Val Glu Ser Met Leu Asp Ser Glu Ser Gly Asp Pro Thr Gly Leu
        1895                1900                1905

Gly Gln Ala Ser Arg Arg Arg Trp Arg Gly Arg Gly Ser Arg Thr
        1910                1915                1920

Ser Val Gln Arg Thr Val Ser Thr Cys Leu His Glu Asp His Ser
        1925                1930                1935

Gly Asp Lys Thr Pro Arg Glu Glu Thr Phe Gly Gly Asp Ala Ala
        1940                1945                1950

Ser Leu Leu Arg Val Ala Ser Ser Val Pro Pro Ser Thr Cys Ser
        1955                1960                1965

Ser Pro Gln Ser Ser Ser Gly Gly Arg Arg Glu Arg Gly Arg Arg
        1970                1975                1980

Gly Val Arg Gly Arg Arg Gly Arg Gly Arg Leu Ile Ser Gln Gln
        1985                1990                1995

Gly Ser Ser Leu Leu Gly Gln Thr Val Ser Ala Gly Ala Leu Ser
        2000                2005                2010
```

```
Ser Gly Asp Thr Ala Gly Ala Ile Ser Thr Glu Gly Glu Asn Arg
    2015                2020                2025

Arg Asn Ala Val Arg Pro Gly Ala Leu Glu His Ser Asp Glu Asp
    2030                2035                2040

Lys Glu Asp Leu Ser Ala Ser Ser Pro Pro Ser Asp Asp Gly Ile
    2045                2050                2055

Ser Gln Arg Ser Ser Gly Ser Gln Gly Asp Ser Ser Ser Ser Gly
    2060                2065                2070

Gly Pro Ser Ser Glu Ala Cys Arg Lys Thr Thr Ser His Val Ala
    2075                2080                2085

Ala Lys Ala Asp Ser Ala Ser Pro Arg Ala Leu His Pro Ser Ala
    2090                2095                2100

Arg Pro Gln Pro Arg Gly Thr Ala Ser Trp Thr Pro Gly Gly Glu
    2105                2110                2115

Pro Ala Val Ser Gly Val Gln His Pro Ser Ala Leu Thr Pro Ser
    2120                2125                2130

Pro Ser Arg Gly Arg Phe Ser Glu Asp Asn Val Ala Ser Arg Val
    2135                2140                2145

Ser Arg Val Ser Ser Val Gly Ala Leu Leu Arg Ser Arg Cys Val
    2150                2155                2160

Val Gly Glu Glu Gln Lys Glu Thr Gln Asn Ser Cys Ser Leu Trp
    2165                2170                2175

Val Val Glu Lys Gly Ala Leu Glu Pro Phe Trp Trp Arg Thr Ala
    2180                2185                2190

Ser Ala Val Gly Cys Val Ser Ala Gly Arg Arg Asp His Ser Asp
    2195                2200                2205

Lys Asp Ala Asn Arg Leu Phe Leu Ala Asp Lys Glu Ala Gly Thr
    2210                2215                2220

Gly Pro Leu Gln Asp Phe Val Leu Pro Asp Phe Ser Gly Ser Ala
    2225                2230                2235

Arg Glu Ile His Gly Asp Glu Arg Gly Ser Asp Ser Asp Ala Ser
    2240                2245                2250

Cys Lys Ser Ala Ala Leu Ser Thr Thr Ser Asp Ser Ser Gly Ile
    2255                2260                2265

Ser Glu Val Ser Leu Asp Leu Glu Ser Thr Val Gln Glu Val Ala
    2270                2275                2280

Leu Gly Thr Ile Leu Ser Ser Ala Leu Ser Ala Leu His Gly Lys
    2285                2290                2295

Thr Gly Asp Gly Asp Thr Gln Glu Ser Asp Ala Glu Arg Glu Ala
    2300                2305                2310

Asn Ala Asp Asp Gly Ser Ala Thr Gly Val Asn Glu Lys Asp Leu
    2315                2320                2325

Arg Gly Glu Ser Arg Pro Glu Leu Pro Ser Pro Ile Pro Gly Lys
    2330                2335                2340

Asp Glu Leu Gly Ser Gln Glu Glu Gly Lys Thr Ala Ser Ser Leu
    2345                2350                2355

Pro Ser Val Lys Ala Glu Gln Gly Gly Ser Glu Arg Gly Gly Ala
    2360                2365                2370

Asp Glu Ile Val Lys Lys Ala Thr Ser Val Leu Arg Ala Cys Lys
    2375                2380                2385

Asp Pro Asp Glu Ala Thr Ser Thr Ser Leu Val Pro Glu Gly Glu
    2390                2395                2400
```

| | | | | | | | | | | | |
|---|---|---|---|---|---|---|---|---|---|---|---|
|Asp|Glu|Asn|Asp|Ala|Cys|Gly|Ala|Leu|Glu|Pro|Asp|Ser|Leu|Val|
|2405| | | | |2410| | | | |2415| | | | |

Ser Val Ser Ala Leu Gly Glu Ser Ser Glu Glu Leu Phe Thr Glu
2420 2425 2430

Val Pro Gln Asn Glu Lys Glu Leu Lys Lys Thr Leu Gln His Val
2435 2440 2445

Asp Pro Arg Leu Cys Gln Gln Met Leu His Gly Gly Leu Cys Phe
2450 2455 2460

Ile Arg Thr Tyr Val Asp Leu Glu Thr Lys Lys Glu Ser Leu Gln
2465 2470 2475

Ala Gly Pro Phe Ala Ala Lys Arg Arg Arg Val Ala Gln Leu Leu
2480 2485 2490

Arg Gly Leu Gln Gly Leu Phe Asp Ala Leu Glu Ser Val Arg Glu
2495 2500 2505

Arg Glu Gly Asp Asp Leu Ser Gly His Glu Gly Asp Ser Ala
2510 2515 2520

Ser Gly Gly Leu Phe Thr Ala Glu Gln Glu Lys Glu Gly Ala Asp
2525 2530 2535

Lys Val Ser Gly Asp Arg Glu Asn Ala Gly Glu Arg Gly Gln Lys
2540 2545 2550

Thr Ala Ala Glu Thr Gly Asp Gln Lys Ala Ser Ile Glu Asp Ala
2555 2560 2565

Val Ala Ala Ala Phe Cys Arg Arg Val Gly Ala Ala Ile Ala Thr
2570 2575 2580

Glu Thr Cys Gly Ser Ile Gln Thr Val Phe Pro Glu Ile Gly Glu
2585 2590 2595

Ala Tyr Asp Val Glu Asp Ser Val Ala Arg Leu Gly Ala Pro Pro
2600 2605 2610

Arg Ala Pro Val Arg Thr Arg Arg Glu Cys Thr Gly Thr Gly Phe
2615 2620 2625

Thr Ser Thr Ala Ala Leu Pro Glu Pro Arg Gly Glu Asp Gly Arg
2630 2635 2640

Lys Gln Glu Thr Ser Glu Pro Leu Gly Val Glu Ala Ala Asp Lys
2645 2650 2655

Thr Asp Ile Gln Gly Glu Tyr Ala Gln Glu Ser Glu His Thr Trp
2660 2665 2670

Thr Gln Glu Met Gly Arg Lys Ala Ser Leu Phe Leu Ser Gly Thr
2675 2680 2685

Leu Glu Leu Ala Gln Leu Lys Glu Glu Gln Val Glu Glu Leu
2690 2695 2700

Gln Gly Glu Gly Asp Pro Leu Thr Ser Phe Leu Leu Pro Ser Asp
2705 2710 2715

Gln Ser Asp Ser Thr Lys Lys Ala Asn Glu Glu Cys Met Gly Gly
2720 2725 2730

Arg Thr Ala Arg Glu Leu Tyr Ala Glu Arg Glu Glu Asp Val Lys
2735 2740 2745

Thr Leu Gly Arg Arg Arg Glu Ala Gln Thr Glu Ser Arg Ala Arg
2750 2755 2760

Gly Pro His Val Asp Ser Ser Ala Glu Ala Ala Ser Val Ala Gln
2765 2770 2775

Gly Asp Glu Gly Gly Glu Glu Ala Arg Lys Arg Lys Lys Asp Glu
2780 2785 2790

Lys Arg Glu Lys Arg Ser Gly Asn Ala Phe Leu Asp Ala Leu Leu 2795                2800               2805

Glu Pro Ala Leu Arg Glu Asp Val Gly Arg Ala Phe Leu Thr Asp
    2810                2815                2820

Phe Gly Ser Gln Ala Pro Gln Asn Ser Thr Asp Ala Gly Lys Pro
    2825                2830                2835

Ile Phe Leu Ser Pro Cys Val Phe Gly Val Arg Gly Gly Ala Arg
    2840                2845                2850

Trp Lys Lys Leu Gly Leu Phe Asn Asp Glu Ala Gln Arg Glu Gly
    2855                2860                2865

Thr Glu Ser Ser Pro Trp Arg Asn Asp Cys Ser Asp Pro Met Ser
    2870                2875                2880

Tyr Arg Ala Asp Ala Pro His Thr Trp Arg Arg His Glu Gly Leu
    2885                2890                2895

Leu Trp Gly Gly Ser Arg His Ala Ala Ser Ala Leu Arg His His
    2900                2905                2910

Gly Arg Lys Ser Pro Ala Phe Leu Ser Pro Gln Trp Glu Asp Asp
    2915                2920                2925

Glu Arg Leu Ser Leu Ser Ser Ser Ala Asp Glu Arg Gly Tyr Thr
    2930                2935                2940

Ser Ser Gly Ser Glu Arg Phe Leu Ser Ile Pro Thr Arg Arg Lys
    2945                2950                2955

Tyr Gly Leu Arg Phe Gln Arg Arg Ser Thr Lys Thr Gly Arg Ala
    2960                2965                2970

Pro Ser Pro Thr Ala Gly Arg Ser Ser Val Asn Arg Ser Gly Trp
    2975                2980                2985

Arg Glu Thr Leu Arg Pro Ser Ser Gly Phe Ser Gly Glu Glu Thr
    2990                2995                3000

Pro Arg Ser Leu Ser Ser Arg Arg Arg Gly Gly Leu Gly Gly
    3005                3010                3015

Ser Ser Pro Thr Ala Phe Arg Pro Pro Met Thr Arg Ala Ala Thr
    3020                3025                3030

Gly Lys Ala Ala Ala Cys Val Arg His Gly Asp Gly Asp Glu Cys
    3035                3040                3045

Ala Glu Pro Asp Ser Gln Phe Gly Ala Phe Gly Ser Ala Asp Leu
    3050                3055                3060

Gly Leu Ser Asp Arg Arg Gly Glu Ala Gly Glu Ala Asp Thr Arg
    3065                3070                3075

Glu Glu Lys Ala Gly Gly Ser Ala Arg His Gly Lys Arg Gly Ser
    3080                3085                3090

Gly Val Arg Ser Gly Gly Ala Arg Glu Ala Gly Ser Asp Ala Gly
    3095                3100                3105

Thr Asp Thr Leu Trp Val Ala Pro Gly Ser Gly Pro Asn Thr Cys
    3110                3115                3120

Arg Ser Gly Arg Lys Ser Pro Ala Ala Ala Ala Leu Ser Ser Leu
    3125                3130                3135

Pro Thr Gly Val Tyr Phe Asp Ala Ser Arg Lys Leu Trp Arg Cys
    3140                3145                3150

Gln Trp Arg Glu Asn Gly Arg Phe Lys Thr Lys Gly Phe Ser Leu
    3155                3160                3165

Asn Val Tyr Lys Thr Leu Lys Glu Ala Arg Arg Ala Cys Val Val
    3170                3175                3180

Tyr Arg Cys Leu Met Gly Gly Trp Glu Val Asp Pro Arg Trp Leu
    3185                3190                3195

-continued

```
Gly Pro Asp Asp Asp Glu Gln Asp Asn Ser Gly Gly Ala Asp Glu
    3200                3205                3210

Val Gly Arg Pro Val Pro Ser Asp Gly Ile Ser Asp Val Val Gly
    3215                3220                3225

Glu Ala Arg Arg Lys Gly Glu Tyr
    3230                3235

<210> SEQ ID NO 12
<211> LENGTH: 1670
<212> TYPE: PRT
<213> ORGANISM: Homo sapiens

<400> SEQUENCE: 12

Met Ile Asn Leu His Gln Leu Phe Arg Val Phe Ser Arg Val Ser Ser
1               5                   10                  15

Ser Ala Ser Asp Pro Ser Ala Ser Asn Pro Ser Pro Ala Ser Leu Val
                20                  25                  30

Ser Val Pro Ala Leu Gln Thr Leu Ser Phe Pro Ala Leu Gln Gln Gln
            35                  40                  45

Asp Leu Leu Ala Ser Leu Ala Ala Ala Ser Leu Pro Gly Pro Asp Ser
        50                  55                  60

Val Thr Met Ser Ser Ser Pro Thr Ser Val Leu Asn Ser Ser Phe Cys
65                  70                  75                  80

Ser Leu Pro Ser Ser Arg Lys Pro Ala Ala Leu Pro Phe Pro Ala Thr
                85                  90                  95

Ser Pro Lys Thr Pro His Leu Ser Asp Ser Phe Pro Ala Ser Ala Ile
            100                 105                 110

Ser Gly Pro Ser Ser Pro Gly Leu Gln Glu Leu Leu Ala Ser Pro Glu
        115                 120                 125

Leu Ala Ala Ala Ala Leu Ala Ser Leu Gln Lys Gln Gln Leu Arg Leu
    130                 135                 140

Ala Leu Gly Thr Glu Arg Gly Gly Cys Gly Ala Arg Gly Asp Glu His
145                 150                 155                 160

Leu His Ser Ile Leu Leu Gln His Lys Ala Thr Ser Glu Asn Ala Met
                165                 170                 175

Arg Trp Ser Trp His Ala Gly Arg Asp Gly Ala Gln Glu Leu Asp Thr
            180                 185                 190

Val Pro Glu Thr Phe Asp Leu Pro Leu Ser Leu Ser Ser Phe Leu Gly
        195                 200                 205

Val Ala Pro Gln Gln Pro Ser Ser Leu Pro Arg Ser Ser Leu Leu Pro
    210                 215                 220

Pro Thr Asp Phe Ser Leu Thr Asp Gly Thr Leu Arg Val Ser Ser Ser
225                 230                 235                 240

Met Leu Pro Ala Leu Ala Thr Gly Ser Glu Ser Gly Ser Ser Arg Gly
                245                 250                 255

Leu Asn Ser Ala Gln Ala Ser Pro Ser Phe Ser Ser Leu Arg Gly Pro
            260                 265                 270

Pro Val Ser Val Pro Glu Glu Val Ser Gly Ser Leu Glu Gly Ser
        275                 280                 285

Pro Gly Pro Phe Ser Ser Gly His Pro Ala Ala Pro Ser His Pro
    290                 295                 300

Cys Ser Thr Val Ser Gly Ala Asp Thr Gln Glu Ala Glu Pro Pro Leu
305                 310                 315                 320

Leu Thr Leu Val Ala Val Asn Thr Pro Asp Ala Gln Asp Pro Ala Val
```

```
                  325                 330                 335
Asp Gly Ala Ser Leu Cys Ala Ser Lys Glu Gly Met Arg Thr Ser Ser
            340                 345                 350
Ala Asp Leu Gly Asp Ser Leu Leu Ala Pro Pro Gly His Gly Ser Ala
            355                 360                 365
Ala Pro Leu Pro Gly Arg His Leu Gly Ser Asp Ala Thr Arg Thr Thr
370                 375                 380
Thr Thr Thr Gly Ser Gly Ala Pro Glu Ser Pro Ser Leu Pro Leu Ala
385                 390                 395                 400
Arg Gly Asp Cys Glu Gly Ala Glu Arg Gly Leu Ala Leu Leu Glu Ala
                405                 410                 415
Pro Val Asn Gly Phe Asn Leu Ala Ala Ser Gln Ser Val Leu Gly Gly
            420                 425                 430
Phe Ala Ala Asp Thr Arg Gly Glu Ala Gly Lys Gly Ile Ala Pro
            435                 440                 445
Gln Ser Arg Lys Ala Arg Lys Pro Gly Thr Ala Val Glu Thr Ala Gly
            450                 455                 460
Ala Pro Glu Ala Val Arg Arg Gly Arg Ala Ala Cys Asn Gly Glu Ala
465                 470                 475                 480
Glu Thr Thr Gly Leu Glu Thr Ala Pro Gln Gln Val Ser Thr Ser Glu
                485                 490                 495
Glu Thr Ala Lys Ser Gly Arg Glu Leu Ala Cys Ala Arg Ala Gly Met
            500                 505                 510
Asp Glu Glu Glu Asp Ala Ala Phe Pro Ser His Val Val Ser Glu Phe
            515                 520                 525
Arg Gly Pro Pro Glu Ile Ser Asn Val Phe Asn Asp Leu Asp Cys Ser
            530                 535                 540
Ser Ala Val Glu Arg Pro Gln Gly Cys Leu Gln His Ala Ala Val Gln
545                 550                 555                 560
Pro Phe Leu Pro Ala Val Ala Pro Glu Val Arg Pro Ser Ala Thr Thr
                565                 570                 575
Ala Gly Arg Thr Pro Met Gly Leu Trp Ser Glu Ala Gly Arg Val Ser
            580                 585                 590
Ser Leu Glu Thr Asp Thr Ala Glu Ile Gly Arg Arg Leu Asp Gly Glu
            595                 600                 605
Ser Ser Gly Ser Pro Asp Arg Trp Gly Asp Ala Arg Leu Ser Ser Pro
            610                 615                 620
Asp Ser Val Pro Ser Ser Ala Asp Val Pro Val Pro Ser Arg Pro Gln
625                 630                 635                 640
Cys Gln Glu Gln Val Pro Gln Val Asp Pro Asp Ser Ser His Pro Leu
                645                 650                 655
Phe Ala Ser Cys Ser Ala Gly Ser Ser Ser Thr Ala Gly Ser Ala Ser
            660                 665                 670
Ala Leu Ala Gly Leu Ala Ser Pro Phe Pro Pro Lys Ser Pro Lys
            675                 680                 685
Thr Gly Ala Asn Asp Pro Arg Met Thr Pro Ser Glu Gly Glu Met Arg
            690                 695                 700
Ala Val Ser Gly Ala Pro Pro Ser Leu His Met Ser Pro Pro Ile Pro
705                 710                 715                 720
Pro Leu Ala Leu Gln Asp Ser Phe Gly Glu Cys Thr Ala Ser Ser Leu
                725                 730                 735
Ala Gly Val Asp Ala Pro Glu Ala Thr Ala Gly Gly Leu Ala Glu Gly
            740                 745                 750
```

```
Val Ala Thr Gly Gly Gly Ser Asp Ser Val Gly Glu Gly Arg Leu Pro
            755                 760                 765
Gly Ala Ala Ser Leu Glu Val Pro Ser Ser Pro Ser Ala Leu Leu Ser
770                 775                 780
Gly Ala Pro Ala Ser Leu Leu Leu Leu Arg Asn Gly Gln Ser Gly
785                 790                 795                 800
Ala Ala Ala Leu Val Ala Ala Met Gln Gln His Gln Ala Leu Ser Gly
                805                 810                 815
Asp Ala Glu Glu Ala Leu Glu Ala Val Leu Ala Gly Gly Ser Asn Val
                820                 825                 830
Gly Asp Met Ala Asn Ser Ser Arg Gly Leu Glu Thr Val Gly Asp Gly
                835                 840                 845
Thr Arg Gly Ser Ala His Thr Thr His Ala Ala His Ser Ser Gly Arg
                850                 855                 860
Asn Ala Val Gly Ala Cys Pro Ala Pro Asp Arg Glu Gly Glu Thr Val
865                 870                 875                 880
Ala Val Pro Thr Ser Val Leu Thr Asn Asn Pro Ala Ser Thr Ser Lys
                885                 890                 895
Thr Met Pro Ser Val Tyr Ser Thr Pro Ala Ser Ala Gly Leu Ser Leu
                900                 905                 910
Thr Ser Ser Ser Thr Pro Pro Val Leu Pro Thr Pro Asn Pro Gly Ala
                915                 920                 925
Gly Met Pro Pro Leu Ala Ser Ala His Ala Ala Ser Pro Ala Val Pro
                930                 935                 940
Gly Asp Ala Asn Leu Gln Ser Leu Phe Phe Trp Ala Pro Gln Ala Cys
945                 950                 955                 960
Pro Leu Gln Pro Gly Ala Leu Ala Val Asp Ala Ser Ala Ser Ser Cys
                965                 970                 975
Gly Gly Val Gly Ser Cys Asn Gly Gly Pro Ala Pro Pro Gly Pro Ser
                980                 985                 990
Pro Val Ala Glu Leu Leu Asp Ala Ser Gly Ser Gly Pro Phe Gly Ala
                995                 1000                1005
Ala Gly Ser Gly Ala Gln Leu Ala Ala Gly Pro Phe Gly Ala Ala
        1010                1015                1020
Thr Pro Ala Ser Ala Thr Phe Gln Gln Gln Leu Leu Leu Leu Ser
        1025                1030                1035
Ala Ala Phe Asp Gln Ile Gly Ser Ser Ser Phe Pro Val Val Gly
        1040                1045                1050
Gly Glu Asn Phe Ile Gly Tyr Ser Ala Leu Ser Ala Ala Arg Pro
        1055                1060                1065
Asp Ala Ser Asp Leu Ser Ala Ser Gly Gly Pro Pro Ala Ser Leu
        1070                1075                1080
Pro Val Leu Leu Ala Ala Ala Asn Ala Gly Val Gly Pro Gly Ala
        1085                1090                1095
Ala Gly Val Gly Asp Gln Pro Asp Phe Leu Ala Leu Leu Gly Gly
        1100                1105                1110
Gly Ser Ala Ser Arg Glu Gly Ala Arg Asp Pro Val Gly Gly Glu
        1115                1120                1125
Leu Gly Gly Ala Gly Asn Ser Ala Thr Ser Met Lys Gly Val Lys
        1130                1135                1140
Arg Gln Phe Val Gln Asn Gly His Gly Thr Ala Ser Gln Thr His
        1145                1150                1155
```

```
Pro Glu Asn Thr Gln Gly Pro Gly Arg Ser Ala Ala Val Val
    1160            1165              1170

Gly Arg Ala Thr Lys Lys Gln Arg Arg Gly Pro Pro His Ser Gly
    1175            1180              1185

Ala Ala Val Ser Ser Gly Ala Pro Ser Gly Val Leu Ala Val Pro
    1190            1195              1200

Gly Cys Leu Gly Pro Pro Ser Val Ala Lys Gly Pro Gly Ser Asp
    1205            1210              1215

Glu Phe Asn Leu Gln Gln Leu Gln Gln Ser Arg Asp Ser Arg His
    1220            1225              1230

Ser Ala Asp Asn Ala Ser Gly Ile Pro Asn Trp Pro Pro Val Phe
    1235            1240              1245

Ser Asn Gly Asn His Thr Leu Gly Val Gly Thr Arg Ser Pro Ser
    1250            1255              1260

Pro Ser Val Cys Ser Ile Ser His Asp Ala Gly Phe Phe Gly Ala
    1265            1270              1275

Ser Gly Ser Asn His Ala Gly Ser Leu Ser Thr Pro Val Cys Leu
    1280            1285              1290

Pro Gln Leu Pro Gly Ala Ala Ser Ala Ser Glu Gly Pro Cys Glu
    1295            1300              1305

Ala Gln Gln Thr Pro Pro Gly Ser Ile Pro Glu Ala Thr Thr Leu
    1310            1315              1320

Gly Gly Leu Ser Ala Ala Ser Gly Asn Pro Asn Ser Thr Phe Ser
    1325            1330              1335

Val Ser Ala Gly Gly Val Ala Pro Ala Ile Leu Asn Leu Ser
    1340            1345              1350

Ser Ala Ser Arg Thr Ser Ser Gln Thr Ser Pro Cys Cys Pro Thr
    1355            1360              1365

Ala Pro Gly Ser Leu Leu Ser Gly Gly Ser Gly Pro Ala Leu Phe
    1370            1375              1380

Phe Ala Gly Pro Pro Ser Pro Leu Gln Lys Ala Pro Val Tyr Ala
    1385            1390              1395

Gly Gly Ser Gly Ser Val Cys Ala Ser Ser Gly Asp Ala Ile Ala
    1400            1405              1410

Ala Ala Ala Leu Leu His Leu Arg Thr Leu Gln Gln Leu Gln Glu
    1415            1420              1425

Leu Gln Arg His Phe Gln Arg Pro Gly Ser Leu Pro Pro Ala Val
    1430            1435              1440

Thr Pro Ala Cys Leu Pro Ser Gly Val Ala Gly Cys Ser Pro Ala
    1445            1450              1455

Gly Leu Gly Ala Ser Thr Pro Gly Thr His Ser Val Val Cys Asn
    1460            1465              1470

Ser Ser Ala Ser Pro Val Pro Gly Ala Ser Arg Val Pro Arg Arg
    1475            1480              1485

Pro Asp Gly Arg Gly Thr Gly Gly Ala Gly Gly Asp Pro Gly Pro
    1490            1495              1500

Ser Lys Arg Gly Ser Val Val Ser Pro Ser Ala Gln Gln Phe
    1505            1510              1515

Val Leu Leu Gln Leu Lys Gln Gln Pro Gly Ser His Gly Asn
    1520            1525              1530

Ala Leu Ser Leu Gly Thr Gln Gly Asn Ser Ser Asn Pro Ala Pro
    1535            1540              1545

Ala Gly Gly Ala Gly Ala Pro Gln Gln His His Pro Gly Val Cys
```

```
            1550                1555                1560

Tyr Ser Pro Pro Lys Asp Val Trp Arg Ala Arg Ile Thr Val Asp
    1565                1570                1575

Gly Arg Gln His Glu Gln Gln Phe Ser Val Lys Arg His Gly Phe
1580                1585                1590

Glu Glu Ala Arg Leu Leu Ala Val Gln Trp Arg Ala His Met Glu
        1595                1600                1605

Asn Leu Arg Leu Gly Gly Ala Ala Lys Gly Lys Gly Asn Ala Ser
    1610                1615                1620

Ala Ser Ser Ala Ser Ala Ala Thr Ala Thr Ser Gln Gly Ser Ser
1625                1630                1635

Gln Ser Ser His Gln Pro Pro Leu Gly Ser Leu Met Val Ser Gly
        1640                1645                1650

Asn Ser Gly Met Ser Gly Pro Gly Ala Gly Pro Leu Ala Asn Arg
    1655                1660                1665

Gly Leu
    1670

<210> SEQ ID NO 13
<211> LENGTH: 2330
<212> TYPE: PRT
<213> ORGANISM: Homo sapiens

<400> SEQUENCE: 13

Met Ser Asp Tyr Ala Pro Ser Arg Phe Ala Ser Pro Gly Asn Ala
1               5                   10                  15

His Pro Lys Ser Pro Leu Phe Ala Arg Pro His Ser Cys Arg Glu Met
                20                  25                  30

Glu Thr Arg Ala Ser Val Gly Thr Ser Arg Gly Ser Arg Gln Pro Leu
        35                  40                  45

Cys Leu Arg Gly Ser Pro His Gly Cys Leu Ser Pro Gln Lys Gly Gln
    50                  55                  60

Asp Arg Leu Pro Ser Phe Ser Pro Leu Arg Thr Gln Pro Thr Leu Leu
65                  70                  75                  80

Ser Pro Pro Phe Pro Ser Lys Gly Cys Phe Ser Ser Cys Leu Pro Ser
                85                  90                  95

Ser Gln Ala Phe Thr Ser His Arg Ala Arg Gly Pro Ser Pro Glu Val
                100                 105                 110

His Ala Val Ser Ala Asp Ala Ser Thr Ser Ser Ser Pro Ile Ser Pro
            115                 120                 125

Ala Ser Arg Ser Ala Ser Glu Gln Gln Pro Arg Arg Glu Met Cys Ser
    130                 135                 140

Pro Pro Gly Ala Ser Ser Asp Ser Thr Ser Pro Thr Gly Ser Ser Ser
145                 150                 155                 160

Cys Ser Ala Glu Gln Asp Asp Val Leu Cys Phe Arg Gln Arg Phe His
                165                 170                 175

Leu Pro Pro Leu Leu His Leu Ser Thr Ser Arg Lys Arg Leu Arg Glu
                180                 185                 190

Glu Asp Ala Ser Ala Ser Ala Cys Ile Ser Ser Leu Gly Asn Leu Pro
            195                 200                 205

Leu Asp Val Asp Thr Lys Arg Arg Gln Glu Tyr Asp Arg Leu Ser
    210                 215                 220

Thr Ala Ser Leu Ser Ser Phe Arg Ser Pro Lys Thr Pro Arg Leu Pro
225                 230                 235                 240
```

```
Ser Cys Leu Ala Arg Arg Asp Pro Glu Glu Ser His Ala Asp Leu Ser
            245                 250                 255
Glu Ser Arg Thr Phe Leu Gln Arg Leu Glu Ala Ala Gly Gln Ser Arg
        260                 265                 270
Lys Gly Asp Thr Ser Arg Glu Thr Ile Glu Ala Asp Glu Lys Lys Val
        275                 280                 285
Leu Ser Thr His Ser Thr Asp Thr Ser Val Gln Arg Ser Pro Ser Glu
    290                 295                 300
Ser Ala Glu Arg Arg Ser Phe Gly Lys Arg Ser Asp Pro Asn Asn Gly
305                 310                 315                 320
Leu Pro Met Ala His Ser Pro Thr Pro Phe Thr Ser Lys Arg Thr Asp
                325                 330                 335
Leu Gly His Ala Leu Asp Asn Ala Leu Ser Met Arg Ala Ala Ser Arg
            340                 345                 350
Cys Gly Phe Pro Gly Pro Ala Glu Ala Thr Val Ala Pro Ala Ala Ser
        355                 360                 365
Gly Ala Ser Arg Thr Ala Ser Pro Leu Pro Phe Thr Val Pro Val Val
    370                 375                 380
Leu Ala Ala Ser Pro Pro Thr Met Pro Ser Ala Cys Ser Pro Asp Leu
385                 390                 395                 400
Cys Arg Ala Ser Thr Ser Pro Leu Ser Cys Ala Gly Val Ser Ser Leu
                405                 410                 415
Asp Ala Pro Gln Ala Val Gly Arg Arg Ser Glu Val Ala Ala Cys Val
            420                 425                 430
Ser Pro Ala Ala Ser Glu Glu Thr Val Gly Asp Thr Arg Glu His Ala
        435                 440                 445
Asp Leu Ser Ser Pro Val Ala Trp Pro Val Ala Cys Leu Ala Ser Ser
    450                 455                 460
Pro Gly Val Ala Lys Lys Pro Leu Asp Leu Gln Ile Asp Pro Glu Gln
465                 470                 475                 480
Pro Arg Gly Asn Asp Lys Leu Val Glu Pro Glu Phe Pro Gly Gly Thr
                485                 490                 495
Ala Ala Val Ser Glu Ser Ala Pro Val Ala Gly Ala Asp Ala Pro Arg
            500                 505                 510
Leu Cys Asp Tyr Gly Leu Ser Glu Ala Gly Val Leu Pro Ala Ser Gly
        515                 520                 525
Pro Trp Leu Arg Lys Pro Asn Pro Met Leu Thr Pro Asp Thr Glu Trp
    530                 535                 540
Ala Ala Pro Ser Ser Gln Glu Asp Arg Ala Cys Thr Gln Lys Glu Thr
545                 550                 555                 560
Ser Ala Ala Arg Leu Ala Pro Asn Leu Leu Tyr Arg Gln Ala Asp Ala
                565                 570                 575
Ala Ala Asp Asn Val Thr Lys Gly His Glu Asp Asp Ser Gln Phe Pro
            580                 585                 590
Leu Arg Ser Gly Ser Phe Thr Ser Ser Ala Val Ala Cys Pro Ser Pro
        595                 600                 605
Pro Asp Val Gln Ala Asp Ser Glu Ala Ala Cys Thr Trp Gly Thr Pro
    610                 615                 620
Gly Asn Gly Asp Thr Cys Glu Ser Thr Gly Gly Trp Arg Gly Ala Thr
625                 630                 635                 640
Asn Val Glu Ala His Thr Cys Leu Thr Gly Glu Asp Gly Ser Arg Tyr
                645                 650                 655
Gly Leu Gln Gly Pro Leu Ser Gln Asp Ser Pro Phe Gln Pro Pro Leu
```

```
                660             665             670
Pro Ser Met Arg Pro Val His Phe Gly Gly Phe Glu Ala Trp Gly Gly
            675             680             685

Asn Ser Glu Ala Ser Gln Gly Asp Ala Gln Gly Leu Gln Phe Pro Arg
            690             695             700

Val Glu Arg Phe Ser Ser Arg Arg Thr Glu His Gly Ser Glu Gly Gly
705             710             715             720

Phe Cys Gly Gln Leu Ala Gly Glu Leu Leu Pro Thr Ser Thr Ser Gly
            725             730             735

Gln Pro His Ser Gln His Val Ala Asp Leu Glu Ser His Thr Gly Ala
            740             745             750

Val Phe Ala Ser Cys Asp Pro Ala Met His Ala His Ala Ser Leu Tyr
            755             760             765

Gly Tyr Pro Gly Ala Phe Tyr Asn Ser Phe Gly Thr Ala Ser Ser Ile
            770             775             780

Phe Asp Leu Thr Gln Pro Pro Gln Ala Phe Leu Tyr Gly Gly Thr Tyr
785             790             795             800

Gly Asn Asn Gly Pro Asp Asp Tyr Cys Val His Arg Thr Asn Ser Thr
            805             810             815

Ser Cys Gln Gly Phe Thr Ala Pro Asp Asn Ile Ser Thr Gly Thr Leu
            820             825             830

Asn Thr Ala Asp Ala Gln Gln Glu Trp Thr Thr Pro Ala Pro Val Ser
            835             840             845

Asp Ala Ala Val Gly His Trp Glu Thr Ser Asp Phe Gly Pro Gln His
            850             855             860

Leu Asn Gly Arg Ala Ser Ser Ser Val Pro Asp His Gly Gly Gly Leu
865             870             875             880

Pro Phe Gly Gly Asn Gly Asn Ser Trp Gly Thr Ser Gly Asn Gly Asp
            885             890             895

Ala Trp Gly Thr Pro Gly Asn Gly Asp Thr Cys Glu Ser Thr Gly Gly
            900             905             910

Trp Arg Gly Thr Thr Asn Val Glu Gly His Thr Cys Leu Thr Gly Glu
            915             920             925

Asp Gly Ser Arg Tyr Gly Leu Gln Ala Pro Leu Ser Gln Asp Ser Pro
            930             935             940

Tyr Gln Pro Pro Leu Pro Pro Met Gln Pro Val His Phe Ala Asn Phe
945             950             955             960

Tyr Ser Ala Cys Phe Pro Leu Pro Pro Pro Val Phe Pro Gly
            965             970             975

Ile Gly Cys Val Ser Ala Ser Tyr Pro Asp Ile Leu Leu Pro Gln Ala
            980             985             990

Arg Phe Leu Ser Gln Ser Cys Pro Gly Pro Pro Ser Val Leu Arg Cys
            995             1000            1005

Pro Pro Pro Ala Ala Leu Leu Arg Gly Ser Ser Pro Leu Asp Cys
            1010            1015            1020

Trp Ser Leu Pro Ala Leu Pro Ser Leu Pro Arg Ile Pro Ser Asp
            1025            1030            1035

Phe Ala Ser Asp Pro Ala Ser Val Pro Leu Pro Ala Ala Val Gln
            1040            1045            1050

Asn Leu Pro Glu Asp Ser Pro Arg Leu Arg Leu Pro Cys Gln Gly
            1055            1060            1065

Ala Ser Thr Arg Asp Gln Ser Pro Leu Gln Tyr Glu Gly Asn Phe
            1070            1075            1080
```

```
Gly Gly Ser Asp Glu Val Leu Arg Pro Gln Val Glu Val Ala Glu
        1085                1090                1095

Asn Arg Gly Thr Pro Asn Phe Leu Ala Ala Ser Tyr Ser Leu Leu
        1100                1105                1110

Gly Ala Phe Ser Cys Glu Gly Asp Asn Arg Asp Asn Glu Tyr Glu
        1115                1120                1125

Thr Gln Leu Trp Gln Gln Leu Asn Glu Ser Gly Glu Leu Gly Val
        1130                1135                1140

Ser Gly Leu Pro Gln Pro Tyr Ser Val Glu Glu Gly Arg Arg Gln
        1145                1150                1155

Glu Leu Gln Ser Pro Tyr Pro Ala Pro Tyr Glu Asn Ile Pro Tyr
        1160                1165                1170

Ser Thr Pro Ser Tyr Asn Ser Val Ser Tyr Thr Ala Ala Ser Lys
        1175                1180                1185

Asp Arg Leu Val Gly Asp Asn Thr Ala Tyr Asn Gly Ala Ala Tyr
        1190                1195                1200

Cys Pro Phe Tyr Gly Gly Ser Gly Met Tyr Glu Thr Pro Gln Arg
        1205                1210                1215

Ser Glu Glu Asn Ser Leu Tyr Ser Ala Asp Pro Gln Val His Phe
        1220                1225                1230

Ser Glu Ser Glu Lys Thr Gly Ser Ser Asp Ser Phe Pro Tyr Ser
        1235                1240                1245

Phe Phe Ser Leu Gly Thr Pro Ala Leu Tyr Pro Gly Gly Ser Leu
        1250                1255                1260

Gln Thr Gly Ala His Leu Glu Glu Val Pro Gly Ser Gly Asp Ala
        1265                1270                1275

Glu Gly Ser Ala Trp Ser Pro Ser Leu Glu Ser Arg Arg Leu Arg
        1280                1285                1290

Gly Arg Thr Arg Ser Pro His Ala Gln Ser Pro Asn Ser Asn Arg
        1295                1300                1305

Ser Arg Gly Ala Ala Trp Thr Phe Ser Pro Ala Ser Leu Pro Phe
        1310                1315                1320

Glu Val Pro Ala Ala Lys Ala Ser Gly Arg Lys Arg Arg Ala
        1325                1330                1335

Pro Gly Ser Leu Pro Ala Gln Thr Asp Arg Gly His Lys Asp Phe
        1340                1345                1350

Leu Leu Glu Leu Leu Ala Ser Arg Leu Glu Pro Val Lys Gly Val
        1355                1360                1365

His Met Asp Arg Leu Arg Lys Thr Trp Val Ala Ser Trp Leu Val
        1370                1375                1380

Gly Lys Arg Arg Ile Thr Arg Ile Phe Ser Phe Gln Lys Phe Gly
        1385                1390                1395

Phe Phe Gly Ala Arg Glu Gln Ala Ile Arg His Arg Arg Glu Ala
        1400                1405                1410

Leu Leu Asn Pro Glu Leu Asp Asn Ser Glu Arg Arg Glu Ala Leu
        1415                1420                1425

Ala Asn Val Glu Arg Ala Thr Asp Asp Glu Leu Gln Gln Ala Ala
        1430                1435                1440

Asp Ala Leu Pro Phe Val Val Gly Val Thr Tyr His Arg Ala Ser
        1445                1450                1455

Arg Cys Trp Val Ala Asn His Arg Lys Pro Met Gly Lys Ile Val
        1460                1465                1470
```

```
Gln Arg Lys Lys Phe Ala Val Ala Glu Leu Gly Phe Leu Glu Ala
1475                1480                1485

Arg Tyr His Ala Ala Val Met Met Phe Cys Trp Asn Lys Gln Gly
1490                1495                1500

Arg Thr Gln Glu Pro Glu Asp Tyr Asp Gln Gly Ala Thr Glu Ala
1505                1510                1515

Phe Asn Ser Arg Gln Val Pro Gln Arg Pro Gly Asp Asp Arg Ala
1520                1525                1530

Phe Glu Phe Ser His Pro Thr Cys Ser Glu Asn Glu Pro Leu Tyr
1535                1540                1545

Thr Leu Lys Ala Leu Asp Ser Gly Thr Cys Asp Asp Ala Met Val
1550                1555                1560

Leu Leu Ala Phe Ile Cys Gly Ser Pro Trp Arg Lys Ile Cys Arg
1565                1570                1575

Gly Gln Gln Cys Gly Asp Asp Pro Thr Leu Leu Glu Ala Ala Ser
1580                1585                1590

Thr Ile Gln Thr Glu Lys Ser Leu Trp Arg Thr Arg Val Lys Ser
1595                1600                1605

Ala Ala Asp Glu Val Arg Glu Gly Pro Gln Arg Arg Leu Glu Gly
1610                1615                1620

Thr Asp Ala Gly Asp Ser Gly Ala Phe Pro Arg Gly Gln Ser Pro
1625                1630                1635

Glu Lys Gly Arg Pro Arg Arg Arg Lys Thr Ala Thr Leu Arg
1640                1645                1650

Glu Gln Glu Asp Val Thr Glu Asp Lys Thr Glu Asp Gly Arg Glu
1655                1660                1665

Asp Lys Thr Glu Asp Gly Gly Glu Asp Lys Thr Glu Asp Gly Gly
1670                1675                1680

Glu Asp Gly Arg Glu Asp Glu Gly Glu Asp Glu Gly Glu Asp Pro
1685                1690                1695

Gly His Gly Trp Gly Glu Arg Arg Arg Cys Arg Lys Ser Asp Arg
1700                1705                1710

Glu Asn Ala Gly Glu Ala Glu Arg Gly Gln Lys Arg Glu Lys Arg
1715                1720                1725

Gln Gln Ser Glu Gly Arg Cys Val Val Ala Glu Val Asp Leu Arg
1730                1735                1740

Asp Ala Lys Asp Thr Val Val Arg Arg Asn Arg Val Ala Arg Arg
1745                1750                1755

Glu Gly Leu Glu Thr Gly Phe Gly Lys Lys Asn Ala Lys Ser Gly
1760                1765                1770

Ala Glu Ser Cys Leu Ser Gln Thr Pro Ala Leu Gly Pro Ser Ser
1775                1780                1785

Pro Pro Phe Pro Val Ser Phe Lys Lys Arg Arg Lys Ser Ser Ser
1790                1795                1800

Arg Glu Ala Asp Leu Arg Gln Ser Arg Pro Arg His Arg Asn
1805                1810                1815

Asp Thr Glu Glu Ala Arg Ser Ile Cys Glu Asp Ser Pro Ser Ser
1820                1825                1830

Glu Val Ala Pro Thr Pro Ala Ser Ser Ser Phe Ser Pro Ala Ala
1835                1840                1845

Ser Leu Ser Ser Asp Gly Ser Arg Leu Gly Ser His Asn His Asp
1850                1855                1860

Leu Thr Asp Ser Gly Arg Ser Ala Ser Val Ser Arg Gly Arg Ser
```

```
              1865                1870                1875

Thr  Asp  Phe  Ser  Met  Phe  Ala  Gly  Leu  Pro  Tyr  Leu  Lys  Ser  Leu
         1880                1885                1890

Glu  Ser  Asn  Thr  Arg  Phe  Val  Pro  Pro  Ser  Arg  Pro  Gly  Glu  Ser
         1895                1900                1905

Gly  Leu  Pro  Asn  Val  Tyr  Ala  Ser  Tyr  Asn  Ser  Gly  Leu  Ala  Phe
         1910                1915                1920

Glu  Ala  Asn  Arg  Pro  Cys  Pro  Leu  Ala  Phe  Asp  Ser  Arg  Ala  Asp
         1925                1930                1935

Pro  Thr  Gly  Trp  Pro  His  Thr  Phe  Pro  His  Pro  Ala  Glu  Ala  Tyr
         1940                1945                1950

Gly  Ser  Gly  Ile  Ala  Ser  Trp  Thr  Pro  Asn  Ala  Asn  Gly  Phe  Phe
         1955                1960                1965

Glu  Ser  Leu  Ala  Tyr  Thr  Gly  Asn  Leu  Glu  Glu  Leu  Arg  Asp  Leu
         1970                1975                1980

Cys  Gly  Arg  Thr  Pro  Asp  Ala  Arg  Asp  Ser  Ser  Asp  His  Trp  Gln
         1985                1990                1995

Glu  Ala  Ala  Ala  Ala  Ser  Ser  Arg  Leu  Pro  Leu  Arg  Pro  Pro
         2000                2005                2010

Ala  Val  His  Ser  Trp  Gln  Asp  Ala  Pro  Cys  Ala  Lys  Asp  Pro  Ala
         2015                2020                2025

Pro  Cys  Val  Glu  Leu  Ala  Arg  Asp  Glu  Cys  Leu  Ala  Gly  Gly  Asp
         2030                2035                2040

Arg  Gln  Thr  Cys  Arg  Phe  His  Ser  Ala  Phe  Asp  Ser  Ala  Asp  Ala
         2045                2050                2055

Gly  Asp  Tyr  Lys  Phe  Asn  Thr  Asp  Ala  Arg  Cys  Leu  Arg  Gly  Pro
         2060                2065                2070

Thr  Phe  Asn  Pro  His  Ser  Asn  Ala  Val  Ala  Thr  Leu  Arg  Arg  Glu
         2075                2080                2085

Gln  Glu  Ala  Ala  Arg  Gly  Ala  Ser  Gly  Gln  Thr  Pro  Ser  Phe  Phe
         2090                2095                2100

Phe  Pro  Arg  Leu  Val  Pro  Val  Ala  Gln  Thr  Asp  Trp  Glu  Ala  Asp
         2105                2110                2115

Pro  Gly  Arg  Gly  Ser  Gly  Asp  Ser  Leu  Ser  Ala  Pro  His  Glu  Ala
         2120                2125                2130

Gly  Glu  Ala  Val  Gly  Val  Glu  Gly  Ser  Glu  Gly  Ala  Pro  Cys  Glu
         2135                2140                2145

Trp  Asn  Phe  Glu  Arg  Asp  Ala  His  Pro  Val  Ile  Leu  Pro  Thr  Ser
         2150                2155                2160

Asn  Cys  Ser  His  Gly  His  Glu  Arg  Leu  Ala  Ser  Ser  Asn  Ala  Phe
         2165                2170                2175

Thr  Glu  Ala  Lys  Gln  Arg  Asn  Ala  Leu  Arg  Cys  Thr  Pro  Gln  Glu
         2180                2185                2190

Thr  Val  Gly  Gly  Val  Asn  Glu  Asn  Gly  Ser  Pro  Leu  Phe  Ser  Thr
         2195                2200                2205

His  Arg  Asp  Ala  Pro  Glu  Ala  Met  Ser  Ala  Leu  Thr  Glu  Val  Ser
         2210                2215                2220

Asp  Arg  Glu  Thr  Gln  Arg  Gly  Pro  Ala  Val  Leu  Gln  Ser  Gly  Asn
         2225                2230                2235

Thr  Glu  Ala  Leu  Leu  Gln  Asp  Ser  Thr  Ser  Asn  Ser  Ala  Ser  Pro
         2240                2245                2250

Thr  Gln  Arg  Arg  Ala  His  Gly  Leu  Asp  Pro  Glu  Pro  Asp  Glu  Ser
         2255                2260                2265
```

```
Lys Ala Arg Gly Glu Arg Ser Lys Glu Glu Asp Arg Glu Thr Leu
    2270            2275            2280

Arg Thr Glu Ala Pro Ser Lys Gly Arg Lys Gln Ile Leu Ser Pro
    2285            2290            2295

Pro Thr Glu Arg Asn Ser Met Tyr Gly Glu Ala Met Ser Ile Asp
    2300            2305            2310

Arg Gln Val Ser Ala Leu Pro Thr Leu Leu Ser His Gly Thr Ala
    2315            2320            2325

Phe Pro
    2330

<210> SEQ ID NO 14
<211> LENGTH: 1438
<212> TYPE: PRT
<213> ORGANISM: Homo sapiens

<400> SEQUENCE: 14

Met Ala Ala Ser Pro Pro Ala Gln Pro Leu Gly Ala Thr Ser Pro
1               5               10              15

Cys Thr Phe Ser Pro Pro Cys Ser Phe Ser Pro Ser Asp Thr Cys Ser
                20              25              30

Val Phe Phe Ala Thr Pro Ser Arg Ala Val Ser Ala Val Pro Glu Leu
                35              40              45

Pro Ala Thr Ser Ser Ala Gln Leu Pro Glu Arg Thr Arg Leu Arg Asn
            50              55              60

Arg Ser Ile Gln Ser Ala Ser Thr Thr Glu Ala Ser Pro Phe Val Asp
65              70              75              80

Ser Ala Ser Leu Phe Pro Glu Ser Leu Ser Glu Ala Pro Lys Ala Val
                85              90              95

Ser Val Asp Gly Glu Ser Arg Arg Thr Arg Glu Arg Arg Lys Ser
                100             105             110

Arg Ser Leu Leu Ala Ala Ala Glu Glu Thr Pro Glu Ala Thr Ala Ala
                115             120             125

Ser Pro Asn Gly Ser Ser Glu Ile Ser Asp Glu Ala Ser Thr Phe
            130             135             140

Val Leu Thr Pro Ala Thr Ala Ser Leu Ala Pro Ala Ala Leu Pro Pro
145             150             155             160

Phe Met Thr Glu Arg Ser Asp Pro Thr Glu Lys Lys Tyr Glu Ala Gln
                165             170             175

Asn Met Gln Val Thr Ala Val Glu Pro Val Gly Leu Ala Pro Arg Ser
                180             185             190

Ala Ser Arg Ser Glu Leu Gly Asp Ala Glu Ser Leu Ser Ala Gly Lys
                195             200             205

Ser Gly Leu Gln Gly Glu Ser Ala Ala Pro Thr Ala Ala Leu Glu Ala
            210             215             220

Asp Ala Gly Glu Thr Arg Leu Thr Gly Leu Ala Gly Glu Pro Val
225             230             235             240

Asn Ser Ser Ser Glu Gly Val Gly Tyr Gly Gly Asp Glu Gln Thr Val
                245             250             255

Ala Gly Glu Thr Arg Glu Pro Gly Thr Ala Glu Lys Leu Gly Asp
                260             265             270

Leu Lys Pro Glu Val Arg Pro Arg Phe His Ala Tyr Ala Glu Gln Asp
            275             280             285

Val Cys Ala Trp Ala Thr Ser Met Leu Ala Arg Lys Glu Leu Arg Lys
```

```
            290                 295                 300
Leu Lys Ala Ala Val Lys Leu Glu Gly Asp Arg Met Pro Arg Ser
305                 310                 315                 320

Asp Val Val Gly Leu Tyr Phe Lys Lys His Arg Pro Cys Trp Ser Val
                325                 330                 335

Asp Tyr His Thr Arg Gln Gly Lys Arg Lys Thr Val Glu Phe Phe Val
                340                 345                 350

Pro Asp Leu Ser Arg Glu Thr Ile Glu Leu Val Leu Val His Ala Ile
                355                 360                 365

Glu Cys Arg Lys Tyr Met Pro Arg Arg Phe Asp Gln Ala Pro Ala Phe
                370                 375                 380

Val Pro Glu Pro Asp Asp Thr Thr Ser Gly Met Pro Tyr Arg Tyr Gly
385                 390                 395                 400

Ala Arg Leu Leu Ser Pro Lys Val Leu Ala Trp Ile Val Glu Asn Thr
                405                 410                 415

Asn Gly Ser Gly Arg Thr Ser Gln His Gly His Gly Gln Ser Arg Arg
                420                 425                 430

Leu Glu Gly Asp Lys Val Gly Glu Gly Asp Ala Gly Ala Gln Leu Leu
                435                 440                 445

Ser Gly Pro Ala Gly Ile Asp Ala Phe Gly Ser Arg Ser Pro Arg Ala
                450                 455                 460

Gly Phe Ala Arg Gln Arg Asp Asn Asn Ser Arg Arg Gln Gly Lys Ala
465                 470                 475                 480

Ser Gly Cys Arg Pro Gly Ala Asp Leu Ala Thr Ser Ser Glu Glu Lys
                485                 490                 495

Ala Thr Arg Glu Gly Glu Thr Glu Leu Pro Gly Gly Ser Ala Gly Pro
                500                 505                 510

Gly Ser Val Pro Ala Gly Thr Ala Tyr Gly Asp Tyr Ala Arg Gln Leu
                515                 520                 525

Pro Ser Glu Gly Tyr Gln Thr Pro Pro Thr Met Glu Gly Arg Met Thr
                530                 535                 540

Pro Ala Gly Leu Leu Ser Gly Gln Glu Phe Gly His Gly Gln Gly Met
545                 550                 555                 560

Gln Gly Ala Gly Val Met Trp Arg Asp Asp Pro Arg Gln Ala Leu Gln
                565                 570                 575

Ala Met Pro Gln Pro Leu Asn Leu Ala Pro His Ala Thr Pro Phe Met
                580                 585                 590

Ser Arg Ala Gly Gly Leu Tyr Asp Gln Arg Glu Ala Ser Val Glu Pro
                595                 600                 605

Gly Arg Asp Val Tyr Pro Val His Tyr Pro Thr Pro Tyr Ala Tyr Gly
610                 615                 620

Pro Gly Ile Pro Ala Asp Ala Gly Ala Pro Ser Ala Gly Pro Gly Pro
625                 630                 635                 640

Tyr Pro His Gln Phe Pro Ser Gly Gly Ala Gly Tyr Val Val Asn Gly
                645                 650                 655

Arg Val Pro Asp Ser Ala Asp His Glu Ala His Ser Pro Arg Ser Pro
                660                 665                 670

Glu Ser Tyr Trp Gly Pro Gln Ala Gly Ser Gly Ala Glu Asp Lys
                675                 680                 685

Asp Cys Gln Val Val Gly Cys Met Leu Pro Asn Gly Ser Glu Met Ala
                690                 695                 700

Met Arg Arg Met Glu Ser Tyr Val Gly Asp Arg Asp Asn Leu Arg Gly
705                 710                 715                 720
```

-continued

```
Ser Ala Ala Phe Ala Gly Asp Gly Arg Thr Gln Ala Glu Gly Leu Ser
            725                 730                 735

Pro Gln Cys Glu Pro Asn Ala Lys Arg Arg Leu Gln Ala Gly Gly
        740                 745                 750

Asp Gly Ser Asn Gly Gly Leu Glu Ala Ser Gly Pro Glu Arg Pro Phe
            755                 760                 765

Pro Gly Ser Gln Met Leu Gln Pro Ser Asp Glu Trp Ala Arg Asn Gly
    770                 775                 780

Gln Arg Ala Phe Ala Val Gln Pro Gly Thr Gly Arg Thr Phe Met
785                 790                 795                 800

Asn Gly Gly Phe Arg Gln Pro Gly Glu Asp Ala Arg Gln Pro Leu
                805                 810                 815

Leu Leu Ser Ser Ala Pro Tyr Ser Pro Pro Ser Val Phe Pro Ala Ala
            820                 825                 830

Pro Pro His Leu Ser His Ala Val Arg Leu Pro Pro Gly Ser Ser Asp
            835                 840                 845

Ala Ala His Arg Thr Pro Met Ser Gly Ala Ala Gly Cys Ala Ser Pro
850                 855                 860

Val Ala Ser Ala Phe Arg Lys Glu Ala Glu Ala Ser Glu Trp Pro Ser
865                 870                 875                 880

Asn Glu Val Tyr Gly Ser Pro Gln Ala Phe Pro Asp Lys Ala Asn Ala
                885                 890                 895

Phe Ala Lys Gly Val Thr Leu Pro Arg Arg Gln Ser Phe Ala Phe Ser
            900                 905                 910

Asp Ala Gly Leu Pro Thr Pro Thr Thr Ser Pro His His Gly Ser Tyr
            915                 920                 925

Cys Ala Ser Thr Ile Ala Ser Ser Pro Lys Ser Ala Ser Pro Val
930                 935                 940

Ser Gln Ser Gly Cys Phe Pro Cys Asp Phe Tyr Pro Ala Thr Ala His
945                 950                 955                 960

Tyr Ser Gly Pro Gly Val Glu Thr Pro Ser Asp Val Ser Ser Phe Val
                965                 970                 975

Pro Ala Pro Ala Glu Thr Ala Glu Gln Gln Ile His Gly Ala Gly Gln
            980                 985                 990

Ala Ala Val Lys Thr Pro Glu Ser  Gly Leu His Met Pro  Ser Ser Gly
            995                  1000                 1005

Trp Pro  Gln Gln Ala Ser Val  Pro Gly Ala His Gly  Ala Glu Phe
    1010                 1015                 1020

Tyr Ala  Ser Arg Ala Phe Ala  Asn Gly Ala His Ala  Pro Ser Leu
    1025                 1030                 1035

Ser Leu  Arg Pro Ser Trp Arg  Tyr Pro Gly Gly Glu  Arg Ser Glu
    1040                 1045                 1050

Gly Asp  Leu Thr Thr Gln Glu  Gln Asn Ala Pro Ala  Gly Ala Ser
    1055                 1060                 1065

Pro Ser  Ser Pro Val Trp Ser  Gly Asn Thr Gly Val  Cys Thr Thr
    1070                 1075                 1080

Glu Gly  Cys Gly Val Trp Leu  Glu Asn Arg Gln Ala  Ala Gly Ser
    1085                 1090                 1095

Val Glu  Gly Ala Ala Asp Pro  Gly Val Gln Gly Ser  Ala Cys Met
    1100                 1105                 1110

Gln Gly  Lys Pro Gln Glu Gly  Gly Arg Cys Ser Pro  Glu Pro Ala
    1115                 1120                 1125
```

-continued

```
Leu Gly Val Arg Arg Pro Ala Glu Phe Ala Gly Ala Pro Val Gly
    1130                1135                1140

Ala Cys Arg Ala Val Glu Asp Arg Thr Met Thr Gly Glu Arg Gly
    1145                1150                1155

Ala Trp Gly Asn Glu Ala Arg Arg Glu Thr Val Thr Gly Asp Gln
    1160                1165                1170

Glu Cys Cys Gly Asp Gln Ala Arg Asp Pro Met Val Phe Ser His
    1175                1180                1185

Met Gly Ser Arg Ala Glu Leu Ser Gly Phe Asp Asp Gly Ser Glu
    1190                1195                1200

Leu Pro Pro Ala Ser Pro Leu Asn Glu Cys Met His Pro Leu Gly
    1205                1210                1215

Lys Pro Gly Ser Arg Ile Phe Pro Glu Phe Gly Ala Trp Pro Gly
    1220                1225                1230

Ser Pro Pro His Glu Gly Ser Phe Val Gln Glu Phe Asp Ile Phe
    1235                1240                1245

Lys Glu Asn Gly Glu Gly Ala Ala Gly Ala Val Asp Asp Ala Met
    1250                1255                1260

Ala Leu Trp Pro Asn Gly Gly Ala Phe Gly Gln Arg Thr Asp Pro
    1265                1270                1275

Leu Ala His Glu Glu Glu Lys Glu Gly Glu Leu Trp Lys Gly Gln
    1280                1285                1290

Pro Thr Pro Phe Cys Ser Ser Pro Ala Leu Trp Cys Val Cys Pro
    1295                1300                1305

Val Glu His Thr Arg Glu Phe Asp Val Met Asp Met Val Thr Leu
    1310                1315                1320

Pro Asp Leu Ser His Thr Ala Gly Pro Val Ser Arg Pro Leu Pro
    1325                1330                1335

Asn Ala Pro Leu Cys Gly Gly Cys Val Val Ala Gly Val Gly Glu
    1340                1345                1350

Ala Gln Ala Gly Asp Gly Glu Ser Lys Gln Gly Ala Lys Leu Ala
    1355                1360                1365

Pro Asp Ser Gln His Leu His Gly Gly Ala Ala Asn Pro Gly Ala
    1370                1375                1380

Val Gly Lys Leu Val Thr Asp Glu Thr Ala Gln Thr Ser Gly Arg
    1385                1390                1395

Glu Gln His Pro Gly Glu Gly Asp Ser Thr Glu Gln Arg Leu Ser
    1400                1405                1410

Gly Leu Ala Ala Arg Ala Thr Pro Gln Arg Glu Thr Lys Arg Pro
    1415                1420                1425

Gly Pro Ser Arg Arg Thr Gly Glu Leu
    1430                1435

<210> SEQ ID NO 15
<211> LENGTH: 3817
<212> TYPE: PRT
<213> ORGANISM: Homo sapiens

<400> SEQUENCE: 15

Met Asp Phe Glu Arg Gly Glu Ser Pro Gly Asp Ser Arg Gly Ser Val
1               5                   10                  15

Ala Phe Leu His His Thr Glu Lys Leu Glu Arg Leu Pro Gly Thr Gly
                20                  25                  30

Glu Thr Thr Ile Arg Gly Met Ser Phe Thr Pro Pro Tyr Ile Cys Met
            35                  40                  45
```

```
Glu Arg Pro Pro Arg Ala Asn Cys Glu Ala Leu Arg Leu Lys Ser Pro
    50                  55                  60

Pro Glu Asn Arg Ala Phe Ser Ser Arg Ser Glu Ser Pro Ser Pro Thr
65                  70                  75                  80

Pro Phe Ala Arg Glu Cys Ala Ser Leu Gly Leu Val Trp Gly Asp Glu
                85                  90                  95

Gly Thr Arg Ala Gly Leu Leu Arg Thr Arg Leu Phe Thr Pro Pro Asp
                100                 105                 110

His Thr Pro His Leu Leu Ala Glu Thr Gly Ala Ser Cys Leu Glu Asp
            115                 120                 125

Leu Phe Pro Gly Thr Val Pro Gln Leu Leu Ser His Leu Pro Ser Pro
    130                 135                 140

Pro Pro Val Pro Gly Val Ala Arg Ala Ser Arg Ser Ser Ser Pro Leu
145                 150                 155                 160

Ala Gly Gly Ser Ser Leu Ala Cys Ala Ser Pro Trp Pro Arg Ser Ala
                165                 170                 175

Thr Pro Phe Phe Ala Ala Asn Met Pro Ala Leu Leu Pro Gly Arg Gly
                180                 185                 190

Pro Met Arg Val Thr Lys Trp Leu Asp Gly Gln Val Ser Asp Pro Gln
    195                 200                 205

Ser Asp Ser Cys Leu Arg Gly Gly Ala Ser Arg Val Glu Arg Ala Ala
    210                 215                 220

Ala Leu Leu Cys Gly Arg Ser Glu Glu Glu Gln Arg Glu Arg Ser
225                 230                 235                 240

Val Asp Glu Arg Arg Leu Arg Lys Ala Ile Gly Val Thr Asp Glu Asp
                245                 250                 255

Glu Ser Glu Arg Glu Arg Glu Thr Glu Gly Gly Val His Glu Arg Leu
                260                 265                 270

Ser Arg Cys Ala Ala Ala Thr Ala Ala Asp Arg Ala Asn Asn Leu Leu
            275                 280                 285

Gly Leu Gly Val Glu Arg Gly Pro Glu Val Ala Gly Gly Arg Leu Gly
    290                 295                 300

Gly Tyr Trp Thr Thr Glu Ser Glu Val Tyr Pro Gln Arg Ile Gly Glu
305                 310                 315                 320

Leu Glu Gly Glu Gly Leu Gly Ser Pro Asp Pro Val Ala Ala Ser Ala
                325                 330                 335

Leu Val Thr Ala Val Gln Asp Ser Arg Glu Asn Leu Asn Cys Leu Thr
            340                 345                 350

Gly Val Leu Thr Thr Leu Arg Leu Ser Ser Arg Asp Ser Glu Gly Asp
    355                 360                 365

Phe Asp Leu Pro Leu Phe Val Gln Ser Arg Lys Trp Arg Ala Lys Tyr
    370                 375                 380

Asn Arg Arg Ser Leu Asp Leu Lys Gly Thr Val Ala Arg Ser Lys Ala
385                 390                 395                 400

Leu Gly Tyr Pro Ala Gly Leu Gln Ile Pro Glu Thr Tyr Arg Asp Leu
                405                 410                 415

Lys Asn Cys Met Gln Arg Pro Ser Ile Asp Ala Ala Asp Ser Arg
                420                 425                 430

Ala Trp Arg Ser Ala Glu Ala Pro Arg Ala Ala Lys Lys Val Phe Ser
            435                 440                 445

Glu Gly Arg Arg Ala Thr Asp Arg Asp Glu Gln Val Ala Phe Val Glu
    450                 455                 460
```

```
Asp Glu Val Thr Glu Gln Leu Leu Phe Asn Ala Asn Ala Ala Val Glu
465                 470                 475                 480

Gly Thr Thr Leu Tyr Asn Asn Leu Leu Cys Lys Tyr Gly Leu Glu Thr
            485                 490                 495

Arg Cys Phe Ser Thr Ser Ser Ala Pro Gly Asn Thr Ala Phe Glu Ser
            500                 505                 510

Arg Leu Ala Arg Ser Asp Ala Asp Pro Thr Ala Ser Ser Gln Ser Ala
            515                 520                 525

Ser Ala Leu Ser His Ala Ala Val Ser Pro Ser Leu Ala Ser Ala Leu
            530                 535                 540

Pro Val Ser Ser Leu Leu Leu Glu Asp Ala Ala Asp Ala Val Gly Asp
545                 550                 555                 560

Arg Ser Glu Leu Glu Thr Gly Ser Gln Ala Glu Ala Ile Pro Thr
            565                 570                 575

Ser Glu Ala Ser Cys Met Arg Arg Glu Lys His Val Gly Glu Ser
            580                 585                 590

Arg Ala Asp Lys Gly Ala Phe Leu Arg Ser Ala Ser Asp Ser Thr His
            595                 600                 605

Ala Glu Glu Asp Gly Leu Ser Gly Gly Lys Asp Ala Ser Ser Arg Glu
610                 615                 620

Gly Gly Ser Glu Glu Arg Glu Glu Ala Ala His Glu Ala Ala Asp Ser
625                 630                 635                 640

Leu Trp Ser Leu Val Leu Asn Arg Asn Ile Ala Ala Leu Pro Gly Phe
            645                 650                 655

Met Thr Val Gly Arg Tyr Glu Cys Asp Leu Leu Pro Lys Arg Ser Ala
            660                 665                 670

Phe Ser Arg Lys Gln Leu Ala Gly Leu Val Ala Gly Ser Arg Pro Leu
            675                 680                 685

Pro Val Leu Pro Ser Ser Asp Thr Pro Gly Ser Ala Ser Thr Glu
690                 695                 700

Leu Leu Ala Glu Arg Val Ala Cys Ala Leu Thr Leu Asp Glu Gly Glu
705                 710                 715                 720

Ala Trp Asn Pro Ser Asp Ala Ser Asp Leu Asp Asp Phe Leu Glu Ser
            725                 730                 735

Ser Cys Ala Pro Asn Ala Leu Arg Arg Gly Arg Gln Ala Val Val Pro
            740                 745                 750

Val Arg Gly Ala Arg Arg Arg Gly Ala Asp Leu Gly Leu Ser Pro
            755                 760                 765

Pro Pro Ser Ser Pro Ala Val Arg Cys Arg Ser Leu Val Arg Trp Ser
770                 775                 780

Gln Gln Arg Pro Phe Phe Ser Asn Val Ser Ala Cys Ala Gly Ala Ala
785                 790                 795                 800

Asp Ser Arg Arg Glu Glu Trp Lys Asp Ala Gly Lys Val Ala Lys Pro
            805                 810                 815

Gly Ser Glu Ser Ala Leu Thr Ser Arg Asp Leu His Ala Ser Thr Gly
            820                 825                 830

Leu Val Asn Ala Ala Leu Asp Ser Ser Glu Gln Lys Ser Gly Glu Arg
            835                 840                 845

Glu Ser Ser Leu Ser Pro Gln Glu Arg Ile Leu Thr Gln Val Lys Lys
            850                 855                 860

Glu Leu Glu Asp Glu Arg Val Arg Glu Lys Gln Thr Ile Arg Asp Lys
865                 870                 875                 880

Asp Ser Glu Lys Gly Gln Gly Gly Glu Ser Asn His His Met Pro Gly
```

```
                885                 890                 895
Thr Ala Asn Gly Gln Arg Thr Pro Asn Glu Gly Glu Ala Pro Met Glu
                900                 905                 910

Thr Glu Glu Ala Pro Thr Leu Glu Pro Ser Asn Gly Met His Arg Asp
                915                 920                 925

Gly Gln Asp Ala Gly Ala Arg Met His Ser Ser Thr Arg Ala Leu
        930                 935                 940

Glu Gly Ala Val Glu Asp Glu Pro Lys Val Thr Leu Pro Asp Lys Asp
945                 950                 955                 960

Glu Pro His Ala Ser Ala Leu Cys Gly Glu Arg Glu Lys Gln Arg Gln
                965                 970                 975

Ser Phe Phe Ser Ser Val Ser Ser Arg Glu Asp Ala Gln Asp Glu Asp
                980                 985                 990

Ser Arg Trp Cys Val Ala Gly Gly Met Tyr Asn Gly Trp Lys Gly Thr
                995                 1000                1005

Tyr Asp Val Trp Ile Tyr Arg Arg Val Ser Ala Ala Leu Arg Glu
        1010                1015                1020

Gly Lys Gly Glu Glu Lys Arg Arg Glu Gly Glu Lys Arg Lys
        1025                1030                1035

Thr Gly Lys Gly Lys Gln Ser Val His Thr Ala Ser Leu Gly Ala
        1040                1045                1050

Gly Gly Ala Gln Gly Leu Ser Pro Gly Glu Thr Gln Ala Ser Gly
        1055                1060                1065

Leu Ala Pro Gly Ser Thr Pro Leu Gly Ser Ala Gly Thr Leu Ser
        1070                1075                1080

Ala Gly Arg Asn Gly Glu Glu Thr Arg Glu Ser Thr Gly Ser Pro
        1085                1090                1095

Ala Gly Ala Phe Ala Ser Ser Ser Ser Leu Ala Ala Lys Gly Gln
        1100                1105                1110

Asn Gly His Ala Ser Val Glu Asp Leu Lys Thr Gln Lys Glu Glu
        1115                1120                1125

Ser Leu Gly Cys Val Leu Ser Ala Ser Ala Leu Pro Leu Asn Pro
        1130                1135                1140

His Ser Gly Glu Thr Arg Glu Asp Ser Ala Gly Arg Asp Glu Glu
        1145                1150                1155

Lys Gly Glu Glu Arg Glu Arg Asp Glu Asn Glu Pro Pro Leu Tyr
        1160                1165                1170

Glu Trp Arg Val Lys Arg Phe Ser Ala Leu Ile His Gly His Glu
        1175                1180                1185

Lys Ala Ser Arg Leu Ala Cys Lys Tyr Cys Val Tyr Leu Glu Arg
        1190                1195                1200

Phe Gly Arg Ile Arg Gly Arg Leu Ser Ile Cys Ser Thr Cys Cys
        1205                1210                1215

Arg Asp Ala Cys Ser Gly Cys Met Pro Ser Lys Lys Arg Ala Ala
        1220                1225                1230

Gly Ala Asp Phe Ser Pro His Cys Arg Asn Gly Arg Asp Ala Gly
        1235                1240                1245

Val Gly Gly Ala Gly Arg Ala Pro Lys Arg Arg Val Gln Ala Lys
        1250                1255                1260

Lys Gly Ala Ala Gly Ala Ala Gly Val Cys Gly Asp Arg Ala Arg
        1265                1270                1275

Lys Gly Lys Gly Glu Asp Glu Pro Glu Arg Asp Gly Leu Asp Arg
        1280                1285                1290
```

```
Arg Glu Glu Gly Gly Thr Pro Ser Ser Lys Gln Thr Ala Glu Arg
    1295                1300                1305

Arg Gly Ala Ala Lys Lys Glu Gly Arg Glu Glu Asp Asp Arg Val
    1310                1315                1320

Asp Gly Lys Gly Thr Ser Leu Ser Leu Glu Asn Asn Ser Phe Glu
    1325                1330                1335

Ser Ser Cys Pro Ala Met Arg Ser Ser Leu Arg Ala Ser Phe Glu
    1340                1345                1350

Val Lys Gly Pro Leu Ser Pro Ser Ser Ala Asp Asp Arg Pro Asn
    1355                1360                1365

Glu Gly Ala Ala Gly Arg Gly Ala Pro Pro Gly Ser Glu Gly Pro
    1370                1375                1380

Ser Arg Asp Leu Ala Leu Arg Ser His Ser Phe Ser Ser Ala Ser
    1385                1390                1395

Ser Ser Arg Lys Ser Ala Lys Asn Ala Ala Glu Ser Leu Arg Arg
    1400                1405                1410

Ile Ala Gly Pro Leu Phe Arg Ser Ser Gly Asp Leu Thr Ala Ser
    1415                1420                1425

Gln Leu Gly Ala Glu Thr Glu Glu Ser Asp Val Leu Gln Asp Val
    1430                1435                1440

Phe Glu Leu Tyr Ser Glu Ala Gly Glu Ala Trp Glu Thr Cys Thr
    1445                1450                1455

Thr Pro Val Ser Phe Ser Pro Ser Leu Ser Val Ala Ser Arg Asp
    1460                1465                1470

Thr Leu Val Val Leu Gly Gly Ser Gln Thr Thr Ala Val Ala Arg
    1475                1480                1485

Leu Asp Ser Gly Lys Met Ser Glu Ala Val Arg Arg Ser Ser Asn
    1490                1495                1500

Ala Leu Ser Ala Ala Ala Ser Ser Phe Pro Lys Gly Lys Gly Phe
    1505                1510                1515

Gly Gly Ala Ser Lys Lys Thr Asp Ser Val Thr Leu Ser Phe Leu
    1520                1525                1530

Ala Arg Val Cys Arg Asn Leu Arg Met Phe Leu Leu Leu Cys Gln
    1535                1540                1545

His Asn Thr Val Ala Gly Gly Leu Pro Gly Asp Ser Lys Cys Val
    1550                1555                1560

Cys Arg Ala Gln Ser Gly Pro Gly Gly Ala Gly Leu Ala Gly Ala
    1565                1570                1575

Asp Gly Arg Ala Pro Gly Asp Leu Gly Asp Ser Lys Gly Thr Ala
    1580                1585                1590

Ile Ala Arg Gly Pro Gly Gly Ala Ala Gly Arg Ala His Gly Ser
    1595                1600                1605

Glu Pro Trp Ala Ser Pro Asn Tyr Thr Gly Gly Pro Phe Phe Pro
    1610                1615                1620

Pro Ala Gly Ser Ala Pro Ser Gly Trp Pro Pro Val Ala Gln Ala
    1625                1630                1635

Asn Ser Arg Pro Glu Val Leu Ser Ala Ile Gln Gly Ala Gln Gly
    1640                1645                1650

Gln Gly Pro His Val Ala His Ser Leu Arg Leu Ala Ala Ser Leu
    1655                1660                1665

Ser Pro Ala Gln Thr Thr Ser Glu Ser Phe Leu Ala Pro Glu Ser
    1670                1675                1680
```

```
Phe Ala Ala Gly Val Arg Pro Leu Leu Glu Gly Ser Leu Ser Val
    1685                1690                1695

Leu Ile Pro Glu Pro Gln Val Gly Leu Gly Pro Ser Ala Gly
    1700                1705                1710

Gln Gln Leu Ala Ser Ser Ser Leu Ser Pro Gly Val Ser Val Lys
    1715                1720                1725

Ala Glu Pro Ser Ser Tyr Phe Gln Ser Ala Gln Gly Thr Cys Arg
    1730                1735                1740

Asp Val Ser Ala Gly Ala Arg Thr Ala Met Pro Ser Ser Phe Leu
    1745                1750                1755

Glu Gln Gly Arg Pro Gly Ala Ala Pro Gly His Ala Pro Ser Gly
    1760                1765                1770

Val Gly Arg Cys Pro Pro Gln Gly Arg Asp Ala Ser Pro Gly Cys
    1775                1780                1785

Pro Gly Phe Arg Thr Pro Pro Ala Gly Phe Asp Gly Pro Ser Ser
    1790                1795                1800

Ser Gly Ala Gly Tyr Ser Leu Ser Pro Tyr Gly Tyr Pro Gly Thr
    1805                1810                1815

Glu Ile Ser Pro His Leu Ala Pro Phe Phe Pro Glu Pro Tyr Arg
    1820                1825                1830

Arg Phe Arg Glu Ser Arg Gly Gly Pro Ala Trp Ile His Ser Pro
    1835                1840                1845

Gly Ser Val Asp Val Pro Ser Ser Gly Leu Gln Ser Pro Phe Thr
    1850                1855                1860

Gly Phe His Ala Thr Ser Gly Ser Ser Pro Pro Arg Leu Gly Pro
    1865                1870                1875

Ser Glu Gly Ala Ser Phe Ala Glu Ala Ser Pro Arg Ala Leu Ala
    1880                1885                1890

Gly Asp Leu Gly Pro Ala Gly Phe Leu Gly Ala Ser Ala Gly Ala
    1895                1900                1905

Pro Ala Ala Glu Gly Arg Gly Pro Leu Phe Asp Pro Ser Ala Glu
    1910                1915                1920

Gly Glu Gly Lys Phe Ala Pro Asp Ala Gly Ala Leu Gly Thr Val
    1925                1930                1935

Glu Gly Pro Ala Asp Cys Arg Thr Gln Gly Glu Thr Gly Arg Thr
    1940                1945                1950

Ala Asp Glu Asp Glu Lys Lys Lys Ala Lys Lys Ala Lys Lys His
    1955                1960                1965

Gly Arg Ile Thr Asp Ile Glu Glu Arg Leu Ala Arg Glu Glu Pro
    1970                1975                1980

Tyr Asp Val Val Glu Glu Gly Asp Asp Pro Glu Pro Thr Arg Gln
    1985                1990                1995

Leu Gly Leu Glu Ala Thr Glu Lys Glu Gln Asp Val Pro Arg Ser
    2000                2005                2010

Gly Asp Ser Lys Ser Pro Asp Gln Asp Ser Pro Gly Gln Pro Ala
    2015                2020                2025

Asp Ile Met His Gly Tyr Phe Lys Ala Arg Val Arg Asn Arg Arg
    2030                2035                2040

Val Lys Asp Gly Leu Leu Leu Arg Met Thr Ala Val Leu Val Gly
    2045                2050                2055

Lys Gly Phe Tyr Asp Leu Glu Thr Val Glu Pro Gly Ala Pro Arg
    2060                2065                2070

Arg Arg Gly Gly Trp Gly Glu Ser Gly Glu Glu Glu Glu Ser
```

```
                2075                2080                2085
Glu Thr Lys Tyr Leu Phe Ser Asn Pro Ala Ser Gln Lys Pro Cys
    2090                2095                2100

Asp Phe Ile Leu Tyr Phe Asp Thr Arg Glu Asn Arg Asp Ala Ser
    2105                2110                2115

Val Ala Ile Leu Asn Gln Ala Leu Pro Ala Pro Pro Pro Arg Leu
    2120                2125                2130

Pro Pro Lys Asn Gly Glu Ser Gln Ala Arg Arg Thr Leu Arg Gln
    2135                2140                2145

Leu Tyr Asp His Phe Leu Glu Pro Lys Cys Gln Cys Leu Glu Asp
    2150                2155                2160

Lys Thr Leu Lys Val Lys His Gly Val Ile Asn Leu Leu Gly Phe
    2165                2170                2175

Pro Arg Leu Tyr Val Lys Leu His Cys Ser Met Ser Trp Asp Glu
    2180                2185                2190

Arg Leu Ser Leu Phe Ser Ser Phe Leu His Trp Leu Cys Arg Glu
    2195                2200                2205

Asp Asp Ser Gln Pro Pro Trp Ser Ser Pro Glu Leu His Pro
    2210                2215                2220

Glu Leu Leu Ala Tyr Leu Val Asp Leu Gly Arg Lys Gly Phe Ala
    2225                2230                2235

Ser Gly Gly Ala Ala Thr Thr Ala Val Val Asn Ala Pro Asp Leu
    2240                2245                2250

Pro Leu Asp Asp Ser Ala Leu Ser Lys Lys Asn Ala Ala Leu Ile
    2255                2260                2265

Arg Ala Tyr Met Gln Gln Asp Thr Gly Ala Ser Gly Pro Ser Gly
    2270                2275                2280

Ser Val Gly Ala Thr Ser Ser Asp Pro Glu Ala Pro Arg Lys Asp
    2285                2290                2295

Asp Glu Ala Glu Glu Gly Glu Lys Asp Asp Ser Asn Ala Ala Leu
    2300                2305                2310

Val Glu Gly Pro Ala Pro Glu Thr Ser Gly Asp Ser Thr Gly Ala
    2315                2320                2325

Ala Gln Pro Cys Gly Lys Gly Arg Glu Glu Arg Glu Ala Gly Asp
    2330                2335                2340

Lys Arg Gly Pro Gly Asn Glu Gly Cys Gly Lys Gly Asp Gly Phe
    2345                2350                2355

Gly Ser Pro Val Ala Val Ala Gly Thr Thr Ala Ala Pro Gly Glu
    2360                2365                2370

Thr Glu Ser Val Ser Cys Pro Ser Ser Thr Ser Gly Gly Gly Ala
    2375                2380                2385

Ser Ser Ala Leu Ser Ser Gly Pro Ser Asp Ser Ala Ala Ala Pro
    2390                2395                2400

Asp Gly Cys Glu Ser Ser Pro Val Ala Leu Glu Ser Ala Ser Leu
    2405                2410                2415

Leu Ser Phe Ser Pro Ser Ala Ala Arg Ala Glu Val Leu Thr Val
    2420                2425                2430

Pro Gly Val Gly Leu Val Asn Phe Ser Leu Pro Asp Gly Val Lys
    2435                2440                2445

Phe Asp Lys Ser Lys Leu Ala Phe Arg Cys Tyr Trp Arg Glu Gly
    2450                2455                2460

His Ala Gly Val Val Thr Val Gly Ala Gly Ala Ala Val Ser Pro
    2465                2470                2475
```

-continued

Ser Ser Gly Ala Gly Thr Phe Val Pro Ser Arg Pro Thr Val Cys
        2480                2485                2490

Thr Ala Gln Asn Lys Ser Arg Thr Phe Ser Cys Arg Lys Tyr Gly
    2495                2500                2505

Leu Tyr Gln Ser Arg Val Leu Ala Leu Gln Ala Arg Leu Leu Ser
    2510                2515                2520

Glu Leu Leu Trp Pro Gln Pro Pro Ser Pro Ala Arg Leu Arg Val
    2525                2530                2535

Ser Ala Met Ala Ala Val Val Tyr Gly Leu Ile Ala Ala Pro Met
    2540                2545                2550

Pro Phe Thr Asp Pro Trp Gln Ala Val Cys Gly Val Ser Val Ala
    2555                2560                2565

Glu Asp Ala Leu Arg Gln Arg Arg Glu Val Trp Lys Asn Leu Leu
    2570                2575                2580

Asp Pro Arg Gln Arg Arg Pro Ala Pro Ala Pro Ile Ser Gln Leu
    2585                2590                2595

Ser Leu Pro Pro Val Ser Gly Pro Pro His Ala Ser Ser Ala Thr
    2600                2605                2610

Gln Glu Leu Pro Asn Arg Pro Gly Thr Pro Trp Pro Gly Gln Glu
    2615                2620                2625

Thr Val Cys Gly Ala Arg Gly Pro Ala Pro Gly Leu Ala Ser Ala
    2630                2635                2640

Trp Ala Thr Tyr Gly Asn Pro Gly Asp Arg Asp Ala Ala Glu Pro
    2645                2650                2655

Gln Ser Thr Tyr Val Gly Arg Gly Pro Ala Gly Ala Glu Gly Pro
    2660                2665                2670

Gly Gly Gly Ile Ala Val His Arg Glu Trp Ala Arg Asn Ser Gly
    2675                2680                2685

Ser Glu Ala Ala Gln Pro Cys Gln Phe Gly Arg Ala Val Glu Arg
    2690                2695                2700

Pro Val Pro Gly Pro Gln Ser Ser Leu Gly Pro Gly Gly Asp Asn
    2705                2710                2715

Arg Gly Asp His Met Ala Tyr Asp Gln Ser Pro Ala Gly Pro Ala
    2720                2725                2730

Ser Asn Ala Pro Gly Pro Thr Pro Pro Phe Val Gly Pro Phe Ser
    2735                2740                2745

Pro Gly Leu Val Leu Arg His Gly Pro Pro Ala Phe Ser Gln Asp
    2750                2755                2760

Pro Ser Leu His Arg Pro Pro Phe Ala Ala Gly Thr Gly Pro Ala
    2765                2770                2775

Gly Gln Arg Leu Ala Ser Asp Ser Pro Tyr Pro Leu Lys Asn Glu
    2780                2785                2790

Ala Ser Pro Gln Leu Ala Met Ala His Ala Pro Gly Phe Glu Asn
    2795                2800                2805

Ser Asp Gly Phe Gln Gly Glu Gln Pro Leu Ala Lys Gln Arg Lys
    2810                2815                2820

Ile Glu Gly Ala Ser Asp Arg Pro Val Pro Asp Glu Gly Gln Val
    2825                2830                2835

Leu Gly Thr Ile Ser His Gly Lys Ser Pro Ala Ala Arg Pro Val
    2840                2845                2850

Asp Gly Asp Phe Ala Pro Asp Gly Arg Ser Pro Leu Phe Ser Gln
    2855                2860                2865

-continued

```
Asp Ala Ser Gly Val Gly Gly Arg Pro Ser Gly Val Gly Gly
2870             2875             2880

Gln Leu Ala Ala Gly Gly Lys Gly His Phe Ala Thr Ala Pro Phe
2885             2890             2895

Gly Ser Gly Thr Leu Pro Thr Thr Arg Gly Pro Ser Gln Pro Gly
2900             2905             2910

Gly Asp Gly Leu Ser His Arg Ser Gly Thr Glu Pro Ala Ala Ala
2915             2920             2925

Tyr Ser Ser Pro Ala Gly Ala Ala Tyr Pro Ser Ala Ser Asn Ala
2930             2935             2940

Ser Pro Ile Tyr Gly Ala Ala Pro Lys Arg Glu Gly Asp Ser Pro
2945             2950             2955

Phe Gly Pro Ala Pro Pro Ser Gly Tyr Cys Arg Pro Gly Ser Pro
2960             2965             2970

Ala Val Asp Pro Lys Leu Pro Gly Ser Val Pro Ser Ser Gly Asn
2975             2980             2985

Leu Asp Ser Val Asn Tyr Gly Ser Phe Phe Pro Gly Gln Gln Ala
2990             2995             3000

Pro Gln Gly Asp Gly Arg Ile Ala Pro Trp Gly Ser Gly His Val
3005             3010             3015

Gly Ala Pro Arg Gly Glu Ala Arg Gly Ser Glu Arg Val Gly His
3020             3025             3030

Ala Gly Ala Ser Arg Gly Leu Thr Gly His Glu Leu Glu Glu Gly
3035             3040             3045

Gln Gly Gly Pro Gly Glu Glu Gly Ala Gly Arg Glu Arg Gln Arg
3050             3055             3060

Lys Arg Arg Lys Ser Ala Met Ser Met Ser Ser Gln Gly Glu Asn
3065             3070             3075

Thr Pro Leu Phe Ala Pro Thr Ser Leu Pro Pro Val Pro Phe Ala
3080             3085             3090

Ser Gly Asp Ser Leu Ala Asp Gly Ser Gly Ser Asp Phe Gly Gln
3095             3100             3105

Gln Leu Gly Pro Pro Phe Ser His Gly Ser His Ala Pro Pro Phe
3110             3115             3120

Pro Glu Ala Asn Ala Val Gly Ser Gln His Phe Thr Ala Asp Asn
3125             3130             3135

Leu Glu Thr Pro Gly Leu Pro Ala Glu Leu Gly Gly Gly Asp Gly
3140             3145             3150

Arg Arg Gln Ser Gly Ser Thr His Glu Glu Val Ser Gly Pro Arg
3155             3160             3165

Ala Gly Gly Glu Lys Gly Glu Phe Ser Leu Glu Gly Ala Pro Gln
3170             3175             3180

Ala Ala Ala Gln Gln Leu Ser Ala Glu Thr Leu Thr Phe Leu Leu
3185             3190             3195

Gly Thr Asn Val Val Trp Glu Glu Asn Glu Lys Arg Trp Arg Val
3200             3205             3210

Gln Val Arg Pro Pro Ser Pro Arg Gly Cys Asp Gly Glu Gly Ala
3215             3220             3225

Asp Gly Lys Leu Gly Gly Glu Lys Lys Lys Arg Lys Arg Asp Gly
3230             3235             3240

Phe Ser Ala Gly Gly Glu Arg Arg Ser Ser Thr Gly Asn Glu
3245             3250             3255

Pro Asp Asp Gln His Lys Ala Gly Thr Leu Glu Trp Val Ser Met
```

```
            3260            3265            3270

Ala Gln Leu His Gln Ala Gln Lys Leu Gln Asn Gln Leu Val Gly
    3275            3280            3285

Lys Met Glu Arg Gly Lys Gly Glu Gly Gly Asp Glu Glu Arg Leu
    3290            3295            3300

Gly Gly Asp Gly Arg Gly Asn Ile Phe Phe Asp Ala Asn Gly Ser
    3305            3310            3315

Asp Glu Asn Ala Lys Lys Ala Ala Leu Leu Lys Ala Arg Arg Trp
    3320            3325            3330

Leu Arg Arg Arg Ile Val Gln Gly Gln Ile Leu Val Thr Gly Leu
    3335            3340            3345

Ser Arg Asp Gly Leu Phe Ser Ser Arg Pro Asp Glu Pro Glu Arg
    3350            3355            3360

Ser Ser Ser Val Ser Thr Gly Ala Phe Thr Gly Ser Ser Pro Asn
    3365            3370            3375

Asp Lys Pro Thr Asp Leu Asn Ala Ala Val Pro Pro Leu Ser Pro
    3380            3385            3390

Phe Phe Ser Pro Ile Pro Phe Gly Ala Thr Thr Ala Pro His Arg
    3395            3400            3405

Pro Ser Pro Gly Phe Tyr Pro Pro Ala Pro Ala His Pro Thr Glu
    3410            3415            3420

Asp Gly Cys Arg Pro Pro Met Pro Ala Pro Val Pro Met His Ala
    3425            3430            3435

Pro Gln Gly Pro Val Asp Ser Arg Thr Tyr Arg Gly Ala Arg Pro
    3440            3445            3450

Val Tyr Pro Gly Ser Asp Val Thr Pro Gln Thr Cys His Gly Val
    3455            3460            3465

Arg Pro Glu Ser Met Gln Glu Gly Arg Ala Ala Leu Leu Ala
    3470            3475            3480

Glu Gln Gly Ser Ala Phe Phe Val Ser Gly Asp Gly Lys Gly Asp
    3485            3490            3495

Asn Arg Gly Ala Thr Val Gly Gln Ile Arg Gln Gly Thr Val Arg
    3500            3505            3510

Val Met Gln Ser Gln Thr Ala Ser Gln Ser Leu Asp Gln Gly Phe
    3515            3520            3525

Asp Leu Pro His Pro Pro Ala Pro Gly Pro Ala Tyr Arg Gly Val
    3530            3535            3540

Pro Val Gly His Gly Pro Ser Gly Pro Tyr Tyr Leu Asn Gly Gly
    3545            3550            3555

Cys Val Ala Gln Arg Pro Tyr Ala Thr Phe Ser Asn Leu Ala Gly
    3560            3565            3570

Pro Val Gln Gly Ser Phe Pro Pro Leu Glu Phe Ser Asn Gly Gly
    3575            3580            3585

Leu Pro Thr Thr Ala Leu Gly Arg Arg Gly Ser Asp Ser Gly Pro
    3590            3595            3600

Gln Gly Ala Gly Arg Asn Ala Ser Gln Met Gln Pro Gly Phe Ala
    3605            3610            3615

Ser Arg Pro His Gly Pro Glu Arg Leu Gly Arg Glu Ser Ala Pro
    3620            3625            3630

Gln Ser Gly Ala Pro Pro Gly Phe Ser Pro His Ala His Gly Arg
    3635            3640            3645

Gly Glu Arg Asp Arg Pro Ser Phe Ser Gly Ala Thr Thr Met Pro
    3650            3655            3660
```

-continued

```
Leu Ala Ser Leu Thr Ala Phe Ser His Pro Ala Ala Gly Pro Met
    3665                3670                3675

Phe Val Gly Thr Glu Gly Arg Gly Gln Gln Gly Asp Ile His Pro
    3680                3685                3690

Asn Leu Cys Gly Val Ala Pro Val Gly Gly Pro Arg Gly Pro Ala
    3695                3700                3705

His Ala Pro Met Pro Ala Tyr Gly Pro Gly Gly Ala Ala Gly Pro
    3710                3715                3720

Pro Arg Asp Asp Arg Arg Ala Glu Gly Gly Ala Pro Gly Val Ser
    3725                3730                3735

His Ser Asp Ile Phe Leu Ala Asn Asp Arg Arg Leu His Pro Glu
    3740                3745                3750

Met Cys Leu His Ser Ala Pro Ser Trp Gly Pro Ala Gly Thr Phe
    3755                3760                3765

Ala Ser Pro Asp Asn Arg Gln Asn Ala Glu Pro Trp Pro Ala Ala
    3770                3775                3780

His Ala Ser Ser Asn Asn Phe Phe Asp Tyr Thr Gly Val Asn Met
    3785                3790                3795

Pro Ala Ala Gly Pro Pro Ile Gln Leu Asp Trp Ser Lys Val Arg
    3800                3805                3810

Gly Ala Gly Gly
    3815

<210> SEQ ID NO 16
<211> LENGTH: 432
<212> TYPE: PRT
<213> ORGANISM: Homo sapiens

<400> SEQUENCE: 16

Met Asp Arg Ala Gly Leu Leu Phe Leu Arg Gly Ala Ala Gly Pro Gly
1               5                   10                  15

Pro Leu Lys Cys Phe Gly Pro Arg Val Glu Ala Phe Ser Gly Ser Ile
                20                  25                  30

Ser Leu Leu Ser Leu Asp Ser Arg Gly Pro Thr Pro Phe Arg Thr Pro
            35                  40                  45

Phe His Thr Thr Ser Ala Leu Ser Lys Ser Arg Gln Pro Pro Lys Glu
        50                  55                  60

Ser Pro Glu Ser Ala Ala Ala Cys Thr Phe Ser Pro Leu Phe Pro Ser
65                  70                  75                  80

Pro Val Arg Ala Ser Pro His Arg Asn Leu Leu Gly Ala Arg Val Ser
                85                  90                  95

Val Pro Cys Lys Pro Leu Ala Cys Val Gly Ala Pro Lys Arg Arg His
            100                 105                 110

Gly Glu Thr Ser Asp Gly Phe Ser Ser Arg Ala Ala Val Ala Ala Glu
        115                 120                 125

Ala Leu Pro Pro Trp Pro Ser Asp Phe Leu Gln Ser Glu Glu Ile Ala
    130                 135                 140

Val Asp Ser Pro Gln Lys Pro Thr Gly Phe Ser Arg Pro Ser Asn Ala
145                 150                 155                 160

Arg Val Ser Pro Ala Pro Asn Ala Trp Glu Ala Ala Val Phe Arg
                165                 170                 175

Arg Leu His Ala Phe Asp Ser Gly Leu Arg Gly Asp Ala Ser Gly Ala
            180                 185                 190

Phe Ala Ala Ser Ala Thr Cys Gly Cys Leu Ala Ala Ala Ser Arg Arg
```

```
                195                 200                 205
Asn Pro Cys Leu Pro Ala Tyr Gln Leu Ser Trp Asn Leu Leu Gln Ala
    210                 215                 220

Arg Met Phe Gly Gly Arg Ala Gly Gly Leu Lys Arg Arg Lys Pro Arg
225                 230                 235                 240

Arg Asp Pro Gly Arg Val Ile Gln Ser Gly Met Gly Arg Arg Gln Glu
                245                 250                 255

Phe Phe Trp Pro Glu Lys Ala Arg Arg Thr Arg Val Pro Leu Tyr Gln
                260                 265                 270

Asn Ser Arg Pro Asn Leu Val Tyr Asp Gln Arg Phe Arg Arg Phe Met
            275                 280                 285

Cys Met Trp Tyr Ala Asn Gly Val Gln Val Phe Arg Pro Phe Ser Cys
    290                 295                 300

Arg Gly Arg Arg Gly Gly Arg Gly Lys Glu Gly Leu Pro Asp Gly Leu
305                 310                 315                 320

Gly Ile Gly Arg Gly Ser Gly Thr Trp Glu Arg Ala Arg Ala Lys Ala
                325                 330                 335

Val Val Leu Leu Lys Gln Leu Gln Arg Gln Gly His Leu Asp Arg Leu
            340                 345                 350

Ala Lys Pro Asp Val Thr Arg Ser Gly Val Arg Gly Val Tyr Phe Asp
        355                 360                 365

Thr Glu Glu Lys Leu Trp Val Ala Thr Trp Asn Glu His Gly Leu Arg
    370                 375                 380

Arg Phe Lys Ala Phe Pro Thr Met Glu Met Gly Phe Asp Ala Ala Tyr
385                 390                 395                 400

Gln Ala Ala Val Ala Val Arg Arg Gln Lys Leu Arg Glu Asn Tyr Ile
                405                 410                 415

Phe Ser Met Gln Arg Asn Arg Lys Lys Ser Gly Arg Pro Pro Phe Lys
            420                 425                 430

<210> SEQ ID NO 17
<211> LENGTH: 1919
<212> TYPE: PRT
<213> ORGANISM: Homo sapiens

<400> SEQUENCE: 17

Met Glu Leu Pro Asp Gln Ala Ala Tyr Gly Arg Gln Leu Ala Lys Arg
1               5                   10                  15

Arg Arg Leu Ser Ala Ser Glu Glu Ala Thr Leu Ala Ser Lys Asn
            20                  25                  30

Asp Gly Lys Glu Gly Leu Gln Glu Pro Ala Gly Ala Thr Ala Gly His
        35                  40                  45

Leu Leu Pro Ala Glu Pro Gly Gln Tyr Thr Pro Glu His Thr Glu
    50                  55                  60

Gly Arg Arg Glu Phe Arg His Pro Val Val Leu Pro Gly Gly Gly
65                  70                  75                  80

Arg Lys Ala Ala Ser Tyr Gly Leu Ile Ala Val Gly Gly Gly Asp Ser
                85                  90                  95

Leu Arg Ala Ser Arg Arg Thr Arg Ser Ser Ala Ser Ile Glu Thr Ser
            100                 105                 110

Ala Glu Glu Lys Glu Thr Tyr Thr Ser Pro Glu Leu Gly Pro Gly Ala
        115                 120                 125

Ser Trp Ser Val Ser Thr Val Lys Gly Ser Lys Gly Arg Ser Asp Glu
    130                 135                 140
```

-continued

```
Glu Gly Arg Ala Gly Lys Arg Ala Gly Ala Cys Ala Ala Arg Asp Ser
145                 150                 155                 160

Ala Ala Gly Ser Arg Thr Leu Ala Gln Ala His Arg Gly Ala Asp Glu
            165                 170                 175

Glu Arg Met Pro Pro His Ser Pro Ala Arg Asp Gly Ser His Gln Val
        180                 185                 190

Cys Trp Asp Ser Asp Ala Leu Pro Ser Pro Tyr Asp Leu Gly Leu Ser
    195                 200                 205

Glu Ala Asp Asp Glu Glu Val Ser Pro Gln Lys Glu Ala Leu Ala Glu
210                 215                 220

Lys Asn Gly Leu Val Leu Phe Ala Glu Gln Ser Leu Gln Gly Val Gly
225                 230                 235                 240

Leu Ala Thr Leu Thr Val Pro Ser Gly Ala Thr Ser Ser Lys Gly Ala
                245                 250                 255

Phe Ser Ala Gly Ser Pro Phe Leu Pro Gly Ser Gly Thr Thr Ala Ser
            260                 265                 270

Pro Arg Ser Pro Val Pro Arg Gly Asp Lys Ser Leu Gly Asp Gly Ser
        275                 280                 285

Val Gly Ser Asp Asp Val Ser Ala Lys Ala Ser Pro His Ala His His
    290                 295                 300

Asn Val Thr Ala Gly Ala Asp Ala Ser Gln Ser Ser Glu Asp Ala Phe
305                 310                 315                 320

Phe Pro Ala Ala Pro Gly Gly Val Pro Gly Thr Leu Thr Val Glu
                325                 330                 335

Asp Leu Leu Thr Met Pro Glu Arg Arg Gln Asp Pro Glu Ala Glu Lys
            340                 345                 350

Ala Ala Lys Thr Asp Phe Asp Cys Leu Ala Ala Leu Ile Gln Asp Ala
        355                 360                 365

Leu Gly Glu Ala Gly Gly Ala Ala Gly Arg Val Ala Pro Lys Arg Arg
    370                 375                 380

Cys Arg Thr Leu Gly Ala Gly Phe Asn Pro Thr His Ser Ala Arg Pro
385                 390                 395                 400

Gly Ser Gly Ser Val Ala Gly Leu Glu Ala Pro Gly Ala Leu Gly Arg
                405                 410                 415

Glu Leu Asp Ala Leu Val Ala Gly Gly Ser Pro Glu Glu Ser Arg Ala
            420                 425                 430

Asp Leu Glu Pro Asp Gly Gln Ala Ala Gly Ala Ser Trp Gln Glu Ser
        435                 440                 445

Leu His Leu Gln Tyr Asp Thr Arg Asn Gly Gly Thr Tyr Glu Glu Asp
    450                 455                 460

Leu Asp Ser Ala Ser Leu Ser Phe Leu Leu Gly His Ser Glu Gly Ser
465                 470                 475                 480

Glu Lys Gly Pro Ala Leu Ser Ala Ser Ala Gly Ala Ser Thr Ala Ala
                485                 490                 495

Ser Val Ser Ser Phe Phe Pro Ser Glu Ala Ala Cys Gly Val Tyr Ala
            500                 505                 510

Pro Gly Gln His Gly Arg Pro Thr Gln Ser Gln Asp Pro Ala Lys Glu
        515                 520                 525

Arg Gln Arg Arg Leu Ala Arg Asp Arg Glu Thr Leu Asn Leu Ser Ala
    530                 535                 540

Gln Ile Ala Ala Arg Phe Lys Ser Cys Arg Thr Glu Asp Val Met Arg
545                 550                 555                 560

Leu Phe Arg Arg Tyr Leu Ala Val Ser Ser Arg Gln Val Arg Asp Pro
```

```
            565                 570                 575
Ala Thr Leu Glu Arg Val Val Ala Ala Cys Cys Tyr Ile Ser Ser Arg
            580                 585                 590

Gln Ala Met Asp Gly Leu Ser Leu Ser Asp Ile Cys His Glu Met Asp
            595                 600                 605

Ala Ser Asn Gly Gln Asp Leu Phe Ala Ala Gly Cys Glu Ala Arg Gly
            610                 615                 620

Lys Lys Leu Ala Asp Gly Glu Gly Met Gly Arg Gly Glu Ser Asp Arg
625                 630                 635                 640

Glu Arg Ala Gly Gly Ala His Ala Ser Met Arg Cys Lys Ser Leu Gly
                    645                 650                 655

Lys Trp Val Val Arg Ile Cys Arg Lys Leu Gln Leu Gln Ala Leu Pro
                    660                 665                 670

Asp Lys Asp Asp Pro Glu Glu Arg Ala Asn Arg Val Leu Ala Arg
            675                 680                 685

Val Lys Gln Leu Leu Ile Ala Lys Met Glu Glu Glu Gln Arg Arg
            690                 695                 700

Pro Gln Leu Val Asn Ala Phe Val Arg Ala Thr Gln Ser Ala Val Glu
705                 710                 715                 720

Lys Gln Arg Leu Lys Ala Glu Gly Asp Arg Ser Glu Ala Asp Ser Leu
                    725                 730                 735

Ala Ser Leu Glu Ser Leu Leu Gly Asp Glu Ala Arg Arg Ala Asp Ala
            740                 745                 750

Arg Ala Asp Ala Glu Ala Arg Arg Gln Thr Pro Ala Glu Ala Gln Leu
            755                 760                 765

Gly Asp Phe Leu Asp Gly His Gln Gly Gly Glu Lys Thr Gly Arg Val
            770                 775                 780

Ser Ser Ala Arg Ile Asn Gly Arg Ala Ala Glu Ala Ser Pro Ala Pro
785                 790                 795                 800

Pro Ala Pro Gln Gly Ser Thr Ala Pro Ala Asp Ser Thr Pro Ala Ala
                    805                 810                 815

Gly Ser Glu Glu Arg Gln Ala Leu Asn Ala Ile Glu Glu Leu Leu Ala
            820                 825                 830

Gln Val Thr Gly Gly Ser Asn Leu Asp Cys Phe Gly Ser Ala Thr Leu
            835                 840                 845

Ala Ala Val Asp Ser Asp Leu Ala Ser Gly Thr Ser His Val Asp Arg
            850                 855                 860

Glu Ser Cys Ala Arg Leu Arg Arg Leu Asp Lys Ser Gly Arg Asp Ala
865                 870                 875                 880

Phe Ala Ala Asp Ala Asp Gly Pro Glu Arg Pro Thr Glu Asn Glu Val
                    885                 890                 895

Glu Pro Glu Ala Arg Pro Gly Ala Gly Val Leu Ala Glu Asp Val
            900                 905                 910

Asp Glu Ala Ser Met Ala Leu Thr Pro Asn Pro Asp Asp Arg Ser Ser
            915                 920                 925

Ser Ala Ser Gly Asp Ala Ala Glu Pro Val Ala Ser Ile Arg Leu Glu
            930                 935                 940

Gln Arg Glu Glu Lys Asn Gly Asp Ala Ser Gly Leu Ser Leu Asp Ile
945                 950                 955                 960

Cys Pro Ser Leu Phe Asp Pro Val Asp Met Pro Ala Leu Ser Ala Ser
                    965                 970                 975

Ser Glu Gly Asp Ser Gly Asp Ser Ser Pro Phe Ser Pro Ile Leu Thr
            980                 985                 990
```

```
Ser Leu Leu Ser Ala Ser Leu Pro  Pro Ser Glu Thr Leu  Ala Gln Ala
        995                 1000                1005

Lys Asp Met Gln Pro Ala Ala  Arg Leu Gln Leu Gln  Arg Phe Thr
    1010                1015                1020

Trp Leu Gln Lys Met Arg Ala  Glu Ala Leu Glu Lys  Leu Lys Lys
    1025                1030                1035

Glu Lys Glu Ala Val Phe Arg  Gly Leu Val Leu Gln  Arg Ile
    1040                1045                1050

Leu Gln Leu Phe Tyr Asp Val  Lys Gln Gly Glu Ser  Asp Gly Glu
    1055                1060                1065

Arg Glu Asp Gly Glu Asp Gly  Glu Gly Lys Lys Arg  Gln Lys Gly
    1070                1075                1080

Trp Thr Glu Glu Asp Pro Leu  Asp Lys Arg Trp Arg  Ala Arg Gly
    1085                1090                1095

Arg Cys Asp Ala Val Ser Leu  Ala Ser Leu Ile Ile  Ile Val Phe
    1100                1105                1110

Lys Trp Met Gln Ile Pro Ile  Pro Gln Arg Ile Ala  Leu Asp Ala
    1115                1120                1125

Leu His Val Asp Arg Lys Ser  Val Tyr Lys Arg Arg  Leu Glu Gln
    1130                1135                1140

Met His Ile Leu Lys Thr Leu  Phe Gly His Leu Arg  Gly Met Val
    1145                1150                1155

Glu Lys Lys Asp Gly Ser Ser  Ser Ser Ala Leu Ala  Glu Glu Leu
    1160                1165                1170

Lys Ala Ser Leu Pro Pro His  Leu Ala Ser Leu Leu  Gln Gln Val
    1175                1180                1185

Val Gly Asn Pro Ala Thr Met  Gln Arg Leu Leu Ala  Leu Ala Asp
    1190                1195                1200

Glu Glu Glu Glu Leu Gly Asn  Phe Ile Ser Ser Gln  Ser Leu Gly
    1205                1210                1215

Ser Asp Gly Glu Ser Gly Lys  Ala Ser Ala Gly Leu  Gly Gly Val
    1220                1225                1230

Pro Pro Pro Ala Ala Ala Ala  Ser Pro Thr Pro Val  Lys Thr Ser
    1235                1240                1245

Gln Ala Ser Phe His Pro Gln  Ala Pro Ala Ala Ser  Ser Pro Glu
    1250                1255                1260

Ser Ser Ala Pro Ser Val Ala  Val Glu Pro Glu Gln  Asp Ala Ala
    1265                1270                1275

Ser Ser Ser Phe Leu Ala Ala  Ile Leu Ala Glu Val  Ala Ala Glu
    1280                1285                1290

Arg Glu Val Gly Ala Val Lys  Thr Arg Gly Pro Gly  Asp Ala Glu
    1295                1300                1305

Arg Thr Ala Ala Glu Leu Gly  Phe Gln Thr Arg Lys  Lys Arg Arg
    1310                1315                1320

Val Ser Glu Leu Asn Ala Gln  Arg Ser Pro Asp Asn  Gly Leu Gly
    1325                1330                1335

Ser Asp Leu Tyr Asp Glu Asp  Arg Glu Ala Ser Ser  Ala Val Pro
    1340                1345                1350

Val Ala Ser Pro Leu Ala Asn  Leu Cys Ser Ser Leu  Ser Ser Ser
    1355                1360                1365

Ser His Arg Asn Pro Ser Glu  Met Ala Ala Val Ala  Ser Val Ala
    1370                1375                1380
```

```
Pro Ser Pro Arg Ala Ala Arg His Pro Arg Ala Pro Asp Glu Met
    1385                1390                1395

Thr Leu Gln Gly Leu Ala Val Gly Lys Asp Ala Gly Thr Pro Arg
    1400                1405                1410

Gln Ala Gly Gly Tyr Ala Gly Thr Phe Leu Pro Gly Asp Gly Asp
    1415                1420                1425

Arg Val Ser Glu Gly Glu Asp Gly Arg Ser Glu Arg Val Arg Ala
    1430                1435                1440

Arg Phe Leu Ala Glu Arg Gly Ser Met Asp Ala Ser Ser Ser Phe
    1445                1450                1455

Ala Leu Gly Phe Ser Leu Ala Glu Ala Leu Leu Arg His Gly Phe
    1460                1465                1470

Cys Leu Pro Ser Pro Ser Asp Pro Pro Ala Gly Leu Ala Asp Ala
    1475                1480                1485

Gln Phe Ala Thr Gly Asp Leu Leu Arg Asp Gly Gly Ser Ser Ser
    1490                1495                1500

Gly Glu Arg Ala Leu Arg Met Gln Pro Glu Gly Phe Ser Ala Thr
    1505                1510                1515

Arg Gly Ser Arg Pro Ala Val Ala Pro Gly Pro Ala Gly Phe Gly
    1520                1525                1530

Ile Gln Ala Glu Ala Glu His Glu Gly Arg Gly Asp Val Asn Ser
    1535                1540                1545

Thr Asp Val Ile Phe Ser Asn Arg Ala Thr Arg Asp Ile Ile Ala
    1550                1555                1560

Ser Phe Leu Ala Ser Ala Ser Thr Glu Gly His Pro Gly Thr Ala
    1565                1570                1575

Ser Leu Thr Gly Arg Gly Leu Glu Asp Gly Arg Ser Pro Arg Leu
    1580                1585                1590

Arg Gly Pro Leu Ala Ala Val Pro Lys Ala Val Ser Gln Ala Asp
    1595                1600                1605

Arg Gly Pro Gly Arg Phe Asn Arg Gly Ala Ser Gly Ser Cys Arg
    1610                1615                1620

Gln Pro Ser Ser Arg Ser Pro Pro Leu Pro Val Ser Pro Tyr Arg
    1625                1630                1635

Gly Arg Thr Gly Asp Ser Ser Arg Gln Arg Pro Leu Ser Pro Ser
    1640                1645                1650

Ser Leu Phe Ala Ala Ala Ala Ser Met Ala Gly Val Leu Pro Gly
    1655                1660                1665

Pro Leu Pro Ser Ser Arg Ser Ala Gly Ser Ser Ala Leu Ser Pro
    1670                1675                1680

Gly Val Glu Arg Ser Pro Arg Glu Arg Val Ala Ala Gln Ala Leu
    1685                1690                1695

Glu Ala Thr Arg Arg Gly Asp Val Asp Arg Ser Leu His Pro
    1700                1705                1710

Ser Ser Ser Val Ser Ala Val Arg Ser Leu Leu Pro Ala Glu Pro
    1715                1720                1725

Ala Leu Gly Gly Ala Ser Pro Phe Ala Ser Ser Ala Leu Ala Met
    1730                1735                1740

Gly Leu Pro Glu Ala Gly Ala Ser Gln Ala Gly Ala Asp Ala Pro
    1745                1750                1755

Leu Ala Ser Pro Ser Ile Ala Leu Ala Thr Val Ala His Leu Lys
    1760                1765                1770

Ala Ala Glu Lys Ala Leu Leu Asp Ser Val Pro Asp Ser Ala Arg
```

-continued

```
            1775                1780                1785

Val Val Ser Leu Gln Phe Glu Arg Thr Gln Gln Arg Trp Val Cys
        1790                1795                1800

Lys Trp Gln Arg His Lys Pro Ala Gly Ala Pro Ala Asn Arg Lys
    1805                1810                1815

Glu Pro Trp His Arg Arg Cys Phe Ser Val Ile Lys Tyr Gly Tyr
    1820                1825                1830

Glu Gly Ala His Ala Leu Ala Ala Val Ala Lys Lys Leu Arg
    1835                1840                1845

Asp Gly Arg Arg Ala Leu Leu Gln Lys Gln Arg Leu Glu Glu
    1850                1855                1860

Glu Gly Leu Ala Glu Ala Glu Ala Pro Arg Glu Glu Glu
    1865                1870                1875

Val Gly Asp Ala Glu Asp Glu Pro Leu Gly Ala Ala Glu Glu
    1880                1885                1890

Ala Glu Glu Thr Val Ser Pro Arg Val Asp Ala Gly Gly Asp Arg
    1895                1900                1905

Ser Ala Ser Gly Ser Ala Glu Ala Gly Lys Gln
    1910                1915

<210> SEQ ID NO 18
<211> LENGTH: 485
<212> TYPE: PRT
<213> ORGANISM: Homo sapiens

<400> SEQUENCE: 18

Met Cys Val Lys Lys Glu Gly Gly Asp Gly Lys Arg Gly Asn Glu Lys
1               5                   10                  15

Asn Gln Val Asn Asp Lys Gly Val Lys Arg Thr Gly Arg Asp Val Glu
            20                  25                  30

Ser Arg His Ala Pro Ser Val Pro His Leu Glu Lys Leu Val Asp Met
        35                  40                  45

Ala Met Val Tyr Ser Ser Cys Leu Pro Pro Cys Asp Ser Ser Gln Gly
    50                  55                  60

Gly Asp Gly Glu Arg Val Lys Arg Asn Ala Gly Ala Lys Arg Lys Gln
65                  70                  75                  80

Gly Gln Gly Glu Ser Gln Asp Arg Leu Lys Ala Leu His Asp Ser His
                85                  90                  95

Pro Leu Gln Cys Val Trp Tyr Leu Glu Ser Ser Pro Ala Thr Asn Ile
            100                 105                 110

Thr Leu Pro Ser Glu Ser Gly Ser Leu Lys Ser Pro Ser Ser Pro Ser
        115                 120                 125

Lys Arg Ala Ser Pro Asp Arg Val Met Glu Val Ser Ala Ser Leu Cys
    130                 135                 140

Lys Glu Glu Gln Lys Arg Arg Glu Gly Pro Arg Glu Gly Gln Trp Cys
145                 150                 155                 160

Cys Ser Trp Ser Phe Pro Arg Gly Arg Pro Thr Gly Thr Lys Phe Ser
                165                 170                 175

Val Lys Leu Phe Gly Tyr Glu Glu Ala Lys Arg Leu Ala Leu Tyr Thr
            180                 185                 190

Ala Leu Tyr Ala Tyr Ser Pro Glu Glu Arg Cys Asp Val Leu Gln Glu
        195                 200                 205

Leu Ile Asp Glu Val Leu Ala Thr Ala Ser Ser Ala Ser Leu Ser Ala
    210                 215                 220
```

```
Ser His Leu Pro Asn Pro Glu Arg Phe Pro Ala Ile Leu Glu Leu Gln
225                 230                 235                 240

Pro Gln Pro Leu Ser Leu Ser Ser Leu Ser Pro Ser Leu Cys Val
            245                 250                 255

Arg Leu Asp Ala Cys Ala Phe Pro Ser Pro Val Leu Ser Gly Ser Pro
            260                 265                 270

Leu Cys Ser Ser Pro Gly Leu Ser Ser Arg Gly Arg Asn Gly Ser Lys
            275                 280                 285

Ala Ala Arg Glu Thr Leu Ser Ile Asp Arg Gly Ile Arg Leu Ser Ser
            290                 295                 300

Gln Ser Ser Ala Ser Ser Asn Ala Met Pro Ser Gln Phe Pro Gln Arg
305                 310                 315                 320

Trp Gln Ala Thr Glu Val Arg Met Ser Leu Leu Cys Arg Ser Ser Phe
            325                 330                 335

Arg Ala Ser Arg Arg Arg Glu Gly Gly Asn His Gly Glu Ala Glu Ala
            340                 345                 350

Glu Ala Lys Arg Ala Gly Gln Thr Arg Glu Lys Thr Gly Arg Arg Asp
            355                 360                 365

Lys Gly Asn His Pro His Asp Leu Ser Val Asn Asn Arg Lys Glu Pro
370                 375                 380

Asn Lys Leu Glu Lys Ser His Ser Ser Cys Ser Pro Arg Arg Ser Leu
385                 390                 395                 400

Phe Ser Ser Ile Gln Val Gln Gln Asp Glu Arg Ser Gly Gly Arg Leu
            405                 410                 415

Leu His Gly Phe Arg Gly Asp Met Glu Glu Gly Lys Arg Ala Ser Arg
            420                 425                 430

Ala Asn Lys His Val Glu Ala Lys Lys Gly Glu Val Thr Gly Arg Arg
            435                 440                 445

Lys Gly Val Cys Gly Gly Ala Leu Phe Gly Cys Phe Pro Ala Arg Arg
            450                 455                 460

Gly Arg Glu Arg Gly Glu Asp Glu Gly Glu Arg Glu Lys Ala Gly Gln
465                 470                 475                 480

Val Asn Ala Gln His
                485

<210> SEQ ID NO 19
<211> LENGTH: 3837
<212> TYPE: PRT
<213> ORGANISM: Homo sapiens

<400> SEQUENCE: 19

Met Ala Phe Ala Pro Arg Thr Ser Pro Arg Leu Ser Ala Gly Ala Gly
1               5                   10                  15

Gly Pro Ser Glu Ala Ser Arg Gly Gly Thr Ala Ala Gly Ala Pro Leu
            20                  25                  30

Gly Pro Val Glu Thr Pro Thr Gly Arg Glu Pro Ser Ser Pro Phe Leu
            35                  40                  45

Arg Ser Ala Ser Ala Lys Arg Val Thr Arg Ala Arg Ala Gly Phe Leu
    50                  55                  60

Ala Ser Ser Pro Asp Asn Gln Ser Arg Ser Thr Ser Pro Leu Arg Pro
65                  70                  75                  80

Ala Asp Ala Leu Arg Ile Ser Glu Ala Ser Ala Ser Ala Pro Gly
            85                  90                  95

Val Arg Arg Ser Leu Arg Ala Ser Asn Ala Arg Pro Pro Val Ser Ala
            100                 105                 110
```

Ser Arg Gly Leu Met Gly Lys Ala Gly Glu Gly Glu Gly Ala Ser
        115                 120                 125

Gly Gly Gly Arg Pro Gly Gly Ala Arg Arg Thr Ser Gly Gly Gly Glu
130                 135                 140

Asp Val Cys Ala Ser Pro Arg Asp Ile Ser Tyr Arg Asp Lys Gly Ala
145                 150                 155                 160

Gly Gly Asp Ala Thr Ala Ser Ser Asn Ser Gln Ser Pro Ser Ser Val
                165                 170                 175

Asp Ala Ala Val Ser Ser Ser Tyr Ser Val Ala Ser Ser Val Ser Ser
                180                 185                 190

Pro Pro Ala Ser Ser Leu Ser Ser Ala Leu Ser Ser Ser Phe Ser Ser
                195                 200                 205

Ser Thr Leu Ser Arg Ser Gly Ser Ser Val Cys Pro Arg Ala Thr Ser
210                 215                 220

Ala Val Ser Ala Thr Leu Gln Gln Gly Glu Arg Ser Gln Glu Ser Ser
225                 230                 235                 240

Leu Leu Ala Gly Glu Arg Glu Thr Asp Arg Asp Ala Asn Arg Pro Gln
                245                 250                 255

Arg Glu Thr Asp Glu Gly Gln Gly Ala Lys Ser Glu Thr Asp Arg Ala
                260                 265                 270

Pro Glu Asp Asp Arg Gly Arg Ser Arg Gly Ser Ala Ser Pro Val
                275                 280                 285

Gln Gly Pro Phe Ser Pro Arg Gly Phe Phe Ser Asn Ala Val Thr Lys
                290                 295                 300

Glu Asn Ser Ala Tyr Pro Ala Thr Ser Gly Gln Ser Gly Gln Glu Val
305                 310                 315                 320

Gly Cys Arg Pro Asn Ser Thr Leu Ser Ser Val Ser Val Cys Ser Leu
                325                 330                 335

Ser Ser Arg Pro Pro Ser Thr Leu Ala Ser Asp Gln Leu Leu Ser Val
                340                 345                 350

Pro Asn Gly Asp Ala Ser Thr Val Ser Thr Ser Ser Pro Ser Leu Ser
                355                 360                 365

Cys Ser Cys Ser Ser Phe Ser Ser Ser Ser Ser Leu Ser Ser Ser
370                 375                 380

Ser Leu Leu Ser Ser Ser Pro Leu Ser Ser Thr Pro Ser Ser Phe Phe
385                 390                 395                 400

Ser Ser Ser Ser Ser Ser Ser Ser Ala Ser Val Ala Pro Pro Gly
                405                 410                 415

Glu Gly Lys Gly Arg Pro Pro Val Arg Ser Gly Arg Gly Ala Cys Pro
                420                 425                 430

Arg Lys Pro Ala Gly Pro Pro Arg Leu Cys Val Pro Tyr Gln Cys
                435                 440                 445

Gln Phe Asn Val Glu Lys Arg Glu Trp Arg Ala Arg Tyr Leu Phe Arg
450                 455                 460

Gly Gln Lys Lys Met Arg Val Phe Ser Leu Ala Arg Tyr Ser Pro Glu
465                 470                 475                 480

Val Ala Val Ser Leu Ala Glu Leu Phe Leu Thr Phe Leu Ala Asp Asn
                485                 490                 495

Asp Gly Ile Pro Arg Ser Glu Val Ile Ala Tyr Trp Ala Glu Thr Leu
                500                 505                 510

Ala Arg Gly Pro Val Thr Ala Thr Thr Gly Thr Asn Pro Lys Gly Gly
                515                 520                 525

```
Asn Leu Leu Gly Pro Gly Ala Ser Glu Glu Thr Val Gly Gly Glu
    530                 535                 540

Gly Gly Glu Asp Ala Glu Ser Arg Ala Ala Glu Lys Glu Arg Glu
545                 550                 555                 560

Glu Gly Lys Ala Ser Ser Ser Gly Ser Ser Asp Gln Asn Ile Thr
                565                 570                 575

Arg Val Glu Ser Ser Glu Ala Lys Glu Asp Gly Glu Glu Asn Ser Ala
            580                 585                 590

Ser Ser Lys Pro Pro Gly Ala Ser Ala Ala Thr Glu Pro Ala Gly
        595                 600                 605

Gly Asp Ala Asp Gly Arg Pro Gly Arg Ala Ala Ser Gly Pro Gly Asp
    610                 615                 620

Ala Cys Arg Ser Val Thr Ser Thr Glu Thr Glu Ala Ala Val Ala Val
625                 630                 635                 640

Ala Pro Glu Ala Lys Gly Gly Pro Ser Ser Asp Val Ser Cys Thr Leu
                645                 650                 655

Asp Lys Ser Arg Glu Ser Arg Gly Asn Gly Val Ala Gly Lys Arg Glu
            660                 665                 670

Asn Pro Ala Trp Ala Val Ser Pro Ser Ser Phe Ala Ala Phe Val Glu
        675                 680                 685

Thr Ala Lys Ala Arg Gln Trp Val Thr Glu Ala Ser Arg Leu Gln Ala
    690                 695                 700

Ala Ser Leu Pro Pro Leu Ala Pro Ala Glu Arg Pro Ala Arg Pro Pro
705                 710                 715                 720

Ile Leu Pro Thr Leu Ala Ser Ser Arg Ala Arg Arg Cys Thr Ser His
                725                 730                 735

Ser Leu Ile Ser Gly Leu Ser Ala Arg Glu Gly Ser Gln Arg Thr Val
            740                 745                 750

Ser Gln Gly Asp Ser Leu Ser Pro Ala Ser Gly Leu Ala Gly Glu Pro
        755                 760                 765

Gly Ala Val Arg Glu Ala Glu Gly Arg Glu Ala Ile Ala Val Asp Asp
    770                 775                 780

Glu Thr Gly Gly Glu His Arg Asp Phe Pro His Ser Gln Gly Pro Ala
785                 790                 795                 800

Gly Arg Gly Arg Leu Ala Gly Ala Arg Pro Ser Ser Ser Asp Met Arg
                805                 810                 815

Gly Glu Lys Arg Gly Arg Arg Ala Leu Arg Glu Gly Glu Ser Lys Arg
            820                 825                 830

Pro Cys Arg Arg Arg Glu Asp Leu Lys Ser Glu Glu Gly Gln Arg Glu
        835                 840                 845

Arg Arg Arg Arg Asp Thr Ala Trp Pro Ala Gly Arg Arg Glu Ala Ser
850                 855                 860

His Gly Arg Gln Asp Ser Arg Val Lys Glu Glu Thr Pro Ala Pro Asp
865                 870                 875                 880

Ala Gly Ala Ala Leu Ala Leu Asp Gly Arg Ala Ala Ala Arg Asp
                885                 890                 895

Arg Pro Gln Lys Ala Pro Ser Pro Phe Gly Thr Pro Glu Ala Leu Ser
            900                 905                 910

Ser Ser Leu Thr Gly Ser Gly Leu His Pro Asp Gly Arg Asn Pro His
        915                 920                 925

Gly His Pro Ala Leu Arg Val Lys Leu Ala Ala Gly Arg Gly Asn Gly
    930                 935                 940

Leu Leu Ala Ala Ser Pro Ala Ser Pro Ser Ser Ala Ser His Ala Ser
```

```
            945                 950                 955                 960
Ser Leu Ala Ser Pro Ser Ala Ser Trp His Ala Ala Gln Gly Glu Ala
                965                 970                 975
Glu Ile Pro Gly Ala Ser Thr Gly Phe Val Asp Ser Pro Cys Ser Ala
                980                 985                 990
Asn Gly Ser Leu Asp Asp Ser Gly Leu Gly Gly Pro Ala Ala Ala Leu
                995                 1000                1005
Gln Lys Ser Trp Arg Asp Arg Lys Arg Asn Arg Lys Lys Leu Ser
    1010                1015                1020
Lys Ser Met His Arg Lys Ser Leu Ala Ser Leu Gly Met Arg Ala
    1025                1030                1035
Pro Pro Gln Asn Ala Cys Leu Ala Asp Pro Ser Asp Val Gly Leu
    1040                1045                1050
Gly Val Gln Met Pro Ser Asp Ala Gly Thr Val Pro Gly Ile Ser
    1055                1060                1065
Pro Pro Ser Phe Gly Ala Ser Glu Gln Lys Ala Ser Ser Ser Ala
    1070                1075                1080
Leu Gly Leu Ala Phe Arg Ala Ser Ser Ser Phe Ser Pro Lys Asn
    1085                1090                1095
Gly Asp Val Glu Pro Ala Gly Arg Asn Pro Pro Gln Phe Leu Pro
    1100                1105                1110
Thr Ala Ser Val Gln Arg Ala Asp Pro Pro Gly Thr Gly Ala Pro
    1115                1120                1125
Pro Ser Gln Gln Val Val Ser Ser Ala Ser Pro Cys Ser Pro Ser
    1130                1135                1140
Ala Leu Ala Ala Thr Ala Ser Pro Gly Ala Cys Arg Gly Gly Ala
    1145                1150                1155
Ser Arg Asn Gly Asp Pro Gln Gly Glu Arg Phe Ser Phe Pro Ala
    1160                1165                1170
Ser Pro Thr Ser Gln Tyr Arg Trp Tyr Ala His Pro Asp Gly Gly
    1175                1180                1185
Ala Thr Gly Pro Ser Cys Cys Arg Gln His Val Gly Gly Ser Gly
    1190                1195                1200
Gly Gly Gly Trp Pro Val Val Trp Leu Lys Gln Leu Glu Met Ala
    1205                1210                1215
Val Asn Gly Pro Pro Lys Phe Cys Ser Tyr Val Glu Ala Val Asp
    1220                1225                1230
Lys His Leu Arg Leu Gly Gly Leu Arg Arg Pro Val Ala Phe Leu
    1235                1240                1245
Pro Leu Ala Ser Arg Pro Ala Ser Pro Thr Gly Leu Gly Gly Gly
    1250                1255                1260
Leu Gly Ala Pro Gly Pro Ala Leu Arg Gln Ala Ser Glu Lys Ala
    1265                1270                1275
Leu Ala Ala Glu Gly Arg Gln Gly Gln Asn Glu Glu Lys Gln Val
    1280                1285                1290
Gly Trp Lys Ser Ala Thr Gly Ser Lys Ala Gly Met Phe Gln Gly
    1295                1300                1305
Asp Ser Gly Glu Thr Thr Ser Glu Arg Gly Ala Glu Glu Ala Glu
    1310                1315                1320
Gly Thr Gly Gly Gly Arg Arg Gly Ile Leu Gly Lys Glu Glu Glu
    1325                1330                1335
Asp Arg Asn Gly Gly Glu Gly Glu Lys Ala Ala Thr Pro Thr Met
    1340                1345                1350
```

-continued

Gly Gly Ala Ser Pro Ala Ala Ser Asp Asp Ala Leu Ser Pro Met
    1355             1360             1365

Lys Ala Asp Arg Pro Ala Glu Ala Leu Gly Thr Gly Gly Ser Ala
    1370             1375             1380

Pro Thr His Ala Asp Ser Arg Arg Ala Pro Gly Met Pro Glu Gly
    1385             1390             1395

Glu Lys Met Thr Gly Pro Ser Lys Glu Gln Glu Met Ala Glu Ala
    1400             1405             1410

Gly Glu Arg Asp Arg Cys Glu Arg Ser Leu Glu Arg Asn Ala Glu
    1415             1420             1425

Leu Val Leu Lys Glu Asn Val Ser Met Thr Ser Ala Ser Asp Val
    1430             1435             1440

Ser Glu Ala Ala Glu Glu Lys Gly Ala Pro Lys Lys Leu Ala Ser
    1445             1450             1455

Ser Pro His Ser Val Glu Ser Pro Cys Gly Arg Thr Ala Glu Lys
    1460             1465             1470

Thr Gly Thr Leu Asn Thr Ser Glu Lys Gly Glu Asn Thr Arg Thr
    1475             1480             1485

Ala Glu Gly Asp Asp Pro Gly Thr Thr Ile Val Lys Glu Glu Phe
    1490             1495             1500

Pro Leu Leu Pro Ala Pro Glu Thr Pro Val Thr Val Thr Ala Gln
    1505             1510             1515

Asp Leu Leu Ser Pro Thr Val Tyr Thr Pro Arg Trp Gln Ala Thr
    1520             1525             1530

Val Gly Lys Ser Leu Glu Leu Gly Ser Leu Asn Cys Glu Lys Ser
    1535             1540             1545

Cys Glu Arg Gly His Trp Ala Asp Ala Ser Ala Cys Asp Leu Glu
    1550             1555             1560

Thr Lys Asp Leu Arg Leu Pro Glu Asp Asn Lys Ser Glu Glu Leu
    1565             1570             1575

Lys Lys Glu Thr Gly Met Phe Leu Gly Val Glu Gly Glu Gln Val
    1580             1585             1590

Glu Glu Ala Lys Ser Ser Lys Glu Ala Phe Ser Pro Glu Glu Arg
    1595             1600             1605

Glu Arg Glu Glu Gln Lys Glu Ser Ser Lys Ala Ala Gly Gly Gly
    1610             1615             1620

Asp Ser Cys Arg Thr Pro Arg Gln Gln Glu Ala Thr Pro Arg Ala
    1625             1630             1635

Ser Glu Glu Cys Gln Pro Glu Ser Arg Ile Asp Met Lys Val Ser
    1640             1645             1650

Pro Asn Thr Glu Met Met Val Glu Lys Leu Glu Glu Thr Arg Val
    1655             1660             1665

Gln Asn Thr Glu Glu Pro Lys Val Glu Glu Lys Glu Glu Gly
    1670             1675             1680

Gly Ser Val Cys Arg Asp Val Ser Val Ala Ser Pro Leu Glu Ser
    1685             1690             1695

Pro Asn Ser Arg Leu Ser Glu Lys Gly Asp Gln Ser Glu Thr Pro
    1700             1705             1710

Ala Gly Val Ala Pro Pro Ser Ser Ser Ala Leu Glu Ala Arg Ala
    1715             1720             1725

Gly Arg Asp Ser Ala Leu Leu Ser Ala Ser Leu Pro Leu Ser Pro
    1730             1735             1740

```
Arg Ala Ser Cys Pro Pro Thr Gln Ser Ala Ser Pro Ala Ser Arg
1745                1750                1755

Asp Pro Thr Pro Ala Ser Leu Arg Val Ser Ser Val Ala Ser Gly
1760                1765                1770

Asp Arg Asn Gly Pro Thr Gly Ile Leu Phe Arg Pro Leu Ser Ser
1775                1780                1785

Pro His Lys Arg Val Ser Phe Cys Leu Arg Gly Gly Ala Glu Pro
1790                1795                1800

Pro Gln Arg Pro Leu Ser Glu Ala Val Pro Tyr Pro Leu Asn Ala
1805                1810                1815

Arg Leu Gln Glu Ile Val Ser Arg Phe Arg Leu Leu Gln Gly Val
1820                1825                1830

Ser Ala Ala Arg Val Ser Ser His Gly Lys Gly Glu Thr Ser Ser
1835                1840                1845

Gln Ala Thr Pro Lys Ala Val Gln Gly Glu Ala Thr Val Lys Glu
1850                1855                1860

Lys Ala Thr Val Thr Pro Thr Glu Ser Ala Lys Ser Leu Ala Gly
1865                1870                1875

Gly Gln Ala Glu Thr Glu Lys Gly Glu Ser Pro Ser Gly Ala Glu
1880                1885                1890

Ala Ala Thr Gln Lys Ala Asp Glu Lys Glu Lys Thr Pro Asp Thr
1895                1900                1905

Asp Ala Thr Gln Ser Arg Ser Thr Ser Ser Gly Phe Glu Thr Gln
1910                1915                1920

Glu Ala Lys Thr Ala Pro Ala Ser Ile Leu Pro Ala Ser Ser Leu
1925                1930                1935

Pro Ser Ser Asp Arg Pro Ser Ala Ser Cys Ser Asp Thr His Ala
1940                1945                1950

Ser Arg Asp Ala Val Pro Leu Ala Ser Ser Pro Ser Ser Ser Ser
1955                1960                1965

Ser Pro Ala Leu Arg Arg Cys Ser Val Arg Gly Lys Asp Leu Val
1970                1975                1980

Ser Ala Pro Val Asp Ser Phe Ser Glu Gly Asp Ser Ser Asp Ala
1985                1990                1995

Arg Pro Phe Val Ser Val Arg Asp Leu Ala Val Lys Leu Tyr Arg
2000                2005                2010

Trp Leu Glu Gln Gly Glu Gly Leu Pro Ala Ala Ala Gly Glu Pro
2015                2020                2025

Gln Gly Ala Cys Gly Val Gly Ala Lys Ala Gln Ala Arg Glu Ala
2030                2035                2040

Leu Arg Ile Asp Thr Val Pro Phe Ile Ser Arg Trp Arg Gln Met
2045                2050                2055

Leu Glu Arg Ser Leu Ser Ile Ala Ser Asp Leu Arg Lys Leu Asp
2060                2065                2070

Leu Gln Val Val His Leu Val Glu Leu Thr Glu Ala Leu His Ile
2075                2080                2085

Ala Val Tyr Ile Cys Gly Gln Leu Arg Arg Arg Leu Arg Glu Gly
2090                2095                2100

Ala Ala Pro Asp Ala Gly Ala Ala Glu Asp Leu Ala Pro Val Asp
2105                2110                2115

Val Asp Asp Pro Arg Gly Cys Ser Gln Gln Ser Gly Asp Thr Arg
2120                2125                2130

Asp Ser Ser Ser Pro Ala Thr Pro Gly Gly Arg Leu Ala Gly Gly
```

-continued

```
            2135                2140                2145
Ala Gly Gly Ala Ala Thr Ser Pro Lys Gly Gln Ala Phe Ala Pro
    2150                2155                2160
Arg Gly Gly Glu Gly Glu Ile Lys Pro Gln Glu Thr Gly Asn Ser
    2165                2170                2175
Gly Asp Ser Lys Ala Glu Gly Lys Glu Ala Ser Gly Asp Ala Asn
    2180                2185                2190
Thr Ser Glu Gly Lys Arg Leu Ser Gly Glu Val Asp Lys Thr Ala
    2195                2200                2205
Glu Val Glu Thr Ala Gly Ser Glu Asp Ile Asn Val Glu Arg Gly
    2210                2215                2220
Val Pro Gly Ala Gln Ala Glu Thr Ala Arg Thr Glu Met Asn Gly
    2225                2230                2235
Gly Val Val Lys Gly Gln Glu Thr Ser Gly Asp Ile Leu Ser Val
    2240                2245                2250
Gly Ser Ser Gln Val Leu Ser Leu Ser Ser Pro Ser Leu Ser His
    2255                2260                2265
Leu Ala Ser Ser Ser Gly Lys Gly Pro Leu Lys Pro Thr Ser Ser
    2270                2275                2280
Pro Ser Ser Ser Leu Tyr Ala Leu Ser Pro Ser Ser Ser Ala Ala
    2285                2290                2295
Ser Pro Phe Ser Ala Gln Leu Ala Ser Pro Ser Ser His Ala Pro
    2300                2305                2310
Leu Ser Leu Ser Phe Arg Ser Ser Ser Pro Thr Ser Leu Ser
    2315                2320                2325
Ser Pro Leu Ala Ser Tyr Pro Phe Pro Gln Thr Leu Gln Gln Thr
    2330                2335                2340
Ser Ala Ser Pro Ser Ser Ser Ala Ser Ala Arg Pro Ser Cys Ala
    2345                2350                2355
Ser Val Lys Pro Leu Arg Glu Ala Gly Asp Leu Val Arg Ala Ala
    2360                2365                2370
Ala Arg Ala Ala Leu Glu Gln Ala Gln Val Phe Gly Val Gly Gly
    2375                2380                2385
Lys Leu Ser Asp Ala Thr His Gln Leu Ala Ala Arg Val Thr Val
    2390                2395                2400
Ala Val Arg Ala Ala Met Leu Ala Lys Gly Glu Gly Gly Leu Thr
    2405                2410                2415
Arg Gly Asp Val Asp Leu Leu Val Glu Glu Thr Glu Arg Phe Val
    2420                2425                2430
Arg Glu Ala Arg Phe Lys Ala Gln Glu Thr Ala Ala Glu Thr Thr
    2435                2440                2445
Ala Leu Pro Asp Gly Val Ala Glu Val Val Ser Ser Glu Ala Gly
    2450                2455                2460
Leu Gly Leu Gln Thr Thr Asn His Ala Pro Val Ser Pro Ala Ala
    2465                2470                2475
Ala Pro Ser Ala Gly Gly Ala Phe Ala Gly Leu Thr Glu Ala Val
    2480                2485                2490
Glu Val Glu Ala Arg Gln Leu Pro Glu Ala Ser Glu Arg Val Gly
    2495                2500                2505
Arg Val Ser Ser Pro Arg Gly Ser Leu Gly Phe Glu Ala Met Asp
    2510                2515                2520
Leu Ala Gly Glu Leu His Leu Val Lys Val Leu Asn Ala Phe His
    2525                2530                2535
```

```
Arg His Thr Glu Cys Leu Met Asn Glu Arg Glu Arg Leu Ile Gln
    2540            2545            2550

Ala Thr Asn Glu Asp Leu Ser Phe Leu Leu His Ala Met Glu Leu
    2555            2560            2565

Ala Leu Pro Ser Gly Leu Asp Thr Pro Leu Leu Ser Ile Leu Glu
    2570            2575            2580

Gly Asp Val Asp Ile Leu Pro Pro Leu Pro Pro Pro Asn Val Glu
    2585            2590            2595

Ala Leu Ile Tyr Leu His Ala Val Ser Leu Ala Gln Ala Asp Ala
    2600            2605            2610

Ser Ala Ser Pro Ser Ser Pro Ser Ala Val Ala Pro Cys Leu Leu
    2615            2620            2625

Ser Pro Ser Ala Arg Leu Leu Leu Ala His Phe Ala Gly Ala Ser
    2630            2635            2640

Pro Thr Ala Gly Gly Leu Gly Gly Asp Ser Ala Lys Gly Arg Thr
    2645            2650            2655

Met Ser Ser Phe Pro Gly Arg Pro Gly Glu Glu Arg His Arg Ala
    2660            2665            2670

Asp Glu Arg Lys Gly Ser Val Leu Pro Val Arg Arg Gly Arg Pro
    2675            2680            2685

Pro Ser Ser Ala Arg Leu Asn Ala Leu Arg Arg Leu His Ala Val
    2690            2695            2700

Gly Glu Pro Ala Ala Asp Ala Gly Leu Asp Thr Val Asn Gly Arg
    2705            2710            2715

Phe Arg Ser Lys Arg Leu Arg Ala Met Ser Gln Glu Glu Ala
    2720            2725            2730

Arg Arg Ala Ala Thr His Ala Ser Pro Thr Ile Pro Tyr Pro Leu
    2735            2740            2745

Ser Arg Tyr Leu His Arg Pro Pro Arg Leu Leu Ser Pro Thr Asp
    2750            2755            2760

Ala Gly His Phe Ala Ser Ser Tyr Ser Ser Pro Leu Ser His Pro
    2765            2770            2775

Leu Ser Lys Gly Ser Ser Leu Thr Ser Pro Lys Arg Gln Arg Arg
    2780            2785            2790

Ser Val Cys Ser Glu Ala Pro Glu His Glu Arg Lys Asn Leu Arg
    2795            2800            2805

Ser Leu Phe Lys Ser Pro Ser Ala Gln Arg Glu Glu Ala Pro Arg
    2810            2815            2820

Ser Leu Thr Arg Pro Phe Gly Pro Leu Lys Gly Glu Gly Phe Ser
    2825            2830            2835

Pro Ala Ser Leu Gly Thr Leu Gly Ser Arg Arg Gln Ser Glu Leu
    2840            2845            2850

Gly Ile Arg Arg Arg Asp Ala Leu Val Ala Phe Pro Pro Ala Gly
    2855            2860            2865

Met Pro Cys His Pro Ala Ser Pro Gly Arg Arg Leu Glu Arg Pro
    2870            2875            2880

Arg Val Asp Gly Ala Asp Met Asp Gly Glu Arg Arg Arg Arg Thr
    2885            2890            2895

Arg Cys Ala Gly Asp Arg Leu Glu Glu Arg Arg Arg Pro Leu Gly
    2900            2905            2910

Pro Val Tyr Ile Pro Thr Lys Val Arg Asp Pro Ala Thr Gly Arg
    2915            2920            2925
```

-continued

| | | | | | | | | | | | |
|---|---|---|---|---|---|---|---|---|---|---|---|
|Val|Ala|Val|Cys|Ala|Cys|Asp|Thr|Glu|Arg|Gly|Glu|
| |2930| | | |2935| | | |2940| | |
|Arg|Val|Arg| | | | | | | | | |

Lys Val Gln Leu Phe Glu Lys Pro His Val Gly Ala Phe Trp Cys
    2945            2950            2955

Ala Arg Tyr Gly Pro Asn Asp Glu Phe Val Arg Cys Phe Ser Ile
    2960            2965            2970

Glu Lys Val Gly Ser Leu Lys Ala Leu Val Ser Ala Val Arg Phe
    2975            2980            2985

Arg Gln Tyr Val Thr Gly His Ser Leu Gly Tyr Gly Val Gly Asn
    2990            2995            3000

Cys Val Pro Val Glu Thr Ile Arg Ser Ala Gly Arg Arg Asp Arg
    3005            3010            3015

Asn Gly Asp Val Ala Pro Asp Arg Pro Leu Lys Gln Ala Ala Ala
    3020            3025            3030

Ser Pro Pro Pro Ala Gly Val Ala Gly Ala Leu Gly Arg Gly Glu
    3035            3040            3045

Val Gly Gln Ala Gln Asp Glu Ser Gly Glu Thr Arg Asp Ala Val
    3050            3055            3060

Glu Glu Glu Gly Arg Gly Gln Glu Pro Leu Gly Ser Gly Glu Gly
    3065            3070            3075

Ala Ser Gly Val Ala Ala Lys Glu Gly His Gly Ser Ser Arg Gly
    3080            3085            3090

Glu Gly Glu Gly Ala Glu Gly Arg Thr Asp Ser Ala Ala Gly Ser
    3095            3100            3105

Thr Ala Gly Asp Arg Ser Thr Glu Asp Ser Ser Arg Leu Leu Ser
    3110            3115            3120

Glu Gly Arg Asp Ala Lys His Gly Ser Ser Pro Ala Gly Gly Ser
    3125            3130            3135

Glu Ala Leu Ala Pro Gly Gly Glu His Ala Leu Ala Glu Gly Ser
    3140            3145            3150

Glu Lys Val Gly Arg Ala Gln Glu Thr Glu Ala Arg Lys Glu Asp
    3155            3160            3165

Leu Arg Thr Ser Gln Asn Glu Thr His Ser Gly Glu Asp Val Ser
    3170            3175            3180

Ser Leu Asn Glu Lys Ala Leu Asp Ser Pro Arg Ser Ser Ala Pro
    3185            3190            3195

Gln Gly Lys Ser Asp Gln Gly Arg Glu Pro Ile Ala Leu Arg Ile
    3200            3205            3210

Arg Ser Thr Leu Pro Pro Ser Glu Val Asp Lys Gln Glu Ala Ala
    3215            3220            3225

Gly Gln Gly Gly Ser Ala Ser Glu Leu Ala Phe Pro Thr Gly Val
    3230            3235            3240

Ser Leu Ala Ser Pro Val Ser Pro Phe Ser Ala Leu Ala Arg Ser
    3245            3250            3255

Pro Ile Ser Ala Arg Ala Ser Ser Val Ser Pro Gly Ala Cys Asp
    3260            3265            3270

Arg Pro Asp Val Ser Arg Arg His Ser Gly Ser Ser Asp Glu Ala
    3275            3280            3285

Ser Glu Ala Leu Trp Asp Leu Gly Glu Asp Leu Gly Phe Ala Gly
    3290            3295            3300

Asp Asp Ala Asn Phe Pro Phe Leu Asp Ser Glu Asn Ser Ala Leu
    3305            3310            3315

Leu Phe Ala Pro Pro Arg His Leu Met Ser Pro Gly Ser Ala Ser

```
                3320                3325                3330
Pro Thr Gly Gly Gly Leu Gly Ile His Tyr Asp Lys Thr Lys His
        3335                3340                3345
Arg Trp Lys Ala Thr Trp Thr Thr Leu Asp Gly Gln Arg Ala Ser
        3350                3355                3360
Thr Ser Phe Ser Val Lys Val Leu Gly Met Glu Arg Ala Arg Glu
        3365                3370                3375
Leu Ala Leu Glu Ala Arg Gln Arg Ala Leu Ala Gly Leu Asp Pro
        3380                3385                3390
Arg Glu Val Arg Asp Glu Met Val Ala Gly Gly Ala Ala Ala Arg
        3395                3400                3405
Asp Arg Glu Arg Glu Arg Gly Arg Gln Asp Gly Arg Arg Glu Gly
        3410                3415                3420
Ser Glu Arg Arg Val Gly Phe Glu Ala Glu Ala Glu Gly Thr Glu
        3425                3430                3435
Ala Ala Ser Glu Arg Leu Arg Arg Arg Gly Glu Arg Glu Asp Gly
        3440                3445                3450
Asp Glu Glu Arg Arg Arg Lys Lys Thr Arg Gly Asp Glu Leu Arg
        3455                3460                3465
Gly Ala Glu Gly Asp Arg Glu Glu Arg Glu Leu Arg Arg Arg Lys
        3470                3475                3480
Thr Ser Glu Glu Arg Arg Lys Gly Lys Asn Glu Ala Ala Lys Asn
        3485                3490                3495
Glu Ala Ala Lys Asn Glu Ala Ala Lys Asn Glu Gly Gly Lys Gly
        3500                3505                3510
Glu Thr Trp Lys Val Arg Glu Gly Gly Lys Thr Pro Leu Gly Val
        3515                3520                3525
Lys Ser His Arg Ala Lys Val Val Gly Gln Thr Val Glu Arg Arg
        3530                3535                3540
Gly Glu Glu Arg Arg Arg Asp Leu Arg Gly Ser Arg Arg Glu Glu
        3545                3550                3555
Gly Lys Thr Val Trp Gly Gln Glu Gln Asp Ala Glu His Gln Val
        3560                3565                3570
Phe Glu Gly Val Lys Glu Asp Asn Glu Arg Gly Arg Arg Arg
        3575                3580                3585
Glu Arg Arg Arg Phe Glu Glu Arg Asp Ser Leu Arg Gly Ser His
        3590                3595                3600
Gly Ala Thr Pro Ser Asp Glu Gln Arg Gln Met Arg Arg Gln Thr
        3605                3610                3615
Ile Leu Gly Ser Arg Glu Val Asp Gly Lys Pro Leu Ser Phe Asp
        3620                3625                3630
Asp Thr His Arg Val Asp Ala Gln Leu Gly Ile Gln Asn Glu Val
        3635                3640                3645
Ala Phe Pro Gly Pro Gln Gly Val Gly Gly Ala Gly Asn Ser Leu
        3650                3655                3660
Gln Phe Gly Arg Glu Gly Glu Arg Phe Ala Ser Ser Ser Pro Val
        3665                3670                3675
Ala Phe Leu Arg Thr Lys Glu Glu Asp Glu Glu Ile Val Glu Val
        3680                3685                3690
Phe Leu Thr Pro Glu Gly Ser Gly Ser Glu Arg Asp Lys Ala Ser
        3695                3700                3705
Ser Val Ser Ala Ser Ser Ala Pro Arg Asp Ser Arg Pro Ala Ser
        3710                3715                3720
```

-continued

```
Pro Arg Leu Arg Ala Ser Arg Leu Arg Glu Ser Ala Arg Leu Gln
    3725                3730                3735

Arg Arg Leu Glu Glu Ala Glu Val His Asp Arg Gly Ser Arg Pro
    3740                3745                3750

Leu Arg Pro Glu Glu Arg Arg Val Ala Lys Arg His Val Ala Glu
    3755                3760                3765

Glu Asn Val Asp Ala Thr Phe Ser Ala Gly Ala Gly Gly Thr Lys
    3770                3775                3780

Lys Ile Arg Pro His Ser Ser His Asp Phe Ser Ala Glu Gly Leu
    3785                3790                3795

Ser Lys Phe Gln Glu Leu Leu Thr Trp Asp Cys Glu Val Glu Ile
    3800                3805                3810

Asp Gly Thr Asp Ala His Val Trp Arg Ala Val Ala Ala Leu Pro
    3815                3820                3825

Gly Pro Arg Pro Arg Pro Tyr Val
    3830                3835

<210> SEQ ID NO 20
<211> LENGTH: 1292
<212> TYPE: PRT
<213> ORGANISM: Homo sapiens

<400> SEQUENCE: 20

Met Cys Gln Glu Arg Lys Pro Arg Glu Leu Ser Leu Arg Asn Asn Ser
1               5                   10                  15

Arg Ala Arg Glu Arg Arg Gly Ser Lys Leu Glu Pro Gly Val Ser Cys
                20                  25                  30

Leu Ser Leu Ser Ala Cys Pro Ser Val Ala Pro Asn Asp Arg Gly Gly
            35                  40                  45

Val Thr Thr Pro Arg Ser Leu His Ala Trp Thr Arg Glu Val Ser Ala
        50                  55                  60

Cys Arg Leu Pro Arg Gln Gln Val Ser Arg Pro Leu Pro Arg Arg Ser
65                  70                  75                  80

Leu Ser Arg Pro Arg Ser Glu Pro Asp Ala Ser Pro Val Lys Gly Pro
                85                  90                  95

Gly Gln Arg Val Glu Ala Ser Ala Val Glu Gly Gly Pro Ser Ala Ser
                100                 105                 110

Ser Ala Glu Arg Leu Gln Val Asp Asp Gly Leu Ala Ala Met Arg Lys
            115                 120                 125

Thr Lys Lys Gly Lys Gly Glu Glu Gly Gly Glu Thr Glu Arg Trp
        130                 135                 140

Ala Thr Gln Ala Val Glu Gln Gln Gly Thr Leu Lys Pro Ala Gly Glu
145                 150                 155                 160

Glu Thr Ala Val Pro Gly Ala Ser Glu Arg Ser Ala Ser Pro Gln Gln
                165                 170                 175

Ala Met Glu Gly Ser Cys Gly Val Glu Thr Pro Glu Thr Phe Phe Gly
                180                 185                 190

Val Ser Thr Gly Asn Ser Gln Gly Ser Pro Ser Pro Glu Ser Val Ala
            195                 200                 205

Gly Glu Glu Ala Arg Pro Glu Arg Glu Asn Ala Glu Lys Ser Ala Thr
        210                 215                 220

Gly Gly Ser Ala Ser Lys Ala Lys Lys Pro Ser Arg Glu Ser Ala Arg
225                 230                 235                 240

Arg Pro Asp Thr Ala Leu Ile Asp Arg His Leu Ile Ala Ala Ser Pro
```

```
                   245                 250                 255
Ser Pro Ser Ser Ala Arg Arg Ser Ser Thr Cys Ser Pro Ser Pro His
            260                 265                 270

Ser Arg Glu Gly Glu Asp Lys Pro Gly Ser Gly Ala Pro Pro Ala Ser
        275                 280                 285

Ser Pro Ser Ala Asn Ala Gly Ala Leu Glu Pro Ala Glu Lys Gly Thr
    290                 295                 300

Leu Gly Ser Pro Pro Gln Asp Val Leu Pro Ala Leu Pro Ala Ser Ser
305                 310                 315                 320

Ser Ser Pro Ser Thr Gly Gly Ser Pro Leu Ser Pro Pro Gly
            325                 330                 335

Gln Ala Pro Arg Ala Glu Ser Gly Ala Pro Gly Ser Gly Ala Leu Ser
            340                 345                 350

Leu Arg Arg Ser Leu Arg His Arg Gln Pro Val Arg Pro Ala Ala Ile
            355                 360                 365

Ala Val Ser Pro Leu Gly Gly Pro Gly Ser Ser Leu Ser Ser Arg Ser
        370                 375                 380

Ala Ser Pro Thr Arg Arg Gly Val Ser Pro Cys Gly Pro Ala Thr
385                 390                 395                 400

Ala Val Gly Lys Gly Ala Gly Ala Ala Ser Gly Ala Ala Leu Pro
                405                 410                 415

Gly Val Gly Ala Lys Ala Pro Pro Ser Ala Thr Pro Leu Ala Gly Leu
            420                 425                 430

Ser Gly Arg Ser Leu Leu Ala Ser Val Ser Pro Ser Ala Ala Ala Leu
        435                 440                 445

Gly Pro Gly Ala Pro Gly Lys Lys Ala Gly Gln Val Gln Gly Ala
    450                 455                 460

Ala Lys Ala Arg Gly Ala Pro Pro Phe Val Leu Ala Glu Tyr Trp Pro
465                 470                 475                 480

Gly Val Thr Leu Asp Glu Met Glu Lys Gly Glu Leu Ser Trp Ala Arg
                485                 490                 495

Ala Ala Ala Gly Leu Pro Leu Pro Ala Ser Pro His Lys Val Pro Gly
            500                 505                 510

Gly Pro Ala Pro Pro Val Gly Gly Pro Pro Ala Arg Asp Glu Asp Ser
        515                 520                 525

Val Ala Ala Cys Ala Gly Glu Lys Gly Lys Glu Lys Ala Phe Leu Gly
    530                 535                 540

Ser Gly Arg Ser Gln Ala Ala Gln Gly Leu Pro Gly Ile Asp Ala Val
545                 550                 555                 560

Ala Ala Ala Cys Trp Gly Gly Ala Gly Val Asp Ser Arg Val Leu Ala
                565                 570                 575

Pro Ala Glu Gly Glu Ala Ser Gly Ala Phe Gly Pro Gly Gly Glu Lys
            580                 585                 590

Lys Lys Val His Ala Ser Ser Asp Ser Ser Gly Gly Ser Arg Ala Ala
        595                 600                 605

Leu Gly Gly Arg Ala Ser Val Gln Gly Lys Ala Arg Lys Pro Ala Gly
    610                 615                 620

Trp Glu Glu Glu Arg Gly Arg Arg Asp Asp Arg Ser Arg Gly Arg Arg
625                 630                 635                 640

Asp Glu Thr Asp Gly Pro Arg Phe Asp Val Thr Trp Phe Val Asp Asp
                645                 650                 655

Ser Pro Leu Ala His Thr Arg Lys Arg Thr Arg Trp Asp Ser Leu Trp
            660                 665                 670
```

```
Val Arg Pro Ala Ser Pro Val Arg Val Gly Asp Ser Ala Pro Glu
        675                 680                 685

Glu Ser Pro Glu Arg Arg Glu Gly Gly Arg Ala Pro Asp Leu Gln
690                 695                 700

Ala Ser Met Ala Lys Arg Arg Thr Ala Asp Ser Gly Leu Glu Glu
705                 710                 715                 720

Ala Gln Val Glu Arg Gly Phe Ser Ser Asp Ser Asp Cys Asp
                725                 730                 735

Trp His Leu Pro Thr Arg Thr Val Ser Ser Leu Ala Pro Phe Ala
                740                 745                 750

Ala Ser Lys Ala His Leu Val Pro Arg Cys Cys Tyr Cys Leu Leu Pro
                755                 760                 765

Arg Arg Leu Pro Gly Arg His Thr Glu Ala Gly Gly Pro Pro Arg Asp
770                 775                 780

Leu Leu Gly Trp Ser Thr Ser Val Glu Ser Glu Glu Thr Arg Gly Arg
785                 790                 795                 800

Tyr Leu Gln Leu Tyr Cys Ala Cys Thr Lys Arg Pro Phe Gly Glu Ser
                805                 810                 815

Val Leu Gln Gly Ala Ala Gly Arg Gly Leu Leu Leu Pro Val Ala
                820                 825                 830

Thr Asn Ala Leu Leu Tyr Ser Val Arg Arg Val Ala Leu Asp Gly Ala
                835                 840                 845

Ala Ser Glu Gln Lys Ser Glu Ala Leu Pro Thr Ser Ala Val Ser Arg
850                 855                 860

Pro Ser Ser Ala Val Ala Arg Ser Ser Cys Ala Ser Ser Gly Cys
865                 870                 875                 880

Asp Asp Gly Arg Ala Glu Val Ala Pro Gly Ala Pro Ala Glu Thr Ile
                885                 890                 895

Tyr Arg Trp Arg Asp Pro Cys Thr Leu Gln Thr Phe Ser Ser Ser Leu
                900                 905                 910

Asp Arg Ile Gln Gly Ser Leu Ala Ala Thr Ala Ala Val Ala Ala Ala
                915                 920                 925

Ala Glu Ser Ala Gly Lys Pro Val Ala Phe Leu Pro Arg Leu Tyr Trp
930                 935                 940

Asp Ser Gln Ala Asp Cys Tyr Ile Ala Ser Cys Leu Arg Trp Glu Glu
945                 950                 955                 960

Glu Ala Gln Pro Thr Pro Ala Ala Glu Arg Gly Glu Lys Arg Asn Gly
                965                 970                 975

Val Glu Arg Pro Ala Glu Ala Arg Glu Arg Gly Arg Asp Glu Lys Lys
                980                 985                 990

Pro Glu Asp Pro Ser Val Pro Gly Leu Arg Arg Arg Ser Leu Lys Leu
                995                 1000                1005

Leu Gln Lys Lys Phe Ser Val Ala Phe Leu Gly Asp Ala Lys Ala
        1010                1015                1020

His Phe Tyr Ala Ser Glu Trp Leu Lys Trp Gln His Lys Gly Gln
        1025                1030                1035

Arg Met Met Asp Glu Glu Asp Arg Arg Gln Glu Val Ala Arg Gln
        1040                1045                1050

Met Leu Leu Val Ser Pro Leu Leu Ala Gly Arg Lys Ala Pro Ala
        1055                1060                1065

Lys Ala Pro Gly Gly Cys Ser Lys Lys Ala Ser Ser Leu Ser Ala
        1070                1075                1080
```

-continued

```
Ala Gln Leu Ala Leu Ala Ser Gly Arg Pro Leu Thr Pro Glu Glu
    1085                1090                1095

Glu Ala Glu Leu Lys Arg Gln Leu Glu Asn Lys Glu Arg Gln Lys
    1100                1105                1110

Lys Gln Lys Leu Leu Arg Gln Trp Arg Arg Gln Gln Ala Arg
    1115                1120                1125

Glu Ala Lys Leu Arg Leu Arg Glu Ala Glu Ala Ala Ala Ala
    1130                1135                1140

Ala Ala Ala Ala Gly Ala Pro Ser Ala Pro Gly Thr Thr Gly Ala
    1145                1150                1155

Ser Gln Thr Arg Ser Pro Gln Ser Gln Gln Lys Ser Glu Ser Leu
    1160                1165                1170

Pro Val Leu Arg Ser Lys Thr Glu Val Leu Gln Pro Ser Pro Gly
    1175                1180                1185

Ala Ser Phe Ala Pro Ala Ser Ser Arg Ser Thr Leu Pro Ala Gly
    1190                1195                1200

Glu Ser Gly Ala Ala Pro Cys Glu Gly Val Gly Thr Arg Arg Ser
    1205                1210                1215

Ala Ala Ser Ala Thr Ser Val Ala Pro Glu Lys Val Thr Gly Arg
    1220                1225                1230

Lys Ser Glu Thr Ala Arg Asp Ala Ala Ser Ala Ser Leu Glu Ala
    1235                1240                1245

Ala Lys Ser Thr Met Val Thr Arg Gly Gly Gly Arg Gly Ser Ser
    1250                1255                1260

Val Val Ala Val Thr Arg Ser Thr Ser Ser Pro Ser Gly Arg Ala
    1265                1270                1275

Ala Ser Val Ala Ser Ser Thr Leu Gly Gly Phe Gly Ala Arg
    1280                1285                1290

<210> SEQ ID NO 21
<211> LENGTH: 2406
<212> TYPE: PRT
<213> ORGANISM: Homo sapiens

<400> SEQUENCE: 21

Met Ala Ala Pro Ala Pro Ser Ala Glu Ala Arg Pro Ala Lys Arg Arg
1               5                   10                  15

Cys Phe Pro Leu Pro Arg Glu Thr Pro Val Ser Ser Glu Asp Glu Thr
                20                  25                  30

Arg Lys Thr Leu Gln His Asp Thr Leu Gly Cys Leu Pro Arg Ser Ser
            35                  40                  45

Ser Gly Gln Pro Glu Leu Ala Ala Ala Ser Ala Ala Ser Gln Val Gly
        50                  55                  60

His Leu Ser Ser Ala Ala Leu Leu Gln Leu Val Gln Thr Gln Ser Ala
65                  70                  75                  80

Gly Gly Val Pro Gln Ala Val Leu Arg Asn Leu Phe Ser Ser Ile His
                85                  90                  95

Arg Asn Pro Lys Pro Leu Pro Ala Asn Ala Leu Ala Ala Thr Pro Asn
            100                 105                 110

Ser Ser Leu Tyr Ala Ser Leu Thr Ser Leu Ser Ser Ala Ala Ala Leu
        115                 120                 125

Pro Gly Ala Gly Pro Ala Tyr Ser Gln Ala Ser Pro Ala Ser Ala
    130                 135                 140

Asp Leu Leu Gln Ser Glu Gln Phe Arg Ser Ala Ala Lys Asn Pro Ser
145                 150                 155                 160
```

-continued

```
Pro Asn Glu Ala Ser Pro Ile Leu Ala Leu Leu Gly Glu Ala Ala Arg
            165                 170                 175

Ala Ala Thr Thr Pro Arg Thr Val Pro Ala Leu Ser Ala Val Cys Pro
        180                 185                 190

Ala Ala Ser Ser Gly Val Ser Leu Pro Pro Ala Ser Asp Thr Leu Ala
    195                 200                 205

Leu Ala Gln Ser Ser Leu Ser Ser Ser Thr Gly Cys Ala Ser Asp Val
210                 215                 220

Lys Ala Ser Arg Pro Glu Glu His Pro Ala Phe Ala Ser Gly Thr Ala
225                 230                 235                 240

Asn Arg Gln Ser Leu Leu Gln Ala Leu Leu Ser Thr Ala Pro Leu
            245                 250                 255

Ala Phe Ser Gly Pro Ser Leu Ser Ser Ala Ser Thr Thr Leu Pro Ala
        260                 265                 270

Ser Ser Gly Ala Val Ser Ser Arg Asn Ala Gly Ala Tyr Gln Phe Glu
    275                 280                 285

Arg Leu Leu Gln Ala Glu Ala Ala Lys Val Lys Ala Leu Leu Pro Asn
290                 295                 300

Thr Thr Ser Lys Ser Met Ser Gln Ser Ser Val Pro Gln Arg Asp Leu
305                 310                 315                 320

Thr Arg Lys Thr Ser Leu Phe Pro Asp Pro Arg Gly Leu Ser Ala Asp
                325                 330                 335

Asp Ala Ser Arg Arg Tyr Asn Thr Arg Gly Ala Asn Ser Gly Gly Ala
            340                 345                 350

Gly Leu Arg Arg Gly Thr Gly Val His Ala Thr Thr Glu Gln Ser Gly
        355                 360                 365

Ala Leu Asp Ala Gly Glu Arg Thr Arg Pro Phe Gly Ala Gly Glu Asp
    370                 375                 380

Glu Ser Ala Gln Gly Lys Pro Asp Ser Arg Gly Arg Gln Arg Pro Gly
385                 390                 395                 400

Ala Leu Asp Ala Ser Asn Ile Leu Gly Leu Leu Ala Ala Phe Gln Pro
                405                 410                 415

Ser Gln Ala Pro Ala Ile Arg Asp Leu Ser Ala Pro Ser His Leu Ser
            420                 425                 430

Ala Ala Ala Thr Gly Ala Leu Pro Leu Thr Ala Ser Phe Thr Ala Ser
        435                 440                 445

Ala Leu Ala Ser Ser Gln Cys Leu Pro Ala Gly Thr Pro Ala Ser Ser
    450                 455                 460

Ser Ala Ser Pro Pro Phe Ser Glu Val Leu Ser Thr Thr Glu Glu Ser
465                 470                 475                 480

Ser Thr Thr Lys Glu Thr Asp Ala Ser Ala Ser Thr Leu Leu Ala Phe
                485                 490                 495

Leu Gln Lys Tyr Ser Ala Val Ser Gly Leu Gly Gly Ala Ser Asp Phe
            500                 505                 510

Leu Gly Gln Leu Gln Gly Lys Thr Ser Leu Pro Leu Ser Leu Ala
        515                 520                 525

Glu Pro Ser Ser Ala Leu Pro Ser Ser Phe Leu Gly Gly Ser Asp Gly
    530                 535                 540

Gly Thr Ile Asp Thr Arg Asn Gly Asn Gly Glu Lys Thr Thr Pro Pro
545                 550                 555                 560

Ile His Leu Phe Gln Ser Ala Phe Arg Met Pro Ser Pro Ser Gln Gln
                565                 570                 575
```

```
Asn Leu Leu Asp Ala Leu Leu Ala Ser Ser Cys Thr Thr Ala Thr Ser
            580                 585                 590

Arg Ser Asp Gly Ser Gly Asn Leu Gly Cys Pro Val Val Asp Glu Arg
        595                 600                 605

Asn Ala Lys Leu Ala Gly Pro Ala His Pro Leu Pro Cys Ser Phe Pro
    610                 615                 620

Gln Ile Ser Ser Ser Gly Glu Pro Gly Arg Lys Thr Gly Gly Arg
625                 630                 635                 640

Val His Arg Gln Gly Thr Ser Gln Ser Gly Gly Arg Val Arg Ser Gly
                645                 650                 655

Lys Asn Gly Gly Ser Ala Ala Pro Pro Arg Gln Ser Ser Ser Asp Asn
                660                 665                 670

Val Pro Ser Thr Pro Thr Val Ser Ser His Glu Ala Pro His Arg Ala
            675                 680                 685

Gly Phe Pro Ser Gln Thr Pro Tyr Glu Leu Ser Ala Ser Pro Ser His
        690                 695                 700

Gln Leu Asp Leu Leu Arg Leu Gly Ala Phe Leu Gly Ala Gly Lys
705                 710                 715                 720

Gln Asp Ala Ser Val His Ser Asp Glu Thr Gly Thr Leu Ser Gly Glu
                725                 730                 735

Pro Ser His Arg Ser Cys Ser Leu Ser Arg Gly Leu Thr Gln Glu Ser
            740                 745                 750

Val Leu Gln Leu Ser Asp Thr Thr Ser Thr Ser Arg Glu Gly Glu Pro
        755                 760                 765

Asn Glu Pro Ser Gln Gly Cys Val Asn Val Ala Ala Ser Leu Pro Ala
770                 775                 780

Phe Gly Pro Gln Pro Ser Ser Gly Ala Ala Lys Ala Arg Glu Gly Arg
785                 790                 795                 800

Arg Gly Ala Gly Gly Ala Gly Ala Ala Pro Pro Val Pro Leu Arg Ala
                805                 810                 815

Asp Val Thr Leu Gly Gly Asn Arg Pro His Tyr His Val Ala Lys Gln
            820                 825                 830

Glu Trp Arg Val Arg Tyr Tyr Met Asn Gly Lys Arg Lys Met Arg Thr
        835                 840                 845

Tyr Ser Ala Lys Phe Tyr Gly Tyr Glu Thr Ala His Thr Met Ala Glu
850                 855                 860

Asp Phe Ala His Tyr Val Asp Lys His Glu Ala Leu Pro Asp Ser Met
865                 870                 875                 880

Met Met Thr Ala Met Met Leu Gln Ala Gln Ala Asn Ser Ala Ala Ser
                885                 890                 895

Ser Gly Gln Thr Val Pro Leu Ala Arg Gly Ile Arg Ala Ser Ser Ala
            900                 905                 910

Ser Thr Gly Ala Gly Gly His Val Ser Lys Ser Ala Thr Lys Gly Ser
        915                 920                 925

Val Ala Ala Ser Ser Glu Gly Ser Thr Ser Met Gly Ser Asp Ala Thr
930                 935                 940

Arg Ser Gln Glu Gly Glu Ala Ala Glu Leu Cys Pro Leu Ala Ala Gly
945                 950                 955                 960

Leu Ser Arg Pro Leu Ala Ser Met His Ser Ala Ala Gly Asn Ala Val
                965                 970                 975

Ala Gln Gly Arg Gln Glu Ser Lys Glu Glu Ala Pro Gly Gly Gln Ala
            980                 985                 990

Trp Phe Gly Glu Pro Gly Lys Phe  Arg Ala Ser Ser Glu  Ala Ala Leu
```

```
                995                 1000                1005
    Cys Gly Ser Gly Ser Ser Ala Glu Gly Arg Asp Gly His Glu Ser
               1010                1015                1020
    Glu Val Leu Trp Ala Thr Leu Gly Lys Val His Asp Ala Ser Gln
               1025                1030                1035
    Gly Lys Lys Ile Lys Pro Glu Lys Pro Leu Thr Val Ala Arg Gly
               1040                1045                1050
    Arg Leu Ala Leu Gly Ala Glu Asp Lys Ser Gln Asn Leu Gly Val
               1055                1060                1065
    Asp Leu Val Asp Ser Gly Glu Ala Gln Gly Leu Pro Gly Val Arg
               1070                1075                1080
    Gln Pro Arg Gln Met Lys Asn Ser Glu Glu Cys Ser Leu Arg Asp
               1085                1090                1095
    Ser Asp Lys Gly Met Ala Leu Ser Lys Arg Phe Gly Phe Leu Pro
               1100                1105                1110
    Ser Gln Thr Pro Ser Cys Asp Ser Met Thr Leu Pro Phe Pro Gly
               1115                1120                1125
    Gly Phe Asp Ala Leu Ser Leu Ser Ser Ala Leu Ser Ser Cys Ala
               1130                1135                1140
    Ser Leu Pro Val Ala His Glu Gly Asn Asn Phe Gln Lys Gly His
               1145                1150                1155
    Thr Gly Asp Ile Val Ala Leu Ala Ser Gln Ser Gly Thr Gln Arg
               1160                1165                1170
    Pro Ala Ser Val Val Leu Ser Arg Asp Ala Asn Val Ser Gly Ser
               1175                1180                1185
    Ser Pro Ser His Pro Thr Trp Gln Arg Glu Gly Ala Ala Val Ser
               1190                1195                1200
    Gly Arg Ala Asp Glu Phe Ser Ser Leu Ser Val Thr Pro Ser Thr
               1205                1210                1215
    Val Pro Leu Ser Ser Phe Thr Met Glu Asp Ile Lys Gly Glu Lys
               1220                1225                1230
    Gly Asp Pro Ser Arg Arg Phe Ala Leu Val Gly Glu Ser Met Lys
               1235                1240                1245
    Asn Val Ser Ala Pro Glu Val Gln Ala Leu Phe Pro Thr Ser Ser
               1250                1255                1260
    Ile Ala Asn Ala Glu Leu Leu Pro Val Asp Phe Leu His Ser Asn
               1265                1270                1275
    Ser Cys Ser Ala Asp Lys Leu Glu Ser Ser Ile Pro Arg Gly Leu
               1280                1285                1290
    Ala Gly Asn Asn Pro Ser Met Thr Ala Thr Ala Val Ala Ala Thr
               1295                1300                1305
    Ala Val Ser His Gln Ile Phe Asp Thr Ile Thr Leu Phe Gly Glu
               1310                1315                1320
    Phe Leu Arg Glu Phe Ala Lys Glu Lys Val Asn Glu Phe His Glu
               1325                1330                1335
    Tyr Gly Leu Glu Ala Ser Pro Leu Thr Val Glu Ala Ser Ser Glu
               1340                1345                1350
    Val Ser Leu Phe Gly Lys Ala Thr Phe Gly Arg Cys Pro Val Ala
               1355                1360                1365
    Gly Gly Ser Thr Pro Ala Gly Ile Ser Lys Met Ser Gly Glu Thr
               1370                1375                1380
    Leu Ser Gly Leu Ser Ala Ser Glu Leu Ser Leu Val Ser Ala Arg
               1385                1390                1395
```

-continued

```
Thr Asn Thr Thr Thr Gly Glu Glu Gln Phe Ala Leu Ala Arg Gly
    1400                1405                1410

Leu Phe Pro Gly Asp Ser Glu Gly Asp Arg Asp Glu Lys Lys Pro
    1415                1420                1425

Gln Leu Ser Gln Gln Glu Leu Leu Val Leu Ser His Ala Leu Val
    1430                1435                1440

Asn Leu Thr Ser Ser Thr Tyr Val Leu Met His Thr Leu Lys Ala
    1445                1450                1455

Ser Leu Ser Lys Ser Thr Glu Ala Val Gln Leu His Gln Pro Leu
    1460                1465                1470

Leu Glu Ala Ala Ser Glu Ala Lys Ala Thr Asp Glu Ala Lys Thr
    1475                1480                1485

Arg Glu Glu Gln Glu Ser Ser Glu Cys Asp His Glu Tyr Pro Pro
    1490                1495                1500

Arg Ser Ser Leu Glu Ala Thr Thr Gly Ala Leu Pro Phe Arg Leu
    1505                1510                1515

Ser Pro Ala Leu Ser Ala Ser Ser Lys Asp Leu Pro Ser Leu Ser
    1520                1525                1530

Ala Ser Ala Ser Leu Glu Ser Val Thr Pro Phe Ala Gly Leu Pro
    1535                1540                1545

Leu Glu Glu Gly Thr Leu Ser Ala Ser Val Gly Leu Ala Ser Ser
    1550                1555                1560

Asp Asp Glu His Asp Thr Ser Leu Leu Phe Lys Thr Glu Ala Ala
    1565                1570                1575

Lys Lys Arg Ser Leu Phe Ser Thr Ala Ala Asp Gly Asp Glu Ser
    1580                1585                1590

Arg Thr Tyr Asn Asp Gly Leu Gly Gln Pro Met Glu Glu Glu Ile
    1595                1600                1605

Arg Ser Cys Val Ser Thr Ser Cys Gly Glu Ala Val Ala Thr Thr
    1610                1615                1620

Thr Leu Ser Ala Ile Gly Pro Gly Thr Gly Ala Ser Gly Ala Leu
    1625                1630                1635

Leu Asp Ser Glu Ser Arg Glu Ser Leu Gly Glu Lys Pro Gly Ala
    1640                1645                1650

Ala Leu Arg Ala Gly Ala His Thr Pro Ala Pro Ser Arg Ala Pro
    1655                1660                1665

Thr Pro Ser Arg Thr Phe Ser Phe Thr Ser Ser Thr Ala Thr
    1670                1675                1680

Ser Ala Ala Leu Leu Cys Asp Ser Asn Val Val His Glu Lys Leu
    1685                1690                1695

Arg Ala Gln Gly Lys Asp Ser Glu Ala Gly Glu Arg Lys Gly Asp
    1700                1705                1710

Ser Glu Lys Glu Glu Glu Val Glu Met Trp Lys Glu Glu Asp Glu
    1715                1720                1725

Glu Val Gln Arg Cys Thr Gly Ser Ala Glu Thr Asp Ser Thr Glu
    1730                1735                1740

Ala Thr Arg Gly Glu Glu Ala Trp Arg Arg Gly Lys Gln Ser Glu
    1745                1750                1755

Lys Lys Pro Ser Val Ile Thr Thr Ala Leu Asn Leu Leu Glu Thr
    1760                1765                1770

His Arg His Leu Ala Leu Thr Ile Ser Gln Leu Lys Arg Pro Val
    1775                1780                1785
```

```
Ala Gln Gln Leu Arg Phe Ile Leu Pro Ile Ala Ala Pro Gln Leu
1790                1795                1800

Leu Pro Cys Ile Leu Pro Pro Ala Ser Phe Gln Gly Pro Gly Glu
1805                1810                1815

Ser Gly Asp Gly Lys Ala Glu Ala Glu Ala Lys Gly Ser Ser Ser
1820                1825                1830

Leu Gly Gln Val Leu Glu Thr Ala Leu Gly His Gly Thr Arg Leu
1835                1840                1845

Ala Pro Ser Ala Ser Ala Met Val Pro Pro Arg Lys Asp Glu Ala
1850                1855                1860

Ala Ser Ala Val Pro Glu Ala Lys Thr Phe Thr Gly Leu Ala Asn
1865                1870                1875

Ala Gly Val Met Arg Glu Ala Ala Ser Arg Thr Leu Glu Ala Glu
1880                1885                1890

Gln Val Ser Arg Lys Arg Ser Arg Glu Glu Val Val Asp Ser Glu
1895                1900                1905

Thr Ala Gly Asp Glu Gly Asp Met Glu Asn Val Pro Glu Thr Leu
1910                1915                1920

Asp Ala Thr Thr Ser Pro Gly Ser Arg Gln Tyr Asp Lys Ser Pro
1925                1930                1935

Ser Asn Gly Gly Thr Lys Pro Pro Ala Thr Ala Lys Ser Arg Val
1940                1945                1950

Ile Arg Asp Gln Ala Ala Leu Glu Arg Leu Leu Leu Ala Pro Phe
1955                1960                1965

Gln Asp Thr Pro Thr Cys Ser Cys Thr Asp Arg Pro Cys Pro Cys
1970                1975                1980

Asp Arg Gln Gln Val Ala Asp Met Ile Tyr Leu Phe Tyr Ala Val
1985                1990                1995

Pro Ala Arg Gln Gln Ala Glu Ser Ser Lys Glu Gly Ser Thr Gln
2000                2005                2010

Arg Leu Gln Phe Ala Ala Arg Asp Thr Asn Glu Arg Lys Asp Ala
2015                2020                2025

Arg Thr Gly Glu Glu Thr Gln Gly Gly Glu Thr Glu Ala Lys Glu
2030                2035                2040

Val Ile Arg Asp Pro Glu Glu Arg Gly Val Cys Glu Gly Ser Ser
2045                2050                2055

Ser Gln Asn Ala His Thr Gln Phe Asp Ala Glu Thr Ala Ser Ser
2060                2065                2070

Ser Met Ser Ser Asp Pro Arg Ala Asp Lys Glu Ser Asn Ala Gln
2075                2080                2085

Asp Ala His Met Ala Asp Lys Thr Ser Phe Val Ser Asp Leu Pro
2090                2095                2100

Gln Pro Ser Gly Glu Phe Ala Pro Ser Leu Leu Ser Glu Thr Ser
2105                2110                2115

Leu Asp Val Ala Met Ala Asp Ser Arg Gly Thr Thr Ser Glu Ile
2120                2125                2130

His Gly Phe Phe Thr Arg Ser Asp Glu Gln Lys Arg Ala Ser Phe
2135                2140                2145

Ser Ser Ser Ser Leu Leu Ala Ala Gly His Ala Val Ala Ser Phe
2150                2155                2160

Ser Ser Ser Leu Ala Gly Val Val Ser Gly Ala Gly Glu Arg Arg
2165                2170                2175

Glu Cys Ala Gly Pro Ser Leu Gly Asp Leu Ser Thr Ile Gly Leu
```

```
                2180                2185                2190
Leu Ser Leu Ser Tyr Pro Ala Met Leu Ala Phe Ile Leu Pro Leu
        2195                2200                2205
Gln Ser Leu Leu His Met Val Ser Gly Met Ile Leu Thr Leu His
    2210                2215                2220
Lys Lys Leu Ile His Arg Phe Ile Cys Ala His Leu Arg Leu Val
2225                2230                2235
Leu Asp Asp Met Arg Arg Pro Ala Gly Gly Ala Leu Lys Ser
    2240                2245                2250
Arg Gly Ala His Gly Asp Thr Glu Ala Ala Glu Ala Gln Val Glu
    2255                2260                2265
Arg Arg Arg Arg Glu His Glu Arg Glu Thr Thr Asn Leu Ala
    2270                2275                2280
Ile Gly Tyr Arg Glu Gly Asn Ala Glu Ala Ser Asn Thr Phe Pro
    2285                2290                2295
Leu Val Asp Thr Val Ser Ser Leu Leu Ser Pro Gly Ser Leu Arg
    2300                2305                2310
Gln Glu Asn Ser Glu Val Glu Arg Arg Asp Asn Asp Glu Glu Arg
    2315                2320                2325
Leu Glu Leu Ile Thr Gly Ile Ala Arg Glu Ser Pro Lys Pro Ser
    2330                2335                2340
Glu Lys Asp Ser Val Ser Pro Phe Leu Ser Thr Ala Pro Cys Pro
    2345                2350                2355
Gly Thr Glu Ala Glu Ser Ser Asp Cys Ser Ala Ser Ser Ala Cys
    2360                2365                2370
Ser Gly Thr Pro Thr Glu Gly Thr Glu Gly Gly Glu Thr Gly Asp
    2375                2380                2385
Ile Ala Ser Phe Leu Ser Pro Ser Gly Asp Val Lys Gln Thr Ile
    2390                2395                2400
Met Leu Ala
    2405

<210> SEQ ID NO 22
<211> LENGTH: 711
<212> TYPE: PRT
<213> ORGANISM: Homo sapiens

<400> SEQUENCE: 22

Met Pro Leu Lys Thr Ser Trp His Cys Ser Cys Asn Ala Thr Phe Pro
1               5                   10                  15

Gly Asp Leu Leu Met Val Val Ala Asn His Asp Arg Val Gly Asn Trp
            20                  25                  30

Asn Pro Gln Asn Ser Val Val Leu Ser Thr Asp Ala Ser Ser Phe Pro
        35                  40                  45

Thr Trp Arg Ser Gly Glu Val Cys Phe Asp Glu Gln Gln Pro Val Arg
    50                  55                  60

Leu Glu Tyr Lys Leu Ile Ile Arg Arg Ala Ser Gly Glu Ile Tyr Trp
65                  70                  75                  80

Glu Pro Ile Pro Thr Asn Arg Val Val Thr Leu Thr Ala Asn Thr Ser
                85                  90                  95

Ser Val Ile Glu Asn Val Trp Gly Ser Leu Ala Thr Cys Ser Ile Thr
            100                 105                 110

Phe Phe Pro Leu Gln Pro Ile Pro Ser Pro Ser Phe Tyr Lys His Ala
        115                 120                 125
```

```
Glu Arg Thr Lys Lys Glu Ala Ser Ser Val His Leu His Ser Ala Ser
130                 135                 140

Ile Ser Asp Asp Ser Gly Ser Asp Thr Gly Thr Cys Ser Gln Val Asp
145                 150                 155                 160

Glu Ser Arg Thr Gln Arg Asn Val Arg Gly Gln Pro Ala Ser Val Gly
                165                 170                 175

Thr Gly Lys Ala Thr Ala Ala Glu Arg Gly Gly Lys Gly Tyr Val Met
            180                 185                 190

Pro His His Gln Cys Ser Thr Ser Gln Arg Arg His Ser Ile Ser Thr
                195                 200                 205

Gln Ala Ala Asp Glu Ala Ala Gly Gly Gly Asn Arg Val Ser Phe Lys
210                 215                 220

Arg Ser Ala Phe Ile Leu Ala Asn Thr Gly Pro Ile Thr Asn Tyr Tyr
225                 230                 235                 240

Thr Val Ser Lys Thr Ile Gly Arg Gly Thr Trp Gly Glu Val Lys Leu
                245                 250                 255

Val Ile Asp Asn Gly Thr Gly Ala Arg Arg Ala Ala Lys Lys Ile Pro
                260                 265                 270

Lys Cys Tyr Val Glu Asp Ala Asp Arg Phe Arg Gln Glu Ile Glu Ile
            275                 280                 285

Met Lys Ser Leu Asp His Pro Asn Ile Val Arg Leu Tyr Glu Thr Phe
290                 295                 300

Glu Asp Met Thr Asp Phe Tyr Leu Val Met Glu Tyr Cys Thr Gly Gly
305                 310                 315                 320

Glu Leu Phe Asp Arg Leu Val His Gln Gly Val Phe Thr Glu Ala Leu
                325                 330                 335

Ala Cys Arg Ile Met Arg Gln Ile Leu Ala Ala Val Ala Tyr Cys His
                340                 345                 350

Ala His Arg Val Ala His Arg Asp Leu Lys Pro Glu Asn Phe Leu Phe
                355                 360                 365

Leu His Asp Asn Pro Glu Ser Pro Ile Lys Leu Ile Asp Phe Gly Leu
                370                 375                 380

Ala Ala Arg Phe Lys Ser Gly Gln Pro Met Arg Thr Arg Ala Gly Thr
385                 390                 395                 400

Pro Tyr Tyr Val Ser Pro Gln Val Leu Glu Gly Arg Tyr Gly Pro Glu
                405                 410                 415

Cys Asp Val Trp Ser Ala Gly Val Met Met Tyr Ile Leu Leu Cys Gly
                420                 425                 430

Tyr Pro Pro Phe Asn Ala Pro Ser Asp Arg Ala Ile Met Asn Lys Val
                435                 440                 445

Arg Ala Gly His Tyr Thr Phe Pro Asp Ser Glu Trp Ser Arg Val Ser
450                 455                 460

Leu Gln Ala Lys Asp Leu Ile Ser Arg Leu Leu Asp Arg His Pro Arg
465                 470                 475                 480

Thr Arg Ile Ser Ala Glu Gln Ala Leu Arg His Ala Trp Phe Ala Met
                485                 490                 495

His Ala Pro Gly Asp His Phe Glu Pro Leu Gly Leu Asp Ile Leu Ser
                500                 505                 510

Lys Phe Arg Arg Phe Gln Gly Leu Ser Arg Leu Lys Lys Leu Ala Leu
                515                 520                 525

Thr Val Ile Ala Gln His Leu Glu Asp Ser Glu Ile Glu Gly Leu Lys
530                 535                 540

Asn Leu Phe Thr Gln Leu Asp Thr Glu Gly Asp Gly Val Leu Thr Val
```

```
            545                 550                 555                 560
        Glu Glu Ile Arg Lys Gly Ile Glu Arg Ser Gly Val His Leu Pro Pro
                        565                 570                 575

Asp Met Val Leu Glu Asp Val Leu Arg Glu Val Asp Thr Ala Gly Thr
                        580                 585                 590

Gly Ser Ile Asp Tyr Thr Glu Phe Ile Ala Ala Cys Leu His Gln Ser
                        595                 600                 605

His Tyr Ile Arg Glu Glu Ala Cys Arg Ala Ala Phe Arg Val Leu Asp
                        610                 615                 620

Ile Asn Gly Asp Gly Leu Val Ser Ala Gln Glu Leu Arg Gln Val Phe
        625                 630                 635                 640

His Met Ala Gly Asp Leu Glu Thr Asp Ala Ala Glu Leu Leu Glu
                        645                 650                 655

Ala Asp Ala Asp Gly Asp Gly His Ile Thr Phe Asp Glu Phe Cys Gly
                        660                 665                 670

Leu Met Arg Lys Val Pro Ser Leu Ala Leu Val Thr Glu His Thr Val
                        675                 680                 685

Ser Met Met Arg Arg Thr Cys Ser Arg Thr Asn Ile Ser Glu Ala Ser
                        690                 695                 700

Leu Thr Pro Arg Ala Thr Gly
        705                 710

<210> SEQ ID NO 23
<211> LENGTH: 368
<212> TYPE: PRT
<213> ORGANISM: Homo sapiens

<400> SEQUENCE: 23

Met Val Ser Arg Thr Leu Ser Leu Ser Met Ser Leu Phe Arg Ala His
        1               5                   10                  15

Leu Val Phe Tyr Arg Cys Ala Leu Asn Leu Asn Ser Ser Tyr Asn Phe
                        20                  25                  30

Gly Phe Leu Val Ala Met Thr Phe Val Leu Gln Ile Ile Thr Gly Ile
                        35                  40                  45

Thr Leu Ala Phe Arg Tyr Thr Ser Glu Ala Ser Cys Ala Phe Ala Ser
                        50                  55                  60

Val Gln His Leu Val Arg Glu Val Ala Ala Gly Trp Glu Phe Arg Met
        65                  70                  75                  80

Leu His Ala Thr Thr Ala Ser Phe Val Phe Leu Cys Ile Leu Ile His
                        85                  90                  95

Met Thr Arg Gly Leu Tyr Asn Trp Ser Tyr Ser Tyr Leu Thr Thr Ala
                        100                 105                 110

Trp Met Ser Gly Leu Val Leu Tyr Leu Leu Thr Ile Ala Thr Ala Phe
                        115                 120                 125

Leu Gly Tyr Val Leu Pro Trp Gly Gln Met Ser Phe Trp Gly Ala Thr
                        130                 135                 140

Val Ile Thr Asn Leu Leu Ser Pro Ile Pro Tyr Leu Val Pro Trp Leu
        145                 150                 155                 160

Leu Gly Gly Tyr Tyr Val Ser Asp Val Thr Leu Lys Arg Phe Phe Val
                        165                 170                 175

Leu His Phe Ile Leu Pro Phe Ile Gly Cys Ile Ile Ile Val Leu His
                        180                 185                 190

Ile Phe Tyr Leu His Leu Asn Gly Ser Ser Asn Pro Ala Gly Ile Asp
                        195                 200                 205
```

```
Thr Ala Leu Lys Val Ala Phe Tyr Pro His Met Leu Met Thr Asp Ala
    210                 215                 220

Lys Cys Leu Ser Tyr Leu Ile Gly Leu Ile Phe Leu Gln Ala Ala Phe
225                 230                 235                 240

Gly Leu Met Glu Leu Ser His Pro Asp Asn Ser Ile Pro Val Asn Arg
                245                 250                 255

Phe Val Thr Pro Leu His Ile Val Pro Glu Trp Tyr Phe Leu Ala Tyr
                260                 265                 270

Tyr Ala Val Leu Lys Val Ile Pro Ser Lys Thr Gly Gly Leu Leu Val
                275                 280                 285

Phe Met Ser Ser Leu Ile Asn Leu Gly Leu Leu Ser Glu Ile Arg Ala
    290                 295                 300

Leu Asn Thr Arg Met Leu Ile Arg Gln Gln Phe Met Thr Arg Asn Val
305                 310                 315                 320

Val Ser Gly Trp Val Ile Trp Val Tyr Ser Met Ile Phe Leu Ile
                325                 330                 335

Ile Ile Gly Ser Ala Ile Pro Gln Ala Thr Tyr Ile Leu Tyr Gly Arg
                340                 345                 350

Leu Ala Thr Ile Leu Tyr Leu Thr Thr Gly Leu Val Leu Cys Leu Tyr
                355                 360                 365
```

<210> SEQ ID NO 24
<211> LENGTH: 84
<212> TYPE: PRT
<213> ORGANISM: Homo sapiens

<400> SEQUENCE: 24

```
Lys Leu Cys Lys Tyr His His Phe Leu Cys Ser Leu Thr Ser Gln Leu
1               5                   10                  15

Ser Tyr Leu Ile Gly Leu Ile Phe Leu Gln Ala Ala Phe Gly Leu Met
                20                  25                  30

Glu Leu Ser His Pro Asp Asn Ser Ile Pro Val Asn Arg Phe Val Thr
                35                  40                  45

Pro Leu His Ile Val Pro Glu Trp Tyr Phe Leu Ala Tyr Tyr Ala Val
        50                  55                  60

Leu Lys Val Ile Pro Ser Lys Thr Gly Gly Leu Leu Val Phe Met Ser
65                  70                  75                  80

Ser Thr Cys Gln
```

<210> SEQ ID NO 25
<211> LENGTH: 244
<212> TYPE: PRT
<213> ORGANISM: Homo sapiens

<400> SEQUENCE: 25

```
Met Ile Ala Val His His Pro Thr Gly Leu Leu Lys Thr Ala Lys
1               5                   10                  15

Ser Val Gly Phe Gln Tyr Pro Thr Thr Leu Arg Leu Phe His Ile Gly
                20                  25                  30

Tyr Val Leu Gly Val Ile Tyr Gly Leu Leu Ser Leu Val Leu Thr
                35                  40                  45

Ala Arg Glu Asn Tyr Tyr Ser Asp Ala Ser Met Ile Ser Thr Ile Val
        50                  55                  60

Leu Gly Val Ile Ile Ser Glu Thr Gly Leu Phe Ile Ser Phe Phe Trp
65                  70                  75                  80

Gly Val Tyr Thr Thr Ser Trp Thr Gly Leu Asp Leu Glu Gly Leu
```

```
                       85                  90                  95

Cys Leu Pro Asp Pro Ser Ser Ile Val Leu Phe Met Thr Ile Met Leu
            100                 105                 110

Ser Ala Leu Ser Ile Val Val Ser Val Tyr Leu Lys Asn Gln His
            115                 120                 125

Leu Tyr Thr Ser Cys Thr Asn Ile Met Ile Phe Thr Leu Val Val Ser
130                 135                 140

Phe Leu Met Leu Val Cys Thr Glu Tyr Leu Gly Leu Ser Ile Tyr Ile
145                 150                 155                 160

Asn Asp Asn Gly Phe Gly Asn Gly Leu Phe Ile Leu Thr Gly Ile His
                165                 170                 175

Phe Ser His Val Ile Val Gly Ala Ile Leu Gly Phe Phe Asn Gln Gly
                180                 185                 190

Met Tyr Ser Ser Leu Val Thr Tyr Leu Pro Val Asn Cys Ile Thr Leu
                195                 200                 205

Ser Lys Cys Lys Gly Thr Leu Cys Lys Ile Phe Ser Glu Pro Phe Thr
            210                 215                 220

Ile Leu Tyr Leu His Phe Val Glu Ala Val Trp Ile Met Ile His Val
225                 230                 235                 240

Thr Phe Tyr Leu

<210> SEQ ID NO 26
<211> LENGTH: 156
<212> TYPE: PRT
<213> ORGANISM: Homo sapiens

<400> SEQUENCE: 26

Met Ser Leu Phe Arg Ala His Leu Val Phe Tyr Arg Cys Ala Leu Asn
1               5                   10                  15

Leu Asn Ser Ser Tyr Asn Phe Gly Phe Leu Val Ala Met Thr Phe Val
                20                  25                  30

Leu Gln Ile Ile Thr Gly Ile Thr Leu Ala Phe Arg Tyr Thr Ser Glu
            35                  40                  45

Ala Ser Cys Ala Phe Ala Ser Val Gln His Leu Val Arg Glu Val Ala
        50                  55                  60

Ala Gly Trp Glu Phe Arg Met Leu His Ala Thr Thr Ala Ser Phe Val
65                  70                  75                  80

Phe Leu Cys Ile Leu Ile His Met Thr Arg Gly Leu Tyr Asn Trp Ser
                85                  90                  95

Tyr Ser Tyr Leu Thr Thr Ala Trp Met Ser Gly Leu Val Leu Tyr Leu
            100                 105                 110

Leu Thr Ile Ala Thr Ala Phe Leu Gly Tyr Ala Thr Ser Asn Tyr Thr
        115                 120                 125

Thr Leu Cys Gln Glu Gly Ser Gln Ile Thr Leu Ile Ile Phe Val Ile
130                 135                 140

Leu Ile His Gly Val Gln Leu Val Leu Phe Leu Gln
145                 150                 155

<210> SEQ ID NO 27
<211> LENGTH: 403
<212> TYPE: PRT
<213> ORGANISM: Homo sapiens

<400> SEQUENCE: 27

Trp Ala His His Met Met Thr Val Gly Leu Glu Val Asp Thr Arg Ala
1               5                   10                  15
```

-continued

```
Tyr Phe Ser Ala Met Thr Ile Met Ile Ala Ile Pro Thr Gly Thr Lys
                 20                  25                  30

Ile Phe Asn Trp Leu Gly Thr Tyr Met Ala Ser His Asn Thr Thr Arg
             35                  40                  45

Thr Ile Asp Leu Trp Ala Ala Leu Cys Phe Ile Leu Leu Phe Thr Leu
         50                  55                  60

Gly Gly Thr Thr Gly Val Val Met Gly Asn Ala Gly Met Asp Ile Ala
65                   70                  75                  80

Leu His Asp Thr Tyr Tyr Ile Val Ala His Phe His Phe Val Leu Ser
                 85                  90                  95

Leu Gly Ala Ile Leu Ala Thr Ile Cys Gly Phe Val Phe Tyr Ser Lys
                100                 105                 110

Asp Met Phe Gly Asp Thr Leu Asn Leu Phe His Val Asn Thr Gly Ser
                115                 120                 125

Ser Pro Tyr Leu Asn Ile Trp Phe Val Val Phe Leu Ala Ser Ile Met
                130                 135                 140

Leu Ile Phe Leu Pro Met His Ile Leu Gly Phe Asn Val Met Pro Arg
145                 150                 155                 160

Arg Ile Pro Asp Tyr Pro Asp Tyr Leu Cys Tyr Ile Asn Thr Trp Cys
                165                 170                 175

Ser Ile Val Gln Leu Val Val Tyr Thr Pro Gln Lys Lys Leu Ile Asn
                180                 185                 190

Asn Pro Val Ser Glu Met Ile Thr Pro Ser Thr Met Val Leu Ile Ile
                195                 200                 205

Leu Ala Ser Glu Tyr Tyr Ser Tyr Leu Thr Thr Ala Trp Met Ser Gly
                210                 215                 220

Leu Val Leu Tyr Leu Leu Thr Ile Ala Thr Ala Phe Leu Gly Tyr Val
225                 230                 235                 240

Leu Pro Trp Gly Gln Met Ser Phe Trp Gly Ala Thr Val Ile Thr Asn
                245                 250                 255

Leu Leu Ser Pro Ile Pro Tyr Leu Val Pro Trp Leu Leu Gly Gly Tyr
                260                 265                 270

Tyr Val Ser Asp Val Thr Leu Lys Arg Phe Phe Val Leu His Phe Ile
                275                 280                 285

Leu Pro Phe Ile Gly Cys Ile Ile Val Leu His Ile Phe Tyr Leu
                290                 295                 300

His Leu Asn Gly Ser Ser Asn Pro Ala Gly Ile Asp Thr Ala Leu Lys
305                 310                 315                 320

Val Ala Phe Tyr Pro His Met Leu Met Thr Asp Ala Lys Cys Leu Ser
                325                 330                 335

Tyr Leu Ile Gly Leu Ile Phe Leu Gln Ala Ala Phe Gly Leu Met Glu
                340                 345                 350

Leu Ser His Pro Asp Asn Ser Ile Pro Val Asn Arg Phe Val Thr Pro
                355                 360                 365

Leu His Ile Val Pro Glu Trp Tyr Phe Leu Ala Tyr Tyr Ala Val Leu
                370                 375                 380

Lys Val Ile Pro Ser Lys Thr Gly Gly Leu Leu Val Phe Met Ser Ser
385                 390                 395                 400

Thr Cys Gln
```